United States Patent
Kouji et al.

(10) Patent No.: US 11,780,841 B2
(45) Date of Patent: Oct. 10, 2023

(54) 3,6-METHANO-1H-PYRROLO[3,2-B]PYRIDINE AND 3,6-METHANO-1H-PYRROLO[3,2-C]PYRIDINE COMPOUNDS AND MEDICAMENTS USING SAME

(71) Applicant: Irimajiri Therapeutics Inc., Kochi (JP)

(72) Inventors: Hiroyuki Kouji, Yufu (JP); Kentaro Yamada, Yufu (JP); Akira Katoh, Yufu (JP); Toshimasa Ishizaki, Yufu (JP); Shigeru Matsuoka, Yufu (JP); Akira Nishizono, Yufu (JP); Tadashi Mishina, Fujisawa (JP); Atsushi Yoshimori, Fujisawa (JP)

(73) Assignee: Irimajiri Therapeutics Inc., Kochi (JP)

( * ) Notice: Subject to any disclaimer, the term of this patent is extended or adjusted under 35 U.S.C. 154(b) by 0 days.

(21) Appl. No.: 17/679,075

(22) Filed: Feb. 23, 2022

(65) Prior Publication Data

US 2022/0194942 A1    Jun. 23, 2022

Related U.S. Application Data

(63) Continuation of application No. 16/791,715, filed on Feb. 14, 2020, now Pat. No. 11,292,794, which is a continuation-in-part of application No. PCT/JP2019/032032, filed on Aug. 15, 2019.

(30) Foreign Application Priority Data

Aug. 16, 2018  (JP) .................. 2018-153227

(51) Int. Cl.
  C07D 471/08   (2006.01)
  C07D 471/18   (2006.01)
  A61P 31/14    (2006.01)
  A61P 35/00    (2006.01)

(52) U.S. Cl.
  CPC ............ C07D 471/18 (2013.01); A61P 31/14 (2018.01); A61P 35/00 (2018.01); C07D 471/08 (2013.01)

(58) Field of Classification Search
  CPC .................................................. C07D 471/08
  See application file for complete search history.

(56) References Cited

FOREIGN PATENT DOCUMENTS

| EP | 3 978 076 A1 | 4/2022 |
|---|---|---|
| WO | 2010/029313 A1 | 3/2010 |
| WO | 2013/154778 A1 | 10/2013 |
| WO | 2020/246503 A1 | 12/2020 |

OTHER PUBLICATIONS

Bromley et al., "Tandem inverse electron demand Diels-Alder, retro-Diels-Alder and intramolecular Diels-Alder sequences: one-pot synthesis of diaza-polycycles," *Tetrahedron* 63:6004-6014, 2007.
Craven et al., "Design, synthesis and decoration of molecular scaffolds for exploitation in the production of alkaloid-like libraries," *Bioorg. Med. Chem.* 23:2629-2635, 2015.
Golub et al., "Molecular Classification of Cancer: Class Discovery and Class Prediction by Gene Expression Monitoring," *Science* 286:531-531, Oct. 15, 1999.
Murrison et al., "Synthesis of Skeletally Diverse Alkaloid-Like Small Molecules," *Eur J. Org. Chem.*:2354-2359, 2011.
Office Action, dated Jul. 13, 2021, for Chinese Application No. 201980068510.3 (w/ English Translation) (10 pages).
Extended European Search Report, dated Mar. 4, 2022, for European Application No. 19849263.9. (8 pages).
Tsiang et al., "Inhibition of Rabies Virus Infection in Cultured Rat Cortical Neurons by an N-Methyl-D-Aspartate Noncompetitive Antagonist, MK-801," *Antimicrobial Agents and Chemotherapy* 35(3):572-574, Mar. 1991.

*Primary Examiner* — Laura L Stockton
(74) *Attorney, Agent, or Firm* — Seed IP Law Group LLP

(57) ABSTRACT

The present disclosure provides a compound that is useful for the treatment and prophylaxis of rabies. The present disclosure provides a compound represented by formula XXIIF or formula XXIIB:

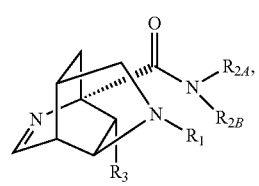

Formula XXIIF

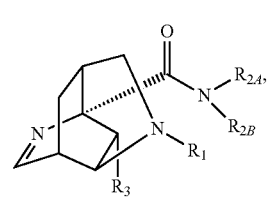

Formula XXIIB wherein $R_1$, $R_{2A}$, $R_{2B}$, $R_3$, and $R_4$ are defined in the specification, a solvent, or a pharmaceutically acceptable salt thereof, use of such a compound, solvate, or pharmaceutically acceptable salt thereof for the treatment or prophylaxis of rabies and cancer, a pharmaceutical composition comprising such a compound, solvate, or pharmaceutically acceptable salt thereof, and a method for the treatment or prophylaxis of rabies and cancer using the same.

14 Claims, 80 Drawing Sheets

3,6-METHANO-1H-PYRROLO[3,2-B]PYRIDINE AND 3,6-METHANO-1H-PYRROLO[3,2-C]PYRIDINE COMPOUNDS AND MEDICAMENTS USING SAME

TECHNICAL FIELD

The present disclosure relates to a novel fused tricyclic compound that is useful as a medicament, an enantiomer thereof, or a pharmaceutically acceptable salt thereof, or a solvate thereof. More specifically, the present disclosure relates to a pharmaceutical composition comprising the fused tricyclic compound or an enantiomer thereof, or a pharmaceutically acceptable salt thereof, or a solvate thereof. The present disclosure also relates to a therapeutic agent comprising the fused tricyclic compound or an enantiomer thereof, or a pharmaceutically acceptable salt thereof, or a solvate thereof.

BACKGROUND ART

Rabies is an infection induced by a rabies virus. The mortality after the onset in humans is almost 100%. While over 15 million people worldwide are vaccinated post-exposure for the prophylaxis of rabies every year, the worldwide number of fatalities due to rabies is about 55000 annually. An effective therapeutic method for rabies still has not been established. There is still a demand for the establishment thereof.

SUMMARY OF INVENTION

Solution to Problem

The present disclosure provides a compound and a method for the treatment of rabies and other diseases.

The present disclosure was completed by the inventors from finding that compounds represented by the following formula IF, IB, IIF, BB, XXIF, XXIB, XXIIF, or XXIIB and the structural formulas related thereto, or a pharmaceutically acceptable salt thereof (hereinafter, also referred to as "the compound(s) of the present disclosure" or "the present compound(s)") can achieve the objects as a result of diligent study.

The present disclosure provides the following items.

[Item 1]
A compound represented by formula XXIF:

[Chemical Formula 1]

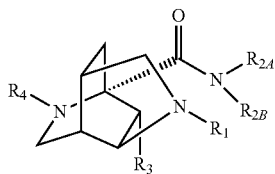

Formula XXIF or an enantiomer thereof, or a salt thereof, or a solvate thereof, wherein
  $R_1$, $R_3$, and $R_4$ are each independently hydrogen, an optionally substituted hydrocarbon group, an optionally substituted heterocycle, optionally substituted carbonyl, or an optionally substituted functional group, and
  $R_{2A}$ and $R_{2B}$ are each independently hydrogen, an optionally substituted hydrocarbon group, an optionally substituted heterocycle, optionally substituted carbonyl, or an optionally substituted functional group, or $R_{2A}$ and $R_{2B}$, together with the nitrogen atom to which they are attached, form a heterocycle, wherein the heterocycles are each independently and optionally substituted.

[Item 1B]
The compound represented by formula XXIF:

[Chemical Formula 2]

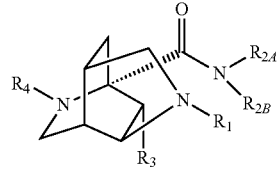

Formula XXIF or an enantiomer thereof, or a salt thereof, or a solvate thereof according to item 1, wherein
  $R_1$, $R_3$, and $R_4$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl,
  $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 2]
A compound represented by formula XXIB:

[Chemical Formula 3]

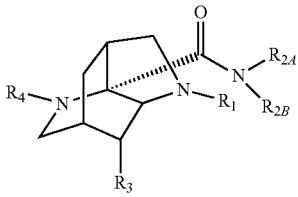

Formula XXIB or an enantiomer thereof, or a salt thereof, or a solvate thereof, wherein
  $R_1$, $R_3$, and $R_4$ are each independently hydrogen, an optionally substituted hydrocarbon group, an optionally substituted heterocycle, optionally substituted carbonyl, or an optionally substituted functional group,
  $R_{2A}$ and $R_{2B}$ are each independently hydrogen, an optionally substituted hydrocarbon group, an optionally substituted heterocycle, optionally substituted carbonyl, or an optionally substituted functional group, or $R_{2A}$ and $R_{2B}$, together with the nitrogen atom to which they are attached, form a heterocycle, wherein the heterocycles are each independently and optionally substituted.

[Item 2B]

The compound represented by formula XXIB:

[Chemical Formula 4]

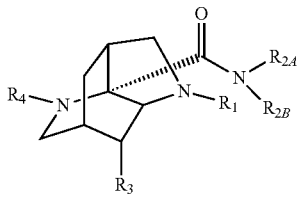

Formula XXIB or an enantiomer thereof, or a salt thereof, or a solvate thereof according to item 2, wherein $R_1$, $R_3$, and $R_4$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 3]

The compound or an enantiomer thereof, or a salt thereof, or a solvate thereof according to any one of the preceding items, wherein the alkyl, alkenyl, alkynyl, cycloalkyl, heterocycloalkyl, aryl, heteroaryl, and carbonyl of $R_1$, $R_3$, and $R_4$ are each independently and optionally substituted with one to the maximum substitutable number of the same or different substituents selected from substituent group I, and the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently and optionally substituted with one to the maximum substitutable number of the same or different substituents selected from substituent group I.

[Item 4]

The compound or an enantiomer thereof, or a salt thereof, or a solvate thereof according to any one of the preceding items, wherein $R_1$, $R_3$, and $R_4$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 4B]

The compound or an enantiomer thereof, or a salt thereof, or a solvate thereof according to any one of the preceding items, wherein $R_1$, $R_3$, and $R_4$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, and $R_{2A}$ and $R_{2B}$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 5]

The compound or an enantiomer thereof, or a salt thereof, or a solvate thereof according to any one of the preceding items, wherein $R_1$, $R_3$, and $R_4$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$, $R_3$, and $R_4$ are optionally substituted with one to the maximum substitutable number of the same or different substituents selected from substituent group II, and $R_{2A}$ and $R_{2B}$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, form a 5- to 6-membered non-aryl heterocycle or heteroaryl ring, wherein the non-aryl heterocycle and the heteroaryl ring are optionally substituted with one to the maximum substitutable number of the same or different substituents selected from substituent group II.

[Item 5B]

The compound or an enantiomer thereof, or a salt thereof, or a solvate thereof according to any one of the preceding items, wherein $R_1$, $R_3$, and $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$, $R_3$, and $R_4$ are optionally substituted with one to the maximum substitutable number of the same or different substituents selected from substituent group III, and $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_{2A}$ and $R_{2B}$ are optionally substituted with one to the maximum substitutable number of the same or different substituents selected from substituent group III, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group V.

[Item 6]

The compound or an enantiomer thereof, or a salt thereof, or a solvate thereof according to any one of the preceding items, wherein $R_1$ and $R_4$ are each independently hydrogen, optionally substituted alkyl, optionally substituted arylalkyl, optionally substituted cycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_4$ are optionally substituted with one to the maximum substitutable number of the same or different substituents selected from substituent group III.

[Item 6B]

The compound or an enantiomer thereof, or a salt thereof, or a solvate thereof according to any one of the preceding items, wherein $R_1$ and $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_4$ are optionally substituted with one to the maximum substitutable number of the same or different substituents selected from substituent group III.

[Item 7]

The compound or an enantiomer thereof, or a salt thereof, or a solvate thereof according to any one of the preceding items, wherein $R_1$ and $R_4$ are each independently hydrogen, optionally substituted alkyl, optionally substituted arylalkyl, formyl, optionally substituted alkylcarbonyl, optionally substituted alkoxycarbonyl, optionally substituted arylcarbonyl, optionally substituted aryloxycarbonyl, carbamoyl, or optionally substituted alkylcarbamoyl, wherein the groups of $R_1$ and $R_4$ are optionally substituted with one to the maximum substitutable number of the same or different substituents selected from substituent group III.

[Item 7B]

The compound or an enantiomer thereof, or a salt thereof, or a solvate thereof according to any one of the preceding items, wherein $R_1$ and $R_4$ are each independently hydrogen, optionally substituted $C_{1-12}$ alkyl, optionally substituted $C_{6-10}$ aryl $C_{1-12}$ alkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, carbamoyl, or optionally substituted $C_{1-12}$ alkylcarbamoyl, wherein the groups of $R_1$ and $R_4$ are optionally substituted with one to the maximum substitutable number of the same or different substituents selected from substituent group III.

[Item 8]

The compound or an enantiomer thereof, or a salt thereof, or a solvate thereof according to any one of the preceding items, wherein $R_1$ and $R_4$ are each independently hydrogen; alkyl; alkyl substituted with one to the maximum substitutable number of the same or different substituents selected from the group consisting of amino, substituted amino, substituted oxy, substituted carbonyl, cycloalkyl, and substituted cycloalkyl; arylalkyl; arylalkyl substituted with one to the maximum substitutable number of the same or different substituents selected from the group consisting of halogen, alkyl, substituted alkyl, hydroxy, substituted oxy, amino, substituted amino, and nitro; formyl; substituted carbonyl; or substituted oxycarbonyl, wherein the substituted amino, substituted oxy, substituted alkyl, substituted carbonyl, substituted cycloalkyl, substituted carbonyl, and substituted oxycarbonyl in $R_1$ and $R_4$ each independently have one to the maximum substitutable number of the same or different substituents selected from substituent group IV.

[Item 8B]

The compound or an enantiomer thereof, or a salt thereof, or a solvate thereof according to any one of the preceding items, wherein $R_1$ and $R_4$ are each independently hydrogen; $C_{1-12}$ alkyl; $C_{1-12}$ alkyl substituted with one to the maximum substitutable number of the same or different substituents selected from the group consisting of amino, substituted amino, substituted oxy, substituted carbonyl, $C_{3-10}$ cycloalkyl, and substituted $C_{3-10}$ cycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, substituted alkyl, hydroxy, substituted oxy, amino, substituted amino, and nitro; formyl; substituted carbonyl; or substituted oxycarbonyl, wherein the substituted amino, substituted oxy, substituted alkyl, substituted carbonyl, substituted cycloalkyl, substituted carbonyl, and substituted oxycarbonyl in $R_1$ and $R_4$ each independently have one to the maximum substitutable number of the same or different substituents selected from substituent group IV.

[Item 9]

The compound or an enantiomer thereof, or a salt thereof, or a solvate thereof according to any one of the preceding items, wherein $R_1$ and $R_4$ are each independently hydrogen; alkyl; alkyl substituted with one to the maximum substitutable number of the same or different substituents selected from the group consisting of amidinoamino, alkoxy, alkoxycarbonyl, carbamoyl, carboxy, hydroxy, trialkylsilyloxy, and cycloalkyl; arylalkyl; arylalkyl substituted with one to the maximum substitutable number of the same or different substituents selected from the group consisting of halogen, alkyl, haloalkyl, alkoxy, haloalkoxy, amino, substituted amino, nitro, and hydroxy; formyl; alkylcarbonyl; arylalkylcarbonyl; arylalkyloxycarbonyl; alkoxycarbonyl; arylcarbonyl; aryloxycarbonyl; carbamoyl; alkylcarbamoyl; or arylalkylcarbamoyl, wherein the substituted amino each independently have one to the maximum substitutable number of the same or different substituents selected from substituent group IV.

[Item 9B]

The compound or an enantiomer thereof, or a salt thereof, or a solvate thereof according to any one of the preceding items, wherein $R_1$ and $R_4$ are each independently hydrogen; $C_{1-12}$ alkyl; $C_{1-12}$ alkyl substituted with one to the maximum substitutable number of the same or different substituents selected from the group consisting of amidinoamino, $C_{1-6}$ alkoxy, $C_{1-6}$ alkoxycarbonyl, carbamoyl, carboxy, hydroxy, tri-$C_{1-6}$ alkylsilyloxy, and $C_{3-10}$ cycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, $C_{1-6}$ haloalkoxy, amino, substituted amino, nitro, and hydroxy; formyl; $C_{1-12}$ alkylcarbonyl; $C_{6-10}$ aryl $C_{1-6}$ alkylcarbonyl; $C_{6-10}$ aryl $C_{1-6}$ alkyloxycarbonyl; $C_{1-12}$ alkoxycarbonyl; $C_{6-10}$ arylcarbonyl; $C_{6-10}$ aryloxycarbonyl; carbamoyl; $C_{1-12}$ alkylcarbamoyl; or $C_{6-10}$ aryl $C_{1-6}$ alkylcarbamoyl, wherein the substituted amino have one to the maximum substitutable number of the same or different substituents selected from substituent group IV.

[Item 10]

The compound or an enantiomer thereof, or a salt thereof, or a solvate thereof according to any one of the preceding items, wherein $R_3$ is hydrogen; alkyl; alkyl substituted with one to the maximum substitutable number of the same or different substituents selected from the group consisting of amino, substituted amino, carboxy, substituted oxycarbonyl, carbamoyl, substituted aminocarbonyl, hydroxy, substituted oxy, cycloalkyl, and substituted cycloalkyl; arylalkyl; or arylalkyl substituted with one to the maximum substitutable number of the same or different substituents selected from the group consisting of halogen, alkyl, substituted alkyl, carboxy, substituted oxycarbonyl, hydroxy, and substituted oxy, wherein the substituted amino, substituted oxy, substituted oxycarbonyl, substituted aminocarbonyl, substituted alkyl, substituted cycloalkyl, substituted carbonyl, and substituted oxycarbonyl in $R_3$ each independently have one to the maximum substitutable number of the same or different substituents selected from substituent group IV.

[Item 11]

The compound or an enantiomer thereof, or a salt thereof, or a solvate thereof according to any one of the preceding items, wherein $R_3$ is hydrogen; alkyl; alkyl substituted with one to the maximum substitutable number of the same or different substituents selected from the group consisting of amidinoamino, alkoxycarbonyl, carbamoyl, carboxy, hydroxy, trialkylsilyloxy, amino, alkoxycarbonylamino, and cycloalkyl; arylalkyl; or arylalkyl substituted with one to the maximum substitutable number of the same or different substituents selected from the group consisting of halogen, alkyl, alkoxycarbonyl, and hydroxy.

[Item 11B]

The compound or an enantiomer thereof, or a salt thereof, or a solvate thereof according to any one of the preceding items, wherein $R_3$ is hydrogen; $C_{1-12}$ alkyl; $C_{1-12}$ alkyl substituted with one to the maximum substitutable number of the same or different substituents selected from the group consisting of amidinoamino, $C_{1-6}$ alkoxycarbonyl, carbamoyl, carboxy, hydroxy, tri-$C_{1-6}$ alkylsilyloxy, amino, $C_{1-6}$ alkoxycarbonylamino, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of halogen, $C_{1-6}$ alkyl, $C_{1-6}$ alkoxycarbonyl, and hydroxy.

[Item 12]

The compound or an enantiomer thereof, or a salt thereof, or a solvate thereof according to any one of the preceding items, wherein $R_{2A}$ and $R_{2B}$ are each independently hydrogen; alkyl; alkyl substituted with one to the maximum substitutable number of the same or different substituents selected from the group consisting of formyl, substituted carbonyl, hydroxy, substituted oxy, amino, substituted amino, cycloalkyl, substituted cycloalkyl, heterocycloalkyl, and substituted heterocycloalkyl; arylalkyl; arylalkyl substituted with one to the maximum substitutable number of the same or different substituents selected from the group consisting of halogen, alkyl, substituted alkyl, hydroxy, and substituted oxy; heteroarylalkyl; substituted heteroarylalkyl; cycloalkyl; or substituted cycloalkyl, wherein the substituted carbonyl, substituted oxy, substituted amino, substituted cycloalkyl, substituted heterocycloalkyl, substituted heteroarylalkyl, and substituted alkyl in $R_{2A}$ and $R_{2B}$ each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

[Item 13]

The compound or an enantiomer thereof, or a salt thereof, or a solvate thereof according to any one of the preceding items, wherein $R_{2A}$ and $R_{2B}$ are each independently hydrogen; alkyl; alkyl substituted with one to the maximum substitutable number of the same or different substituents selected from the group consisting of amidinoamino, alkoxy, alkoxycarbonyl, carbamoyl, carboxy, hydroxy, amino, alkoxycarbonylamino, cycloalkyl, and heterocycloalkyl; arylalkyl; arylalkyl substituted with one to the maximum substitutable number of the same or different substituents selected from the group consisting of halogen, alkyl, haloalkyl, alkoxy, and hydroxy; heteroarylalkyl; alkoxycarbonyl-substituted heteroarylalkyl; or cycloalkyl, or $R_{2A}$ and $R_{2B}$, together with the nitrogen atom to which they are attached, form a 5- to 6-membered non-aryl heterocycle, wherein the non-aryl heterocycle is optionally substituted with one or up to the maximum substitutable number of the same or different substituents selected from substituent group VI.

[Item 13B]

The compound or an enantiomer thereof, or a salt thereof, or a solvate thereof according to any one of the preceding items, wherein $R_{2A}$ and $R_{2B}$ are each independently hydrogen; $C_{1-12}$ alkyl; $C_{1-12}$ alkyl substituted with one to the maximum substitutable number of the same or different substituents selected from the group consisting of amidinoamino, $C_{1-6}$ alkoxy, $C_{1-6}$ alkoxycarbonyl, carbamoyl, carboxy, hydroxy, amino, $C_{1-6}$ alkoxycarbonylamino, $C_{3-10}$ cycloalkyl, and 5- to 10-membered heterocycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, and hydroxy; 5- to 10-membered heteroaryl $C_{1-6}$ alkyl; $C_{1-6}$ alkoxycarbonyl-substituted 5- to 10-membered heteroaryl $C_{1-6}$ alkyl; or $C_{3-10}$ cycloalkyl, or $R_{2A}$ and $R_{2B}$, together with the nitrogen atom to which they are attached, form a 5- to 6-membered non-aryl heterocycle, wherein the non-aryl heterocycle is optionally substituted with one or up to the maximum substitutable number of the same or different substituents selected from substituent group VI.

[Item 14]

The compound or an enantiomer thereof, or a salt thereof, or a solvate thereof according to any one of the preceding items, wherein $R_1$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of halogen, alkyl, haloalkyl, alkoxy, substituted amino, and hydroxy, wherein the substituted amino has one to the maximum substitutable number of the same or different substituents selected from substituent group IV.

[Item 14B]

The compound or an enantiomer thereof, or a salt thereof, or a solvate thereof according to any one of the preceding items, wherein $R_1$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, substituted amino, and hydroxy, wherein the substituted amino has one to the maximum substitutable number of the same or different substituents selected from substituent group IV.

[Item 15]

The compound or an enantiomer thereof, or a salt thereof, or a solvate thereof according to any one of the preceding items, wherein $R_{2A}$ is hydrogen, and $R_{2B}$ is alkyl; alkyl substituted with one to the maximum substitutable number of the same or different substituents selected from the group consisting of amidinoamino, carbamoyl, carboxy, hydroxy, and cycloalkyl; arylalkyl; arylalkyl substituted with one to the maximum substitutable number of the same or different substituents selected from the group consisting of halogen, alkyl, haloalkyl, alkoxy, and hydroxy; or cycloalkyl.

[Item 15B]

The compound or an enantiomer thereof, or a salt thereof, or a solvate thereof according to any one of the preceding items, wherein $R_{2A}$ is hydrogen, and $R_{2B}$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, and hydroxy; or $C_{3-10}$ cycloalkyl.

[Item 16]

The compound or an enantiomer thereof, or a salt thereof, or a solvate thereof according to any one of the preceding items, wherein $R_3$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of alkyl and hydroxy.

[Item 16B]

The compound or an enantiomer thereof, or a salt thereof, or a solvate thereof according to any one of the preceding items, wherein $R_3$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of $C_{1-6}$ alkyl and hydroxy.

[Item 17]

The compound or an enantiomer thereof, or a salt thereof, or a solvate thereof according to any one of the preceding items, wherein $R_4$ is hydrogen, alkyl, alkylcarbonyl, arylalkylcarbonyl, arylalkyloxycarbonyl, alkoxycarbonyl, carbamoyl, or arylalkylcarbamoyl.

[Item 17B]

The compound or an enantiomer thereof, or a salt thereof, or a solvate thereof according to any one of the preceding items, wherein $R_4$ is hydrogen, $C_{1-12}$ alkyl, $C_{1-12}$ alkylcarbonyl, $C_{6-10}$ aryl $C_{1-6}$ alkylcarbonyl, $C_{6-10}$ aryl $C_{1-6}$ alkyloxycarbonyl, $C_{1-12}$ alkoxycarbonyl, carbamoyl, or $C_{6-10}$ aryl $C_{1-6}$ alkylcarbamoyl.

[Item 17C]

The compound or an enantiomer thereof, or a salt thereof, or a solvate thereof according to any one of the preceding items, wherein $R_1$ is hydrogen, methyl, ethyl, isobutyl, isopentyl, amidinoaminopropyl, tert-butoxyethyl, tert-butoxypropyl, (tert-butoxycarbonyl)ethyl, carbamoylmethyl, carboxyethyl, hydroxyethyl, hydroxypropyl, cyclopentylmethyl, cyclohexylmethyl, benzyl, phenylethyl, naphthalenylmethyl, fluorobenzyl, chlorobenzyl, dichlorobenzyl, methylbenzyl, tert-butylbenzyl, (trifluoromethyl)benzyl, methoxybenzyl, ethoxybenzyl, tert-butoxybenzyl, aminobenzyl, (cyclopentylcarbonylamino)benzyl, (cyclopentylmethylamino)benzyl, (dimethylamino)benzyl, (carbamoylethylcarbonylamino)benzyl, (carboxyethylcarbonylamino)benzyl, nitrobenzyl, hydroxybenzyl, 3-methylbutanoyl, isobutylcarbonyl, 2-phenylacetyl, isopropyloxycarbonyl, benzoyl, or phenyloxycarbonyl.

[Item 17D]

The compound or an enantiomer thereof, or a salt thereof, or a solvate thereof according to any one of the preceding items, wherein $R_{2A}$ is hydrogen, $R_{2B}$ is methyl, isopropyl, isobutyl, n-pentyl, isopentyl, n-hexyl, heptyl, amidinoaminopropyl, tert-butoxyethyl, tert-butoxycarbonylmethyl, carbamoylmethyl, carbamoylethyl, carboxyethyl, hydroxyethyl, aminobutyl, ((tert-butoxycarbonyl)amino)butyl, cyclohexylmethyl, (tetrahydro-2H-pyran-2-yl)methyl, benzyl, phenylethyl, naphthalenylmethyl, naphthalenylethyl, fluorobenzyl, chlorobenzyl, dichlorobenzyl, (fluorophenyl)ethyl, methylbenzyl, (trifluoromethyl)benzyl, methoxybenzyl, tert-butoxybenzyl, hydroxybenzyl, α-hydroxymethylphenethyl, β-hydroxyphenethyl, pyridinylmethyl, (1H-indol-3-yl)ethyl, (1-(tert-butoxycarbonyl)-1H-indol-3-yl)ethyl, cyclopentyl, or cyclohexyl, or $R_{2A}$ and $R_{2B}$, together with the nitrogen atom to which they are attached, form a pyrrolidine ring or piperidine ring.

[Item 17E]

The compound or an enantiomer thereof, or a salt thereof, or a solvate thereof according to any one of the preceding items, wherein $R_3$ is n-propyl, isobutyl, isopentyl, amidinoaminopropyl, (methoxycarbonyl)ethyl, (tert-butoxycarbonyl)ethyl, carbamoylmethyl, carboxyethyl, hydroxymethyl, hydroxyethyl, (tert-butyldimethyl silyloxy)ethyl, aminobutyl, ((tert-butoxycarbonyl)amino)butyl, cyclohexylmethyl, cyclohexylethyl, benzyl, phenylethyl, phenylpropyl, phenylbutyl, naphthalenylmethyl, naphthalenylethyl, chlorobenzyl, methylbenzyl, (methylphenyl)ethyl, (isopropylphenyl)ethyl, or hydroxybenzyl.

[Item 17F]

The compound or an enantiomer thereof, or a salt thereof, or a solvate thereof according to any one of the preceding items, wherein $R_4$ is hydrogen, methyl, ethyl, isobutyl, formyl, acetyl, 3-methylbutanoyl, 2-phenylacetyl, methoxycarbonyl, ethoxycarbonyl, 2-methylpropyloxycarbonyl, tert-butoxycarbonyl, benzoyl, benzyl, benzyloxycarbonyl, aminocarbonyl, N-benzylaminocarbonyl, propylcarbamoyl, N-isobutylaminocarbonyl, or N-benzylaminocarbonyl.

[Item 17G]

The compound or an enantiomer thereof, or a salt thereof, or a solvate thereof according to any one of the preceding items, wherein the compound is a compound selected from the group consisting of compound numbers IB-1 to IB-995 and IF-1 to IF-931.

[Item 18]
A compound represented by formula XXIIF:

[Chemical Formula 5]

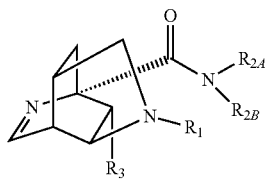

Formula XXIIF or an enantiomer thereof, or a salt thereof, or a solvate thereof, wherein
  $R_1$ and $R_3$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and
  $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 19]
A compound represented by formula XXIIB:

[Chemical Formula 6]

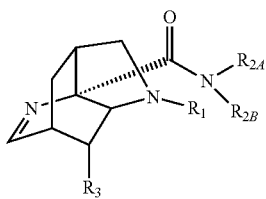

Formula XXIIB or an enantiomer thereof, or a salt thereof, or a solvate thereof, wherein
  $R_1$ and $R_3$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and
  $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 20]
The compound or an enantiomer thereof, or a salt thereof, or a solvate thereof according to any one of the preceding items, wherein
  the alkyl, alkenyl, alkynyl, cycloalkyl, heterocycloalkyl, aryl, heteroaryl, and carbonyl of $R_1$ and $R_3$ are each independently and optionally substituted with one to the maximum substitutable number of the same or different substituents selected from substituent group I, and
  the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently and optionally substituted with one to the maximum substitutable number of the same or different substituents selected from substituent group I.

[Item 21]
The compound or an enantiomer thereof, or a salt thereof, or a solvate thereof according to any one of the preceding items, wherein
  $R_1$ and $R_3$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and
  $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

[Item 22]
The compound or an enantiomer thereof, or a salt thereof, or a solvate thereof according to any one of the preceding items, wherein
  $R_1$ and $R_3$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_3$ are optionally substituted with one to the maximum substitutable number of the same or different substituents selected from substituent group II, and
  $R_{2A}$ and $R_{2B}$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group II.

[Item 23]

The compound or an enantiomer thereof, or a salt thereof, or a solvate thereof according to any one of the preceding items, wherein $R_1$ and $R_3$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_3$ are optionally substituted with one to the maximum substitutable number of the same or different substituents selected from substituent group III, and $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_{2A}$ and $R_{2B}$ are optionally substituted with one to the maximum substitutable number of the same or different substituents selected from substituent group III, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group III.

[Item 24]

The compound or an enantiomer thereof, or a salt thereof, or a solvate thereof according to any one of the preceding items, wherein $R_1$ and $R_3$ are each independently hydrogen, optionally substituted alkyl, optionally substituted arylalkyl, optionally substituted cycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_3$ are optionally substituted with one to the maximum substitutable number of the same or different substituents selected from substituent group III.

[Item 25B]

The compound or an enantiomer thereof, or a salt thereof, or a solvate thereof according to any one of the preceding items, wherein $R_1$ and $R_3$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_3$ are optionally substituted with one to the maximum substitutable number of the same or different substituents selected from substituent group III.

[Item 25]

The compound or an enantiomer thereof, or a salt thereof, or a solvate thereof according to any one of the preceding items, wherein $R_1$ is hydrogen; alkyl; $C_{1-12}$ alkyl substituted with one to the maximum substitutable number of the same or different substituents selected from the group consisting of amino, substituted amino, hydroxy, substituted oxy, formyl, substituted carbonyl, cycloalkyl, and substituted cycloalkyl; arylalkyl; arylalkyl substituted with one to the maximum substitutable number of the same or different substituents selected from the group consisting of halogen, alkyl, substituted alkyl, hydroxy, substituted oxy, amino, substituted amino, and nitro; formyl; or substituted carbonyl, wherein the substituted amino, substituted oxy, substituted carbonyl, substituted cycloalkyl, and substituted alkyl in $R_1$ each independently have one to the maximum substitutable number of the same or different substituents selected from substituent group IV.

[Item 26]

The compound or an enantiomer thereof, or a salt thereof, or a solvate thereof according to any one of the preceding items, wherein $R_1$ is hydrogen; alkyl; $C_{1-12}$ alkyl substituted with one to the maximum substitutable number of the same or different substituents selected from the group consisting of amidinoamino, alkoxycarbonyl-substituted amidinoamino, alkoxy, alkoxycarbonyl, carbamoyl, carboxy, hydroxy, trialkylsilyloxy, and cycloalkyl; arylalkyl; arylalkyl substituted with one to the maximum substitutable number of the same or different substituents selected from the group consisting of halogen, alkyl, haloalkyl, alkoxy, haloalkoxy, amino, substituted amino, nitro, and hydroxy; formyl; alkylcarbonyl; arylalkylcarbonyl; alkoxycarbonyl; arylcarbonyl; aryloxycarbonyl; carbamoyl; alkylcarbamoyl; or arylalkylcarbamoyl, wherein the substituted amino has one to the maximum substitutable number of the same or different substituents selected from substituent group IV.

[Item 27B]

The compound or an enantiomer thereof, or a salt thereof, or a solvate thereof according to any one of the preceding items, wherein $R_1$ is hydrogen; $C_{1-12}$ alkyl; $C_{1-12}$ alkyl substituted with one to the maximum substitutable number of the same or different substituents selected from the group consisting of amidinoamino, $C_{1-6}$ alkoxycarbonyl-substituted amidinoamino, $C_{1-6}$ alkoxy, $C_{1-6}$ alkoxycarbonyl, carbamoyl, carboxy, hydroxy, tri-$C_{1-6}$ alkylsilyloxy, and $C_{3-10}$ cycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, $C_{1-6}$ haloalkoxy, amino, substituted amino, nitro, and hydroxy; formyl; $C_{1-12}$ alkylcarbonyl; $C_{6-10}$ aryl $C_{1-6}$ alkylcarbonyl; $C_{1-12}$ alkoxycarbonyl; $C_{6-10}$ arylcarbonyl; $C_{6-10}$ aryloxycarbonyl; carbamoyl; $C_{1-12}$ alkylcarbamoyl; or $C_{6-10}$ aryl $C_{1-6}$ alkylcarbamoyl, wherein the substituted amino has one to the maximum substitutable number of the same or different substituents selected from substituent group IV.

[Item 27C]

The compound or an enantiomer thereof, or a salt thereof, or a solvate thereof according to any one of the preceding items, wherein $R_1$ is $C_{1-12}$ alkyl; $C_{1-12}$ alkyl substituted with one to the maximum substitutable number of the same or different substituents selected from the group consisting of amidinoamino, $C_{1-6}$ alkoxycarbonyl-substituted amidinoamino, $C_{1-6}$ alkoxy, $C_{1-6}$ alkoxycarbonyl, carbamoyl, carboxy, hydroxy, tri-$C_{1-6}$ alkylsilyloxy, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, $C_{1-6}$ haloalkoxy, amino, substituted amino, nitro, and hydroxy, wherein the substituted amino has one to the maximum substitutable number of the same or different substituents selected from substituent group IV.

[Item 28]

The compound or an enantiomer thereof, or a salt thereof, or a solvate thereof according to any one of the preceding items, wherein $R_3$ is hydrogen; alkyl; formyl; substituted carbonyl; alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl; arylalkyl; arylalkyl substituted with one to the maximum substitutable number of the same or different substituents selected from the group consisting of halogen, nitro, hydroxy, substituted oxy, amino, substituted amino, alkyl, and substituted alkyl; heteroarylalkyl; or substituted heteroarylalkyl, wherein the substituted carbonyl, substituted oxy, substituted amino, substituted cycloalkyl, substituted heterocycloalkyl, substituted alkyl, and substituted heteroarylalkyl in $R_3$ each independently have one to the maximum substitutable number of the same or different substituents selected from substituent group IV.

[Item 29B]

The compound or an enantiomer thereof, or a salt thereof, or a solvate thereof according to any one of the preceding items, wherein $R_3$ is hydrogen; alkyl; formyl; alkylcarbonyl; arylalkylcarbonyl; alkyl substituted with one to the maximum substitutable number of the same or different substituents selected from the group consisting of hydroxy, trialkylsilyloxy, alkoxy, alkoxycarbonyl, alkoxycarbonylamino, cycloalkyl, carboxy, amino, amidinoamino, alkoxycarbonyl-substituted amidinoamino, carbamoyl, and heterocycloalkyl; arylalkyl; arylalkyl substituted with one to the maximum substitutable number of the same or different substituents selected from the group consisting of halogen, nitro, hydroxy, amino, monoalkylamino, dialkylamino, alkyl, haloalkyl, alkoxy, haloalkoxy, carboxyalkylcarbonylamino, carbamoylalkylcarbonylamino, cycloalkylcarbonylamino, and cycloalkylalkylamino; heteroarylalkyl; or alkoxycarbonyl-substituted heteroarylalkyl.

[Item 29C]

The compound or an enantiomer thereof, or a salt thereof, or a solvate thereof according to any one of the preceding items, wherein $R_3$ is hydrogen; $C_{1-12}$ alkyl; formyl; $C_{1-6}$ alkylcarbonyl; $C_{6-10}$ aryl $C_{1-6}$ alkylcarbonyl; $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-6}$ cycloalkyl, carboxy, amino, amidinoamino, $C_{1-6}$ alkoxycarbonyl-substituted amidinoamino, carbamoyl, and 5- to 6-membered heterocycloalkyl; $C_{6-10}$ aryl $C_{1-6}$ alkyl; $C_{6-10}$ aryl $C_{1-12}$ alkyl substituted with one to the maximum substitutable number of the same or different substituents selected from the group consisting of halogen, nitro, hydroxy, amino, mono- $C_{1-6}$ alkylamino, di-$C_{1-6}$ alkylamino, $C_{1-6}$ alkyl, $C_{1-6}$ haloalkyl, $C_{1-6}$ alkoxy, $C_{1-6}$ haloalkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino; 5- to 10-membered heteroaryl $C_{1-6}$ alkyl; or $C_{1-6}$ alkoxycarbonyl-substituted 5- to 10-membered heteroaryl $C_{1-6}$ alkyl.

[Item 29D]

The compound or an enantiomer thereof, or a salt thereof, or a solvate thereof according to any one of the preceding items, wherein $R_3$ is $C_{1-12}$ alkyl; $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-6}$ cycloalkyl, carboxy, amino, amidinoamino, $C_{1-6}$ alkoxycarbonyl-substituted amidinoamino, carbamoyl, and 5- to 6-membered heterocycloalkyl; $C_{6-10}$ aryl $C_{1-6}$ alkyl; or $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, $C_{1-6}$ haloalkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino.

[Item 29]

The compound or an enantiomer thereof, or a salt thereof, or a solvate thereof according to any one of the preceding items, wherein $R_{2A}$ and $R_{2B}$ are each independently hydrogen; alkyl; formyl; substituted carbonyl; alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl; arylalkyl; arylalkyl substituted with one to the maximum substitutable number of the same or different substituents selected from the group consisting of halogen, nitro, hydroxy, substituted oxy, amino, substituted amino, alkyl, and substituted alkyl; heteroarylalkyl; or substituted heteroarylalkyl, wherein the substituted carbonyl, substituted oxy, substituted amino, substituted cycloalkyl, substituted heterocycloalkyl, substituted alkyl, and substituted heteroarylalkyl in $R_{2A}$ and $R_{2B}$ each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

[Item 30B]

The compound or an enantiomer thereof, or a salt thereof, or a solvate thereof according to any one of the preceding items, wherein $R_{2A}$ and $R_{2B}$ are each independently hydrogen; alkyl; formyl; alkylcarbonyl; arylalkylcarbonyl; alkyl substituted with one to the maximum substitutable number of the same or different substituents selected from the group consisting of hydroxy, trialkylsilyloxy, alkoxy, alkoxycarbonyl, alkoxycarbonylamino, cycloalkyl, carboxy, amino, amidinoamino, alkoxycarbonyl-substituted amidinoamino, carbamoyl, and heterocycloalkyl; arylalkyl; arylalkyl substituted with one to the maximum substitutable number of the same or different substituents selected from the group consisting of halogen, nitro, hydroxy, amino, monoalkylamino, dialkylamino, alkyl, haloalkyl, alkoxy, carboxyalkylcarbonylamino, carbamoylalkylcarbonylamino, cycloalkylcarbonylamino, and cycloalalkylalkylamino; heteroarylalkyl; or alkoxycarbonyl-substituted heteroarylalkyl, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

[Item 30C]

The compound or an enantiomer thereof, or a salt thereof, or a solvate thereof according to any one of the preceding items, wherein $R_{2A}$ and $R_{2B}$ are each independently hydrogen; $C_{1-12}$ alkyl; formyl; $C_{1-6}$ alkylcarbonyl; $C_{6-10}$ aryl $C_{1-6}$ alkylcarbonyl; $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-10}$ cycloalkyl, carboxy, amino, amidinoamino, $C_{1-6}$ alkoxycarbonyl-substituted amidinoamino, carbamoyl, and 5- to 6-membered heterocycloalkyl; $C_{6-10}$ aryl $C_{1-12}$ alkyl; $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino; 5- to 10-membered heteroaryl $C_{1-12}$ alkyl; or $C_{1-6}$ alkoxycarbonyl-substituted 5- to 10-membered heteroaryl $C_{1-12}$ alkyl, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from the group consisting of halogen, nitro, hydroxy, amino, $C_{1-6}$ alkyl, $C_{1-6}$ haloalkyl, $C_{1-6}$ alkoxy, $C_{1-6}$ alkoxycarbonyl, $C_{3-6}$ cycloalkylcarbonylamino, and $C_{3-6}$ cycloalkyl $C_{1-6}$ alkylamino.

[Item 30D]

The compound or an enantiomer thereof, or a salt thereof, or a solvate thereof according to any one of the preceding items, wherein $R_{2A}$ and $R_{2B}$ are each independently hydrogen; $C_{1-12}$ alkyl; $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-10}$ cycloalkyl, carboxy, amino, amidinoamino, $C_{1-6}$ alkoxycarbonyl-substituted amidinoamino, carbamoyl, and 5- to 6-membered heterocycloalkyl; $C_{6-10}$ aryl $C_{1-12}$ alkyl; $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, carboxy C$_{1-6}$ alkylcarbonylamino, carbamoyl C$_{1-6}$ alkylcarbonylamino, C$_{3-6}$ cycloalkylcarbonylamino, and C$_{3-6}$ cycloalkyl C$_{1-6}$ alkylamino; 5- to 10-membered heteroaryl C$_{1-12}$ alkyl; or C$_{1-6}$ alkoxycarbonyl-substituted 5- to 10-membered heteroaryl C$_{1-12}$ alkyl, or R$_{2A}$ and R$_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from the group consisting of halogen, nitro, hydroxy, amino, C$_{1-6}$ alkyl, C$_{1-6}$ haloalkyl, C$_{1-6}$ alkoxy, C$_{1-6}$ alkoxycarbonyl, C$_{3-6}$ cycloalkylcarbonylamino, and C$_{3-6}$ cycloalkyl C$_{1-6}$ alkylamino.

[Item 30]

The compound or an enantiomer thereof, or a salt thereof, or a solvate thereof according to any one of the preceding items, wherein R$_1$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of halogen, alkyl, haloalkyl, alkoxy, haloalkoxy, substituted amino, and hydroxy, wherein the substituted amino has one to the maximum substitutable number of the same or different substituents selected from substituent group IV.

[Item 31B]

The compound or an enantiomer thereof, or a salt thereof, or a solvate thereof according to any one of the preceding items, wherein R$_1$ is C$_{1-12}$ alkyl; C$_{1-12}$ alkyl substituted with one to the maximum substitutable number of the same or different substituents selected from the group consisting of amidinoamino, carbamoyl, carboxy, hydroxy, and C$_{3-10}$ cycloalkyl; C$_{6-10}$ aryl C$_{1-6}$ alkyl; or C$_{6-10}$ aryl C$_{1-6}$ alkyl substituted with one to the maximum substitutable number of the same or different substituents selected from the group consisting of halogen, C$_{1-6}$ alkyl, C$_{1-6}$ haloalkyl, C$_{1-6}$ alkoxy, C$_{1-6}$ haloalkoxy, substituted amino, and hydroxy, wherein the substituted amino has one to the maximum substitutable number of the same or different substituents selected from substituent group IV.

[Item 31]

The compound or an enantiomer thereof, or a salt thereof, or a solvate thereof according to any one of the preceding items, wherein R$_{2A}$ is hydrogen, and R$_{2B}$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of halogen and alkyl.

[Item 32B]

The compound or an enantiomer thereof, or a salt thereof, or a solvate thereof according to any one of the preceding items, wherein R$_{2A}$ is hydrogen, and R$_{2B}$ is C$_{1-12}$ alkyl; C$_{1-12}$ alkyl substituted with one to the maximum substitutable number of the same or different substituents selected from the group consisting of amidinoamino, carbamoyl, carboxy, hydroxy, and C$_{3-10}$ cycloalkyl; C$_{6-10}$ aryl C$_{1-6}$ alkyl; or C$_{6-10}$ aryl C$_{1-6}$ alkyl substituted with one to the maximum substitutable number of the same or different substituents selected from the group consisting of halogen and C$_{1-6}$ alkyl.

[Item 32]

The compound or an enantiomer thereof, or a salt thereof, or a solvate thereof according to any one of the preceding items, wherein R$_3$ is alkyl; alkyl substituted with one to the maximum substitutable number of the same or different substituents selected from the group consisting of amidinoamino, carbamoyl, carboxy, hydroxy, and cycloalkyl; or arylalkyl.

[Item 32B]

The compound or an enantiomer thereof, or a salt thereof, or a solvate thereof according to any one of the preceding items, wherein R$_3$ is C$_{1-12}$ alkyl; alkyl substituted with one to the maximum substitutable number of the same or different substituents selected from the group consisting of amidinoamino, carbamoyl, carboxy, hydroxy, and cycloalkyl; C$_{6-10}$ aryl C$_{1-6}$ alkyl; or arylalkyl substituted with one to the maximum substitutable number of the same or different substituents selected from the group consisting of alkyl and hydroxy.

[Item 32C]

The compound or an enantiomer thereof, or a salt thereof, or a solvate thereof according to any one of the preceding items, wherein R$_1$ is methyl, n-propyl, isobutyl, isopentyl, amidinoaminopropyl, tert-butoxycarbonyl-substituted amidinoaminopropyl, tert-butoxyethyl, tert-butoxypropyl, (tert-butoxycarbonyl)ethyl, carboxyethyl, hydroxyethyl, hydroxypropyl, aminopropyl, 2-(tert-butyl-dimethylsilyloxy)ethyl, cyclopentylmethyl, cyclohexylmethyl, benzyl, phenylethyl, naphthalenylmethyl, fluorobenzyl, chlorobenzyl, dichlorobenzyl, methylbenzyl, (tert-butyl)benzyl, methoxybenzyl, ethoxybenzyl, (tert-butoxy)benzyl, (trifluoromethoxy)benzyl, (dimethylamino)benzyl, nitrobenzyl, or hydroxybenzyl.

[Item 32D]

The compound or an enantiomer thereof, or a salt thereof, or a solvate thereof according to any one of the preceding items, wherein R$_{2A}$ and R$_{2B}$ are each independently isopropyl, isobutyl, sec-butyl, pentyl, isopentyl, n-hexyl, heptyl, amidinoaminopropyl, tert-butoxycarbonyl-substituted amidinoaminopropyl, tert-butoxyethyl, tert-butoxycarbonylmethyl, (tert-butoxycarbonyl)ethyl, carbamoylethyl, carboxyethyl, hydroxyethyl, aminopropyl, aminobutyl, ((tert-butoxycarbonyl)amino)butyl, cyclopentylmethyl, cyclohexylmethyl, (1,2,3,4-tetrahydronaphthalenyl)methyl, (tetrahydro-2H-pyranyl)methyl, benzyl, phenylethyl, naphthalenylmethyl, (naphthalenyl)ethyl, β-hydroxyphenethyl, α-(hydroxymethyl)phenethyl, fluorobenzyl, chlorobenzyl, dichlorobenzyl, (fluorophenyl)ethyl, methylbenzyl, (trifluoromethyl)benzyl, methoxybenzyl, (tert-butoxy)benzyl, hydroxybenzyl, pyridinylmethyl, quinolinylethyl, (1-(tert-butoxycarbonyl)-1H-indolyl)ethyl, cyclopentyl, or cyclohexyl, or R$_{2A}$ and R$_{2B}$, together with the nitrogen atom to which they are attached, form a pyrrolidine ring or piperidine ring.

[Item 32E]

The compound or an enantiomer thereof, or a salt thereof, or a solvate thereof according to any one of the preceding items, wherein
R$_3$ is n-propyl, isobutyl, isopentyl, amidinoaminopropyl, tert-butoxycarbonyl-substituted amidinoaminopropyl, (methoxycarbonyl)ethyl, (tert-butoxycarbonyl)ethyl, carboxyethyl, hydroxyethyl, aminopropyl, (tert-butyldimethylsilyloxy)ethyl, ((tert-butoxycarbonyl)amino)butyl, cyclopentylmethyl, cyclohexylmethyl, cyclohexylethyl, benzyl, phenylethyl, phenylpropyl, phenylbutyl, naphthalenylmethyl, naphthalenylethyl, chlorobenzyl, methylbenzyl, (methylphenyl)ethyl, (isopropylphenyl)ethyl, (tert-butoxy)benzyl, or hydroxybenzyl.

[Item 32F]

The compound or an enantiomer thereof, or a salt thereof, or a solvate thereof according to any one of the preceding items, wherein
the compound is a compound selected from the group consisting of compound numbers IIB-1 to IIB-1129 and IIF-1 to IIF-1047.

[Item 33]

An antiviral agent for a virus in the Lyssavirus genus, comprising the compound according to any one of the preceding items or a pharmaceutically acceptable salt thereof.

[Item 34]

The antiviral agent according to any one of the preceding items, wherein the virus in the Lyssavirus genus comprises a rabies virus.

[Item 35]

A medicament comprising the compound according to any one of the preceding items or a pharmaceutically acceptable salt thereof.

[Item 36]

The medicament according to any one of the preceding items, which is a prophylactic agent or a therapeutic agent for rabies.

[Item 37]

A pharmaceutical composition comprising the compound according to any one of the preceding items or a pharmaceutically acceptable salt thereof, and a pharmaceutically acceptable carrier.

[Item 38]

A pharmaceutical composition for the prophylaxis or treatment of rabies, comprising the compound according to any one of the preceding items or a pharmaceutically acceptable salt thereof, and a pharmaceutically acceptable carrier.

[Item 39]

An anticancer agent comprising the compound according to any one of the preceding items or a pharmaceutically acceptable salt thereof.

[Item 40]

The medicament according to any one of the preceding items, which is a prophylactic agent or a therapeutic agent for cancer.

[Item 41]

A pharmaceutical composition for the prophylaxis or treatment of cancer, comprising the compound according to any one of the preceding items or a pharmaceutically acceptable salt thereof, and a pharmaceutically acceptable carrier.

[Item 42]

A method for the prophylaxis or treatment of rabies, characterized by administering a prophylactically or therapeutically effective amount of the compound according to any one of the preceding items or a pharmaceutically acceptable salt thereof, the antiviral agent according to any one of the preceding items, the medicament according to any one of the preceding items, or the pharmaceutical composition according to any one of the preceding items to a patient in need thereof.

[Item 43]

Use of the compound according to any one of the preceding items or a pharmaceutically acceptable salt thereof, or the antiviral agent according to any one of the preceding items, for the manufacture of a medicament for the prophylaxis or treatment of rabies.

[Item 44]

A method for the prophylaxis or treatment of cancer, characterized by administering a prophylactically or therapeutically effective amount of the compound according to any one of the preceding items or a pharmaceutically acceptable salt thereof, the anticancer agent according to any one of the preceding items, the medicament according to any one of the preceding items, or the pharmaceutical composition according to any one of the preceding items to a patient in need thereof.

[Item 45]

Use of the compound according to any one of the preceding items or a pharmaceutically acceptable salt thereof, or the anticancer agent according to any one of the preceding items, for the manufacture of a medicament for the prophylaxis or treatment of cancer.

[Item 46]

A method for the prophylaxis or treatment of rabies, comprising administering an effective amount of the compound according to any one of the preceding items or a pharmaceutically acceptable salt thereof to a subject in need thereof.

[Item 47]

A method for the prophylaxis or treatment of cancer, comprising administering an effective amount of the compound according to any one of the preceding items or a pharmaceutically acceptable salt thereof to a subject in need thereof.

The present disclosure also provides the following items.

[Item A1]

A compound represented by formula IF:

[Chemical Formula 7]

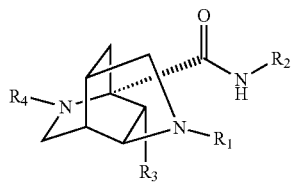

Formula IF or an enantiomer thereof, or a salt thereof, or a solvate thereof, wherein
R$_1$, R$_2$ and R$_3$ are each independently optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and
R$_4$ is hydrogen, optionally substituted alkyl, optionally substituted alkenyl, optionally substituted alkynyl, optionally substituted arylalkyl, optionally substituted heteroarylalkyl, optionally substituted cycloalkylalkyl, optionally substituted heterocycloalkylalkyl, optionally substituted alkylcarbonyl, optionally substituted alkoxycarbonyl, optionally substituted arylcarbonyl, optionally substituted heteroarylcarbonyl, or optionally substituted carbamoyl.

[Item A2]

A compound represented by formula IB:

[Chemical Formula 8]

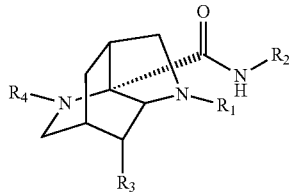

Formula IB or an enantiomer thereof, or a salt thereof, or a solvate thereof, wherein $R_1$, $R_2$ and $R_3$ are each independently optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $R_4$ is hydrogen, optionally substituted alkyl, optionally substituted alkenyl, optionally substituted alkynyl, optionally substituted arylalkyl, optionally substituted heteroarylalkyl, optionally substituted cycloalkylalkyl, optionally substituted heterocycloalkylalkyl, optionally substituted alkylcarbonyl, optionally substituted alkoxycarbonyl, optionally substituted arylcarbonyl, optionally substituted heteroarylcarbonyl, or optionally substituted carbamoyl.

[Item A3]

The compound or an enantiomer thereof, or a salt thereof, or a solvate thereof according to any one of the preceding items, wherein $R_1$, $R_2$ and $R_3$ are each independently optionally substituted alkyl, optionally substituted arylalkyl, optionally substituted heteroarylalkyl, or optionally substituted cycloalkylalkyl, and $R_4$ is hydrogen, optionally substituted alkyl, optionally substituted alkylcarbonyl, optionally substituted arylcarbonyl, optionally substituted alkoxycarbonyl, or optionally substituted carbamoyl.

[Item A3a]

The compound or an enantiomer thereof, or a salt thereof, or a solvate thereof according to any one of the preceding items, wherein $R_1$, $R_2$ and $R_3$ are each independently optionally substituted alkyl, optionally substituted arylalkyl, optionally substituted heteroarylalkyl, or optionally substituted cycloalkylalkyl, and $R_4$ is hydrogen, optionally substituted alkyl, optionally substituted alkylcarbonyl, optionally substituted arylcarbonyl, or optionally substituted alkoxycarbonyl.

[Item A4]

The compound or an enantiomer thereof, or a salt thereof, or a solvate thereof according to any one of the preceding items, wherein $R_1$, $R_2$ and $R_3$ are each independently optionally substituted $C_{1-6}$ alkyl, optionally substituted $C_{6-10}$ aryl $C_{1-6}$ alkyl, optionally substituted 5- to 10-membered heteroaryl $C_{1-6}$ alkyl, or optionally substituted $C_{3-6}$ cycloalkyl $C_{1-6}$ alkyl, and $R_4$ is hydrogen, optionally substituted $C_{1-6}$ alkyl, optionally substituted $C_{1-6}$ alkylcarbonyl, optionally substituted $C_{6-10}$ arylcarbonyl, optionally substituted $C_{1-6}$ alkoxycarbonyl, or optionally substituted $C_{1-6}$ alkylcarbamoyl.

[Item A4b]

The compound or an enantiomer thereof, or a salt thereof, or a solvate thereof according to any one of the preceding items, wherein $R_1$, $R_2$ and $R_3$ are each independently optionally substituted $C_{1-6}$ alkyl, optionally substituted $C_{6-10}$ aryl $C_{1-6}$ alkyl, optionally substituted 5- to 10-membered heteroaryl $C_{1-6}$ alkyl, or optionally substituted $C_{3-6}$ cycloalkyl $C_{1-6}$ alkyl, and $R_4$ is hydrogen, optionally substituted $C_{1-6}$ alkyl, optionally substituted $C_{1-6}$ alkylcarbonyl, optionally substituted $C_{6-10}$ arylcarbonyl, or optionally substituted $C_{1-6}$ alkoxycarbonyl.

[Item A5]

The compound or an enantiomer thereof, or a salt thereof, or a solvate thereof according to any one of the preceding items, wherein $R_1$, $R_2$ and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, (optionally substituted amino)-$C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl $C_{1-6}$ alkyl.

[Item A5a]

The compound or an enantiomer thereof, or a salt thereof, or a solvate thereof according to any one of the preceding items, wherein $R_1$, $R_2$ and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl $C_{1-6}$ alkyl.

[Item A5b]

The compound or an enantiomer thereof, or a salt thereof, or a solvate thereof according to any one of the preceding items, wherein $R_4$ is hydrogen, optionally substituted $C_{1-6}$ alkyl, optionally substituted $C_{1-6}$ alkylcarbonyl, optionally substituted $C_{6-10}$ aryl $C_{1-6}$ alkylcarbonyl, optionally substituted $C_{6-10}$ arylcarbonyl, optionally substituted $C_{1-6}$ alkoxycarbonyl, optionally substituted $C_{6-10}$ aryl $C_{1-6}$ alkoxycarbonyl, carbamoyl, optionally substituted $C_{1-6}$ alkylcarbamoyl, or optionally substituted $C_{6-10}$ aryl $C_{1-6}$ alkylcarbamoyl.

[Item A5c]

The compound or an enantiomer thereof, or a salt thereof, or a solvate thereof according to any one of the preceding items, wherein $R_1$, $R_2$ and $R_3$ are each independently optionally substituted alkyl or optionally substituted arylalkyl.

[Item A5d]

The compound or an enantiomer thereof, or a salt thereof, or a solvate thereof according to any one of the preceding items, wherein $R_1$, $R_2$ and $R_3$ are each independently optionally substituted $C_{1-6}$ alkyl or optionally substituted $C_{6-10}$ aryl $C_{1-6}$ alkyl.

[Item A5e]

The compound or an enantiomer thereof, or a salt thereof, or a solvate thereof according to any one of the preceding items, wherein $R_1$, $R_2$ and $R_3$ are each independently $C_{1-6}$ alkyl, $C_{6-10}$ aryl $C_{1-6}$ alkyl, $C_{1-4}$ alkyl-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, or (optionally substituted amino)-$C_{6-10}$ aryl $C_{1-6}$ alkyl.

[Item A5f]

The compound or an enantiomer thereof, or a salt thereof, or a solvate thereof according to any one of the preceding items, wherein $R_2$ is naphthalen-1-ylmethyl or optionally substituted benzyl.

[Item A5g]

The compound or an enantiomer thereof, or a salt thereof, or a solvate thereof according to any one of the preceding items, wherein $R_1$ and $R_3$ are each independently alkyl or optionally substituted benzyl, and $R_2$ is optionally substituted benzyl.

[Item A5h]

The compound or an enantiomer thereof, or a salt thereof, or a solvate thereof according to any one of the preceding items, wherein $R_1$ and $R_3$ are each independently $C_{1-6}$ alkyl, benzyl, $C_{1-4}$ alkyl-substituted benzyl, chloro-substituted benzyl, $C_{1-4}$ alkoxy-substituted benzyl, or amino-substituted benzyl, and $R_2$ is benzyl or chloro-substituted benzyl.

[Item A5i]

The compound or an enantiomer thereof, or a salt thereof, or a solvate thereof according to any one of the preceding items, wherein $R_1$ and $R_3$ are each independently isobutyl, isopentyl, 4-(dimethylamino)benzyl, 4-methylbenzyl, 4-methoxybenzyl, 3-chlorobenzyl, 4-chlorobenzyl, or 3,4-dichlorobenzyl, and $R_2$ is benzyl, 3-chlorobenzyl, or 3,4-dichlorobenzyl.

[Item A6]

The compound or an enantiomer thereof, or a salt thereof, or a solvate thereof according to any one of the preceding items, wherein $R_4$ is hydrogen, $C_{1-6}$ alkyl, $C_{1-6}$ alkylcarbonyl, $C_{6-10}$ arylcarbonyl, $C_{6-10}$ aryl $C_{1-6}$ alkylcarbonyl, $C_{1-6}$ alkoxycarbonyl, $C_{6-10}$ aryl $C_{1-6}$ alkoxycarbonyl, carbamoyl, $C_{1-6}$ alkylcarbamoyl, or $C_{6-10}$ aryl $C_{1-6}$ alkylcarbamoyl.

[Item A6b]

The compound or an enantiomer thereof, or a salt thereof, or a solvate thereof according to any one of the preceding items, wherein $R_4$ is hydrogen, $C_{1-6}$ alkyl, $C_{1-6}$ alkylcarbonyl, $C_{6-10}$ arylcarbonyl, or $C_{1-6}$ alkoxycarbonyl.

[Item A7]

The compound or an enantiomer thereof, or a salt thereof, or a solvate thereof according to any one of the preceding items, wherein $R_4$ is hydrogen, $C_{1-4}$ alkyl, $C_{1-4}$ alkylcarbonyl, $C_6$ arylcarbonyl, $C_6$ aryl $C_{1-4}$ alkylcarbonyl, $C_{1-4}$ alkoxycarbonyl, $C_6$ aryl $C_{1-4}$ alkoxycarbonyl, carbamoyl, $C_{1-4}$ alkylcarbamoyl, or $C_6$ aryl $C_{1-4}$ alkylcarbamoyl.

[Item A1b]

The compound or an enantiomer thereof, or a salt thereof, or a solvate thereof according to any one of the preceding items, wherein $R_4$ is hydrogen, $C_{1-4}$ alkyl, $C_{1-4}$ alkylcarbonyl, $C_6$ arylcarbonyl, or $C_{1-4}$ alkoxycarbonyl.

[Item A8]

The compound or an enantiomer thereof, or a salt thereof, or a solvate thereof according to any one of the preceding items, wherein $R_4$ is hydrogen, methyl, ethyl, acetyl, benzoyl, methoxycarbonyl, tert-butoxycarbonyl, or propylcarbamoyl.

[Item A8b]

The compound or an enantiomer thereof, or a salt thereof, or a solvate thereof according to any one of the preceding items, wherein $R_4$ is hydrogen, methyl, ethyl, acetyl, benzoyl, methoxycarbonyl, or tert-butoxycarbonyl.

[Item A9]

The compound or an enantiomer thereof, or a salt thereof, or a solvate thereof according to any one of the preceding items, wherein $R_2$ is $C_{1-4}$ alkyl, hydroxy-substituted $C_{1-4}$ alkyl, carbamoyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkoxycarbonyl-substituted 5- to 10-membered heteroaryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, halogen-substituted $C_{6-10}$ aryl $C_{1-4}$ alkyl, $C_{1-4}$ alkoxy-substituted $C_{6-10}$ aryl $C_{1-4}$ alkyl, $C_{1-4}$ alkoxycarbonyl-substituted $C_{1-4}$ alkyl, $C_{1-4}$ alkoxycarbonylamino-substituted $C_{1-4}$ alkyl, 5- to 6-membered heterocycloalkyl-substituted $C_{1-4}$ alkyl, or $C_{5-6}$ cycloalkyl $C_{1-4}$ alkyl.

[Item A9b]

The compound or an enantiomer thereof, or a salt thereof, or a solvate thereof according to any one of the preceding items, wherein $R_2$ is isopropyl, 1-methylpropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 4-fluorobenzyl, 3-chlorobenzyl, 4-chlorobenzyl, 3,4-dichlorobenzyl, 4-(tert-butoxy)benzyl, 2-(tert-butoxy)-2-oxoethyl, 4-((tert-butoxycarbonyl)amino)butyl, (tetrahydro-2H-pyran-2-yl)methyl, or cyclohexylmethyl.

[Item A10]

The compound or an enantiomer thereof, or a salt thereof, or a solvate thereof according to any one of the preceding items, wherein R₂ is isobutyl, 2-hydroxyethyl, 3-amino-3-oxopropyl, 4-aminobutyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 3-chlorobenzyl, 4-chlorobenzyl, 3,4-dichlorobenzyl, 4-(tert-butoxy)benzyl, 2-(tert-butoxy)-2-oxoethyl, 4-((tert-butoxycarbonyl)amino)butyl, (tetrahydro-2H-pyran-2-yl)methyl, or cyclohexylmethyl.

[Item A10b]

The compound or an enantiomer thereof, or a salt thereof, or a solvate thereof according to any one of the preceding items, wherein R₂ is 1-methylpropyl, isopropyl, isobutyl, isopentyl, n-hexyl, benzyl, 4-hydroxybenzyl, 4-fluorobenzyl, 2-carboxyethyl, carbamoylmethyl, carbamoylethyl, 3-(amidinoamino)propyl, hydroxymethyl, 2-hydroxyethyl, phenethyl, naphthalen-1-ylmethyl, or cyclohexylmethyl.

[Item A11]

The compound or an enantiomer thereof, or a salt thereof, or a solvate thereof according to any one of the preceding items, wherein R₂ is isopropyl, isobutyl, isopentyl, benzyl, 4-hydroxybenzyl, 4-fluorobenzyl, 2-carboxyethyl, carbamoylmethyl, 3-(amidinoamino)propyl, 2-hydroxyethyl, phenethyl, naphthalen-1-ylmethyl, or n-hexyl.

[Item A11b]

The compound or an enantiomer thereof, or a salt thereof, or a solvate thereof according to any one of the preceding items, wherein R₂ is 1-methylpropyl, isopropyl, isobutyl, benzyl, 4-hydroxybenzyl, 2-carboxyethyl, 3-(amidinoamino)propyl, or naphthalen-1-ylmethyl.

[Item A12]

The compound or an enantiomer thereof, or a salt thereof, or a solvate thereof according to any one of the preceding items, wherein R₁ is $C_{1-6}$ alkyl, hydroxy-substituted $C_{1-4}$ alkyl, carbamoyl-substituted $C_{1-4}$ alkyl, amino-substituted $C_{1-6}$ alkyl, amidinoamino-substituted $C_{1-4}$ alkyl, carboxy-substituted $C_{1-4}$ alkyl, $C_{1-4}$ alkoxycarbonyl-substituted $C_{1-4}$ alkyl, $C_{6-10}$ aryl $C_{1-4}$ alkyl, hydroxy-substituted $C_{6-10}$ aryl $C_{1-4}$ alkyl, $C_{1-4}$ alkoxy-substituted $C_{6-10}$ aryl $C_{1-4}$ alkyl, halo-substituted $C_{6-10}$ aryl $C_{1-4}$ alkyl, or $C_{5-6}$ cycloalkyl $C_{1-4}$ alkyl.

[Item A12b]

The compound or an enantiomer thereof, or a salt thereof, or a solvate thereof according to any one of the preceding items, wherein R₁ is methyl, isopropyl, isobutyl, isopentyl, n-hexyl, 3-amino-3-oxopropyl, 3-(tert-butoxy)-3-oxopropyl, benzyl, naphthalen-1-ylmethyl, 2-carboxyethyl, carbamoylmethyl, 3-(amidinoamino)propyl, 4-fluorobenzyl, 4-hydroxybenzyl, 4-(tert-butoxy)benzyl, 3,4-dichlorobenzyl, naphthalen-1-ylmethyl, phenethyl, hydroxymethyl, 2-hydroxyethyl, or cyclohexylmethyl.

[Item A13]

The compound or an enantiomer thereof, or a salt thereof, or a solvate thereof according to any one of the preceding items, wherein R₁ is methyl, isobutyl, isopentyl, 3-(tert-butoxy)-3-oxopropyl, benzyl, naphthalen-1-ylmethyl, 4-hydroxybenzyl, 4-(tert-butoxy)benzyl, 3,4-dichlorobenzyl, or cyclohexylmethyl.

[Item A14]

The compound or an enantiomer thereof, or a salt thereof, or a solvate thereof according to any one of the preceding items, wherein R₁ is isopropyl, isobutyl, isopentyl, n-hexyl, cyclohexylmethyl, benzyl, phenethyl, naphthalen-1-ylmethyl, 4-hydroxybenzyl, 4-fluorobenzyl, 2-carboxyethyl, carbamoylmethyl, carbamoylethyl, 3-(amidinoamino)propyl, hydroxymethyl, or hydroxyethyl.

[Item A14b]

The compound or an enantiomer thereof, or a salt thereof, or a solvate thereof according to any one of the preceding items, wherein R₁ is isobutyl, isopentyl, cyclohexylmethyl, benzyl, phenethyl, naphthalen-1-ylmethyl, 4-hydroxybenzyl, 4-fluorobenzyl, 2-carboxyethyl, carbamoylmethyl, 3-(amidinoamino)propyl, or hydroxyethyl.

[Item A14c]

The compound or an enantiomer thereof, or a salt thereof, or a solvate thereof according to any one of the preceding items, wherein R₁ is isobutyl, benzyl, 4-hydroxybenzyl, 2-carboxyethyl, 3-(amidinoamino)propyl, or naphthalen-1-ylmethyl.

[Item A15]

The compound or an enantiomer thereof, or a salt thereof, or a solvate thereof according to any one of the preceding items, wherein R₃ is $C_{1-4}$ alkyl, hydroxy-substituted $C_{1-4}$ alkyl, carbamoyl-substituted $C_{1-4}$ alkyl, $C_{1-4}$ alkoxycarbonyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, or $C_{5-6}$ cycloalkyl $C_{1-4}$ alkyl.

[Item A15b]

The compound or an enantiomer thereof, or a salt thereof, or a solvate thereof according to any one of the preceding items, which is isopropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 4-hydroxybenzyl, 4-fluorobenzyl, 3-methylbenzyl, 4-methylbenzyl, 3-methoxy-3-oxopropyl, 4-((tert-butoxycarbonyl)amino)butyl, or cyclohexylmethyl.

[Item A16]

The compound or an enantiomer thereof, or a salt thereof, or a solvate thereof according to any one of the preceding items, wherein R₃ is isobutyl, isopentyl, 3-amino-3-oxopropyl, 3-methoxy-3-oxopropyl, 4-aminobutyl, 2-carboxyethyl, benzyl, phenethyl, 3-methylbenzyl, 4-methylbenzyl, 4-hydroxybenzyl, 4-((tert-butoxycarbonyl)amino)butyl, or cyclohexylmethyl.

[Item A17]

The compound or an enantiomer thereof, or a salt thereof, or a solvate thereof according to any one of the preceding items, wherein R₃ is isopropyl, isobutyl, isopentyl, n-hexyl, cyclohexylmethyl, benzyl, phenethyl, naphthalen-1-ylmethyl, 4-hydroxybenzyl, 4-fluorobenzyl, 2-carboxyethyl, carbamoylmethyl, carbamoylethyl, 3-(amidinoamino)propyl, hydroxymethyl, or hydroxyethyl.

[Item A17b]

The compound or an enantiomer thereof, or a salt thereof, or a solvate thereof according to any one of the preceding items, wherein R₃ is isobutyl, isopentyl, benzyl, phenethyl, 4-hydroxybenzyl, 2-carboxyethyl, carbamoylmethyl, 3-(amidinoamino)propyl, hydroxymethyl, or naphthalen-1-ylmethyl.

[Item A17c]

The compound or an enantiomer thereof, or a salt thereof, or a solvate thereof according to any one of the preceding items, wherein R₃ is isobutyl, benzyl, 4-hydroxybenzyl, 2-carboxyethyl, 3-(amidinoamino)propyl, or naphthalen-1-ylmethyl.

[Item A18]

The compound or an enantiomer thereof, or a salt thereof, or a solvate thereof according to any one of the preceding items, wherein R₄ is hydrogen or alkyl.

[Item A18a]

The compound or an enantiomer thereof, or a salt thereof, or a solvate thereof according to any one of the preceding items, wherein R₄ is hydrogen or $C_{1-6}$ alkyl.

[Item A18b]

The compound or an enantiomer thereof, or a salt thereof, or a solvate thereof according to any one of the preceding items, wherein R₄ is hydrogen or ethyl.

[Item A19]

The compound or an enantiomer thereof, or a salt thereof, or a solvate thereof according to any one of the preceding items, wherein R₄ is hydrogen.

[Item A20]

The compound or an enantiomer thereof, or a salt thereof, or a solvate thereof according to any one of the preceding items, wherein R₁ is $C_{1-6}$ alkyl or $C_{6-10}$ aryl $C_{1-6}$ alkyl, and R₂ and R₃ are each independently $C_{1-6}$ alkyl or optionally substituted $C_{6-10}$ aryl $C_{1-6}$ alkyl.

[Item A21]

The compound or an enantiomer thereof, or a salt thereof, or a solvate thereof according to any one of the preceding items, wherein R₁ is isobutyl, isopentyl, or benzyl, R₂ is isobutyl, benzyl, phenethyl, 3-methylbenzyl, 4-methylbenzyl, or 3,4-dichlorobenzyl, and R₃ is isobutyl, benzyl, phenethyl, 3-methylbenzyl, or 4-methylbenzyl.

[Item A22]

The compound or an enantiomer thereof, or a salt thereof, or a solvate thereof according to any one of the preceding items, wherein the compound is a compound of formula IF, R₁ is isobutyl, R₂ is benzyl, and R₃ is benzyl.

[Item A23]

The compound or an enantiomer thereof, or a salt thereof, or a solvate thereof according to any one of the preceding items, wherein the compound is compound of formula IF, R₁ is benzyl, R₂ is benzyl, and R₃ is isobutyl.

[Item A24]

The compound or an enantiomer thereof, or a salt thereof, or a solvate thereof according to any one of the preceding items, wherein the compound is a compound of formula IF, R₁ is isobutyl, R₂ is benzyl, and R₃ is 3-methylbenzyl.

[Item A25]

The compound or an enantiomer thereof, or a salt thereof, or a solvate thereof according to any one of the preceding items, wherein the compound is a compound of formula IF, R₁ is benzyl, R₂ is 3,4-dichlorobenzyl, and R₃ is isobutyl.

[Item A26]

The compound or an enantiomer thereof, or a salt thereof, or a solvate thereof according to any one of the preceding items, wherein the compound of formula IF is a compound selected from the group consisting of IF-1, IF-2, IF-3, IF-4, IF-5, IF-6, IF-7, IF-8, IF-9, IF-10, IF-11, IF-12, IF-13, IF-14, IF-15, IF-16, IF-17, IF-18, IF-19, IF-20, IF-22, IF-23, IF-24, IF-25, IF-26, IF-27, IF-28, IF-29, IF-30, IF-31, IF-32, IF-33, IF-34, IF-35, IF-36, IF-38, IF-39, IF-40, IF-41, IF-42, IF-43, IF-44, IF-45, IF-46, IF-47, IF-49, IF-50, IF-54, IF-57, IF-58, IF-68, IF-69, IF-70, IF-71, IF-72, IF-73, IF-74, IF-76, IF-77, IF-80, and IF-81 to IF-884.

[Item A26b]

The compound or an enantiomer thereof, or a salt thereof, or a solvate thereof according to any one of the preceding items, wherein the compound of formula IF is (3S*,3aS*,6S*,7R*,7aS*)-N,7-dibenzyl-1-isobutyloctahydro-6H-3,6-methanopyrrolo[3,2-c]pyridine-6-caboxamide, (3S*,3aS*,6S*,7R*,7aS*)-1,7-dibenzyl-N-isobutyloctahydro-6H-3,6-methanopyrrolo[3,2-c]pyridine-6-caboxamide, (3S*,3aS*,6S*,7R*,7aS*)-N,1-dibenzyl-7-isobutyloctahydro-6H-3,6-methanopyrrolo[3,2-c]pyridine-6-caboxamide, (3S*,3aS*,6S*,7R*,7aS*)-N,7-dibenzyl-1-isopentyloctahydro-6H-3,6-methanopyrrolo[3,2-c]pyridine-6-caboxamide, (3S*,3aS*,6S*,7R*,7aS*)-N-benzyl-1-isobutyl-7-phenethyloctahydro-6H-3,6-methanopyrrolo[3,2-c]pyridine-6-caboxamide, (3S*,3aS*,6S*,7R*,7aS*)-N-benzyl-1-isobutyl-7-(3-methylbenzyl)octahydro-6H-3,6-methanopyrrolo[3,2-c]pyridine-6-caboxamide, (3S*,3aS*,6S*,7R*,7aS*)-N-benzyl-1-isobutyl-7-(4-methylbenzyl)octahydro-6H-3,6-methanopyrrolo[3,2-c]pyridine-6-caboxamide, (3S*,3aS*,6S*,7R*,7aS*)-7-benzyl-1-isobutyl-N-(3-methylbenzyl)octahydro-6H-3,6-methanopyrrolo[3,2-c]pyridine-6-caboxamide, (3S*,3aS*,6S*,7R*,7aS*)-1-benzyl-N-(3,4-dichlorobenzyl)-7-isobutyloctahydro-6H-3,6-methanopyrrolo[3,2-c]pyridine-6-caboxamide, or (3S*,3aS*,6S*,7R*,7aS*)-N,7-dibenzyl-4-ethyl-1-isobutyloctahydro-6H-3,6-methanopyrrolo[3,2-c]pyridine-6-caboxamide.

[Item A27]

The compound or an enantiomer thereof, or a salt thereof, or a solvate thereof according to any one of the preceding items, wherein the compound of formula IB is a compound selected from the group consisting of D3-1, IB-2, IB-3, IB-4, IB-5, IB-6, IB-7, IB-8, IB-9, D3-10, D3-11, IB-12, IB-13, IB-14, IB-15, IB-16, IB-17, IB-18, IB-19, IB-20, IB-21, IB-22, IB-23, IB-24, IB-25, IB-26, IB-27, IB-28, IB-29, IB-30, IB-31, IB-32, IB-33, IB-34, IB-35, IB-36, IB-37, IB-38, IB-39, IB-40, IB-41, IB-42, IB-43, IB-44, IB-45, IB-46, IB-47, IB-49, IB-50, IB-54, IB-57, IB-58, IB-64, IB-68, IB-69, IB-70, IB-71, IB-72, IB-73, IB-74, IB-75, IB-76, IB-77, IB-78, IB-79, IB-80, and IB-81 to IB-923.

[Item A27b]

The compound or an enantiomer thereof, or a salt thereof, or a solvate thereof according to any one of the preceding items, wherein the compound of formula IB is (3S*,3aS*,6R*,7R*,7aS*)-7-benzyl-N,1-diisobutyloctahydro-3 aH-3,6-methanopyrrolo[3,2-b]pyridine-3a-caboxamide, (3S*,3aS*,6R*,7R*,7aS*)-1-benzyl-N,7-diisobutyloctahydro-3aH-3,6-methanopyrrolo[3,2-b]pyridine-3a-caboxamide, (3S*,3aS*,6R*,7R*,7aS*)-N-benzyl-1,7-diisobutyloctahydro-4,6-methanopyrrolo[3,2-b]pyridine-3a-caboxamide, (3S*,3aS*,6R*,7R*,7aS*)-N,7-dibenzyl-1-isopentyloctahydro-3aH-3,6-methanopyrrolo[3,2-b]pyridine-3a-caboxamide, (3S*,3aS*,6R*,7R*,7aS*)-1-benzyl-7- isobutyl-N-phenethyloctahydro-3aH-3,6-methanopyrrolo[3,2-b]pyridine-3a-caboxamide, (3S*,3aS*,6R*,7R*,7aS*)-N-benzyl-1-isobutyl-7-(3-methylbenzyl)octahydro-3aH-3,6-methanopyrrolo[3,2-b]pyridine-3a-caboxamide, or (3S*,3aS*,6R*,7R*,7aS*)-7-benzyl-1-isobutyl-N-(3-methylbenzyl)octahydro-3aH-3,6-methanopyrrolo[3,2-b]pyridine-3a-caboxamide.

[Item A28]

A compound represented by formula IIF:

[Chemical Formula 9]

Formula IIF or an enantiomer thereof, or a salt thereof, or a solvate thereof, wherein
$R_1$, $R_2$ and $R_3$ are each independently optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl.

[Item A29]

A compound represented by formula IIB:

[Chemical Formula 10]

Formula IIB or an enantiomer thereof, or a salt thereof, or a solvate thereof, wherein
$R_1$, $R_2$ and $R_3$ are each independently optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl.

[Item A30]

The compound or an enantiomer thereof, or a salt thereof, or a solvate thereof according to any one of the preceding items, wherein
$R_1$, $R_2$ and $R_3$ are each independently optionally substituted alkyl, optionally substituted arylalkyl, optionally substituted heteroarylalkyl, or optionally substituted cycloalkylalkyl.

[Item A31]

The compound or an enantiomer thereof, or a salt thereof, or a solvate thereof according to any one of the preceding items, wherein
$R_1$, $R_2$ and $R_3$ are each independently optionally substituted $C_{1-6}$ alkyl, optionally substituted $C_{6-10}$ aryl $C_{1-6}$ alkyl, optionally substituted 5- to 10-membered heteroaryl $C_{1-6}$ alkyl, or optionally substituted $C_{3-6}$ cycloalkyl $C_{1-6}$ alkyl.

[Item A32]

The compound or an enantiomer thereof, or a salt thereof, or a solvate thereof according to any one of the preceding items, wherein
$R_1$, $R_2$ and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, (optionally substituted amino)-$C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl $C_{1-6}$ alkyl.

[Item A32a]

The compound or an enantiomer thereof, or a salt thereof, or a solvate thereof according to any one of the preceding items, wherein
$R_1$, $R_2$ and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl$C_{1-6}$ alkyl.

[Item A32b]

The compound or an enantiomer thereof, or a salt thereof, or a solvate thereof according to any one of the preceding items, wherein
$R_1$, $R_2$ and $R_3$ are each independently optionally substituted alkyl or optionally substituted arylalkyl.

[Item A32c]

The compound or an enantiomer thereof, or a salt thereof, or a solvate thereof according to any one of the preceding items, wherein
$R_1$, $R_2$ and $R_3$ are each independently optionally substituted $C_{1-6}$ alkyl or optionally substituted $C_{6-10}$ aryl $C_{1-6}$ alkyl.

[Item A33]

The compound or an enantiomer thereof, or a salt thereof, or a solvate thereof according to any one of the preceding items, wherein
$R_2$ is $C_{1-4}$ alkyl, hydroxy-substituted $C_{1-4}$ alkyl, carbamoyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkoxycarbonyl-substituted 5- to 10-membered heteroaryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, halogen-substituted $C_{6-10}$ aryl $C_{1-4}$ alkyl, $C_{1-4}$ alkoxy-substituted $C_{6-10}$ aryl $C_{1-4}$ alkyl, $C_{1-4}$ alkoxycarbonyl-substituted $C_{1-4}$ alkyl, $C_{1-4}$ alkoxycarbonylamino-substituted $C_{1-4}$ alkyl, 5- to 6-membered heterocycloalkyl-substituted $C_{1-4}$ alkyl, or $C_{5-6}$ cycloalkyl $C_{1-4}$ alkyl.

[Item A33b]

The compound or an enantiomer thereof, or a salt thereof, or a solvate thereof according to any one of the preceding items, wherein $R_2$ is isopropyl, 1-methylpropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 4-fluorobenzyl, 3-chlorobenzyl, 4-chlorobenzyl, 3,4-dichlorobenzyl, 4-(tert-butoxy)benzyl, 2-(tert-butoxy)-2-oxoethyl, 3-(tert-butoxy)-3-oxopropyl, 4-((tert-butoxycarbonyl)amino)butyl, (tetrahydro-2H-pyran-2-yl)methyl, cyclohexylmethyl, or

[Chemical Formula 11]

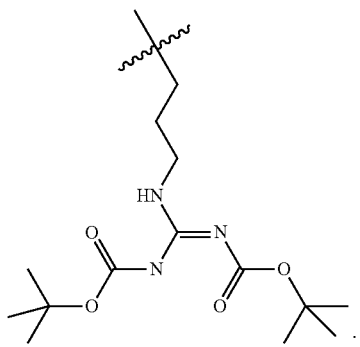

[Item A34]

The compound or an enantiomer thereof, or a salt thereof, or a solvate thereof according to any one of the preceding items, wherein $R_2$ is isobutyl, 2-hydroxyethyl, 3-amino-3-oxopropyl, 4-aminobutyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 3-chlorobenzyl, 4-chlorobenzyl, 3,4-dichlorobenzyl, 4-(tert-butoxy)benzyl, 2-(tert-butoxy)-2-oxoethyl, 4-((tert-butoxycarbonyl)amino)butyl, (tetrahydro-2H-pyran-2-yl)methyl, or cyclohexylmethyl.

[Item A35]

The compound or an enantiomer thereof, or a salt thereof, or a solvate thereof according to any one of the preceding items, wherein $R_2$ is isopropyl, isobutyl, isopentyl, benzyl, 4-hydroxybenzyl, 4-fluorobenzyl, 2-carboxyethyl, carbamoylmethyl, 3-(amidinoamino)propyl, hydroxyethyl, phenethyl, naphthalen-1-ylmethyl, or n-hexyl.

[Item A35b]

The compound or an enantiomer thereof, or a salt thereof, or a solvate thereof according to any one of the preceding items, wherein $R_2$ is isopropyl, 1-methylpropyl, isobutyl, 3-(amidinoamino)propyl, 2-carboxyethyl, benzyl, naphthalen-1-ylmethyl, 4-hydroxybenzyl, 4-(tert-butoxy)benzyl, 3-(tert-butoxy)-3-oxopropyl, or

[Chemical Formula 12]

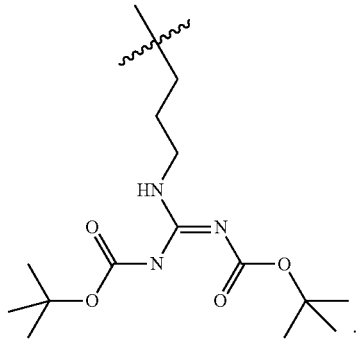

[Item A36]

The compound or an enantiomer thereof, or a salt thereof, or a solvate thereof according to any one of the preceding items, wherein $R_1$ is $C_{1-6}$ alkyl, hydroxy-substituted $C_{1-4}$ alkyl, carbamoyl-substituted $C_{1-4}$ alkyl, amino-substituted $C_{1-6}$ alkyl, amidinoamino-substituted $C_{1-4}$ alkyl, carboxy-substituted $C_{1-4}$ alkyl, $C_{1-4}$ alkoxycarbonyl-substituted $C_{1-4}$ alkyl, $C_{6-10}$ aryl $C_{1-4}$ alkyl, hydroxy-substituted $C_{6-10}$ aryl $C_{1-4}$ alkyl, $C_{1-4}$ alkoxy-substituted $C_{6-10}$ aryl $C_{1-4}$ alkyl, halo-substituted $C_{6-10}$ aryl $C_{1-4}$ alkyl, or $C_{5-6}$ cycloalkyl $C_{1-4}$ alkyl.

[Item A36b]

The compound or an enantiomer thereof, or a salt thereof, or a solvate thereof according to any one of the preceding items, wherein $R_1$ is methyl, isopropyl, isobutyl, isopentyl, n-hexyl, 2-hydroxyethyl, carbamoylmethyl, 3-amino-3-oxopropyl, 3-(amidinoamino)propyl, 2-carboxyethyl, benzyl, phenethyl, naphthalen-1-ylmethyl, 4-hydroxybenzyl, 4-fluorobenzyl, 3,4-dichlorobenzyl, 4-(tert-butoxy)benzyl, 3-(tert-butoxy)-3-oxopropyl, hydroxymethyl, cyclohexylmethyl, or

[Chemical Formula 13]

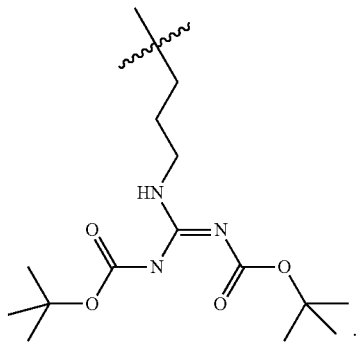

[Item A37]

The compound or an enantiomer thereof, or a salt thereof, or a solvate thereof according to any one of the preceding items, wherein $R_1$ is methyl, isobutyl, isopentyl, 3-(tert-butoxy)-3-oxopropyl, benzyl, naphthalen-1-ylmethyl, 4-hydroxybenzyl, 4-(tert-butoxy)benzyl, 3,4-dichlorobenzyl, or cyclohexylmethyl.

[Item A38]

The compound or an enantiomer thereof, or a salt thereof, or a solvate thereof according to any one of the preceding items, wherein R₁ is isobutyl, isopentyl, cyclohexylmethyl, benzyl, phenethyl, naphthalen-1-ylmethyl, 4-hydroxybenzyl, 4-fluorobenzyl, 2-carboxyethyl, carbamoylmethyl, 3-(amidinoamino)propyl, or hydroxyethyl.

[Item A38b]

The compound or an enantiomer thereof, or a salt thereof, or a solvate thereof according to any one of the preceding items, wherein R₁ is isobutyl, 3-(amidinoamino)propyl, 2-carboxyethyl, benzyl, naphthalen-1-ylmethyl, 4-hydroxybenzyl, 4-(tert-butoxy)benzyl, 3-(tert-butoxy)-3-oxopropyl, or

[Chemical Formula 14]

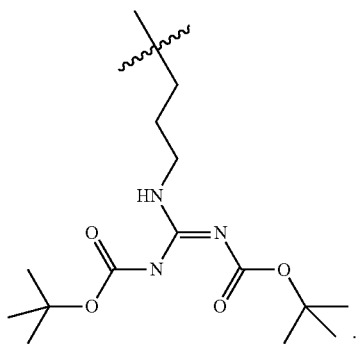

[Item A39]

The compound or an enantiomer thereof, or a salt thereof, or a solvate thereof according to any one of the preceding items, wherein R₃ is $C_{1-4}$ alkyl, hydroxy-substituted $C_{1-4}$ alkyl, carbamoyl-substituted $C_{1-4}$ alkyl, $C_{1-4}$ alkoxycarbonyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, or $C_{5-6}$ cycloalkyl $C_{1-4}$ alkyl.

[Item A39b]

The compound or an enantiomer thereof, or a salt thereof, or a solvate thereof according to any one of the preceding items, wherein R₃ is isopropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 3-methylbenzyl, 4-methylbenzyl, 4-hydroxybenzyl, 4-fluorobenzyl, 4-(tert-butoxy)benzyl, 3-methoxy-3-oxopropyl, 3-(tert-butoxy)-3-oxopropyl, 4-((tert-butoxycarbonyl)amino)butyl, cyclohexylmethyl, or

[Chemical Formula 15]

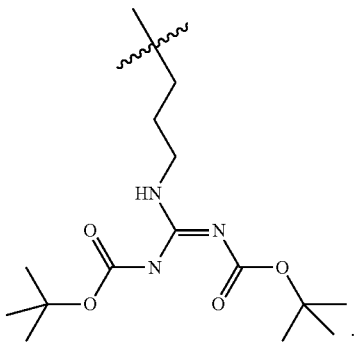

[Item A40]

The compound or an enantiomer thereof, or a salt thereof, or a solvate thereof according to any one of the preceding items, wherein R₃ is isobutyl, isopentyl, 3-amino-3-oxopropyl, 3-methoxy-3-oxopropyl, 4-aminobutyl, 2-carboxyethyl, benzyl, phenethyl, 3-methylbenzyl, 4-methylbenzyl, 4-hydroxybenzyl, 4-((tert-butoxycarbonyl)amino)butyl, or cyclohexylmethyl.

[Item A41]

The compound or an enantiomer thereof, or a salt thereof, or a solvate thereof according to any one of the preceding items, wherein R₃ is isobutyl, isopentyl, benzyl, phenethyl, 4-hydroxybenzyl, 2-carboxyethyl, carbamoylmethyl, 3-(amidinoamino)propyl, hydroxymethyl, or naphthalen-1-ylmethyl.

[Item A41b]

The compound or an enantiomer thereof, or a salt thereof, or a solvate thereof according to any one of the preceding items, wherein R₃ is isobutyl, 2-carboxyethyl, 3-(amidinoamino)propyl, benzyl, naphthalen-1-ylmethyl, 4-hydroxybenzyl, 4-(tert-butoxy)benzyl, 3-(tert-butoxy)-3-oxopropyl, or

[Chemical Formula 16]

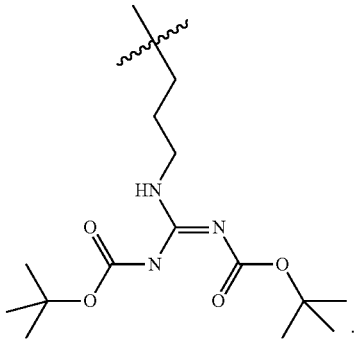

[Item A42]

The compound or an enantiomer thereof, or a salt thereof, or a solvate thereof according to any one of the preceding items, wherein R₁ is $C_{1-6}$ alkyl or $C_{6-10}$ aryl $C_{1-6}$ alkyl, R₂ and R₃ are each independently $C_{1-6}$ alkyl or optionally substituted $C_{6-10}$ aryl $C_{1-6}$ alkyl.

[Item A42b]

The compound or an enantiomer thereof, or a salt thereof, or a solvate thereof according to any one of the preceding items, wherein R₁, R₂, and R₃ are each independently $C_{1-6}$ alkyl or optionally substituted $C_{6-10}$ aryl $C_{1-6}$ alkyl.

[Item A42c]

The compound or an enantiomer thereof, or a salt thereof, or a solvate thereof according to any one of the preceding items, wherein R₁, R₂, and R₃ are each independently $C_{1-6}$ alkyl, $C_{6-10}$ aryl $C_{1-6}$ alkyl, $C_{1-4}$ alkyl-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, or (optionally substituted amino)-$C_{6-10}$ aryl $C_{1-6}$ alkyl.

[Item A42d]

The compound or an enantiomer thereof, or a salt thereof, or a solvate thereof according to any one of the preceding items, wherein R₁ is $C_{1-6}$ alkyl or $C_6$ aryl $C_{1-4}$ alkyl, R₂ is $C_{1-6}$ alkyl or $C_{1-4}$ alkyl-substituted benzyl, and R₃ is $C_{1-6}$ alkyl or $C_6$ aryl $C_{1-4}$ alkyl.

[Item A43]

The compound or an enantiomer thereof, or a salt thereof, or a solvate thereof according to any one of the preceding items, wherein R₁ is isobutyl, benzyl, 4-(dimethylamino)benzyl, 4-methylbenzyl, 4-tert-butylbenzyl, 4-methoxybenzyl, 3-chlorobenzyl, 4-chlorobenzyl, or 3,4-dichlorobenzyl, R₂ is isobutyl, benzyl, naphthalen-1-ylmethyl, 4-methylbenzyl, 4-chlorobenzyl, or 3,4-dichlorobenzyl, and R₃ is isobutyl, isopentyl, or benzyl.

[Item A43b]

The compound or an enantiomer thereof, or a salt thereof, or a solvate thereof according to any one of the preceding items, wherein R₁ is isobutyl, isopentyl, or benzyl, R₂ is isobutyl, benzyl, phenethyl, 3-methylbenzyl, 4-methylbenzyl, or 3,4-dichlorobenzyl, and R₃ is isobutyl, benzyl, phenethyl, 3-methylbenzyl, or 4-methylbenzyl.

[Item A44]

The compound or an enantiomer thereof, or a salt thereof, or a solvate thereof according to any one of the preceding items, wherein the compound is a compound of formula IIF, R₁ is isobutyl, R₂ is 4-methylbenzyl, and R₃ is benzyl.

[Item A45]

The compound or an enantiomer thereof, or a salt thereof, or a solvate thereof according to any one of the preceding items, wherein the compound is a compound of formula IIB, R₁ is benzyl, R₂ is isobutyl, and R₃ is isobutyl.

[Item A46]

An antiviral agent for a virus in the Lyssavirus genus, comprising the compound according to any one of the preceding items or a pharmaceutically acceptable salt thereof.

[Item A47]

The antiviral agent according to any one of the preceding items, wherein the virus in the Lyssavirus genus comprises a rabies virus.

[Item A48]

A medicament comprising the compound according to any one of the preceding items or a pharmaceutically acceptable salt thereof, or the antiviral agent according to any one of the preceding items.

[Item A49]

The medicament according to any one of the preceding items, which is a prophylactic agent or a therapeutic agent for rabies.

[Item A50]

A pharmaceutical composition comprising the compound according to any one of the preceding items or a pharmaceutically acceptable salt thereof, or the antiviral agent according to any one of the preceding items, and a pharmaceutically acceptable carrier.

[Item A51]

A pharmaceutical composition for the prophylaxis or treatment of rabies, comprising the compound according to any one of the preceding items or a pharmaceutically acceptable salt thereof, or the antiviral agent according to any one of the preceding items, and a pharmaceutically acceptable carrier.

[Item A52]

The compound according to any one of the preceding items or a pharmaceutically acceptable salt thereof for use as an antiviral agent for a virus in the Lyssavirus genus, preferably a rabies virus, or for the prophylaxis or treatment of rabies.

[Item A53]

A method for the prophylaxis or treatment of rabies, characterized by administering a prophylactically or therapeutically effective amount of the compound according to any one of the preceding items or a pharmaceutically acceptable salt thereof, the antiviral agent according to any one of the preceding items, the medicament according to any one of the preceding items, or the pharmaceutical composition according to any one of the preceding items to a patient in need thereof

[Item A54]

Use of the compound according to any one of the preceding items or a pharmaceutically acceptable salt thereof, or the antiviral agent according to any one of the preceding items, for the manufacture of a medicament for the prophylaxis or treatment of rabies.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The compounds of the present disclosure exhibit an excellent antiviral action on viruses in the Lyssavirus genus including the rabies virus. Therefore, the compounds of the present disclosure are useful as a therapeutic agent and/or prophylactic agent for rabies.

DESCRIPTION OF EMBODIMENTS

Figure 1:
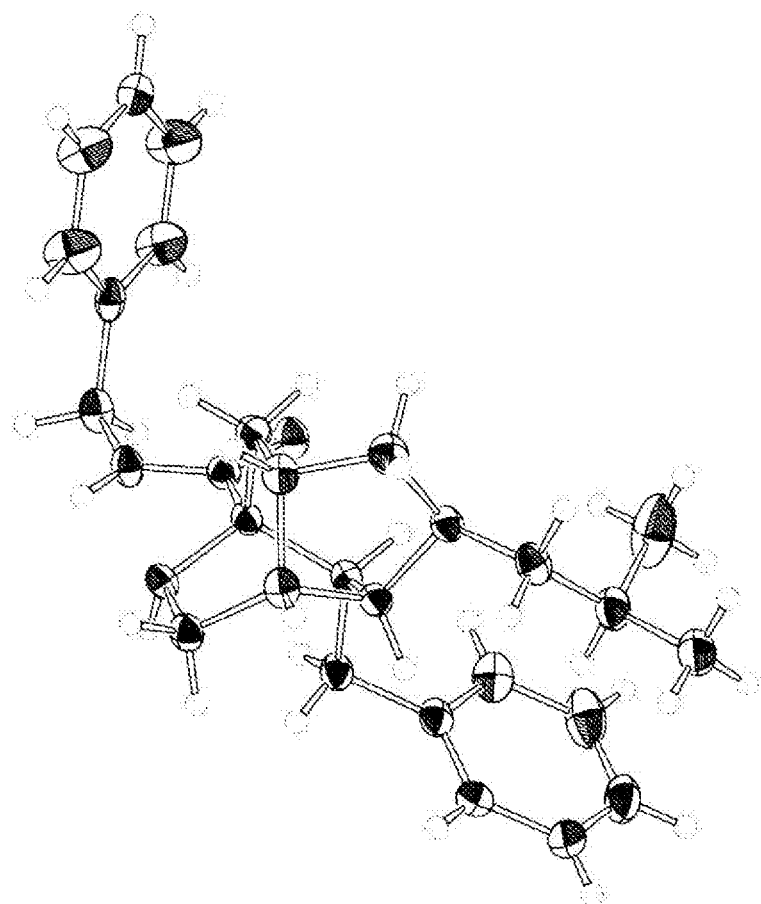
FIG. 1 shows an ORTEP diagram for the results of X-ray crystallography in Synthesis Example: IF-1.

Hereinafter, the present disclosure is described in more detail.

Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

Definitions

The terms and the general technology used in the present disclosure are first described.

As used herein, the term "group" refers to a monovalent group, unless especially noted otherwise. Examples of a group that is not a monovalent group include alkylene group (divalent) and the like. The term "group" may also be abbreviated in the following description of substituents or the like.

As used herein, the number of substituents when a group is defined as "optionally substituted" or "substituted" is not particularly limited as long as it is substitutable and is one or more. The description for each group is also applicable when the substituent is a part of or a substituent on another substituent, unless specifically noted otherwise.

As used herein, "maximum substitutable number" is the maximum number of substituents that a group can have. The number can vary for each group. For example, the number is 3 for a methyl group, 5 for an ethyl group, 7 for a benzyl group, and 10 for a naphthalenyl ethyl group.

For a group that is modified by "optionally substituted" or "substituted" herein, any portion of the group can be substituted. For example, "optionally substituted arylalkyl" and "substituted arylalkyl" can have the aryl moiety substituted, the alkyl moiety substituted, or both the aryl moiety and the alkyl moiety substituted.

As used herein, the substituent used when "optionally substituted" can be one or more of the same or different substituents selected from any one of the following substituent groups I to VI. While the types of atoms within a substituent associated with attachment are not particularly limited by the type of substituent, if the atom to which a substituent attaches is an oxygen atom, a nitrogen atom, or a sulfur atom, the atom is limited to and selected from those with an attachment point in the following substituents that is a carbon atom.

Substituent group I consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, unsubstituted or substituted alkyl, unsubstituted or substituted alkenyl, unsubstituted or substituted alkynyl, unsubstituted or substituted aryl, unsubstituted or substituted cycloalkyl, unsubstituted or substituted heteroaryl, unsubstituted or substituted heterocycloalkyl, unsubstituted or substituted alkyloxy, unsubstituted or substituted alkenyloxy, unsubstituted or substituted alkynyloxy, unsubstituted or substituted aryl-Lx-oxy, unsubstituted or substituted cycloalkyl-Lx-oxy, unsubstituted or substituted heteroaryl-Lx-oxy, unsubstituted or substituted heterocycloalkyl-Lx-oxy, unsubstituted or substituted alkyloxyalkyl, unsubstituted or substituted alkenyloxyalkyl, unsubstituted or substituted alkynyloxyalkyl, unsubstituted or substituted aryloxyalkyl, unsubstituted or substituted cycloalkyloxyalkyl, unsubstituted or substituted heteroaryloxyalkyl, unsubstituted or substituted heterocycloalkyloxyalkyl, unsubstituted or substituted alkyloxyalkyloxy, unsubstituted or substituted alkenyloxyalkyloxy, unsubstituted or substituted alkynyloxyalkyloxy, unsubstituted or substituted aryloxyalkyloxy, unsubstituted or substituted cycloalkyloxyalkyloxy, unsubstituted or substituted heteroaryloxyalkyloxy, unsubstituted or substituted heterocycloalkyloxyalkyloxy, unsubstituted or substituted alkylcarbonyl, unsubstituted or substituted alkenylcarbonyl, unsubstituted or substituted alkynylcarbonyl, unsubstituted or substituted aryl-Lx-carbonyl, unsubstituted or substituted cycloalkyl-Lx-carbonyl, unsubstituted or substituted heteroaryl-Lx-carbonyl, unsubstituted or substituted heterocycloalkyl-Lx-carbonyl, unsubstituted or substituted alkylcarbonyloxy, unsubstituted or substituted alkenylcarbonyloxy, unsubstituted or substituted alkynylcarbonyloxy, unsubstituted or substituted aryl-Lx-carbonyloxy, unsubstituted or substituted cycloalkyl-Lx-carbonyloxy, unsubstituted or substituted heteroaryl-Lx-carbonyloxy, unsubstituted or substituted heterocycloalkyl-Lx-carbonyloxy, unsubstituted or substituted alkylcarbonylamino, unsubstituted or substituted alkenylcarbonylamino, unsubstituted or substituted alkynylcarbonylamino, unsubstituted or substituted aryl-Lx-carbonylamino, unsubstituted or substituted cycloalkyl-Lx-carbonylamino, unsubstituted or substituted heteroaryl-Lx-carbonylamino, unsubstituted or substituted heterocycloalkyl-Lx-carbonylamino, unsubstituted or substituted alkylcarbonylthio, unsubstituted or substituted alkenylcarbonylthio, unsubstituted or substituted alkynylcarbonylthio, unsubstituted or substituted aryl-Lx-carbonylthio, unsubstituted or substituted cycloalkyl-Lx-carbonylthio, unsubstituted or substituted heteroaryl-Lx-carbonylthio, unsubstituted or substituted heterocycloalkyl-Lx-carbonylthio, unsubstituted or substituted alkylcarbonylimino, unsubstituted or substituted alkenylcarbonylimino, unsubstituted or substituted alkynylcarbonylimino, unsubstituted or substituted aryl-Lx-carbonylimino, unsubstituted or substituted cycloalkyl-Lx-carbonylimino, unsubstituted or substituted heteroaryl-Lx-carbonylimino, unsubstituted or substituted heterocycloalkyl-Lx-carbonylimino, unsubstituted or substituted alkylthio, unsubstituted or substituted alkenylthio, unsubstituted or substituted alkynylthio, unsubstituted or substituted aryl-Lx-thio, unsubstituted or substituted cycloalkyl-Lx-thio, unsubstituted or substituted heteroaryl-Lx-thio, unsubstituted or substituted heterocycloalkyl-Lx-thio, unsubstituted or substituted alkylamino, unsubstituted or substituted alkenylamino, unsubstituted or substituted alkynylamino, unsubstituted or substituted alkynylamino, unsubstituted or substituted aryl-Lx-amino, unsubstituted or substituted cycloalkyl-Lx-amino, unsubstituted or substituted heteroaryl-Lx-amino, unsubstituted or substituted heterocycloalkyl-Lx-amino, unsubstituted or substituted alkylsulfonyl, unsubstituted or substituted alkenyl sulfonyl, unsubstituted or substituted alkynylsulfonyl, unsubstituted or substituted aryl-Lx-sulfonyl, unsubstituted or substituted cycloalkyl-Lx-sulfonyl, unsubstituted or substituted heteroaryl-Lx-sulfonyl, unsubstituted or substituted heterocycloalkyl-Lx-sulfonyl, unsubstituted or substituted alkyl sulfonyl amino, unsubstituted or substituted alkenylsulfonylamino, unsubstituted or substituted alkynyl sulfonylamino, unsubstituted or substituted aryl-Lx-sulfonylamino, unsubstituted or substituted cycloalkyl-Lx-sulfonylamino, unsubstituted or substituted heteroaryl-Lx-sulfonylamino, unsubstituted or substituted heterocycloalkyl-Lx-sulfonylamino, unsubstituted or substituted alkylimino, unsubstituted or substituted alkenylimino, unsubstituted or substituted alkynylimino, unsubstituted or substituted aryl-Lx-imino, unsubstituted or substituted cycloalkyl-Lx-imino, unsubstituted or substituted heteroaryl-Lx-imino, unsubstituted or substituted heterocycloalkyl-Lx-imino, unsubstituted or substituted alkyloxyimino, unsubstituted or substituted alkenyloxyimino, unsubstituted or substituted alkynyloxyimino, unsubstituted or substituted aryl-Lx-oxyimino, unsubstituted or substituted cycloalkyl-Lx-oxyimino, unsubstituted or substituted heteroaryl-Lx-oxyimino, unsubstituted or substituted heterocycloalkyl-Lx-oxyimino, unsubstituted or substituted alkyloxycarbonyl, unsubstituted or substituted alkenyloxycarbonyl, unsubstituted or substituted alkynyloxycarbonyl, unsubstituted or substituted aryl-Lx-oxycarbonyl, unsubstituted or substituted cycloalkyl-Lx-oxycarbonyl, unsubstituted or substituted heteroaryl-Lx-oxycarbonyl, unsubstituted or substituted heterocycloalkyl-Lx-oxycarbonyl, unsubstituted or substituted alkyloxycarbonylamino, unsubstituted or substituted alkenyloxycarbonylamino, unsubstituted or substituted alkynyloxycarbonylamino, unsubstituted or substituted aryl-Lx-oxycarbonylamino, unsubstituted or substituted cycloalkyl-Lx-oxycarbonylamino, unsubstituted or substituted heteroaryl-Lx-oxycarbonylamino, unsubstituted or substituted heterocycloalkyl-Lx-oxycarbonylamino, unsubstituted or substituted alkylsulfanyl, unsubstituted or substituted alkenyl sulfanyl, unsubstituted or substituted alkynylsulfanyl, unsubstituted or substituted aryl-Lx-sulfanyl, unsubstituted or substituted cycloalkyl-Lx-sulfanyl, unsubstituted or substituted heteroaryl-Lx-sulfanyl, unsubstituted or substituted heterocycloalkyl-Lx-sulfanyl, unsubstituted or substituted alkylsulfinyl, unsubstituted or substituted alkenylsulfinyl, unsubstituted or substituted alkynylsulfinyl, unsubstituted or substituted aryl-Lx-sulfinyl, unsubstituted or substituted cycloalkyl-Lx-sulfinyl, unsubstituted or substituted heteroaryl-Lx-sulfinyl, unsubstituted or substituted heterocycloalkyl-Lx-sulfinyl, unsubstituted or substituted alkylcarbamoyl, unsubstituted or substituted alkenylcarbamoyl, unsubstituted or substituted alkynylcarbamoyl, unsubstituted or substituted aryl-Lx-carbamoyl, unsubstituted or substituted cycloalkyl-Lx-carbamoyl, unsubstituted or substituted heteroaryl-Lx-carbamoyl, unsubstituted or substituted heterocycloalkyl-Lx-carbamoyl, unsubstituted or substituted alkyl sulfamoyl, unsubstituted or substituted alkenylsulfamoyl, unsubstituted or substituted alkynylsulfamoyl, unsubstituted or substituted aryl-Lx-sulfamoyl, unsubstituted or substituted cycloalkyl-Lx-sulfamoyl, unsubstituted or substituted heteroaryl-Lx-sulfamoyl, and unsubstituted or substituted heterocycloalkyl-Lx-sulfamoyl, wherein Lx is a single bond or unsubstituted or substituted alkylene, wherein the substituted alkyl, substituted alkenyl, substituted alkynyl, substituted aryl, substituted cycloalkyl, substituted heteroaryl, substituted heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, alkyl, alkenyl, alkynyl, aryl, cycloalkyl, heteroaryl, heterocycloalkyl, alkyloxy, alkenyloxy, alkynyloxy, aryl-Lx-oxy, cycloalkyl-Lx-oxy, heteroaryl-Lx-oxy, heterocycloalkyl-Lx-oxy, alkyloxyalkyl, alkenyloxyalkyl, alkynyloxyalkyl, aryloxyalkyl, cycloalkyloxyalkyl, heteroaryloxyalkyl, heterocycloalkyloxyalkyl, alkyloxyalkyloxy, alkenyloxyalkyloxy, alkynyloxyalkyloxy, aryloxyalkyloxy, cycloalkyloxyalkyloxy, heteroaryloxyalkyloxy, heterocycloalkyloxyalkyloxy, alkylcarbonyl, alkenylcarbonyl, alkynylcarbonyl, aryl-Lx-carbonyl, cycloalkyl-Lx-carbonyl, heteroaryl-Lx-carbonyl, heterocycloalkyl-Lx-carbonyl, alkylcarbonyloxy, alkenylcarbonyloxy, alkynylcarbonyloxy, aryl-Lx-carbonyloxy, cycloalkyl-Lx-carbonyloxy, heteroaryl-Lx-carbonyloxy, heterocycloalkyl-Lx-carbonyloxy, alkylcarbonylamino, alkenylcarbonylamino, alkynylcarbonylamino, aryl-Lx-carbonylamino, cycloalkyl-Lx-carbonylamino, heteroaryl-Lx-carbonylamino, heterocycloalkyl-Lx-carbonylamino, alkylcarbonylthio, alkenylcarbonylthio, alkynylcarbonylthio, aryl-Lx-carbonylthio, cycloalkyl-Lx-carbonylthio, heteroaryl-Lx-carbonylthio, heterocycloalkyl-Lx-carbonylthio, alkylcarbonylimino, alkenylcarbonylimino, alkynylcarbonylimino, aryl-Lx-carbonylimino, cycloalkyl-Lx-carbonylimino, heteroaryl-Lx-carbonylimino, heterocycloalkyl-Lx-carbonylimino, alkylthio, alkenylthio, alkynylthio, aryl-Lx-thio, cycloalkyl-Lx-thio, heteroaryl-Lx-thio, heterocycloalkyl-Lx-thio, alkylamino, alkenylamino, alkynylamino, alkynylamino, aryl-Lx-amino, cycloalkyl-Lx-amino, heteroaryl-Lx-amino, heterocycloalkyl-Lx-amino, alkylsulfonyl, alkenyl sulfonyl, alkynylsulfonyl, aryl-Lx-sulfonyl, cycloalkyl-Lx-sulfonyl, heteroaryl-Lx-sulfonyl, heterocycloalkyl-Lx-sulfonyl, alkyl sulfonylamino, alkenyl sulfonylamino, alkynylsulfonylamino, aryl-Lx-sulfonylamino, cycloalkyl-Lx-sulfonylamino, heteroaryl-Lx-sulfonylamino, heterocycloalkyl-Lx-sulfonylamino, alkylimino, alkenylimino, alkynylimino, aryl-Lx-imino, cycloalkyl-Lx-imino, heteroaryl-Lx-imino, heterocycloalkyl-Lx-imino, alkyloxyimino, alkenyloxyimino, alkynyloxyimino, aryl-Lx-oxyimino, cycloalkyl-Lx-oxyimino, heteroaryl-Lx-oxyimino, heterocycloalkyl-Lx-oxyimino, alkyloxycarbonyl, alkenyloxycarbonyl, alkynyloxycarbonyl, aryl-Lx-oxycarbonyl, cycloalkyl-Lx-oxycarbonyl, heteroaryl-Lx-oxycarbonyl, heterocycloalkyl-Lx-oxycarbonyl, alkyloxycarbonylamino, alkenyloxycarbonylamino, alkynyloxycarbonylamino, aryl-Lx-oxycarbonylamino, cycloalkyl-Lx-oxycarbonylamino, heteroaryl-Lx-oxycarbonylamino, heterocycloalkyl-Lx-oxycarbonylamino, alkylsulfanyl, alkenylsulfanyl, alkynylsulfanyl, aryl-Lx-sulfanyl, cycloalkyl-Lx-sulfanyl, heteroaryl-Lx-sulfanyl, heterocycloalkyl-Lx-sulfanyl, alkylsulfinyl, alkenylsulfinyl, alkynylsulfinyl, aryl-Lx-sulfinyl, cycloalkyl-Lx-sulfinyl, heteroaryl-Lx-sulfinyl, heterocycloalkyl-Lx-sulfinyl, alkylcarbamoyl, alkenylcarbamoyl, alkynylcarbamoyl, aryl-Lx-carbamoyl, cycloalkyl-Lx-carbamoyl, heteroaryl-Lx-carbamoyl, heterocycloalkyl-Lx-carbamoyl, alkylsulfamoyl, alkenylsulfamoyl, alkynylsulfamoyl, aryl-Lx-sulfamoyl, cycloalkyl-Lx-sulfamoyl, heteroaryl-Lx-sulfamoyl, and heterocycloalkyl-Lx-sulfamoyl.

Substituent group II consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, unsubstituted or substituted $C_{1-12}$ alkyl, unsubstituted or substituted $C_{2-12}$ alkenyl, unsubstituted or substituted $C_{2-12}$ alkynyl, unsubstituted or substituted $C_{6-10}$ aryl, unsubstituted or substituted $C_{3-10}$ cycloalkyl, unsubstituted or substituted 5- to 10-membered heteroaryl, unsubstituted or substituted 5- to 10-membered heterocycloalkyl, unsubstituted or substituted $C_{1-12}$ alkyloxy, unsubstituted or substituted $C_{2-12}$ alkenyloxy, unsubstituted or substituted $C_{2-12}$ alkynyloxy, unsubstituted or substituted $C_{6-10}$ aryl-Lx-oxy, unsubstituted or substituted $C_{3-10}$ cycloalkyl-Lx-oxy, unsubstituted or substituted 5- to 10-membered heteroaryl-Lx-oxy, unsubstituted or substituted 5- to 10-membered heterocycloalkyl-Lx-oxy, unsubstituted or substituted $C_{1-12}$ alkyloxy $C_{1-12}$ alkyl, unsubstituted or substituted $C_{2-12}$ alkenyloxy $C_{1-12}$ alkyl, unsubstituted or substituted $C_{2-12}$ alkynyloxy $C_{1-12}$ alkyl, unsubstituted or substituted $C_{6-10}$ aryloxy $C_{1-12}$ alkyl, unsubstituted or substituted $C_{3-10}$ cycloalkyloxy $C_{1-12}$ alkyl, unsubstituted or substituted 5- to 10-membered heteroaryloxy $C_{1-12}$ alkyl, unsubstituted or substituted 5- to 10-membered heterocycloalkyloxy $C_{1-12}$ alkyl, unsubstituted or substituted $C_{1-12}$ alkyloxy $C_{1-12}$ alkyloxy, unsubstituted or substituted $C_{2-12}$ alkenyloxy $C_{1-12}$ alkyloxy, unsubstituted or substituted $C_{2-12}$ alkynyloxy $C_{1-12}$ alkyloxy, unsubstituted or substituted $C_{6-10}$ aryloxy $C_{1-12}$ alkyloxy, unsubstituted or substituted $C_{3-10}$ cycloalkyloxy $C_{1-12}$ alkyloxy, unsubstituted or substituted 5- to 10-membered heteroaryloxy $C_{1-12}$ alkyloxy, unsubstituted or substituted 5- to 10-membered heterocycloalkyloxy $C_{1-12}$ alkyloxy, unsubstituted or substituted $C_{1-12}$ alkylcarbonyl, unsubstituted or substituted $C_{2-12}$ alkenylcarbonyl, unsubstituted or substituted $C_{2-12}$ alkynylcarbonyl, unsubstituted or substituted $C_{6-10}$ aryl-Lx-carbonyl, unsubstituted or substituted $C_{3-10}$ cycloalkyl-Lx-carbonyl, unsubstituted or substituted 5- to 10-membered heteroaryl-Lx-carbonyl, unsubstituted or substituted 5- to 10-membered heterocycloalkyl-Lx-carbonyl, unsubstituted or substituted $C_{1-12}$ alkylcarbonyloxy, unsubstituted or substituted $C_{2-12}$ alkenylcarbonyloxy, unsubstituted or substituted $C_{2-12}$ alkynylcarbonyloxy, unsubstituted or substituted $C_{6-10}$ aryl-Lx-carbonyloxy, unsubstituted or substituted $C_{3-10}$ cycloalkyl-Lx-carbonyloxy, unsubstituted or substituted 5- to 10-membered heteroaryl-Lx-carbonyloxy, unsubstituted or substituted 5- to 10-membered heterocycloalkyl-Lx-carbonyloxy, unsubstituted or substituted $C_{1-12}$ alkylcarbonylamino, unsubstituted or substituted $C_{2-12}$ alkenylcarbonylamino, unsubstituted or substituted $C_{2-12}$ alkynylcarbonylamino, unsubstituted or substituted $C_{6-10}$ aryl-Lx-carbonylamino, unsubstituted or substituted $C_{3-10}$ cycloalkyl-Lx-carbonylamino, unsubstituted or substituted 5- to 10-membered heteroaryl-Lx-carbonylamino, unsubstituted or substituted 5- to 10-membered heterocycloalkyl-Lx-carbonylamino, unsubstituted or substituted $C_{1-12}$ alkylcarbonylthio, unsubstituted or substituted $C_{2-12}$ alkenylcarbonylthio, unsubstituted or substituted $C_{2-12}$ alkynylcarbonylthio, unsubstituted or substituted $C_{6-10}$ aryl-Lx-carbonylthio, unsubstituted or substituted $C_{3-10}$ cycloalkyl-Lx-carbonylthio, unsubstituted or substituted 5- to 10-membered heteroaryl-Lx-carbonylthio, unsubstituted or substituted 5- to 10-membered heterocycloalkyl-Lx-carbonylthio, unsubstituted or substituted $C_{1-12}$ alkylcarbonylimino, unsubstituted or substituted $C_{2-12}$ alkenylcarbonylimino, unsubstituted or substituted $C_{2-12}$ alkynylcarbonylimino, unsubstituted or substituted $C_{6-10}$ aryl-Lx-carbonylimino, unsubstituted or substituted $C_{3-10}$ cycloalkyl-Lx-carbonylimino, unsubstituted or substituted 5- to 10-membered heteroaryl-Lx-carbonylimino, unsubstituted or substituted 5- to 10-membered heterocycloalkyl-Lx-carbonylimino, unsubstituted or substituted $C_{1-12}$ alkylthio, unsubstituted or substituted $C_{2-12}$ alkenylthio, unsubstituted or substituted $C_{2-12}$ alkynylthio, unsubstituted or substituted $C_{6-10}$ aryl-Lx-thio, unsubstituted or substituted $C_{3-10}$ cycloalkyl-Lx-thio, unsubstituted or substituted 5- to 10-membered heteroaryl-Lx-thio, unsubstituted or substituted 5- to 10-membered heterocycloalkyl-Lx-thio, unsubstituted or substituted $C_{1-12}$ alkylamino, unsubstituted or substituted $C_{2-12}$ alkenylamino, unsubstituted or substituted $C_{2-12}$ alkynylamino, unsubstituted or substituted $C_{6-10}$ aryl-Lx-amino, unsubstituted or substituted $C_{3-10}$ cycloalkyl-Lx-amino, unsubstituted or substituted 5- to 10-membered heteroaryl-Lx-amino, unsubstituted or substituted 5- to 10-membered heterocycloalkyl-Lx-amino, unsubstituted or substituted $C_{1-12}$ alkylsulfonyl, unsubstituted or substituted $C_{2-12}$ alkenylsulfonyl, unsubstituted or substituted $C_{2-12}$ alkynylsulfonyl, unsubstituted or substituted $C_{6-10}$ aryl-Lx-sulfonyl, unsubstituted or substituted $C_{3-10}$ cycloalkyl-Lx-sulfonyl, unsubstituted or substituted 5- to 10-membered heteroaryl-Lx-sulfonyl, unsubstituted or substituted 5- to 10-membered heterocycloalkyl-Lx-sulfonyl, unsubstituted or substituted $C_{1-12}$ alkylsulfonylamino, unsubstituted or substituted $C_{2-12}$ alkenyl sulfonylamino, unsubstituted or substituted $C_{2-12}$ alkynyl sulfonylamino, unsubstituted or substituted $C_{6-10}$ aryl-Lx-sulfonylamino, unsubstituted or substituted $C_{3-10}$ cycloalkyl-Lx-sulfonylamino, unsubstituted or substituted 5- to 10-membered heteroaryl-Lx-sulfonylamino, unsubstituted or substituted 5- to 10-membered heterocycloalkyl-Lx-sulfonylamino, unsubstituted or substituted $C_{1-12}$ alkylimino, unsubstituted or substituted $C_{2-12}$ alkenylimino, unsubstituted or substituted $C_{2-12}$ alkynylimino, unsubstituted or substituted $C_{6-10}$ aryl-Lx-imino, unsubstituted or substituted $C_{3-10}$ cycloalkyl-Lx-imino, unsubstituted or substituted 5- to 10-membered heteroaryl-Lx-imino, unsubstituted or substituted 5- to 10-membered heterocycloalkyl-Lx-imino, unsubstituted or substituted $C_{1-12}$ alkyloxyimino, unsubstituted or substituted $C_{2-12}$ alkenyloxyimino, unsubstituted or substituted $C_{2-12}$ alkynyloxyimino, unsubstituted or substituted $C_{6-10}$ aryl-Lx-oxyimino, unsubstituted or substituted $C_{3-10}$ cycloalkyl-Lx-oxyimino, unsubstituted or substituted 5- to 10-membered heteroaryl-Lx-oxyimino, unsubstituted or substituted 5- to 10-membered heterocycloalkyl-Lx-oxyimino, unsubstituted or substituted $C_{1-12}$ alkyloxycarbonyl, unsubstituted or substituted $C_{2-12}$ alkenyloxycarbonyl, unsubstituted or substituted $C_{2-12}$ alkynyloxycarbonyl, unsubstituted or substituted $C_{6-10}$ aryl-Lx-oxycarbonyl, unsubstituted or substituted $C_{3-10}$ cycloalkyl-Lx-oxycarbonyl, unsubstituted or substituted 5- to 10-membered heteroaryl-Lx-oxycarbonyl, unsubstituted or substituted 5- to 10-membered heterocycloalkyl- Lx-oxycarbonyl, unsubstituted or substituted $C_{1-12}$ alkyloxycarbonylamino, unsubstituted or substituted $C_{2-12}$ alkenyloxycarbonylamino, unsubstituted or substituted $C_{2-12}$ alkynyloxycarbonylamino, unsubstituted or substituted $C_{6-10}$ aryl-Lx-oxycarbonylamino, unsubstituted or substituted $C_{3-10}$ cycloalkyl-Lx-oxycarbonylamino, unsubstituted or substituted 5- to 10-membered heteroaryl-Lx-oxycarbonylamino, unsubstituted or substituted 5- to 10-membered heterocycloalkyl-Lx-oxycarbonylamino, unsubstituted or substituted $C_{1-12}$ alkylsulfanyl, unsubstituted or substituted $C_{2-12}$ alkenylsulfanyl, unsubstituted or substituted $C_{2-12}$ alkynylsulfanyl, unsubstituted or substituted $C_{6-10}$ aryl-Lx-sulfanyl, unsubstituted or substituted $C_{3-10}$ cycloalkyl-Lx-sulfanyl, unsubstituted or substituted 5- to 10-membered heteroaryl-Lx-sulfanyl, unsubstituted or substituted 5- to 10-membered heterocycloalkyl-Lx-sulfanyl, unsubstituted or substituted $C_{1-12}$ alkylsulfinyl, unsubstituted or substituted $C_{2-12}$ alkenylsulfinyl, unsubstituted or substituted $C_{2-12}$ alkynylsulfinyl, unsubstituted or substituted $C_{6-10}$ aryl-Lx-sulfinyl, unsubstituted or substituted $C_{3-10}$ cycloalkyl-Lx-sulfinyl, unsubstituted or substituted 5- to 10-membered heteroaryl-Lx-sulfinyl, unsubstituted or substituted 5- to 10-membered heterocycloalkyl-Lx-sulfinyl, unsubstituted or substituted $C_{1-12}$ alkylcarbamoyl, unsubstituted or substituted $C_{2-12}$ alkenylcarbamoyl, unsubstituted or substituted $C_{2-12}$ alkynylcarbamoyl, unsubstituted or substituted $C_{6-10}$ aryl-Lx-carbamoyl, unsubstituted or substituted $C_{3-10}$ cycloalkyl-Lx-carbamoyl, unsubstituted or substituted 5- to 10-membered heteroaryl-Lx-carbamoyl, unsubstituted or substituted 5- to 10-membered heterocycloalkyl-Lx-carbamoyl, unsubstituted or substituted $C_{1-12}$ alkyl sulfamoyl, unsubstituted or substituted $C_{2-12}$ alkenylsulfamoyl, unsubstituted or substituted $C_{2-12}$ alkynylsulfamoyl, unsubstituted or substituted $C_{6-10}$ aryl-Lx-sulfamoyl, unsubstituted or substituted $C_{3-10}$ cycloalkyl-Lx-sulfamoyl, unsubstituted or substituted 5- to 10-membered heteroaryl-Lx-sulfamoyl, and unsubstituted or substituted 5- to 10-membered heterocycloalkyl-Lx-sulfamoyl, wherein Lx is a single bond or unsubstituted or substituted $C_{1-12}$ alkylene, wherein the substituted $C_{1-12}$ alkyl, substituted $C_{2-12}$ alkenyl, substituted $C_{2-12}$ alkynyl, substituted $C_{6-10}$ aryl, substituted $C_{3-10}$ cycloalkyl, substituted 5- to 10-membered heteroaryl, substituted 5- to 10-membered heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, $C_{1-12}$ alkyl, $C_{1-12}$ haloalkyl, $C_{2-12}$ alkenyl, $C_{2-12}$ alkynyl, $C_{6-10}$ aryl, $C_{3-10}$ cycloalkyl, 5- to 10-membered heteroaryl, 5- to 10-membered heterocycloalkyl, $C_{1-12}$ alkyloxy, $C_{1-12}$ haloalkyloxy, $C_{2-12}$ alkenyloxy, $C_{2-12}$ alkynyloxy, $C_{6-10}$ aryl-Lx-oxy, $C_{3-10}$ cycloalkyl-Lx-oxy, 5- to 10-membered heteroaryl-Lx-oxy, 5- to 10-membered heterocycloalkyl-Lx-oxy, $C_{1-12}$ alkyloxyalkyl, $C_{2-12}$ alkenyloxyalkyl, $C_{2-12}$ alkynyloxyalkyl, $C_{6-10}$ aryloxyalkyl, $C_{3-10}$ cycloalkyloxyalkyl, 5- to 10-membered heteroaryloxyalkyl, 5- to 10-membered heterocycloalkyloxyalkyl, $C_{1-12}$ alkyloxyalkyloxy, $C_{2-12}$ alkenyloxyalkyloxy, $C_{2-12}$ alkynyloxyalkyloxy, $C_{6-10}$ aryloxyalkyloxy, $C_{3-10}$ cycloalkyloxyalkyloxy, 5- to 10-membered heteroaryloxyalkyloxy, 5- to 10-membered heterocycloalkyloxyalkyloxy, $C_{1-12}$ alkylcarbonyl, $C_{2-12}$ alkenylcarbonyl, $C_{2-12}$ alkynylcarbonyl, $C_{6-10}$ aryl-Lx-carbonyl, $C_{3-10}$ cycloalkyl-Lx-carbonyl, 5- to 10-membered heteroaryl-Lx-carbonyl, 5- to 10-membered heterocycloalkyl-Lx-carbonyl, $C_{1-12}$ alkylcarbonyloxy, $C_{2-12}$ alkenylcarbonyloxy, $C_{2-12}$ alkynylcarbonyloxy, $C_{6-10}$ aryl-Lx-carbonyloxy, $C_{3-10}$ cycloalkyl-Lx-carbonyloxy, 5- to 10-membered heteroaryl-Lx-carbonyloxy, 5- to 10-membered heterocycloalkyl-Lx-carbonyloxy, $C_{1-12}$ alkylcarbonylamino, $C_{2-12}$ alkenylcarbonylamino, $C_{2-12}$ alkynylcarbonylamino, $C_{6-10}$ aryl-Lx-carbonylamino, $C_{3-10}$ cycloalkyl-Lx-carbonylamino, 5- to 10-membered heteroaryl-Lx-carbonylamino, 5- to 10-membered heterocycloalkyl-Lx-carbonylamino, $C_{1-12}$ alkylcarbonylthio, $C_{2-12}$ alkenylcarbonylthio, $C_{2-12}$ alkynylcarbonylthio, $C_{6-10}$ aryl-Lx-carbonylthio, $C_{3-10}$ cycloalkyl-Lx-carbonylthio, 5- to 10-membered heteroaryl-Lx-carbonylthio, 5- to 10-membered heterocycloalkyl-Lx-carbonylthio, $C_{1-12}$ alkylcarbonylimino, $C_{2-12}$ alkenylcarbonylimino, $C_{2-12}$ alkynylcarbonylimino, $C_{6-10}$ aryl-Lx-carbonylimino, $C_{3-10}$ cycloalkyl-Lx-carbonylimino, 5- to 10-membered heteroaryl-Lx-carbonylimino, 5- to 10-membered heterocycloalkyl-Lx-carbonylimino, $C_{1-12}$ alkylthio, $C_{2-12}$ alkenylthio, $C_{2-12}$ alkynylthio, $C_{6-10}$ aryl-Lx-thio, $C_{3-10}$ cycloalkyl-Lx-thio, 5- to 10-membered heteroaryl-Lx-thio, 5- to 10-membered heterocycloalkyl-Lx-thio, $C_{1-12}$ alkylamino, $C_{2-12}$ alkenylamino, $C_{2-12}$ alkynylamino, $C_{2-12}$ alkynylamino, $C_{6-10}$ aryl-Lx-amino, $C_{3-10}$ cycloalkyl-Lx-amino, 5- to 10-membered heteroaryl-Lx-amino, 5- to 10-membered heterocycloalkyl-Lx-amino, $C_{1-12}$ alkylsulfonyl, $C_{2-12}$ alkenylsulfonyl, $C_{2-12}$ alkynylsulfonyl, $C_{6-10}$ aryl-Lx-sulfonyl, $C_{3-10}$ cycloalkyl-Lx-sulfonyl, 5- to 10-membered heteroaryl-Lx-sulfonyl, 5- to 10-membered heterocycloalkyl-Lx-sulfonyl, $C_{1-12}$ alkyl sulfonyl amino, $C_{2-12}$ alkenyl sulfonyl amino, $C_{2-12}$ alkynylsulfonylamino, $C_{6-10}$ aryl-Lx-sulfonylamino, $C_{3-10}$ cycloalkyl-Lx-sulfonylamino, 5- to 10-membered heteroaryl-Lx-sulfonylamino, 5- to 10-membered heterocycloalkyl-Lx-sulfonylamino, $C_{1-12}$ alkylimino, $C_{2-12}$ alkenylimino, $C_{2-12}$ alkynylimino, $C_{6-10}$ aryl-Lx-imino, $C_{3-10}$ cycloalkyl-Lx-imino, 5- to 10-membered heteroaryl-Lx-imino, 5- to 10-membered heterocycloalkyl-Lx-imino, $C_{1-12}$ alkyloxyimino, $C_{2-12}$ alkenyloxyimino, $C_{2-12}$ alkynyloxyimino, $C_{6-10}$ aryl-Lx-oxyimino, $C_{3-10}$ cycloalkyl-Lx-oxyimino, 5- to 10-membered heteroaryl-Lx-oxyimino, 5- to 10-membered heterocycloalkyl-Lx-oxyimino, $C_{1-12}$ alkyloxycarbonyl, $C_{2-12}$ alkenyloxycarbonyl, $C_{2-12}$ alkynyloxycarbonyl, $C_{6-10}$ aryl-Lx-oxycarbonyl, $C_{3-10}$ cycloalkyl-Lx-oxycarbonyl, 5- to 10-membered heteroaryl-Lx-oxycarbonyl, 5- to 10-membered heterocycloalkyl-Lx-oxycarbonyl, $C_{1-12}$ alkyloxycarbonylamino, $C_{2-12}$ alkenyloxycarbonylamino, $C_{2-12}$ alkynyloxycarbonylamino, $C_{6-10}$ aryl-Lx-oxycarbonylamino, $C_{3-10}$ cycloalkyl-Lx-oxycarbonylamino, 5- to 10-membered heteroaryl-Lx-oxycarbonylamino, 5- to 10-membered heterocycloalkyl-Lx-oxycarbonylamino, $C_{1-12}$ alkyl sulfanyl, $C_{2-12}$ alkenyl sulfanyl, $C_{2-12}$ alkynyl sulfanyl, $C_{6-10}$ aryl-Lx-sulfanyl, $C_{3-10}$ cycloalkyl-Lx-sulfanyl, 5- to 10-membered heteroaryl-Lx-sulfanyl, 5- to 10-membered heterocycloalkyl-Lx-sulfanyl, $C_{1-12}$ alkylsulfinyl, $C_{2-12}$ alkenylsulfinyl, $C_{2-12}$ alkynylsulfinyl, $C_{6-10}$ aryl-Lx-sulfinyl, $C_{3-10}$ cycloalkyl-Lx-sulfinyl, 5- to 10-membered heteroaryl-Lx-sulfinyl, 5- to 10-membered heterocycloalkyl-Lx-sulfinyl, $C_{1-12}$ alkylcarbamoyl, $C_{2-12}$ alkenylcarbamoyl, $C_{2-12}$ alkynylcarbamoyl, $C_{6-10}$ aryl-Lx-carbamoyl, $C_{3-10}$ cycloalkyl-Lx-carbamoyl, 5- to 10-membered heteroaryl-Lx-carbamoyl, 5- to 10-membered heterocycloalkyl-Lx-carbamoyl, $C_{1-12}$ alkylsulfamoyl, $C_{2-12}$ alkenylsulfamoyl, $C_{2-12}$ alkynylsulfamoyl, $C_{6-10}$ aryl-Lx-sulfamoyl, $C_{3-10}$ cycloalkyl-Lx-sulfamoyl, 5- to 10-membered heteroaryl-Lx-sulfamoyl, and 5- to 10-membered heterocycloalkyl-Lx-sulfamoyl. [0021]

Substituent group III consists of halogen, hydroxy, carboxy, amino, carbamoyl, nitro, amidinoamino, alkyl, aryl, cycloalkyl, heteroaryl, alkyloxy, alkylcarbonyl, cycloalkylcarbonyl, alkylcarbonylamino, cycloalkylcarbonylamino, alkylamino, cycloalkylalkylamino, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

Substituent group III is preferably substituent group III', which consists of halogen, hydroxy, carboxy, amino, carbamoyl, nitro, amidinoamino, $C_{1-12}$ alkyl, $C_{6-10}$ aryl, $C_{3-10}$ cycloalkyl, 5- to 10-membered heteroaryl, $C_{1-12}$ alkyloxy, $C_{1-12}$ alkylcarbonyl, $C_{3-10}$ cycloalkylcarbonyl, $C_{1-12}$ alkylcarbonylamino, $C_{3-10}$ cycloalkylcarbonylamino, $C_{1-12}$ alkylamino, $C_{3-10}$ cycloalkyl $C_{1-6}$ alkylamino, $C_{1-12}$ alkyloxycarbonyl, and tri-$C_{1-6}$ alkylsilyloxy, wherein these groups of the substituent group are optionally substituted with one to the maximum substitutable number of the same or different substituents selected from the group consisting of halogen, hydroxy, carboxy, amino, carbamoyl, nitro, $C_{1-12}$ alkyl, $C_{1-12}$ haloalkyl, $C_{1-12}$ alkyloxy, $C_{1-12}$ haloalkyloxy, and $C_{1-12}$ alkyloxycarbonyl.

Substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

Substituent group IV is preferably substituent group IV', which consists of halogen, hydroxy, carboxy, amino, carbamoyl, nitro, amidino, $C_{1-6}$ alkyl, $C_{6-10}$ aryl, $C_{3-10}$ cycloalkyl, 5- to 10-membered heteroaryl, 5- to 10-membered heterocycloalkyl, $C_{6-10}$ aryl $C_{1-6}$ alkyl, $C_{3-10}$ cycloalkyl $C_{1-6}$ alkyl, $C_{1-6}$ alkyloxy, $C_{6-10}$ aryloxy, $C_{1-6}$ alkylcarbonyl, $C_{3-10}$ cycloalkylcarbonyl, $C_{1-6}$ alkyloxycarbonyl, and tri-$C_{1-6}$ alkylsilyloxy, and these groups of the substituent group are each independently and optionally substituted with one to the maximum substitutable number of the same or different substituents selected from the group consisting of halogen, hydroxy, carboxy, amino, carbamoyl, nitro, $C_{1-6}$ alkyl, $C_{1-6}$ haloalkyl, $C_{1-6}$ alkyloxy, $C_{1-6}$ haloalkyloxy, and $C_{1-6}$ alkyloxycarbonyl.

Substituent group V consists of halogen, hydroxy, carboxy, amino, formyl, carbamoyl, cyano, nitro, amidino, amidinoamino, alkyl, aryl, cycloalkyl, heteroaryl, heterocycloalkyl, alkyloxy, aryloxy, cycloalkyloxy, heteroaryloxy, heterocycloalkyloxy, alkyloxyoxy, alkylamino, arylamino, cycloalkylamino, heteroarylamino, heterocycloalkylamino, formyl, alkylcarbonyl, arylcarbonyl, cycloalkylcarbonyl, heteroarylcarbonyl, heterocycloalkylcarbonyl, alkyloxycarbonyl, aryloxycarbonyl, cycloalkyloxycarbonyl, heteroaryloxycarbonyl, heterocycloalkyloxycarbonyl, alkylcarbamoyl, arylcarbamoyl, cycloalkylcarbamoyl, heteroarylcarbamoyl, and heterocycloalkylcarbamoyl, wherein these groups of the substituent group are each independently and optionally substituted with one to the maximum substitutable number of the same or different substituents selected from the group consisting of halogen, hydroxy, carboxy, amino, formyl, carbamoyl, cyano, nitro, amidino, amidinoamino, alkyl, alkyloxy, haloalkyl, haloalkyloxy, alkylamino, formyl, alkylcarbonyl, alkyloxycarbonyl, and alkylcarbamoyl.

Substituent group V is preferably substituent group V', which consists of halogen, hydroxy, carboxy, amino, formyl, carbamoyl, cyano, nitro, amidino, amidinoamino, $C_{1-12}$ alkyl, $C_{6-10}$ aryl, $C_{3-10}$ cycloalkyl, 5- to 10-membered heteroaryl, 5- to 10-membered heterocycloalkyl, $C_{1-12}$ alkyloxy, $C_{6-10}$ aryloxy, $C_{3-10}$ cycloalkyloxy, 5- to 10-membered heteroaryloxy, 5- to 10-membered heterocycloalkyloxy, $C_{1-12}$ alkylamino, $C_{6-10}$ arylamino, $C_{3-10}$ cycloalkylamino, 5- to 10-membered heteroarylamino, 5- to 10-membered heterocycloalkylamino, formyl, $C_{1-12}$ alkylcarbonyl, $C_{6-10}$ arylcarbonyl, $C_{3-10}$ cycloalkylcarbonyl, 5- to 10-membered heteroarylcarbonyl, 5- to 10-membered heterocycloalkylcarbonyl, $C_{1-12}$ alkyloxycarbonyl, $C_{6-10}$ aryloxycarbonyl, $C_{3-10}$ cycloalkyloxycarbonyl, 5- to 10-membered heteroaryloxycarbonyl, 5- to 10-membered heterocycloalkyloxycarbonyl, $C_{1-12}$ alkylcarbamoyl, $C_{6-10}$ arylcarbamoyl, $C_{3-10}$ cycloalkylcarbamoyl, 5- to 10-membered heteroarylcarbamoyl, and 5- to 10-membered heterocycloalkylcarbamoyl, wherein these groups of the substituent group are each independently and optionally substituted with one to the maximum substitutable number of the same or different substituents selected from the group consisting of halogen, hydroxy, carboxy, amino, formyl, carbamoyl, cyano, nitro, amidino, amidinoamino, $C_{1-6}$ alkyl, $C_{1-6}$ alkyloxy, $C_{1-6}$ haloalkyl, $C_{1-6}$ haloalkyloxy, $C_{1-6}$ alkylamino, formyl, $C_{1-6}$ alkylcarbonyl, $C_{1-6}$ alkyloxycarbonyl, and $C_{1-6}$ alkylcarbamoyl.

Substituent group VI consists of halogen, hydroxy, carboxy, amino, formyl, carbamoyl, cyano, nitro, amidino, amidinoamino, alkyl, alkyloxy, haloalkyl, haloalkyloxy, alkylamino, formyl, alkylcarbonyl, alkyloxycarbonyl, and alkylcarbamoyl.

Substituent group VI is preferably substituent group VI', which consists of halogen, hydroxy, carboxy, amino, formyl, carbamoyl, cyano, nitro, amidino, amidinoamino, $C_{1-6}$ alkyl, $C_{1-6}$ alkyloxy, $C_{1-6}$ haloalkyl, $C_{1-6}$ haloalkyloxy, $C_{1-6}$ alkylamino, formyl, $C_{1-6}$ alkylcarbonyl, $C_{1-6}$ alkyloxycarbonyl, and $C_{1-6}$ alkylcarbamoyl.

As used herein, examples of substituents used when "optionally substituted" include substituent group α and substituent group β. Substituent group α can be substituent group α1, substituent group α2, or substituent group α3. Substituent group β can be substituent group β1, substituent group β2, or substituent group β3. Substituents used when "optionally substituted" can be selected from substituent group α1, and substitution can be performed with 1 to 5 of the same or different substituents. While the types of atoms within a substituent associated with attachment are not particularly limited by the type of substituent, if the atom to which a substituent attaches is an oxygen atom, a nitrogen atom, or a sulfur atom, the substituent is limited to those with an attaching atom that is a carbon atom from the following substituents.

Substituent group α1 includes
1) halogen atom
2) hydroxyl group 3) carboxyl group
4) cyano group
5) $C_{1-6}$ alkyl
6) $C_{2-6}$ alkenyl
7) $C_{2-6}$ alkynyl
8) $C_{1-6}$ alkoxy
9) $C_{1-6}$ alkylthio
10) $C_{1-6}$ alkylcarbonyl
11) $C_{1-6}$ alkylsulfonyl
(however, each substituent from 5) to 11) is optionally substituted with 1 to 5 of the same or different substituents selected from substituent group β1)
12) $C_{3-10}$ alicyclic group
13) $C_{3-10}$ alicyclic oxy
14) $C_{6-10}$ aryloxy
15) 5- to 6-membered heteroaryloxy
16) 4- to 10-membered non-aryl heterocyclyloxy
17) $C_{3-10}$ alicyclic thio
18) $C_{6-10}$ arylthio
19) 5- to 6-membered heteroarylthio
20) 4- to 10-membered non-aryl heterocyclylthio
21) $C_{6-10}$ aryl
22) 5- to 6-membered heteroaryl
23) 4- to 10-membered non-aryl heterocycle
24) $C_{3-10}$ alicyclic carbonyl
25) $C_{6-10}$ arylcarbonyl
26) 5- to 6-membered heteroarylcarbonyl
27) 4- to 10-membered non-aryl heterocyclylcarbonyl
28) $C_{3-10}$ alicyclic sulfonyl
29) $C_{6-10}$ aryl sulfonyl
30) 5- to 6-membered heteroarylsulfonyl
31) 4- to 10-membered non-aryl heterocyclylsulfonyl
(however, each substituent from 12) to 31) is optionally substituted with 1 to 5 substituents in substituent group (31 or 5) $C_{1-6}$ alkyl)
32) —NR$^{10a}$R$^{11a}$
33) —SO$_2$—NR$^{10b}$R$^{11b}$
34) —NR$^{10c}$—C(=O)R$^{11c}$
35) —NR$^{10d}$—C(=O)OR$^{11d}$
36) —NR$^{12a}$—C(=O)NR$^{10e}$R$^{11e}$
37) —NR$^{10i}$—SO$_2$—R$^{11i}$
38) —NR$^{12c}$—SO$_2$—NR$^{10j}$R$^{11j}$
39) —C(=O)OR$^{10k}$
40) —C(=O)NR$^{10l}$R$^{11k}$
41) —C(=O)NR$^{10m}$OR$^{11l}$
42) —C(=O)NR$^{12d}$—NR$^{10n}$R$^{11m}$
43) —C(=NR$^{13a}$)R$^{10s}$
44) —C(=NR$^{13c}$)NR$^{10t}$R$^{11q}$
45) —C(=NR$^{13d}$)NR$^{12f}$—NR$^{10u}$R$^{11r}$
46) —NR$^{17c}$—C(=NR$^{13k}$)R$^{17d}$
47) —NR$^{12g}$—C(=NR$^{13e}$)—NR$^{10v}$R$^{11s}$
48) —NR$^{14}$—C(=NR$^{13f}$)—NR$^{12h}$—NR$^{10w}$R$^{11t}$
49) —OC(=O)R$^{10x}$
50) —OC(=O)OR$^{10y}$
51) —OC(=O)NR$^{10z1}$R$^{11a}$
52) —NR$^{12i}$—NR$^{10z2}$R$^{1v}$
53) —NR$^{10z3}$OR$^{11w}$, and
54) protecting group, and
substituent group β1 is a group consisting of
1) halogen atom,
2) hydroxyl group,
3) carboxyl group,
4) cyano group,
5) $C_{3-10}$ alicyclic group,
6) $C_{1-6}$ alkoxy,
7) $C_{3-10}$ alicyclic oxy,
8) $C_{1-6}$ alkylthio,
9) 5- to 6-membered heteroarylthio,
10) $C_{6-10}$ aryl,
11) 5- to 6-membered heteroaryl,
12) 4- to 10-membered non-aryl heterocycle,
13) $C_{1-6}$ alkylcarbonyl,
14) $C_{3-10}$ alicyclic carbonyl,
15) $C_{6-10}$ arylcarbonyl,
16) 5- to 6-membered heteroarylcarbonyl,
17) 4- to 10-membered non-aryl heterocyclylcarbonyl,
18) —NR$^{15a}$R$^{16a}$,
19) —SO$_2$—NR$^{15b}$R$^{16b}$,
20) —NR$^{15c}$—C(=O)R$^{16c}$
21) —NR$^{17a}$—C(=O)NR$^{15d}$R$^{16d}$,
22) —C(=O)NR$^{15e}$R$^{16e}$,
23) —C(=NR$^{13g}$)R$^{15f}$,
24) —C(=NR$^{13h}$)NR$^{15g}$R$^{16f}$
25) —NR$^{16g}$—C(=NR$^{13i}$)R$^{15h}$
26) —NR$^{17h}$—C(=NR$^{13j}$)—NR$^{15i}$R$^{16h}$, and
27) protecting group
(however, each substituent from 5) to 17) in substituent group β1 is optionally substituted with 1 to 5 substituents selected from the group consisting of a halogen atom, hydroxyl group, cyano group, carboxyl group, and —NR$^{18a}$R$^{18b}$), wherein R$^{13a}$, R$^{13a2}$, R$^{13c}$, R$^{13c2}$, R$^{13d}$, R$^{13d2}$, R$^{13e}$, R$^{13f}$, R$^{13g}$, R$^{13g2}$, R$^{13h}$, R$^{13h2}$, R$^{13i}$, R$^{13j}$, and R$^{13k}$ are each independently the same or different hydrogen atom, hydroxyl group, $C_{1-6}$ alkyl, $C_{1-6}$ alkoxy, or $C_{1-6}$ alkoxycarbonyl, R$^{10a}$, R$^{10b}$, R$^{10c}$, R$^{10d}$, R$^{10e}$, R$^{10i}$, R$^{10j}$, R$^{10k}$, R$^{10l}$, R$^{10m}$, R$^{10n}$, R$^{10s}$, R$^{10s2}$, R$^{10t}$, R$^{10t2}$, R$^{10u}$, R$^{10u2}$, R$^{10v}$, R$^{10w}$, R$^{10x}$, R$^{10y}$, R$^{10z1}$, R$^{10z2}$, R$^{10z3}$, R$^{11a}$, R$^{11b}$, R$^{11c}$, R$^{11d}$, R$^{11e}$, R$^{11i}$, R$^{11j}$, R$^{11k}$, R$^{11l}$, R$^{11m}$, R$^{11q}$, R$^{11q2}$, R$^{11r}$, R$^{11r2}$, R$^{11s}$, R$^{11t}$, R$^{11u}$, R$^{11v}$, R$^{11w}$, R$^{12a}$, R$^{12c}$, R$^{12d}$, R$^{12f}$, R$^{12f2}$, R$^{12g}$, R$^{12h}$, R$^{12i}$, R$^{14}$, R$^{15a}$, R$^{15b}$, R$^{15c}$, R$^{15d}$, R$^{15e}$, R$^{15f}$, R$^{15f2}$, R$^{15g}$, R$^{15g2}$, R$^{15h}$, R$^{15i}$, R$^{16a}$, R$^{16b}$, R$^{16c}$, R$^{16d}$, R$^{16e}$, R$^{16f}$, R$^{16f2}$, R$^{16g}$, R$^{16h}$, R$^{17a}$, R$^{17b}$, R$^{17c}$, and R$^{17d}$ are each independently the same or different hydrogen atom, $C_{1-6}$ alkyl (the $C_{1-6}$ alkyl is optionally substituted with 1 to 3 of the same or different substituents selected from a hydroxyl group, cyano group, $C_{1-6}$ alkoxy, and —NR$^{18a}$R$^{18b}$), or $C_{1-6}$ alkoxycarbonyl, and R$^{18a}$ and R$^{18b}$ are each independently the same or different hydrogen atom or $C_{1-6}$ alkyl.

In an exemplary embodiment, hydrogen of any hydroxyl group in substituent groups α1 and β1 is optionally substituted with a protecting group.

Examples of preferred substituents as the substituent used when "optionally substituted" herein include the following.

Substituent group a2 preferably includes
1) halogen atom
2) hydroxyl group
3) carboxyl group
4) cyano group
5) $C_{1-6}$ alkyl
6) $C_{1-6}$ alkoxy
7) $C_{1-6}$ alkylthio
8) $C_{1-6}$ alkylcarbonyl
(however, each substituent from 5) to 8) is optionally substituted with 1 to 5 same or different substituents selected from substituent group β2)
9) $C_{3-10}$ alicyclic group
10) $C_{3-10}$ alicyclic oxy
11) $C_{6-10}$ aryloxy
12) 5- to 6-membered heteroaryloxy 13) 4- to 10-membered non-aryl heterocyclyloxy
14) $C_{3-10}$ alicyclic thio
15) $C_{6-10}$ arylthio
16) 5- to 6-membered heteroarylthio
17) 4- to 10-membered non-aryl heterocyclylthio
18) $C_{6-10}$ aryl
19) 5- to 6-membered heteroaryl
20) 4- to 10-membered non-aryl heterocycle
21) $C_{3-10}$ alicyclic carbonyl
22) $C_{6-10}$ arylcarbonyl
23) 5- to 6-membered heteroarylcarbonyl
24) 4- to 10-membered non-aryl heterocyclylcarbonyl
(however, each substituent from 9) to 24) is optionally substituted with 1 to 5 substituents in substituent group β2 or 1) $C_{1-6}$ alkyl)
25) —$NR^{10a}R^{11a}$
26) —$SO_2$—$NR^{10b}R^{11b}$
27) —$NR^{10c}$—C(=O)$R^{11c}$
28) —$NR^{12a}$—C(=O)$NR^{10d}R^{11d}$
29) —$NR^{10e}$—$SO_2$—$R^{11e}$
30) —$NR^{12b}$—$SO_2$—$NR^{10f}R^{11f}$
31) —C(=O)$NR^{10g}R^{11g}$
32) —C(=$NR^{13a}$)$R^{10h}$
33) —C(=$NR^{13b}$)$NR^{10i}R^{11h}$
34) —$NR^{11f2}$—C(=$NR^{13c}$)$R^{10g2}$, and
35) —$NR^{12c}$—C(=$NR^{13d}$)—$NR^{10j}R^{11i}$, and
substituent group β2 is preferably a group consisting of
1) halogen atom
2) hydroxyl group
3) cyano group
4) $C_{3-10}$ alicyclic group
5) $C_{1-6}$ alkoxy
6) $C_{1-6}$ alkylthio
7) 5- to 6-membered heteroarylthio
8) 5- to 6-membered heteroaryl
9) 4- to 10-membered non-aryl heterocycle
10) $C_{1-6}$ alkylcarbonyl
11) $C_{3-10}$ alicyclic carbonyl
12) $C_{6-10}$ arylcarbonyl
13) 5- to 6-membered heteroarylcarbonyl
14) 4- to 10-membered non-aryl heterocyclylcarbonyl
15) —$NR^{15a}R^{16a}$
16) —$NR^{15b}$—C(=O)$R^{16b}$
17) —$NR^{17a}$—C(=O)$NR^{15c}R^{16c}$
18) —C(=O)$NR^{15d}R^{16d}$
19) —C(=$NR^{13e}$)$R^{15e}$
20) —C(=$NR^{13f}$)$NR^{15f}R^{16e}$
21) —$NR^{16f}$—C(=$NR^{13g}$)$R^{15g}$
22) —$NR^{17b}$—C(=$NR^{13h}$)—$NR^{15h}R^{16g}$
23) —C(=N—$OR^{13e2}$)$R^{15e2}$, and
24) —C(=N—$OR^{13f2}$)$NR^{15f2}R^{16e2}$
(however, each substituent from 4) to 14) in substituent group β2 is optionally substituted with 1 to 5 substituents selected from the group consisting of a halogen atom, hydroxyl group, cyano group, carboxyl group, and —$NR^{18a}R^{18b}$,
$R^{13a}$, $R^{13a2}$, $R^{13b}$, $R^{13b2}$, $R^{13c}$, $R^{13d}$, $R^{13e}$, $R^{13e2}$, $R^{13f}$, $R^{13f2}$, $R^{13g}$, and $R^{13h}$ are each independently the same or different hydrogen atom, hydroxyl group, $C_{1-6}$ alkyl, $C_{1-6}$ alkoxy, or $C_{1-6}$ alkoxycarbonyl,
$R^{10a}$, $R^{10b}$, $R^{10c}$, $R^{10d}$, $R^{10e}$, $R^{10f}$, $R^{10g}$, $R^{10g2}$, $R^{10h}$, $R^{10i}$, $R^{10i2}$, $R^{10j}$, $R^{11a}$, $R^{11b}$, $R^{11c}$, $R^{11d}$, $R^{11e}$, $R^{11f}$, $R^{11f2}$, $R^{11g}$, $R^{11h}$, $R^{11h2}$, $R^{11i}$, $R^{12a}$, $R^{12b}$, $R^{12c}$, $R^{15a}$, $R^{15b}$, $R^{15c}$, $R^{15d}$, $R^{15e}$, $R^{15e2}$, $R^{15f}$, $R^{15f2}$, $R^{15g}$, $R^{15h}$, $R^{16a}$, $R^{16b}$, $R^{16c}$, $R^{16d}$, $R^{16e}$, $R^{16e2}$, $R^{16f}$, $R^{16g}$, $R^{17a}$, and $R^{17b}$ are each independently the same or different hydrogen atom, $C_{1-6}$ alkyl (the $C_{1-6}$ alkyl is optionally substituted with 1 to 3 same or different substituents selected from a hydroxyl group, cyano group, $C_{1-6}$ alkoxy, and —$NR^{18a}R^{18b}$), or $C_{1-6}$ alkoxycarbonyl, and
$R^{18a}$ and $R^{18b}$ are each independently the same or different hydrogen atom or $C_{1-6}$ alkyl.

In an exemplary embodiment, hydrogen of any hydroxy group in substituent groups α2 and β2 is optionally substituted with a protecting group.

Examples of more preferred substituents used when "optionally substituted" herein include the following substituents.

Substituent group α3 more preferably includes
1) halogen atom
2) hydroxyl group
3) cyano group
4) $C_{1-6}$ alkyl
5) $C_{1-6}$ alkoxy
6) $C_{1-6}$ alkylthio
7) $C_{1-6}$ alkylcarbonyl
(however, each substituent from 4) to 7) is optionally substituted with 1 to 5 same or different substituents selected from substituent group (33)
8) $C_{3-10}$ alicyclic group
9) 5- to 6-membered heteroaryloxy
10) 4- to 10-membered non-aryl heterocyclyloxy
11) 5- to 6-membered heteroarylthio
12) 4- to 10-membered non-aryl heterocyclylthio
13) $C_{6-10}$ aryl
14) 5- to 6-membered heteroaryl
15) 4- to 10-membered non-aryl heterocycle
(however, each substituent from 8) to 15) is optionally substituted with 1 to 5 substituents in substituent group β3 or 1) $C_{1-6}$ alkyl)
16) —$NR^{10a}R^{11a}$
17) —$NR^{11b}$—C(=O)$R^{10b}$
18) —$NR^{12a}$—C(=O)$NR^{10c}R^{11c}$
19) —C(=O)$NR^{10d}R^{11d}$
20) —C(=$NR^{13a}$)$R^{10e}$
21) —C(=$NR^{13b}$)$NR^{10f}R^{11e}$
22) —$NR^{11f}$—C(=$NR^{13c}$)$R^{10g}$, and
23) —$NR^{12b}$—C(=$NR^{13d}$)—$NR^{10h}R^{11g}$, and
substituent group β3 is more preferably
1) halogen atom,
2) hydroxyl group,
3) cyano group,
4) —$NR^{15a}R^{16a}$,
5) —$NR^{15b}$—C(=O)$R^{16b}$,
6) —$NR^{17a}$—C(=O)$NR^{15c}R^{16c}$,
7) —C(=O)$NR^{15d}R^{16d}$,
8) —C(=$NR^{13e}$)$R^{15e}$,
9) —C(=$NR^{13f}$)$NR^{15f}R^{16e}$,
10) —$NR^{16f}$—C(=$NR^{13g}$)$R^{15g}$, and
11) —$NR^{17b}$—C(=$NR^{13h}$)—$NR^{15h}R^{16g}$, wherein
$R^{13a}$, $R^{13a2}$, $R^{13b}$, $R^{13b2}$, $R^{13c}$, $R^{13d}$, $R^{13e}$, $R^{13e2}$, $R^{13f}$, $R^{13f2}$, $R^{13g}$, and $R^{13h}$ are each independently the same or different hydrogen atom, hydroxyl group, $C_{1-6}$ alkyl, $C_{1-6}$ alkoxy, or $C_{1-6}$ alkoxycarbonyl,
$R^{10a}$, $R^{10b}$, $R^{10c}$, $R^{10d}$, $R^{10e}$, $R^{10f}$, $R^{10e2}$, $R^{10f2}$, $R^{10g}$, $R^{10h}$, $R^{11a}$, $R^{11b}$, $R^{11c}$, $R^{11d}$, $R^{11e}$, $R^{11e2}$, $R^{11f}$, $R^{11g}$, $R^{12a}$, $R^{12b}$, $R^{15a}$, $R^{15b}$, $R^{15c}$, $R^{15d}$, $R^{15e}$, $R^{15e2}$, $R^{15f}$, $R^{15f2}$, $R^{15g}$, $R^{15h}$, $R^{16a}$, $R^{16b}$, $R^{16c}$, $R^{16d}$, $R^{16e}$, $R^{16e2}$, $R^{16f}$, $R^{16g}$, $R^{17a}$, and $R^{17b}$ are each independently the same or different hydrogen atom, $C_{1-6}$ alkyl (the $C_{1-6}$ alkyl is optionally substituted with 1 to 3 same or different substituents selected from hydroxyl group, cyano group, $C_{1-6}$ alkoxy, and —$NR^{18a}R^{18b}$), or $C_{1-6}$ alkoxycarbonyl, and R$^{18a}$, and R$^{18b}$ are each independently the same or different hydrogen atom or C$_{1-6}$ alkyl.

In an exemplary embodiment, hydrogen of any hydroxyl group in substituent groups α3 and β3 is optionally substituted with a protecting group.

In an exemplary embodiment, a hydroxyl group in the aforementioned substituent group (e.g., α (α1 or the like) β (β1 or the like), or I to VI) is also optionally substituted with a protecting group. In an exemplary embodiment, an amino group in substituent groups I to VI is also optionally protected with a nitrogen protecting group.

As used herein, "C$_{1-6}$" means that the number of carbon atoms is 1 to 6. The same applies to other numbers. For example, "C$_{1-4}$" means that the number of carbon atoms is 1 to 4, and "C$_{1-3}$" means that the number of carbon atoms is 1 to 3. A description with a limitation in the number of carbons herein is only a preferred numerical range. It is intended so that groups with a substituent with a number of carbons other than the number of carbons specified in the present disclosure are also within the scope of the present disclosure.

As used herein, "hydrocarbon group" is also referred to as a hydrocarbyl group, referring to a group generated by removing at least one hydrogen from "hydrocarbon" comprising at least one carbon and at least one hydrogen.

As used herein, "functional group" refers to any group conferring some type of functionality, encompassing a carboxyl group, nitrile group, carbonyl group, hydroxyl group, amino group, imino group, nitro group, halogen group, as well as alkyl group, and more broadly acid anhydrides and groups formed by a bond such as an ester bond, amide bond, or ether bond.

As used herein, "heteroatom" refers to atoms other than carbon atoms and hydrogen atoms such as oxygen atoms, nitrogen atoms, and sulfur atoms. A group comprising a heteroatom is also known as a hetero . . . group (e.g., heteroaryl group (means that an aryl group comprises at least a heteroatom) or heterocyclic group (means that a cyclic group (carbon ring group) comprises at least one heteroatom)) or the like.

As used herein, "halogen atom" is an atom belonging to the halogen group, referring to a fluorine atom, chlorine atom, bromine atom, iodine atom, or the like, and is preferably a fluorine atom or chlorine atom, and still more preferably a fluorine atom. A "halogen atom" is also referred to as "halogen" or "halo".

As used herein, "hydroxyl group" is a monovalent group of —OH. This group is also referred to as a "hydroxy group" or "hydroxy".

As used herein, "carboxyl group" is a monovalent group of —COOH. This group is also referred to as a "carboxy group", "carboxy", or "carboxyl".

As used herein, "cyano group" is a monovalent group of —CN.

As used herein, "amino" is a monovalent group of —NH$_2$. This group is also referred to as an "amino group".

As used herein, "alkyl" refers to a linear or branched saturated aliphatic hydrocarbon group. "C$_{1-12}$ alkyl" is an alkyl group with 1 to 12 carbon atoms. Examples thereof include, but are not limited to, C$_{1-6}$ alkyl, heptyl, isoheptyl, octyl, isooctyl, nonyl, isononyl, decyl, isodecyl, undecyl, isoundecyl, dodecyl, isododecy, and the like. "C$_{1-6}$ alkyl" is an alkyl group with 1 to 6 carbon atoms, which is preferably "C$_{1-4}$ alkyl", more preferably "C$_{1-3}$ alkyl", and still more preferably "C$_{1-2}$ alkyl". Specific examples of "C$_{1-4}$ alkyl" include methyl, ethyl, propyl, isopropyl, n-butyl, isobutyl, tert-butyl, sec-butyl, and the like. Specific examples of "C$_{1-6}$ alkyl" include, but are not limited to, C$_{1-4}$ alkyl, n-pentyl, isopentyl, neopentyl, tert-pentyl, 1,2-dimethylpropyl, n-hexyl, and the like.

As used herein, "alkenyl" refers to a linear or branched unsaturated aliphatic hydrocarbon group comprising at least one carbon-carbon double bond. "C$_{2-12}$ alkenyl" is an alkenyl group with 2 to 12 carbon atoms. Examples thereof include, but are not limited to, heptenyl, isoheptenyl, octenyl, isooctenyl, nonenyl, isononenyl, decenyl, isodecenyl, undecenyl, isoundecenyl, dodecenyl, isododecenyl, and the like. "C$_{2-6}$ alkenyl" is an alkenyl group with 2 to 6 carbon atoms. Preferred examples thereof include "C$_{2-4}$ alkenyl". Specific examples of "C$_{2-6}$ alkenyl" include, but are not limited to, vinyl, 1-propenyl, 2-propenyl, 1-butenyl, 2-butenyl, 3-butenyl, 2-methyl-1-propenyl, 2-methyl-2-propenyl, and the like.

As used herein, "alkynyl" refers to a linear or branched unsaturated aliphatic hydrocarbon group comprising at least one carbon-carbon triple bond. "C$_{2-12}$ alkynyl" is an alkynyl group with 2 to 12 carbon atoms. Examples thereof include, but are not limited to, heptynyl, isoheptynyl, octynyl, isooctynyl, nonynyl, isononynyl, decynyl, isodecynyl, undecynyl, isoundecynyl, dodecynyl, isododecynyl, and the like. "C$_{2-6}$ alkynyl" is an alkynyl group with 2 to 6 carbon atoms. Preferred examples thereof include "C$_{2-4}$ alkynyl". Specific examples of "C$_{2-6}$ alkynyl" include, but are not limited to, ethynyl, 1-propynyl, 2-propynyl, 1-butynyl, 1-methyl-2-propynyl, 3-butynyl, 1-pentynyl, 1-hexynyl, and the like.

As used herein, "aryl" refers to a monovalent group of a monocyclic or bicyclic aromatic hydrocarbon ring. "C$_{6-10}$ aryl" refers to an aryl group with 6 to 10 carbon atoms. Examples of "aryl" include, but are not limited to, C$_6$ aryl, C$_{10}$ aryl, and the like. Specific examples of C$_6$ aryl include, but are not limited to, phenyl and the like. Specific examples of C$_{10}$ aryl include, but are not limited to, 1-naphthyl, 2-naphthyl, and the like.

An aryl group as a substituent or a portion thereof may be fused to an alicyclic group. For example, a phenyl group may be fused to a cyclohexane ring to form a 1,2,3,4-tetrahydronaphthalenyl group. In such a case, one of the possible carbon atoms on a benzene ring attaches to the backbone, or to a group near the backbone, or to its atom. An aryl group encompasses 5,6,7,8-tetrahydronaphthalen-1-yl and 5,6,7,8-tetrahy dronaphthalen-2-yl.

As used herein, "arylalkyl" refers to alkyl substituted with at least one aryl. "C$_{6-10}$ aryl C$_{1-6}$ alkyl" refers to C$_{1-6}$ alkyl substituted with at least one C$_{6-10}$ aryl. Specific examples of C$_{6-10}$ aryl C$_{1-6}$ alkyl include, but are not limited to, benzyl (phenyl-CH$_2$—), phenethyl(phenyl-CH$_2$CH$_2$—), naphthalen-1-ylmethyl, naphthalen-2-ylmethyl, 2-(naphthalen-1-yl)ethyl, 2-(naphthalen-2-yl)ethyl, and the like.

As used herein, "(optionally substituted amino)-arylalkyl" refers to arylalkyl substituted with an optionally substituted amino group, wherein the alkyl group, the aryl group, or both is substituted with an amino group. An amino group of such an arylalkyl group may be unsubstituted, or substituted with 1, 2, or 3 substituents, such as optionally substituted alkyl (e.g., unsubstituted C$_{1-6}$ alkyl, C$_{3-6}$ cycloalkyl-C$_{1-6}$ alkyl, C$_{3-6}$ cycloalkylcarbonyl, or the like). Examples of (optionally substituted amino)-C$_{6-10}$ aryl C$_{1-6}$ alkyl include, but are not limited to, (di(alkyl)amino)benzyl, ((cycloalkylalkyl)amino)benzyl, ((cycloalkylcarbonyl)amino)benzyl, ((carbamoylalkyl)carbonylamino)benzyl, ((carboxyalkyl)carbonyl)aminobenzyl, (di(alkyl)amino)naphthalenylmethyl, ((cycloalkylalkyl)amino)naphthalenylmethyl, ((cycloalkylcarbonyl)amino)naphthalenylmethyl, ((carbamoylalkyl)carbonylamino)naphthalenylmethyl, ((carboxyalkyl)carbonyl)aminonaphthalenylmethyl, and the like.

As used herein, the aryl moiety of "arylthio" is defined the same as the aforementioned aryl. Preferred examples of "$C_{6-10}$ arylthio" include "$C_6$ or $C_{10}$ arylthio". Specific examples of "$C_{6-10}$ aryloxy" include, but are not limited to, phenylthio, 1-naphthylthio, 2-naphthylthio, and the like.

As used herein, "aryl sulfonyl" refers to sulfonyl substituted with the aforementioned "aryl". "$C_{6-10}$ aryl sulfonyl" is preferably "$C_6$ or $C_{10}$ aryl sulfonyl". Specific examples of "$C_{6-10}$ aryl sulfonyl" include, but are not limited to, phenylsulfonyl, 1-naphthylsulfonyl, 2-naphthylsulfonyl, and the like.

As used herein, "heteroaryl" refers to a monovalent group of a monocyclic or bicyclic aromatic heterocycle comprising 1 to 4 same or different heteroatoms selected from the group consisting of an oxygen atom, nitrogen atom, and sulfur atom.

As used herein, "5- to 6-membered heteroaryl" refers to a monovalent group of a monocyclic aromatic heterocycle consisting 5 to 6 atoms, comprising 1 to 4 same or different heteroatoms selected from the group consisting of an oxygen atom, nitrogen atom, and sulfur atom. Specific examples of "5- to 6-membered heteroaryl" include, but are not limited to, pyrrolyl, furyl, thienyl, pyrazolyl, imidazolyl, oxazolyl, isooxazolyl, oxadiazolyl, thiazolyl, isothiazolyl, thiadiazolyl, tetrazolyl, pyridyl, furyl, pyridazinyl, pyrimidinyl, pyrazinyl, and the like.

As used herein, "5- to 10-membered heteroaryl" refers to a monovalent group of a monocyclic or bicyclic aromatic heterocycle consisting of 5 to 10 atoms, comprising 1 to 4 same or different heteroatoms selected from the group consisting of an oxygen atom, nitrogen atom, and sulfur atom. Specific examples of "5- to 10-membered heteroaryl" include, but are not limited to, 5- to 6-membered heteroaryl, quinolyl, isoquinolyl, naphthyridinyl, quinoxalinyl, cinnolinyl, quinazolinyl, phthalazinyl, imidazopyridyl, imidazothiazolyl, imidazooxazolyl, benzothiazolyl, benzooxazolyl, benzoimidazolyl, indolyl, isoindolyl, indazolyl, pyrrolopyridyl, thienopyridyl, furopyridyl, benzothiadiazolyl, benzooxadiazolyl, pyridopyrimidinyl, benzofuryl, benzothienyl, benzo[1,3]dioxole, thienofuryl, chromenyl, chromanyl, coumarinyl, quinolonyl, and the like.

As used herein, "heteroarylalkyl" refers to alkyl substituted with at least one heteroaryl. "5- to 10-membered heteroaryl $C_{1-6}$ alkyl" refers to $C_{1-6}$ alkyl substituted with at least one 5- to 10-membered heteroaryl. Specific examples of 5- to 10-membered heteroaryl $C_{1-6}$ alkyl include, but are not limited to, pyridin-2-ylmethyl, pyridin-4-ylmethyl, 2-(quinolin-8-yl)ethyl, 2-(quinolin-5-yl)ethyl, 2-(quinoxalin-5-yl)ethyl, 2-(1H-indol-3-yl)ethyl, and the like.

As used herein, "alicyclic group" refers to a monovalent group of a monocyclic, bicyclic, or tricyclic non-aromatic hydrocarbon ring, including those that have a partially unsaturated bond, those that have a partially crosslinked structure, those that are partially a spiro, and those having 1, 2, or more carbonyl structures. An "alicyclic group" encompasses cycloalkyl, cycloalkenyl, and cycloalkynyl. "$C_{3-20}$ alicyclic group" is preferably a "$C_{3-10}$ alicyclic group", more preferably a "$C_{3-6}$ alicyclic group". Specific examples of "$C_{3-20}$ alicyclic group" include, but are not limited to, cyclopropyl, cyclobutyl, cyclopentyl, cyclohexyl, cycloheptyl, cyclooctyl, cyclohexadinyl, cycloheptadinyl, cyclooctadinyl, adamantyl, norbornyl, and the like.

An alicyclic group can be a fused ring between a non-aryl ring and an aryl and/or heteroaryl ring. For example, cycloalkyl fused with $C_{6-10}$ aryl or 5- to 6-membered heteroaryl is encompassed by an alicyclic group. Examples of fused alicyclic groups include a monovalent group with one hydrogen atom removed from 1,2,3,4-tetrahydronaphthalene, indane, 1,2,3,4-tetrahydroanthracene, and 5,6,7,8-tetrahydroquinoline. Specific examples thereof include 1,2,3,4-tetrahydronaphthalen-1-yl, 1,2,3,4-tetrahydronaphthalen-2-yl, indan-1-yl, indan-2-yl, 5,6,7,8-tetrahydroquinolin-5-yl, 5,6,7,8-tetrahydroquinolin-6-yl, and the like. A fused alicyclic group attaches from any one of the possible cyclic structure atoms on a non-aryl ring to the backbone.

As used herein, "$C_{3-10}$ alicyclic group" refers to a substituent with "$C_{3-10}$ alicyclic group" that is a monovalent group among the aforementioned "$C_{3-20}$ alicyclic group".

As used herein, "alicyclic oxy" refers to an (alicyclic group)-O— group, and the alicyclic moiety is defined the same as an alicyclic group. "$C_{3-6}$ alicyclic oxy" refers to a ($C_{3-6}$ alicyclic group)-O— group, and the $C_{3-6}$ alicyclic moiety is defined the same as a $C_{3-6}$ alicyclic group. "$C_{3-6}$ alicyclic oxy" is preferably "$C_{3-5}$ alicyclic oxy". Specific examples of "$C_{3-6}$ alicyclic oxy" include, but are not limited to, cyclopropyloxy, cyclobutyloxy, cyclopentyloxy, cyclohexyloxy, and the like.

As used herein, "alicyclic carbonyl" refers to carbonyl substituted with the "alicyclic group" described above. "$C_{3-10}$ alicyclic carbonyl" is preferably "$C_{3-6}$ alicyclic carbonyl". Specific examples of "$C_{3-10}$ alicyclic carbonyl" include, but are not limited to, cyclopropylcarbonyl, cyclobutylcarbonyl, cyclopentylcarbonyl, cyclohexylcarbonyl, and the like.

As used herein, "alicyclic thio" refers to an (alicyclic group)-S— group, and the alicyclic moiety is defined the same as above. "$C_{3-10}$ alicyclic thio" is preferably "$C_{3-6}$ alicyclic thio". Specific examples of "$C_{3-6}$ alicyclic thio" include, but are not limited to, cyclopropylthio, cyclobutylthio, cyclopentylthio, cyclohexylthio, and the like.

As used herein, "alicyclic sulfonyl" refers to a sulfonyl group substituted with the "alicyclic group" described above. "$C_{3-10}$ alicyclic sulfonyl" is preferably "$C_{3-6}$ alicyclic sulfonyl". Specific examples of "$C_{3-10}$ alicyclic sulfonyl" include, but are not limited to, cyclopropylsulfonyl, cyclobutylsulfonyl, cyclopentylsulfonyl, cyclohexylsulfonyl, and the like.

As used herein, "cycloalkyl" refers to a non-aromatic saturated hydrocarbon ring group, including those that have a partially crosslinked structure, those that are partially spiro, those having 1, 2, or more carbonyl structures. "$C_{3-20}$ cycloalkyl" refers to monocyclic or bicyclic cycloalkyl with 3 to 20 carbon atoms. "$C_{3-6}$ cycloalkyl" refers to monocyclic cycloalkyl with 3 to 6 carbon atoms. Specific examples of $C_{3-6}$ cycloalkyl include, but are not limited to, cyclopropyl, cyclobutyl, cyclopentyl, and cyclohexyl.

A cycloalkyl group can be fused to aryl and/or heteroaryl ring as a substituent or a portion thereof. For example, a cyclohexyl group can be fused to a benzene ring to form a 1,2,3,4-tetrahydronaphthalenyl group. In such a case, one of the possible carbon atoms on the cyclohexane ring attaches to the backbone, to a group near the backbone, or to its atom. A cycloalkyl group encompasses 1,2,3,4-tetrahydronaphthalen-1-yl, 1,2,3,4-tetrahydronaphthalen-2-yl, indan-1-yl, indan-2-yl, 5,6,7,8-tetrahydroquinolin-5-yl, and 5,6,7,8-tetrahydroquinolin-6-yl.

As used herein, "cycloalkylalkyl" refers to alkyl substituted with at least one cycloalkyl. "$C_{3-6}$ cycloalkyl $C_{1-6}$ alkyl" refers to $C_{1-6}$ alkyl substituted with at least one $C_{3-6}$ cycloalkyl. Specific examples of $C_{3-6}$ cycloalkyl $C_{1-6}$ alkyl include, but are not limited to, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 3-cyclopropylpropyl, 3-cyclobutylpropyl, 3-cyclopentylpropyl, 3-cyclohexylpropyl, and the like.

As used herein, "heterocycloalkyl" refers to a non-aromatic saturated or partially unsaturated heterocycle comprised of 3 or more atoms, comprising 1, 2, or more same or different heteroatoms selected from the group consisting of an oxygen atom, nitrogen atom, and sulfur atom, including those that have a partially crosslinked structure and those that are partially spiro. "Heterocycloalkyl" encompasses "non-aryl heterocycle". Heterocycloalkyl can have a structure where a non-aromatic heterocycle is fused to an aryl ring and/or heteroaryl ring.

As used herein, "non-aryl heterocycle" refers to a monocyclic or bicyclic non-aromatic heterocycle comprised of 3 or more atoms, comprising 1, 2, or more same or different heteroatoms selected from the group consisting of an oxygen atom, nitrogen atom, and sulfur atom, including saturated non-aryl heterocycles, those that have a partially unsaturated attachment, those that have a partially crosslinked structure, and those that are partially spiro. A non-aryl heterocycle can form a fused ring with aryl or heteroaryl. For example, a non-aryl heterocycle fused to $C_{6-10}$ aryl or 5- to 6-membered heteroaryl is also encompassed by a heterocycle. 1, 2, or more carbonyl, thiocarbonyl, sulfinyl, or sulfonyl can be comprised to constitute the non-aryl heterocycle. For example, lactam, thiolactam, lactone, thiolactone, cyclic imide, cyclic carbamate, cyclic thiocarbamate, and other cyclic groups are also encompassed by the non-aryl heterocycle. In this regard, an oxygen atom of carbonyl, sulfinyl, and sulfonyl and a sulfur atom of thiocarbonyl are not included in the number of members of the ring (ring size) or the number of heteroatoms constituting the ring.

As used herein, "4- to 10-membered non-aryl heterocycle" refers to a substituent with "4- to 10-membered non-aryl heterocycle" that is a monovalent group among the "non-aryl heterocycle" described above.

As used herein, the non-aryl heterocycle moiety of "non-aryl heterocyclyloxy" is defined the same as the "non-aryl heterocycle" described above. "4- to 10-membered non-aryl heterocyclyloxy" is preferably "4- to 6-membered non-aryl heterocyclyloxy". Specific examples of "4- to 10-membered non-aryl heterocyclyloxy" include, but are not limited to, tetrahydrofuranyloxy, tetrahydropyranyloxy, azetidinyloxy, pyrrolidinyloxy, piperidinyloxy, and the like.

As used herein, the non-aryl heterocycle moiety of "non-aryl heterocyclylthio" is defined the same as the "non-aryl heterocycle" described above. "4- to 10-membered non-aryl heterocyclylthio" is preferably "4- to 6-membered non-aryl heterocyclylthio". Specific examples of "4- to 10-membered non-aryl heterocyclylthio" include, but are not limited to, tetrahydropyranylthio, piperidinylthio, and the like.

As used herein, "non-aryl heterocyclylcarbonyl" refers to a carbonyl group substituted with the "non-aryl heterocycle" described above. "4- to 10-membered non-aryl heterocyclylcarbonyl" is preferably "4- to 6-membered non-aryl heterocyclylcarbonyl". Specific examples of "4- to 10-membered non-aryl heterocyclylcarbonyl" include, but are not limited to, azetidinylcarbonyl, pyrrolidinylcarbonyl, piperidinylcarbonyl, morpholinylcarbonyl, and the like.

As used herein, "non-aryl heterocyclylsulfonyl" refers to a sulfonyl group substituted with the "non-aryl heterocycle" described above. "4- to 10-membered non-aryl heterocyclylsulfonyl" is preferably "4- to 6-membered non-aryl heterocyclylsulfonyl". Specific examples of "4- to 10-membered non-aryl heterocyclylsulfonyl" include, but are not limited to, azetidinylsulfonyl, pyrrolidinylsulfonyl, piperidinylsulfonyl, morpholinylsulfonyl, and the like.

As used herein, "5- to 6-membered heterocycloalkyl" refers to heterocycloalkyl comprised of 5 to 6 cyclic atoms, comprising 1 or more same or different heteroatoms selected from the group consisting of an oxygen atom, nitrogen atom, and sulfur atom.

As used herein, "heterocycloalkylalkyl" refers to alkyl substituted with at least one heterocycloalkyl.

As used herein, "alkylcarbonyl" is a monovalent group of —C(=O)-alkyl. Preferred examples of alkylcarbonyl include $C_{1-6}$ alkylcarbonyl. Specific examples of $C_{1-6}$ alkylcarbonyl include, but are not limited to, acetyl ($CH_3C(=O)—$), n-propanoyl ($CH_3CH_2C(=O)—$), n-butanoyl ($CH_3CH_2CH_2C(=O)—$), n-pentanoyl ($CH_3(CH_2)_3C(=O)—$), n-hexanoyl ($CH_3(CH_2)_4C(=O)—$), n-heptanoyl ($CH_3(CH_2)_5C(=O)—$), and the like.

As used herein, "alkoxy" is a monovalent group of —O-alkyl. Preferred examples of alkoxy include $C_{1-6}$ alkoxy (i.e., $C_{1-6}$ alkyl-O—), $C_{1-4}$ alkoxy (i.e., $C_{1-4}$ alkyl-O—), and the like. Specific examples of $C_{1-4}$ alkoxy include methoxy ($CH_3O—$), ethoxy ($CH_3CH_2O—$), n-propoxy ($CH_3(CH_2)_2O—$), isopropoxy (($CH_3)_2CHO—$), n-butoxy ($CH_3(CH_2)_3O—$), isobutoxy (($CH_3)_2CHCH_2O—$), tert-butoxy (($CH_3)_3CO—$), sec-butoxy ($CH_3CH_2CH(CH_3)O—$), and the like. Specific examples of $C_{1-6}$ alkoxy include, but are not limited to, $C_{1-4}$ alkoxy, n-pentyloxy ($CH_3(CH_2)_4O—$), isopentyloxy (($CH_3)_2CHCH_2CH_2O—$), neopentyloxy (($CH_3)_3CCH_2O—$), tert-pentyloxy ($CH_3CH_2C(CH_3)_2O—$), 1,2-dimethylpropoxy ($CH_3CH(CH_3)CH(CH_3)O—$), and the like.

As used herein, "alkoxycarbonyl" is a monovalent group of —C(=O)—O-alkyl. Examples of alkoxycarbonyl include, but are not limited to, $C_{1-6}$ alkoxycarbonyl, preferably $C_{1-4}$ alkoxycarbony. Specific examples of $C_{1-4}$ alkoxycarbonyl include methoxycarbonyl, ethoxycarbonyl, n-propoxycarbonyl, isopropoxycarbonyl, n-butoxycarbonyl, sec-butoxycarbonyl, tert-butoxycarbonyl, isobutoxycarbonyl, and the like. Specific examples of $C_{1-6}$ alkoxycarbonyl include, but are not limited to, $C_{1-4}$ alkoxycarbonyl, n-pentyloxycarbonyl, i sopentyloxycarbonyl, neopentyloxycarbonyl, tert-pentyloxycarbonyl, 1,2-dimethylpropyloxycarbonyl, n-hexyl oxycarbonyl, and the like.

As used herein, "alkoxycarbonylamino" is a monovalent group of —NH—C(=O)—O-alkyl. Examples of alkoxycarbonylamino include, but are not limited to, $C_{1-6}$ alkoxycarbonylamino, preferably $C_{1-4}$ alkoxycarbonylamino. Specific examples of $C_{1-4}$ alkoxycarbonylamino include methoxycarbonylamino, ethoxycarbonylamino, n-propoxycarbonylamino, isopropoxycarbonylamino, n-butoxycarbonylamino, sec-butoxycarbonylamino, tert-butoxycarbonylamino, isobutoxycarbonylamino, and the like. Specific examples of $C_{1-6}$ alkoxycarbonylamino include, but are not limited to, $C_{1-4}$ alkoxycarbonylamino, n-pentyloxycarbonylamino, isopentyloxycarbonylamino, neopentyloxycarbonylamino, tert-pentyloxycarbonylamino, 1,2-dimethylpropyloxycarbonylamino, n-hexyloxycarbonylamino, and the like.

As used herein, "haloalkyl" is a monovalent group of halogenated alkyl, having one or more hydrogen on an alkyl group substituted with halogen. The term "perhaloalkyl" refers to haloalkyl with all hydrogen on the alkyl group substituted with halogen. For example, perfluoroethyl is —$CF_2CF_3$, and perchloro-n-propyl is —$CCl_2CCl_2CCl_3$. Examples of haloalkyl include $C_{1-6}$ haloalkyl, $C_{1-4}$ haloalkyl, $C_{1-3}$ haloalkyl, and the like. Specific examples of $C_{1-3}$ alkyl include, but are not limited to, fluoromethyl, chloromethyl, bromomethyl, difluoromethyl, dichloromethyl, dibromomethyl, trifluoromethyl, trichloromethyl, tribromomethyl, fluorochloromethyl, difluorochloromethyl, fluorodichloromethyl, fluoroethyl, chloroethyl, bromoethyl, trifluoroethyl, trichloroethyl, tribromoethyl, perfluoroethyl, perchloroethyl, perbromoethyl, perfluoropropyl, perchloropropyl, perbromopropyl, perfluoroisopropyl, perchloroisopropyl, perbromoisopropyl, and the like. Specific examples of $C_{1-4}$ alkyl include, but are not limited to, $C_{1-3}$ haloalkyl, perfluorobutyl, perchlorobutyl, perbromobutyl, perfluoroisobutyl, perfluoro-t-butyl, and the like. Specific examples of $C_{1-6}$ alkyl include, but are not limited to, $C_{1-4}$ haloalkyl, perfluoro-n-pentyl, perfluoroisopentyl, perfluoroneopentyl, perfluorotert-pentyl, perfluoro-1,2-dimethylpropyl, and the like.

As used herein, "haloalkoxy" as well as "haloalkyloxy" is a monovalent group of —O-haloalkyl with one or more hydrogen on the alkyl group substituted with halogen. The term "perhaloalkoxy" refers to haloalkoxy with all hydrogen on the alkyl group substituted with halogen. For example, perfluoroethoxy is —OCF$_2$CF$_3$, and perchloro-n-propoxy is —OCCl$_2$CCl$_2$CCl$_3$. Preferred examples of haloalkoxy include $C_{1-6}$ haloalkoxy, $C_{1-4}$ haloalkoxy, $C_{1-3}$ haloalkoxy, and the like. Specific examples of $C_{1-3}$ alkoxy include, but are not limited to, fluoromethoxy, chloromethoxy, bromomethoxy, difluoromethoxy, dichloromethoxy, dibromomethoxy, trifluoromethoxy, trichloromethoxy, tribromomethoxy, fluorochloromethoxy, difluorochloromethoxy, fluorodichloromethoxy, fluoroethoxy, chloroethoxy, bromoethoxy, trifluoroethoxy, trichloroethoxy, tribromoethoxy, perfluoroethoxy, perchloroethoxy, perbromoethoxy, perfluoropropoxy, perchloropropoxy, perbromopropoxy, perfluoroisopropoxy, perchloroisopropoxy, perbromoisopropoxy, and the like. Specific examples of $C_{1-4}$ alkoxy include, but are not limited to, $C_{1-3}$ haloalkoxy, perfluorobutoxy, perchlorobutoxy, perbromobutoxy, perfluoroisobutoxy, perfluoro-t-butoxy, and the like. Specific examples of $C_{1-6}$ alkoxy include, but are not limited to, $C_{1-4}$ haloalkoxy, perfluoro-n-pentyloxy, perfluoroisopentyloxy, perfluoroneopentyloxy, perfluorotert-pentyloxy, perfluoro-1,2-dimethylpropoxy, and the like.

As used herein, "alkylsulfonyl" refers to a sulfonyl group substituted with the "alkyl" described above. "$C_{1-6}$ alkylsulfonyl" is preferably "$C_{1-4}$ alkylsulfonyl". Specific examples of "$C_{1-6}$ alkylsulfonyl" include, but are not limited to, methylsulfonyl, propionylsulfonyl, butyrylsulfonyl, and the like.

As used herein, the alkyl moiety of "alkylthio" is defined the same as the alkyl described above. Examples of "$C_{1-6}$ alkylthio" include "$C_{1-4}$ alkylthio", and preferred examples thereof include "$C_{1-3}$ alkylthio". Specific examples of "$C_{1-6}$ alkylthio" include, but are not limited to, methylthio, ethylthio, propylthio, butylthio, isopropylthio, isobutylthio, tert-butylthio, sec-butylthio, isopentylthio, neopentylthio, tert-pentylthio, 1,2-dimethylpropylthio, and the like.

As used herein, "arylcarbonyl" is a monovalent group of —C(=O)-aryl. Preferred examples of arylcarbonyl include $C_{6-10}$ arylcarbonyl. Specific examples of $C_{6-10}$ arylcarbonyl include, but are not limited to, benzoyl (i.e., phenyl-C(=O)—), 1-naphthylcarbonyl, 2-naphthylcarbonyl, and the like.

As used herein, the aryl moiety of "aryloxy" is defined the same as the aryl described above. Preferred examples of "$C_{6-10}$ aryloxy" include "$C_6$ or $C_{10}$ aryloxy". Specific examples of "$C_{6-10}$ aryloxy group" include, but are not limited to, a phenoxy group, 1-naphthyloxy group, 2-naphthyloxy group, and the like.

As used herein, "heteroarylcarbonyl" is a monovalent group of —C(=O)-heteroaryl.

As used herein, "heteroarylcarbonyl group" refers to a carbonyl group substituted with the "heteroaryl" described above. Specific examples of "5- to 6-membered heteroarylcarbonyl group" include, but are not limited to, pyrazoylcarbonyl group, triazoylcarbonyl group, thiazoylcarbonyl group, thiadiazoylcarbonyl group, pyridylcarbonyl group, pyridazoylcarbonyl group, and the like.

As used herein, the heteroaryl moiety of the "heteroaryloxy group" is defined the same as the "heteroaryl" described above. The 5- to 6-membered heteroaryl moiety of the "5- to 6-membered heteroaryloxy group" is defined the same as "5-membered heteroaryl" or "6-membered heteroaryl", respectively. Specific examples of "5- to 6-membered heteroaryloxy group" include, but are not limited to, a pyrazoyloxy group, triazoyloxy group, thiazoyloxy group, thiadiazoyloxy group, pyridyloxy group, pyridazoyloxy group, and the like.

As used herein, the heteroaryl moiety of a "heteroarylthio group" is defined the same as the "heteroaryl" described above. The 5- to 6-membered heteroaryl moiety of "5- to 6-membered heteroarylthio group" is defined the same as "5-membered heteroaryl" or "6-membered heteroaryl", respectively. Specific examples of "5- to 6-membered heteroarylthio group" include, but are not limited to, pyrazoylthio group, triazoylthio group, thiazoylthio group, thiadiazoylthio group, pyridylthio group, pyridazoylthio group, and the like.

As used herein, the heteroaryl moiety of a "heteroarylsulfonyl group" is defined the same as the "heteroaryl" described above. A "5- to 6-membered heteroarylsulfonyl group" refers to a sulfonyl group substituted with a "5- to 6-membered heteroaryl". Specific examples of "5- to 6-membered heteroarylsulfonyl group" include, but are not limited to, pyrazoylsulfonyl group, triazoylsulfonyl group, thiazoylsulfonyl group, thiadiazoylsulfonyl group, pyridylsulfonyl group, pyridazoylsulfonyl group, and the like.

As used herein, "acyl" refers to a monovalent group of —C(=O)—$R_{acyl}$, wherein $R_{acyl}$ is hydrogen, optionally substituted alkyl, optionally substituted alkenyl, optionally substituted alkynyl, optionally substituted aryl, optionally substituted heteroaryl, or optionally substituted heterocycloalkyl. Specific examples of acyl include, but are not limited to, formyl, groups exemplified as alkylcarbonyl, arylcarbonyl, and heteroarylcarbonyl, and the like.

As used herein, "optionally substituted carbonyl" group refers to a monovalent group of —C(=O)— (hydrogen or any group selected from a substituent group described herein). Examples of "optionally substituted carbonyl" group include, but are not limited to, formyl, and optionally substituted carbamoyl, alkylcarbonyl, alkoxycarbonyl, alkenylcarbonyl, alkenyloxycarbonyl, alkynylcarbonyl, alkynyloxycarbonyl, arylcarbonyl, aryloxycarbonyl, cycloalkylcarbonyl, cycloalkyloxycarbonyl, heteroarylcarbonyl, heteroaryloxycarbonyl, heterocycloalkylcarbonyl, heterocycloalkyloxycarbonyl, and the like. A carbonyl group substituted with hydrogen is a formyl group. A carbonyl group substituted with amino is a carbamoyl group.

As used herein, "optionally substituted oxy" group refers to a monovalent group of —O— (hydrogen or any group selected from a substituent group described herein). Examples of "optionally substituted oxy" group include, but are not limited to, hydroxy, and optionally substituted alkyloxy, alkenyloxy, alkynyloxy, aryloxy, heteroaryloxy, heterocycloalkyloxy, alkylcarbonyloxy, alkenylcarbonyloxy, alkynylcarbonyloxy, arylcarbonyloxy, heteroarylcarbonyloxy, heterocycloalkylcarbonyloxy, and the like. An oxy group substituted with hydrogen is a hydroxy group.

As used herein, "carbamoyl" is a monovalent group of —C(=O)—NH$_2$.

As used herein, "amidinoamino" is a monovalent group of —NH—C(=NH)—NH$_2$.

As used herein, the phrase "a substituent-substituted group" means that the group is substituted with at least one substituent. For example, "hydroxy-substituted C$_{1-6}$ alkyl" refers to C$_{1-6}$ alkyl that has at least one hydroxy substitution.

As used herein, "carbamoyl-substituted C$_{1-6}$ alkyl" is C$_{1-6}$ alkyl substituted with at least one —C(=O)—NH$_2$ group. Examples of "carbamoyl-substituted C$_{1-6}$ alkyl" include, but are not limited to, carbamoyl-substituted C$_{1-4}$ alkyl. Specific examples of "carbamoyl-substituted C$_{1-4}$ alkyl" include, but are not limited to, 2-amino-2-oxoethyl (i.e., H$_2$NC(=O)—CH$_2$— or carbamoylmethyl), 3-amino-3-oxopropyl (i.e., H$_2$NC(=O)—CH$_2$CH$_2$— or carbamoylethyl), 4-amino-4-oxobutyl (i.e., H$_2$NC(=O)—(CH$_2$)$_3$— or carbamoylpropyl), 5-amino-5-oxopentyl (i.e., H$_2$NC(=O)—(CH$_2$)$_4$— or carbamoylbutyl), and the like. Specific examples of "carbamoyl-substituted C$_{1-6}$ alkyl" include, but are not limited to, carbamoyl-substituted C$_{1-4}$ alkyl, 6-amino-6-oxohexyl (i.e., H$_2$NC(=O)—(CH$_2$)$_5$— or carbamoylpentyl), 7-amino-7-oxoheptyl (i.e., H$_2$NC(=O)—(CH$_2$)$_6$— or carbamoylhexyl), and the like.

As used herein, "amidinoamino-substituted alkyl" or "guanidino-substituted alkyl" is alkyl substituted with at least one —NH—C(=NH)—NH$_2$ group, wherein the nitrogen atom of the amidinoamino group can be protected with a nitrogen protecting group (e.g., tert-butoxycarbonyl group). Examples of "amidinoamino-substituted C$_{1-6}$ alkyl" include, but are not limited to, "amidinoamino-substituted C$_{1-4}$ alkyl" and the like. Specific examples of "amidinoamino-substituted C$_{1-4}$ alkyl" include, but are not limited to, (amidinoamino)methyl, 2-(amidinoamino)ethyl, 3-(amidinoamino)propyl, 4-(amidinoamino)butyl, and the like. Specific examples of "amidinoamino-substituted C$_{1-6}$ alkyl" include, but are not limited to, amidinoamino-substituted C$_{1-4}$ alkyl, 5-(amidinoamino)pentyl, 6-(amidinoamino) hexyl, and the like. Examples of amidinoamino groups protected with a nitrogen protecting group include

[Chemical Formula 17]

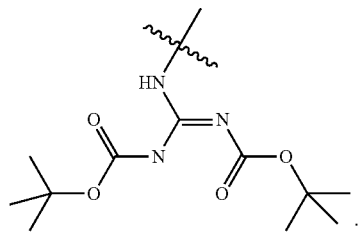

As used herein, "amidinoamino" is synonymous with "guanidino".

As used herein, "carboxy-substituted alkyl" is alkyl substituted with at least one —COOH group. Examples of "carboxy-substituted C$_{1-6}$ alkyl" include, but are not limited to, "carboxy-substituted C$_{1-4}$ alkyl" and the like. Specific examples of "carboxy-substituted C$_{1-4}$ alkyl" include, but are not limited to, carboxymethyl, 2-carboxyethyl, 3-carboxypropyl, 4-carboxybutyl, and the like. Specific examples of "carboxy-substituted C$_{1-6}$ alkyl" include, but are not limited to, carboxy-substituted C$_{1-4}$ alkyl, 5-carboxypentyl, 6-carboxyhexyl, and the like.

A "protecting group" refers to a group of atoms that blocks, reduces, or prevents reactivity of a functional group when attached to a reactive functional group in a molecule. The compound of the present disclosure can have a substitution with a protecting group when appropriate or needed at any of R$_1$ to R$_4$ or any position of a substituent thereof or other substituents or the like. Compounds comprising such a protecting group are also within the scope of the present disclosure. Typically, a protecting group can be selectively removed during a synthesis process if desired. Examples of protecting groups are found in Greene and Wuts, Protective Groups in Organic Chemistry, 5th Edition, 2014, John Wiley & Sons, NY and Harrison et al., Compendium of Synthetic Organic Methods, Vol. 1 to 8, John Wiley & Sons, NY, or the like. As used herein, a "protecting group" can fall under the definitions for 1) to 53) of substituent α and 1) to 26) of substituent β. In such a case, "54) protecting group" can be described as "54) protecting group other than 1) to 53)" in substituent group α1, and "27) protecting group" can be described as "protecting group other than 1) to 26)" in substituent group β1. Representative examples of nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("TES"), trityl and substituted trityl group, allyloxycarbonyl, 9-fluorenylmethyloxycarbonyl ("FMOC"), nitro-veratryloxycarbonyl ("NVOC"), groups represented by "Protect" herein, and the like. Representative examples of hydroxyl protecting groups include, but are not limited to, groups that acylate (esterify) or alkylate a hydroxyl group, such as benzyl and trityl ether, as well as alkyl ether, tetrahydropyranyl ether, trialkylsilyl ether (e.g., TMS, triethylsilyl, t-butyldimethylsilyl (TBDMS), and triisopropylsilyl (TIPS)), alkyldiarylsilyl ether (e.g., t-butyldiphenylsilyl (TBDPS)), triarylsilyl ether (e.g., triphenylsilyl), glycol ether (e.g., ethylene glycol ether, propylene glycol ether, and the like), and allyl ether.

An amino group of the compound of the present disclosure (e.g., amino group of the backbone, amino group as a substituent, amino group in a substituent of said compound, or the like) can be protected with a nitrogen protecting group or a group represented by "Protect". An amino group in a substituent listed in a substituent group can be further protected with a nitrogen protecting group or a group represented by "Protect". A protected substituent can also be used as a substituent.

A hydroxy group of the compound of the present disclosure (e.g., hydroxy group as a substituent, a hydroxy group in a substituent of said compound, a hydroxy group in a substituent group described above, or the like) can also be protected with a protecting group of a hydroxy group. A hydroxy group in a substituent listed in a substituent group can be further protected with a hydroxyl protecting group described herein. A protected substituent can also be used as a substituent.

Preferred Embodiments

The preferred embodiments of the present disclosure are described hereinafter. It is understood that the embodiments provided hereinafter are provided for the better understanding of the present disclosure, so that the scope of the present disclosure should not be limited by the following descriptions. Thus, it is apparent that those skilled in the art can refer to the descriptions herein to make appropriate modifications within the scope of the present disclosure. It is also understood that the following embodiments of the present disclosure can be used individually or as a combination.

(Compound and Composition of the Present Disclosure)

In one aspect, the compound of the present disclosure can be exemplified as a compound represented by formula XXIF:

[Chemical Formula 18]

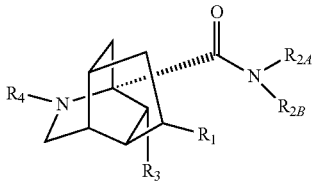

Formula XXIF or an enantiomer thereof, or a salt thereof, or a solvate thereof, wherein $R_1$, $R_3$, and $R_4$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

If one of $R_{2A}$ or $R_{2B}$ is hydrogen herein, it is understood that the same definition as $R_2$ described herein can be used.

In another aspect, the compound of the present disclosure can be exemplified as a compound represented by formula XXIB:

[Chemical Formula 19]

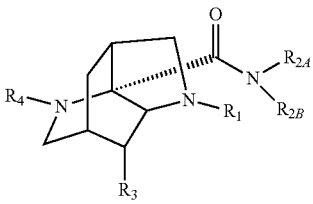

Formula XXIB or an enantiomer thereof, or a salt thereof, or a solvate thereof, wherein $R_1$, $R_{2a}$, $R_{2B}$, and $R_3$ are defined the same as those for formula XXIF described herein.

In still another aspect, the compound of the present disclosure can be exemplified as a compound represented by formula XXIIF:

[Chemical Formula 20]

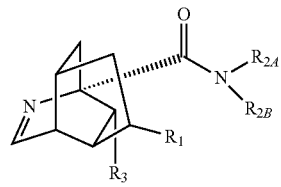

Formula XXIIF or an enantiomer thereof, or a salt thereof, or a solvate thereof, wherein $R_1$, $R_{2A}$, $R_{2B}$, and $R_3$ are defined the same as those for formula XXIF described herein.

In still another aspect, the compound of the present disclosure can be exemplified as a compound represented by formula XXIIB:

[Chemical Formula 21]

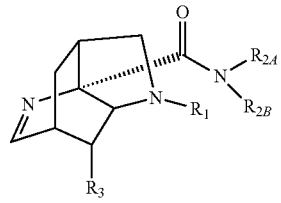

Formula XXIIB or an enantiomer thereof, or a salt thereof, or a solvate thereof, wherein $R_1$, $R_2$, and $R_3$ are defined the same as those for formula XXIF described herein.

In one embodiment, the alkyl, alkenyl, alkynyl, cycloalkyl, heterocycloalkyl, aryl, heteroaryl, and carbonyl of $R_1$, $R_3$, and if present $R_4$ are each independently and optionally substituted with one to the maximum substitutable number of the same or different substituents selected from substituent group I, and the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently and optionally substituted with one to the maximum substitutable number of the same or different substituents selected from substituent group I.

In one embodiment, $R_1$, $R_3$, and if present $R_4$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

In some cases for substituents in this embodiment, $R_{2A}$ and $R_{2B}$ are each independently hydrogen, optionally substituted alkyl, optionally substituted cycloalkyl, optionally substituted heterocycloalkyl, optionally substituted aryl, or optionally substituted heteroaryl and/or $R_{2A}$ and $R_{2B}$, together with the nitrogen atom to which they are attached, form a non-aryl heterocycle, wherein the non-aryl heterocycles are each independently and optionally substituted.

Alternatively, in another embodiment for (an imine form), $R_1$ and $R_3$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

In some cases, $R_1$ and $R_3$ are each independently hydrogen, optionally substituted alkyl, optionally substituted cycloalkyl, optionally substituted heterocycloalkyl, optionally substituted aryl, or optionally substituted heteroaryl, and $R_{2A}$ and $R_{2B}$ are each independently hydrogen, optionally substituted alkyl, optionally substituted cycloalkyl, optionally substituted heterocycloalkyl, optionally substituted aryl, or optionally substituted heteroaryl, and/or $R_{2A}$ and $R_{2B}$, together with the nitrogen atom to which they are attached, form a non-aryl heterocycle, wherein the non-aryl heterocycles are each independently and optionally substituted.

In one embodiment, $R_1$, $R_3$, and if present $R_4$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, and $R_{2A}$ and $R_{2B}$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

In some cases, $R_{2A}$ and $R_{2B}$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, or optionally substituted 5- to 10-membered heteroaryl, and/or $R_{2A}$ and $R_{2B}$, together with the nitrogen atom to which they are attached, form a non-aryl heterocycle, wherein the non-aryl heterocycles are each independently and optionally substituted.

In one embodiment, $R_1$, $R_3$, and if present $R_4$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$, $R_3$, and $R_4$ are optionally substituted with one to the maximum substitutable number of the same or different substituents selected from substituent group II, and $R_{2A}$ and $R_{2B}$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, form a 5- to 6-membered non-aryl heterocycle or heteroaryl ring, wherein the non-aryl heterocycle and the heteroaryl ring are optionally substituted with one to the maximum substitutable number of the same or different substituents selected from substituent group II.

In one embodiment, $R_1$, $R_3$, and if present $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$, $R_3$, and $R_4$ are optionally substituted with one to the maximum substitutable number of the same or different substituents selected from substituent group III, and $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_{2A}$ and $R_{2B}$ are optionally substituted with one to the maximum substitutable number of the same or different substituents selected from substituent group III, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group V.

In some cases, $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, or formyl, wherein the groups of $R_{2A}$ and $R_{2B}$ are optionally substituted with one to the maximum substitutable number of the same or different substituents selected from substituent group III.

In one embodiment, $R_1$ and if present $R_4$ are each independently hydrogen, optionally substituted alkyl, optionally substituted arylalkyl, optionally substituted cycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_4$ are optionally substituted with one to the maximum substitutable number of the same or different substituents selected from substituent group III.

In some cases, $R_1$ and if present $R_4$ are each independently hydrogen, optionally substituted alkyl, optionally substituted arylalkyl, optionally substituted cycloalkyl, or formyl, wherein the groups of $R_1$ and $R_4$ are optionally substituted with one to the maximum substitutable number of the same or different substituents selected from substituent group III.

In one embodiment, $R_1$ and if present $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_4$ are optionally substituted with one to the maximum substitutable number of the same or different substituents selected from substituent group III.

In one embodiment, $R_1$ and if present $R_4$ are each independently hydrogen, optionally substituted alkyl, optionally substituted arylalkyl, formyl, optionally substituted alkylcarbonyl, optionally substituted alkoxycarbonyl, optionally substituted arylcarbonyl, optionally substituted aryloxycarbonyl, carbamoyl, or optionally substituted alkylcarbamoyl, wherein the groups of $R_1$ and $R_4$ are optionally substituted with one to the maximum substitutable number of the same or different substituents selected from substituent group III.

In one embodiment, $R_1$ and if present $R_4$ are each independently hydrogen, optionally substituted $C_{1-12}$ alkyl, optionally substituted $C_{6-10}$ aryl $C_{1-12}$ alkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, carbamoyl, or optionally substituted $C_{1-12}$ alkylcarbamoyl, wherein the groups of $R_1$ and $R_4$ are optionally substituted with one to the maximum substitutable number of the same or different substituents selected from substituent group III.

In one embodiment, $R_1$ and if present $R_4$ are each independently hydrogen, alkyl, alkyl substituted with one to the maximum substitutable number of the same or different substituents selected from the group consisting of amino, substituted amino, substituted oxy, substituted carbonyl, cycloalkyl, and substituted cycloalkyl, arylalkyl, arylalkyl substituted with one to the maximum substitutable number of the same or different substituents selected from the group consisting of halogen, alkyl, substituted alkyl, hydroxy, substituted oxy, amino, substituted amino, and nitro, formyl, substituted carbonyl, or substituted oxycarbonyl, wherein the substituted amino, substituted oxy, substituted alkyl, substituted carbonyl, substituted cycloalkyl, substituted carbonyl, and substituted oxycarbonyl in $R_1$ and $R_4$ each independently have one to the maximum substitutable number of the same or different substituents selected from substituent group IV.

In one embodiment, $R_1$ and if present $R_4$ are each independently hydrogen, $C_{1-12}$ alkyl, $C_{1-12}$ alkyl substituted with one to the maximum substitutable number of the same or different substituents selected from the group consisting of amino, substituted amino, substituted oxy, substituted carbonyl, $C_{3-10}$ cycloalkyl, and substituted $C_{3-10}$ cycloalkyl, $C_{6-10}$ aryl $C_{1-6}$ alkyl, $C_{6-10}$ aryl $C_{1-6}$ alkyl substituted with one to the maximum substitutable number of the same or different substituents selected from the group consisting of halogen, $C_{1-6}$ alkyl, substituted alkyl, hydroxy, substituted oxy, amino, substituted amino, and nitro, formyl, substituted carbonyl, or substituted oxycarbonyl, wherein the substituted amino, substituted oxy, substituted alkyl, substituted carbonyl, substituted cycloalkyl, substituted carbonyl, and substituted oxycarbonyl in $R_1$ and $R_4$ each independently have one to the maximum substitutable number of the same or different substituents selected from substituent group IV.

In one embodiment, $R_1$ and $R_3$ are each independently hydrogen, optionally substituted alkyl, optionally substituted arylalkyl, optionally substituted cycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_3$ are optionally substituted with one to the maximum substitutable number of the same or different substituents selected from substituent group III.

In one embodiment, and $R_3$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_3$ are optionally substituted with one to the maximum substitutable number of the same or different substituents selected from substituent group III.

In one embodiment, $R_1$ and if present $R_4$ are each independently hydrogen, alkyl, alkyl substituted with one to the maximum substitutable number of the same or different substituents selected from the group consisting of amidinoamino, alkoxy, alkoxycarbonyl, carbamoyl, carboxy, hydroxy, tri alkylsilyloxy, and cycloalkyl, arylalkyl, arylalkyl substituted with one to the maximum substitutable number of the same or different substituents selected from the group consisting of halogen, alkyl, haloalkyl, alkoxy, haloalkoxy, amino, substituted amino, nitro, and hydroxy, formyl, alkylcarbonyl, arylalkylcarbonyl, arylalkyloxycarbonyl, alkoxycarbonyl, arylcarbonyl, aryloxycarbonyl, carbamoyl, alkylcarbamoyl, or arylalkylcarbamoyl, wherein the substituted amino each independently has one to the maximum substitutable number of the same or different substituents selected from substituent group IV.

In one embodiment, $R_1$ and if present $R_4$ are each independently hydrogen, $C_{1-12}$ alkyl, $C_{1-12}$ alkyl substituted with one to the maximum substitutable number of the same or different substituents selected from the group consisting of amidinoamino, $C_{1-6}$ alkoxy, $C_{1-6}$ alkoxycarbonyl, carbamoyl, carboxy, hydroxy, tri-$C_{1-6}$ alkylsilyloxy, and $C_{3-10}$ cycloalkyl, $C_{6-10}$ aryl $C_{1-6}$ alkyl, $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, $C_{1-6}$ haloalkoxy, amino, substituted amino, nitro, and hydroxy, formyl, $C_{1-12}$ alkylcarbonyl, $C_{6-10}$ aryl $C_{1-6}$ alkylcarbonyl, $C_{6-10}$ aryl $C_{1-6}$ alkyloxycarbonyl, $C_{1-12}$ alkoxycarbonyl, $C_{6-10}$ arylcarbonyl, $C_{6-10}$ aryloxycarbonyl, carbamoyl, $C_{1-12}$ alkylcarbamoyl, or $C_{6-10}$ aryl $C_{1-6}$ alkylcarbamoyl, wherein the substituted amino has one to the maximum substitutable number of the same or different substituents selected from substituent group IV.

In one embodiment, $R_1$ and if present $R_4$ are each independently, $C_{1-12}$ alkyl, $C_{1-12}$ alkyl substituted with one to the maximum substitutable number of the same or different substituents selected from the group consisting of amidinoamino, $C_{1-6}$ alkoxycarbonyl-substituted amidinoamino, $C_{1-6}$ alkoxy, $C_{1-6}$ alkoxycarbonyl, carbamoyl, carboxy, hydroxy, tri-$C_{1-6}$ alkylsilyloxy, and $C_{3-10}$ cycloalkyl, $C_{6-10}$ aryl $C_{1-6}$ alkyl, or $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, $C_{1-6}$ haloalkoxy, amino, substituted amino, nitro, and hydroxy, wherein the substituted amino optionally has one to the maximum substitutable number of the same or different substituents selected from substituent group IV.

In one embodiment, $R_3$ is hydrogen, alkyl, alkyl substituted with one to the maximum substitutable number of the same or different substituents selected from the group consisting of formyl, substituted carbonyl, hydroxy, substituted oxy, substituted carbonyl, amino, substituted amino, cycloalkyl, substituted cycloalkyl, heterocycloalkyl, and substituted heterocycloalkyl, arylalkyl, arylalkyl substituted with one to the maximum substitutable number of the same or different substituents selected from the group consisting of halogen, nitro, hydroxy, substituted oxy, amino, substituted amino, alkyl, and substituted alkyl, heteroarylalkyl, or substituted heteroarylalkyl, wherein the substituted carbonyl, substituted oxy, substituted amino, substituted cycloalkyl, substituted heterocycloalkyl, substituted alkyl, and substituted heteroarylalkyl in $R_3$ each independently and optionally have one to the maximum substitutable number of the same or different substituents selected from substituent group IV.

In some cases, $R_3$ is hydrogen, alkyl, alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl, arylalkyl, arylalkyl substituted with one to the maximum substitutable number of the same or different substituents selected from the group consisting of halogen, nitro, hydroxy, substituted oxy, amino, substituted amino, alkyl, and substituted alkyl, heteroarylalkyl, or substituted heteroarylalkyl, wherein the substituted oxy, substituted amino, substituted cycloalkyl, substituted heterocycloalkyl, substituted alkyl, and substituted heteroarylalkyl in $R_3$ each independently and optionally have one to the maximum substitutable number of the same or different substituents selected from substituent group IV.

In one embodiment, $R_3$ can be hydrogen, alkyl, formyl, alkylcarbonyl, arylalkylcarbonyl, alkyl substituted with one to the maximum substitutable number of the same or different substituents selected from the group consisting of hydroxy, trialkylsilyloxy, alkoxy, alkoxycarbonyl, alkoxycarbonylamino, cycloalkyl, carboxy, amino, amidinoamino, alkoxycarbonyl-substituted amidinoamino, carbamoyl, and heterocycloalkyl, arylalkyl, arylalkyl substituted with one to the maximum substitutable number of the same or different substituents selected from the group consisting of halogen, nitro, hydroxy, amino, monoalkylamino, dialkylamino, alkyl, haloalkyl, alkoxy, haloalkoxy, carboxyalkylcarbonylamino, carbamoylalkylcarbonylamino, cycloalkylcarbonylamino, and cycloalkylalkylamino, heteroarylalkyl, or alkoxycarbonyl-substituted heteroarylalkyl.

In some cases, $R_3$ can be hydrogen, alkyl, alkyl substituted with one to the maximum substitutable number of the same or different substituents selected from the group consisting of hydroxy, trialkylsilyloxy, alkoxy, alkoxycarbonyl, alkoxycarbonylamino, cycloalkyl, carboxy, amino, amidinoamino, alkoxycarbonyl-substituted amidinoamino, carbamoyl, and heterocycloalkyl, arylalkyl, arylalkyl substituted with one to the maximum substitutable number of the same or different substituents selected from the group consisting of halogen, nitro, hydroxy, amino, monoalkylamino, dialkylamino, alkyl, haloalkyl, alkoxy, haloalkoxy, carboxyalkylcarbonylamino, carbamoylalkylcarbonylamino, cycloalkylcarbonylamino, and cycloalkylalkylamino, heteroarylalkyl, or alkoxycarbonyl-substituted heteroarylalkyl.

In one embodiment, $R_3$ can be hydrogen, $C_{1-12}$ alkyl, formyl, $C_{1-6}$ alkylcarbonyl, $C_{6-10}$ aryl $C_{1-6}$ alkylcarbonyl, $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-6}$ cycloalkyl, carboxy, amino, amidinoamino, $C_{1-6}$ alkoxycarbonyl-substituted amidinoamino, carbamoyl, and 5- to 6-membered heterocycloalkyl, $C_{6-10}$ aryl $C_{1-6}$ alkyl, $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, $C_{1-6}$ haloalkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino, 5- to 10-membered heteroaryl $C_{1-6}$ alkyl, or $C_{1-6}$ alkoxycarbonyl-substituted 5- to 10-membered heteroaryl $C_{1-6}$ alkyl.

In some cases, $R_3$ can be hydrogen, $C_{1-12}$ alkyl, $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-6}$ cycloalkyl, carboxy, amino, amidinoamino, $C_{1-6}$ alkoxycarbonyl-substituted amidinoamino, carbamoyl, and 5- to 6-membered heterocycloalkyl, $C_{6-10}$ aryl $C_{1-6}$ alkyl, $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, $C_{1-6}$ haloalkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino, 5- to 10-membered heteroaryl $C_{1-6}$ alkyl, or $C_{1-6}$ alkoxycarbonyl-substituted 5- to 10-membered heteroaryl $C_{1-6}$ alkyl.

In one embodiment, $R_3$ can be $C_{1-12}$ alkyl, $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-6}$ cycloalkyl, carboxy, amino, amidinoamino, $C_{1-6}$ alkoxycarbonyl-substituted amidinoamino, carbamoyl, and 5- to 6-membered heterocycloalkyl, $C_{6-10}$ aryl $C_{1-6}$ alkyl, or $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, $C_{1-6}$ haloalkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino.

In one embodiment, $R_3$ is hydrogen, alkyl, alkyl substituted with one to the maximum substitutable number of the same or different substituents selected from the group consisting of amino, substituted amino, carboxy, substituted oxycarbonyl, carbamoyl, substituted aminocarbonyl, hydroxy, substituted oxy, cycloalkyl, and substituted cycloalkyl, arylalkyl, or arylalkyl substituted with one to the maximum substitutable number of the same or different substituents selected from the group consisting of halogen, alkyl, substituted alkyl, carboxy, substituted oxycarbonyl, hydroxy, and substituted oxy, wherein the substituted amino, substituted oxy, substituted oxycarbonyl, substituted aminocarbonyl, substituted alkyl, substituted cycloalkyl, substituted carbonyl, and substituted oxycarbonyl in $R_3$ each independently have one to the maximum substitutable number of the same or different substituents selected from substituent group IV.

In one embodiment, $R_3$ is hydrogen, alkyl, alkyl substituted with one to the maximum substitutable number of the same or different substituents selected from the group consisting of amidinoamino, alkoxycarbonyl, carbamoyl, carboxy, hydroxy, trialkylsilyloxy, amino, alkoxycarbonylamino, and cycloalkyl, arylalkyl, or arylalkyl substituted with one to the maximum substitutable number of the same or different substituents selected from the group consisting of halogen, alkyl, alkoxycarbonyl, and hydroxy.

In one embodiment, $R_3$ is hydrogen, $C_{1-12}$ alkyl, $C_{1-12}$ alkyl substituted with one to the maximum substitutable number of the same or different substituents selected from the group consisting of amidinoamino, $C_{1-6}$ alkoxycarbonyl, carbamoyl, carboxy, hydroxy, tri-$C_{1-6}$ alkylsilyloxy, amino, $C_{1-6}$ alkoxycarbonylamino, and $C_{3-10}$ cycloalkyl, $C_{6-10}$ aryl $C_{1-6}$ alkyl, or $C_{6-10}$ aryl $C_{1-6}$ alkyl substituted with one to the maximum substitutable number of the same or different substituents selected from the group consisting of halogen, $C_{1-6}$ alkyl, $C_{1-6}$ alkoxycarbonyl, and hydroxy.

In one embodiment, $R_{2A}$ and $R_{2B}$ are each independently hydrogen, alkyl, alkyl substituted with one to the maximum substitutable number of the same or different substituents selected from the group consisting of formyl, substituted carbonyl, hydroxy, substituted oxy, amino, substituted amino, cycloalkyl, substituted cycloalkyl, heterocycloalkyl, and substituted heterocycloalkyl, arylalkyl, arylalkyl substituted with one to the maximum substitutable number of the same or different substituents selected from the group consisting of halogen, alkyl, substituted alkyl, hydroxy, and substituted oxy, heteroarylalkyl, substituted heteroarylalkyl, cycloalkyl, or substituted cycloalkyl, wherein the substituted carbonyl, substituted oxy, substituted amino, substituted cycloalkyl, substituted heterocycloalkyl, substituted heteroarylalkyl, and substituted alkyl in $R_{2A}$ and $R_{2B}$ each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

In one embodiment, $R_{2A}$ and $R_{2B}$ are each independently hydrogen, alkyl, alkyl substituted with one to the maximum substitutable number of the same or different substituents selected from the group consisting of amidinoamino, alkoxy, alkoxycarbonyl, carbamoyl, carboxy, hydroxy, amino, alkoxycarbonylamino, cycloalkyl, and heterocycloalkyl, arylalkyl, arylalkyl substituted with one to the maximum substitutable number of the same or different substituents selected from the group consisting of halogen, alkyl, haloalkyl, alkoxy, and hydroxy, heteroarylalkyl, alkoxycarbonyl-substituted heteroarylalkyl, or cycloalkyl, or $R_{2A}$ and $R_{2B}$, together with the nitrogen atom to which they are attached, form a 5- to 6-membered non-aryl heterocycle, wherein the non-aryl heterocycle is optionally substituted with one or up to the maximum substitutable number of the same or different substituents selected from substituent group VI.

In one embodiment, $R_{2A}$ and $R_{2B}$ are each independently hydrogen, $C_{1-12}$ alkyl substituted with one to the maximum substitutable number of the same or different substituents selected from the group consisting of amidinoamino, $C_{1-6}$ alkoxy, $C_{1-6}$ alkoxycarbonyl, carbamoyl, carboxy, hydroxy, amino, $C_{1-6}$ alkoxycarbonylamino, $C_{3-10}$ cycloalkyl, and 5- to 10-membered heterocycloalkyl, $C_{6-10}$ aryl $C_{1-6}$ alkyl, $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, and hydroxy, 5- to 10-membered heteroaryl $C_{1-6}$ alkyl, $C_{1-6}$ alkoxycarbonyl-substituted 5- to 10-membered heteroaryl $C_{1-6}$ alkyl, or $C_{3-10}$ cycloalkyl, $R_{2A}$ and $R_{2B}$, together with the nitrogen atom to which they are attached, form a 5- to 6-membered non-aryl heterocycle, wherein the non-aryl heterocycle is optionally substituted with one or up to the maximum substitutable number of the same or different substituents selected from substituent group VI.

In one embodiment, $R_{2A}$ and $R_{2B}$ are each independently hydrogen, alkyl, alkyl substituted with one to the maximum substitutable number of the same or different substituents selected from the group consisting of formyl, substituted carbonyl, hydroxy, substituted oxy, substituted carbonyl, amino, substituted amino, cycloalkyl, substituted cycloalkyl, heterocycloalkyl, and substituted heterocycloalkyl, arylalkyl, arylalkyl substituted with one to the maximum substitutable number of the same or different substituents selected from the group consisting of halogen, nitro, hydroxy, substituted oxy, amino, substituted amino, alkyl, and substituted alkyl, heteroarylalkyl, or substituted heteroarylalkyl, wherein the substituted carbonyl, substituted oxy, substituted amino, substituted cycloalkyl, substituted heterocycloalkyl, substituted alkyl, and substituted heteroarylalkyl in $R_{2A}$ and $R_{2B}$ each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

In some cases, $R_{2A}$ and $R_{2B}$ are each independently hydrogen, alkyl, alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl, arylalkyl, arylalkyl substituted with one to the maximum substitutable number of the same or different substituents selected from the group consisting of halogen, nitro, hydroxy, substituted oxy, amino, substituted amino, alkyl, and substituted alkyl, heteroarylalkyl, or substituted heteroarylalkyl, wherein the substituted oxy, substituted amino, substituted cycloalkyl, substituted heterocycloalkyl, substituted alkyl, and substituted heteroarylalkyl in $R_{2A}$ and $R_{2B}$ each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

In one embodiment, $R_{2A}$ and $R_{2B}$ are each independently hydrogen, alkyl, alkyl substituted with one to the maximum substitutable number of the same or different substituents selected from the group consisting of formyl, alkylcarbonyl, arylalkylcarbonyl, hydroxy, tri alkyl silyloxy, alkoxy, alkoxycarbonyl, alkoxycarbonylamino, cycloalkyl, carboxy, amino, amidinoamino, alkoxycarbonyl-substituted amidinoamino, carbamoyl, and heterocycloalkyl, arylalkyl, arylalkyl substituted with one to the maximum substitutable number of the same or different substituents selected from the group consisting of halogen, nitro, hydroxy, amino, monoalkylamino, dialkylamino, alkyl, haloalkyl, alkoxy, carboxyalkylcarbonylamino, carbamoylalkylcarbonylamino, cycloalkylcarbonylamino, and cycloalkylalkylamino, heteroarylalkyl, or alkoxycarbonyl-substituted heteroarylalkyl, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

In some cases, $R_{2A}$ and $R_{2B}$ are each independently hydrogen, alkyl, alkyl substituted with one to the maximum substitutable number of the same or different substituents selected from the group consisting of hydroxy, trialkylsilyloxy, alkoxy, alkoxycarbonylamino, cycloalkyl, carboxy, amino, amidinoamino, alkoxycarbonyl-substituted amidinoamino, and heterocycloalkyl, arylalkyl, arylalkyl substituted with one to the maximum substitutable number of the same or different substituents selected from the group consisting of halogen, nitro, hydroxy, amino, monoalkylamino, dialkylamino, alkyl, haloalkyl, alkoxy, carboxyalkylcarbonylamino, carbamoylalkylcarbonylamino, cycloalkylcarbonylamino, and cycloalkylalkylamino, heteroarylalkyl, or alkoxycarbonyl-substituted heteroarylalkyl, or $R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI.

In one embodiment, $R_{2A}$ and $R_{2B}$ are each independently hydrogen, $C_{1-12}$ alkyl, $C_{1-12}$ alkyl substituted with one to the maximum substitutable number of the same or different substituents selected from the group consisting of formyl, $C_{1-6}$ alkylcarbonyl, $C_{6-10}$ aryl $C_{1-6}$ alkylcarbonyl, hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-10}$ cycloalkyl, carboxy, amino, amidinoamino, $C_{1-6}$ alkoxycarbonyl-substituted amidinoamino, carbamoyl, and 5- to 6-membered heterocycloalkyl, $C_{6-10}$ aryl $C_{1-12}$ alkyl, $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino, 5- to 10-membered heteroaryl $C_{1-12}$ alkyl, or $C_{1-6}$ alkoxycarbonyl-substituted 5- to 10-membered heteroaryl $C_{1-12}$ alkyl, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from the group consisting of halogen, nitro, hydroxy, amino, $C_{1-6}$ alkyl, $C_{1-6}$ haloalkyl, $C_{1-6}$ alkoxy, $C_{1-6}$ alkoxycarbonyl, $C_{3-6}$ cycloalkylcarbonylamino, and $C_{3-6}$ cycloalkyl $C_{1-6}$ alkylamino.

In some cases, $R_{2A}$ and $R_{2B}$ are each independently hydrogen, $C_{1-12}$ alkyl, $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonylamino, $C_{3-10}$ cycloalkyl, carboxy, amino, amidinoamino, $C_{1-6}$ alkoxycarbonyl-substituted amidinoamino, and 5- to 6-membered heterocycloalkyl, $C_{6-10}$ aryl $C_{1-12}$ alkyl, $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino, 5- to 10-membered heteroaryl $C_{1-12}$ alkyl, or $C_{1-6}$ alkoxycarbonyl-substituted 5- to 10-membered heteroaryl $C_{1-12}$ alkyl, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from the group consisting of halogen, nitro, hydroxy, amino, $C_{1-6}$ alkyl, $C_{1-6}$ haloalkyl, $C_{1-6}$ alkoxy, $C_{1-6}$ alkoxycarbonyl, $C_{3-6}$ cycloalkylcarbonylamino, and $C_{3-6}$ cycloalkyl $C_{1-6}$ alkylamino.

In one embodiment, $R_{2A}$ and $R_{2B}$ are each independently hydrogen, $C_{1-12}$ alkyl, $C_{1-12}$ alkyl substituted with one to the maximum substitutable number of the same or different substituents selected from the group consisting of hydroxy, tri-$C_{1-6}$ alkylsilyloxy, $C_{1-6}$ alkoxy, $C_{1-6}$ alkoxycarbonyl, $C_{1-6}$ alkoxycarbonylamino, $C_{3-10}$ cycloalkyl, carboxy, amino, amidinoamino, $C_{1-6}$ alkoxycarbonyl-substituted amidinoamino, carbamoyl, and 5- to 6-membered heterocycloalkyl, $C_{6-10}$ aryl $C_{1-12}$ alkyl, $C_{6-10}$ aryl $C_{1-12}$ alkyl substituted with one to the maximum substitutable number of the same or different substituents selected from the group consisting of halogen, nitro, hydroxy, amino, mono-$C_{1-6}$ alkylamino, di-$C_{1-6}$ alkylamino, $C_{1-6}$ alkyl, $C_{1-6}$ haloalkyl, $C_{1-6}$ alkoxy, carboxy $C_{1-6}$ alkylcarbonylamino, carbamoyl $C_{1-6}$ alkylcarbonylamino, $C_{3-6}$ cycloalkylcarbonylamino, and $C_{3-6}$ cycloalkyl $C_{1-6}$ alkylamino, 5- to 10-membered heteroaryl $C_{1-12}$ alkyl, or $C_{1-6}$ alkoxycarbonyl-substituted 5- to 10-membered heteroaryl $C_{1-12}$ alkyl, or $R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group consisting of halogen, nitro, hydroxy, amino, $C_{1-6}$ alkyl, $C_{1-6}$ haloalkyl, $C_{1-6}$ alkoxy, $C_{1-6}$ alkoxycarbonyl, $C_{3-6}$ cycloalkylcarbonylamino, and $C_{3-6}$ cycloalkyl $C_{1-6}$ alkylamino.

In one embodiment, $R_1$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of halogen, alkyl, haloalkyl, alkoxy, substituted amino, and hydroxy, wherein the substituted amino has one to the maximum substitutable number of the same or different substituents selected from substituent group IV. Alternatively, $R_1$ is alkyl; arylalkyl; or arylalkyl substituted with one to the maximum substitutable number of the same or different substituents selected from the group consisting of halogen, alkyl, haloalkyl, alkoxy, substituted amino, and hydroxy, wherein the substituted amino has one to the maximum substitutable number of the same or different substituents selected from substituent group IV.

In one embodiment, $R_1$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, substituted amino, and hydroxy, wherein the substituted amino has one to the maximum substitutable number of the same or different substituents selected from substituent group IV. Alternatively, $R_1$ is $C_{1-12}$ alkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, substituted amino, and hydroxy, wherein the substituted amino has one to the maximum substitutable number of the same or different substituents selected from substituent group IV.

In one embodiment, $R_{2A}$ is hydrogen, and $R_{2B}$ is alkyl; alkyl substituted with one to the maximum substitutable number of the same or different substituents selected from the group consisting of amidinoamino, carbamoyl, carboxy, hydroxy, and cycloalkyl; arylalkyl; arylalkyl substituted with one to the maximum substitutable number of the same or different substituents selected from the group consisting of halogen, alkyl, haloalkyl, alkoxy, and hydroxy; or cycloalkyl. Alternatively, $R_{2A}$ is hydrogen, and $R_{2B}$ is alkyl; arylalkyl; arylalkyl substituted with one to the maximum substitutable number of the same or different substituents selected from the group consisting of halogen, alkyl, haloalkyl, alkoxy, and hydroxy; or cycloalkyl.

In one embodiment, $R_{2A}$ is hydrogen, and $R_{2B}$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, and hydroxy; or $C_{3-10}$ cycloalkyl. Alternatively, $R_{2A}$ is hydrogen, and $R_{2B}$ is $C_{1-12}$ alkyl; $C_{6-10}$ aryl $C_{1-6}$ alkyl; $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, $C_{1-6}$ alkoxy, and hydroxy; or $C_{3-10}$ cycloalkyl.

In one embodiment, $R_3$ is alkyl; alkyl substituted with one to the maximum substitutable number of the same or different substituents selected from the group consisting of amidinoamino, carbamoyl, carboxy, hydroxy, and cycloalkyl; arylalkyl; or arylalkyl substituted with one to the maximum substitutable number of the same or different substituents selected from the group consisting of alkyl and hydroxy. Alternatively, $R_3$ is alkyl or arylalkyl.

In one embodiment, $R_3$ is $C_{1-12}$ alkyl; $C_{1-12}$ alkyl substituted with one to the maximum substitutable number of the same or different substituents selected from the group consisting of amidinoamino, carbamoyl, carboxy, hydroxy, and $C_{3-10}$ cycloalkyl; $C_{6-10}$ aryl $C_{1-6}$ alkyl; or $C_{6-10}$ aryl $C_{1-6}$ alkyl substituted with one to the maximum substitutable number of the same or different substituents selected from the group consisting of $C_{1-6}$ alkyl and hydroxy. Alternatively, in one embodiment, $R_3$ is $C_{1-12}$ alkyl or $C_{6-10}$ aryl $C_{1-6}$ alkyl.

In one embodiment, $R_4$ is hydrogen, alkyl, alkylcarbonyl, arylalkylcarbonyl, arylalkyloxycarbonyl, alkoxycarbonyl, carbamoyl, or arylalkylcarbamoyl.

In one embodiment, $R_4$ is hydrogen, $C_{1-12}$ alkyl, $C_{1-12}$ alkylcarbonyl, $C_{6-10}$ aryl $C_{1-6}$ alkylcarbonyl, $C_{6-10}$ aryl $C_{1-6}$ alkyloxycarbonyl, $C_{1-12}$ alkoxycarbonyl, carbamoyl, or $C_{6-10}$ aryl $C_{1-6}$ alkylcarbamoyl.

In one embodiment, $R_1$ is hydrogen, methyl, ethyl, isobutyl, isopentyl, amidinoaminopropyl, tert-butoxyethyl, tert-butoxypropyl, (tert-butoxycarbonyl)ethyl, carbamoyl methyl, carboxyethyl, hydroxyethyl, hydroxypropyl, cyclopentylmethyl, cyclohexylmethyl, benzyl, phenylethyl, naphthalenylmethyl, fluorobenzyl, chlorobenzyl, dichlorobenzyl, methylbenzyl, tert-butylbenzyl, (trifluoromethyl)benzyl, methoxybenzyl, ethoxybenzyl, tert-butoxybenzyl, aminobenzyl, (cyclopentylcarbonylamino)benzyl, (cyclopentylmethylamino)benzyl, (dimethylamino)benzyl, (carbamoylethylcarbonylamino)benzyl, (carboxyethylcarbonylamino)benzyl, nitrobenzyl, hydroxybenzyl, 3-methylbutanoyl, isobutylcarbonyl, 2-phenylacetyl, isopropyloxycarbonyl, benzoyl, or phenyloxycarbonyl.

In another embodiment, $R_1$ is methyl, n-propyl, isobutyl, isopentyl, amidinoaminopropyl, tert-butoxycarbonyl-substituted amidinoaminopropyl, tert-butoxyethyl, tert-butoxypropyl, (tert-butoxycarbonyl)ethyl, carboxyethyl, hydroxyethyl, hydroxypropyl, aminopropyl, 2-(tert-butyl-dimethyl silyloxy)ethyl, cyclopentylmethyl, cyclohexylmethyl, benzyl, phenylethyl, naphthalenylmethyl, fluorobenzyl, chlorobenzyl, dichlorobenzyl, methylbenzyl, (tert-butyl)benzyl, methoxybenzyl, ethoxybenzyl, (tert-butoxy)benzyl, (trifluoromethoxy)benzyl, (dimethylamino)benzyl, nitrobenzyl, or hydroxybenzyl.

In one embodiment, $R_{2A}$ is hydrogen, and $R_{2B}$ is methyl, isopropyl, isobutyl, n-pentyl, isopentyl, n-hexyl, heptyl, amidinoaminopropyl, tert-butoxyethyl, tert-butoxycarbonylmethyl, carbamoylmethyl, carbamoylethyl, carboxyethyl, hydroxyethyl, aminobutyl, ((tert-butoxycarbonyl)amino)butyl, cyclohexylmethyl, (tetrahydro-2H-pyran-2-yl)methyl, benzyl, phenylethyl, naphthalenylmethyl, naphthalenylethyl, fluorobenzyl, chlorobenzyl, dichlorobenzyl, (fluorophenyl)ethyl, methylbenzyl, (trifluoromethyl)benzyl, methoxybenzyl, tert-butoxybenzyl, hydroxybenzyl, α-hydroxymethylphenethyl, β-hydroxyphenethyl, pyridinylmethyl, (1H-indol-3-yl)ethyl, (1-(tert-butoxycarbonyl)-1H-indol-3-yl)ethyl, cyclopentyl, or cyclohexyl, or $R_{2A}$ and $R_{2B}$, together with the nitrogen atom to which they are attached, form a pyrrolidine ring or piperidine ring.

In one embodiment, $R_{2A}$ and $R_{2B}$ are each independently isopropyl, isobutyl, sec-butyl, pentyl, isopentyl, n-hexyl, heptyl, amidinoaminopropyl, tert-butoxycarbonyl-substituted amidinoaminopropyl, tert-butoxyethyl, tert-butoxycarbonylmethyl, (tert-butoxycarbonyl)ethylcarbamoylethyl, carboxyethyl, hydroxyethyl, aminopropyl, aminobutyl, ((tert-butoxycarbonyl)amino)butyl, cyclopentylmethyl, cyclohexylmethyl, (1,2,3,4-tetrahydronaphthalenyl)methyl, (tetrahydro-2H-pyranyl)methyl, benzyl, phenylethyl, naphthalenylmethyl, (naphthalenyl)ethyl, β-hydroxyphenethyl, α-(hydroxymethyl)phenethyl, fluorobenzyl, chlorobenzyl, dichlorobenzyl, (fluorophenyl)ethyl, methylbenzyl, (trifluoromethyl)benzyl, methoxybenzyl, (tert-butoxy)benzyl, hydroxybenzyl, pyridinylmethyl, quinolinylethyl, (1-(tert-butoxycarbonyl)-1H-indolyl)ethyl, cyclopentyl, or cyclohexyl, or $R_{2A}$ and $R_{2B}$, together with the nitrogen atom to which they are attached, form a pyrrolidine ring or piperidine ring.

In one embodiment, $R_3$ is n-propyl, isobutyl, isopentyl, amidinoaminopropyl, (methoxycarbonyl)ethyl, (tert-butoxycarbonyl)ethyl, carbamoylmethyl, carboxyethyl, hydroxymethyl, hydroxyethyl, (tert-butyl di methyl silyloxy)ethyl, aminobutyl, ((tert-butoxycarbonyl)amino)butyl, cyclohexylmethyl, cyclohexylethyl, benzyl, phenylethyl, phenylpropyl, phenylbutyl, naphthalenylmethyl, naphthalenylethyl, chlorobenzyl, methylbenzyl, (methylphenyl)ethyl, (isopropylphenyl)ethyl, or hydroxybenzyl.

In one embodiment, $R_3$ is n-propyl, isobutyl, isopentyl, amidinoaminopropyl, tert-butoxycarbonyl-substituted amidinoaminopropyl, (methoxycarbonyl)ethyl, (tert-butoxycarbonyl)ethyl, carboxyethyl, hydroxyethyl, aminopropyl, (tert-butyldimethylsilyloxy)ethyl, ((tert-butoxycarbonyl)amino)butyl, cyclopentylmethyl, cyclohexylmethyl, cyclohexylethyl, benzyl, phenylethyl, phenylpropyl, phenylbutyl, naphthalenylmethyl, naphthalenylethyl, chlorobenzyl, methylbenzyl, (methylphenyl)ethyl, (isopropylphenyl)ethyl, (tert-butoxy)benzyl, or hydroxybenzyl.

In one embodiment, $R_4$ is hydrogen, methyl, ethyl, isobutyl, formyl, acetyl, 3-methylbutanoyl, 2-phenylacetyl, methoxycarbonyl, ethoxycarbonyl, 2-methylpropyloxycarbonyl, tert-butoxycarbonyl, benzoyl, benzyl, benzyloxycarbonyl, aminocarbonyl, N-benzylaminocarbonyl, propylcarbamoyl, N-isobutylaminocarbonyl, or N-benzylaminocarbonyl.

In some embodiments, the compound of the present disclosure can be exemplified as a compound represented by formula IF:

[Chemical Formula 22]

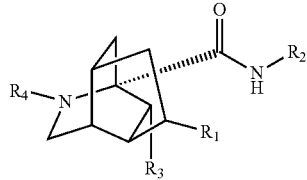

Formula IF or an enantiomer thereof, or a salt thereof, or a solvate thereof, wherein
  $R_1$, $R_2$, and $R_3$ are each independently optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and
  $R_4$ is hydrogen, optionally substituted alkyl, optionally substituted alkenyl, optionally substituted alkynyl, optionally substituted arylalkyl, optionally substituted heteroarylalkyl, optionally substituted cycloalkylalkyl, optionally substituted heterocycloalkylalkyl, optionally substituted alkylcarbonyl, optionally substituted alkoxycarbonyl, optionally substituted arylcarbonyl, optionally substituted heteroarylcarbonyl, or optionally substituted carbamoyl.

In one embodiment, $R_1$, $R_2$, and $R_3$ are each independently optionally substituted alkyl, optionally substituted arylalkyl, optionally substituted heteroarylalkyl, or optionally substituted cycloalkylalkyl.

In one embodiment, $R_1$, $R_2$, and $R_3$ are each independently optionally substituted $C_{1-6}$ alkyl, optionally substituted $C_{6-10}$ aryl $C_{1-6}$ alkyl, optionally substituted 5- to 10-membered heteroaryl $C_{1-6}$ alkyl, or optionally substituted $C_{3-6}$ cycloalkyl $C_{1-6}$ alkyl.

In one embodiment, $R_1$, $R_2$, and $R_3$ are each independently optionally substituted alkyl, optionally substituted arylalkyl, optionally substituted heteroarylalkyl, or optionally substituted cycloalkylalkyl, and $R_4$ is hydrogen, optionally substituted alkyl, optionally substituted alkylcarbonyl, optionally substituted arylcarbonyl, optionally substituted alkoxycarbonyl, or optionally substituted alkylcarbamoyl.

In one embodiment, $R_1$, $R_2$, and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, (optionally substituted amino)-$C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl $C_{1-6}$ alkyl.

In one embodiment, $R_1$, $R_2$, and $R_3$ are each independently $C_{1-6}$ alkyl, hydroxy-substituted $C_{1-6}$ alkyl, carbamoyl-substituted $C_{1-6}$ alkyl, amino-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkoxycarbonyl-substituted 5- to 10-membered heteroaryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, (optionally substituted amino)-$C_{6-10}$ aryl $C_{1-6}$ alkyl, $C_{1-4}$ alkoxycarbonyl-substituted $C_{1-6}$ alkyl, $C_{1-4}$ alkoxycarbonylamino-substituted $C_{1-6}$ alkyl, 5- to 6-membered heterocycloalkyl-substituted $C_{1-6}$ alkyl, or $C_{3-6}$ cycloalkyl $C_{1-6}$ alkyl.

In one embodiment, $R_1$, $R_2$, and $R_3$ are each independently alkyl or optionally substituted arylalkyl.

In one embodiment, $R_1$, $R_2$, and $R_3$ are each independently $C_{1-6}$ alkyl or optionally substituted $C_{6-10}$ aryl $C_{1-6}$ alkyl.

In one embodiment, $R_1$, $R_2$, and $R_3$ are each independently $C_{1-6}$ alkyl, $C_{6-10}$ aryl $C_{1-6}$ alkyl, $C_{1-4}$ alkyl-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, or (optionally substituted amino)-$C_{6-10}$ aryl $C_{1-6}$ alkyl.

In one embodiment, $R_1$, $R_2$, and $R_3$ are each independently $C_{1-6}$ alkyl, $C_{6-10}$ aryl $C_{1-6}$ alkyl, $C_{1-4}$ alkyl-substituted $C_{6-10}$ aryl $C_{1-6}$ alkyl, chloro-substituted $C_{6-10}$ aryl $C_{1-6}$ alkyl, $C_{1-4}$ alkoxy-substituted $C_{6-10}$ aryl $C_{1-6}$ alkyl, or (optionally substituted amino)-$C_{6-10}$ aryl $C_{1-6}$ alkyl.

In one embodiment, $R_1$ is $C_{1-6}$ alkyl or $C_6$ aryl $C_{1-4}$ alkyl, $R_2$ is $C_{1-6}$ alkyl or $C_{1-4}$ alkyl-substituted benzyl, and $R_3$ is $C_{1-6}$ alkyl or $C_6$ aryl $C_{1-4}$ alkyl.

In one embodiment, $R_1$ and $R_3$ are each independently alkyl or optionally substituted benzyl, and $R_2$ is optionally substituted benzyl.

In one embodiment, $R_1$ and $R_3$ are each independently $C_{1-6}$ alkyl, benzyl, $C_{1-4}$ alkyl-substituted benzyl, chloro-substituted benzyl, $C_{1-4}$ alkoxy-substituted benzyl, or amino-substituted benzyl, and $R_2$ is benzyl or chloro-substituted benzyl.

In one embodiment, $R_1$ and $R_3$ are each independently isobutyl, isopentyl, 4-(dimethylamino)benzyl, 4-methylbenzyl, 4-methoxybenzyl, 3-chlorobenzyl, 4-chlorobenzyl, or 3,4-dichlorobenzyl, and $R_2$ is benzyl, 3-chlorobenzyl, or 3,4-dichlorobenzyl.

In one embodiment, $R_1$ is isobutyl, benzyl, 4-(dimethylamino)benzyl, 4-methylbenzyl, 4-tert-butylbenzyl, 4-methoxybenzyl, 3-chlorobenzyl, 4-chlorobenzyl, or 3,4-dichlorobenzyl, $R_2$ is isobutyl, benzyl, naphthalen-1-ylmethyl, 4-methylbenzyl, 4-chlorobenzyl, or 3,4-dichlorobenzyl, and $R_3$ is isobutyl, isopentyl, or benzyl.

In one embodiment, $R_1$ is $C_{1-6}$ alkyl, hydroxy-substituted $C_{1-4}$ alkyl, carbamoyl-substituted $C_{1-4}$ alkyl, amino-substituted $C_{1-6}$ alkyl, amidinoamino-substituted $C_{1-4}$ alkyl, carboxy-substituted $C_{1-4}$ alkyl, $C_{1-4}$ alkoxycarbonyl-substituted $C_{1-4}$ alkyl, $C_{6-10}$ aryl $C_{1-4}$ alkyl, hydroxy-substituted $C_{6-10}$ aryl $C_{1-4}$ alkyl, $C_{1-4}$ alkoxy-substituted $C_{6-10}$ aryl $C_{1-4}$ alkyl, halo-substituted $C_{6-10}$ aryl $C_{1-4}$ alkyl, or $C_{5-6}$ cycloalkyl $C_{1-4}$ alkyl.

In one embodiment, $R_1$ is methyl, isopropyl, isobutyl, isopentyl, n-hexyl, 3-amino-3-oxopropyl, 3-(tert-butoxy)-3-oxopropyl, benzyl, naphthalen-1-ylmethyl, 2-carboxyethyl, carbamoylmethyl, 3-(amidinoamino)propyl, 4-fluorobenzyl, 4-hydroxybenzyl, 4-(tert-butoxy)benzyl, 3,4-dichlorobenzyl, naphthalen-1-ylmethyl, phenethyl, hydroxymethyl, 2-hydroxyethyl, or cyclohexylmethyl.

In one embodiment, $R_1$ is methyl, isopropyl, isobutyl, isopentyl, n-hexyl, 2-hydroxyethyl, carbamoylmethyl, 3-amino-3-oxopropyl, 3-(amidinoamino)propyl, 2-carboxyethyl, benzyl, phenethyl, naphthalen-1-ylmethyl, 4-hydroxybenzyl, 4-fluorobenzyl, 3,4-dichlorobenzyl, 4-(tert-butoxy)benzyl, 3-(tert-butoxy)-3-oxopropyl, hydroxymethyl, cyclohexylmethyl, or

[Chemical Formula 23]

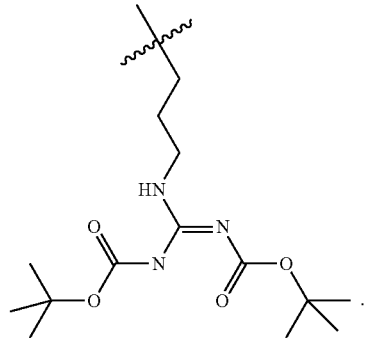

(This group is also represented as (tBOC)Gun-Pr)

In one embodiment, $R_1$ is methyl, isobutyl, isopentyl, 3-(tert-butoxy)-3-oxopropyl, benzyl, naphthalen-1-ylmethyl, 4-hydroxybenzyl, 4-(tert-butoxy)benzyl, 3,4-dichlorobenzyl, or cyclohexylmethyl.

In one embodiment, $R_1$ is isopropyl, isobutyl, isopentyl, n-hexyl, cyclohexylmethyl, benzyl, phenethyl, naphthalen-1-ylmethyl, 4-hydroxybenzyl, 4-fluorobenzyl, 2-carboxyethyl, carbamoylmethyl, carbamoylethyl, 3-(amidinoamino)propyl, hydroxymethyl, or hydroxyethyl.

In one embodiment, $R_1$ is isobutyl, isopentyl, cyclohexylmethyl, benzyl, phenethyl, naphthalen-1-ylmethyl, 4-hydroxybenzyl, 4-fluorobenzyl, 2-carboxyethyl, carbamoylmethyl, 3-(amidinoamino)propyl, or hydroxyethyl.

In one embodiment, $R_1$ is isobutyl, benzyl, 4-hydroxybenzyl, 2-carboxyethyl, 3-(amidinoamino)propyl, or naphthalen-1-ylmethyl.

In one embodiment, $R_1$ is isobutyl, 3-(amidinoamino)propyl, 2-carboxyethyl, benzyl, naphthalen-1-ylmethyl, 4-hydroxybenzyl, 4-(tert-butoxy)benzyl, 3-(tert-butoxy)-3-oxopropyl, or

[Chemical Formula 24]

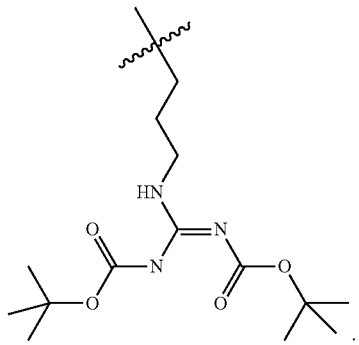

In one embodiment, $R_1$ is isobutyl, 3-hydroxypropyl, 3-amino-3-oxopropyl, 6-aminohexyl, 2-carboxyethyl, benzyl, naphthalen-1-ylmethyl, 4-hydroxybenzyl, or cyclohexylmethyl.

In one embodiment, $R_2$ is $C_{1-4}$ alkyl, hydroxy-substituted $C_{1-4}$ alkyl, carbamoyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkoxycarbonyl-substituted 5- to 10-membered heteroaryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, halogen-substituted $C_{6-10}$ aryl $C_{1-4}$ alkyl, $C_{1-4}$ alkoxy-substituted $C_{6-10}$ aryl $C_{1-4}$ alkyl, $C_{1-4}$ alkoxycarbonyl-substituted $C_{1-4}$ alkyl, $C_{1-4}$ alkoxycarbonylamino-substituted $C_{1-4}$ alkyl, 5- to 6-membered heterocycloalkyl-substituted $C_{1-4}$ alkyl, or $C_{5-6}$ cycloalkyl $C_{1-4}$ alkyl.

In one embodiment, $R_2$ is naphthalen-1-ylmethyl or optionally substituted benzyl.

In one embodiment, $R_2$ is isopropyl, 1-methylpropyl, isobutyl, isopentyl, n-hexyl, hydroxymethyl, 2-hydroxyethyl, carbamoylmethyl, 3-amino-3-oxopropyl, 3-(amidinoamino)propyl, 4-aminobutyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 4-fluorobenzyl, 3-chlorobenzyl, 4-chlorobenzyl, 3,4-dichlorobenzyl, 4-(tert-butoxy)benzyl, 2-(tert-butoxy)-2-oxoethyl, 4-((tert-butoxycarbonyl)amino)butyl, (tetrahydro-2H-pyran-2-yl)methyl, or cyclohexylmethyl.

In one embodiment, $R_2$ is isopropyl, 1-methylpropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 2-naphthalen-1-yl)ethyl, 2-(1-(tert-butoxycarbonyl)-1H-indol-3-yl)ethyl, 3-methylbenzyl, 4-methylbenzyl, 4-hydroxybenzyl, 4-fluorobenzyl, 3-chlorobenzyl, 4-chlorobenzyl, 3,4-dichlorobenzyl, 4-(tert-butoxy)benzyl, 2-(tert-butoxy)-2-oxoethyl, 3-(tert-butoxy)-3-oxopropyl, 4-((tert-butoxycarbonyl)amino)butyl, (tetrahydro-2H-pyran-2-yl)methyl, cyclohexylmethyl, or

[Chemical Formula 25]

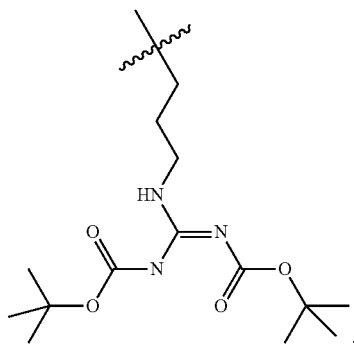

In one embodiment, $R_2$ is isobutyl, 2-hydroxyethyl, 3-amino-3-oxopropyl, 4-aminobutyl, 2-carboxyethyl, benzyl, phenethyl, naphthalen-1-ylmethyl, 2-(naphthalen-1-yl)ethyl, 2-(1-(tert-butoxycarbonyl)-1H-indol-3-yl)ethyl, 3-methylbenzyl, 4-methylbenzyl, 4-hydroxybenzyl, 3-chlorobenzyl, 4-chlorobenzyl, 3,4-dichlorobenzyl, 4-(tert-butoxy)benzyl, 2-(tert-butoxy)-2-oxoethyl, 4-((tert-butoxycarbonyl)amino)butyl, (tetrahydro-2H-pyran-2-yl)methyl, or cyclohexylmethyl.

In one embodiment, $R_2$ is 1-methylpropyl, isopropyl, isobutyl, isopentyl, n-hexyl, benzyl, 4-hydroxybenzyl, 4-fluorobenzyl, 2-carboxyethyl, carbamoylmethyl, carbamoylethyl, 3-(amidinoamino)propyl, hydroxymethyl, 2-hydroxyethyl, phenethyl, naphthalen-1-ylmethyl, or cyclohexylmethyl.

In one embodiment, $R_2$ is isopropyl, 1-methylpropyl, isobutyl, 3-(amidinoamino)propyl, 2-carboxyethyl, benzyl, naphthalen-1-ylmethyl, 4-hydroxybenzyl, 4-(tert-butoxy)benzyl, 3-(tert-butoxy)-3-oxopropyl, or

[Chemical Formula 26]

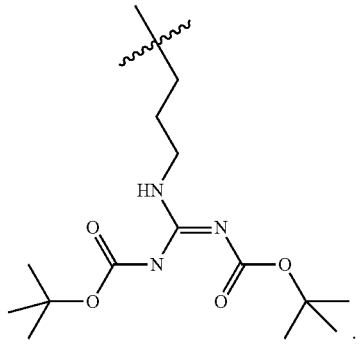

In one embodiment, $R_2$ is isopropyl, isobutyl, isopentyl, benzyl, 4-hydroxybenzyl, 4-fluorobenzyl, 2-carboxyethyl, carbamoylmethyl, 3-(amidinoamino)propyl, hydroxyethyl, phenethyl, naphthalen-1-ylmethyl, or n-hexyl.

In one embodiment, $R_2$ is isobutyl, 2-hydroxyethyl, 3-amino-3-oxopropyl, 4-aminobutyl, 2-carboxyethyl, benzyl, phenethyl, naphthalen-1-ylmethyl, 3-methylbenzyl, 4-methylbenzyl, 4-hydroxybenzyl, cyclohexylmethyl, or 2-(1H-indol-3-yl)ethyl.

In one embodiment, $R_2$ is 1-methylpropyl, isopropyl, isobutyl, benzyl, 4-hydroxybenzyl, 2-carboxyethyl, 3-(amidinoamino)propyl, or naphthalen-1-ylmethyl.

In one embodiment, $R_3$ is $C_{1-4}$ alkyl, hydroxy-substituted $C_{1-4}$ alkyl, carbamoyl-substituted $C_{1-4}$ alkyl, $C_{1-4}$ alkoxycarbonyl-substituted $C_{1-4}$ alkyl, amino-substituted $C_{1-4}$ alkyl, amidinoamino-substituted $C_{1-4}$ alkyl, carboxy-substituted $C_{1-4}$ alkyl, $C_{6-10}$ aryl $C_{1-4}$ alkyl, $C_{1-4}$ alkyl-substituted $C_{6-10}$ aryl $C_{1-4}$ alkyl, hydroxy-substituted $C_{6-10}$ aryl $C_{1-4}$ alkyl, or $C_{5-6}$ cycloalkyl $C_{1-4}$ alkyl.

In one embodiment, $R_3$ is isopropyl, isobutyl, isopentyl, n-hexyl, 3-amino-3-oxopropyl, 3-methoxy-3-oxopropyl, 4-aminobutyl, 2-carboxyethyl, carbamoylmethyl, 3-(amidinoamino)propyl, benzyl, naphthalen-1-ylmethyl, phenethyl, hydroxymethyl, 2-hydroxyethyl, 4-fluorobenzyl, 3-methylbenzyl, 4-methylbenzyl, 4-hydroxybenzyl, 4-((tert-butoxycarbonyl)amino)butyl, or cyclohexylmethyl.

In one embodiment, $R_3$ is isopropyl, isobutyl, isopentyl, n-hexyl, hydroxymethyl, 2-hydroxyethyl, carbamoylmethyl, 3-amino-3-oxopropyl, 4-aminobutyl, 3-(amidinoamino)propyl, 2-carboxyethyl, benzyl, phenethyl, naphthalen-1-ylmethyl, 3-methylbenzyl, 4-methylbenzyl, 4-hydroxybenzyl, 4-fluorobenzyl, 4-(tert-butoxy)benzyl, 3-methoxy-3-oxopropyl, 3-(tert-butoxy)-3-oxopropyl, 4-((tert-butoxycarbonyl)amino)butyl, cyclohexylmethyl, or

[Chemical Formula 27]

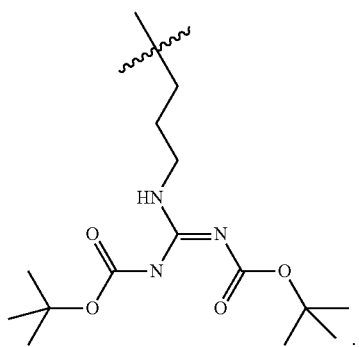

In one embodiment, $R_3$ is isobutyl, isopentyl, 3-amino-3-oxopropyl, 3-methoxy-3-oxopropyl, 4-aminobutyl, 2-carboxyethyl, benzyl, phenethyl, 3-methylbenzyl, 4-methylbenzyl, 4-hydroxybenzyl, 4-((tert-butoxycarbonyl)amino)butyl, or cyclohexylmethyl.

In one embodiment, $R_3$ is isopropyl, isobutyl, isopentyl, n-hexyl, cyclohexylmethyl, benzyl, phenethyl, naphthalen-1-ylmethyl, 4-hydroxybenzyl, 4-fluorobenzyl, 2-carboxyethyl, carbamoylmethyl, carbamoylethyl, 3-(amidinoamino)propyl, hydroxymethyl, or hydroxyethyl.

In one embodiment, $R_3$ is isobutyl, isopentyl, benzyl, phenethyl, 4-hydroxybenzyl, 2-carboxyethyl, carbamoylmethyl, 3-(amidinoamino)propyl, hydroxymethyl, or naphthalen-1-ylmethyl.

In one embodiment, $R_3$ is isobutyl, benzyl, 4-hydroxybenzyl, 2-carboxyethyl, 3-(amidinoamino)propyl, or naphthalen-1-ylmethyl.

In one embodiment, $R_3$ is isobutyl, 2-carboxyethyl, 3-(amidinoamino)propyl, benzyl, naphthalen-1-ylmethyl, 4-hydroxybenzyl, 4-(tert-butoxy)benzyl, 3-(tert-butoxy)-3-oxopropyl, or

[Chemical Formula 28]

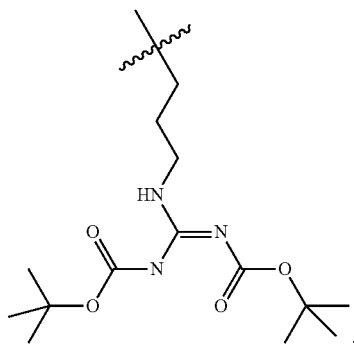

In one embodiment, $R_3$ is isobutyl, hydroxymethyl, 3-amino-3-oxopropyl, 4-aminobutyl, 2-carboxyethyl, benzyl, 2-naphthylmethyl, 4-hydroxybenzyl, or cyclohexylmethyl.

In one embodiment, $R_1$ is $C_{1-6}$ alkyl or $C_{6-10}$ aryl $C_{1-6}$ alkyl, and $R_2$ and $R_3$ are each independently $C_{1-6}$ alkyl or optionally substituted $C_{6-10}$ aryl $C_{1-6}$ alkyl.

In one embodiment, $R_1$ is isobutyl, isopentyl, or benzyl, $R_2$ is isobutyl, benzyl, phenethyl, 3-methylbenzyl, 4-methylbenzyl, or 3,4-dichlorobenzyl, and $R_3$ is isobutyl, benzyl, phenethyl, 3-methylbenzyl, or 4-methylbenzyl.

In one embodiment, $R_1$ is isobutyl, $R_2$ is benzyl, and $R_3$ is benzyl.

In one embodiment, $R_1$ is benzyl, $R_2$ is benzyl, and $R_3$ is isobutyl.

In one embodiment, $R_1$ is isobutyl, $R_2$ is benzyl, and $R_3$ is 3-methylbenzyl.

In one embodiment, $R_1$ is benzyl, $R_2$ is 3,4-dichlorobenzyl, and $R_3$ is isobutyl.

In one embodiment, $R_1$ is isobutyl, $R_2$ is 4-methylbenzyl, and $R_3$ is benzyl.

In one embodiment, $R_1$ is benzyl, $R_2$ is isobutyl, and $R_3$ is isobutyl.

In one embodiment, $R_4$ is hydrogen, optionally substituted alkyl, optionally substituted alkylcarbonyl, optionally substituted arylcarbonyl, or optionally substituted alkoxycarbonyl.

In one embodiment, $R_4$ is hydrogen, optionally substituted $C_{1-6}$ alkyl, optionally substituted $C_{1-6}$ alkylcarbonyl, optionally substituted $C_{6-10}$ arylcarbonyl, optionally substituted $C_{1-6}$ alkoxycarbonyl, or optionally substituted $C_{1-6}$ alkylcarbamoyl.

In one embodiment, $R_4$ is hydrogen, optionally substituted $C_{1-6}$ alkyl, optionally substituted $C_{1-6}$ alkylcarbonyl, optionally substituted $C_{6-10}$ arylcarbonyl, or optionally substituted $C_{1-6}$ alkoxycarbonyl.

In one embodiment, $R_4$ is hydrogen, $C_{1-6}$ alkyl, $C_{1-6}$ alkylcarbonyl, $C_{6-10}$ arylcarbonyl, $C_{1-6}$ alkoxycarbonyl, or $C_{1-6}$ alkylcarbamoyl.

In one embodiment, $R_4$ is hydrogen, $C_{1-6}$ alkyl, $C_{1-6}$ alkylcarbonyl, $C_{6-10}$ arylcarbonyl, or $C_{1-6}$ alkoxycarbonyl.

In one embodiment, $R_4$ is hydrogen, $C_{1-4}$ alkyl, $C_{1-4}$ alkylcarbonyl, $C_6$ arylcarbonyl, $C_{1-4}$ alkoxycarbonyl, or $C_{1-4}$ alkylcarbamoyl.

In one embodiment, $R_4$ is hydrogen, $C_{1-4}$ alkyl, $C_{1-4}$ alkylcarbonyl, $C_6$ arylcarbonyl, or $C_{1-4}$ alkoxycarbonyl.

In one embodiment, $R_4$ is hydrogen or alkyl.

In one embodiment, $R_4$ is hydrogen or $C_{1-6}$ alkyl.

In one embodiment, $R_4$ is hydrogen, methyl, ethyl, acetyl, benzoyl, methoxycarbonyl, tert-butoxycarbonyl, or propylcarbamoyl.

In one embodiment, $R_4$ is hydrogen, methyl, ethyl, acetyl, benzoyl, methoxycarbonyl, or tert-butoxycarbonyl.

In one embodiment, $R_4$ is hydrogen or ethyl. In a preferred embodiment, $R_4$ is hydrogen.

A hydroxyl group, amino group, and/or carboxyl group in $R_1$, $R_2$, $R_3$, and/or $R_4$, when present, can be independently protected with a protecting group. Such a compound is also within the scope of the present disclosure.

In some embodiments, the compound of the present disclosure can be exemplified as a compound represented by formula IB:

[Chemical Formula 29]

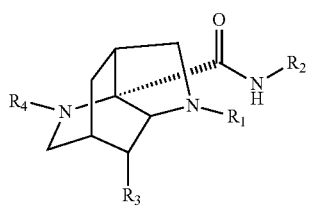

Formula IB or an enantiomer thereof, or a salt thereof, or a solvate thereof. $R_1$, $R_2$, and $R_3$ in formula IB are defined the same as those in formula IF.

In some embodiments, the compound of the present disclosure can be exemplified as a compound represented by formula IIF:

[Chemical Formula 30]

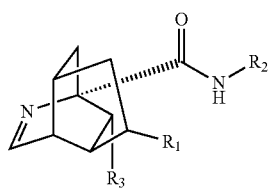

Formula IIF or an enantiomer thereof, or a salt thereof, or a solvate thereof. $R_1$, $R_2$, and $R_3$ in formula IIF are defined the same as those in formula IF.

In some embodiments, the compound of the present disclosure can be exemplified as a compound represented by formula IIB:

[Chemical Formula 31]

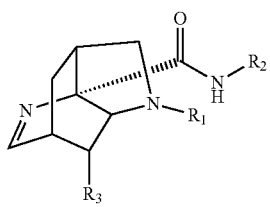

Formula IIB or an enantiomer thereof, or a salt thereof, or a solvate thereof. $R_1$, $R_2$, and $R_3$ in formula IIB are defined the same as those in formula IF.

The compound of the present disclosure is further described hereinafter.

While the compound of the present disclosure can have enantiomers and stereoisomers such as tautomers and geometric isomers depending on the type of substituent, they are also encompassed by the present disclosure. Specifically, if there is one or more asymmetric carbon atoms in the compound of the present disclosure, there is a diastereomer or enantiomer, and a mixture of such a diastereomer and enantiomer, and isolated diastereomers and enantiomers are also encompassed by the compound of the present disclosure.

The present disclosure is also intended to encompass various hydrates, solvates, and crystalline polymorphisms.

Furthermore, the compound of the present disclosure can be substituted with an isotope (e.g., $^2$H (or D), $^3$H (or T), $^{11}$C, $^{13}$C, $^{14}$C, $^{13}$N, $^{15}$N, $^{15}$O, $^{35}$S, $^{18}$F, $^{125}$I, or the like). These compounds are also encompassed by the compound of the present disclosure.

Furthermore, the scope of the present disclosure encompasses prodrugs of the compound of the present disclosure. In the present disclosure, a prodrug refers to a derivative that yields a compound represented by formula IF, IB, IIF, IIB, XXIF, XXIB, XXIIF, or XXIIB, or a related structural formula by acid hydrolysis or enzymatic degradation in the body. For example, if a compound represented by formula IF, IB, IIF, IIB, XXIF, XXIB, XXIIF, or XXIIB, or a related structural formula thereof has a functional group such as a hydroxyl group, amino group, or carboxyl group or other substituents, these groups can be modified by a conventional method to manufacture a prodrug. Prodrug technologies are described in, for example, C. G. Wermuth, "The Practice of Medicinal Chemistry", 4$^{th}$Ed., Academic Press, (2015), Chapter 28.

Examples for compounds having a carboxy group include compound whose carboxyl group is modified to be an alkoxycarbonyl group, alkylthiocarbonyl group, or alkylaminocarbonyl group.

Examples of compounds having an amino group include compounds whose amino group is substituted with an alkanoyl group to be an alkanoylamino group, compounds substituted with an alkoxycarbonyl group to be an alkoxycarbonylamino group, compounds modified to have an alkanoyloxymethylamino group, and compounds modified to have hydroxylamine.

Examples for compounds having a hydroxyl group include compounds whose hydroxyl group is substituted with an alkanoyl group to be an alkanoyloxy group, phosphate ester, or alkanoyloxymethyloxy group.

Examples of the alkyl moiety of a group used for preparing a prodrug thereof include the alkyl group. The alkyl group is optionally substituted with, for example, an alkoxy group or the like. Preferred examples thereof include the following.

For compounds whose carboxyl group is modified to be an alkoxycarbonyl group, examples thereof include alkoxycarbonyl such as methoxycarbonyl and ethoxycarbony, and alkoxycarbonyl substituted with an alkoxy group such as methoxymethoxycarbonyl, ethoxymethoxycarbonyl, 2-methoxyethoxycarbonyl, and 2-methoxyethoxymethoxycarbonyl, or privaloyloxymethoxycarbonyl.

As used herein, "pharmaceutically acceptable salt" refers to an acid addition salt or base addition salt which is pharmaceutically acceptable for use. Specific examples of "pharmaceutically acceptable salts" include, but are not limited to, acid addition salts such as acetate, propionate, butyrate, formate, trifluoroacetate, maleate, fumarate, tartrate, citrate, stearate, succinate, ethylsuccinate, malonate, lactobionate, gluconate, glucoheptonate, benzoate, methanesulfonate, benzenesulfonate, para-toluenesulfonate (tosylate), laurylsulfate, malate, ascorbate, mandelate, saccharinate, xinafoate, pamoate, cinnamate, adipate, cysteine salt, N-acetyl cysteine salt, hydrochloride, hydrobromide, phosphate, sulfate, hydroiodide, nicotinate, oxalate, picrate, thiocyanate, undecanoate, acrylic acid polymer salt, and carboxyvinyl polymer; inorganic base addition salts such as lithium salt, sodium salt, potassium salt, and calcium salt; organic base addition salts such as morpholine and piperidine; amino acid addition salts such as aspartic acid and glutamic acid; and the like.

In one embodiment, the compound of the present disclosure can be administered directly, or as a formulation, medicament, or a pharmaceutical composition using a suitable dosage form, by oral or parenteral administration. Specific examples of such dosage forms include, but are not limited to, tablets, capsules, powdered agents, granules, liquid agents, suspension, injection agents, patch-on agents, poultice, and the like. These formulations can be manufactured by a known method using an additive that is commonly used as a pharmaceutical additive.

As these additives, an excipient, disintegrant, binding agent, fluidizer, lubricant, coating agent, solubilizing agent, solubilizing promotor, thickener, dispersant, stabilizer, sweetener, flavoring agent, or the like can be used depending on the objective. Specific examples of these additives include, but are not limited to, lactose, mannitol, crystalline cellulose, low-substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, talc, and the like.

The dosage of the compound of the present disclosure is appropriately selected depending on the subject targeted for administration, route of administration, disease, age of subject, body weight, and symptom. For example, the dosage is 0.01 mg as the lower limit (preferably 100 mg) and 10000 mg as the upper limit (preferably 6000 mg) per day for adults for oral administration. This amount can be administered once daily, or divided into several doses.

In one embodiment, the compound of the present disclosure is a compound with an antiviral activity for a virus in the Lyssavirus genus. The virus in the Lyssavirus genus comprises a rabies virus, Lagos bat virus, mokola virus, Duvenhage virus, European bat 1 lyssavirus, European bat 2 lyssavirus, Australian bat lyssavirus, and the like. The virus in the Lyssavirus genus preferably comprises a rabies virus.

In one embodiment, the compound of the present disclosure is a compound with the ability to suppress or kill tumor or cancer. The tumor or cancer can be any tumor or cancer such as carcinoma, lymphoma, blastoma, sarcoma, or leukemia. Tumor and cancer can be squamous cell carcinoma, lung cancer such as small cell lung cancer, non-small cell lung cancer, or pulmonary adenocarcinoma, squamous cell carcinoma of the lung, peritoneal cancer, hepatoma, esophageal cancer, gastrointestinal cancer, pancreatic cancer, glioblastoma, uterine cancer such as cervical cancer, ovarian cancer, liver cancer, hepatocellular cancer, bladder cancer, hepatocellular carcinoma, breast cancer, colon cancer, colorectal cancer, epithelial or uterine carcinoma, salivary gland carcinoma, kidney cancer, liver cancer, prostate cancer, vulvar cancer, thyroid cancer, liver carcinoma, various types of head and neck cancer, blood cancer (leukemia), prostate cancer, gastric cancer, fibrous cancer, glioma, melanoma, or the like.

The timing of dosing of the compound of the present disclosure and therapeutic agents thereof is not limited. The compound and therapeutic agent can be administered concurrently or sequentially to a subject being administered therewith. The compound of the present disclosure and therapeutic agent thereof can be formulated as a combined agent. The dosage of the therapeutic agent can be appropriately selected based on the clinically used dose. The ratio of the compound of the present disclosure and therapeutic agent thereof can be appropriately selected depending on the subject of administration, route of administration, target disease, symptom, combination, or the like.

In one embodiment of the present disclosure, the compound of the present disclosure can be combined and administered concurrently or at different times upon use of a pharmaceutical composition. Such a pharmaceutical composition is also within the scope of the present disclosure.

Such a medicament, formulation, or pharmaceutical composition can be manufactured by mixing the compound of the present disclosure and/or an addition agent (e.g., anti-rabies gamma globulin formulation, antimicrobial agent, antiviral agent (e.g., ribavirin, amantadine, or the like), sedative (e.g., ketamine, midazolam, or the like) or the like) with any suitable component, together or separately, as a combined agent, or as separate agents using any technology that is known in the art. An appropriate formulation such as a tablet, capsule, powder, granule, liquid agent, suspension, injection, patch, or poultice can be formulated by using any technology that is known in the art. If the compound of the present disclosure and/or an addition agent (e.g., anti-rabies gamma globulin formulation, antimicrobial agent, antiviral agent (e.g., ribavirin, amantadine, or the like), sedative (e.g., ketamine, midazolam, or the like) or the like) are prepared as separate agents, they can be provided as a kit of two agents. The kit can provide one of the components as a single agent, with instructions (package insert or the like) instructing to combine and administer the other component (for the compound of the present disclosure, the additional agent; for the addition agent (e.g., anti-rabies gamma globulin formulation, antimicrobial agent, antiviral agent (e.g., ribavirin, amantadine, or the like), sedative (e.g., ketamine, midazolam, or the like) or the like), the compound of the present disclosure) concurrently or at different times.

If the compound of the present disclosure is used as an active ingredient of a medicament, the compound is intended for use in not just humans, but also other animals other than humans (cat, dog, cow, horse, bat, fox, mangoose, raccoon, and the like).

(Method of Manufacturing the Compound of the Present Disclosure)

Hereinafter, the method of manufacturing the compound of the present disclosure is described with examples, but the present disclosure is not limited thereto.

The compound of the present disclosure can be manufactured by, for example, the following manufacturing methods, but are not limited to such methods. These manufacturing methods can be appropriately improved upon based on the expertise of those skilled in the art of organic synthetic chemistry. Salts of the compounds used as a raw material can be used in the following manufacturing method, as long as the reaction is not affected.

In the following manufacturing methods, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in the document (Peter G. M. Wuts, "Greene's Protective Groups in Organic Synthesis", 5th Ed., John Wiley & Sons, Inc., Hoboken, New Jersey (2014)) or the like can be used as the protecting groups used in these processes. A protecting group can be introduced or removed by a method that is commonly used in organic synthetic chemistry (e.g., method described in the aforementioned document or the like) or a method in accordance thereto.

The starting material and intermediate in the following manufacturing methods can be purchased as a commercially available product or are available by synthesis in accordance with a method described in a known document or a known method from a known compound. Salts of the starting material and intermediate can also be used, as long as the reaction is not affected.

The intermediate and compound of interest in the following manufacturing methods can also be converted into another compound encompassed by the present disclosure by appropriately converting their functional groups. A functional group can be converted in doing so by a method that is commonly used in organic synthetic chemistry (e.g., method described in R. C. Larock, "Comprehensive Organic Transformations", 2nd Ed., John Wiley and Sons, Inc., New York (1999) or the like) or a method in accordance therewith.

An inert solvent in the following manufacturing methods refers to a solvent that does not react with a raw material, reagent, base, acid, catalyst, ligand, or the like used in the reaction (hereinafter, also referred to as "raw material or the like used in the reaction"). A solvent used in each step can be used as an inert solvent even if the solvent reacts with the raw material or the like used in the reaction, as long as the reaction of interest proceeds to result in a compound of interest.

The overview of compound synthesis related to the present disclosure is shown below. "B" and "F" following the Roman numeral compound number indicate that a 5-membered ring comprising nitrogen is located in the "back" and "front", respectively. In other words, a —C(=O)NH—R$_2$ group attached to a 5-membered ring comprising nitrogen referred to as "back", and a —C(=O)NH—R$_2$ that is not attached to a 5-membered ring comprising nitrogen is referred to as "front".

Synthesis Scheme 1

Synthesis of Compound III

Compound III can be manufactured by, for example, the following manufacturing method.

(1) Route 1-1 Synthesis from Compound VII and Compound VIII

[Chemical Formula 32]

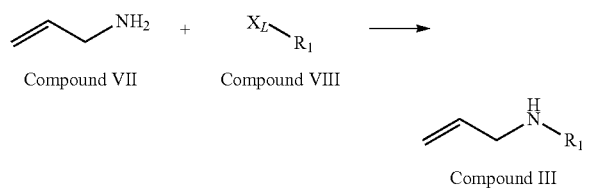

(2) Route 1-2 Synthesis from Compound VII and Compound VIII through Protection of Amine

[Chemical Formula 33]

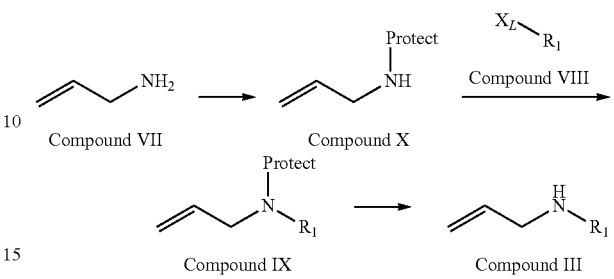

(3) Route 1-3 Synthesis from Compound XI and Compound XII

[Chemical Formula 34]

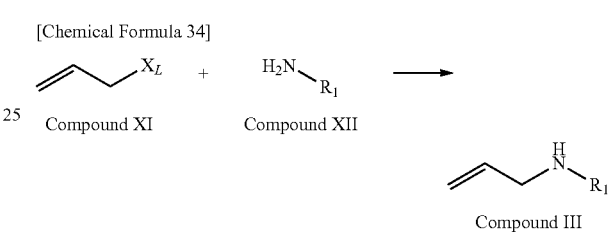

wherein $X_L$ represents a leaving group in a nucleophilic substitution reaction. Examples thereof include halogen (e.g., chlorine, bromine, or iodine), sulfate esters (—OSO$_3$H and the like), and sulfonyl-O— groups (e.g., methanesulfonyl-O—, toluenesulfonyl-O—, and the like).

(4) Route 1-4 Synthesis from Compound XI and Compound XIII

[Chemical Formula 35]

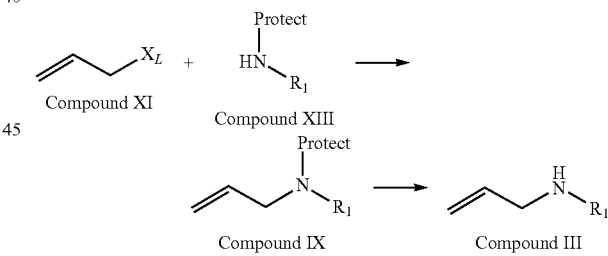

(5) Route 1-5 Synthesis from Compound VII and Compound XIV

[Chemical Formula 36]

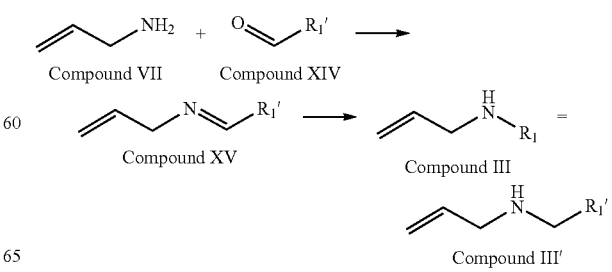

wherein if $R_1$ in compound III can be expressed as —$CH_2$—$R_1'$, $R_1$ in compound III can be replaced with —$CH_2$—$R_1'$ to express compound III as compound III'.

In the formula, $R_1$ is as defined in item 1 or A1 herein, and "Protect" is a protecting group of amino group. Examples of protecting groups of an amino group include an ethoxycarbonyl group, tert-butoxycarbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, trimethylsilyl group, benzyloxycarbonyl group, 3- or 4-chlorobenzyloxycarbonyl group, benzyl sulfonyl group, benzyl group, 4-nitrobenzyl group, 4-methoxybenzyl group, methyl group, ethyl group, and the like.

A compound that is commercially available or a compound manufactured by a known method can be used as a starting raw material compound.

Synthesis Scheme 2
Synthesis of compound V
A compound of formula V can be manufactured by, for example, the following manufacturing method.
(1) Route 2-1 Synthesis from Compound XVI and Compound XVII

[Chemical Formula 37]

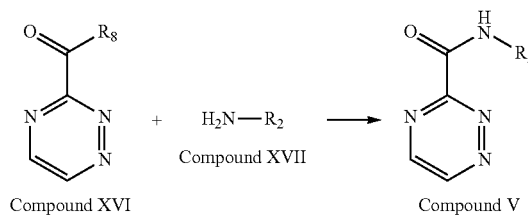

Compound XVI        Compound V wherein $R_8$ indicates alkoxy, aryloxy, hydroxy, or halogen. Examples thereof include an ethoxy group. This synthesis is achieved by various reactions known to those skilled in the art. If $R_2$ is aryl, compound V can be synthesized in accordance with the method described in C. W. Cheung, M. L. Ploeger, and X. Hu, Nature Communications 2017, 8, 14878.
(2) Route 2-2 Synthesis from Compound XVIII

[Chemical Formula 38]

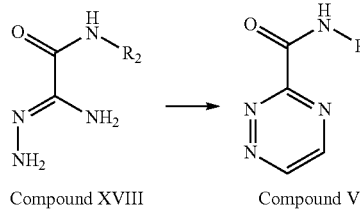

Compound XVIII        Compound V wherein $R_2$ is as defined in item 1 or A1 herein. A compound that is commercially available or a compound that is manufactured by a known method can be used as the starting compound.

Synthesis Scheme 3
Synthesis of Compound VI
A compound of formula VI can be manufactured from compound III and compound IV by, for example, the following manufacturing method.

[Chemical Formula 39]

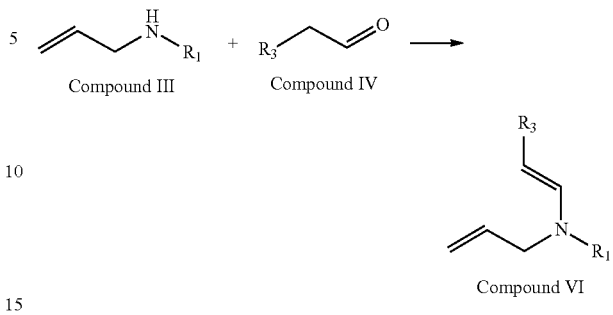

wherein $R_1$ and $R_3$ are as defined in item 1 or A1 herein.

Synthesis Scheme 4
Compound of Formula IIF and Compound of Formula IIB-Route 1
A compound of formula IIF and compound of formula IIB can be manufactured, for example, from three components through one-pot synthesis in accordance with a known method (e.g., method described in Bioorg. Med. Chem. 23 (2015) 2629-2635, Tetrahedron 63 (2007) 6004-6014, Eur. J. Org. Chem. 2009, 2185-2189, Eur. J. Org. Chem. 2011, 2354-2359 or the like).

[Chemical Formula 40]

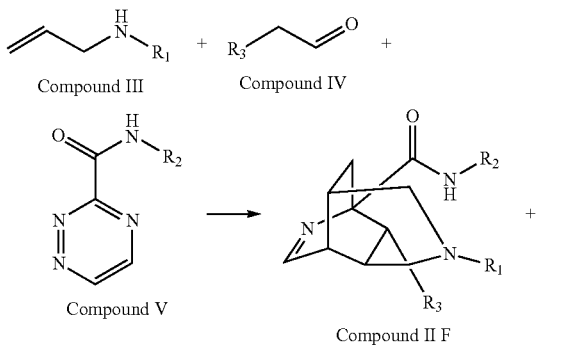

wherein $R_1$, $R_2$, and $R_3$ are as defined in item 1 or A1 herein.

Synthesis Scheme 5
Compound of Formula IIF and Compound of Formula IIB-Route 2
A compound of formula IIF and compound of formula IIB can be manufactured, for example, from two components as described below.

[Chemical Formula 41]

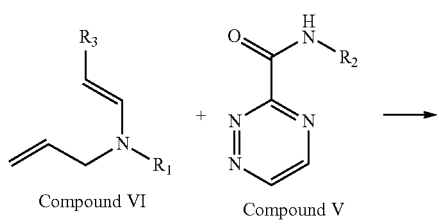

Compound VI    Compound V

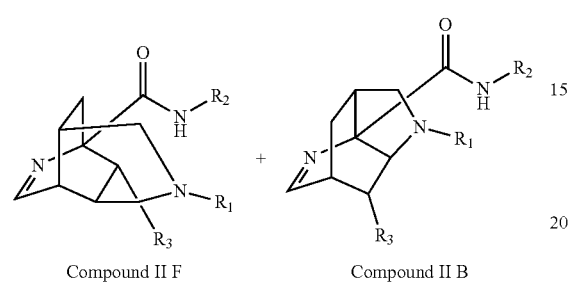

Compound II F    Compound II B wherein $R_1$, $R_2$, and $R_3$ are as defined in item 1 or A1 herein.

Synthesis Scheme 6

Synthesis of Compound IF and Compound IB

Step 6-1

Reduction of Imine

Compound IF (i.e., compound of formula IF) or compound IB (i.e., compound of formula IB) can be manufactured, for example, from compound IIF (i.e., compound of formula BF) or compound IIB (i.e., compound of formula IIB) by reduction as described below. However, $R_4$ therein is H.

[Chemical Formula 42]

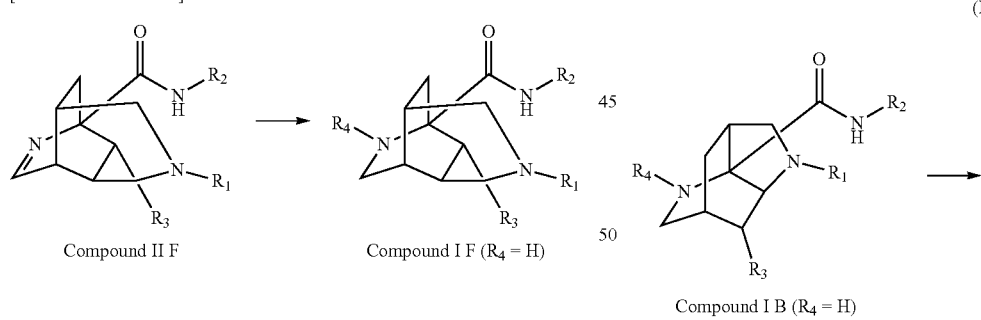

Compound II F    Compound I F ($R_4$ = H)

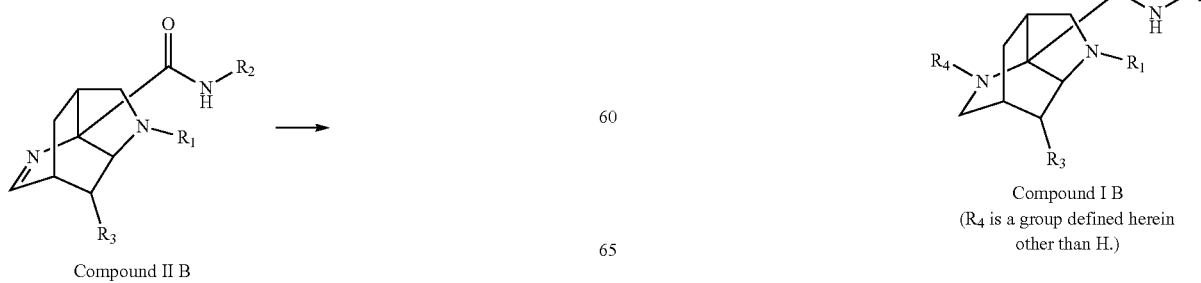

Compound II B

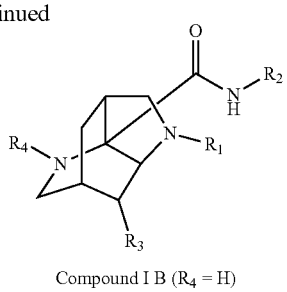

Compound I B ($R_4$ = H)

Step 6-2

Modification of Amine of Piperidine ring

Amine of a piperidine ring of compound IF or compound IB can be modified, for example by alkylation, amidation, or the like as follows.

[Chemical Formula 43]

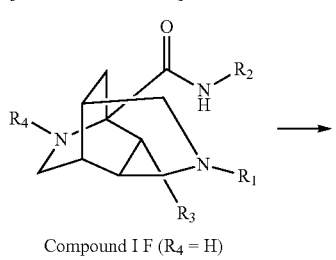

Compound I F ($R_4$ = H)

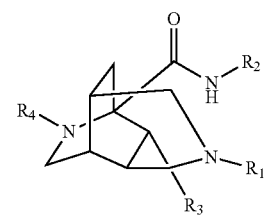

Compound I F
($R_4$ is a group defined herein other than H.)

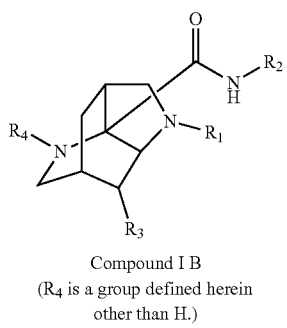

Compound I B ($R_4$ = H)

Compound I B
($R_4$ is a group defined herein other than H.)

Synthesis Scheme 7
Synthesis of Compound V'
A compound of formula V' can be manufactured by, for example, the following manufacturing method.
(1) Route 7-1 Synthesis from Compound XVI and Compound XVII'

[Chemical Formula 44]

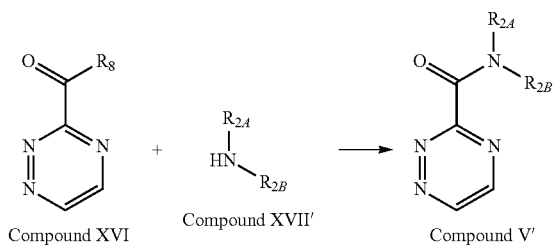

Compound XVI + Compound XVII' → Compound V'

A compound of formula V' can be manufactured under the same condition as Route 2-1 of Synthesis Scheme 2. $R_8$ indicates alkoxy, aryloxy, hydroxy, or halogen.
(2) Route 7-2 Synthesis from Compound XVIII'

[Chemical Formula 45]

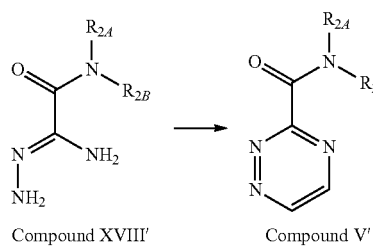

Compound XVIII' → Compound V' wherein $R_{2A}$ and $R_{2B}$ are as defined in item 1 herein. A compound that is commercially available or a compound manufactured by a known method can be used as a starting raw material compound.

Synthesis Scheme 8
Synthesis of Compound of Formula XXIIF and Compound of Formula XXIIB-Route 1
A compound of formula XXIIF and a compound of formula XXIIB can be synthesized under the same condition as Synthesis Scheme 4.

[Chemical Formula 46]

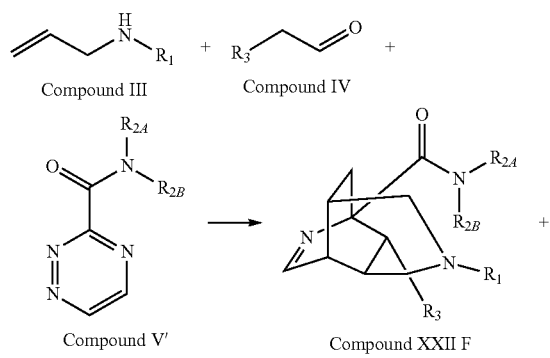

Compound III + Compound IV

Compound V' → Compound XXII F

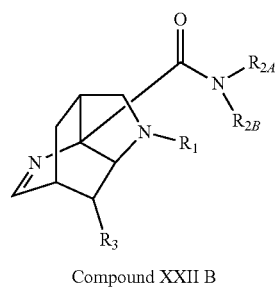

Compound XXII B wherein $R_1$, $R_{2A}$, $R_{2B}$, and $R_3$ are as defined in item 1 herein.

Synthesis Scheme 9
Synthesis of Compound of Formula XXIIF and Compound of Formula XXIIB-Route 2
A compound of formula XXIIF and compound of formula XXIIB can be manufactured, for example, from two components as described below.

[Chemical Formula 47]

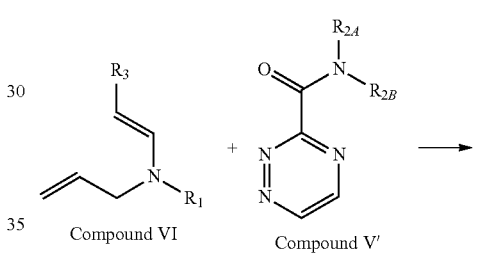

Compound VI + Compound V'

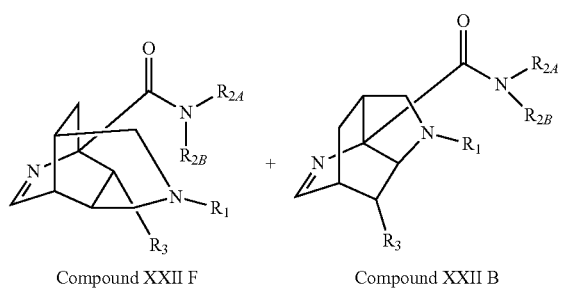

Compound XXII F       Compound XXII B wherein $R_1$, $R_{2A}$, $R_{2B}$, and $R_3$ are as defined in item 1 herein.

Synthesis Scheme 10
Synthesis of Compound XXIF and Compound XXIB
Step 10-1
Reduction of Imine
Under the same condition as step 6-1 of Synthesis Scheme 6, compound XXIF (i.e., compound of formula XXIF) or compound XXIB (i.e., compound of formula XXIB) can be manufactured, for example, from compound XXIIF (i.e., compound of formula XXIIF) or compound XXIIB (i.e., compound of formula XXIIB) by reduction as described below. However, $R_4$ therein is H.

[Chemical Formula 48]

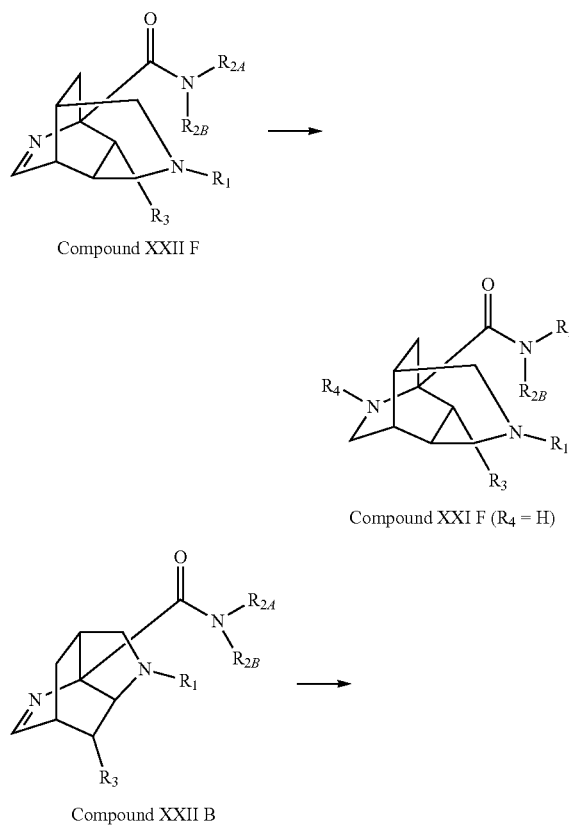

Compound XXII F

Compound XXI F (R₄ = H)

Compound XXII B

Compound XXI B (R₄ = H)

Step 10-2

Modification of Amine of Piperidine Ring

Amine of a piperidine ring in compound XXIF or compound XXIIB can be modified by, for example, alkylation, amidation, or the like as follows.

[Chemical Formula 49]

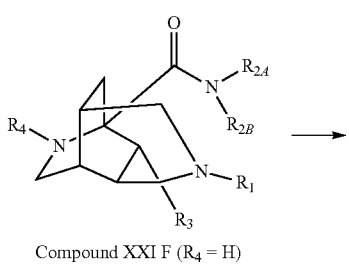

Compound XXI F (R₄ = H)

-continued

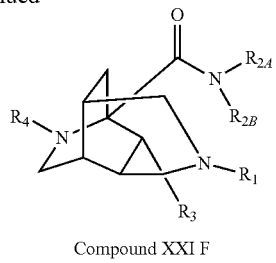

Compound XXI F

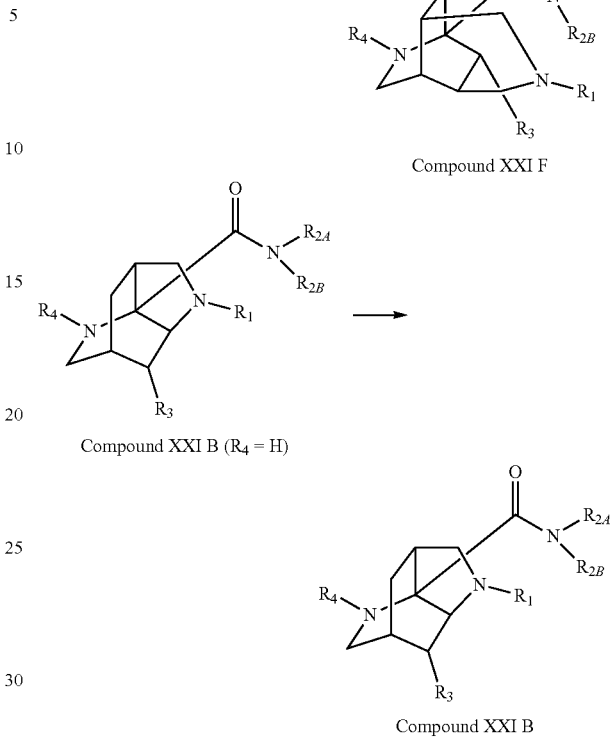

Compound XXI B (R₄ = H)

Compound XXI B

R₄ in the product of this step is a group defined herein other than H.

The intermediate and compound of interest in the manufacturing methods described above can be isolated and purified by subjecting them to a purification method that is commonly used in organic synthesis chemistry (e.g., neutralization, filtration, extraction, washing, drying, concentration, recrystallization, various chromatography, or the like). Each intermediate can also be subjected to the subsequent reaction without any particular purification.

Optically active forms of the compound of the present disclosure can be manufactured by using an optically active starting material or intermediate, or by optically resolving a racemate of the final product or intermediate. Examples of optional resolution methods include, but are not limited to, separation method using an optically active column or a separation method such as fractional crystallization method. A diastereomer of the compound of the present disclosure can be manufactured by, for example, but not limited to, a separation method such as column chromatography or fractional crystallization.

A pharmaceutically acceptable salt of a compound represented by formula IF, IB, IIF, IIB, XXIF, XXIB, XXIIF, or XXIIB, or a related structural formula can be manufactured by, for example, but not limited to, mixing a compound represented by formula IF, IB, IIF, IIB, XXIF, XXIB, XXIIF, or XXIIB, or a related structural formula with a pharmaceutically acceptable acid or base in a solvent such as water, methanol, ethanol, 2-propanol, ethyl acetate, or acetone.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure is specifically described based on the Examples. The scope of the present disclosure is not limited to the Examples described below.

For Thin Layer Chromatography (TLC), Merck's TLC Silica gel 60 F254 (25 glass plate, 20×20 cm) and Fuji Silysia Chemical's CHROMATOREX NH-TLC Plates (20× 20 cm) were used. As the developing solvent, chloroform-methanol mixed solvent system, ethyl acetate-methanol mixed solvent system, or ethyl acetate-hexane mixed solvent system was used. Spots were checked using coloring with UV irradiation, ninhydrin, iodine, or phosphomolybdic acid (ethanol solution). An organic solvent was dried using anhydrous sodium sulfate and anhydrous magnesium sulfate. For column chromatography, Fuji Silysia Chemical's cartridge column CHROMATOREX Q-PACKS 130 (SIZE 10, 20, or 60) and DNH (SIZE 20) or Shoko Science's Purif-Pack®-EX SI50 (SIZE 20 or 60) were used in accordance with the amount of raw product to be purified. Silica gel thin layer chromatography for separation (PTLC: Preparative Thin Layer Chromatography) used Merck's PLC Silica gel 60 F254 (20×20 cm; thickness: 0.5 mm; product number: 1.05744.0001; thickness: 1 mm; product number: 1.13895.0001) and Fuji Silysia Chemical's CHROMATOREX NH-PLC05 (20×20 cm; thickness: 0.5 mm). Synthesized compounds were identified by LC/MS (Liquid Chromatography/Mass Spectrometry). Tables 1 to 4 show the retention (tR) and m/z value $[M+1]^+$. For measurement, Shimadzu's LCMS-2020 system was used, and Chemicals Evaluation and Research Institute's L-column2 ODS, 3 µm, 3.0×50 mm was used as the analysis column. The column oven was set to 40° C., and compounds were detected by using both UV absorption (220 nm, 254 nm) and mass spectrometry. Elution condition A or B shown below was used.

Elution Condition A:

Flow rate 1.5 mL/min, mobile phase a=aqueous 0.05% (v/v) trifluoroacetic acid solution, mobile phase b=0.05% (v/v) trifluoroacetic acid containing acetonitrile; 0-0.9 minutes, linear gradient, A:B (95:5)-A:B (10:90), 0.9-2 minutes Elution Condition B:

Flow rate 1.0 mL/min, mobile phase a=aqueous 0.05% (v/v) formic acid solution, mobile phase b=0.05% (v/v) formic acid containing acetonitril; 0-0.9 minutes, linear gradient, A:B (95:5)-A:B (10:90), 0.9-2 minutes Elution Condition B1:

Flow rate 1.0 mL/min, mobile phase a=aqueous 0.05% (v/v) formic acid solution, mobile phase b=0.05% (v/v) formic acid containing acetonitrile; 0.1-2.0 minutes, linear gradient, A:B (95:5)-A:B (60:40), 2.0-3.0 minutes, linear gradient, A:B (60:40)-A:B (10:90), 3.0-4.0 minutes Furthermore, LC/MS measurement used the following instrument and measurement conditions.

Measurement Condition C:

Shimadzu's LCMS-2020 system was used, and Chemicals Evaluation and Research Institute's L-column2 ODS, 3 µm, 3.0×50 mm was used as the analysis column. The column oven was set to 40° C., and the compound was detected by using both UV absorption (220 nm, 254 nm) and mass spectrometry.

Elution condition: flow rate of 1.5 mL/min, mobile phase a=aqueous 0.05% (v/v) trifluoroacetic acid solution, mobile phase b=0.05% (v/v) trifluoroacetic acid containing acetonitrile

TABLE A1

| Time (min) | Ratio of mobile phase b (%) |
| --- | --- |
| 0.0 | 5 |
| 0.01-0..89 | 5-90 linear gradient |
| 0.9 | 90 |
| 2.00 | 90 |

Measurement Condition D:

The same apparatus as measurement condition C was used.

Elution condition: flow rate of 1.5 mL/min, mobile phase a=aqueous 0.05% (v/v) trifluoroacetic acid solution, mobile phase b=0.05% (v/v) trifluoroacetic acid containing acetonitrile

TABLE A2

| Time (min) | Ratio of mobile phase b (%) |
| --- | --- |
| 0.0 | 0 |
| 0.5 | 0 |
| 0.51-1.39 | 0-70 linear gradient |
| 1.4 | 70 |
| 1.5 | 90 |
| 2.00 | 90 |

Measurement Condition E:

The same apparatus as measurement condition C was used.

Elution condition: flow rate of 1.5 mL/min, mobile phase a=5 mM $NH_4HCO_3$ containing water/acetonitrile=900/100 (v/v), mobile phase b=5 mM $NH_4HCO_3$ containing water/acetonitrile=100/900 (v/v)

TABLE A3

| Time (min) | Ratio of mobile phase b (%) |
| --- | --- |
| 0.0 | 0 |
| 0.5 | 0 |
| 0.51-1.39 | 0-70 linear gradient |
| 1.4 | 70 |
| 1.5 | 90 |
| 2.00 | 90 |

Measurement Condition F:

Waters' Alliance 2695 Separation Module system was used, and YMC's YMC-Triart C18, 5 µm, 3.0×50 mm was used as the analysis column. The column oven was set to 30° C., and the compound was detected using both UV absorption (220 nm) and mass spectrometry.

Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A4

| Time (min) | Ratio of mobile phase b (%) |
| --- | --- |
| 0.0 | 10 |
| 1.0 | 10 |
| 1.0-1.5 | 10-30 gradient |
| 1.5-4.5 | 30-70 gradient |
| 4.5-5.0 | 70-90 gradient |
| 6.0 | 90 |

Measurement Condition G:

The same apparatus as measurement condition F was used.

Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A5

| Time (min) | Ratio of mobile phase b (%) |
| --- | --- |
| 0.0 | 1 |
| 1.0 | 1 |
| 1.0-4.0 | 1-40 gradient |
| 4.0-5.0 | 40-90 gradient |
| 6.0 | 90 |

Measurement Condition H:

Waters' 2767 system was used, and YMC's YMC-Triart C18, 5 μm, 4.6×50 mm was used as the analysis column. The column oven was set to 25° C., and compound was detected using UV absorption (220 nm), mass spectrometry, and ELS (Evaporative Light Scattering).

Elution condition: flow rate of 2 mL/min, mobile phase a=aqueous 0.1% (v/v) trifluoroacetic acid solution, mobile phase b=0.1% (v/v) trifluoroacetic acid containing acetonitrile

TABLE A6

| Time (min) | Ratio of mobile phase b (%) |
| --- | --- |
| 0.0 | 5 |
| 0.5 | 5 |
| 0.5-3.0 | 5-95 gradient |
| 5.0 | 95 |

Measurement Condition I:

Waters' H-class/SQD2 system was used, and Waters' ACQUITY UPLC BEH C18 1.7 μm, 2.1×50 mm was used as the analysis column. A compound was detected using both UV absorption (220 nm) and mass spectrometry.

Elution condition: flow rate of 0.6 mL/min, mobile phase a=aqueous 0.1% (v/v) formic acid solution, mobile phase b=0.1% (v/v) formic acid containing acetonitrile

TABLE A7

| Time (min) | Ratio of mobile phase b (%) |
| --- | --- |
| 0.0 | 2 |
| 2.0-2.6 | 2-100 |
| 2.6-3.0 | 100 |

Measurement Condition J:

The same apparatus as measurement condition F was used.

Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A8

| Time (min) | Ratio of mobile phase b (%) |
| --- | --- |
| 0.0 | 10 |
| 1.0 | 10 |
| 1.0-2.0 | 10-60 gradient |
| 2.0-5.0 | 60-99 gradient |
| 5.0-6.0 | 99 |

Nuclear Magnetic Resonance (NMR) was measured using Bruker AVANCE III 400 MHz Spectrometer (resonant frequency: $^1$H: 400 MHz, $^{13}$C: 100 MHz) and Bruker AVANCE III 300 MHz Spectrometer (resonant frequency: $^1$H: 300 MHz, $^{13}$C: 75 MHz). For the measurement of X-ray crystal structure, Rigaku Corporation's single crystal X-ray diffractometer XtaLAB P200 was used. Cu-K$_\alpha$ rays monochromed with a multilayer mirror were used as the source. The structure was determined by a direct method using SIR2008. The structure was refined by the full-matrix least-squares method with respect to F2 using SHELEX-2014/7. Non-hydrogen atoms were refined with anisotropic atomic displacement parameters.

The abbreviations described above and the following abbreviations are also used in the Examples to simplify the description.

s: singlet
d: doublet
t: triplet
m: multiplet
dd: double doublet
J: coupling constant
Hz: Hertz
δ: chemical shift
min: minute
RT and tR: retention
CDCl$_3$: deuterated chloroform
Me: methyl
Et: ethyl
Pr: propyl
i-Pr: isopropyl
i-Bu: isobutyl
s-Bu and sec-Bu: secondary butyl
$^t$Bu, tBu and tert-Bu: tertiary butyl
i-Pnt: isopentyl
Hxy: n-hexyl
Ac: acetyl
Bz: benzoyl
Bnzl: benzyl
3-Me-Bnzl: 3-methylbenzyl
4-Me-Bnzl: 4-methylbenzyl
3-MeO-Bnzl: 3-methoxybenzyl
4-MeO-Bnzl: 4-methoxybenzyl
4-OH-Bnzl: 4-hydroxybenzyl
3-F-Bnzl: 3-fluorobenzyl
4-F-Bnzl: 4-fluorobenzyl
3-Cl-Bnzl: 3-chlorobenzyl
4-Cl-Bnzl: 4-chlorobenzyl
3,4-Cl$_2$-Bnzl: 3,4-dichlorobenzyl
4-tBuO-Bnzl: 4-(tert-butoxy)benzyl
4-Nt-Bnzl: 4-nitrobenzyl
Cbx-E and 2-Cbx-Et: 2-carboxyethyl
Cbm-M: 2-amino-2-oxoethyl or carbamoylmethyl Cbm-E: 3-amino-3-oxopropyl or 2-carbamoylethyl
tBOC-E: 2-(tert-butoxycarbonyl)ethyl or 3-(tert-butoxy)-3-oxopropyl
Gun-Pr and 3-Gun-Pr: 3-guanidinopropyl
Hdr-M: hydroxymethyl
Hdr-E and 2-OH-Et: 2-hydroxyethyl
tBuO-E and 2-OtBu-Et: 2-(tert-butoxy)ethyl
Ph-Et: 2-phenylethyl
Ph-Pr: 3-phenylpropyl
Ph-Bu: 4-phenylbutyl
Np-M and 1-Npm: naphthalen-1-ylmethyl
2-Npm: naphthalen-2-ylmethyl
Np-E: 2-(naphthalen-1-yl)ethyl
Cpm: cyclopentylmethyl
Chm: cyclohexylmethyl
Boc and tBOC and 'BOC: tert-butoxycarbonyl
TBSO-E and 2-OTBS-Et: 2-(tert-butyldimethylsilyloxy)ethyl

[Chemical Formula 50]

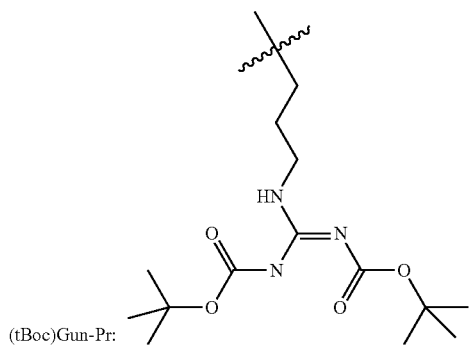

(tBoc)Gun-Pr:

Example 1: Synthesis of Compound

Synthesis Example for Compound V

Synthesis of N-benzyl-1,2,4-triazine-3-carboxamide

Ethyl 1,2,4-triazine-3-carboxylate (1.53 g, 10.0 mmol) was dissolved in methanol (10.0 mL), and phenylmethaneamine (1.18 g, 11.0 mmol) was added. The mixture was then stirred for 3 hours at 50° C. Methanol was evaporated under reduced pressure, and the resulting residue was purified by column chromatography (column: Purif-Pack Si50, Size 60, eluent: ethyl acetate-methanol (gradient from 0% to 15%)). A fraction of a compound of interest was concentrated. The eluted crystal was filtered out to obtain the aforementioned compound (1.25 g, yield: 58%).

Under the same conditions as this reaction, the following compounds were synthesized.
  N-(naphthalen-1-ylmethyl)-1,2,4-triazine-3-carboxamide
  tert-butyl (4-(1,2,4-triazine-3-carboxamide)butyl)carbamate
  N-(4-(tert-butoxy)benzyl)-1,2,4-triazine-3-carboxamide
  N-isobutyl-1,2,4-triazine-3-carboxamide
  N-(4-methylbenzyl)-1,2,4-triazine-3-carboxamide
  N-phenethyl-1,2,4-triazine-3-carboxamide
  N-(3-methylbenzyl)-1,2,4-triazine-3-carboxamide
  N-(3-chlorobenzyl)-1,2,4-triazine-3-carboxamide
  N-(4-chlorobenzyl)-1,2,4-triazine-3-carboxamide
  N-(2-(naphthalen-1-yl)ethyl)-1,2,4-triazine-3-carboxamide
  tert-butyl 3-(2-(1,2,4-triazine-3-carboxamide)ethyl)-1H-indol-1-carboxylate
  N-(3,4-dichlorobenzyl)-1,2,4-triazine-3-carboxamide Synthesis Example for Compound V Synthesis of N-(2-hydroxyethyl)-1,2,4-triazine-3-carboxamide Ethyl 1,2,4-triazine-3-carboxylate (76.5 mg, 0.500 mmol) was dissolved in ethanol (1.00 mL), and 2-aminoethanol (24.2 mg, 0.525 mmol) was added. The mixture was then stirred for 3 hours at room temperature. Methanol was evaporated under reduced pressure, and the resulting residue was purified by column chromatography (column: Purif-Pack Si50, Size 20, eluent: ethyl acetate-methanol (gradient from 0% to 30%)). A fraction of a compound of interest was concentrated to obtain the aforementioned compound (44.8 mg, yield: 53%).

Under the same conditions as this reaction, the following compound was synthesized.

N-(cyclohexylmethyl)-1,2,4-triazine-3-carboxamide

Synthesis Example for Compound V

Synthesis of tert-butyl 3-(1,2,4-triazine-3-carboxamide)propanoate

Triethylamine (0.245 mL, 1.75 mmol) was added to an ethanol (2.00 mL) solution of tert-butyl 3-aminopropanoate·HCl (272 mg, 1.50 mmol). A methanol (1.00 mL) suspension of ethyl 1,2,4-triazine-3-carboxylate (76.0 mg, 0.500 mmol) was added thereto. The mixture was stirred for 4 hours at room temperature. Ethanol was evaporated under reduced pressure. The residue was dissolved in ethyl acetate. The organic layer was washed with 10% citric acid water and 5% bicarbonate aqueous solution and dried with anhydrous sodium sulfate. The solvent was evaporated. The resulting residue was purified by column chromatography (column: Purif-Pack Si50, Size 20, eluent: hexane-ethyl acetate (gradient from 60% to 100%)) to obtain the aforementioned compound (65.7 mg, yield: 52%).

Synthesis Example for Compound XV

Synthesis of 4-methylpentanal

A methylene chloride (40.0 mL) solution of acetic acid (0.0994 mL, 1.30 mmol) and 4-methylpentan-1-ol (1.49 mL, 11.8 mmol) was slowly added dropwise into a methylene chloride (45.0 mL) solution of 1,1,1-triacetoxy-1,1-dihydro-1,2-benziodoxol-3-(1H)-one (Dess-Martin periodinane) (5.25 g, 12.4 mmol) at room temperature. After completion of the addition, the mixture was stirred for another hour, and then diethyl ether (280 mL) was added. An aqueous 1.30M sodium hydroxide solution (200 mL) was added to the organic layer and stirred for 10 minutes at room temperature. The organic layer was washed with an aqueous 1.30M sodium hydroxide solution (90.0 mL) and (50.0 mL). After drying with anhydrous sodium magnesium sulfate, the solvent was carefully evaporated to obtain the aforementioned compound (1.01 g, 86%).

Under the same conditions as this reaction, the following compound was synthesized.

5-methylhexanal

Synthesis Example for Compound III

Synthesis of N-benzylprop-2-en-1-amine (Bromomethyl)benzene (0.992 mL, 8.35 mmol) was gradually added dropwise to a suspension of anhydrous potassium carbonate (1.39 g, 10.0 mmol) and prop-2-en-1-amine (7.53 mL, 100 mmol) and then stirred for 3 hours at room temperature. The solids were filtered and washed with methylene chloride. The combined organic layer was evaporated under reduced pressure. The resulting residue was purified with CHROMATOREX Q-PACK SI30 SIZE 20 (hexane: ethyl acetate=50%:50% to 0%:100%) to obtain the aforementioned compound (934 mg, yield: 76%).

Under the same conditions as this reaction, the following compound was synthesized.

N-(3,4-dichlorobenzyl)prop-2-en-1-amine

Synthesis Example for Compound III

Synthesis of N-(cyclohexylmethyl)prop-2-en-1-amine

Prop-2-en-1-amine (3.42 g, 60.0 mmol) was added dropwise to a methanol (40.0 mL) solution of cyclohexanecarbaldehyde (7.06 g, 63.0 mmol) while cooling with ice. After the completion of the addition, sodium tetrahydroborate (0.850 g, 22.0 mmol) was resolved and added while cooling with ice, and the mixture was stirred for another hour. Methanol was evaporated under reduced pressure. Ethyl ether was added to the residue. The organic layer was washed with saturated saline and dried with anhydrous sodium sulfate and then concentrated under reduce pressure. The residue was evaporated under reduced pressure to obtain the aforementioned compound (7.35 g, 80%, boiling point, 79 to 84° C./9.1 mmHg).

Under the same conditions as this reaction, the following compounds were synthesized.
N-isobutylprop-2-en-1-amine
N-allyl-3-methylbutan-1-amine

Synthesis Example for Compound III

Synthesis of N-(4-tert-butoxybenzyl)prop-2-en-1-amine

A methanol (2.00 mL) solution of 4-tert-butoxybenzaldehyde (468 mg, 2.63 mmol) was added dropwise to a methanol (3.00 mL) solution of prop-2-en-1-amine (143 mg, 2.50 mmol) while cooling with ice. After the completion of the addition, sodium tetrahydroborate (35.0 mg, 0.920 mmol) was resolved and added while cooling with ice, and the mixture was stirred for another hour. Methanol was evaporated under reduced pressure. Ethyl acetate was added to the residue. The organic layer was washed with saturated saline and dried with anhydrous sodium sulfate and then concentrated under reduce pressure. The resulting residue was purified by column chromatography (column: Purif-Pack Si50, Size 60, eluent: hexane-ethyl acetate (gradient from 20% to 100%) and then ethyl acetate-methanol (gradient from 0% to 15%)) to obtain the aforementioned compound (370 mg, yield: 68%).

Under the same conditions as this reaction, the following compounds were synthesized.
N-(naphthalen-1-ylmethyl)prop-2-en-1-amine
N-(3,4-dichlorobenzyl)prop-2-en-1-amine

Synthesis Example: IIB-1 and IIF-1

Synthesis of (3S*,3aS*,6R*,7R*,7aS*)-N,7-dibenzyl-1-isobutyl-1,2,3,6,7,7a-hexahydro-3aH-3,6-methanopyrrolo[3,2-b]pyridine-3a-carboxamide (IIB-1) and (3S*,3aR*,6S*,7R*,7aR*)-N,7-dibenzyl-1-isobutyl-1,2,3,3a,7,7a-hexahydro-6H-3,6-methanopyrrolo[3,2-c]pyridine-6-carboxamide (IIF-1)

4 A molecular sieves (850 mg), 3-phenylpropanal (0.157 mL, 1.19 mmol), and N-isobutylprop-2-en-1-amine (purity: 90%, 150 mg, 1.19 mmol) were added to a chloroform (8.50 mL) solution of N-benzyl-1,2,4-triazine-3-carboxamide (III) (170 mg, 0.794 mmol), and heated and refluxed for 10 hours. The molecular sieves were filtered and washed twice with chloroform (5.00 mL). The combined organic layer was evaporated under reduced pressure. The resulting residue was purified with CHROMATOREX Q-PACK SI30 SIZE 60 (ethyl acetate:methanol=100%:0% to 96%:4%) to obtain the aforementioned compounds (IIF-1) (86.9 mg, yield: 26%, RT=1.14 minutes (B method), [M+1]$^+$=416) and (IIB-1) (149 mg, yield: 45%, RT=1.19 minutes (B method), [M+1]$^+$=416).

Synthesis Example: IIB-29

Synthesis of (3S*,3aS*,6R*,7R*,7aS*)-N-(4-aminobutyl)-7-benzyl-1-isobutyl-1,2,3,6,7,7a-hexahydro-3aH-3,6-methanopyrrolo[3,2-b]pyridine-3a-carboxamide (JIB-29)

Formic acid (300 μL) was added to (3S*,3aS*,6R*,7R*,7aS*)-7-benzyl-1-isobutyl-N-(4-((tert-butoxycarbonyl)amino)butyl)-1,2,3,6,7,7a-hexahydro-3aH-3,6-methanopyrrolo[3,2-b]pyridine-3a-carboxamide (IIB-30) (9.30 mg, 0.0187 mmol) and incubated overnight at room temperature. Formic acid was evaporated under reduced pressure to obtain a diformic acid salt of the aforementioned compound (7.70 mg, yield: 84%, RT=0.71 minutes (A method), [M+1]$^+$=397).

Synthesis Example: IIF-26

Synthesis of 3-((3S*,3aR*,6S*,7R*,7aR*)-7-benzyl-1-isobutyl-1,2,3,3a,7,7a-hexahydro-1H-3,6-methanopyrrolo[3,2-c]pyridine-6-carboxamide)propanoic acid (II-26)

Formic acid (1.00 mL) was added to (3S*,3aR*,6S*,7R*,7aR*)-7-benzyl-1-isobutyl-N-(2-(tert-butoxy)-2-oxoethyl)-1,2,3,3a,7,7a-hexahydro-6H-3,6-methanopyrrolo[3,2-c]pyridine-6-carboxamide (IIF-27) (30.4 mg, 0.0660 mmol), and heated overnight at 50° C. Formic acid was evaporated under reduced pressure to obtain a monoformic acid salt of the aforementioned compound (29.7 mg, yield: 100%, RT=0.75 minutes (A method), [M+1]$^+$=398).

Synthesis Example: IIB-28

Synthesis of (3S*,3aS*,6R*,7R*,7aS*)-N-(3-amino-3-oxopropyl)-7-benzyl-1-isobutyl-1,2,3,6,7,7a-hexahydro-3aH-3,6-methanopyrrolo[3,2-b]pyridine-3a-carboxamide (JIB-28)

3-((3S*,3aS*,6R*,7R*,7aS*)-7-benzyl-1-isobutyl-1,2,3,6,7,7a-hexahydro-1H-3,6-methanopyrrolo[3,2-b]pyridine- 3a-carboxamide)propanoic acid (IIB-26) (15.0 mg, 0.0380 mmol) was dissolved in methanol (2.00 mL), and ammonium water (25.0 μL) and 4-(4,6-dimethoxy-1,3,5-triazin-2-yl)-4-methylmorpholinium chloride (110 mg, 0.397 mmol) were resolved and added 4 times each at room temperature. The solvent was evaporated under reduced pressure. The resulting residue was purified by preparative PLC (Fuji Silysia Chemical's CHROMATOREX NH-PLC05 (layer thickness 0.500 mm) (ethyl acetate:methanol=9:1) to obtain the aforementioned compound (7.10 mg, yield: 47%, RT=0.79 minutes (A method), [M+1]$^+$=397).

Tables 1 to 4 summarize the synthesized compounds of formula IIB and compounds of IIF. The following abbreviations are used in the following tables.

INT-iBu: N-isobutyl-1,2,4-triazine-3-carboxamide
INT-Bnzl: N-benzyl-1,2,4-triazine-3-carboxamide
SM1-iBu: N-isobutylprop-2-en-1-amine
SM1-Bnzl: N-benzylprop-2-en-1-amine
SM2-Ph: 3-phenylpropanal
SM2-Pnt: 4-methylpentanal Since samples with a blank entry under Mass in the following tables are prepared based on Mass Number in HPLC, it can be understood that the molecular weight is inferred and confirmed based on the time of retension (UV) of HPLC to identify the structure.

TABLE 1

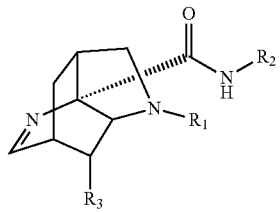

| Compound number | $R_1$ | $R_2$ | $R_3$ | Synthesis method | Intermediate | Raw material 1 | Raw material 2 |
|---|---|---|---|---|---|---|---|
| IIB-1 | i-Bu | Bnzl | Bnzl | EX | INT-Bnzl | SM1-iBu | SM2-Ph |
| IIB-2 | i-Bu | i-Bu | i-Bu | IIB-1, IIF-1 | INT-iBu | SM1-iBu | SM2-Pnt |
| IIB-3 | i-Bu | i-Bu | Bnzl | IIB-1, IIF-1 | INT-iBu | SM1-iBu | SM2-Ph |
| IIB-4 | Bnzl | i-Bu | i-Bu | IIB-1, IIF-1 | INT-iBu | SM1-Bnzl | SM2-Pnt |
| IIB-5 | i-Bu | Bnzl | i-Bu | IIB-1, IIF-1 | INT-Bnzl | SM1-iBu | SM2-Pnt |
| IIB-6 | Bnzl | i-Bu | Bnzl | IIB-1, IIF-1 | INT-iBu | SM1-Bnzl | SM2-Ph |
| IIB-7 | Bnzl | Bnzl | i-Bu | IIB-1, IIF-1 | INT-Bnzl | SM1-Bnzl | SM2-Pnt |
| IIB-8 | Bnzl | Bnzl | Bnzl | IIB-1, IIF-1 | INT-Bnzl | SM1-Bnzl | SM2-Ph |
| IIB-9 | i-Pnt | Bnzl | Bnzl | IIB-1, IIF-1 | INT-Bnzl | N-allyl-3-methyl-butan-1-amine | SM2-Ph |
| IIB-10 | Bnzl | Bnzl | i-Pnt | IIB-1, IIF-1 | INT-Bnzl | SM1-Bnzl | 5-methyl-hexanal |
| IIB-11 | i-Bu | Bnzl | Ph-Et | IIB-1, IIF-1 | INT-Bnzl phenyl- | SM1-iBu | 4-phenyl butanal |
| IIB-12 | i-Bu | Ph-Et | Bnzl | IIB-1, IIF-1 | N-phenethyl-1,2,4-triazine-3-carboxamide | SM1-iBu | SM2-Ph |
| IIB-13 | i-Bu | Bnzl | 3-Me-Bnzl | IIB-1, IIF-1 | INT-Bnzl | SM1-iBu | 3-(m-tolyl)propanal |
| IIB-14 | i-Bu | Bnzl | 4-Me-Bnzl | IIB-1, IIF-1 | INT-Bnzl | SM1-iBu | 3-(p-tolyl)propanal |
| IIB-15 | i-Bu | 3-Me-Bnzl | Bnzl | IIB-1, IIF-1 | N-(3-methylbenzyl)-1,2,4-triazine-3-carboxamide | SM1-iBu | SM2-Ph |
| IIB-16 | i-Bu | 4-Me-Bnzl | Bnzl | IIB-1, IIF-1 | N-(4-methylbenzyl)-1,2,4-triazine-3-carboxamide | SM1-iBu | SM2-Ph |

TABLE 1-continued

| | | | | | | | |
|---|---|---|---|---|---|---|---|
| IIB-17 | i-Bu | 3-Cl-Bnzl | Bnzl | IIB-1, IIF-1 | N-(3-chlorobenzyl)-1,2,4-triazine-3-carboxamide | SM1-iBu | SM2-Ph |
| IIB-18 | i-Bu | 4-Cl-Bnzl | Bnzl | IIB-1, IIF-1 | N-(4-chlorobenzyl)-1,2,4-triazine-3-carboxamide | SM1-iBu | SM2-Ph |
| IIB-19 | 3,4-Cl$_2$-Bnzl | Bnzl | i-Bu | IIB-1, IIF-1 | INT-Bnzl | N-(3,4-dichlorobenzyl)prop-2-en-1-amine | SM2-Pnt |
| IIB-20 | Bnzl | 3,4-Cl$_2$-Bnzl | i-Bu | IIB-1, IIF-1 | N-(3,4-dichloro-benzyl)-1,2,4-triazine-3-carboxamide | SM1-Bnzl | SM2-Pnt |
| IIB-21 | Me | Np-E | Bnzl | IIB-1, IIF-1 | N-(2-(naphthalen-1-yl)ethyl)-1,2,4-triazine-3-carboxamide | N-methyl-prop-2-en-1-amine | SM2-Ph |
| IIB-23 | i-Bu | 4-(tert-butoxy)benzyl | Bnzl | IIB-1, IIF-1 | N-(4-tert-butoxybenzyl)-1,2,4-triazine-3-carboxamide | SM1-iBu | SM2-Ph |
| IIB-24 | i-Bu | Np-M | Bnzl | IIB-1, IIF-1 | N-((naphthalen-1-yl)methyl)-1,2,4-triazine-3-carboxamide | SM1-iBu | SM2-Ph |
| IIB-25 | i-Bu | Hdr-E | Bnzl | IIB-1, IIF-1 | N-(2-hydroxyethyl)-1,2,4-triazine-3-carboxamide | SM1-iBu | SM2-Ph |
| IIB-26 | i-Bu | Cbx-E | Bnzl | IB-40 | | IIB-27 | |
| IIB-27 | i-Bu | 2-(tert-butoxy)-2-oxoethyl | Bnzl | IIB-1, IIF-1 | tert-butyl 3-(1,2,4-triazine-3-carboxamide)propanoate | SM1-iBu | SM2-Ph |
| IIB-28 | i-Bu | Cbm-E | Bnzl | EX | | IIB-26 | |
| IIB-29 | i-Bu | 4-aminobutyl | Bnzl | EX | | IIB-30 | |
| IIB-30 | i-Bu | 4-((tert-butoxy-carbonyl)amino)butyl | Bnzl | IIB-1, IIF-1 | tert-butyl 4-(1,2,4-triazine-3-carboxamide)butyl-carbamate | SM1-iBu | SM2-Ph |
| IIB-31 | i-Bu | Chm | Bnzl | IIB-1, IIF-1 | N-(cyclohexyl-methyl)-1,2,4-triazine-3-carboxamide | SM1-iBu | SM2-Ph |
| IIB-32 | i-Bu | (tetra-hydro-2H-pyran-2-yl)methyl | Bnzl | IIB-1, IIF-1 | N-((tetrahydro-2H-pyran-2-yl)methyl)-1,2,4-triazine-3-carboxamide | SM1-iBu | SM2-Ph |

TABLE 1-continued

| | | | | | | | |
|---|---|---|---|---|---|---|---|
| IIB-34 | i-Bu | Bnzl | 4-((tert-butoxy carbonyl) amino) butyl | IIB-1, IIF-1 | INT-Bnzl | SM1-iBu | tert-butyl 5-formyl pentyl-carbamate |
| IIB-36 | i-Bu | Bnzl | 3-methoxy-3-oxo-propyl | IIB-1, IIF-1 | INT-Bnzl | SM1-iBu | methyl 4-formyl butanoate |
| IIB-38 | i-Bu | Bnzl | Chm | IIB-1, IIF-1 | INT-Bnzl | SM1-iBu | 3-cyclo-hexyl-propanal |
| IIB-39 | Chm | Bnzl | Bnzl | IIB-1, IIF-1 | INT-Bnzl | N-(cyclo-hexyl-methyl) prop-2-en-1-amine | SM2-Ph |
| IIB-40 | 4-OH-Bnzl | Bnzl | Bnzl | IB-40 | | IIB-41 | |
| IIB-41 | 4-(tert-butoxy) benzyl | Bnzl | Bnzl | IIB-1, IIF-1 | INT-Bnzl | N-(4-tert-butoxy-benzyl)prop-2-en-1-amine | SM2-Ph |
| IIB-42 | Np-M | Bnzl | Bnzl | IIB-1, IIF-1 | INT-Bnzl | N-((naphthalen-1-yl)methyl) prop-2-en-1-amine | SM2-Ph |
| IIB-76 | 3-(tert-butoxy)-3-oxopropyl | Bnzl | Bnzl | IIB-1, IIF-1 | INT-Bnzl | N-(3-(tert-butoxy)-3-oxopropyl)-prop-2-en-1-amine | SM2-Ph |
| IIB-77 | Bnzl | Bnzl | 4-OH-Bnzl | IIB-1, IIF-1 | INT-Bnzl | SM1-Bnzl | 3-(4-hydroxy-phenyl) propanal |
| IIB-78 | Me | 2-(1-(tert-butoxy-carbonyl)-1H-indol-3-yl)ethyl | Bnzl | IIB-1, IIF-1 | N-(2-(1-(tert-butoxy-carbonyl)-1H-indol-3-yl)ethyl)-1,2,4-triazine-3-carboxamide | N-methyl-prop-2-en-1-amine | SM2-Ph |
| IIB-80 | Np-M | Bnzl | Pr | IIB-1, IIF-1 | INT-Bnzl | N-((naphthalen-1-yl)methyl)prop-2-en-1-amine | pentanal |
| IIB-81 | benzyl | naphthalen-en-1-ylmethyl | iso-butyl | IIB-1, IIF-1 | | | |

EX: described in the Examples

| Compound number | $R_1$ | $R_2$ | $R_3$ | LCMS tR (min) | Mass $(M + H)^+$ | Measurement conditon |
|---|---|---|---|---|---|---|
| IIB-81 | benzyl | naphthalen-1-ylmethyl | isobutyl | 1.29 | 467 | B |
| IIB-82 | benzyl | 4-(trifluoro-methyl) benzyl | isobutyl | 1.29 | 484 | B |
| IIB-83 | 4-chlorobenzyl | benzyl | isobutyl | 1.29 | 450 | B |
| IIB-84 | 3-chlorobenzyl | benzyl | isobutyl | 1.30 | 450 | B |

TABLE 1-continued

| | | | | | | |
|---|---|---|---|---|---|---|
| IIB-85 | 4-methoxybenzyl | benzyl | isobutyl | 1.23 | 446 | B |
| IIB-86 | 4-methylbenzyl | benzyl | isobutyl | 1.27 | 430 | B |
| IIB-88 | isobutyl | isobutyl | 4-chloro-benzyl | 1.26 | 416 | B |
| IIB-89 | isobutyl | 4-chloro-benzyl | isobutyl | 1.27 | 416 | B |
| IIB-90 | isobutyl | benzyl | isopentyl | 1.26 | 396 | B |
| IIB-91 | isobutyl | benzyl | isobutyl | 1.26 | 396 | B |
| IIB-92 | isobutyl | isopentyl | benzyl | 1.27 | 396 | B |
| IIB-93 | 4-hydroxy-benzyl | benzyl | isobutyl | 1.19 | 432 | B |
| IIB-94 | 4-(dimethyl-amino)benzyl | benzyl | isobutyl | 1.27 | 459 | B |
| IIB-95 | 4-(tert-butyl)benzyl | benzyl | isobutyl | 1.31 | 472 | B |
| IIB-96 | 4-(trifluoro-methoxy)benzyl | benzyl | isobutyl | 1.32 | 500 | B |
| IIB-97 | 4-ethoxybenzyl | benzyl | isobutyl | 1.25 | 460 | B |
| IIB-98 | isopentyl | isobutyl | benzyl | 1.26 | 396 | B |
| IIB-99 | benzyl | 4-hydroxy-benzyl | isobutyl | 1.17 | 432 | B |
| IIB-100 | 4-methoxy-benzyl | 4-hydroxy-benzyl | isobutyl | 1.17 | 462 | B |
| IIB-101 | 4-hydroxy-benzyl | benzyl | isopentyl | 1.20 | 446 | B |
| IIB-102 | benzyl | naphthalen-2-ylmethyl | isobutyl | 1.27 | 466 | B |
| IIB-103 | isopentyl | 4-chloro-benzyl | isobutyl | 1.28 | 431 | B |
| IIB-104 | isopentyl | 4-fluoro-benzyl | isobutyl | 1.26 | 414 | B |
| IIB-105 | benzyl | pyridin-4-yl methyl | isobutyl | 1.06 | 417 | B |
| IIB-106 | 4-methoxy-benzyl | benzyl | benzyl | 0.99 | 480 | C |
| IIB-107 | phenethyl | benzyl | 2-(tert-butyldimethyl-silyloxy)ethyl | 1.12 | 532 | C |
| IIB-108 | cyclopentyl-methyl | 4-hydroxy-benzyl | 2-carboxy-ethyl | 0.78 | 440 | C |
| IIB-109 | 4-nitrobenzyl | 4-(tert-butoxy)benzyl | 2-(tert-butoxy-carbonyl)ethyl | 1.03 | 605 | C |
| IIB-110 | i-Bu | i-Pr | Bnzl | 3.09 | 368 | F |
| IIB-111 | i-Bu | i-Bu | 4-tBuO-Bnzl | 3.95 | 454 | F |
| IIB-112 | i-Bu | Bnzl | 4-tBuO-Bnzl | 4.05 | 488 | F |
| IIB-113 | i-Bu | tBOC-E | 4-tBuO-Bnzl | 4.12 | 526 | F |
| IIB-114 | i-Bu | s-Bu | 4-tBuO-Bnzl | 3.93 | 454 | F |
| IIB-115 | i-Bu | 1-Npm | 4-tBuO-Bnzl | 4.48 | 538 | F |
| IIB-116 | i-Bu | i-Pr | 4-tBuO-Bnzl | 3.64 | 440 | F |
| IIB-117 | i-Bu | 1-Npm | tBOC-E | 4.11 | 504 | F |
| IIB-118 | i-Bu | i-Pr | tBOC-E | 3.18 | 406 | F |
| IIB-119 | i-Bu | 1-Npm | 1-Npm | 4.39 | 516 | F |
| IIB-120 | i-Bu | i-Pr | 1-Npm | 3.52 | 418 | F |
| IIB-121 | Bnzl | 4-tBuO-Bnzl | Bnzl | 4.23 | 522 | F |
| IIB-122 | Bnzl | i-Bu | 4-tBuO-Bnzl | 4.11 | 488 | F |
| IIB-123 | Bnzl | Bnzl | 4-tBuO-Bnzl | 4.20 | 522 | F |
| IIB-124 | Bnzl | tBOC-E | 4-tBuO-Bnzl | 4.27 | 560 | F |
| IIB-125 | Bnzl | Bnzl | tBOC-E | 3.72 | 488 | F |
| IIB-126 | Bnzl | 4-tBuO-Bnzl | tBOC-E | 4.22 | 560 | F |
| IIB-127 | Bnzl | 1-Npm | tBOC-E | 4.18 | 538 | F |
| IIB-128 | Bnzl | i-Bu | 1-Npm | 3.98 | 466 | F |
| IIB-129 | Bnzl | Bnzl | 1-Npm | 4.09 | 500 | F |
| IIB-130 | Bnzl | 4-tBuO-Bnzl | 1-Npm | 4.55 | 572 | F |
| IIB-131 | Bnzl | tBOC-E | 1-Npm | 4.17 | 538 | F |
| IIB-132 | Bnzl | s-Bu | 1-Npm | 3.96 | 466 | F |
| IIB-133 | Bnzl | 1-Npm | 1-Npm | 4.49 | 550 | F |
| IIB-134 | Bnzl | i-Pr | 1-Npm | 3.71 | 452 | F |
| IIB-135 | 4-tBuO-Bnzl | i-Bu | Bnzl | 3.92 | 488 | F |
| IIB-136 | 4-tBuO-Bnzl | Bnzl | Bnzl | 4.57 | 522 | F |

TABLE 1-continued

| | | | | | | |
|---|---|---|---|---|---|---|
| IIB-137 | 4-tBuO-Bnzl | 1-Npm | Bnzl | 5.10 | 572 | F |
| IIB-138 | 4-tBuO-Bnzl | Bnzl | tBOC-E | 3.95 | 560 | F |
| IIB-139 | 4-tBuO-Bnzl | 1-Npm | tBOC-E | 4.35 | 610 | F |
| IIB-140 | 4-tBuO-Bnzl | i-Bu | 1-Npm | 4.07 | 538 | F |
| IIB-141 | 4-tBuO-Bnzl | Bnzl | 1-Npm | 5.00 | 572 | F |
| IIB-142 | 4-tBuO-Bnzl | tBOC-E | 1-Npm | 4.14 | 610 | F |
| IIB-143 | 4-tBuO-Bnzl | s-Bu | 1-Npm | 4.27 | 538 | F |
| IIB-144 | 4-tBuO-Bnzl | 1-Npm | 1-Npm | 5.40 | 622 | F |
| IIB-145 | i-Bu | 4-tBuO-Bnzl | Bnzl | 4.13 | 488 | F |
| IIB-146 | i-Bu | tBOC-E | Bnzl | 3.66 | 454 | F |
| IIB-147 | i-Bu | s-Bu | Bnzl | 3.38 | 382 | F |
| IIB-148 | i-Bu | i-Bu | tBOC-E | 3.44 | 420 | F |
| IIB-149 | i-Bu | Bnzl | tBOC-E | 3.63 | 454 | F |
| IIB-150 | i-Bu | 4-tBuO-Bnzl | tBOC-E | 4.18 | 526 | F |
| IIB-151 | i-Bu | s-Bu | tBOC-E | 3.46 | 420 | F |
| IIB-152 | i-Bu | i-Bu | 1-Npm | 3.87 | 432 | F |
| IIB-153 | i-Bu | Bnzl | 1-Npm | 3.98 | 466 | F |
| IIB-154 | i-Bu | 4-tBuO-Bnzl | 1-Npm | 4.44 | 538 | F |
| IIB-155 | i-Bu | tBOC-E | 1-Npm | 4.04 | 504 | F |
| IIB-156 | Bnzl | tBOC-E | Bnzl | 3.82 | 488 | F |
| IIB-157 | Bnzl | s-Bu | Bnzl | 3.55 | 416 | F |
| IIB-158 | Bnzl | 1-Npm | Bnzl | 4.21 | 500 | F |
| IIB-159 | Bnzl | i-Pr | Bnzl | 3.31 | 402 | F |
| IIB-160 | Bnzl | s-Bu | 4-tBuO-Bnzl | 4.08 | 488 | F |
| IIB-161 | Bnzl | 1-Npm | 4-tBuO-Bnzl | 4.61 | 572 | F |
| IIB-162 | Bnzl | i-Pr | 4-tBuO-Bnzl | 3.83 | 474 | F |
| IIB-163 | Bnzl | s-Bu | tBOC-E | 3.60 | 454 | F |
| IIB-164 | Bnzl | i-Pr | tBOC-E | 3.28 | 440 | F |
| IIB-165 | 4-tBuO-Bnzl | i-Pr | Bnzl | 3.70 | 474 | F |
| IIB-166 | 4-tBuO-Bnzl | i-Pr | tBOC-E | 3.75 | 512 | F |
| IIB-167 | 4-tBuO-Bnzl | i-Pr | 1-Npm | 4.07 | 524 | F |
| IIB-168 | tBOC-E | i-Bu | Bnzl | 3.77 | 454 | F |
| IIB-169 | tBOC-E | Bnzl | Bnzl | 3.86 | 488 | F |
| IIB-170 | tBOC-E | 4-tBuO-Bnzl | Bnzl | 4.34 | 560 | F |
| IIB-171 | tBOC-E | s-Bu | Bnzl | 3.76 | 454 | F |
| IIB-172 | tBOC-E | 1-Npm | Bnzl | 4.34 | 538 | F |
| IIB-173 | tBOC-E | i-Bu | 4-tBuO-Bnzl | 4.30 | 526 | F |
| IIB-174 | tBOC-E | Bnzl | 4-tBuO-Bnzl | 4.40 | 560 | F |
| IIB-175 | tBOC-E | s-Bu | 4-tBuO-Bnzl | 4.31 | 526 | F |
| IIB-176 | tBOC-E | 1-Npm | 4-tBuO-Bnzl | 4.80 | 610 | F |
| IIB-177 | tBOC-E | i-Pr | 4-tBuO-Bnzl | 4.05 | 512 | F |
| IIB-178 | tBOC-E | i-Bu | 1-Npm | 4.13 | 504 | F |
| IIB-179 | tBOC-E | 4-tBuO-Bnzl | 1-Npm | 4.66 | 610 | F |
| IIB-180 | tBOC-E | s-Bu | 1-Npm | 4.09 | 504 | F |
| IIB-181 | tBOC-E | 1-Npm | 1-Npm | 4.63 | 588 | F |
| IIB-182 | 1-Npm | 4-tBuO-Bnzl | Bnzl | 4.18 | 572 | F |
| IIB-183 | 1-Npm | s-Bu | Bnzl | 3.82 | 466 | F |
| IIB-184 | 1-Npm | Bnzl | 4-tBuO-Bnzl | 4.68 | 572 | F |
| IIB-185 | 1-Npm | tBOC-E | 4-tBuO-Bnzl | 4.24 | 610 | F |
| IIB-186 | 1-Npm | s-Bu | 4-tBuO-Bnzl | 4.84 | 538 | F |
| IIB-187 | 1-Npm | 1-Npm | 4-tBuO-Bnzl | 4.85 | 622 | F |
| IIB-188 | 1-Npm | i-Pr | 4-tBuO-Bnzl | 4.20 | 524 | F |
| IIB-189 | 1-Npm | i-Bu | tBOC-E | 3.80 | 504 | F |
| IIB-190 | 1-Npm | Bnzl | tBOC-E | 4.45 | 538 | F |
| IIB-191 | 1-Npm | 4-tBuO-Bnzl | tBOC-E | 4.84 | 610 | F |
| IIB-192 | 1-Npm | s-Bu | tBOC-E | 4.29 | 504 | F |
| IIB-193 | 1-Npm | 1-Npm | tBOC-E | 4.49 | 588 | F |
| IIB-194 | 1-Npm | Bnzl | 1-Npm | 4.75 | 550 | F |
| IIB-195 | 1-Npm | 4-tBuO-Bnzl | 1-Npm | 4.74 | 622 | F |
| IIB-196 | 1-Npm | tBOC-E | 1-Npm | 4.59 | 588 | F |
| IIB-197 | 1-Npm | s-Bu | 1-Npm | 4.57 | 516 | F |
| IIB-198 | i-Bu | 4-tBuO-Bnzl | i-Bu | 4.04 | 454 | F |
| IIB-199 | i-Bu | tBOC-E | i-Bu | 3.35 | 420 | F |
| IIB-200 | i-Bu | s-Bu | i-Bu | 3.25 | 348 | F |
| IIB-201 | i-Bu | 1-Npm | i-Bu | 4.00 | 432 | F |
| IIB-202 | i-Bu | i-Pr | i-Bu | 2.97 | 334 | F |

TABLE 1-continued

| | | | | | | |
|---|---|---|---|---|---|---|
| IIB-203 | i-Bu | (tBOC)Gun-Pr | 4-tBuO-Bnzl | 2.81 | 641 | J |
| IIB-204 | i-Bu | 1-Npm | (tBOC)Gun-Pr | 3.27 | 675 | J |
| IIB-205 | i-Bu | s-Bu | 1-Npm | 3.85 | 432 | F |
| IIB-206 | Bnzl | 4-tBuO-Bnzl | i-Bu | 4.13 | 488 | F |
| IIB-207 | Bnzl | s-Bu | i-Bu | 3.45 | 382 | F |
| IIB-208 | Bnzl | i-Pr | i-Bu | 3.14 | 368 | F |
| IIB-209 | Bnzl | i-Bu | (tBOC)Gun-Pr | 3.22 | 625 | J |
| IIB-210 | Bnzl | 4-tBuO-Bnzl | (tBOC)Gun-Pr | 2.96 | 675 | J |
| IIB-211 | tBOC-E | i-Bu | i-Bu | 3.63 | 420 | F |
| IIB-212 | tBOC-E | Bnzl | i-Bu | 3.83 | 454 | F |
| IIB-213 | tBOC-E | 4-tBuO-Bnzl | i-Bu | 4.35 | 526 | F |
| IIB-214 | tBOC-E | s-Bu | i-Bu | 3.68 | 420 | F |
| IIB-215 | tBOC-E | 1-Npm | i-Bu | 4.32 | 504 | F |
| IIB-216 | tBOC-E | i-Pr | i-Bu | 3.41 | 406 | F |
| IIB-217 | tBOC-E | Bnzl | 1-Npm | 4.19 | 538 | F |
| IIB-218 | tBOC-E | i-Pr | 1-Npm | 3.87 | 490 | F |
| IIB-219 | 1-Npm | Bnzl | i-Bu | 3.62 | 466 | F |
| IIB-220 | 1-Npm | i-Bu | Bnzl | 3.67 | 466 | F |
| IIB-221 | 1-Npm | (tBOC)Gun-Pr | Bnzl | 3.97 | 709 | F |
| IIB-222 | 1-Npm | i-Bu | 4-tBuO-Bnzl | 4.18 | 538 | F |
| IIB-223 | 1-Npm | i-Pr | tBOC-E | 3.62 | 490 | F |
| IIB-224 | 1-Npm | 1-Npm | (tBOC)Gun-Pr | 5.14 | 759 | F |
| IIB-225 | 1-Npm | i-Pr | (tBOC)Gun-Pr | 3.15 | 661 | F |
| IIB-226 | 1-Npm | i-Bu | 1-Npm | 4.07 | 516 | F |
| IIB-227 | 1-Npm | (tBOC)Gun-Pr | 1-Npm | 2.99 | 459 | F |
| IIB-228 | 1-Npm | i-Pr | 1-Npm | 3.90 | 502 | F |
| IIB-229 | i-Bu | (tBOC)Gun-Pr | i-Bu | 3.10 | 591 | J |
| IIB-230 | i-Bu | (tBOC)Gun-Pr | Bnzl | 3.03 | 625 | J |
| IIB-231 | i-Bu | i-Bu | (tBOC)Gun-Pr | 3.01 | 591 | J |
| IIB-232 | i-Bu | Bnzl | (tBOC)Gun-Pr | 3.02 | 625 | J |
| IIB-233 | i-Bu | 4-tBuO-Bnzl | (tBOC)Gun-Pr | 2.84 | 641 | J |
| IIB-234 | i-Bu | s-Bu | (tBOC)Gun-Pr | 2.99 | 591 | J |
| IIB-235 | i-Bu | i-Pr | (tBOC)Gun-Pr | 2.90 | 577 | J |
| IIB-236 | i-Bu | (tBOC)Gun-Pr | 1-Npm | 3.17 | 675 | J |
| IIB-237 | Bnzl | (tBOC)Gun-Pr | i-Bu | 3.19 | 625 | J |
| IIB-238 | Bnzl | (tBOC)Gun-Pr | Bnzl | 3.26 | 659 | J |
| IIB-239 | Bnzl | (tBOC)Gun-Pr | 4-tBuO-Bnzl | 2.84 | 675 | J |
| IIB-240 | Bnzl | i-Bu | tBOC-E | 3.56 | 454 | F |
| IIB-241 | Bnzl | Bnzl | (tBOC)Gun-Pr | 3.28 | 659 | J |
| IIB-242 | Bnzl | s-Bu | (tBOC)Gun-Pr | 3.04 | 625 | J |
| IIB-243 | Bnzl | i-Pr | (tBOC)Gun-Pr | 2.99 | 611 | J |
| IIB-244 | Bnzl | (tBOC)Gun-Pr | 1-Npm | 3.36 | 709 | J |
| IIB-245 | tBOC-E | i-Pr | Bnzl | 3.45 | 440 | F |
| IIB-246 | (tBOC)Gun-Pr | 1-Npm | i-Bu | 3.65 | 657 | J |
| IIB-247 | (tBOC)Gun-Pr | i-Pr | i-Bu | 3.21 | 577 | J |
| IIB-248 | (tBOC)Gun-Pr | 1-Npm | Bnzl | 3.75 | 709 | J |
| IIB-249 | (tBOC)Gun-Pr | i-Pr | Bnzl | 3.24 | 611 | J |
| IIB-250 | (tBOC)Gun-Pr | 1-Npm | 4-tBuO-Bnzl | 3.30 | 725 | J |
| IIB-251 | (tBOC)Gun-Pr | i-Pr | 4-tBuO-Bnzl | 2.92 | 627 | J |
| IIB-252 | (tBOC)Gun-Pr | 1-Npm | 1-Npm | 3.86 | 759 | J |
| IIB-253 | (tBOC)Gun-Pr | i-Pr | 1-Npm | 3.38 | 661 | J |
| IIB-254 | 1-Npm | (tBOC)Gun-Pr | i-Bu | 4.29 | 675 | F |
| IIB-255 | 1-Npm | 1-Npm | i-Bu | 4.05 | 516 | F |
| IIB-256 | 1-Npm | 1-Npm | Bnzl | 4.92 | 550 | F |
| IIB-257 | Bnzl | tBOC-E | i-Bu | 3.73 | 454 | F |
| IIB-258 | Bnzl | 1-Npm | (tBOC)Gun-Pr | 3.80 | 709 | J |
| IIB-259 | 4-tBuO-Bnzl | i-Bu | i-Bu | 3.67 | 454 | F |
| IIB-260 | 4-tBuO-Bnzl | Bnzl | i-Bu | 3.67 | 488 | F |
| IIB-261 | 4-tBuO-Bnzl | tBOC-E | i-Bu | 3.82 | 526 | F |
| IIB-262 | 4-tBuO-Bnzl | (tBOC)Gun-Pr | i-Bu | 3.38 | 641 | F |
| IIB-263 | 4-tBuO-Bnzl | s-Bu | i-Bu | 3.75 | 454 | F |

TABLE 1-continued

| | | | | | | |
|---|---|---|---|---|---|---|
| IIB-264 | 4-tBuO-Bnzl | 1-Npm | i-Bu | 4.22 | 538 | F |
| IIB-265 | 4-tBuO-Bnzl | i-Pr | i-Bu | 3.47 | 440 | F |
| IIB-266 | 4-tBuO-Bnzl | tBOC-E | Bnzl | 3.88 | 560 | F |
| IIB-267 | 4-tBuO-Bnzl | (tBOC)Gun-Pr | Bnzl | 3.24 | 675 | F |
| IIB-268 | 4-tBuO-Bnzl | s-Bu | Bnzl | 3.85 | 488 | F |
| IIB-269 | 4-tBuO-Bnzl | i-Bu | tBOC-E | 3.88 | 526 | F |
| IIB-270 | 4-tBuO-Bnzl | s-Bu | tBOC-E | 3.79 | 526 | F |
| IIB-271 | 4-tBuO-Bnzl | i-Bu | (tBOC)Gun-Pr | 3.45 | 641 | F |
| IIB-272 | 4-tBuO-Bnzl | Bnzl | (tBOC)Gun-Pr | 3.82 | 675 | F |
| IIB-273 | 4-tBuO-Bnzl | s-Bu | (tBOC)Gun-Pr | 3.38 | 641 | F |
| IIB-274 | 4-tBuO-Bnzl | 1-Npm | (tBOC)Gun-Pr | 3.88 | 725 | F |
| IIB-275 | 4-tBuO-Bnzl | i-Pr | (tBOC)Gun-Pr | 3.27 | 627 | F |
| IIB-276 | 4-tBuO-Bnzl | (tBOC)Gun-Pr | 1-Npm | 3.74 | 725 | F |
| IIB-277 | (tBOC)Gun-Pr | i-Bu | i-Bu | 4.52 | 591 | F |
| IIB-278 | (tBOC)Gun-Pr | Bnzl | i-Bu | 4.25 | 625 | F |
| IIB-279 | (tBOC)Gun-Pr | 4-tBuO-Bnzl | i-Bu | 3.79 | 641 | F |
| IIB-280 | (tBOC)Gun-Pr | s-Bu | i-Bu | 4.04 | 591 | F |
| IIB-281 | (tBOC)Gun-Pr | i-Bu | Bnzl | 4.39 | 625 | F |
| IIB-282 | (tBOC)Gun-Pr | Bnzl | Bnzl | 4.30 | 659 | F |
| IIB-283 | (tBOC)Gun-Pr | 4-tBuO-Bnzl | Bnzl | 3.82 | 675 | F |
| IIB-284 | (tBOC)Gun-Pr | s-Bu | Bnzl | 4.09 | 625 | F |
| IIB-285 | (tBOC)Gun-Pr | i-Bu | 4-tBuO-Bnzl | 3.80 | 641 | F |
| IIB-286 | (tBOC)Gun-Pr | Bnzl | 1-Npm | 4.57 | 709 | F |
| IIB-287 | (tBOC)Gun-Pr | s-Bu | 1-Npm | 4.49 | 675 | F |
| IIB-288 | 1-Npm | i-Bu | i-Bu | 3.65 | 432 | F |
| IIB-289 | 1-Npm | 4-tBuO-Bnzl | i-Bu | 4.09 | 538 | F |
| IIB-290 | 1-Npm | tBOC-E | i-Bu | 3.77 | 504 | F |
| IIB-291 | 1-Npm | s-Bu | i-Bu | 3.71 | 432 | F |
| IIB-292 | 1-Npm | i-Pr | i-Bu | 3.54 | 418 | F |
| IIB-293 | 1-Npm | tBOC-E | Bnzl | 3.99 | 538 | F |
| IIB-294 | 1-Npm | i-Pr | Bnzl | 3.69 | 452 | F |
| IIB-295 | 1-Npm | (tBOC)Gun-Pr | 4-tBuO-Bnzl | 3.59 | 725 | F |
| IIB-296 | 1-Npm | i-Bu | (tBOC)Gun-Pr | 4.00 | 675 | F |
| IIB-297 | 1-Npm | Bnzl | (tBOC)Gun-Pr | 4.17 | 709 | F |
| IIB-298 | 1-Npm | 4-tBuO-Bnzl | (tBOC)Gun-Pr | 3.65 | 725 | F |
| IIB-299 | Bnzl | 1-Npm | 3-Gun-Pr | 2.70 | 509 | F |
| IIB-300 | 4-OH-Bnzl | 3-Gun-Pr | i-Bu | 2.47 | 441 | F |
| IIB-301 | 4-OH-Bnzl | 1-Npm | 3-Gun-Pr | 2.90 | 525 | F |
| IIB-302 | 1-Npm | 3-Gun-Pr | 4-OH-Bnzl | 2.70 | 525 | F |
| IIB-303 | 1-Npm | i-Bu | 3-Gun-Pr | 2.82 | 475 | F |
| IIB-304 | 1-Npm | Bnzl | 3-Gun-Pr | 2.97 | 509 | F |
| IIB-305 | 1-Npm | 4-OH-Bnzl | 3-Gun-Pr | 2.77 | 525 | F |
| IIB-306 | 1-Npm | s-Bu | 3-Gun-Pr | 2.82 | 475 | F |
| IIB-307 | Bnzl | Ph-Et | i-Bu | 0.97 | 430 | C |
| IIB-308 | Ph-Et | i-Bu | Bnzl | 1.00 | 430 | C |
| IIB-309 | Chm | i-Bu | Bnzl | 1.05 | 422 | C |
| IIB-310 | Bnzl | 4-F-Bnzl | i-Bu | 0.98 | 434 | C |
| IIB-311 | Chm | Bnzl | i-Bu | 1.04 | 422 | C |
| IIB-312 | Bnzl | Hxy | i-Bu | 1.08 | 410 | C |
| IIB-313 | Ph-Et | i-Bu | i-Bu | 0.99 | 396 | C |
| IIB-314 | Ph-Et | i-Bu | 1-Npm | 1.04 | 480 | C |
| IIB-315 | Bnzl | i-Bu | Ph-Et | 1.00 | 430 | C |
| IIB-316 | 4-F-Bnzl | i-Bu | Bnzl | 1.00 | 434 | C |
| IIB-317 | i-Bu | 4-F-Bnzl | Bnzl | 0.99 | 434 | C |
| IIB-318 | Ph-Et | Bnzl | i-Bu | 0.98 | 430 | C |
| IIB-319 | Bnzl | i-Pnt | i-Bu | 1.00 | 396 | C |
| IIB-320 | i-Bu | Hxy | Bnzl | 1.05 | 410 | C |
| IIB-321 | 4-F-Bnzl | Bnzl | Bnzl | 0.99 | 468 | C |
| IIB-322 | Ph-Et | Bnzl | Bnzl | 1.00 | 464 | C |
| IIB-323 | Bnzl | i-Bu | i-Pnt | 1.03 | 396 | C |
| IIB-324 | 4-F-Bnzl | Bnzl | i-Bu | 0.98 | 434 | C |

TABLE 1-continued

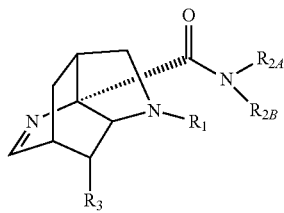

Formula XXIIB

| Compound number | $R_1$ | $R_{2A}$ | $R_{2B}$ | $R_3$ | LCMS RT (min) | Mass $(M + H)^+$ | Measurement condition |
|---|---|---|---|---|---|---|---|
| IIB-325 | 2-Npm | H | Bnzl | i-Bu | 2.89 | 466 | B1 |
| IIB-326 | i-Pnt | H | 3-Cl-Bnzl | Bnzl | 2.85 | 464 | B1 |
| IIB-327 | i-Pnt | H | 4-Me-Bnzl | Bnzl | 2.83 | 444 | B1 |
| IIB-328 | i-Pnt | H | 4-MeO-Bnzl | Bnzl | 2.71 | 460 | B1 |
| IIB- | Me | H | quinolin-8-yl ethyl | Bnzl | 2.09 | 439 | B1 |
| IIB- | Me | H | quinolin-5-yl ethyl | Bnzl | 1.62 | 439 | B1 |
| IIB-331 | i-Bu | H | 4-Cl-Bnzl | Ph-Et | 2.84 | 464 | B1 |
| IIB-332 | i-Bu | H | 3-Cl-Bnzl | Ph-Et | 2.68 | 464 | B1 |
| IIB-333 | i-Bu | H | 4-MeO-Bnzl | Ph-Et | 2.70 | 460 | B1 |
| IIB-334 | i-Bu | H | 4-Me-Bnzl | Ph-Et | 2.83 | 445 | B1 |
| IIB-335 | i-Bu | H | 2-Npm | Ph-Et | 2.92 | 480 | B1 |
| IIB-336 | i-Bu | H | Bnzl | Ph-Pr | 2.82 | 444 | B1 |
| IIB-337 | i-Bu | H | 3-Cl-Bnzl | Ph-Pr | 1.29 | 478 | B |
| IIB-338 | i-Bu | H | 3-F-Bnzl | Ph-Pr | 1.33 | 462 | B |
| IIB-339 | Cpm | H | 4-OH-Bnzl | Cbx-E | 1.10 | 440 | B |
| IIB-340 | i-Bu | H | 3-Me-Bnzl | Ph-Pr | 1.33 | 458 | B |
| IIB-341 | i-Bu | H | 3-MeO-Bnzl | Ph-Pr | 1.29 | 474 | B |
| IIB-342 | i-Bu | H | 3-Cl-Bnzl | Ph-Bu | 1.33 | 492 | B |
| IIB-343 | i-Bu | H | 3-F-Bnzl | Ph-Bu | 1.29 | 476 | B |
| IIB-344 | i-Bu | H | 3-Me-Bnzl | Ph-Bu | 1.31 | 473 | B |
| IIB-345 | i-Bu | H | 3-MeO-Bnzl | Ph-Bu | 1.36 | 488 | B |
| IIB-346 | i-Bu | H | Bnzl | Ph-Bu | 1.29 | 458 | B |

TABLE 1-continued

| | | | | | | | |
|---|---|---|---|---|---|---|---|
| IIB-347 | i-Pnt | H | 3-F-Bnzl | Ph-Pr | 1.25 | 476 | B |
| IIB-348 | 1-Npm | H | pentyl | Ph-Et | 1.08 | 494 | C |
| IIB-349 | 1-Npm | | pyrrolidine † | Ph-Et | 0.96 | 478 | C |
| IIB-350 | 1-Npm | H | cyclohexyl | Ph-Et | 1.07 | 506 | C |
| IIB-351 | 1-Npm | H | cyclopentyl | Ph-Et | 1.05 | 492 | C |
| IIB-352 | 1-Npm | | piperidine † | Ph-Et | 1.01 | 492 | C |
| IIB-353 | 1-Npm | H | heptyl | Ph-Et | 1.14 | 522 | C |
| IIB-354 | Hdr-E | H | 4-fluorophenethyl | 1-Npm | 0.93 | 486 | C |
| IIB-355 | tBuO-E | H | 4-fluorophenethyl | 1-Npm | 1.07 | 542 | C |
| IIB-356 | Pr | H | Chm | Bnzl | 1.00 | 408 | C |
| IIB-357 | 1-Npm | H | Hxy | 4-methylphenethyl | 1.13 | 522 | C |
| IIB-358 | 1-Npm | H | Hxy | 4-isopropylphenethyl | 1.18 | 550 | C |
| IIB-359 | 1-Npm | H | Hxy | 2-(naphthalen-2-yl)ethyl | 1.15 | 558 | C |
| IIB-360 | 1-Npm | H | Hxy | cyclohexylethyl | 1.19 | 514 | C |
| IIB-361 | tBuO-E | H | 4-Cl-Bnzl | 1-Npm | 1.07 | 545 | C |
| IIB-362 | tBuO-E | H | 4-Me-Bnzl | 1-Npm | 1.07 | 524 | C |
| IIB-363 | Pr | H | Bnzl | Chm | 1.00 | 408 | C |
| IIB-364 | Pr | H | 2-methylbenzyl | Bnzl | 0.95 | 416 | C |
| IIB-365 | Pr | H | (1,2,3,4-tetrahydronaphthalen-1-yl)methyl | Bnzl | 1.01 | 456 | C |
| IIB-366 | Pr | H | Cpm | Bnzl | 0.96 | 394 | C |
| IIB-367 | Pr | H | Bnzl | Cpm | 0.95 | 394 | C |
| IIB-368 | 1-Npm | H | Hxy | 3-methylphenethyl | 1.13 | 522 | C |
| IIB-369 | 4-Nt-Bnzl | H | Bnzl | Bnzl | 0.96 | 495 | C |
| IIB-370 | 4-Nt-Bnzl | H | Hxy | Ph-Et | 1.04 | 503 | C |
| IIB-371 | i-Pnt | H | 4-F-Bnzl | Bnzl | 2.73 | 448 | B1 |
| IIB-372 | i-Pnt | H | Ph-Et | Bnzl | 2.76 | 444 | B1 |
| IIB-373 | i-Pnt | H | 1-Npm | Bnzl | 2.93 | 480 | B1 |
| IIB-374 | i-Bu | H | 4-F-Bnzl | Ph-Et | 2.73 | 448 | B1 |
| IIB-375 | i-Bu | H | Ph-Et | Ph-Et | 2.76 | 444 | B1 |

TABLE 1-continued

| | | | | | | | |
|---|---|---|---|---|---|---|---|
| IIB-376 | i-Bu | H | 1-Npm | Ph-Et | 2.93 | 480 | B1 |
| IIB-377 | 4-F-Bnzl | H | 1-Npm | Bnzl | 2.98 | 518 | B1 |
| IIB-378 | 4-F-Bnzl | H | 1-Npm | i-Bu | 1.30 | 484 | B |
| IIB-379 | tBuO-E | H | 4-F-Bnzl | 1-Npm | 1.06 | 528 | C |
| IIB-380 | tBOC-E | H | Bnzl | Ph-Et | 1.02 | 502 | C |
| IIB-381 | 4-tBuO-Bnzl | H | Bnzl | Ph-Et | 1.06 | 536 | C |
| IIB-382 | tBuO-E | H | Bnzl | 1-Npm | 1.05 | 510 | C |
| IIB-383 | Chm | H | tBuO-E | 1-Npm | 1.07 | 516 | C |
| IIB-384 | 1-Npm | H | 4-F-Bnzl | TBSO-E | 1.16 | 586 | C |
| IIB-385 | i-Pnt | H | Bnzl | Ph-Et | 1.01 | 444 | C |
| IIB-386 | 1-Npm | H | 4-F-Bnzl | Hdr-E | 0.91 | 472 | C |
| IIB-387 | Hdr-E | H | 4-F-Bnzl | 1-Npm | 0.91 | 472 | C |
| IIB-388 | Cbx-E | H | Bnzl | Ph-Et | 0.88 | 446 | C |
| IIB-389 | TBSO-E | H | Ph-Et | 1-Npm | 1.07 | 524 | C |
| IIB-390 | Ph-Et | H | Hxy | 1-Npm | 1.08 | 508 | C |
| IIB-391 | Ph-Et | H | i-Bu | 4-tBuO-Bnzl | 1.06 | 502 | C |
| IIB-392 | Ph-Et | H | i-Bu | 4-OH-Bnzl | 0.89 | 446 | C |
| IIB-393 | Ph-Et | H | i-Bu | TBSO-E | 1.13 | 498 | C |
| IIB-394 | Ph-Et | H | i-Bu | Hdr-E | 0.82 | 384 | C |
| IIB-395 | Ph-Et | H | i-Bu | i-Pnt | 1.02 | 410 | C |
| IIB-396 | i-Bu | H | i-Bu | 4-OH-Bnzl | 0.85 | 398 | C |
| IIB-397 | i-Bu | H | Bnzl | 4-OH-Bnzl | 0.87 | 432 | C |
| IIB-398 | i-Bu | H | 2-Cbx-Et | 4-OH-Bnzl | 0.69 | 414 | C |
| IIB-399 | i-Bu | H | s-Bu | 4-OH-Bnzl | 0.85 | 398 | C |
| IIB-400 | i-Bu | H | 1-Npm | 4-OH-Bnzl | 0.95 | 482 | C |
| IIB-401 | i-Bu | H | i-Pr | 4-OH-Bnzl | 0.80 | 384 | C |
| IIB-402 | i-Bu | H | 1-Npm | 2-Cbx-Et | 0.89 | 448 | C |
| IIB-403 | i-Bu | H | i-Pr | 2-Cbx-Et | 0.72 | 350 | C |
| IIB-404 | Bnzl | H | 4-OH-Bnzl | Bnzl | 0.90 | 466 | C |
| IIB-405 | Bnzl | H | i-Bu | 4-OH-Bnzl | 0.89 | 432 | C |
| IIB-406 | Bnzl | H | 2-Cbx-Et | 4-OH-Bnzl | 0.74 | 448 | C |
| IIB-407 | Bnzl | H | Bnzl | 2-Cbx-Et | 0.82 | 432 | C |
| IIB-408 | Bnzl | H | 4-OH-Bnzl | 2-Cbx-Et | 0.73 | 448 | C |
| IIB-409 | Bnzl | H | 1-Npm | 2-Cbx-Et | 0.90 | 482 | C |
| IIB-410* | Bnzl | H | 4-OH-Bnzl | 1-Npm | 0.93, 0.95 | 516 | C |
| IIB-411 | Bnzl | H | 2-Cbx-Et | 1-Npm | 0.88 | 482 | C |
| IIB-412 | 4-OH-Bnzl | H | i-Bu | Bnzl | 0.89 | 432 | C |
| IIB-413 | 4-OH-Bnzl | H | 1-Npm | Bnzl | 0.97 | 516 | C |
| IIB-414 | 4-OH-Bnzl | H | Bnzl | 2-Cbx-Et | 0.76 | 448 | C |
| IIB-415 | 4-OH-Bnzl | H | 1-Npm | 2-Cbx-Et | 0.84 | 498 | C |
| IIB-416* | 4-OH-Bnzl | H | i-Bu | 1-Npm | 0.93, 0.94 | 482 | C |
| IIB-417 | 4-OH-Bnzl | H | Bnzl | 1-Npm | 0.95 | 516 | C |
| IIB-418 | 4-OH-Bnzl | H | 2-Cbx-Et | 1-Npm | 0.82 | 498 | C |

TABLE 1-continued

| | | | | | | | |
|---|---|---|---|---|---|---|---|
| IIB-419 | 4-OH-Bnzl | H | s-Bu | 1-Npm | 0.94 | 482 | C |
| IIB-420* | 4-OH-Bnzl | H | 1-Npm | 1-Npm | 0.98, 1.00 | 566 | C |
| IIB-421 | i-Bu | H | 4-OH-Bnzl | Bnzl | 0.88 | 432 | C |
| IIB-422 | i-Bu | H | i-Bu | 2-Cbx-Et | 0.78 | 364 | C |
| IIB-423 | i-Bu | H | Bnzl | 2-Cbx-Et | 0.81 | 398 | C |
| IIB-424 | i-Bu | H | 4-OH-Bnzl | 2-Cbx-Et | 0.71 | 414 | C |
| IIB-425 | i-Bu | H | s-Bu | 2-Cbx-Et | 0.77 | 364 | C |
| IIB-426 | i-Bu | H | 4-OH-Bnzl | 1-Npm | 0.94 | 482 | C |
| IIB-427 | i-Bu | H | 2-Cbx-Et | 1-Npm | 0.87 | 448 | C |
| IIB-428 | Bnzl | H | 2-Cbx-Et | Bnzl | 0.83 | 432 | C |
| IIB-429 | Bnzl | H | s-Bu | 4-OH-Bnzl | 0.88 | 432 | C |
| IIB-430 | Bnzl | H | 1-Npm | 4-OH-Bnzl | 0.97 | 516 | C |
| IIB-431 | Bnzl | H | i-Pr | 4-OH-Bnzl | 0.84 | 418 | C |
| IIB-432 | Bnzl | H | s-Bu | 2-Cbx-Et | 0.79 | 398 | C |
| IIB-433 | Bnzl | H | i-Pr | 2-Cbx-Et | 0.74 | 384 | C |
| IIB-434 | 4-OH-Bnzl | H | i-Pr | Bnzl | 0.85 | 418 | C |
| IIB-435 | 4-OH-Bnzl | H | i-Pr | 2-Cbx-Et | 0.68 | 400 | C |
| IIB-436 | 4-OH-Bnzl | H | i-Pr | 1-Npm | 0.90 | 468 | C |
| IIB-437 | 2-Cbx-Et | H | i-Bu | Bnzl | 0.82 | 398 | C |
| IIB-438 | 2-Cbx-Et | H | Bnzl | Bnzl | 0.84 | 432 | C |
| IIB-439 | 2-Cbx-Et | H | 4-OH-Bnzl | Bnzl | 0.76 | 448 | C |
| IIB-440 | 2-Cbx-Et | H | s-Bu | Bnzl | 0.81 | 398 | C |
| IIB-441 | 2-Cbx-Et | H | 1-Npm | Bnzl | 0.91 | 482 | C |
| IIB-442 | 2-Cbx-Et | H | i-Bu | 4-OH-Bnzl | 0.76 | 414 | C |
| IIB-443 | 2-Cbx-Et | H | Bnzl | 4-OH-Bnzl | 0.78 | 448 | C |
| IIB-444 | 2-Cbx-Et | H | s-Bu | 4-OH-Bnzl | 0.75 | 414 | C |
| IIB-445 | 2-Cbx-Et | H | 1-Npm | 4-OH-Bnzl | 0.86 | 498 | C |
| IIB-446 | 2-Cbx-Et | H | i-Pr | 4-OH-Bnzl | 0.71 | 400 | C |
| IIB-447 | 2-Cbx-Et | H | i-Bu | 1-Npm | 0.88 | 448 | C |
| IIB-448 | 2-Cbx-Et | H | 4-OH-Bnzl | 1-Npm | 0.83 | 498 | C |
| IIB-449 | 2-Cbx-Et | H | s-Bu | 1-Npm | 0.87 | 448 | C |
| IIB-450 | 2-Cbx-Et | H | 1-Npm | 1-Npm | 0.96 | 532 | C |
| IIB-451 | 1-Npm | H | 4-OH-Bnzl | Bnzl | 0.95 | 516 | C |
| IIB-452 | 1-Npm | H | Bnzl | 4-OH-Bnzl | 0.95 | 516 | C |
| IIB-453 | 1-Npm | H | 2-Cbx-Et | 4-OH-Bnzl | 0.80 | 498 | C |
| IIB-454 | 1-Npm | H | s-Bu | 4-OH-Bnzl | 0.94 | 482 | C |
| IIB-455 | 1-Npm | H | 1-Npm | 4-OH-Bnzl | 1.01 | 566 | C |
| IIB-456 | 1-Npm | H | i-Pr | 4-OH-Bnzl | 0.90 | 468 | C |
| IIB-457 | 1-Npm | H | i-Bu | 2-Cbx-Et | 0.88 | 448 | C |
| IIB-458 | 1-Npm | H | Bnzl | 2-Cbx-Et | 0.89 | 482 | C |
| IIB-459 | 1-Npm | H | 4-OH-Bnzl | 2-Cbx-Et | 0.81 | 498 | C |
| IIB-460 | 1-Npm | H | s-Bu | 2-Cbx-Et | 0.88 | 448 | C |
| IIB-461 | 1-Npm | H | 1-Npm | 2-Cbx-Et | 0.96 | 532 | C |
| IIB-462* | 1-Npm | H | 4-OH-Bnzl | 1-Npm | 0.97, 1.00 | 566 | C |
| IIB-463* | 1-Npm | H | 2-Cbx-Et | 1-Npm | 0.93, 0.95 | 532 | C |
| IIB-464 | i-Bu | H | 4-OH-Bnzl | i-Bu | 0.86 | 398 | C |

TABLE 1-continued

| | | | | | | | |
|---|---|---|---|---|---|---|---|
| IIB-465 | i-Bu | H | 2-Cbx-Et | i-Bu | 0.78 | 364 | C |
| IIB-466 | i-Bu | H | 1-Npm | 3-Gun-Pr | 0.78 | 475 | C |
| IIB-467 | Bnzl | H | i-Bu | 3-Gun-Pr | 0.69 | 425 | C |
| IIB-468 | 2-Cbx-Et | H | i-Bu | i-Bu | 0.81 | 364 | C |
| IIB-469 | 2-Cbx-Et | H | Bnzl | i-Bu | 0.83 | 398 | C |
| IIB-470 | 2-Cbx-Et | H | 4-OH-Bnzl | i-Bu | 0.75 | 414 | C |
| IIB-471 | 2-Cbx-Et | H | s-Bu | i-Bu | 0.81 | 364 | C |
| IIB-472 | 2-Cbx-Et | H | 1-Npm | i-Bu | 0.91 | 448 | C |
| IIB-473 | 2-Cbx-Et | H | i-Pr | i-Bu | 0.76 | 350 | C |
| IIB-474 | 2-Cbx-Et | H | Bnzl | 1-Npm | 0.89 | 482 | C |
| IIB-475 | 2-Cbx-Et | H | i-Pr | 1-Npm | 0.84 | 434 | C |
| IIB-476 | 1-Npm | H | 3-Gun-Pr | Bnzl | 0.78 | 509 | C |
| IIB-477 | 1-Npm | H | i-Bu | 4-OH-Bnzl | 0.94 | 482 | C |
| IIB-478 | 1-Npm | H | i-Pr | 2-Cbx-Et | 0.83 | 434 | C |
| IIB-479 | 1-Npm | H | 1-Npm | 3-Gun-Pr | 0.84 | 559 | C |
| IIB-480 | 1-Npm | H | i-Pr | 3-Gun-Pr | 0.72 | 461 | C |
| IIB-481 | 1-Npm | H | 3-Gun-Pr | 1-Npm | 0.83 | 559 | C |
| IIB-482 | i-Bu | H | 3-Gun-Pr | i-Bu | 0.69 | 391 | C |
| IIB-483 | i-Bu | H | 3-Gun-Pr | Bnzl | 0.70 | 425 | C |
| IIB-484 | i-Bu | H | i-Bu | 3-Gun-Pr | 0.68 | 391 | C |
| IIB-485 | i-Bu | H | Bnzl | 3-Gun-Pr | 0.71 | 425 | C |
| IIB-486 | i-Bu | H | s-Bu | 3-Gun-Pr | 0.67 | 391 | C |
| IIB-487 | i-Bu | H | i-Pr | 3-Gun-Pr | 0.63 | 377 | C |
| IIB-488 | i-Bu | H | 3-Gun-Pr | 1-Npm | 0.76 | 475 | C |
| IIB-489 | Bnzl | H | 3-Gun-Pr | i-Bu | 0.71 | 425 | C |
| IIB-490 | Bnzl | H | 3-Gun-Pr | Bnzl | 0.73 | 459 | C |
| IIB-491 | Bnzl | H | Bnzl | 3-Gun-Pr | 0.71 | 459 | C |
| IIB-492 | Bnzl | H | s-Bu | 3-Gun-Pr | 0.68 | 425 | C |
| IIB-493 | Bnzl | H | i-Pr | 3-Gun-Pr | 0.64 | 411 | C |
| IIB-494 | Bnzl | H | 3-Gun-Pr | 1-Npm | 0.78 | 509 | C |
| IIB-495 | 2-Cbx-Et | H | i-Pr | Bnzl | 0.77 | 384 | C |
| IIB-496 | 3-Gun-Pr | H | 1-Npm | i-Bu | 0.79 | 475 | C |
| IIB-497 | 3-Gun-Pr | H | i-Pr | i-Bu | 0.66 | 377 | C |
| IIB-498 | 3-Gun-Pr | H | 1-Npm | Bnzl | 0.79 | 509 | C |
| IIB-499* | 3-Gun-Pr | H | i-Pr | Bnzl | 0.66, 0.67 | 411 | C |
| IIB-500 | 3-Gun-Pr | H | 1-Npm | 1-Npm | 0.82 | 559 | C |
| IIB-501* | 3-Gun-Pr | H | i-Pr | 1-Npm | 0.71, 0.74 | 461 | C |
| IIB-502 | 1-Npm | H | 3-Gun-Pr | i-Bu | 0.77 | 475 | C |
| IIB-503 | 3-tertbutoxy-propyl | H | 4-F-Bnzl | 1-Npm | 1.05 | 542 | C |
| IIB-504 | 3-hydroxypropyl | H | 4-F-Bnzl | 1-Npm | 0.9 | 486 | C |
| IIB-505 | Hdr-E | H | 4-Cl-Bnzl | 1-Npm | 0.93 | 488 | C |
| IIB-506 | 3-aminopropyl | H | 3-aminopropyl | 3-aminopropyl | 1.06 | 751 | C |
| IIB-507 | 1-Npm | H | β-hydroxy-phenethyl | Ph-Et | 0.98 | 544 | C |

TABLE 1-continued

| | | | | | | | |
|---|---|---|---|---|---|---|---|
| IIB-508 | 1-Npm | H | α-(hydroxymethyl)phenethyl | Ph-Et | 0.97 | 558 | C |
| IIB-509 | 1-Npm | H | α-(hydroxymethyl)phenethyl | Ph-Et | 1.00 | 558 | C |
| IIB-510 | 4-Nt-Bnzl | H | Bnzl | tBOC-E | 0.96 | 533 | C |
| IIB-511 | 2-OH-Et | H | Ph-Et | 1-Npm | 0.89 | 468.3 | C |
| IIB-512 | Chm | H | 2-OH-Et | 1-Npm | 0.86 | 460.3 | C |
| IIB-513 | i-Bu | H | i-Pr | 3-Gun-Pr | 0.58 | 377.3 | C |
| IIB-514 | Bnzl | H | 4-OH-Bnzl | i-Bu | 0.81 | 432.2 | C |
| IIB-515 | Bnzl | H | i-Bu | 4-OH-Bnzl | 0.81 | 432.2 | C |
| IIB-516 | i-Bu | H | Bnzl | 4-OH-Bnzl | 0.81 | 432.3 | C |
| IIB-517 | i-Bu | H | 4-OH-Bnzl | Bnzl | 0.81 | 432.3 | C |
| IIB-518 | 2-OH-Et | H | Bnzl | 1-Npm | 0.87 | 454.3 | C |
| IIB-519 | Ph-Et | H | 1-Npm | Hxy | 1.10 | 508.4 | C |
| IIB-520 | 1-Npm | H | Ph-Et | Hxy | 1.10 | 508.4 | C |
| IIB-521 | Hxy | H | Ph-Et | 1-Npm | 1.08 | 508.4 | C |
| IIB-522 | Hxy | H | 1-Npm | Ph-Et | 1.09 | 508.4 | C |
| IIB-523 | i-Pnt | H | i-Pr | i-Bu | 3.52 | 348 | F |
| IIB-524 | Chm | H | i-Pr | i-Bu | 3.94 | 374 | F |
| IIB-525 | Chm | H | i-Pr | i-Pnt | 4.35 | 388 | F |
| IIB-526 | i-Bu | H | s-Bu | i-Pnt | 3.95 | 362 | F |
| IIB-527 | i-Pnt | H | s-Bu | i-Bu | 3.75 | 362 | F |
| IIB-528 | i-Pnt | H | s-Bu | Ph-Et | 4.29 | 410 | F |
| IIB-529 | Chm | H | s-Bu | i-Bu | 4.22 | 388 | F |
| IIB-530 | Chm | H | s-Bu | Ph-Et | 4.32 | 436 | F |
| IIB-531 | Chm | H | s-Bu | i-Pnt | 4.52 | 402 | F |
| IIB-532 | Chm | H | i-Pnt | i-Bu | 4.7 | 402 | F |
| IIB-533 | i-Pnt | H | Hxy | i-Bu | 4.55 | 390 | F |
| IIB-534 | 2-Cbx-Et | H | Bnzl | 2-OH-Et | 2.27 | 386 | F |
| IIB-535 | 2-Cbx-Et | H | Bnzl | i-Pnt | 3.49 | 412 | F |
| IIB-536 | Ph-Et | H | Bnzl | 2-Cbx-Et | 3.02 | 446 | F |
| IIB-537 | 4-F-Bnzl | H | Bnzl | 2-Cbx-Et | 3.13 | 450 | F |
| IIB-538 | 2-OH-Et | H | Bnzl | 2-Cbx-Et | 2.52 | 386 | F |
| IIB-539 | i-Pnt | H | Bnzl | 2-Cbx-Et | 3.15 | 412 | F |
| IIB-540 | i-Pnt | H | Bnzl | 2-OH-Et | 3.07 | 384 | F |
| IIB-541 | Chm | H | Bnzl | 2-Cbx-Et | 3.42 | 438 | F |
| IIB-542 | 2-Cbx-Et | H | i-Bu | Ph-Et | 3.3 | 412 | F |
| IIB-543 | 2-Cbx-Et | H | i-Bu | i-Pnt | 3.29 | 378 | F |
| IIB-544 | Ph-Et | H | i-Bu | 2-Cbx-Et | 3.13 | 412 | F |
| IIB-545 | 4-F-Bnzl | H | i-Bu | 2-Cbx-Et | 2.98 | 416 | F |
| IIB-546 | 2-OH-Et | H | i-Bu | 2-Cbx-Et | 3.57 | 352 | G |
| IIB-547 | i-Pnt | H | i-Bu | 4-OH-Bnzl | 3.38 | 412 | F |
| IIB-548 | i-Pnt | H | i-Bu | 2-Cbx-Et | 2.99 | 378 | F |
| IIB-549 | Chm | H | i-Bu | 4-OH-Bnzl | 3.63 | 438 | F |
| IIB-550 | Chm | H | i-Bu | 2-Cbx-Et | 3.29 | 404 | F |
| IIB-551 | 2-Cbx-Et | H | 1-Npm | Ph-Et | 3.84 | 496 | F |
| IIB-552 | 2-Cbx-Et | H | 1-Npm | 2-OH-Et | 2.82 | 436 | F |
| IIB-553 | 2-Cbx-Et | H | 1-Npm | i-Pnt | 3.92 | 462 | F |
| IIB-554 | Ph-Et | H | 1-Npm | 2-Cbx-Et | 3.72 | 496 | F |
| IIB-555 | 4-F-Bnzl | H | 1-Npm | 2-Cbx-Et | 3.62 | 500 | F |
| IIB-556 | 2-OH-Et | H | 1-Npm | 2-Cbx-Et | 2.95 | 436 | F |
| IIB-557 | i-Pnt | H | 1-Npm | 2-Cbx-Et | 3.65 | 462 | F |
| IIB-558 | Chm | H | 1-Npm | 2-Cbx-Et | 3.94 | 488 | F |
| IIB-559 | 4-OH-Bnzl | H | i-Pr | Ph-Et | 3.3 | 432 | F |
| IIB-560 | 4-OH-Bnzl | H | i-Pr | i-Pnt | 3.1 | 398 | F |
| IIB-561 | 2-Cbx-Et | H | i-Pr | Ph-Et | 3.04 | 398 | F |
| IIB-562 | 2-Cbx-Et | H | i-Pr | 2-OH-Et | 2.82 | 338 | G |
| IIB-563 | 2-Cbx-Et | H | i-Pr | i-Pnt | 3 | 364 | F |
| IIB-564 | Ph-Et | H | i-Pr | 2-Cbx-Et | 2.87 | 398 | F |
| IIB-565 | Ph-Et | H | i-Pr | 2-OH-Et | 2.82 | 370 | F |
| IIB-566 | 4-F-Bnzl | H | i-Pr | 2-OH-Et | 2.77 | 374 | F |
| IIB-567 | 2-OH-Et | H | i-Pr | Bnzl | 2.77 | 356 | F |
| IIB-568 | 2-OH-Et | H | i-Pr | 1-Npm | 3.24 | 406 | F |
| IIB-569 | 2-OH-Et | H | i-Pr | 4-OH-Bnzl | 2.52 | 372 | F |
| IIB-570 | 2-OH-Et | H | i-Pr | 2-Cbx-Et | 3.09 | 338 | G |
| IIB-571 | 2-OH-Et | H | i-Pr | Ph-Et | 3.02 | 370 | F |
| IIB-572 | i-Pnt | H | i-Pr | 4-OH-Bnzl | 3.04 | 398 | F |
| IIB-573 | i-Pnt | H | i-Pr | 2-Cbx-Et | 2.69 | 364 | F |
| IIB-574 | i-Pnt | H | i-Pr | 2-OH-Et | 2.65 | 336 | F |
| IIB-575 | Chm | H | i-Pr | 4-OH-Bnzl | 3.34 | 424 | F |
| IIB-576 | Chm | H | i-Pr | 2-Cbx-Et | 2.94 | 390 | F |

TABLE 1-continued

| | | | | | | | |
|---|---|---|---|---|---|---|---|
| IIB-577 | i-Bu | H | s-Bu | 2-OH-Et | 2.62 | 336 | F |
| IIB-578 | 4-OH-Bnzl | H | s-Bu | Ph-Et | 3.50 | 446 | F |
| IIB-579 | 4-OH-Bnzl | H | s-Bu | i-Pnt | 3.38 | 412 | F |
| IIB-580 | 2-Cbx-Et | H | s-Bu | Ph-Et | 3.22 | 412 | F |
| IIB-581 | 2-Cbx-Et | H | s-Bu | i-Pnt | 3.27 | 378 | F |
| IIB-582 | Ph-Et | H | s-Bu | 2-Cbx-Et | 3.10 | 412 | F |
| IIB-583 | 4-F-Bnzl | H | s-Bu | 2-Cbx-Et | 2.88 | 416 | F |
| IIB-584 | 2-OH-Et | H | s-Bu | 4-OH-Bnzl | 2.69 | 386 | F |
| IIB-585 | 2-OH-Et | H | s-Bu | 2-Cbx-Et | 3.47 | 352 | G |
| IIB-586 | 2-OH-Et | H | s-Bu | i-Pnt | 3.24 | 350 | F |
| IIB-587 | i-Pnt | H | s-Bu | 4-OH-Bnzl | 3.34 | 412 | F |
| IIB-588 | i-Pnt | H | s-Bu | 2-Cbx-Et | 2.90 | 378 | F |
| IIB-589 | i-Pnt | H | s-Bu | 2-OH-Et | 2.90 | 350 | F |
| IIB-590 | Chm | H | s-Bu | 4-OH-Bnzl | 3.62 | 438 | F |
| IIB-591 | Chm | H | s-Bu | 2-Cbx-Et | 3.24 | 404 | F |
| IIB-592 | i-Bu | H | 4-OH-Bnzl | i-Pnt | 3.52 | 412 | F |
| IIB-593 | 2-Cbx-Et | H | 4-OH-Bnzl | Ph-Et | 3.04 | 462 | F |
| IIB-594 | 2-Cbx-Et | H | 4-OH-Bnzl | i-Pnt | 2.92 | 428 | F |
| IIB-595 | Ph-Et | H | 4-OH-Bnzl | 2-Cbx-Et | 2.85 | 462 | F |
| IIB-596 | 4-F-Bnzl | H | 4-OH-Bnzl | 2-Cbx-Et | 2.77 | 466 | F |
| IIB-597 | 2-OH-Et | H | 4-OH-Bnzl | 2-Cbx-Et | 3.24 | 402 | G |
| IIB-598 | i-Pnt | H | 4-OH-Bnzl | 2-Cbx-Et | 2.72 | 428 | F |
| IIB-599 | Chm | H | 4-OH-Bnzl | 2-Cbx-Et | 2.97 | 454 | F |
| IIB-600 | i-Bu | H | 2-Cbx-Et | Ph-Et | 3.12 | 412 | F |
| IIB-601 | i-Bu | H | 2-Cbx-Et | i-Pnt | 3.12 | 378 | F |
| IIB-602 | 2-OH-Et | H | 2-Cbx-Et | i-Bu | 3.5 | 352 | G |
| IIB-603 | i-Pnt | H | 2-Cbx-Et | i-Bu | 3.04 | 378 | F |
| IIB-604 | i-Pnt | H | 2-Cbx-Et | 4-OH-Bnzl | 2.63 | 428 | F |
| IIB-605 | Chm | H | 2-Cbx-Et | i-Bu | 3.34 | 404 | F |
| IIB-606 | Chm | H | 2-Cbx-Et | 4-OH-Bnzl | 2.85 | 454 | F |
| IIB-607 | Chm | H | 2-Cbx-Et | i-Pnt | 3.59 | 418 | F |
| IIB-608 | Bnzl | H | 4-F-Bnzl | 4-OH-Bnzl | 3.63 | 484 | F |
| IIB-609 | Bnzl | H | 4-F-Bnzl | 2-Cbx-Et | 3.12 | 450 | F |
| IIB-610 | i-Bu | H | 4-F-Bnzl | 4-OH-Bnzl | 3.44 | 450 | F |
| IIB-611 | i-Bu | H | 4-F-Bnzl | 2-Cbx-Et | 3.02 | 416 | F |
| IIB-612 | 1-Npm | H | 4-F-Bnzl | 4-OH-Bnzl | 3.99 | 534 | F |
| IIB-613 | 1-Npm | H | 4-F-Bnzl | 2-Cbx-Et | 3.57 | 500 | F |
| IIB-614 | 4-OH-Bnzl | H | 4-F-Bnzl | 2-Cbx-Et | 2.85 | 466 | F |
| IIB-615 | 4-OH-Bnzl | H | 4-F-Bnzl | Ph-Et | 3.63 | 498 | F |
| IIB-616 | 4-OH-Bnzl | H | 4-F-Bnzl | i-Pnt | 3.57 | 464 | F |
| IIB-617 | 2-Cbx-Et | H | 4-F-Bnzl | 4-OH-Bnzl | 2.95 | 466 | F |
| IIB-618 | 2-Cbx-Et | H | 4-F-Bnzl | Ph-Et | 3.48 | 464 | F |
| IIB-619 | 2-Cbx-Et | H | 4-F-Bnzl | i-Pnt | 3.42 | 430 | F |

TABLE 1-continued

| | | | | | | | |
|---|---|---|---|---|---|---|---|
| IIB-620 | Ph-Et | H | 4-F-Bnzl | 4-OH-Bnzl | 3.67 | 498 | F |
| IIB-621 | Ph-Et | H | 4-F-Bnzl | 2-Cbx-Et | 3.32 | 464 | F |
| IIB-622 | 2-OH-Et | H | 4-F-Bnzl | 4-OH-Bnzl | 2.95 | 438 | F |
| IIB-623 | 2-OH-Et | H | 4-F-Bnzl | 2-Cbx-Et | 2.57 | 404 | F |
| IIB-624 | i-Pnt | H | 4-F-Bnzl | 4-OH-Bnzl | 3.54 | 464 | F |
| IIB-625 | i-Pnt | H | 4-F-Bnzl | 2-Cbx-Et | 3.19 | 430 | F |
| IIB-626 | Chm | H | 4-F-Bnzl | 4-OH-Bnzl | 3.80 | 490 | F |
| IIB-627 | Chm | H | 4-F-Bnzl | 2-Cbx-Et | 3.45 | 456 | F |
| IIB-628 | i-Bu | H | i-Pnt | 2-Cbx-Et | 3.05 | 378 | F |
| IIB-629 | 4-OH-Bnzl | H | i-Pnt | 2-Cbx-Et | 2.80 | 428 | F |
| IIB-630 | 2-Cbx-Et | H | i-Pnt | i-Bu | 3.25 | 378 | F |
| IIB-631 | 2-Cbx-Et | H | i-Pnt | 4-OH-Bnzl | 2.90 | 428 | F |
| IIB-632 | 2-OH-Et | H | i-Pnt | i-Bu | 3.20 | 350 | F |
| IIB-633 | 2-OH-Et | H | i-Pnt | 2-Cbx-Et | 2.59 | 366 | F |
| IIB-634 | Chm | H | i-Pnt | 2-Cbx-Et | 3.54 | 418 | F |
| IIB-635 | i-Bu | H | 2-OH-Et | i-Bu | 2.69 | 336 | F |
| IIB-636 | i-Bu | H | 2-OH-Et | 4-OH-Bnzl | 2.35 | 386 | F |
| IIB-637 | i-Npm | H | 2-OH-Et | 4-OH-Bnzl | 2.94 | 470 | F |
| IIB-638 | i-Npm | H | 2-OH-Et | 2-Cbx-Et | 2.63 | 436 | F |
| IIB-639 | 4-OH-Bnzl | H | 2-OH-Et | Bnzl | 2.67 | 420 | F |
| IIB-640 | 4-OH-Bnzl | H | 2-OH-Et | 1-Npm | 3.04 | 470 | F |
| IIB-641 | 4-OH-Bnzl | H | 2-OH-Et | Ph-Et | 2.75 | 434 | F |
| IIB-642 | 4-OH-Bnzl | H | 2-OH-Et | i-Pnt | 2.60 | 400 | F |
| IIB-643 | 2-Cbx-Et | H | 2-OH-Et | Bnzl | 3.60 | 386 | F |
| IIB-644 | 2-Cbx-Et | H | 2-OH-Et | i-Bu | 3.40 | 352 | F |
| IIB-645 | 2-Cbx-Et | H | 2-OH-Et | 1-Npm | 2.84 | 436 | F |
| IIB-646 | 2-Cbx-Et | H | 2-OH-Et | Ph-Et | 2.57 | 400 | F |
| IIB-647 | 2-Cbx-Et | H | 2-OH-Et | i-Pnt | 2.52 | 366 | F |
| IIB-648 | Ph-Et | H | 2-OH-Et | 2-Cbx-Et | 2.37 | 400 | F |
| IIB-649 | 4-F-Bnzl | H | 2-OH-Et | 2-Cbx-Et | 2.12 | 404 | F |
| IIB-650 | i-Pnt | H | 2-OH-Et | i-Bu | 2.94 | 350 | F |
| IIB-651 | i-Pnt | H | 2-OH-Et | 2-Cbx-Et | 3.34 | 366 | F |
| IIB-652 | Chm | H | 2-OH-Et | i-Bu | 3.17 | 376 | F |
| IIB-653 | Chm | H | 2-OH-Et | 2-Cbx-Et | 2.47 | 392 | F |
| IIB-654 | Bnzl | H | Ph-Et | 4-OH-Bnzl | 3.69 | 480 | F |
| IIB-655 | Bnzl | H | Ph-Et | 2-Cbx-Et | 3.15 | 446 | F |
| IIB-656 | i-Bu | H | Ph-Et | 4-OH-Bnzl | 3.47 | 446 | F |
| IIB-657 | i-Bu | H | Ph-Et | 2-Cbx-Et | 3.05 | 412 | F |
| IIB-658 | 1-Npm | H | Ph-Et | 4-OH-Bnzl | 4.02 | 530 | F |
| IIB-659 | 1-Npm | H | Ph-Et | 2-Cbx-Et | 3.62 | 496 | F |
| IIB-660 | 4-OH-Bnzl | H | Ph-Et | 2-Cbx-Et | 2.85 | 462 | F |
| IIB-661 | 4-OH-Bnzl | H | Ph-Et | i-Pnt | 3.74 | 460 | F |
| IIB-662 | 2-Cbx-Et | H | Ph-Et | 4-OH-Bnzl | 3.02 | 462 | F |
| IIB-663 | 2-Cbx-Et | H | Ph-Et | i-Pnt | 3.55 | 426 | F |
| IIB-664 | 4-F-Bnzl | H | Ph-Et | 4-OH-Bnzl | 3.69 | 498 | F |
| IIB-665 | 4-F-Bnzl | H | Ph-Et | 2-Cbx-Et | 3.22 | 464 | F |
| IIB-666 | 2-OH-Et | H | Ph-Et | 4-OH-Bnzl | 2.99 | 434 | F |
| IIB-667 | 2-OH-Et | H | Ph-Et | 2-Cbx-Et | 2.62 | 400 | F |
| IIB-668 | i-Pnt | H | Ph-Et | 4-OH-Bnzl | 3.63 | 460 | F |
| IIB-669 | i-Pnt | H | Ph-Et | 2-Cbx-Et | 3.27 | 426 | F |
| IIB-670 | Chm | H | Ph-Et | 4-OH-Bnzl | 3.92 | 486 | F |
| IIB-671 | Chm | H | Ph-Et | 2-Cbx-Et | 3.55 | 452 | F |
| IIB-672 | Bnzl | H | Hxy | 2-Cbx-Et | 3.54 | 426 | F |

TABLE 1-continued

| | | | | | | | |
|---|---|---|---|---|---|---|---|
| IIB-673 | i-Bu | H | Hxy | 2-Cbx-Et | 3.42 | 392 | F |
| IIB-674 | 1-Npm | H | Hxy | 2-Cbx-Et | 4 | 476 | F |
| IIB-675 | 4-OH-Bnzl | H | Hxy | 2-Cbx-Et | 3.17 | 442 | F |
| IIB-676 | 2-Cbx-Et | H | Hxy | i-Bu | 3.54 | 392 | F |
| IIB-677 | 2-Cbx-Et | H | Hxy | 4-OH-Bnzl | 3.25 | 442 | F |
| IIB-678 | 2-Cbx-Et | H | Hxy | i-Put | 3.84 | 406 | F |
| IIB-679 | Ph-Et | H | Hxy | 2-Cbx-Et | 3.75 | 440 | F |
| IIB-680 | 4-F-Bnzl | H | Hxy | 2-Cbx-Et | 3.6 | 444 | F |
| IIB-681 | 2-OH-Et | H | Hxy | i-Bu | 3.6 | 364 | F |
| IIB-682 | 2-OH-Et | H | Hxy | 4-OH-Bnzl | 3.29 | 414 | F |
| IIB-683 | 2-OH-Et | H | Hxy | 2-Cbx-Et | 2.88 | 380 | F |
| IIB-684 | 2-OH-Et | H | Hxy | i-Pnt | 3.87 | 378 | F |
| IIB-685 | i-Put | H | Hxy | 4-OH-Bnzl | 3.98 | 440 | F |
| IIB-686 | i-Put | H | Hxy | 2-Cbx-Et | 3.59 | 406 | F |
| IIB-687 | i-Put | H | Hxy | 2-OH-Et | 3.52 | 378 | F |
| IIB-688 | Chm | H | Hxy | 4-OH-Bnzl | 4.24 | 466 | F |
| IIB-689 | Chm | H | Hxy | 2-Cbx-Et | 3.88 | 432 | F |
| IIB-690 | tBOC-E | H | Bnzl | i-Pnt | 4.47 | 468 | F |
| IIB-691 | Ph-Et | H | Bnzl | tBOC-E | 4.34 | 502 | F |
| IIB-692 | 4-F-Bnzl | H | Bnzl | tBOC-E | 4.09 | 506 | F |
| IIB-693 | 2-OtBu-Et | H | Bnzl | tBOC-E | 4.27 | 498 | F |
| IIB-694 | i-Put | H | Bnzl | tBOC-E | 4.25 | 468 | F |
| IIB-695 | Chm | H | Bnzl | tBOC-E | 4.5 | 494 | F |
| IIB-696 | tBOC-E | H | i-Bu | Ph-Et | 4.25 | 468 | F |
| IIB-697 | tBOC-E | H | i-Bu | i-Pnt | 4.3 | 434 | F |
| IIB-698 | Ph-Et | H | i-Bu | tBOC-E | 4.18 | 468 | F |
| IIB-699 | 2-OtBu-Et | H | i-Bu | tBOC-E | 4.09 | 464 | F |
| IIB-700 | i-Pnt | H | i-Bu | 4-tBuO-Bnzl | 4.43 | 468 | F |
| IIB-701 | i-Pnt | H | i-Bu | tBOC-E | 3.97 | 434 | F |
| IIB-702 | Chm | H | i-Bu | 4-tBuO-Bnzl | 4.67 | 494 | F |
| IIB-703 | Chm | H | i-Bu | tBOC-E | 4.43 | 460 | F |
| IIB-704 | tBOC-E | H | 1-Npm | Ph-Et | 4.78 | 552 | F |
| IIB-705 | tBOC-E | H | 1-Npm | i-Pnt | 4.89 | 518 | F |
| IIB-706 | Ph-Et | H | 1-Npm | tBOC-E | 4.72 | 552 | F |
| IIB-707 | 4-F-Bnzl | H | 1-Npm | tBOC-E | 4.52 | 556 | F |
| IIB-708 | 2-OtBu-Et | H | 1-Npm | tBOC-E | 5.37 | 548 | F |
| IIB-709 | i-Pnt | H | 1-Npm | tBOC-E | 4.68 | 518 | F |
| IIB-710 | Chm | H | 1-Npm | tBOC-E | 4.9 | 544 | F |
| IIB-711 | 4-tBuO-Bnzl | H | i-Pr | Ph-Et | 4.29 | 488 | F |
| IIB-712 | tBOC-E | H | i-Pr | Ph-Et | 3.92 | 454 | F |
| IIB-713 | tBOC-E | H | i-Pr | i-Pnt | 4 | 420 | F |
| IIB-714 | Ph-Et | H | i-Pr | tBOC-E | 3.92 | 454 | F |
| IIB-715 | 2-OtBu-Et | H | i-Pr | Bnzl | 3.77 | 412 | F |
| IIB-716 | 2-OtBu-Et | H | i-Pr | 1-Npm | 4.24 | 462 | F |
| IIB-717 | 2-OtBu-Et | H | i-Pr | 4-tBuO-Bnzl | 4.37 | 484 | F |
| IIB-718 | 2-OtBu-Et | H | i-Pr | tBOC-E | 3.94 | 450 | F |
| IIB-719 | 2-OtBu-Et | H | i-Pr | i-Pnt | 4.04 | 392 | F |
| IIB-720 | i-Pnt | H | i-Pr | 4-tBuO-Bnzl | 4.22 | 454 | F |
| IIB-721 | i-Pnt | H | i-Pr | tBOC-E | 4.82 | 420 | F |
| IIB-722 | Chm | H | i-Pr | 4-tBuO-Bnzl | 4.57 | 480 | F |
| IIB-723 | 4-tBuO-Bnzl | H | s-Bu | Ph-Et | 4.5 | 502 | F |
| IIB-724 | 4-tBuO-Bnzl | H | s-Bu | i-Pnt | 4.62 | 468 | F |
| IIB-725 | tBOC-E | H | s-Bu | Ph-Et | 4.29 | 468 | F |
| IIB-726 | tBOC-E | H | s-Bu | i-Pnt | 4.3 | 434 | F |
| IIB-727 | Ph-Et | H | s-Bu | tBOC-E | 4.14 | 468 | F |
| IIB-728 | 4-F-Bnzl | H | s-Bu | tBOC-E | 4.52 | 472 | F |
| IIB-729 | 2-OtBu-Et | H | s-Bu | 4-tBuO-Bnzl | 4.68 | 498 | F |
| IIB-730 | 2-OtBu-Et | H | s-Bu | tBOC-E | 4.17 | 464 | F |
| IIB-731 | i-Pnt | H | s-Bu | 4-tBuO-Bnzl | 4.74 | 468 | F |
| IIB-732 | i-Pnt | H | s-Bu | tBOC-E | 4.27 | 434 | F |
| IIB-733 | Chm | H | s-Bu | 4-tBuO-Bnzl | 4.74 | 494 | F |
| IIB-734 | i-Bu | H | 4-tBuO-Bnzl | i-Pnt | 4.57 | 468 | F |
| IIB-735 | tBOC-E | H | 4-tBuO-Bnzl | Ph-Et | 5.2 | 574 | F |
| IIB-736 | tBOC-E | H | 4-tBuO-Bnzl | i-Pnt | 4.6 | 540 | F |

TABLE 1-continued

| | | | | | | | |
|---|---|---|---|---|---|---|---|
| IIB-737 | Ph-Et | H | 4-tBuO-Bnzl | tBOC-E | 4.59 | 574 | F |
| IIB-738 | 4-F-Bnzl | H | 4-tBuO-Bnzl | tBOC-E | 4.5 | 578 | F |
| IIB-739 | 2-OtBu-Et | H | 4-tBuO-Bnzl | tBOC-E | 4.79 | 570 | F |
| IIB-740 | i-Pnt | H | 4-tBuO-Bnzl | tBOC-E | 4.8 | 540 | F |
| IIB-741 | Chm | H | 4-tBuO-Bnzl | tBOC-E | 4.99 | 566 | F |
| IIB-742 | i-Bu | H | tBOC-E | Ph-Et | 4.12 | 468 | F |
| IIB-743 | i-Bu | H | tBOC-E | i-Pnt | 4.18 | 434 | F |
| IIB-744 | 2-OtBu-Et | H | tBOC-E | i-Bu | 4.1 | 464 | F |
| IIB-745 | i-Pnt | H | tBOC-E | i-Bu | 4.17 | 434 | F |
| IIB-746 | Chm | H | tBOC-E | 4-tBuO-Bnzl | 4.95 | 566 | F |
| IIB-747 | Chm | H | tBOC-E | i-Pnt | 4.55 | 474 | F |
| IIB-748 | Bnzl | H | 4-F-Bnzl | 4-tBuO-Bnzl | 4.54 | 540 | F |
| IIB-749 | Bnzl | H | 4-F-Bnzl | tBOC-E | 4.05 | 506 | F |
| IIB-750 | i-Bu | H | 4-F-Bnzl | 4-tBuO-Bnzl | 4.39 | 506 | F |
| IIB-751 | i-Bu | H | 4-F-Bnzl | tBOC-E | 3.97 | 472 | F |
| IIB-752 | 1-Npm | H | 4-F-Bnzl | 4-tBuO-Bnzl | 4.92 | 590 | F |
| IIB-753 | 1-Npm | H | 4-F-Bnzl | tBOC-E | 4.57 | 556 | F |
| IIB-754 | 4-tBuO-Bnzl | H | 4-F-Bnzl | tBOC-E | 4.62 | 578 | F |
| IIB-755 | 4-tBuO-Bnzl | H | 4-F-Bnzl | Ph-Et | 4.6 | 554 | F |
| IIB-756 | 4-tBuO-Bnzl | H | 4-F-Bnzl | i-Pnt | 4.47 | 520 | F |
| IIB-757 | tBOC-E | H | 4-F-Bnzl | 4-tBuO-Bnzl | 4.74 | 578 | F |
| IIB-758 | tBOC-E | H | 4-F-Bnzl | Ph-Et | 4.24 | 520 | F |
| IIB-759 | tBOC-E | H | 4-F-Bnzl | i-Pnt | 4.4 | 486 | F |
| IIB-760 | Ph-Et | H | 4-F-Bnzl | 4-tBuO-Bnzl | 4.59 | 554 | F |
| IIB-761 | Ph-Et | H | 4-F-Bnzl | tBOC-E | 4.4 | 520 | F |
| IIB-762 | 2-OtBu-Et | H | 4-F-Bnzl | 4-tBuO-Bnzl | 4.72 | 550 | F |
| IIB-763 | 2-OtBu-Et | H | 4-F-Bnzl | tBOC-E | 4.3 | 516 | F |
| IIB-764 | i-Pnt | H | 4-F-Bnzl | 4-tBuO-Bnzl | 4.57 | 520 | F |
| IIB-765 | i-Pnt | H | 4-F-Bnzl | tBOC-E | 4.22 | 486 | F |
| IIB-766 | Chm | H | 4-F-Bnzl | 4-tBuO-Bnzl | 4.89 | 546 | F |
| IIB-767 | Chm | H | 4-F-Bnzl | tBOC-E | 4.39 | 512 | F |
| IIB-768 | i-Bu | H | i-Pnt | tBOC-E | 4 | 434 | F |
| IIB-769 | 4-tBuO-Bnzl | H | i-Pnt | tBOC-E | 4.77 | 540 | F |
| IIB-770 | tBOC-E | H | i-Pnt | i-Bu | 4.37 | 434 | F |
| IIB-771 | tBOC-E | H | i-Pnt | 4-tBuO-Bnzl | 4.79 | 540 | F |
| IIB-772 | 2-OtBu-Et | H | i-Pnt | i-Bu | 4.5 | 406 | F |
| IIB-773 | 2-OtBu-Et | H | i-Pnt | tBOC-E | 4.67 | 478 | F |
| IIB-774 | i-Bu | H | 2-OtBu-Et | i-Bu | 3.49 | 392 | F |
| IIB-775 | i-Bu | H | 2-OtBu-Et | 4-tBuO-Bnzl | 4.34 | 498 | F |

TABLE 1-continued

| | | | | | | | |
|---|---|---|---|---|---|---|---|
| IIB-776 | i-Bu | H | 2-OtBu-Et | tBOC-E | 3.74 | 464 | F |
| IIB-777 | 1-Npm | H | 2-OtBu-Et | 4-tBuO-Bnzl | 4.75 | 582 | F |
| IIB-778 | 1-Npm | H | 2-OtBu-Et | tBOC-E | 4.42 | 548 | F |
| IIB-779 | 4-tBuO-Bnzl | H | 2-OtBu-Et | Bnzl | 4.42 | 532 | F |
| IIB-780 | 4-tBuO-Bnzl | H | 2-OtBu-Et | 1-Npm | 4.82 | 582 | F |
| IIB-781 | 4-tBuO-Bnzl | H | 2-OtBu-Et | tBOC-E | 4.4 | 570 | F |
| IIB-782 | 4-tBuO-Bnzl | H | 2-OtBu-Et | i-Pnt | 4.64 | 512 | F |
| IIB-783 | tBOC-E | H | 2-OtBu-Et | Bnzl | 3.99 | 498 | F |
| IIB-784 | tBOC-E | H | 2-OtBu-Et | i-Bu | 4.15 | 464 | F |
| IIB-785 | tBOC-E | H | 2-OtBu-Et | 4-tBuO-Bnzl | 4.54 | 570 | F |
| IIB-786 | tBOC-E | H | 2-OtBu-Et | i-Pnt | 4.22 | 478 | F |
| IIB-787 | Ph-Et | H | 2-OtBu-Et | tBOC-E | 4.04 | 512 | F |
| IIB-788 | Chm | H | 2-OtBu-Et | i-Bu | 4.12 | 432 | F |
| IIB-789 | Chm | H | 2-OtBu-Et | tBOC-E | 4.32 | 504 | F |
| IIB-790 | Bnzl | H | Ph-Et | 4-tBuO-Bnzl | 4.62 | 536 | F |
| IIB-791 | Bnzl | H | Ph-Et | tBOC-E | 4.15 | 502 | F |
| IIB-792 | i-Bu | H | Ph-Et | 4-tBuO-Bnzl | 4.47 | 502 | F |
| IIB-793 | i-Bu | H | Ph-Et | tBOC-E | 4.09 | 468 | F |
| IIB-794 | 1-Npm | H | Ph-Et | 4-tBuO-Bnzl | 4.95 | 586 | F |
| IIB-795 | 1-Npm | H | Ph-Et | tBOC-E | 4.62 | 552 | F |
| IIB-796 | 4-tBuO-Bnzl | H | Ph-Et | tBOC-E | 4.72 | 574 | F |
| IIB-797 | 4-tBuO-Bnzl | H | Ph-Et | i-Pnt | 4.74 | 516 | F |
| IIB-798 | tBOC-E | H | Ph-Et | i-Pnt | 4.65 | 482 | F |
| IIB-799 | 4-F-Bnzl | H | Ph-Et | 4-tBuO-Bnzl | 4.67 | 554 | F |
| IIB-800 | 4-F-Bnzl | H | Ph-Et | tBOC-E | 4.24 | 520 | F |
| IIB-801 | 2-OtBu-Et | H | Ph-Et | 4-tBuO-Bnzl | 4.8 | 546 | F |
| IIB-802 | 2-OtBu-Et | H | Ph-Et | tBOC-E | 4.3 | 512 | F |
| IIB-803 | i-Pnt | H | Ph-Et | 4-tBuO-Bnzl | 4.67 | 516 | F |
| IIB-804 | i-Pnt | H | Ph-Et | tBOC-E | 4.34 | 482 | F |
| IIB-805 | Chm | H | Ph-Et | 4-tBuO-Bnzl | 4.93 | 542 | F |
| IIB-806 | Chm | H | Ph-Et | tBOC-E | 4.6 | 508 | F |
| IIB-807 | Bnzl | H | Hxy | tBOC-E | 4.49 | 482 | F |
| IIB-808 | 1-Npm | H | Hxy | tBOC-E | 5 | 532 | F |
| IIB-809 | 4-tBuO-Bnzl | H | Hxy | 1-Npm | 5.37 | 566 | F |
| IIB-810 | 4-tBuO-Bnzl | H | Hxy | tBOC-E | 5.05 | 554 | F |
| IIB-811 | tBOC-E | H | Hxy | i-Bu | 4.75 | 448 | F |
| IIB-812 | tBOC-E | H | Hxy | 1-Npm | 4.92 | 532 | F |
| IIB-813 | tBOC-E | H | Hxy | 4-tBuO-Bnzl | 5.04 | 554 | F |
| IIB-814 | tBOC-E | H | Hxy | i-Pnt | 5 | 462 | F |
| IIB-815 | Ph-Et | H | Hxy | tBOC-E | 4.72 | 496 | F |
| IIB-816 | 4-F-Bnzl | H | Hxy | tBOC-E | 4.6 | 500 | F |
| IIB-817 | 2-OtBu-Et | H | Hxy | 4-tBuO-Bnzl | 5.17 | 526 | F |
| IIB-818 | 2-OtBu-Et | H | Hxy | tBOC-E | 4.87 | 492 | F |

TABLE 1-continued

| | | | | | | | |
|---|---|---|---|---|---|---|---|
| IIB-819 | 2-OtBu-Et | H | Hxy | i-Pnt | 4.95 | 434 | F |
| IIB-820 | i-Pnt | H | Hxy | 4-tBuO-Bnzl | 5.05 | 496 | F |
| IIB-821 | i-Pnt | H | Hxy | tBOC-E | 4.7 | 462 | F |
| IIB-822 | Chm | H | Hxy | 4-tBuO-Bnzl | 5.29 | 522 | F |
| IIB-823 | i-Bu | H | i-Bu | Ph-Et | 3.33 | 396 | H |
| IIB-824 | i-Bu | H | i-Bu | i-Pnt | 3.17 | 362 | H |
| IIB-825 | 1-Npm | H | i-Bu | i-Pnt | 3.45 | 446 | H |
| IIB-826 | 4-F-Bnzl | H | i-Bu | i-Bu | 3.03 | 400 | H |
| IIB-827 | 4-F-Bnzl | H | i-Bu | 1-Npm | 3.26 | 484 | H |
| IIB-828 | 4-F-Bnzl | H | i-Bu | Ph-Et | 3.15 | 448 | H |
| IIB-829 | 4-F-Bnzl | H | i-Bu | i-Pnt | 3.15 | 414 | H |
| IIB-830 | i-Pnt | H | i-Bu | i-Bu | 3.13 | 362 | H |
| IIB-831 | i-Pnt | H | i-Bu | 1-Npm | 3.3 | 446 | H |
| IIB-832 | i-Pnt | H | i-Bu | Ph-Et | 3.17 | 410 | H |
| IIB-833 | Chm | H | i-Bu | i-Bu | 3.26 | 388 | H |
| IIB-834 | Chm | H | i-Bu | 1-Npm | 3.48 | 472 | H |
| IIB-835 | Chm | H | i-Bu | Ph-Et | 3.32 | 436 | H |
| IIB-836 | Bnzl | H | Bnzl | Ph-Et | 3.39 | 464 | H |
| IIB-837 | 1-Npm | H | Bnzl | i-Pnt | 3.37 | 480 | H |
| IIB-838 | Ph-Et | H | Bnzl | 1-Npm | 3.4 | 514 | H |
| IIB-839 | Ph-Et | H | Bnzl | i-Pnt | 3.26 | 444 | H |
| IIB-840 | 4-F-Bnzl | H | Bnzl | 1-Npm | 3.34 | 518 | H |
| IIB-841 | 4-F-Bnzl | H | Bnzl | Ph-Et | 3.17 | 482 | H |
| IIB-842 | 4-F-Bnzl | H | Bnzl | i-Pnt | 3.21 | 448 | H |
| IIB-843 | i-Pnt | H | Bnzl | 1-Npm | 3.36 | 480 | H |
| IIB-844 | Chm | H | Bnzl | 1-Npm | 3.47 | 506 | H |
| IIB-845 | Chm | H | Bnzl | Ph-Et | 3.33 | 470 | H |
| IIB-846 | Chm | H | Bnzl | i-Pnt | 3.37 | 436 | H |
| IIB-847 | Bnzl | H | 1-Npm | Ph-Et | 3.39 | 514 | H |
| IIB-848 | Bnzl | H | 1-Npm | i-Pnt | 3.44 | 480 | H |
| IIB-849 | i-Bu | H | 1-Npm | i-Pnt | 3.3 | 446 | H |
| IIB-850 | 1-Npm | H | 1-Npm | Ph-Et | 3.56 | 564 | H |
| IIB-851 | 1-Npm | H | 1-Npm | i-Pnt | 3.59 | 530 | H |
| IIB-852 | Ph-Et | H | 1-Npm | Bnzl | 3.41 | 514 | H |
| IIB-853 | Ph-Et | H | 1-Npm | i-Bu | 3.38 | 480 | H |
| IIB-854 | Ph-Et | H | 1-Npm | 1-Npm | 3.53 | 564 | H |
| IIB-855 | Ph-Et | H | 1-Npm | i-Pnt | 3.46 | 494 | H |
| IIB-856 | 4-F-Bnzl | H | 1-Npm | 1-Npm | 3.48 | 568 | H |
| IIB-857 | 4-F-Bnzl | H | 1-Npm | Ph-Et | 3.39 | 532 | H |
| IIB-858 | 4-F-Bnzl | H | 1-Npm | i-Pnt | 3.4 | 498 | H |
| IIB-859 | i-Pnt | H | 1-Npm | i-Bu | 3.42 | 446 | H |
| IIB-860 | i-Pnt | H | 1-Npm | 1-Npm | 3.51 | 530 | H |
| IIB-861 | i-Pnt | H | 1-Npm | Ph-Et | 3.42 | 494 | H |
| IIB-862 | Chm | H | 1-Npm | Bnzl | 3.58 | 506 | H |
| IIB-863 | Chm | H | 1-Npm | i-Bu | 3.54 | 472 | H |
| IIB-864 | Chm | H | 1-Npm | 1-Npm | 3.67 | 556 | H |
| IIB-865 | Chm | H | 1-Npm | Ph-Et | 3.57 | 520 | H |
| IIB-866 | Chm | H | 1-Npm | i-Pnt | 3.59 | 486 | H |

TABLE 1-continued

| | | | | | | | |
|---|---|---|---|---|---|---|---|
| IIB-867 | Bnzl | H | i-Pr | Ph-Et | 3.16 | 416 | H |
| IIB-868 | Bnzl | H | i-Pr | i-Pnt | 3.17 | 382 | H |
| IIB-869 | i-Bu | H | i-Pr | Ph-Et | 3.12 | 382 | H |
| IIB-870 | 1-Npm | H | i-Pr | Ph-Et | 3.34 | 466 | H |
| IIB-871 | 1-Npm | H | i-Pr | i-Pnt | 3.38 | 432 | H |
| IIB-872 | Ph-Et | H | i-Pr | Bnzl | 3.15 | 416 | H |
| IIB-873 | Ph-Et | H | i-Pr | i-Bu | 3.12 | 382 | H |
| IIB-874 | Ph-Et | H | i-Pr | 1-Npm | 3.34 | 466 | H |
| IIB-875 | Ph-Et | H | i-Pr | i-Pnt | 3.22 | 396 | H |
| IIB-876 | 4-F-Bnzl | H | i-Pr | Bnzl | 3.11 | 420 | H |
| IIB-877 | 4-F-Bnzl | H | i-Pr | i-Bu | 3.04 | 386 | H |
| IIB-878 | 4-F-Bnzl | H | i-Pr | 1-Npm | 3.28 | 470 | H |
| IIB-879 | 4-F-Bnzl | H | i-Pr | Ph-Et | 3.13 | 434 | H |
| IIB-880 | 4-F-Bnzl | H | i-Pr | i-Pnt | 3.11 | 400 | H |
| IIB-881 | i-Pnt | H | i-Pr | Bnzl | 3.08 | 382 | H |
| IIB-882 | i-Pnt | H | i-Pr | 1-Npm | 3.31 | 432 | H |
| IIB-883 | i-Pnt | H | i-Pr | Ph-Et | 3.19 | 396 | H |
| IIB-884 | Chm | H | i-Pr | Bnzl | 3.27 | 408 | H |
| IIB-885 | Chm | H | i-Pr | 1-Npm | 3.45 | 458 | H |
| IIB-886 | Chm | H | i-Pr | Ph-Et | 3.32 | 422 | H |
| IIB-887 | Bnzl | H | s-Bu | Ph-Et | 3.22 | 430 | H |
| IIB-888 | Bnzl | H | s-Bu | i-Pnt | 3.25 | 396 | H |
| IIB-889 | i-Bu | H | s-Bu | Ph-Et | 3.19 | 396 | H |
| IIB-890 | 1-Npm | H | s-Bu | Ph-Et | 3.41 | 480 | H |
| IIB-891 | 1-Npm | H | s-Bu | i-Pnt | 3.42 | 446 | H |
| IIB-892 | Ph-Et | H | s-Bu | Bnzl | 3.24 | 430 | H |
| IIB-893 | Ph-Et | H | s-Bu | i-Bu | 3.22 | 396 | H |
| IIB-894 | Ph-Et | H | s-Bu | 1-Npm | 3.39 | 480 | H |
| IIB-895 | Ph-Et | H | s-Bu | i-Pnt | 3.32 | 410 | H |
| IIB-896 | 4-F-Bnzl | H | s-Bu | Bnzl | 3.25 | 434 | H |
| IIB-897 | 4-F-Bnzl | H | s-Bu | i-Bu | 3.13 | 400 | H |
| IIB-898 | 4-F-Bnzl | H | s-Bu | 1-Npm | 3.35 | 484 | H |
| IIB-899 | 4-F-Bnzl | H | s-Bu | Ph-Et | 3.23 | 448 | H |
| IIB-900 | 4-F-Bnzl | H | s-Bu | i-Pnt | 3.25 | 414 | H |
| IIB-901 | i-Pnt | H | s-Bu | Bnzl | 3.23 | 396 | H |
| IIB-902 | i-Pnt | H | s-Bu | 1-Npm | 3.39 | 446 | H |
| IIB-903 | Chm | H | s-Bu | Bnzl | 3.38 | 422 | H |
| IIB-904 | Chm | H | s-Bu | 1-Npm | 3.51 | 472 | H |
| IIB-905 | Bnzl | H | Ph-Et | Bnzl | 3.24 | 464 | H |
| IIB-906 | Bnzl | H | Ph-Et | 1-Npm | 3.43 | 514 | H |

TABLE 1-continued

| | | | | | | | |
|---|---|---|---|---|---|---|---|
| IIB-907 | Bnzl | H | Ph-Et | i-Pnt | 3.28 | 444 | H |
| IIB-908 | i-Bu | H | Ph-Et | i-Bu | 3.15 | 396 | H |
| IIB-909 | i-Bu | H | Ph-Et | 1-Npm | 3.38 | 480 | H |
| IIB-910 | i-Bu | H | Ph-Et | i-Pnt | 4.41 | 410 | H |
| IIB-911 | 1-Npm | H | Ph-Et | Bnzl | 3.47 | 514 | H |
| IIB-912 | 1-Npm | H | Ph-Et | i-Bu | 3.43 | 480 | H |
| IIB-913 | 1-Npm | H | Ph-Et | 1-Npm | 3.58 | 564 | H |
| IIB-914 | 4-F-Bnzl | H | Ph-Et | Bnzl | 3.23 | 482 | H |
| IIB-915 | 4-F-Bnzl | H | Ph-Et | i-Bu | 3.17 | 448 | H |
| IIB-916 | 4-F-Bnzl | H | Ph-Et | 1-Npm | 3.38 | 532 | H |
| IIB-917 | 4-F-Bnzl | H | Ph-Et | i-Pnt | 3.26 | 462 | H |
| IIB-918 | i-Pnt | H | Ph-Et | i-Bu | 3.24 | 410 | H |
| IIB-919 | i-Pnt | H | Ph-Et | 1-Npm | 3.42 | 494 | H |
| IIB-920 | Chm | H | Ph-Et | Bnzl | 3.38 | 470 | H |
| IIB-921 | Chm | H | Ph-Et | i-Bu | 3.33 | 436 | H |
| IIB-922 | Chm | H | Ph-Et | 1-Npm | 3.49 | 520 | H |
| IIB-923 | Chm | H | Ph-Et | i-Pnt | 3.45 | 450 | H |
| IIB-924 | Bnzl | H | 4-F-Bnzl | Bnzl | 3.2 | 468 | H |
| IIB-925 | Bnzl | H | 4-F-Bnzl | 1-Npm | 3.34 | 518 | H |
| IIB-926 | Bnzl | H | 4-F-Bnzl | Ph-Et | 3.2 | 482 | H |
| IIB-927 | Bnzl | H | 4-F-Bnzl | i-Pnt | 3.23 | 448 | H |
| IIB-928 | i-Bu | H | 4-F-Bnzl | i-Bu | 3.13 | 400 | H |
| IIB-929 | i-Bu | H | 4-F-Bnzl | 1-Npm | 3.32 | 484 | H |
| IIB-930 | i-Bu | H | 4-F-Bnzl | i-Pnt | 3.21 | 414 | H |
| IIB-931 | 1-Npm | H | 4-F-Bnzl | Bnzl | 3.47 | 518 | H |
| IIB-932 | 1-Npm | H | 4-F-Bnzl | i-Bu | 3.43 | 484 | H |
| IIB-933 | 1-Npm | H | 4-F-Bnzl | 1-Npm | 3.63 | 568 | H |
| IIB-934 | 1-Npm | H | 4-F-Bnzl | Ph-Et | 3.48 | 532 | H |
| IIB-935 | 1-Npm | H | 4-F-Bnzl | i-Pnt | 3.5 | 498 | H |
| IIB-936 | Ph-Et | H | 4-F-Bnzl | Bnzl | 3.28 | 482 | H |
| IIB-937 | Ph-Et | H | 4-F-Bnzl | i-Bu | 3.27 | 448 | H |
| IIB-938 | Ph-Et | H | 4-F-Bnzl | 1-Npm | 3.42 | 532 | H |
| IIB-939 | Ph-Et | H | 4-F-Bnzl | i-Pnt | 3.33 | 462 | H |
| IIB-940 | i-Pnt | H | 4-F-Bnzl | 1-Npm | 3.33 | 498 | H |
| IIB-941 | i-Pnt | H | 4-F-Bnzl | Ph-Et | 3.28 | 462 | H |
| IIB-942 | Chm | H | 4-F-Bnzl | Bnzl | 3.31 | 474 | H |
| IIB-943 | Chm | H | 4-F-Bnzl | i-Bu | 3.29 | 440 | H |
| IIB-944 | Chm | H | 4-F-Bnzl | 1-Npm | 3.47 | 524 | H |
| IIB-945 | Chm | H | 4-F-Bnzl | Ph-Et | 3.42 | 488 | H |
| IIB-946 | Chm | H | 4-F-Bnzl | i-Pnt | 3.38 | 454 | H |

TABLE 1-continued

| | | | | | | | |
|---|---|---|---|---|---|---|---|
| IIB-947 | Bnzl | H | i-Pnt | Bnzl | 3.27 | 430 | H |
| IIB-948 | Bnzl | H | i-Pnt | 1-Npm | 3.42 | 480 | H |
| IIB-949 | Bnzl | H | i-Pnt | Ph-Et | 3.29 | 444 | H |
| IIB-950 | i-Bu | H | i-Pnt | 1-Npm | 3.38 | 446 | H |
| IIB-951 | i-Bu | H | i-Pnt | Ph-Et | 3.3 | 410 | H |
| IIB-952 | 1-Npm | H | i-Pnt | Bnzl | 3.45 | 480 | H |
| IIB-953 | 1-Npm | H | i-Pnt | i-Bu | 3.42 | 446 | H |
| IIB-954 | 1-Npm | H | i-Pnt | 1-Npm | 3.56 | 530 | H |
| IIB-955 | Ph-Et | H | i-Pnt | Bnzl | 3.29 | 444 | H |
| IIB-956 | Ph-Et | H | i-Pnt | i-Bu | 3.28 | 410 | H |
| IIB-957 | Ph-Et | H | i-Pnt | 1-Npm | 3.43 | 494 | H |
| IIB-958 | 4-F-Bnzl | H | i-Pnt | Bnzl | 3.27 | 448 | H |
| IIB-959 | 4-F-Bnzl | H | i-Pnt | i-Bu | 3.2 | 414 | H |
| IIB-960 | 4-F-Bnzl | H | i-Pnt | 1-Npm | 3.42 | 498 | H |
| IIB-961 | 4-F-Bnzl | H | i-Pnt | Ph-Et | 3.28 | 462 | H |
| IIB-962 | Chm | H | i-Pnt | Bnzl | 3.44 | 436 | H |
| IIB-963 | Chm | H | i-Pnt | 1-Npm | 3.58 | 486 | H |
| IIB-964 | Chm | H | i-Pnt | Ph-Et | 3.45 | 450 | H |
| IIB-965 | Bnzl | H | Hxy | Bnzl | 3.42 | 444 | H |
| IIB-966 | Bnzl | H | Hxy | 1-Npm | 3.53 | 494 | H |
| IIB-967 | Bnzl | H | Hxy | i-Pnt | 3.43 | 424 | H |
| IIB-968 | i-Bu | H | Hxy | 1-Npm | 3.49 | 460 | H |
| IIB-969 | 1-Npm | H | Hxy | 1-Npm | 3.67 | 544 | H |
| IIB-970 | 1-Npm | H | Hxy | i-Pnt | 3.63 | 474 | H |
| IIB-971 | Ph-Et | H | Hxy | Bnzl | 3.43 | 458 | H |
| IIB-972 | Ph-Et | H | Hxy | i-Bu | 3.39 | 424 | H |
| IIB-973 | Ph-Et | H | Hxy | i-Pnt | 3.49 | 438 | H |
| IIB-974 | 4-F-Bnzl | H | Hxy | Bnzl | 3.41 | 462 | H |
| IIB-975 | 4-F-Bnzl | H | Hxy | i-Bu | 3.33 | 428 | H |
| IIB-976 | 4-F-Bnzl | H | Hxy | 1-Npm | 3.52 | 512 | H |
| IIB-977 | 4-F-Bnzl | H | Hxy | Ph-Et | 3.4 | 476 | H |
| IIB-978 | 4-F-Bnzl | H | Hxy | i-Pnt | 3.42 | 442 | H |
| IIB-979 | i-Pnt | H | Hxy | Bnzl | 3.41 | 424 | H |
| IIB-980 | i-Pnt | H | Hxy | 1-Npm | 3.58 | 474 | H |
| IIB-981 | Chm | H | Hxy | Bnzl | 3.54 | 450 | H |
| IIB-982 | Chm | H | Hxy | 1-Npm | 3.64 | 500 | H |
| IIB-983 | 2-OtBu-Et | H | i-Bu | Bnzl | 4.35 | 426 | H |
| IIB-984 | 2-OtBu-Et | H | i-Bu | 1-Npm | 4.49 | 476 | H |
| IIB-985 | 2-OtBu-Et | H | Bnzl | i-Pnt | 4.48 | 440 | H |
| IIB-986 | i-Pnt | H | Bnzl | 4-tBuO-Bnzl | 3.42 | 502 | H |

TABLE 1-continued

| | | | | | | | |
|---|---|---|---|---|---|---|---|
| IIB-987 | Chm | H | Bnzl | 4-tBuO-Bnzl | 3.53 | 528 | H |
| IIB-988 | 4-tBuO-Bnzl | H | 1-Npm | Ph-Et | 3.58 | 586 | H |
| IIB-989 | 4-tBuO-Bnzl | H | 1-Npm | i-Pnt | 3.58 | 552 | H |
| IIB-990 | Ph-Et | H | 1-Npm | 4-tBuO-Bnzl | 3.53 | 586 | H |
| IIB-991 | 4-F-Bnzl | H | 1-Npm | 4-tBuO-Bnzl | 3.54 | 590 | H |
| IIB-992 | 2-OtBu-Et | H | 1-Npm | Bnzl | 4.52 | 510 | H |
| IIB-993 | 2-OtBu-Et | H | 1-Npm | i-Bu | 4.52 | 476 | H |
| IIB-994 | 2-OtBu-Et | H | 1-Npm | 1-Npm | 4.6 | 560 | H |
| IIB-995 | i-Pnt | H | 1-Npm | 4-tBuO-Bnzl | 3.58 | 552 | H |
| IIB-996 | Chm | H | 1-Npm | 4-tBuO-Bnzl | 3.69 | 578 | H |
| IIB-997 | Bnzl | H | 4-tBuO-Bnzl | Ph-Et | 3.46 | 536 | H |
| IIB-998 | Bnzl | H | 4-tBuO-Bnzl | i-Pnt | 3.46 | 502 | H |
| IIB-999 | i-Bu | H | 4-tBuO-Bnzl | Ph-Et | 3.42 | 502 | H |
| IIB-1000 | 1-Npm | H | 4-tBuO-Bnzl | Ph-Et | 3.6 | 586 | H |
| IIB-1001 | 1-Npm | H | 4-tBuO-Bnzl | i-Pnt | 3.61 | 552 | H |
| IIB-1002 | Ph-Et | H | 4-tBuO-Bnzl | Bnzl | 3.47 | 536 | H |
| IIB-1003 | Ph-Et | H | 4-tBuO-Bnzl | 1-Npm | 3.53 | 586 | H |
| IIB-1004 | Ph-Et | H | 4-tBuO-Bnzl | i-Pnt | 3.53 | 516 | H |
| IIB-1005 | 4-F-Bnzl | H | 4-tBuO-Bnzl | Bnzl | 3.39 | 540 | H |
| IIB-1006 | 4-F-Bnzl | H | 4-tBuO-Bnzl | 1-Npm | 3.53 | 590 | H |
| IIB-1007 | 4-F-Bnzl | H | 4-tBuO-Bnzl | Ph-Et | 3.43 | 554 | H |
| IIB-1008 | 4-F-Bnzl | H | 4-tBuO-Bnzl | i-Pnt | 3.44 | 520 | H |
| IIB-1009 | 2-OtBu-Et | H | 4-tBuO-Bnzl | 1-Npm | 3.63 | 582 | H |
| IIB-1010 | i-Pnt | H | 4-tBuO-Bnzl | i-Bu | 3.38 | 468 | H |
| IIB-1011 | i-Pnt | H | 4-tBuO-Bnzl | 1-Npm | 3.58 | 552 | H |
| IIB-1012 | i-Pnt | H | 4-tBuO-Bnzl | Ph-Et | 3.48 | 516 | H |
| IIB-1013 | Chm | H | 4-tBuO-Bnzl | Bnzl | 3.54 | 528 | H |
| IIB-1014 | Chm | H | 4-tBuO-Bnzl | i-Bu | 3.43 | 494 | H |
| IIB-1015 | Chm | H | 4-tBuO-Bnzl | 1-Npm | 3.66 | 578 | H |
| IIB-1016 | Chm | H | 4-tBuO-Bnzl | Ph-Et | 3.63 | 542 | H |

TABLE 1-continued

| | | | | | | | |
|---|---|---|---|---|---|---|---|
| IIB-1017 | Chm | H | 4-tBuO-Bnzl | i-Pnt | 3.63 | 508 | H |
| IIB-1018 | Bnzl | H | tBOC-E | Ph-Et | 3.27 | 502 | H |
| IIB-1019 | Bnzl | H | tBOC-E | i-Pnt | 3.25 | 468 | H |
| IIB-1020 | 1-Npm | H | tBOC-E | Ph-Et | 3.45 | 552 | H |
| IIB-1021 | 1-Npm | H | tBOC-E | i-Pnt | 3.47 | 518 | H |
| IIB-1022 | 4-tBuO-Bnzl | H | tBOC-E | Ph-Et | 3.48 | 574 | H |
| IIB-1023 | 4-tBuO-Bnzl | H | tBOC-E | i-Pnt | 3.53 | 540 | H |
| IIB-1024 | Ph-Et | H | tBOC-E | Bnzl | 3.23 | 502 | H |
| IIB-1025 | Ph-Et | H | tBOC-E | i-Bu | 3.29 | 468 | H |
| IIB-1026 | Ph-Et | H | tBOC-E | 1-Npm | 3.41 | 552 | H |
| IIB-1027 | Ph-Et | H | tBOC-E | 4-tBuO-Bnzl | 3.47 | 574 | H |
| IIB-1028 | Ph-Et | H | tBOC-E | i-Pnt | 3.32 | 482 | H |
| IIB-1029 | 4-F-Bnzl | H | tBOC-E | Bnzl | 3.26 | 506 | H |
| IIB-1030 | 4-F-Bnzl | H | tBOC-E | i-Bu | 3.21 | 472 | H |
| IIB-1031 | 4-F-Bnzl | H | tBOC-E | 1-Npm | 3.42 | 556 | H |
| IIB-1032 | 4-F-Bnzl | H | tBOC-E | 4-tBuO-Bnzl | 3.44 | 578 | H |
| IIB-1033 | 4-F-Bnzl | H | tBOC-E | Ph-Et | 3.27 | 520 | H |
| IIB-1034 | 4-F-Bnzl | H | tBOC-E | i-Pnt | 3.29 | 486 | H |
| IIB-1035 | 2-OtBu-Et | H | tBOC-E | Bnzl | 3.34 | 498 | H |
| IIB-1036 | 2-OtBu-Et | H | tBOC-E | 1-Npm | 3.46 | 548 | H |
| IIB-1037 | 2-OtBu-Et | H | tBOC-E | 4-tBuO-Bnzl | 3.52 | 570 | H |
| IIB-1038 | 2-OtBu-Et | H | tBOC-E | Ph-Et | 3.36 | 512 | H |
| IIB-1039 | i-Pnt | H | tBOC-E | Bnzl | 3.25 | 468 | H |
| IIB-1040 | i-Pnt | H | tBOC-E | 1-Npm | 3.38 | 518 | H |
| IIB-1041 | i-Pnt | H | tBOC-E | Ph-Et | 3.27 | 482 | H |
| IIB-1042 | Chm | H | tBOC-E | Bnzl | 3.39 | 494 | H |
| IIB-1043 | Chm | H | tBOC-E | 1-Npm | 3.54 | 544 | H |
| IIB-1044 | Chm | H | tBOC-E | Ph-Et | 3.5 | 508 | H |
| IIB-1045 | Ph-Et | H | i-Pr | 4-tBuO-Bnzl | 3.36 | 488 | H |
| IIB-1046 | 4-F-Bnzl | H | i-Pr | 4-tBuO-Bnzl | 3.33 | 492 | H |
| IIB-1047 | Ph-Et | H | s-Bu | 4-tBuO-Bnzl | 3.43 | 502 | H |
| IIB-1048 | 4-F-Bnzl | H | s-Bu | 4-tBuO-Bnzl | 3.46 | 506 | H |
| IIB-1049 | 2-OtBu-Et | H | s-Bu | Bnzl | 3.28 | 426 | H |
| IIB-1050 | 2-OtBu-Et | H | s-Bu | i-Bu | 3.26 | 392 | H |
| IIB-1051 | 2-OtBu-Et | H | s-Bu | 1-Npm | 3.48 | 476 | H |
| IIB-1052 | 2-OtBu-Et | H | s-Bu | Ph-Et | 3.39 | 440 | H |
| IIB-1053 | 4-tBuO-Bnzl | H | Ph-Et | Bnzl | 3.48 | 536 | H |
| IIB-1054 | 4-tBuO-Bnzl | H | Ph-Et | i-Bu | 3.38 | 502 | H |
| IIB-1055 | 4-tBuO-Bnzl | H | Ph-Et | 1-Npm | 3.58 | 586 | H |

TABLE 1-continued

| | | | | | | | |
|---|---|---|---|---|---|---|---|
| IIB-1056 | tBOC-E | H | Ph-Et | Bnzl | 3.3 | 502 | H |
| IIB-1057 | tBOC-E | H | Ph-Et | i-Bu | 3.28 | 468 | H |
| IIB-1058 | tBOC-E | H | Ph-Et | 1-Npm | 3.47 | 552 | H |
| IIB-1059 | 2-OtBu-Et | H | Ph-Et | Bnzl | 3.29 | 474 | H |
| IIB-1060 | 2-OtBu-Et | H | Ph-Et | i-Bu | 3.27 | 440 | H |
| IIB-1061 | 2-OtBu-Et | H | Ph-Et | i-Pnt | 3.36 | 454 | H |
| IIB-1062 | 4-tBuO-Bnzl | H | 4-F-Bnzl | Bnzl | 3.52 | 540 | H |
| IIB-1063 | 4-tBuO-Bnzl | H | 4-F-Bnzl | i-Bu | 3.42 | 506 | H |
| IIB-1064 | 4-tBuO-Bnzl | H | 4-F-Bnzl | 1-Npm | 3.6 | 590 | H |
| IIB-1065 | tBOC-E | H | 4-F-Bnzl | Bnzl | 3.27 | 506 | H |
| IIB-1066 | tBOC-E | H | 4-F-Bnzl | i-Bu | 3.28 | 472 | H |
| IIB-1067 | tBOC-E | H | 4-F-Bnzl | 1-Npm | 3.45 | 556 | H |
| IIB-1068 | 2-OtBu-Et | H | 4-F-Bnzl | i-Bu | 3.22 | 444 | H |
| IIB-1069 | 2-OtBu-Et | H | 4-F-Bnzl | Ph-Et | 3.33 | 492 | H |
| IIB-1070 | 2-OtBu-Et | H | 4-F-Bnzl | i-Pnt | 3.33 | 458 | H |
| IIB-1071 | Bnzl | H | 2-OtBu-Et | Bnzl | 4.32 | 460 | H |
| IIB-1072 | Bnzl | H | 2-OtBu-Et | i-Bu | 4.25 | 426 | H |
| IIB-1073 | Bnzl | H | 2-OtBu-Et | 1-Npm | 4.42 | 510 | H |
| IIB-1074 | Bnzl | H | 2-OtBu-Et | Ph-Et | 4.31 | 474 | H |
| IIB-1075 | Bnzl | H | 2-OtBu-Et | i-Pnt | 4.34 | 440 | H |
| IIB-1076 | i-Bu | H | 2-OtBu-Et | Bnzl | 4.33 | 426 | H |
| IIB-1077 | i-Bu | H | 2-OtBu-Et | 1-Npm | 4.42 | 476 | H |
| IIB-1078 | i-Bu | H | 2-OtBu-Et | Ph-Et | 4.35 | 440 | H |
| IIB-1079 | 1-Npm | H | 2-OtBu-Et | Bnzl | 4.45 | 510 | H |
| IIB-1080 | 1-Npm | H | 2-OtBu-Et | i-Bu | 4.48 | 476 | H |
| IIB-1081 | 1-Npm | H | 2-OtBu-Et | Ph-Et | 4.48 | 524 | H |
| IIB-1082 | 1-Npm | H | 2-OtBu-Et | i-Pnt | 4.53 | 490 | H |
| IIB-1083 | 4-tBuO-Bnzl | H | 2-OtBu-Et | i-Bu | 4.43 | 498 | H |
| IIB-1084 | Ph-Et | H | 2-OtBu-Et | Bnzl | 4.33 | 474 | H |
| IIB-1085 | Ph-Et | H | 2-OtBu-Et | i-Bu | 4.33 | 440 | H |
| IIB-1086 | Ph-Et | H | 2-OtBu-Et | 1-Npm | 4.47 | 524 | H |

TABLE 1-continued

| | | | | | | | |
|---|---|---|---|---|---|---|---|
| IIB-1087 | Ph-Et | H | 2-OtBu-Et | 4-tBuO-Bnzl | 4.49 | 546 | H |
| IIB-1088 | Ph-Et | H | 2-OtBu-Et | i-Pnt | 4.41 | 454 | H |
| IIB-1089 | 4-F-Bnzl | H | 2-OtBu-Et | Bnzl | 4.33 | 478 | H |
| IIB-1090 | 4-F-Bnzl | H | 2-OtBu-Et | i-Bu | 4.26 | 444 | H |
| IIB-1091 | 4-F-Bnzl | H | 2-OtBu-Et | 1-Npm | 4.43 | 528 | H |
| IIB-1092 | 4-F-Bnzl | H | 2-OtBu-Et | 4-tBuO-Bnzl | 4.47 | 550 | H |
| IIB-1093 | 4-F-Bnzl | H | 2-OtBu-Et | Ph-Et | 4.32 | 492 | H |
| IIB-1094 | 4-F-Bnzl | H | 2-OtBu-Et | i-Pnt | 4.37 | 458 | H |
| IIB-1095 | i-Pnt | H | 2-OtBu-Et | Bnzl | 4.29 | 440 | H |
| IIB-1096 | i-Pnt | H | 2-OtBu-Et | 1-Npm | 4.43 | 490 | H |
| IIB-1097 | i-Pnt | H | 2-OtBu-Et | 4-tBuO-Bnzl | 4.47 | 512 | H |
| IIB-1098 | Chm | H | 2-OtBu-Et | Bnzl | 4.43 | 466 | H |
| IIB-1099 | Chm | H | 2-OtBu-Et | 4-tBuO-Bnzl | 4.56 | 538 | H |
| IIB-1100 | Chm | H | 2-OtBu-Et | Ph-Et | 4.46 | 480 | H |
| IIB-1101 | Bnzl | H | i-Pnt | 4-tBuO-Bnzl | 3.43 | 502 | H |
| IIB-1102 | Bnzl | H | i-Pnt | tBOC-E | 3.23 | 468 | H |
| IIB-1103 | 1-Npm | H | i-Pnt | 4-tBuO-Bnzl | 3.6 | 552 | H |
| IIB-1104 | 1-Npm | H | i-Pnt | tBOC-E | 3.45 | 518 | H |
| IIB-1105 | 4-tBuO-Bnzl | H | i-Pnt | Bnzl | 3.48 | 502 | H |
| IIB-1106 | 4-tBuO-Bnzl | H | i-Pnt | i-Bu | 3.47 | 468 | H |
| IIB-1107 | 4-tBuO-Bnzl | H | i-Pnt | 1-Npm | 3.64 | 552 | H |
| IIB-1108 | 4-tBuO-Bnzl | H | i-Pnt | Ph-Et | 3.53 | 516 | H |
| IIB-1109 | tBOC-E | H | i-Pnt | Bnzl | 3.33 | 468 | H |
| IIB-1110 | tBOC-E | H | i-Pnt | 1-Npm | 3.49 | 518 | H |
| IIB-1111 | tBOC-E | H | i-Pnt | Ph-Et | 3.38 | 482 | H |
| IIB-1112 | Ph-Et | H | i-Pnt | 4-tBuO-Bnzl | 3.53 | 516 | H |
| IIB-1113 | Ph-Et | H | i-Pnt | tBOC-E | 3.34 | 482 | H |
| IIB-1114 | 4-F-Bnzl | H | i-Pnt | 4-tBuO-Bnzl | 3.44 | 520 | H |
| IIB-1115 | 4-F-Bnzl | H | i-Pnt | tBOC-E | 2.47 | 486 | H |
| IIB-1116 | Chm | H | i-Pnt | 4-tBuO-Bnzl | 2.82 | 508 | H |
| IIB-1117 | Bnzl | H | Hxy | 4-tBuO-Bnzl | 2.73 | 516 | H |
| IIB-1118 | i-Bu | H | Hxy | 4-tBuO-Bnzl | 2.7 | 482 | H |
| IIB-1119 | 1-Npm | H | Hxy | 4-tBuO-Bnzl | 2.88 | 566 | H |

TABLE 1-continued

| | | | | | | | |
|---|---|---|---|---|---|---|---|
| IIB-1120 | 4-tBuO-Bnzl | H | Hxy | Bnzl | 2.78 | 516 | H |
| IIB-1121 | 4-tBuO-Bnzl | H | Hxy | Ph-Et | 2.83 | 530 | H |
| IIB-1122 | 4-tBuO-Bnzl | H | Hxy | i-Pnt | 2.85 | 496 | H |
| IIB-1123 | tBOC-E | H | Hxy | Bnzl | 2.62 | 482 | H |
| IIB-1124 | tBOC-E | H | Hxy | Ph-Et | 2.68 | 496 | H |
| IIB-1125 | Ph-Et | H | Hxy | 4-tBuO-Bnzl | 2.77 | 530 | H |
| IIB-1126 | 4-F-Bnzl | H | Hxy | 4-tBuO-Bnzl | 2.75 | 534 | H |
| IIB-1127 | 2-OtBu-Et | H | Hxy | Bnzl | 2.48 | 454 | H |
| IIB-1128 | 2-OtBu-Et | H | Hxy | 1-Npm | 2.75 | 504 | H |
| IIB-1129 | 2-OtBu-Et | H | Hxy | Ph-Et | 2.68 | 468 | H |

† Ring formed together by $R_{2A}$ and $R_{2B}$
* IIB-410, 416, 420, 462, 463, 499, and 501 are mixtures of conformational isomers.

| Compound number | Name of compound | LCMS $t_R$ (min) | Mass $(M + H)^+$ | Measurement condition | Yield (%) |
|---|---|---|---|---|---|
| IIB-1 | (3S*,3aS*,6R*,7R*,7aS*)-N,7-dibenzyl-1-isobutyl-1,2,3,6,7,7a-hexahydro-3aH-3,6-methanopyrrolo[3,2-b]pyridine-3a-carboxamide | 1.19 | 416 | B | 18 |
| IIB-2 | (3S*,3aS*,6R*,7R*,7aS*)-N,1,7-triisobutyl-1,2,3,6,7,7a-hexahydro-3aH-3,6-methanopyrrolo[3,2-b]pyridine-3a-carboxamide | 1.17 | 348 | B | 33 |
| IIB-3 | (3S*,3aS*,6R*,7R*,7aS*)-7-benzyl-N,1-diisobutyl-1,2,3,6,7,7a-hexahydro-3aH-3,6-methanopyrrolo[3,2-b]pyridine-3a-carboxamide | 1.18 | 382 | B | 26 |
| IIB-4 | (3S*,3aS*,6R*,7R*,7aS*)-1-benzyl-N,7-diisobutyl-1,2,3,6,7,7a-hexahydro-3aH-3,6-methanopyrrolo[3,2-b]pyridine-3a-carboxamide | 1.17 | 382 | B | 40 |
| IIB-5 | (3S*,3aS*,6R*,7R*,7aS*)-N-benzyl-1,7-diisobutyl-1,2,3,6,7,7a-hexahydro-3aH-3,6-methanopyrrolo[3,2-b]pyridine-3a-carboxamide | 1.18 | 382 | B | 36 |
| IIB-6 | (3S*,3aS*,6R*,7R*,7aS*)-1,7-dibenzyl-N-isobutyl-1,2,3,6,7,7a-hexahydro-3aH-3,6-methanopyrrolo[3,2-b]pyridine-3a-carboxamide | 1.19 | 416 | B | 47 |
| IIB-7 | (3S*,3aS*,6R*,7R*,7aS*)-N,1-dibenzyl-7-isobutyl-1,2,3,6,7,7a-hexahydro-3aH-3,6-methanopyrrolo[3,2-b]pyridine-3a-carboxamide | 1.19 | 416 | B | 35 |
| IIB-8 | (3S*,3aS*,6R*,7R*,7aS*)-N,1,7-tribenzyl-1,2,3,6,7,7a-hexahydro-3aH-3,6-methanopyrrolo[3,2-b]pyridine-3a-carboxamide | 1.21 | 450 | B | 36 |
| IIB-9 | (3S*,3aS*,6R*,7R*,7aS*)-N,7-dibenzyl-1-isopentyl-1,2,3,6,7,7a-hexahydro-3aH-3,6-methanopyrrolo[3,2-b]pyridine-3a-carboxamide | 1.22 | 430 | B | 35 |
| IIB-10 | (3S*,3aS*,6R*,7R*,7aS*)-N,1-dibenzyl-7-isopentyl-1,2,3,6,7,7a-hexahydro-3aH-3,6-methanopyrrolo[3,2-b]pyridine-3a-carboxamide | 1.22 | 430 | B | 27 |

TABLE 1-continued

| | | | | | |
|---|---|---|---|---|---|
| IIB-11 | (3S*,3aS*,6R*,7R*,7aS*)-N-benzyl-1-isobutyl-7-phenethyl-1,2,3,6,7,7a-hexahydro-3aH-3,6-methanopyrrolo[3,2-b]pyridine-3a-carboxamide | 1.21 | 430 | B | 35 |
| IIB-12 | (3S*,3aS*,6R*,7R*,7aS*)-1-benzyl-7-isobutyl-N-phenethyl-1,2,3,6,7,7a-hexahydro-3aH-3,6-methanopyrrolo[3,2-b]pyridine-3a-carboxamide | 1.21 | 430 | B | 19 |
| IIB-13 | (3S*,3aS*,6R*,7R*,7aS*)-N-benzyl-1-isobutyl-7-(3-methylbenzyl)-1,2,3,6,7,7a-hexahydro-3aH-3,6-methanopyrrolo[3,2-b]pyridine-3a-carboxamide | 1.22 | 430 | B | 39 |
| IIB-14 | (3S*,3aS*,6R*,7R*,7aS*)-N-benzyl-1-isobutyl-7-(4-methylbenzyl)-1,2,3,6,7,7a-hexahydro-3aH-3,6-methanopyrrolo[3,2-b]pyridine-3a-carboxamide | 1.21 | 430 | B | 37 |
| IIB-15 | (3S*,3aS*,6R*,7R*,7aS*)-7-benzyl-1-isobutyl-N-(3-methylbenzyl)-1,2,3,6,7,7a-hexahydro-3aH-3,6-methanopyrrolo[3,2-b]pyridine-3a-carboxamide | 1.22 | 430 | B | 20 |
| IIB-16 | (3S*,3aS*,6R*,7R*,7aS*)-7-benzyl-1-isobutyl-N-(4-methylbenzyl)-1,2,3,6,7,7a-hexahydro-3aH-3,6-methanopyrrolo[3,2-b]pyridine-3a-carboxamide | 1.23 | 430 | B | 30 |
| IIB-17 | (3S*,3aS*,6R*,7R*,7aS*)-7-benzyl-N-(3-chlorobenzyl)-1-isobutyl-1,2,3,6,7,7a-hexahydro-3aH-3,6-methanopyrrolo[3,2-b]pyridine-3a-carboxamide | 1.22 | 450 | B | 34 |
| IIB-18 | (3S*,3aS*,6R*,7R*,7aS*)-7-benzyl-N-(4-chlorobenzyl)-1-isobutyl-1,2,3,6,7,7a-hexahydro-3aH-3,6-methanopyrrolo[3,2-b]pyridine-3a-carboxamide | 1.22 | 450 | B | 24 |
| IIB-19 | (3S*,3aS*,6R*,7R*,7aS*)-N-benzyl-1-(3,4-dichlorobenzyl)-7-isobutyl-1,2,3,6,7,7a-hexahydro-3aH-3,6-methanopyrrolo[3,2-b]pyridine-3a-carboxamide | 1.28 | 484 | B | 27 |
| IIB-20 | (3S*,3aS*,6R*,7R*,7aS*)-1-benzyl-N-(3,4-dichlorobenzyl)-7-isobutyl-1,2,3,6,7,7a-hexahydro-3aH-3,6-methanopyrrolo[3,2-b]pyridine-3a-carboxamide | 1.25 | 484 | B | 31 |
| IIB-21 | (3S*,3aS*,6R*,7R*,7aS*)-7-benzyl-1-isobutyl-N-(2-(naphthalen-1-yl)ethyl)-1,2,3,6,7,7a-hexahydro-3aH-3,6-methanopyrrolo[3,2-b]pyridine-3a-carboxamide | 1.18 | 438 | B | 54 |
| IIB-23 | (3S*,3aS*,6R*,7R*,7aS*)-7-benzyl-1-isobutyl-N-(4-(tert-butoxy)benzyl)-1,2,3,6,7,7a-hexahydro-3aH-3,6-methanopyrrolo[3,2-b]pyridine-3a-carboxamide | 1.05 | 488 | A | 28 |
| IIB-24 | (3S*,3aS*,6R*,7R*,7aS*)-7-benzyl-1-isobutyl-N-(naphthalen-1-ylmethyl)-1,2,3,6,7,7a-hexahydro-3aH-3,6-methanopyrrolo[3,2-b]pyridine-3a-carboxamide | 1.03 | 466 | A | 30 |
| IIB-25 | (3S*,3aS*,6R*,7R*,7aS*)-7-benzyl-N-(2-hydroxyethyl)-1-isobutyl-1,2,3,6,7,7a-hexahydro-3aH-3,6-methanopyrrolo[3,2-b]pyridine-3a-carboxamide | 0.79 | 370 | A | 20 |
| IIB-26 | 3-((3S*,3aS*,6R*,7R*,7aS*)-7-benzyl-1-isobutyl-1,2,3,6,7,7a-hexahydro-1H-3,6-methanopyrrolo[3,2-b]pyridine-3a-carboxamide)propanoic acid | 0.80 | 398 | A | 95 |

TABLE 1-continued

| | | | | | |
|---|---|---|---|---|---|
| IIB-27 | (3S*,3aS*,6R*,7R*,7aS*)-7-benzyl-1-isobutyl-N-(2-(tert-butoxy)-2-oxoethyl)-1,2,3,6,7,7a-hexahydro-3aH-3,6-methanopyrrolo[3,2-b]pyridine-3a-carboxamide | 0.98 | 454 | A | 11 |
| IIB-28 | (3S*,3aS*,6R*,7R*,7aS*)-N-(3-amino-3-oxopropyl)-7-benzyl-1-isobutyl-1,2,3,6,7,7a-hexahydro-3aH-3,6-methanopyrrolo[3,2-b]pyridine-3a-carboxamide | 0.79 | 397 | A | 80 |
| IIB-29 | (3S*,3aS*,6R*,7R*,7aS*)-N-(4-aminobutyl)-7-benzyl-1-isobutyl-1,2,3,6,7,7a-hexahydro-3aH-3,6-methanopyrrolo[3,2-b]pyridine-3a-carboxamide | 0.71 | 397 | A | 93 |
| IIB-30 | (3S*,3aS*,6R*,7R*,7aS*)-7-benzyl-1-isobutyl-N-(4-((tert-butoxycarbonyl)amino)butyl)-1,2,3,6,7,7a-hexahydro-3aH-3,6-methanopyrrolo[3,2-b]pyridine-3a-carboxamide | 0.97 | 497 | A | 18 |
| IIB-31 | (3S*,3aS*,6R*,7R*,7aS*)-7-benzyl-N-cyclohexylmethyl-1-isobutyl-1,2,3,6,7,7a-hexahydro-3aH-3,6-methanopyrrolo[3,2-b]pyridine-3a-carboxamide | 1.04 | 422 | A | 5 |
| IIB-32 | (3S*,3aS*,6R*,7R*,7aS*)-7-benzyl-1-isobutyl-N-((tetrahydro-2H-pyran-2-yl)methyl)-1,2,3,6,7,7a-hexahydro-3aH-3,6-methanopyrrolo[3,2-b]pyridine-3a-carboxamide | 0.93 | 424 | A | 38 |
| IIB-34 | (3S*,3aS*,6R*,7R*,7aS*)-N-benzyl-1-isobutyl-7-(4-((tert-butoxycarbonyl)amino)butyl)-1,2,3,6,7,7a-hexahydro-3aH-3,6-methanopyrrolo[3,2-b]pyridine-3a-carboxamide | 0.99 | 497 | A | 36 |
| IIB-36 | (3S*,3aS*,6R*,7R*,7aS*)-N-benzyl-1-isobutyl-7-(3-methoxy-3-oxopropyl)-1,2,3,6,7,7a-hexahydro-3aH-3,6-methanopyrrolo[3,2-b]pyridine-3a-carboxamide | 0.89 | 412 | A | 22 |
| IIB-38 | (3S*,3aS*,6R*,7R*,7aS*)-N-benzyl-7-(cyclohexylmethyl)-1-isobutyl-1,2,3,6,7,7a-hexahydro-3aH-3,6-methanopyrrolo[3,2-b]pyridine-3a-carboxamide | 1.05 | 422 | A | 59 |
| IIB-39 | (3S*,3aS*,6R*,7R*,7aS*)-N,7-dibenzyl-1-cyclohexylmethyl-1,2,3,6,7,7a-hexahydro-3aH-3,6-methanopyrrolo[3,2-b]pyridine-3a-carboxamide | 1.04 | 456 | A | 12 |
| IIB-40 | (3S*,3aS*,6R*,7R*,7aS*)-N,7-dibenzyl-1-(4-hydroxybenzyl)-1,2,3,6,7,7a-hexahydro-3aH-3,6-methanopyrrolo[3,2-b]pyridine-3a-carboxamide | 0.91 | 466 | A | 92 |
| IIB-41 | (3S*,3aS*,6R*,7R*,7aS*)-N,7-dibenzyl-1-(4-(tert-butoxy)benzyl)-1,2,3,6,7,7a-hexahydro-3aH-3,6-methanopyrrolo[3,2-b]pyridine-3a-carboxamide | 1.05 | 522 | A | 10 |
| IIB-42 | (3S*,3aS*,6R*,7R*,7aS*)-N,7-dibenzyl-1-(naphthalen-1-ylmethyl)-1,2,3,6,7,7a-hexahydro-3aH-3,6-methanopyrrolo[3,2-b]pyridine-3a-carboxamide | 1.04 | 500 | A | 4 |
| IIB-76 | tert-butyl 3-((3S*,3aS*,6R*,7R*,7aS*)-7-benzyl-3a-(benzylcarbamoyl)-2,3,3a,6,7,7a-hexahydro-1H-3,6-methanopyrrolo[3,2-b]pyridin-1-yl)propanoate | 0.83 | 488 | B | 34 |
| IIB-77 | (3S*,3aS*,6R*,7R*,7aS*)-N,1-dibenzyl-7-(4-hydroxybenzyl)-1,2,3,6,7,7a-hexahydro-3aH-3,6-methanopyrrolo[3,2-b]pyridine-3a-carboxamide | 0.85 | 466 | B | 34 |

TABLE 1-continued

| | | | | | |
|---|---|---|---|---|---|
| IIB-78 | tert-butyl 3-((3S*,3aS*,6R*,7R*,7aS*)-2-(7-benzyl-1-methyl-2,3,3a,6,7,7a-hexahydro-1H-3,6-methanopyrrolo[3,2-b]pyridine-3a-carboxamide)ethyl)-1H-indole-1-carboxylate | 1.00 | 527 | B | 49 |
| IIB-80 | (3S*,3aS*,6R*,7R*,7aS*)-N-benzyl-1-(naphthalen-1-ylmethyl)-7-propyl-1,2,3,6,7,7a-hexahydro-3aH-3,6-methanopyrrolo[3,2-b]pyridine-3a-carboxamide | 0.95 | 452 | A | 9 |

TABLE 2

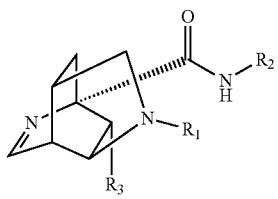

| Compound number | $R_1$ | $R_2$ | $R_3$ | Synthesis method | Intermediate | Raw material 1 | Raw material 2 |
|---|---|---|---|---|---|---|---|
| IIF-1 | i-Bu | Bnzl | Bnzl | EX | INT-Bnzl | SM1-iBu | SM2-Ph |
| IIF-2 | i-Bu | i-Bu | i-Bu | IIB-1, IIF-1 | INT-iBu | SM1-iBu | SM2-Pnt |
| IIF-3 | i-Bu | i-Bu | Bnzl | IIB-1, IIF-1 | INT-iBu | SM1-iBu | SM2-Ph |
| IIF-4 | Bnzl | i-Bu | i-Bu | IIB-1, IIF-1 | INT-iBu | SM1-Bnzl | SM2-Pnt |
| IIF-5 | i-Bu | Bnzl | i-Bu | IIB-1, IIF-1 | INT-Bnzl | SM1-iBu | SM2-Pnt |
| IIF-6 | Bnzl | i-Bu | Bnzl | IIB-1, IIF-1 | INT-iBu | SM1-Bnzl | SM2-Ph |
| IIF-7 | Bnzl | Bnzl | i-Bu | IIB-1, IIF-1 | N-(benzyl-1,2,4-triazine-3-carboxamide | SM1-Bnzl | SM2-Pnt |
| IIF-8 | Bnzl | Bnzl | Bnzl | IIB-1, IIF-1 | INT-Bnzl | SM1-Bnzl | SM2-Ph |
| IIF-9 | i-Pnt | Bnzl | Bnzl | IIB-1, IIF-1 | INT-Bnzl | N-allyl-3-methylbutan-1-amine | SM2-Ph |
| IIF-10 | Bnzl | Bnzl | i-Pnt | IIB-1, IIF-1 | INT-Bnzl | SM1-Bnzl | 5-methyl-hexanal |
| IIF-11 | i-Bu | Bnzl | Ph-Et | IIB-1, IIF-1 | INT-Bnzl | SM1-iBu | 4-phenyl-butanal |
| IIF-12 | i-Bu | Ph-Et | Bnzl | IIB-1, IIF-1 | N-phenethyl-1,2,4-triazine-3-carboxamide | SM1-iBu | SM2-Ph |
| IIF-13 | i-Bu | Bnzl | 3-Me-Bnzl | IIB-1, IIF-1 | INT-Bnzl | SM1-iBu | 3-(m-tolyl)propanal |
| IIF-14 | i-Bu | Bnzl | 4-Me-Bnzl | IIB-1, IIF-1 | INT-Bnzl | SM1-iBu | 3-(p-tolyl)propanal |
| IIF-15 | i-Bu | 3-Me-Bnzl | Bnzl | IIB-1, IIF-1 | N-(3-methylbenzyl)-1,2,4-triazine-3-carboxamide | SM1-iBu | SM2-Ph |
| IIF-16 | i-Bu | 4-Me-Bnzl | Bnzl | IIB-1, IIF-1 | N-(4-methylbenzyl)-1,2,4-triazine-3-carboxamide | SM1-iBu | SM2-Ph |

TABLE 2-continued

| ID | R1 | R2 | R3 | Method | Name | SM1 | SM2 |
|---|---|---|---|---|---|---|---|
| IIF-17 | i-Bu | 3-Cl-Bnzl | Bnzl | IIB-1, IIF-1 | N-(3-chlorobenzyl)-1,2,4-triazine-3-carboxamide | SM1-iBu | SM2-Ph |
| IIF-18 | i-Bu | 4-Cl-Bnzl | Bnzl | IIB-1, IIF-1 | N-(4-chlorobenzyl)-1,2,4-triazine-3-carboxamide | SM1-iBu | SM2-Ph |
| IIF-19 | 3,4-Cl$_2$-Bnzl | Bnzl | i-Bu | IIB-1, IIF-1 | INT-Bnzl | N-(3,4-dichlorobenzyl)prop-2-en-1-amine | SM2-Pnt |
| IIF-20 | Bnzl | 3,4-Cl$_2$-Bnzl | i-Bu | IIB-1, IIF-1 | N-(3,4-dichlorobenzyl)-1,2,4-triazine-3-carboxamide | SM1-Bnzl | SM2-Pnt |
| IIF-23 | i-Bu | 4-(tert-butoxy)benzyl | Bnzl | IIB-1, IIF-1 | N-(4-tert-butoxybenzyl)-1,2,4-triazine-3-carboxamide | SM1-iBu | SM2-Ph |
| IIF-24 | i-Bu | Np-M | Bnzl | IIB-1, IIF-1 | N-((naphthalen-1-yl)methyl)-1,2,4-triazine-3-carboxamide | SM1-iBu | SM2-Ph |
| IIF-25 | i-Bu | Hdr-E | Bnzl | IIB-1, IIF-1 | N-(2-hydroxyethyl)-1,2,4-triazine-3-carboxamide | SM1-iBu | SM2-Ph |
| IIF-26 | i-Bu | Cbx-E | Bnzl | EX | | IIB-27 | |
| IIF-27 | i-Bu | 2-(tert-butoxy)-2-oxo-ethyl | Bnzl | IIB-1, IIF-1 | tert-butyl 3-(1,2,4-triazine-3-carboxamide)propanoate | SM1-iBu | SM2-Ph |
| IIF-28 | i-Bu | Cbm-E | Bnzl | IIB-28 | | IIF-26 | |
| IIF-29 | i-Bu | 4-amino-butyl | Bnzl | IIB-29 | | IIF-30 | |
| IIF-30 | i-Bu | 4-((tert-butoxy-carbonyl)amino butyl | Bnzl | IIB-1, IIF-1 | tert-butyl 4-(1,2,4-triazine-3-carboxamide)butyl-carbamate | SM1-iBu | SM2-Ph |
| IIF-31 | i-Bu | Chm | Bnzl | IIB-1, IIF-1 | N-(cyclohexylmethyl)-1,2,4-triazine-3-carboxamide | SM1-iBu | SM2-Ph |
| IIF-32 | i-Bu | (tetrahydro-2H-pyran-2-yl)methyl | Bnzl | IIB-1, IIF-1 | N-((tetrahydro-2H-pyran-2-yl)methyl)-1,2,4-triazine-3-carboxamide | SM1-iBu | SM2-Ph |
| IIF-34 | i-Bu | Bnzl | 4-((tert-butoxy-carbonyl)amino)butyl | IIB-1, IIF-1 | INT-Bnzl | SM1-iBu | tert-butyl 5-formyl-pentyl-carbamate |

TABLE 2-continued

| | | | | | | | |
|---|---|---|---|---|---|---|---|
| IIF-36 | i-Bu | Bnzl | 3-methoxy-3-oxopropyl | IIB-1, IIF-1 | INT-Bnzl | SM1-iBu | methyl 4-formyl-butanoate |
| IIF-38 | i-Bu | Bnzl | Chm | IIB-1, IIF-1 | INT-Bnzl | SM1-iBu | 3-cyclohexylpropanal |
| IIF-39 | Chm | Bnzl | Bnzl | IIB-1, IIF-1 | INT-Bnzl | N-(cyclohexylmethyl)prop-2-en-1-amine | SM2-Ph |
| IIF-40 | 4-OH-Bnzl | Bnzl | Bnzl | IF-40 | | IIF-41 | |
| IIF-41 | 4-(tert-butoxy)benzyl | Bnzl | Bnzl | IIB-1, IIF-1 | INT-Bnzl | N-(4-tert-butoxybenzyl)prop-2-en-1-amine | SM2-Ph |
| IIF-42 | Np-M | Bnzl | Bnzl | IIB-1, IIF-1 | INT-Bnzl | N-((naphthalen-1-yl)methyl)prop-2-en-1-amine | SM2-Ph |
| IIF-76 | 3-(tert-butoxy)-3-oxopropyl | Bnzl | Bnzl | IIB-1, IIF-1 | N-benzyl-1,2,4-triazine-3-carboxamide | N-(3-(tert-butoxy)-3-oxopropyl)-prop-2-en-1-amine | SM2-Ph |
| IIF-77 | Bnzl | Bnzl | 4-OH-Bnzl | IIB-1, IIF-1 | N-benzyl-1,2,4-triazine-3-carboxamide | SM1-Bnzl | 3-(4-hydroxyphenyl)propanal |
| IIF-80 | Np-M | Bnzl | Pr | IIB-1, IIF-1 | N-benzyl 1,2,4-triazine-3-carboxamide | N-((naphthalen-1-yl)methyl)prop-2-en-1-amine | pentanal |

| Compound number | R1 | R2 | R3 | LCMS tR (min) | Mass (M + H)+ | Measurement condition |
|---|---|---|---|---|---|---|
| IIF-81 | benzyl | naphthalen-1-ylmethyl | isobutyl | 1.29 | 467 | B |
| IIF-82 | benzyl | 4-(trifluoromethyl)benzyl | isobutyl | 1.29 | 484 | B |
| IIF-83 | 4-chlorobenzyl | benzyl | isobutyl | 1.29 | 450 | B |
| IIF-84 | 3-chlorobenzyl | benzyl | isobutyl | 1.30 | 450 | B |
| IIF-85 | 4-methoxybenzyl | benzyl | isobutyl | 1.23 | 446 | B |
| IIF-86 | 4-methylbenzyl | benzyl | isobutyl | 1.24 | 430 | B |
| IIF-88 | isobutyl | isobutyl | 4-chlorobenzyl | 1.26 | 416 | B |
| IIF-89 | isobutyl | 4-chlorobenzyl | isobutyl | 1.22 | 416 | B |
| IIF-90 | isobutyl | benzyl | isopentyl | 1.23 | 396 | B |
| IIF-91 | isopentyl | benzyl | isobutyl | 1.26 | 396 | B |
| IIF-92 | isobutyl | isopentyl | benzyl | 1.23 | 396 | B |
| IIF-93 | 4-hydroxybenzyl | benzyl | isobutyl | 1.19 | 432 | B |
| IIF-94 | 4-(dimethylamino)benzyl | benzyl | isobutyl | 1.27 | 459 | B |
| IIF-95 | 4-(tert-butyl)benzyl | benzyl | isobutyl | 1.29 | 472 | B |
| IIF-96 | 4-(trifluoromethoxy)benzyl | benzyl | isobutyl | 1.32 | 500 | B |

TABLE 2-continued

| | | | | | | |
|---|---|---|---|---|---|---|
| IIF-97 | 4-ethoxybenzyl | benzyl | isobutyl | 1.25 | 460 | B |
| IIF-98 | isopentyl | isobutyl | benzyl | 1.22 | 396 | B |
| IIF-99 | benzyl | 4-hydroxy-benzyl | isobutyl | 1.17 | 432 | B |
| IIF-100 | 4-methoxy-benzyl | 4-hydroxy-benzyl | isobutyl | 1.17 | 462 | B |
| IIF-101 | 4-hydroxy-benzyl | benzyl | isopentyl | 1.20 | 446 | B |
| IIF-102 | benzyl | naphthalen-2-ylmethyl | isobutyl | 1.27 | 466 | B |
| IIF-103 | isopentyl | 4-chloro-benzyl | isobutyl | 1.28 | 431 | B |
| IIF-104 | isopentyl | 4-fluoro-benzyl | isobutyl | 1.26 | 414 | B |
| IIF-105 | benzyl | pyridin-4-ylmethyl | isobutyl | 1.06 | 417 | B |
| IIF-106 | 4-methoxy-benzyl | benzyl | benzyl | 0.93 | 480 | C |
| IIF-107 | phenethyl | benzyl | 2-(tert-butyl-dimethyl-silyloxy)ethyl | 1.08 | 532 | C |
| IIF-109 | 4-nitro-benzyl | 4-(tert-butoxy)benzyl | 2-(tert-butoxy carbonyl)ethyl | 1.00 | 605 | C |
| IIF-110 | i-Bu | i-Pr | Bnzl | 2.92 | 368 | F |
| IIF-111 | i-Bu | i-Bu | 4-tBuO-Bnzl | 3.64 | 454 | F |
| IIF-112 | i-Bu | Bnzl | 4-tBuO-Bnzl | 3.75 | 488 | F |
| IIF-113 | i-Bu | tBOC-E | 4-tBuO-Bnzl | 3.73 | 526 | F |
| IIF-114 | i-Bu | s-Bu | 4-tBuO-Bnzl | 3.64 | 454 | F |
| IIF-115 | i-Bu | 1-Npm | 4-tBuO-Bnzl | 4.18 | 538 | F |
| IIF-116 | i-Bu | i-Pr | 4-tBuO-Bnzl | 3.4 | 440 | F |
| IIF-117 | i-Bu | 1-Npm | tBOC-E | 3.92 | 504 | F |
| IIF-118 | i-Bu | 1-Npm | 1-Npm | 4.25 | 516 | F |
| IIF-119 | i-Bu | i-Pr | 1-Npm | 3.4 | 418 | F |
| IIF-120 | Bnzl | 4-tBuO-Bnzl | Bnzl | 3.95 | 522 | F |
| IIF-121 | Bnzl | i-Bu | 4-tBuO-Bnzl | 3.79 | 488 | F |
| IIF-122 | Bnzl | Bnzl | 4-tBuO-Bnzl | 3.91 | 522 | F |
| IIF-123 | Bnzl | tBOC-E | 4-tBuO-Bnzl | 3.94 | 560 | F |
| IIF-124 | Bnzl | Bnzl | tBOC-E | 3.47 | 488 | F |
| IIF-125 | Bnzl | 4-tBuO-Bnzl | tBOC-E | 3.98 | 560 | F |
| IIF-126 | Bnzl | 1-Npm | tBOC-E | 3.96 | 538 | F |
| IIF-127 | Bnzl | i-Bu | 1-Npm | 3.74 | 466 | F |
| IIF-128 | Bnzl | Bnzl | 1-Npm | 3.92 | 500 | F |
| IIF-129 | Bnzl | 4-tBuO-Bnzl | 1-Npm | 4.27 | 572 | F |
| IIF-130 | Bnzl | tBOC-E | 1-Npm | 3.8 | 538 | F |
| IIF-131 | Bnzl | s-Bu | 1-Npm | 3.74 | 466 | F |
| IIF-132 | Bnzl | 1-Npm | 1-Npm | 4.31 | 550 | F |
| IIF-133 | 4-tBuO-Bnzl | Bnzl | Bnzl | 4.1 | 522 | F |
| IIF-134 | 4-tBuO-Bnzl | tBOC-E | Bnzl | 3.6 | 560 | F |
| IIF-135 | 4-tBuO-Bnzl | s-Bu | Bnzl | 3.47 | 488 | F |
| IIF-136 | 4-tBuO-Bnzl | 1-Npm | Bnzl | 4.75 | 572 | F |
| IIF-137 | 4-tBuO-Bnzl | Bnzl | tBOC-E | 3.69 | 560 | F |
| IIF-138 | 4-tBuO-Bnzl | 1-Npm | tBOC-E | 4.04 | 610 | F |
| IIF-139 | 4-tBuO-Bnzl | i-Bu | 1-Npm | 3.82 | 538 | F |
| IIF-140 | 4-tBuO-Bnzl | Bnzl | 1-Npm | 4.68 | 572 | F |
| IIF-141 | 4-tBuO-Bnzl | tBOC-E | 1-Npm | 3.8 | 610 | F |
| IIF-142 | 4-tBuO-Bnzl | s-Bu | 1-Npm | 3.92 | 538 | F |

TABLE 2-continued

| | | | | | | |
|---|---|---|---|---|---|---|
| IIF-143 | 4-tBuO-Bnzl | 1-Npm | 1-Npm | 4.65 | 622 | F |
| IIF-144 | i-Bu | 4-tBuO-Bnzl | Bnzl | 3.87 | 488 | F |
| IIF-145 | i-Bu | tBOC-E | Bnzl | 3.25 | 454 | F |
| IIF-146 | i-Bu | s-Bu | Bnzl | 3.12 | 382 | F |
| IIF-147 | i-Bu | i-Bu | tBOC-E | 3.19 | 420 | F |
| IIF-148 | i-Bu | Bnzl | tBOC-E | 3.37 | 454 | F |
| IIF-149 | i-Bu | 4-tBuO-Bnzl | tBOC-E | 3.93 | 526 | F |
| IIF-150 | i-Bu | i-Pr | tBOC-E | 2.93 | 406 | F |
| IIF-151 | i-Bu | i-Bu | 1-Npm | 3.68 | 432 | F |
| IIF-152 | i-Bu | Bnzl | 1-Npm | 3.72 | 466 | F |
| IIF-153 | i-Bu | 4-tBuO-Bnzl | 1-Npm | 4.24 | 538 | F |
| IIF-154 | i-Bu | tBOC-E | 1-Npm | 3.74 | 504 | F |
| IIF-155 | Bnzl | tBOC-E | Bnzl | 3.44 | 488 | F |
| IIF-156 | Bnzl | s-Bu | Bnzl | 3.24 | 416 | F |
| IIF-157 | Bnzl | 1-Npm | Bnzl | 3.87 | 500 | F |
| IIF-158 | Bnzl | i-Pr | Bnzl | 3.01 | 402 | F |
| IIF-159 | Bnzl | s-Bu | 4-tBuO-Bnzl | 3.82 | 488 | F |
| IIF-160 | Bnzl | 1-Npm | 4-tBuO-Bnzl | 4.43 | 572 | F |
| IIF-161 | Bnzl | i-Pr | 4-tBuO-Bnzl | 3.51 | 474 | F |
| IIF-162 | Bnzl | s-Bu | tBOC-E | 3.34 | 454 | F |
| IIF-163 | Bnzl | i-Pr | tBOC-E | 3.15 | 440 | F |
| IIF-164 | Bnzl | i-Pr | 1-Npm | 3.5 | 452 | F |
| IIF-165 | 4-tBuO-Bnzl | i-Pr | Bnzl | 3.49 | 474 | F |
| IIF-166 | 4-tBuO-Bnzl | i-Pr | tBOC-E | 3.38 | 512 | F |
| IIF-167 | 4-tBuO-Bnzl | i-Pr | 1-Npm | 3.82 | 524 | F |
| IIF-168 | tBOC-E | i-Bu | Bnzl | 3.5 | 454 | F |
| IIF-169 | 1-Npm | i-Bu | Bnzl | 3.54 | 466 | F |
| IIF-170 | 1-Npm | 4-tBuO-Bnzl | Bnzl | 3.95 | 572 | F |
| IIF-171 | 1-Npm | s-Bu | Bnzl | 3.52 | 466 | F |
| IIF-172 | 1-Npm | i-Pr | Bnzl | 3.19 | 452 | F |
| IIF-173 | 1-Npm | Bnzl | 4-tBuO-Bnzl | 4.3 | 572 | F |
| IIF-174 | 1-Npm | tBOC-E | 4-tBuO-Bnzl | 3.95 | 610 | F |
| IIF-175 | 1-Npm | s-Bu | 4-tBuO-Bnzl | 3.87 | 538 | F |
| IIF-176 | 1-Npm | 1-Npm | 4-tBuO-Bnzl | 4.62 | 622 | F |
| IIF-177 | 1-Npm | i-Pr | 4-tBuO-Bnzl | 3.84 | 524 | F |
| IIF-178 | 1-Npm | Bnzl | tBOC-E | 3.8 | 538 | F |
| IIF-179 | 1-Npm | 4-tBuO-Bnzl | tBOC-E | 4.5 | 610 | F |
| IIF-180 | 1-Npm | s-Bu | tBOC-E | 3.62 | 504 | F |
| IIF-181 | 1-Npm | 1-Npm | tBOC-E | 4.15 | 588 | F |
| IIF-182 | 1-Npm | Bnzl | 1-Npm | 4.3 | 550 | F |
| IIF-183 | 1-Npm | 4-tBuO-Bnzl | 1-Npm | 4.75 | 622 | F |
| IIF-184 | 1-Npm | tBOC-E | 1-Npm | 4.02 | 588 | F |
| IIF-185 | 1-Npm | s-Bu | 1-Npm | 4.25 | 516 | F |
| IIF-186 | i-Bu | 4-tBuO-Bnzl | i-Bu | 3.68 | 454 | F |
| IIF-187 | i-Bu | tBOC-E | i-Bu | 3.05 | 420 | F |
| IIF-188 | i-Bu | s-Bu | i-Bu | 2.84 | 348 | F |
| IIF-189 | i-Bu | 1-Npm | i-Bu | 3.71 | 432 | F |
| IIF-190 | i-Bu | i-Pr | i-Bu | 2.66 | 334 | F |
| IIF-191 | i-Bu | (tBOC)Gun-Pr | 4-tBuO-Bnzl | 2.71 | 641 | J |
| IIF-192 | i-Bu | 1-Npm | (tBOC)Gun-Pr | 3.47 | 675 | J |
| IIF-193 | i-Bu | s-Bu | 1-Npm | 3.64 | 432 | F |
| IIF-194 | Bnzl | 4-tBuO-Bnzl | i-Bu | 3.93 | 488 | F |
| IIF-195 | Bnzl | i-Pr | i-Bu | 3.01 | 368 | F |
| IIF-196 | Bnzl | i-Bu | tBOC-E | 3.32 | 454 | F |
| IIF-197 | tBOC-E | Bnzl | i-Bu | 3.52 | 454 | F |
| IIF-198 | tBOC-E | 4-tBuO-Bnzl | i-Bu | 4.01 | 526 | F |
| IIF-199 | tBOC-E | s-Bu | i-Bu | 3.26 | 420 | F |
| IIF-200 | tBOC-E | 1-Npm | i-Bu | 4.09 | 504 | F |
| IIF-201 | tBOC-E | i-Pr | i-Bu | 3.03 | 406 | F |
| IIF-202 | tBOC-E | 1-Npm | Bnzl | 4.06 | 538 | F |
| IIF-203 | tBOC-E | Bnzl | 4-tBuO-Bnzl | 4.19 | 560 | F |
| IIF-204 | tBOC-E | 1-Npm | 4-tBuO-Bnzl | 4.62 | 610 | F |
| IIF-205 | tBOC-E | i-Bu | 1-Npm | 3.96 | 504 | F |
| IIF-206 | tBOC-E | 4-tBuO-Bnzl | 1-Npm | 4.41 | 610 | F |

TABLE 2-continued

| | | | | | | |
|---|---|---|---|---|---|---|
| IIF-207 | tBOC-E | 1-Npm | 1-Npm | 4.48 | 588 | F |
| IIF-208 | tBOC-E | i-Pr | 1-Npm | 3.71 | 490 | F |
| IIF-209 | 1-Npm | i-Bu | i-Bu | 3.32 | 432 | F |
| IIF-210 | 1-Npm | Bnzl | i-Bu | 3.38 | 466 | F |
| IIF-211 | 1-Npm | 4-tBuO-Bnzl | i-Bu | 3.67 | 538 | F |
| IIF-212 | 1-Npm | s-Bu | i-Bu | 3.35 | 432 | F |
| IIF-213 | 1-Npm | 1-Npm | i-Bu | 3.8 | 516 | F |
| IIF-214 | 1-Npm | i-Pr | i-Bu | 3.17 | 418 | F |
| IIF-215 | 1-Npm | i-Bu | 4-tBuO-Bnzl | 3.92 | 538 | F |
| IIF-216 | 1-Npm | i-Bu | tBOC-E | 3.5 | 504 | F |
| IIF-217 | 1-Npm | i-Pr | tBOC-E | 3.34 | 490 | F |
| IIF-218 | 1-Npm | i-Bu | 1-Npm | 3.79 | 516 | F |
| IIF-219 | 1-Npm | (tBOC)Gun-Pr | 1-Npm | 3.82 | 759 | F |
| IIF-220 | 1-Npm | i-Pr | 1-Npm | 3.65 | 502 | F |
| IIF-221 | i-Bu | (tBOC)Gun-Pr | i-Bu | 2.89 | 591 | J |
| IIF-222 | i-Bu | (tBOC)Gun-Pr | Bnzl | 2.96 | 625 | J |
| IIF-223 | i-Bu | s-Bu | tBOC-E | 3.13 | 420 | F |
| IIF-224 | i-Bu | i-Bu | (tBOC)Gun-Pr | 2.96 | 591 | J |
| IIF-225 | i-Bu | Bnzl | (tBOC)Gun-Pr | 3 | 625 | J |
| IIF-226 | i-Bu | 4-tBuO-Bnzl | (tBOC)Gun-Pr | 2.78 | 641 | J |
| IIF-227 | i-Bu | s-Bu | (tBOC)Gun-Pr | 2.95 | 591 | J |
| IIF-228 | i-Bu | i-Pr | (tBOC)Gun-Pr | 2.81 | 577 | J |
| IIF-229 | i-Bu | (tBOC)Gun-Pr | 1-Npm | 3.08 | 675 | J |
| IIF-230 | Bnzl | (tBOC)Gun-Pr | i-Bu | 2.93 | 625 | J |
| IIF-231 | Bnzl | s-Bu | i-Bu | 3.23 | 382 | F |
| IIF-232 | Bnzl | (tBOC)Gun-Pr | Bnzl | 2.94 | 659 | J |
| IIF-233 | Bnzl | (tBOC)Gun-Pr | 4-tBuO-Bnzl | 2.74 | 675 | J |
| IIF-234 | Bnzl | i-Bu | (tBOC)Gun-Pr | 3.49 | 698? | J |
| IIF-235 | Bnzl | Bnzl | (tBOC)Gun-Pr | 3.18 | 659 | J |
| IIF-236 | Bnzl | 4-tBuO-Bnzl | (tBOC)Gun-Pr | 2.95 | 675 | J |
| IIF-237 | Bnzl | s-Bu | (tBOC)Gun-Pr | 3.04 | 625 | J |
| IIF-238 | Bnzl | 1-Npm | (tBOC)Gun-Pr | 4.09 | 709 | J |
| IIF-239 | Bnzl | (tBOC)Gun-Pr | 1-Npm | 3.36 | 709 | J |
| IIF-240 | tBOC-E | i-Bu | i-Bu | 3.25 | 420 | F |
| IIF-241 | tBOC-E | Bnzl | Bnzl | 3.62 | 488 | F |
| IIF-242 | tBOC-E | 4-tBuO-Bnzl | Bnzl | 4.1 | 560 | F |
| IIF-243 | tBOC-E | s-Bu | Bnzl | 4.48 | 454 | F |
| IIF-244 | tBOC-E | i-Pr | Bnzl | 3.24 | 440 | F |
| IIF-245 | tBOC-E | i-Bu | 4-tBuO-Bnzl | 4.15 | 526 | F |
| IIF-246 | tBOC-E | i-Pr | 4-tBuO-Bnzl | 3.89 | 512 | F |
| IIF-247 | tBOC-E | Bnzl | 1-Npm | 4.03 | 538 | F |
| IIF-248 | tBOC-E | s-Bu | 1-Npm | 3.96 | 504 | F |
| IIF-249 | (tBOC)Gun-Pr | 1-Npm | i-Bu | 3.77 | 657 | J |
| IIF-250 | (tBOC)Gun-Pr | i-Pr | i-Bu | 3.16 | 577 | J |
| IIF-251 | (tBOC)Gun-Pr | 1-Npm | Bnzl | 3.71 | 709 | J |
| IIF-252 | (tBOC)Gun-Pr | i-Pr | Bnzl | 3.18 | 611 | J |
| IIF-253 | (tBOC)Gun-Pr | 1-Npm | 4-tBuO-Bnzl | 3.39 | 725 | J |
| IIF-254 | (tBOC)Gun-Pr | i-Pr | 4-tBuO-Bnzl | 2.96 | 627 | J |
| IIF-255 | (tBOC)Gun-Pr | 1-Npm | 1-Npm | 3.97 | 759 | J |
| IIF-256 | (tBOC)Gun-Pr | i-Pr | 1-Npm | 3.47 | 661 | J |
| IIF-257 | 1-Npm | 1-Npm | Bnzl | 4.5 | 550 | F |

TABLE 2-continued

| | | | | | | |
|---|---|---|---|---|---|---|
| IIF-258 | Bnzl | tBOC-E | i-Bu | 3.51 | 454 | F |
| IIF-259 | Bnzl | i-Pr | (tBOC)Gun-Pr | 2.99 | 611 | J |
| IIF-260 | 4-tBuO-Bnzl | i-Bu | i-Bu | 3.42 | 454 | F |
| IIF-261 | 4-tBuO-Bnzl | Bnzl | i-Bu | 3.44 | 488 | F |
| IIF-262 | 4-tBuO-Bnzl | tBOC-E | i-Bu | 3.5 | 526 | F |
| IIF-263 | 4-tBuO-Bnzl | (tBOC)Gun-Pr | i-Bu | 3.29 | 641 | F |
| IIF-264 | 4-tBuO-Bnzl | s-Bu | i-Bu | 3.45 | 454 | F |
| IIF-265 | 4-tBuO-Bnzl | 1-Npm | i-Bu | 3.9 | 538 | F |
| IIF-266 | 4-tBuO-Bnzl | i-Pr | i-Bu | 3.24 | 440 | F |
| IIF-267 | 4-tBuO-Bnzl | i-Bu | Bnzl | 3.57 | 488 | F |
| IIF-268 | 4-tBuO-Bnzl | (tBOC)Gun-Pr | Bnzl | 3.1 | 675 | F |
| IIF-269 | 4-tBuO-Bnzl | i-Bu | tBOC-E | 3.6 | 526 | F |
| IIF-270 | 4-tBuO-Bnzl | s-Bu | tBOC-E | 3.59 | 526 | F |
| IIF-271 | 4-tBuO-Bnzl | i-Bu | (tBOC)Gun-Pr | 3.38 | 641 | F |
| IIF-272 | 4-tBuO-Bnzl | Bnzl | (tBOC)Gun-Pr | 3.72 | 675 | F |
| IIF-273 | 4-tBuO-Bnzl | s-Bu | (tBOC)Gun-Pr | 3.38 | 641 | F |
| IIF-274 | 4-tBuO-Bnzl | 1-Npm | (tBOC)Gun-Pr | 3.79 | 725 | F |
| IIF-275 | 4-tBuO-Bnzl | i-Pr | (tBOC)Gun-Pr | 3.27 | 627 | F |
| IIF-276 | 4-tBuO-Bnzl | (tBOC)Gun-Pr | 1-Npm | 3.54 | 725 | F |
| IIF-277 | tBOC-E | s-Bu | 4-tBuO-Bnzl | 4.09 | 526 | F |
| IIF-278 | (tBOC)Gun-Pr | i-Bu | i-Bu | 4.24 | 591 | F |
| IIF-279 | (tBOC)Gun-Pr | Bnzl | i-Bu | 3.99 | 625 | F |
| IIF-280 | (tBOC)Gun-Pr | 4-tBuO-Bnzl | i-Bu | 3.51 | 641 | F |
| IIF-281 | (tBOC)Gun-Pr | s-Bu | i-Bu | 3.82 | 591 | F |
| IIF-282 | (tBOC)Gun-Pr | i-Bu | Bnzl | 4.27 | 625 | F |
| IIF-283 | (tBOC)Gun-Pr | Bnzl | Bnzl | 4.14 | 659 | F |
| IIF-284 | (tBOC)Gun-Pr | 4-tBuO-Bnzl | Bnzl | 3.72 | 675 | F |
| IIF-285 | (tBOC)Gun-Pr | s-Bu | Bnzl | 3.99 | 625 | F |
| IIF-286 | (tBOC)Gun-Pr | i-Bu | 4-tBuO-Bnzl | 3.59 | 641 | F |
| IIF-287 | (tBOC)Gun-Pr | Bnzl | 4-tBuO-Bnzl | 4.32 | 675 | F |
| IIF-288 | (tBOC)Gun-Pr | Bnzl | 1-Npm | 4.57 | 709 | F |
| IIF-289 | (tBOC)Gun-Pr | s-Bu | 1-Npm | 4.49 | 675 | F |
| IIF-290 | 1-Npm | tBOC-E | i-Bu | 3.35 | 504 | F |
| IIF-291 | 1-Npm | (tBOC)Gun-Pr | i-Bu | 3.95 | 675 | F |
| IIF-292 | 1-Npm | (tBOC)Gun-Pr | Bnzl | 3.7 | 709 | F |
| IIF-293 | 1-Npm | (tBOC)Gun-Pr | 4-tBuO-Bnzl | 3.3 | 725 | F |
| IIF-294 | 1-Npm | i-Bu | (tBOC)Gun-Pr | 3.77 | 675 | F |
| IIF-295 | 1-Npm | Bnzl | (tBOC)Gun-Pr | 3.82 | 709 | F |
| IIF-296 | 1-Npm | 4-tBuO-Bnzl | (tBOC)Gun-Pr | 3.6 | 725 | F |
| IIF-297 | 1-Npm | s-Bu | (tBOC)Gun-Pr | 4.15 | 675 | F |
| IIF-298 | 1-Npm | 1-Npm | (tBOC)Gun-Pr | 4.91 | 759 | F |

TABLE 2-continued

| | | | | | | |
|---|---|---|---|---|---|---|
| IIF-299 | 1-Npm | i-Pr | (tBOC)Gun-Pr | 3.5 | 661 | F |
| IIF-300 | 1-Npm | tBOC-E | Bnzl | 3.47 | 538 | F |
| IIF-301 | Bnzl | i-Pr | 3-Gun-Pr | 1.47 | 411 | F |
| IIF-302 | 4-OH-Bnzl | i-Pr | 3-Gun-Pr | 1.37 | 427 | F |
| IIF-303 | 1-Npm | 3-Gun-Pr | i-Bu | 2.75 | 475 | F |
| IIF-304 | 1-Npm | i-Bu | 3-Gun-Pr | 2.6 | 475 | F |
| IIF-305 | 1-Npm | Bnzl | 3-Gun-Pr | 2.69 | 509 | F |
| IIF-306 | 1-Npm | i-Pr | 3-Gun-Pr | 2.49 | 461 | F |
| IIF-307 | Bnzl | Ph-Et | i-Bu | 0.93 | 430 | C |
| IIF-308 | Chm | i-Bu | Bnzl | 0.97 | 422 | C |
| IIF-309 | Bnzl | 4-F-Bnzl | i-Bu | 0.93 | 434 | C |
| IIF-310 | Chm | Bnzl | i-Bu | 0.97 | 422 | C |
| IIF-311 | Bnzl | Hxy | i-Bu | 1.02 | 410 | C |
| IIF-312 | Ph-Et | i-Bu | i-Bu | 0.94 | 396 | C |
| IIF-313 | Ph-Et | i-Bu | 1-Npm | 1.01 | 480 | C |
| IIF-314 | Bnzl | i-Bu | Ph-Et | 0.97 | 430 | C |
| IIF-315 | 4-F-Bnzl | i-Bu | Bnzl | 0.94 | 434 | C |
| IIF-316 | i-Bu | 4-F-Bnzl | Bnzl | 0.93 | 434 | C |
| IIF-317 | Ph-Et | Bnzl | i-Bu | 0.94 | 430 | C |
| IIF-318 | Bnzl | i-Pnt | i-Bu | 0.96 | 396 | C |
| IIF-319 | i-Bu | Hxy | Bnzl | 0.98 | 410 | C |
| IIF-320 | 4-F-Bnzl | Bnzl | Bnzl | 0.94 | 468 | C |
| IIF-321 | Ph-Et | Bnzl | Bnzl | 0.96 | 464 | C |
| IIF-322 | Bnzl | i-Bu | i-Pnt | 0.97 | 396 | C |
| IIF-323 | 4-F-Bnzl | Bnzl | i-Bu | 0.94 | 434 | C |

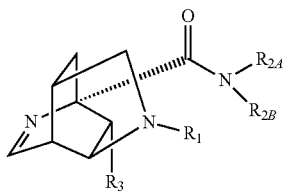

Formula XXIIF

| Compound number | $R_1$ | $R_{2A}$ | $R_{2B}$ | $R_3$ | LCMS RT (min) | Mass $(M + H)^+$ | Measurement condition |
|---|---|---|---|---|---|---|---|
| IIF-324 | 2-Npm | H | Bnzl | i-Bu | 2.89 | 466 | B1 |
| IIF-325 | i-Pnt | H | 3-Cl-Bnzl | Bnzl | 2.85 | 464 | B1 |
| IIF-326 | i-Pnt | H | 4-Cl-Bnzl | Bnzl | 2.85 | 464 | B1 |
| IIF-327 | i-Pnt | H | 4-F-Bnzl | Bnzl | 2.73 | 448 | B1 |
| IIF-328 | i-Pnt | H | 4-Me-Bnzl | Bnzl | 2.83 | 444 | B1 |
| IIF-329 | i-Pnt | H | 4-MeO-Bnzl | Bnzl | 2.71 | 460 | B1 |
| IIF-330 | i-Bu | H | 4-Cl-Bnzl | Ph-Et | 2.68 | 464 | B1 |
| IIF-331 | i-Bu | H | 3-Cl-Bnzl | Ph-Et | 2.85 | 464 | B1 |
| IIF-332 | i-Bu | H | 4-MeO-Bnzl | Ph-Et | 2.50 | 460 | B1 |
| IIF-333 | i-Bu | H | 4-Me-Bnzl | Ph-Et | 2.65 | 444 | B1 |
| IIF-334 | i-Bu | H | 2-Npm | Ph-Et | 2.77 | 480 | B1 |
| IIF-335 | i-Bu | H | Bnzl | Ph-Pr | 2.65 | 444 | B1 |
| IIF-336 | i-Bu | H | 3-Cl-Bnzl | Ph-Pr | 1.27 | 478 | B |
| IIF-337 | i-Bu | H | 3-F-Bnzl | Ph-Pr | 1.25 | 462 | B |
| IIF-338 | Cpm | H | 4-OH-Bnzl | Cbx-E | 0.96 | 440 | B |
| IIF-339 | i-Bu | H | 3-Me-Bnzl | Ph-Pr | 1.26 | 458 | B |
| IIF-340 | i-Bu | H | 3-MeO-Bnzl | Ph-Pr | 1.25 | 474 | B |
| IIF-341 | i-Bu | H | 3-Cl-Bnzl | Ph-Bu | 1.30 | 492 | B |
| IIF-342 | i-Bu | H | 3-F-Bnzl | Ph-Bu | 1.26 | 476 | B |
| IIF-343 | i-Bu | H | 3-Me-Bnzl | Ph-Bu | 1.29 | 472 | B |
| IIF-344 | i-Bu | H | 3-MeO-Bnzl | Ph-Bu | 1.26 | 488 | B |
| IIF-345 | i-Bu | H | Bnzl | Ph-Bu | 1.25 | 458 | B |
| IIF-346 | i-Pnt | H | 3-F-Bnzl | Ph-Pr | 1.25 | 476 | B |
| IIF-347 | Hdr-E | H | 4-fluorophenethyl | 1-Npm | 0.9 | 486 | C |

TABLE 2-continued

| | | | | | | | |
|---|---|---|---|---|---|---|---|
| IIF-348 | 1-Npm | H | cyclohexyl | Ph-Et | 1.02 | 506 | C |
| IIF-349 | 1-Npm | H | cyclopentyl | Ph-Et | 0.99 | 492 | C |
| IIF-350 | 1-Npm | H | pentyl | Ph-Et | 1.01 | 494 | C |
| IIF-351 | 1-Npm | H | heptyl | Ph-Et | 1.08 | 522 | C |
| IIF-352 | propyl | H | Chm | Bnzl | 0.95 | 408 | C |
| IIF-353 | 1-Npm | H | hexyl | 4-methylphenethyl | 1.07 | 522 | C |
| IIF-354 | 1-Npm | H | hexyl | 2-(naphthalen-2-yl)ethyl | 1.10 | 558 | C |
| IIF-355 | 1-Npm | H | hexyl | 4-isopropylphenethyl | 1.12 | 550 | C |
| IIF-356 | 1-Npm | H | hexyl | cyclohexylethyl | 1.13 | 514 | C |
| IIF-357 | tBuO-E | H | 4-fluorophenethyl | 1-Npm | 1.01 | 542 | C |
| IIF-358 | tBuO-E | H | 4-Cl-Bnzl | 1-Npm | 1.03 | 545 | C |
| IIF-359 | tBuO-E | H | 4-Me-Bnzl | 1-Npm | 1.02 | 524 | C |
| IIF-360 | 1-Npm | | piperidine † | Ph-Et | 0.95 | 492 | C |
| IIF-361 | 1-Npm | | pyrrolidine † | Ph-Et | 0.93 | 478 | C |
| IIF-362 | propyl | H | Bnzl | Chm | 0.94 | 408 | C |
| IIF-363 | propyl | H | 2-methylbenzyl | Bnzl | 0.91 | 416 | C |
| IIF-364 | propyl | H | (1,2,3,4-tetrahydronaphthalen-1-yl)methyl | Bnzl | 0.97 | 456 | C |
| IIF-365 | propyl | H | Cpm | Bnzl | 0.92 | 394 | C |
| IIF-366 | propyl | H | Bnzl | Cpm | 0.91 | 394 | C |
| IIF-367 | 1-Npm | H | Hxy | 3-methylphenethyl | 1.07 | 522 | C |
| IIF-368 | 4-Nt-Bnzl | H | Bnzl | Bnzl | 0.92 | 495 | C |
| IIF-369 | 4-Nt-Bnzl | H | Hxy | Ph-Et | 1.01 | 503 | C |
| IIF-370 | i-Pnt | H | Ph-Et | Bnzl | 2.76 | 444 | B1 |
| IIF-371 | i-Pnt | H | 1-Npm | Bnzl | 2.93 | 480 | B1 |
| IIF-372 | i-Bu | H | 4-F-Bnzl | Ph-Et | 2.56 | 448 | B1 |
| IIF-373 | i-Bu | H | Ph-Et | Ph-Et | 2.60 | 444 | B1 |
| IIF-374 | i-Bu | H | 1-Npm | Ph-Et | 2.79 | 480 | B1 |
| IIF-375 | 4-F-Bnzl | H | 1-Npm | Bnzl | 2.80 | 518 | B1 |
| IIF-376 | 4-F-Bnzl | H | 1-Npm | i-Bu | 1.26 | 484 | B |
| IIF-377 | tBuO-E | H | 4-F-Bnzl | 1-Npm | 1.01 | 528 | C |
| IIF-378 | 4-tBuO-Bnzl | H | Bnzl | Ph-Et | 1.01 | 536 | C |
| IIF-379 | tBuO-E | H | Bnzl | 1-Npm | 1.00 | 510 | C |
| IIF-380 | Chm | H | tBuO-E | 1-Npm | 1.01 | 516 | C |
| IIF-381 | tBOC-E | H | Bnzl | Ph-Et | 0.97 | 502 | C |
| IIF-382 | i-Pnt | H | Bnzl | Ph-Et | 0.96 | 444 | C |
| IIF-383 | 1-Npm | H | 4-F-Bnzl | Hdr-E | 0.83 | 472 | C |

TABLE 2-continued

| | | | | | | | |
|---|---|---|---|---|---|---|---|
| IIF-384 | Hdr-E | H | 4-F-Bnzl | 1-Npm | 0.88 | 472 | C |
| IIF-385 | Cbx-E | H | Bnzl | Ph-Et | 0.86 | 446 | C |
| IIF-386 | tBuO-E | H | Ph-Et | 1-Npm | 1.02 | 524 | C |
| IIF-387 | Ph-Et | H | Hxy | 1-Npm | 1.06 | 508 | C |
| IIF-388 | Ph-Et | H | i-Bu | TBSO-E | 1.09 | 498 | C |
| IIF-389 | Ph-Et | H | i-Bu | Hdr-E | 0.77 | 384 | C |
| IIF-390 | Ph-Et | H | i-Bu | i-Pnt | 0.96 | 410 | C |
| IIF-391 | Ph-Et | H | i-Bu | 4-tBuO-Bnzl | 1.02 | 502 | C |
| IIF-392 | Ph-Et | H | i-Bu | 4-OH-Bnzl | 0.85 | 446 | C |
| IIF-393 | i-Bu | H | i-Bu | 4-OH-Bnzl | 0.80 | 398 | C |
| IIF-394 | i-Bu | H | Bnzl | 4-OH-Bnzl | 0.82 | 432 | C |
| IIF-395 | i-Bu | H | 2-Cbx-Et | 4-OH-Bnzl | 0.63 | 414 | C |
| IIF-396 | i-Bu | H | s-Bu | 4-OH-Bnzl | 0.79 | 398 | C |
| IIF-397 | i-Bu | H | 1-Npm | 4-OH-Bnzl | 0.89 | 482 | C |
| IIF-398 | i-Bu | H | i-Pr | 4-OH-Bnzl | 0.75 | 384 | C |
| IIF-399 | i-Bu | H | 1-Npm | 2-Cbx-Et | 0.82 | 448 | C |
| IIF-400 | Bnzl | H | 4-OH-Bnzl | Bnzl | 0.83 | 466 | C |
| IIF-401 | Bnzl | H | i-Bu | 4-OH-Bnzl | 0.82 | 432 | C |
| IIF-402 | Bnzl | H | 2-Cbx-Et | 4-OH-Bnzl | 0.67 | 448 | C |
| IIF-403 | Bnzl | H | Bnzl | 2-Cbx-Et | 0.76 | 432 | C |
| IIF-404 | Bnzl | H | 4-OH-Bnzl | 2-Cbx-Et | 0.68 | 448 | C |
| IIF-405 | Bnzl | H | 1-Npm | 2-Cbx-Et | 0.84 | 482 | C |
| IIF-406 | Bnzl | H | 4-OH-Bnzl | 1-Npm | 0.89 | 516 | C |
| IIF-407 | Bnzl | H | 2-Cbx-Et | 1-Npm | 0.83 | 482 | C |
| IIF-408 | 4-OH-Bnzl | H | 2-Cbx-Et | Bnzl | 0.69 | 448 | C |
| IIF-409 | 4-OH-Bnzl | H | s-Bu | Bnzl | 0.84 | 432 | C |
| IIF-410 | 4-OH-Bnzl | H | 1-Npm | Bnzl | 0.93 | 516 | C |
| IIF-411 | 4-OH-Bnzl | H | Bnzl | 2-Cbx-Et | 0.73 | 448 | C |
| IIF-412 | 4-OH-Bnzl | H | 1-Npm | 2-Cbx-Et | 0.81 | 498 | C |
| IIF-413 | 4-OH-Bnzl | H | i-Bu | 1-Npm | 0.91 | 482 | C |
| IIF-414 | 4-OH-Bnzl | H | Bnzl | 1-Npm | 0.92 | 516 | C |
| IIF-415 | 4-OH-Bnzl | H | 2-Cbx-Et | 1-Npm | 0.76 | 498 | C |
| IIF-416 | 4-OH-Bnzl | H | s-Bu | 1-Npm | 0.91 | 482 | C |
| IIF-417 | 4-OH-Bnzl | H | 1-Npm | 1-Npm | 0.98 | 566 | C |
| IIF-418 | i-Bu | H | 4-OH-Bnzl | Bnzl | 0.81 | 432 | C |
| IIF-419 | i-Bu | H | i-Bu | 2-Cbx-Et | 0.71 | 364 | C |
| IIF-420 | i-Bu | H | Bnzl | 2-Cbx-Et | 0.73 | 398 | C |
| IIF-421 | i-Bu | H | 4-OH-Bnzl | 2-Cbx-Et | 0.65 | 414 | C |
| IIF-422 | i-Bu | H | i-Pr | 2-Cbx-Et | 0.65 | 350 | C |
| IIF-423 | i-Bu | H | 4-OH-Bnzl | 1-Npm | 0.87 | 482 | C |
| IIF-424 | i-Bu | H | 2-Cbx-Et | 1-Npm | 0.81 | 448 | C |
| IIF-425 | Bnzl | H | 2-Cbx-Et | Bnzl | 0.76 | 432 | C |
| IIF-426 | Bnzl | H | s-Bu | 4-OH-Bnzl | 0.81 | 432 | C |
| IIF-427 | Bnzl | H | 1-Npm | 4-OH-Bnzl | 0.90 | 516 | C |
| IIF-428 | Bnzl | H | i-Pr | 4-OH-Bnzl | 0.77 | 418 | C |

TABLE 2-continued

| | | | | | | | |
|---|---|---|---|---|---|---|---|
| IIF-429 | Bnzl | H | s-Bu | 2-Cbx-Et | 0.73 | 398 | C |
| IIF-430 | Bnzl | H | i-Pr | 2-Cbx-Et | 0.69 | 384 | C |
| IIF-431 | 4-OH-Bnzl | H | i-Pr | Bnzl | 0.8 | 418 | C |
| IIF-432 | 4-OH-Bnzl | H | i-Pr | 2-Cbx-Et | 0.65 | 400 | C |
| IIF-433 | 4-OH-Bnzl | H | i-Pr | 1-Npm | 0.87 | 468 | C |
| IIF-434 | 2-Cbx-Et | H | i-Bu | Bnzl | 0.80 | 398 | C |
| IIF-435 | 1-Npm | H | 4-OH-Bnzl | Bnzl | 0.89 | 516 | C |
| IIF-436 | 1-Npm | H | Bnzl | 4-OH-Bnzl | 0.87 | 516 | C |
| IIF-437 | 1-Npm | H | 2-Cbx-Et | 4-OH-Bnzl | 0.73 | 498 | C |
| IIF-438 | 1-Npm | H | s-Bu | 4-OH-Bnzl | 0.86 | 482 | C |
| IIF-439 | 1-Npm | H | 1-Npm | 4-OH-Bnzl | 0.94 | 566 | C |
| IIF-440 | 1-Npm | H | i-Pr | 4-OH-Bnzl | 0.82 | 468 | C |
| IIF-441 | 1-Npm | H | Bnzl | 2-Cbx-Et | 0.81 | 482 | C |
| IIF-442 | 1-Npm | H | 4-OH-Bnzl | 2-Cbx-Et | 0.74 | 498 | C |
| IIF-443 | 1-Npm | H | s-Bu | 2-Cbx-Et | 0.79 | 448 | C |
| IIF-444 | 1-Npm | H | 1-Npm | 2-Cbx-Et | 0.88 | 532 | C |
| IIF-445 | 1-Npm | H | 4-OH-Bnzl | 1-Npm | 0.96 | 566 | C |
| IIF-446 | 1-Npm | H | 2-Cbx-Et | 1-Npm | 0.88 | 532 | C |
| IIF-447 | i-Bu | H | 4-OH-Bnzl | i-Bu | 0.78 | 398 | C |
| IIF-448 | i-Bu | H | 2-Cbx-Et | i-Bu | 0.70 | 364 | C |
| IIF-449 | i-Bu | H | 1-Npm | 3-Gun-Pr | 0.72 | 475 | C |
| IIF-450 | Bnzl | H | i-Bu | 2-Cbx-Et | 0.73 | 398 | C |
| IIF-451 | 2-Cbx-Et | H | Bnzl | i-Bu | 0.80 | 398 | C |
| IIF-452 | 2-Cbx-Et | H | 4-OH-Bnzl | i-Bu | 0.70 | 414 | C |
| IIF-453 | 2-Cbx-Et | H | s-Bu | i-Bu | 0.78 | 364 | C |
| IIF-454 | 2-Cbx-Et | H | 1-Npm | i-Bu | 0.88 | 448 | C |
| IIF-455 | 2-Cbx-Et | H | i-Pr | i-Bu | 0.74 | 350 | C |
| IIF-456 | 2-Cbx-Et | H | 1-Npm | Bnzl | 0.88 | 482 | C |
| IIF-457 | 2-Cbx-Et | H | Bnzl | 4-OH-Bnzl | 0.77 | 448 | C |
| IIF-458 | 2-Cbx-Et | H | 1-Npm | 4-OH-Bnzl | 0.84 | 498 | C |
| IIF-459 | 2-Cbx-Et | H | i-Bu | 1-Npm | 0.86 | 448 | C |
| IIF-460 | 2-Cbx-Et | H | 4-OH-Bnzl | 1-Npm | 0.77 | 498 | C |
| IIF-461 | 2-Cbx-Et | H | 1-Npm | 1-Npm | 0.94 | 532 | C |
| IIF-462 | 2-Cbx-Et | H | i-Pr | 1-Npm | 0.82 | 434 | C |

TABLE 2-continued

| | | | | | | | |
|---|---|---|---|---|---|---|---|
| IIF-463 | 1-Npm | H | 4-OH-Bnzl | i-Bu | 0.87 | 482 | C |
| IIF-464 | 1-Npm | H | i-Bu | 4-OH-Bnzl | 0.85 | 482 | C |
| IIF-465 | 1-Npm | H | i-Bu | 2-Cbx-Et | 0.78 | 448 | C |
| IIF-466 | 1-Npm | H | i-Pr | 2-Cbx-Et | 0.75 | 434 | C |
| IIF-467 | 1-Npm | H | 3-Gun-Pr | 1-Npm | 0.78 | 559 | C |
| IIF-468 | i-Bu | H | 3-Gun-Pr | i-Bu | 0.63 | 391 | C |
| IIF-469 | i-Bu | H | 3-Gun-Pr | Bnzl | 0.66 | 425 | C |
| IIF-470 | i-Bu | H | s-Bu | 2-Cbx-Et | 0.70 | 364 | C |
| IIF-471 | i-Bu | H | i-Bu | 3-Gun-Pr | 0.62 | 391 | C |
| IIF-472 | i-Bu | H | Bnzl | 3-Gun-Pr | 0.65 | 425 | C |
| IIF-473 | i-Bu | H | s-Bu | 3-Gun-Pr | 0.62 | 391 | C |
| IIF-474 | i-Bu | H | i-Pr | 3-Gun-Pr | 0.58 | 377 | C |
| IIF-475 | i-Bu | H | 3-Gun-Pr | 1-Npm | 0.72 | 475 | C |
| IIF-476 | Bnzl | H | 3-Gun-Pr | i-Bu | 0.67 | 425 | C |
| IIF-477 | Bnzl | H | 3-Gun-Pr | Bnzl | 0.69 | 459 | C |
| IIF-478 | Bnzl | H | i-Bu | 3-Gun-Pr | 0.64 | 425 | C |
| IIF-479 | Bnzl | H | Bnzl | 3-Gun-Pr | 0.66 | 459 | C |
| IIF-480 | Bnzl | H | s-Bu | 3-Gun-Pr | 0.64 | 425 | C |
| IIF-481 | Bnzl | H | 1-Npm | 3-Gun-Pr | 0.73 | 509 | C |
| IIF-482 | Bnzl | H | 3-Gun-Pr | 1-Npm | 0.74 | 509 | C |
| IIF-483 | 2-Cbx-Et | H | i-Bu | i-Bu | 0.79 | 364 | C |
| IIF-484 | 2-Cbx-Et | H | Bnzl | Bnzl | 0.81 | 432 | C |
| IIF-485 | 2-Cbx-Et | H | 4-OH-Bnzl | Bnzl | 0.72 | 448 | C |
| IIF-486 | 2-Cbx-Et | H | s-Bu | Bnzl | 0.79 | 398 | C |
| IIF-487 | 2-Cbx-Et | H | i-Pr | Bnzl | 0.75 | 384 | C |
| IIF-488 | 2-Cbx-Et | H | i-Bu | 4-OH-Bnzl | 0.75 | 414 | C |
| IIF-489 | 2-Cbx-Et | H | i-Pr | 4-OH-Bnzl | 0.70 | 400 | C |
| IIF-490 | 2-Cbx-Et | H | Bnzl | 1-Npm | 0.87 | 482 | C |
| IIF-491 | 2-Cbx-Et | H | s-Bu | 1-Npm | 0.86 | 448 | C |
| IIF-492 | 3-Gun-Pr | H | 1-Npm | i-Bu | 0.79 | 475 | C |
| IIF-493 | 3-Gun-Pr | H | i-Pr | i-Bu | 0.67 | 377 | C |
| IIF-494 | 3-Gun-Pr | H | i-Pr | Bnzl | 0.66 | 411 | C |
| IIF-495 | 3-Gun-Pr | H | 1-Npm | 1-Npm | 0.83 | 559 | C |
| IIF-496 | 3-Gun-Pr | H | i-Pr | 1-Npm | 0.73 | 461 | C |
| IIF-497 | 3-tert-butoxy-propyl | H | 4-F-Bnzl | 1-Npm | 1.00 | 542 | C |
| IIF-498 | 3-hydroxy-propyl | H | 4-F-Bnzl | 1-Npm | 0.88 | 486 | C |
| IIF-499 | 3-amino-propyl | H | 3-amino-propyl | 3-aminopropyl | 1.02 | 751 | C |
| IIF-500 | 1-Npm | H | β-hydroxy-phenethyl | Ph-Et | 0.93 | 544 | C |

TABLE 2-continued

| | | | | | | | |
|---|---|---|---|---|---|---|---|
| IIF-501 | 1-Npm | H | α-(hydroxy-methyl)phenethyl | Ph-Et | 0.92 | 558 | C |
| IIF-502 | 1-Npm | H | α-(hydroxy-methyl)phenethyl | Ph-Et | 0.95 | 558 | C |
| IIF-503 | 4-Nt-Bnzl | H | Bnzl | tBOC-E | 0.93 | 533 | C |
| IIF-504 | 2-OH-Et | H | Ph-Et | 1-Npm | 0.89 | 468.3 | C |
| IIF-505 | Chm | H | 2-OH-Et | 1-Npm | 0.86 | 460.3 | C |
| IIF-506 | 2-OH-Et | H | Bnzl | 1-Npm | 0.87 | 454.3 | C |
| IIF-507 | Ph-Et | H | 1-Npm | Hxy | 1.06 | 508.4 | C |
| IIF-508 | 1-Npm | H | Ph-Et | Hxy | 1.04 | 508.4 | C |
| IIF-509 | Hxy | H | Ph-Et | 1-Npm | 1.04 | 508.4 | C |
| IIF-510 | Hxy | H | 1-Npm | Ph-Et | 1.03 | 508.4 | C |
| IIF-511 | i-Pnt | H | i-Pr | i-Bu | 3.25 | 348 | F |
| IIF-512 | Chm | H | i-Pr | i-Bu | 3.49 | 374 | F |
| IIF-513 | Chm | H | i-Pr | i-Pnt | 3.74 | 388 | F |
| IIF-514 | i-Bu | H | s-Bu | i-Pnt | 3.55 | 362 | F |
| IIF-515 | i-Pnt | H | s-Bu | i-Bu | 3.45 | 362 | F |
| IIF-516 | Chm | H | s-Bu | i-Bu | 3.72 | 388 | F |
| IIF-517 | Chm | H | s-Bu | Ph-Et | 4 | 436 | F |
| IIF-518 | Chm | H | s-Bu | i-Pnt | 4.02 | 402 | F |
| IIF-519 | i-Bu | H | i-Pnt | i-Bu | 3.52 | 362 | F |
| IIF-520 | Chm | H | i-Pnt | i-Bu | 3.99 | 402 | F |
| IIF-521 | i-Bu | H | Hxy | i-Bu | 3.88 | 376 | F |
| IIF-522 | Chm | H | Hxy | i-Bu | 4.34 | 416 | F |
| IIF-523 | 2-Cbx-Et | H | Bnzl | i-Pnt | 3.3 | 412 | F |
| IIF-524 | Ph-Et | H | Bnzl | 2-Cbx-Et | 3.02 | 446 | F |
| IIF-525 | 4-F-Bnzl | H | Bnzl | 2-Cbx-Et | 2.85 | 450 | F |
| IIF-526 | 2-OH-Et | H | Bnzl | 2-Cbx-Et | 2.45 | 386 | F |
| IIF-527 | i-Pnt | H | Bnzl | 2-Cbx-Et | 2.85 | 412 | F |
| IIF-528 | i-Pnt | H | Bnzl | 2-OH-Et | 2.84 | 384 | F |
| IIF-529 | Chm | H | Bnzl | 2-Cbx-Et | 3 | 438 | F |
| IIF-530 | 2-Cbx-Et | H | i-Bu | Ph-Et | 3.17 | 412 | F |
| IIF-531 | 2-Cbx-Et | H | i-Bu | i-Pnt | 3.12 | 378 | F |
| IIF-532 | 4-F-Bnzl | H | i-Bu | 2-Cbx-Et | 2.69 | 416 | F |
| IIF-533 | 2-OH-Et | H | i-Bu | 2-Cbx-Et | 3.49 | 352 | G |
| IIF-534 | i-Pnt | H | i-Bu | 4-OH-Bnzl | 3.12 | 412 | F |
| IIF-535 | Chm | H | i-Bu | 2-Cbx-Et | 2.84 | 404 | F |
| IIF-536 | 2-Cbx-Et | H | 1-Npm | Ph-Et | 3.72 | 496 | F |
| IIF-537 | 2-Cbx-Et | H | 1-Npm | i-Pnt | 3.65 | 462 | F |
| IIF-538 | Ph-Et | H | 1-Npm | 2-Cbx-Et | 3.47 | 496 | F |
| IIF-539 | 4-F-Bnzl | H | 1-Npm | 2-Cbx-Et | 3.3 | 500 | F |
| IIF-540 | 2-OH-Et | H | 1-Npm | 2-Cbx-Et | 2.87 | 436 | F |

TABLE 2-continued

| IIF-541 | i-Pnt | H | 1-Npm | 2-Cbx-Et | 3.34 | 462 | F |
|---|---|---|---|---|---|---|---|
| IIF-542 | Chm | H | 1-Npm | 2-Cbx-Et | 3.4 | 488 | F |
| IIF-543 | 4-OH-Bnzl | H | i-Pr | Ph-Et | 3.19 | 432 | F |
| IIF-544 | 4-OH-Bnzl | H | i-Pr | i-Pnt | 3.09 | 398 | F |
| IIF-545 | 2-Cbx-Et | H | i-Pr | Ph-Et | 2.92 | 398 | F |
| IIF-546 | 2-Cbx-Et | H | i-Pr | 2-OH-Et | 3.02 | 338 | G |
| IIF-547 | Ph-Et | H | i-Pr | 2-Cbx-Et | 2.65 | 398 | F |
| IIF-548 | Ph-Et | H | i-Pr | 2-OH-Et | 2.62 | 370 | F |
| IIF-549 | 4-F-Bnzl | H | i-Pr | 2-Cbx-Et | 2.5 | 402 | F |
| IIF-550 | 4-F-Bnzl | H | i-Pr | 2-OH-Et | 2.47 | 374 | F |
| IIF-551 | 2-OH-Et | H | i-Pr | Bnzl | 2.69 | 356 | F |
| IIF-552 | 2-OH-Et | H | i-Pr | i-Bu | 2.57 | 322 | F |
| IIF-553 | 2-OH-Et | H | i-Pr | 1-Npm | 3.07 | 406 | F |
| IIF-554 | 2-OH-Et | H | i-Pr | 4-OH-Bnzl | 2.45 | 372 | F |
| IIF-555 | 2-OH-Et | H | i-Pr | 2-Cbx-Et | 3.12 | 338 | G |
| IIF-556 | 2-OH-Et | H | i-Pr | Ph-Et | 2.9 | 370 | F |
| IIF-557 | 2-OH-Et | H | i-Pr | i-Pnt | 2.82 | 336 | F |
| IIF-558 | i-Pnt | H | i-Pr | 4-OH-Bnzl | 2.88 | 398 | F |
| IIF-559 | i-Pnt | H | i-Pr | 2-Cbx-Et | 2.49 | 364 | F |
| IIF-560 | i-Pnt | H | i-Pr | 2-OH-Et | 3.67 | 336 | G |
| IIF-561 | i-Bu | H | s-Bu | 2-OH-Et | 3.69 | 336 | G |
| IIF-562 | 4-OH-Bnzl | H | s-Bu | Ph-Et | 3.35 | 446 | F |
| IIF-563 | 4-OH-Bnzl | H | s-Bu | i-Pnt | 3.2 | 412 | F |
| IIF-564 | 2-Cbx-Et | H | s-Bu | i-Pnt | 3.09 | 378 | F |
| IIF-565 | Ph-Et | H | s-Bu | 2-Cbx-Et | 2.8 | 412 | F |
| IIF-566 | 4-F-Bnzl | H | s-Bu | 2-Cbx-Et | 2.69 | 416 | F |
| IIF-567 | 2-OH-Et | H | s-Bu | 4-OH-Bnzl | 2.67 | 386 | F |
| IIF-568 | 2-OH-Et | H | s-Bu | 2-Cbx-Et | 3.47 | 352 | G |
| IIF-569 | i-Pnt | H | s-Bu | 4-OH-Bnzl | 3.07 | 412 | F |
| IIF-570 | i-Pnt | H | s-Bu | 2-Cbx-Et | 2.67 | 378 | F |
| IIF-571 | Chm | H | s-Bu | 4-OH-Bnzl | 3.2 | 438 | F |
| IIF-572 | Chm | H | s-Bu | 2-Cbx-Et | 2.8 | 404 | F |
| IIF-573 | i-Bu | H | 4-OH-Bnzl | i-Pnt | 3.1 | 412 | F |

| | | | | | | | |
|---|---|---|---|---|---|---|---|
| IIF-574 | 2-Cbx-Et | H | 4-OH-Bnzl | Ph-Et | 2.77 | 462 | F |
| IIF-575 | 2-Cbx-Et | H | 4-OH-Bnzl | i-Pnt | 2.72 | 428 | F |
| IIF-576 | Ph-Et | H | 4-OH-Bnzl | 2-Cbx-Et | 2.67 | 462 | F |
| IIF-577 | 4-F-Bnzl | H | 4-OH-Bnzl | 2-Cbx-Et | 2.55 | 466 | F |
| IIF-578 | 2-OH-Et | H | 4-OH-Bnzl | 2-Cbx-Et | 3.2 | 402 | G |
| IIF-579 | i-Pnt | H | 4-OH-Bnzl | 2-Cbx-Et | 2.52 | 428 | F |
| IIF-580 | Chm | H | 4-OH-Bnzl | 2-Cbx-Et | 2.67 | 454 | F |
| IIF-581 | i-Bu | H | 2-Cbx-Et | Ph-Et | 2.82 | 412 | F |
| IIF-582 | i-Bu | H | 2-Cbx-Et | i-Pnt | 2.72 | 378 | F |
| IIF-583 | i-Pnt | H | 2-Cbx-Et | i-Bu | 2.74 | 378 | F |
| IIF-584 | i-Pnt | H | 2-Cbx-Et | 4-OH-Bnzl | 2.45 | 428 | F |
| IIF-585 | Chm | H | 2-Cbx-Et | i-Bu | 2.94 | 404 | F |
| IIF-586 | Chm | H | 2-Cbx-Et | i-Pnt | 3.17 | 418 | F |
| IIF-587 | Bnzl | H | 4-F-Bnzl | 4-OH-Bnzl | 3.25 | 484 | F |
| IIF-588 | Bnzl | H | 4-F-Bnzl | 2-Cbx-Et | 2.88 | 450 | F |
| IIF-589 | i-Bu | H | 4-F-Bnzl | 4-OH-Bnzl | 3.12 | 450 | F |
| IIF-590 | i-Bu | H | 4-F-Bnzl | 2-Cbx-Et | 2.72 | 416 | F |
| IIF-591 | 1-Npm | H | 4-F-Bnzl | 4-OH-Bnzl | 3.5 | 534 | F |
| IIF-592 | 1-Npm | H | 4-F-Bnzl | 2-Cbx-Et | 3.13 | 500 | F |
| IIF-593 | 4-OH-Bnzl | H | 4-F-Bnzl | 2-Cbx-Et | 2.7 | 466 | F |
| IIF-594 | 4-OH-Bnzl | H | 4-F-Bnzl | Ph-Et | 3.5 | 498 | F |
| IIF-595 | 4-OH-Bnzl | H | 4-F-Bnzl | i-Pnt | 3.44 | 464 | F |
| IIF-596 | 2-Cbx-Et | H | 4-F-Bnzl | 4-OH-Bnzl | 2.9 | 466 | F |
| IIF-597 | 2-Cbx-Et | H | 4-F-Bnzl | Ph-Et | 3.32 | 464 | F |
| IIF-598 | 2-Cbx-Et | H | 4-F-Bnzl | i-Pnt | 3.25 | 430 | F |
| IIF-599 | Ph-Et | H | 4-F-Bnzl | 4-OH-Bnzl | 3.42 | 498 | F |
| IIF-600 | Ph-Et | H | 4-F-Bnzl | 2-Cbx-Et | 3.07 | 464 | F |
| IIF-601 | 2-OH-Et | H | 4-F-Bnzl | 4-OH-Bnzl | 2.84 | 438 | F |
| IIF-602 | 2-OH-Et | H | 4-F-Bnzl | 2-Cbx-Et | 2.52 | 404 | F |
| IIF-603 | i-Pnt | H | 4-F-Bnzl | 4-OH-Bnzl | 3.27 | 464 | F |
| IIF-604 | Chm | H | 4-F-Bnzl | 4-OH-Bnzl | 3.37 | 490 | F |
| IIF-605 | Chm | H | 4-F-Bnzl | 2-Cbx-Et | 3 | 456 | F |
| IIF-606 | i-Bu | H | i-Pnt | 2-Cbx-Et | 2.72 | 378 | F |
| IIF-607 | 4-OH-Bnzl | H | i-Pnt | 2-Cbx-Et | 2.72 | 428 | F |
| IIF-608 | 2-Cbx-Et | H | i-Pnt | i-Bu | 3.1 | 378 | F |
| IIF-609 | 2-Cbx-Et | H | i-Pnt | 4-OH-Bnzl | 2.94 | 428 | F |
| IIF-610 | 2-OH-Et | H | i-Pnt | i-Bu | 3.04 | 350 | F |
| IIF-611 | Chm | H | i-Pnt | 2-Cbx-Et | 3.05 | 418 | F |
| IIF-612 | i-Bu | H | 2-OH-Et | i-Bu | 2.43 | 336 | F |

TABLE 2-continued

| | | | | | | | |
|---|---|---|---|---|---|---|---|
| IIF-613 | i-Bu | H | 2-OH-Et | 4-OH-Bnzl | 1.34 | 386 | F |
| IIF-614 | i-Bu | H | 2-OH-Et | 2-Cbx-Et | 2.57 | 352 | F |
| IIF-615 | 1-Npm | H | 2-OH-Et | 4-OH-Bnzl | 2.62 | 470 | F |
| IIF-616 | 1-Npm | H | 2-OH-Et | 2-Cbx-Et | 2.45 | 436 | F |
| IIF-617 | 4-OH-Bnzl | H | 2-OH-Et | Bnzl | 2.43 | 420 | F |
| IIF-618 | 4-OH-Bnzl | H | 2-OH-Et | 1-Npm | 2.74 | 470 | F |
| IIF-619 | 4-OH-Bnzl | H | 2-OH-Et | i-Pnt | 2.45 | 400 | F |
| IIF-620 | 2-Cbx-Et | H | 2-OH-Et | Bnzl | 3.32 | 386 | F |
| IIF-621 | 2-Cbx-Et | H | 2-OH-Et | 4-OH-Bnzl | 2.94 | 402 | G |
| IIF-622 | 2-Cbx-Et | H | 2-OH-Et | i-Pnt | 3.42 | 366 | G |
| IIF-623 | Bnzl | H | Ph-Et | 4-OH-Bnzl | 3.29 | 480 | F |
| IIF-624 | Bnzl | H | Ph-Et | 2-Cbx-Et | 2.9 | 446 | F |
| IIF-625 | i-Bu | H | Ph-Et | 4-OH-Bnzl | 3.15 | 446 | F |
| IIF-626 | i-Bu | H | Ph-Et | 2-Cbx-Et | 2.77 | 412 | F |
| IIF-627 | 1-Npm | H | Ph-Et | 4-OH-Bnzl | 3.55 | 530 | F |
| IIF-628 | 4-OH-Bnzl | H | Ph-Et | i-Pnt | 3.57 | 460 | F |
| IIF-629 | 2-Cbx-Et | H | Ph-Et | 4-OH-Bnzl | 2.95 | 462 | F |
| IIF-630 | 4-F-Bnzl | H | Ph-Et | 4-OH-Bnzl | 3.3 | 498 | F |
| IIF-631 | 2-OH-Et | H | Ph-Et | 4-OH-Bnzl | 2.88 | 434 | F |
| IIF-632 | i-Pnt | H | Ph-Et | 4-OH-Bnzl | 3.37 | 460 | F |
| IIF-633 | i-Pnt | H | Ph-Et | 2-Cbx-Et | 2.99 | 426 | F |
| IIF-634 | Chm | H | Ph-Et | 4-OH-Bnzl | 3.47 | 486 | F |
| IIF-635 | Chm | H | Ph-Et | 2-Cbx-Et | 3.1 | 452 | F |
| IIF-636 | Bnzl | H | Hxy | 2-Cbx-Et | 3.15 | 426 | F |
| IIF-637 | 4-OH-Bnzl | H | Hxy | 1-Npm | 4.15 | 510 | F |
| IIF-638 | 4-OH-Bnzl | H | Hxy | 2-Cbx-Et | 3 | 442 | F |
| IIF-639 | 2-Cbx-Et | H | Hxy | i-Bu | 3.4 | 392 | F |
| IIF-640 | 2-Cbx-Et | H | Hxy | 1-Npm | 3.85 | 476 | F |
| IIF-641 | 2-Cbx-Et | H | Hxy | 4-OH-Bnzl | 3.22 | 442 | F |
| IIF-642 | 2-Cbx-Et | H | Hxy | i-Pnt | 3.65 | 406 | F |
| IIF-643 | Ph-Et | H | Hxy | 2-Cbx-Et | 3.37 | 440 | F |
| IIF-644 | 4-F-Bnzl | H | Hxy | 2-Cbx-Et | 3.2 | 444 | F |
| IIF-645 | 2-OH-Et | H | Hxy | i-Bu | 3.35 | 364 | F |
| IIF-646 | 2-OH-Et | H | Hxy | 4-OH-Bnzl | 3.15 | 414 | F |
| IIF-647 | 2-OH-Et | H | Hxy | 2-Cbx-Et | 2.79 | 380 | F |

TABLE 2-continued

| | | | | | | | |
|---|---|---|---|---|---|---|---|
| IIF-648 | 2-OH-Et | H | Hxy | i-Pnt | 3.55 | 378 | F |
| IIF-649 | i-Pnt | H | Hxy | 4-OH-Bnzl | 3.69 | 440 | F |
| IIF-650 | i-Pnt | H | Hxy | 2-Cbx-Et | 3.24 | 406 | F |
| IIF-651 | i-Pnt | H | Hxy | 2-OH-Et | 3.24 | 378 | F |
| IIF-652 | Chm | H | Hxy | 4-OH-Bnzl | 3.75 | 466 | F |
| IIF-653 | Chm | H | Hxy | 2-Cbx-Et | 3.35 | 432 | F |
| IIF-654 | tBOC-E | H | Bnzl | i-Pnt | 4.09 | 468 | F |
| IIF-655 | Ph-Et | H | Bnzl | tBOC-E | 4.04 | 502 | F |
| IIF-656 | 4-F-Bnzl | H | Bnzl | tBOC-E | 3.8 | 506 | F |
| IIF-657 | tBOC-E | H | i-Bu | Ph-Et | 3.92 | 468 | F |
| IIF-658 | 4-F-Bnzl | H | i-Bu | tBOC-E | 3.7 | 472 | F |
| IIF-659 | i-Pnt | H | i-Bu | 4-tBuO-Bnzl | 4.39 | 468 | F |
| IIF-660 | Chm | H | i-Bu | 4-tBuO-Bnzl | 4.35 | 494 | F |
| IIF-661 | Chm | H | i-Bu | tBOC-E | 3.94 | 460 | F |
| IIF-662 | tBOC-E | H | 1-Npm | Ph-Et | 4.47 | 552 | F |
| IIF-663 | tBOC-E | H | 1-Npm | i-Pnt | 4.52 | 518 | F |
| IIF-664 | Ph-Et | H | 1-Npm | tBOC-E | 4.39 | 552 | F |
| IIF-665 | 4-F-Bnzl | H | 1-Npm | tBOC-E | 4.25 | 556 | F |
| IIF-666 | 2-OtBu-Et | H | 1-Npm | tBOC-E | 4.89 | 548 | F |
| IIF-667 | i-Pnt | H | 1-Npm | tBOC-E | 4.35 | 518 | F |
| IIF-668 | Chm | H | 1-Npm | tBOC-E | 4.54 | 544 | F |
| IIF-669 | 4-tBuO-Bnzl | H | i-Pr | i-Pnt | 4.07 | 454 | F |
| IIF-670 | tBOC-E | H | i-Pr | Ph-Et | 3.72 | 454 | F |
| IIF-671 | 2-OtBu-Et | H | i-Pr | 1-Npm | 3.87 | 462 | F |
| IIF-672 | 2-OtBu-Et | H | i-Pr | 4-tBuO-Bnzl | 3.9 | 484 | F |
| IIF-673 | Chm | H | i-Pr | 4-tBuO-Bnzl | 4.07 | 480 | F |
| IIF-674 | 4-tBuO-Bnzl | H | s-Bu | Ph-Et | 4.22 | 502 | F |
| IIF-675 | 4-tBuO-Bnzl | H | s-Bu | i-Pnt | 4.07 | 468 | F |
| IIF-676 | tBOC-E | H | s-Bu | i-Pnt | 3.82 | 434 | F |
| IIF-677 | Ph-Et | H | s-Bu | tBOC-E | 3.84 | 468 | F |
| IIF-678 | 4-F-Bnzl | H | s-Bu | tBOC-E | 3.95 | 472 | F |
| IIF-679 | 2-OtBu-Et | H | s-Bu | tBOC-E | 3.7 | 464 | F |
| IIF-680 | i-Pnt | H | s-Bu | 4-tBuO-Bnzl | 4.12 | 468 | F |
| IIF-681 | i-Pnt | H | s-Bu | tBOC-E | 3.7 | 434 | F |
| IIF-682 | Chm | H | s-Bu | 4-tBuO-Bnzl | 4.35 | 494 | F |
| IIF-683 | i-Bu | H | 4-tBuO-Bnzl | i-Pnt | 4.07 | 468 | F |
| IIF-684 | tBOC-E | H | 4-tBuO-Bnzl | Ph-Et | 4.52 | 574 | F |
| IIF-685 | tBOC-E | H | 4-tBuO-Bnzl | i-Pnt | 4.42 | 540 | F |
| IIF-686 | Ph-Et | H | 4-tBuO-Bnzl | tBOC-E | 4.52 | 574 | F |
| IIF-687 | 4-F-Bnzl | H | 4-tBuO-Bnzl | tBOC-E | 4.22 | 578 | F |
| IIF-688 | Chm | H | 4-tBuO-Bnzl | tBOC-E | 4.54 | 566 | F |
| IIF-689 | i-Bu | H | tBOC-E | i-Pnt | 3.7 | 434 | F |
| IIF-690 | Bnzl | H | 4-F-Bnzl | 4-tBuO-Bnzl | 4.17 | 540 | F |
| IIF-691 | i-Bu | H | 4-F-Bnzl | 4-tBuO-Bnzl | 3.99 | 506 | F |
| IIF-692 | i-Bu | H | 4-F-Bnzl | tBOC-E | 3.67 | 472 | F |

TABLE 2-continued

| | | | | | | | |
|---|---|---|---|---|---|---|---|
| IIF-693 | 1-Npm | H | 4-F-Bnzl | 4-tBuO-Bnzl | 4.59 | 590 | F |
| IIF-694 | 1-Npm | H | 4-F-Bnzl | tBOC-E | 4.17 | 556 | F |
| IIF-695 | 4-tBuO-Bnzl | H | 4-F-Bnzl | tBOC-E | 4.34 | 578 | F |
| IIF-696 | 4-tBuO-Bnzl | H | 4-F-Bnzl | Ph-Et | 4.75 | 554 | F |
| IIF-697 | 4-tBuO-Bnzl | H | 4-F-Bnzl | i-Pnt | 4.42 | 520 | F |
| IIF-698 | tBOC-E | H | 4-F-Bnzl | 4-tBuO-Bnzl | 4.39 | 578 | F |
| IIF-699 | tBOC-E | H | 4-F-Bnzl | i-Pnt | 4.09 | 486 | F |
| IIF-700 | Ph-Et | H | 4-F-Bnzl | 4-tBuO-Bnzl | 4.34 | 554 | F |
| IIF-701 | 2-OtBu-Et | H | 4-F-Bnzl | 4-tBuO-Bnzl | 4.32 | 550 | F |
| IIF-702 | i-Pnt | H | 4-F-Bnzl | 4-tBuO-Bnzl | 4.29 | 520 | F |
| IIF-703 | Chm | H | 4-F-Bnzl | 4-tBuO-Bnzl | 4.39 | 546 | F |
| IIF-704 | Chm | H | 4-F-Bnzl | tBOC-E | 4.05 | 512 | F |
| IIF-705 | 4-tBuO-Bnzl | H | i-Pnt | tBOC-E | 4.32 | 540 | F |
| IIF-706 | tBOC-E | H | i-Pnt | 4-tBuO-Bnzl | 4.54 | 540 | F |
| IIF-707 | i-Bu | H | 2-OtBu-Et | 4-tBuO-Bnzl | 3.87 | 498 | F |
| IIF-708 | 1-Npm | H | 2-OtBu-Et | 4-tBuO-Bnzl | 4.47 | 582 | F |
| IIF-709 | 1-Npm | H | 2-OtBu-Et | tBOC-E | 4 | 548 | F |
| IIF-710 | 4-tBuO-Bnzl | H | 2-OtBu-Et | Bnzl | 4.02 | 532 | F |
| IIF-711 | 4-tBuO-Bnzl | H | 2-OtBu-Et | i-Pnt | 4.25 | 512 | F |
| IIF-712 | tBOC-E | H | 2-OtBu-Et | Bnzl | 3.67 | 498 | F |
| IIF-713 | tBOC-E | H | 2-OtBu-Et | 4-tBuO-Bnzl | 4.17 | 570 | F |
| IIF-714 | Bnzl | H | Ph-Et | 4-tBuO-Bnzl | 4.25 | 536 | F |
| IIF-715 | i-Bu | H | Ph-Et | 4-tBuO-Bnzl | 4.1 | 502 | F |
| IIF-716 | 1-Npm | H | Ph-Et | 4-tBuO-Bnzl | 4.59 | 586 | F |
| IIF-717 | 1-Npm | H | Ph-Et | tBOC-E | 4.2 | 552 | F |
| IIF-718 | 4-F-Bnzl | H | Ph-Et | 4-tBuO-Bnzl | 4.29 | 554 | F |
| IIF-719 | 2-OtBu-Et | H | Ph-Et | 4-tBuO-Bnzl | 4.39 | 546 | F |
| IIF-720 | i-Pnt | H | Ph-Et | 4-tBuO-Bnzl | 4.37 | 516 | F |
| IIF-721 | Chm | H | Ph-Et | 4-tBuO-Bnzl | 4.54 | 542 | F |
| IIF-722 | Chm | H | Ph-Et | tBOC-E | 4.05 | 508 | F |
| IIF-723 | 4-tBuO-Bnzl | H | Hxy | 1-Npm | 5.09 | 566 | F |
| IIF-724 | 4-tBuO-Bnzl | H | Hxy | tBOC-E | 4.74 | 554 | F |
| IIF-725 | tBOC-E | H | Hxy | 4-tBuO-Bnzl | 4.8 | 554 | F |
| IIF-726 | Ph-Et | H | Hxy | tBOC-E | 4.45 | 496 | F |
| IIF-727 | 4-F-Bnzl | H | Hxy | tBOC-E | 4.27 | 500 | F |
| IIF-728 | 2-OtBu-Et | H | Hxy | 4-tBuO-Bnzl | 4.79 | 526 | F |
| IIF-729 | 2-OtBu-Et | H | Hxy | i-Pnt | 4.42 | 434 | F |
| IIF-730 | i-Pnt | H | Hxy | 4-tBuO-Bnzl | 4.74 | 496 | F |
| IIF-731 | Chm | H | Hxy | 4-tBuO-Bnzl | 4.87 | 522 | F |
| IIF-732 | i-Bu | H | i-Bu | Ph-Et | 3.11 | 396 | H |
| IIF-733 | i-Bu | H | i-Bu | i-Pnt | 2.96 | 362 | H |
| IIF-734 | 1-Npm | H | i-Bu | i-Pnt | 3.25 | 446 | H |
| IIF-735 | 4-F-Bnzl | H | i-Bu | i-Bu | 2.88 | 400 | H |

TABLE 2-continued

| | | | | | | | |
|---|---|---|---|---|---|---|---|
| IIF-736 | 4-F-Bnzl | H | i-Bu | 1-Npm | 3.12 | 484 | H |
| IIF-737 | 4-F-Bnzl | H | i-Bu | Ph-Et | 2.98 | 448 | H |
| IIF-738 | 4-F-Bnzl | H | i-Bu | i-Pnt | 2.98 | 414 | H |
| IIF-739 | i-Pnt | H | i-Bu | i-Bu | 2.92 | 362 | H |
| IIF-740 | i-Pnt | H | i-Bu | 1-Npm | 3.17 | 446 | H |
| IIF-741 | i-Pnt | H | i-Bu | Ph-Et | 2.99 | 410 | H |
| IIF-742 | Chm | H | i-Bu | i-Bu | 2.99 | 388 | H |
| IIF-743 | Chm | H | i-Bu | 1-Npm | 3.31 | 472 | H |
| IIF-744 | Chm | H | i-Bu | Ph-Et | 3.1 | 436 | H |
| IIF-745 | Chm | H | i-Bu | i-Pnt | 3.13 | 402 | H |
| IIF-746 | Bnzl | H | Bnzl | Ph-Et | 3.22 | 464 | H |
| IIF-747 | 1-Npm | H | Bnzl | i-Pnt | 3.17 | 480 | H |
| IIF-748 | Ph-Et | H | Bnzl | 1-Npm | 3.27 | 514 | H |
| IIF-749 | Ph-Et | H | Bnzl | i-Pnt | 3.12 | 444 | H |
| IIF-750 | 4-F-Bnzl | H | Bnzl | 1-Npm | 3.19 | 518 | H |
| IIF-751 | 4-F-Bnzl | H | Bnzl | Ph-Et | 3.02 | 482 | H |
| IIF-752 | 4-F-Bnzl | H | Bnzl | i-Pnt | 3.05 | 448 | H |
| IIF-753 | i-Pnt | H | Bnzl | 1-Npm | 3.2 | 480 | H |
| IIF-754 | Chm | H | Bnzl | 1-Npm | 3.3 | 506 | H |
| IIF-755 | Chm | H | Bnzl | Ph-Et | 3.12 | 470 | H |
| IIF-756 | Chm | H | Bnzl | i-Pnt | 3.15 | 436 | H |
| IIF-757 | Bnzl | H | 1-Npm | Ph-Et | 3.22 | 514 | H |
| IIF-758 | Bnzl | H | 1-Npm | i-Pnt | 3.27 | 480 | H |
| IIF-759 | i-Bu | H | 1-Npm | i-Pnt | 3.13 | 446 | H |
| IIF-760 | 1-Npm | H | 1-Npm | Ph-Et | 3.34 | 564 | H |
| IIF-761 | 1-Npm | H | 1-Npm | i-Pnt | 3.38 | 530 | H |
| IIF-762 | Ph-Et | H | 1-Npm | Bnzl | 3.27 | 514 | H |
| IIF-763 | Ph-Et | H | 1-Npm | i-Bu | 3.22 | 480 | H |
| IIF-764 | Ph-Et | H | 1-Npm | 1-Npm | 3.42 | 564 | H |
| IIF-765 | Ph-Et | H | 1-Npm | i-Pnt | 3.32 | 494 | H |
| IIF-766 | 4-F-Bnzl | H | 1-Npm | 1-Npm | 3.36 | 568 | H |
| IIF-767 | 4-F-Bnzl | H | 1-Npm | Ph-Et | 3.22 | 532 | H |
| IIF-768 | 4-F-Bnzl | H | 1-Npm | i-Pnt | 3.24 | 498 | H |
| IIF-769 | i-Pnt | H | 1-Npm | i-Bu | 3.22 | 446 | H |
| IIF-770 | i-Pnt | H | 1-Npm | 1-Npm | 3.39 | 530 | H |
| IIF-771 | i-Pnt | H | 1-Npm | Ph-Et | 3.27 | 494 | H |
| IIF-772 | Chm | H | 1-Npm | Bnzl | 3.38 | 506 | H |
| IIF-773 | Chm | H | 1-Npm | i-Bu | 3.3 | 472 | H |
| IIF-774 | Chm | H | 1-Npm | 1-Npm | 3.49 | 556 | H |
| IIF-775 | Chm | H | 1-Npm | Ph-Et | 3.36 | 520 | H |
| IIF-776 | Chm | H | 1-Npm | i-Pnt | 3.38 | 486 | H |
| IIF-777 | Bnzl | H | i-Pr | Ph-Et | 3 | 416 | H |
| IIF-778 | Bnzl | H | i-Pr | i-Pnt | 3.01 | 382 | H |
| IIF-779 | i-Bu | H | i-Pr | Ph-Et | 2.93 | 382 | H |
| IIF-780 | 1-Npm | H | i-Pr | Ph-Et | 3.14 | 466 | H |
| IIF-781 | 1-Npm | H | i-Pr | i-Pnt | 3.17 | 432 | H |
| IIF-782 | Ph-Et | H | i-Pr | Bnzl | 2.99 | 416 | H |
| IIF-783 | Ph-Et | H | i-Pr | i-Bu | 2.95 | 382 | H |
| IIF-784 | Ph-Et | H | i-Pr | 1-Npm | 3.22 | 466 | H |
| IIF-785 | Ph-Et | H | i-Pr | i-Pnt | 3.08 | 396 | H |
| IIF-786 | 4-F-Bnzl | H | i-Pr | Bnzl | 2.92 | 420 | H |
| IIF-787 | 4-F-Bnzl | H | i-Pr | i-Bu | 2.92 | 386 | H |

TABLE 2-continued

| | | | | | | | |
|---|---|---|---|---|---|---|---|
| IIF-788 | 4-F-Bnzl | H | i-Pr | 1-Npm | 3.14 | 470 | H |
| IIF-789 | 4-F-Bnzl | H | i-Pr | Ph-Et | 2.98 | 434 | H |
| IIF-790 | 4-F-Bnzl | H | i-Pr | i-Pnt | 2.97 | 400 | H |
| IIF-791 | i-Pnt | H | i-Pr | Bnzl | 2.91 | 382 | H |
| IIF-792 | i-Pnt | H | i-Pr | 1-Npm | 3.16 | 432 | H |
| IIF-793 | i-Pnt | H | i-Pr | Ph-Et | 3.02 | 396 | H |
| IIF-794 | Chm | H | i-Pr | Bnzl | 3.05 | 408 | H |
| IIF-795 | Chm | H | i-Pr | 1-Npm | 3.28 | 458 | H |
| IIF-796 | Chm | H | i-Pr | Ph-Et | 3.09 | 422 | H |
| IIF-797 | Bnzl | H | s-Bu | Ph-Et | 3.07 | 430 | H |
| IIF-798 | Bnzl | H | s-Bu | i-Pnt | 3.07 | 396 | H |
| IIF-799 | i-Bu | H | s-Bu | Ph-Et | 3 | 396 | H |
| IIF-800 | 1-Npm | H | s-Bu | Ph-Et | 3.21 | 480 | H |
| IIF-801 | 1-Npm | H | s-Bu | i-Pnt | 3.22 | 446 | H |
| IIF-802 | Ph-Et | H | s-Bu | Bnzl | 3.09 | 430 | H |
| IIF-803 | Ph-Et | H | s-Bu | i-Bu | 3.05 | 396 | H |
| IIF-804 | Ph-Et | H | s-Bu | 1-Npm | 3.28 | 480 | H |
| IIF-805 | Ph-Et | H | s-Bu | i-Pnt | 3.17 | 410 | H |
| IIF-806 | 4-F-Bnzl | H | s-Bu | Bnzl | 3.07 | 434 | H |
| IIF-807 | 4-F-Bnzl | H | s-Bu | i-Bu | 2.97 | 400 | H |
| IIF-808 | 4-F-Bnzl | H | s-Bu | 1-Npm | 3.22 | 484 | H |
| IIF-809 | 4-F-Bnzl | H | s-Bu | Ph-Et | 3.06 | 448 | H |
| IIF-810 | 4-F-Bnzl | H | s-Bu | i-Pnt | 3.1 | 414 | H |
| IIF-811 | i-Pnt | H | s-Bu | Bnzl | 3.05 | 396 | H |
| IIF-812 | i-Pnt | H | s-Bu | 1-Npm | 3.25 | 446 | H |
| IIF-813 | Chm | H | s-Bu | Bnzl | 3.15 | 422 | H |
| IIF-814 | Chm | H | s-Bu | 1-Npm | 3.34 | 472 | H |
| IIF-815 | Bnzl | H | Ph-Et | Bnzl | 3.07 | 464 | H |
| IIF-816 | Bnzl | H | Ph-Et | 1-Npm | 3.31 | 514 | H |
| IIF-817 | Bnzl | H | Ph-Et | i-Pnt | 3.15 | 444 | H |
| IIF-818 | i-Bu | H | Ph-Et | i-Bu | 2.96 | 396 | H |
| IIF-819 | i-Bu | H | Ph-Et | 1-Npm | 3.22 | 480 | H |
| IIF-820 | i-Bu | H | Ph-Et | i-Pnt | 4.26 | 410 | H |
| IIF-821 | 1-Npm | H | Ph-Et | Bnzl | 3.29 | 514 | H |
| IIF-822 | 1-Npm | H | Ph-Et | i-Bu | 3.26 | 480 | H |
| IIF-823 | 1-Npm | H | Ph-Et | 1-Npm | 3.42 | 564 | H |
| IIF-824 | 4-F-Bnzl | H | Ph-Et | Bnzl | 3.08 | 482 | H |
| IIF-825 | 4-F-Bnzl | H | Ph-Et | i-Bu | 3.04 | 448 | H |
| IIF-826 | 4-F-Bnzl | H | Ph-Et | 1-Npm | 3.24 | 532 | H |
| IIF-827 | 4-F-Bnzl | H | Ph-Et | i-Pnt | 3.13 | 462 | H |
| IIF-828 | i-Pnt | H | Ph-Et | i-Bu | 3.07 | 410 | H |
| IIF-829 | i-Pnt | H | Ph-Et | 1-Npm | 3.28 | 494 | H |
| IIF-830 | Chm | H | Ph-Et | Bnzl | 3.19 | 470 | H |
| IIF-831 | Chm | H | Ph-Et | i-Bu | 3.12 | 436 | H |
| IIF-832 | Chm | H | Ph-Et | 1-Npm | 3.34 | 520 | H |
| IIF-833 | Chm | H | Ph-Et | i-Pnt | 3.24 | 450 | H |
| IIF-834 | Bnzl | H | 4-F-Bnzl | Bnzl | 3.03 | 468 | H |
| IIF-835 | Bnzl | H | 4-F-Bnzl | 1-Npm | 3.19 | 518 | H |
| IIF-836 | Bnzl | H | 4-F-Bnzl | Ph-Et | 3.06 | 482 | H |
| IIF-837 | Bnzl | H | 4-F-Bnzl | i-Pnt | 3.08 | 448 | H |
| IIF-838 | i-Bu | H | 4-F-Bnzl | i-Bu | 2.92 | 400 | H |
| IIF-839 | i-Bu | H | 4-F-Bnzl | 1-Npm | 3.16 | 484 | H |

TABLE 2-continued

| | | | | | | | |
|---|---|---|---|---|---|---|---|
| IIF-840 | i-Bu | H | 4-F-Bnzl | i-Pnt | 3.03 | 414 | H |
| IIF-841 | 1-Npm | H | 4-F-Bnzl | Bnzl | 3.31 | 518 | H |
| IIF-842 | 1-Npm | H | 4-F-Bnzl | i-Bu | 3.23 | 484 | H |
| IIF-843 | 1-Npm | H | 4-F-Bnzl | 1-Npm | 3.47 | 568 | H |
| IIF-844 | 1-Npm | H | 4-F-Bnzl | Ph-Et | 3.29 | 532 | H |
| IIF-845 | 1-Npm | H | 4-F-Bnzl | i-Pnt | 3.31 | 498 | H |
| IIF-846 | Ph-Et | H | 4-F-Bnzl | Bnzl | 3.16 | 482 | H |
| IIF-847 | Ph-Et | H | 4-F-Bnzl | i-Bu | 3.11 | 448 | H |
| IIF-848 | Ph-Et | H | 4-F-Bnzl | 1-Npm | 3.31 | 532 | H |
| IIF-849 | Ph-Et | H | 4-F-Bnzl | i-Pnt | 3.2 | 462 | H |
| IIF-850 | i-Pnt | H | 4-F-Bnzl | Bnzl | 3.05 | 448 | H |
| IIF-851 | i-Pnt | H | 4-F-Bnzl | 1-Npm | 3.21 | 498 | H |
| IIF-852 | i-Pnt | H | 4-F-Bnzl | Ph-Et | 3.13 | 462 | H |
| IIF-853 | Chm | H | 4-F-Bnzl | Bnzl | 3.12 | 474 | H |
| IIF-854 | Chm | H | 4-F-Bnzl | i-Bu | 3.09 | 440 | H |
| IIF-855 | Chm | H | 4-F-Bnzl | 1-Npm | 3.3 | 524 | H |
| IIF-856 | Chm | H | 4-F-Bnzl | Ph-Et | 3.21 | 488 | H |
| IIF-857 | Chm | H | 4-F-Bnzl | i-Pnt | 3.17 | 454 | H |
| IIF-858 | Bnzl | H | i-Pnt | Bnzl | 3.08 | 430 | H |
| IIF-859 | Bnzl | H | i-Pnt | 1-Npm | 3.28 | 480 | H |
| IIF-860 | Bnzl | H | i-Pnt | Ph-Et | 3.12 | 444 | H |
| IIF-861 | i-Bu | H | i-Pnt | 1-Npm | 3.23 | 446 | H |
| IIF-862 | i-Bu | H | i-Pnt | Ph-Et | 3.11 | 410 | H |
| IIF-863 | 1-Npm | H | i-Pnt | Bnzl | 3.25 | 480 | H |
| IIF-864 | 1-Npm | H | i-Pnt | i-Bu | 3.22 | 446 | H |
| IIF-865 | 1-Npm | H | i-Pnt | 1-Npm | 3.42 | 530 | H |
| IIF-866 | Ph-Et | H | i-Pnt | Bnzl | 3.16 | 444 | H |
| IIF-867 | Ph-Et | H | i-Pnt | i-Bu | 3.13 | 410 | H |
| IIF-868 | Ph-Et | H | i-Pnt | 1-Npm | 3.33 | 494 | H |
| IIF-869 | 4-F-Bnzl | H | i-Pnt | Bnzl | 3.09 | 448 | H |
| IIF-870 | 4-F-Bnzl | H | i-Pnt | i-Bu | 3.05 | 414 | H |
| IIF-871 | 4-F-Bnzl | H | i-Pnt | 1-Npm | 3.29 | 498 | H |
| IIF-872 | 4-F-Bnzl | H | i-Pnt | Ph-Et | 3.13 | 462 | H |
| IIF-873 | Chm | H | i-Pnt | Bnzl | 3.23 | 436 | H |
| IIF-874 | Chm | H | i-Pnt | 1-Npm | 3.42 | 486 | H |
| IIF-875 | Chm | H | i-Pnt | Ph-Et | 3.25 | 450 | H |
| IIF-876 | Bnzl | H | Hxy | Bnzl | 3.24 | 444 | H |
| IIF-877 | Bnzl | H | Hxy | 1-Npm | 3.39 | 494 | H |
| IIF-878 | Bnzl | H | Hxy | i-Pnt | 3.27 | 424 | H |
| IIF-879 | i-Bu | H | Hxy | 1-Npm | 3.36 | 460 | H |
| IIF-880 | 1-Npm | H | Hxy | 1-Npm | 3.54 | 544 | H |
| IIF-881 | 1-Npm | H | Hxy | i-Pnt | 3.43 | 474 | H |
| IIF-882 | Ph-Et | H | Hxy | Bnzl | 3.3 | 458 | H |
| IIF-883 | Ph-Et | H | Hxy | i-Bu | 3.24 | 424 | H |
| IIF-884 | Ph-Et | H | Hxy | i-Pnt | 3.35 | 438 | H |
| IIF-885 | 4-F-Bnzl | H | Hxy | Bnzl | 3.23 | 462 | H |
| IIF-886 | 4-F-Bnzl | H | Hxy | i-Bu | 3.17 | 428 | H |
| IIF-887 | 4-F-Bnzl | H | Hxy | 1-Npm | 3.4 | 512 | H |
| IIF-888 | 4-F-Bnzl | H | Hxy | Ph-Et | 3.24 | 476 | H |
| IIF-889 | 4-F-Bnzl | H | Hxy | i-Pnt | 3.28 | 442 | H |
| IIF-890 | i-Pnt | H | Hxy | Bnzl | 3.26 | 424 | H |
| IIF-891 | i-Pnt | H | Hxy | 1-Npm | 3.47 | 474 | H |
| IIF-892 | Chm | H | Hxy | Bnzl | 3.34 | 450 | H |
| IIF-893 | Chm | H | Hxy | 1-Npm | 3.5 | 500 | H |
| IIF-894 | 2-OtBu-Et | H | i-Bu | Bnzl | 4.15 | 426 | H |

TABLE 2-continued

| | | | | | | | |
|---|---|---|---|---|---|---|---|
| IIF-895 | 2-OtBu-Et | H | i-Bu | i-Bu | 4.18 | 392 | H |
| IIF-896 | 2-OtBu-Et | H | i-Bu | 1-Npm | 4.31 | 476 | H |
| IIF-897 | 2-OtBu-Et | H | i-Bu | 4-tBuO-Bnzl | 4.37 | 498 | H |
| IIF-898 | 2-OtBu-Et | H | i-Bu | Ph-Et | 4.18 | 440 | H |
| IIF-899 | 2-OtBu-Et | H | i-Bu | i-Pnt | 4.28 | 406 | H |
| IIF-900 | 2-OtBu-Et | H | Bnzl | Bnzl | 4.2 | 460 | H |
| IIF-901 | 2-OtBu-Et | H | Bnzl | i-Bu | 4.17 | 426 | H |
| IIF-902 | 2-OtBu-Et | H | Bnzl | 4-tBuO-Bnzl | 4.32 | 532 | H |
| IIF-903 | 2-OtBu-Et | H | Bnzl | Ph-Et | 4.29 | 474 | H |
| IIF-904 | 2-OtBu-Et | H | Bnzl | i-Pnt | 4.27 | 440 | H |
| IIF-905 | i-Pnt | H | Bnzl | 4-tBuO-Bnzl | 3.26 | 502 | H |
| IIF-906 | Chm | H | Bnzl | 4-tBuO-Bnzl | 3.32 | 528 | H |
| IIF-907 | 4-tBuO-Bnzl | H | 1-Npm | Ph-Et | 3.42 | 586 | H |
| IIF-908 | 4-tBuO-Bnzl | H | 1-Npm | i-Pnt | 3.42 | 552 | H |
| IIF-909 | Ph-Et | H | 1-Npm | 4-tBuO-Bnzl | 3.4 | 586 | H |
| IIF-910 | 4-F-Bnzl | H | 1-Npm | 4-tBuO-Bnzl | 3.4 | 590 | H |
| IIF-911 | 2-OtBu-Et | H | 1-Npm | Bnzl | 4.38 | 510 | H |
| IIF-912 | 2-OtBu-Et | H | 1-Npm | i-Bu | 4.35 | 476 | H |
| IIF-913 | 2-OtBu-Et | H | 1-Npm | 1-Npm | 4.5 | 560 | H |
| IIF-914 | i-Pnt | H | 1-Npm | 4-tBuO-Bnzl | 3.43 | 552 | H |
| IIF-915 | Chm | H | 1-Npm | 4-tBuO-Bnzl | 3.5 | 578 | H |
| IIF-916 | Bnzl | H | 4-tBuO-Bnzl | Ph-Et | 3.31 | 536 | H |
| IIF-917 | Bnzl | H | 4-tBuO-Bnzl | i-Pnt | 3.29 | 502 | H |
| IIF-918 | i-Bu | H | 4-tBuO-Bnzl | Ph-Et | 3.22 | 502 | H |
| IIF-919 | 1-Npm | H | 4-tBuO-Bnzl | Ph-Et | 3.41 | 586 | H |
| IIF-920 | 1-Npm | H | 4-tBuO-Bnzl | i-Pnt | 3.41 | 552 | H |
| IIF-921 | Ph-Et | H | 4-tBuO-Bnzl | Bnzl | 3.32 | 536 | H |
| IIF-922 | Ph-Et | H | 4-tBuO-Bnzl | 1-Npm | 3.43 | 586 | H |
| IIF-923 | Ph-Et | H | 4-tBuO-Bnzl | i-Pnt | 3.37 | 516 | H |
| IIF-924 | 4-F-Bnzl | H | 4-tBuO-Bnzl | Bnzl | 3.22 | 540 | H |
| IIF-925 | 4-F-Bnzl | H | 4-tBuO-Bnzl | 1-Npm | 3.38 | 590 | H |
| IIF-926 | 4-F-Bnzl | H | 4-tBuO-Bnzl | Ph-Et | 3.28 | 554 | H |
| IIF-927 | 4-F-Bnzl | H | 4-tBuO-Bnzl | i-Pnt | 3.29 | 520 | H |
| IIF-928 | 2-OtBu-Et | H | 4-tBuO-Bnzl | 1-Npm | 3.46 | 582 | H |

TABLE 2-continued

| | | | | | | | |
|---|---|---|---|---|---|---|---|
| IIF-929 | i-Pnt | H | 4-tBuO-Bnzl | i-Bu | 3.2 | 468 | H |
| IIF-930 | i-Pnt | H | 4-tBuO-Bnzl | 1-Npm | 3.42 | 552 | H |
| IIF-931 | i-Pnt | H | 4-tBuO-Bnzl | Ph-Et | 3.33 | 516 | H |
| IIF-932 | Chm | H | 4-tBuO-Bnzl | Bnzl | 3.33 | 528 | H |
| IIF-933 | Chm | H | 4-tBuO-Bnzl | i-Bu | 3.24 | 494 | H |
| IIF-934 | Chm | H | 4-tBuO-Bnzl | 1-Npm | 3.5 | 578 | H |
| IIF-935 | Chm | H | 4-tBuO-Bnzl | Ph-Et | 3.41 | 542 | H |
| IIF-936 | Chm | H | 4-tBuO-Bnzl | i-Pnt | 3.42 | 508 | H |
| IIF-937 | Bnzl | H | tBOC-E | Ph-Et | 3.08 | 502 | H |
| IIF-938 | Bnzl | H | tBOC-E | i-Pnt | 3.08 | 468 | H |
| IIF-939 | 1-Npm | H | tBOC-E | Ph-Et | 3.25 | 552 | H |
| IIF-940 | 1-Npm | H | tBOC-E | i-Pnt | 3.26 | 518 | H |
| IIF-941 | 4-tBuO-Bnzl | H | tBOC-E | Ph-Et | 3.32 | 574 | H |
| IIF-942 | 4-tBuO-Bnzl | H | tBOC-E | i-Pnt | 3.34 | 540 | H |
| IIF-943 | Ph-Et | H | tBOC-E | Bnzl | 3.08 | 502 | H |
| IIF-944 | Ph-Et | H | tBOC-E | i-Bu | 3.12 | 468 | H |
| IIF-945 | Ph-Et | H | tBOC-E | 1-Npm | 3.27 | 552 | H |
| IIF-946 | Ph-Et | H | tBOC-E | 4-tBuO-Bnzl | 3.33 | 574 | H |
| IIF-947 | Ph-Et | H | tBOC-E | i-Pnt | 3.18 | 482 | H |
| IIF-948 | 4-F-Bnzl | H | tBOC-E | Bnzl | 3.06 | 506 | H |
| IIF-949 | 4-F-Bnzl | H | tBOC-E | i-Bu | 3.04 | 472 | H |
| IIF-950 | 4-F-Bnzl | H | tBOC-E | 1-Npm | 3.23 | 556 | H |
| IIF-951 | 4-F-Bnzl | H | tBOC-E | 4-tBuO-Bnzl | 3.27 | 578 | H |
| IIF-952 | 4-F-Bnzl | H | tBOC-E | Ph-Et | 3.12 | 520 | H |
| IIF-953 | 4-F-Bnzl | H | tBOC-E | i-Pnt | 3.13 | 486 | H |
| IIF-954 | 2-OtBu-Et | H | tBOC-E | Bnzl | 3.11 | 498 | H |
| IIF-955 | 2-OtBu-Et | H | tBOC-E | 1-Npm | 3.27 | 548 | H |
| IIF-956 | 2-OtBu-Et | H | tBOC-E | 4-tBuO-Bnzl | 3.37 | 570 | H |
| IIF-957 | 2-OtBu-Et | H | tBOC-E | Ph-Et | 3.17 | 512 | H |
| IIF-958 | i-Pnt | H | tBOC-E | Bnzl | 3.08 | 468 | H |
| IIF-959 | i-Pnt | H | tBOC-E | 1-Npm | 3.22 | 518 | H |
| IIF-960 | i-Pnt | H | tBOC-E | Ph-Et | 3.13 | 482 | H |
| IIF-961 | Chm | H | tBOC-E | Bnzl | 3.17 | 494 | H |
| IIF-962 | Chm | H | tBOC-E | 1-Npm | 3.34 | 544 | H |
| IIF-963 | Ph-Et | H | i-Pr | 4-tBuO-Bnzl | 3.22 | 488 | H |
| IIF-964 | 4-F-Bnzl | H | i-Pr | 4-tBuO-Bnzl | 3.16 | 492 | H |
| IIF-965 | Ph-Et | H | s-Bu | 4-tBuO-Bnzl | 3.29 | 502 | H |
| IIF-966 | 4-F-Bnzl | H | s-Bu | 4-tBuO-Bnzl | 3.29 | 506 | H |
| IIF-967 | 2-OtBu-Et | H | s-Bu | Bnzl | 3.04 | 426 | H |
| IIF-968 | 2-OtBu-Et | H | s-Bu | i-Bu | 3.03 | 392 | H |
| IIF-969 | 2-OtBu-Et | H | s-Bu | 1-Npm | 3.3 | 476 | H |
| IIF-970 | 2-OtBu-Et | H | s-Bu | Ph-Et | 3.15 | 440 | H |

TABLE 2-continued

| | | | | | | | |
|---|---|---|---|---|---|---|---|
| IIF-971 | 4-tBuO-Bnzl | H | Ph-Et | Bnzl | 3.33 | 536 | H |
| IIF-972 | 4-tBuO-Bnzl | H | Ph-Et | i-Bu | 3.25 | 502 | H |
| IIF-973 | 4-tBuO-Bnzl | H | Ph-Et | 1-Npm | 3.47 | 586 | H |
| IIF-974 | tBOC-E | H | Ph-Et | Bnzl | 3.16 | 502 | H |
| IIF-975 | tBOC-E | H | Ph-Et | i-Bu | 3.13 | 468 | H |
| IIF-976 | tBOC-E | H | Ph-Et | 1-Npm | 3.35 | 552 | H |
| IIF-977 | 2-OtBu-Et | H | Ph-Et | Bnzl | 3.1 | 474 | H |
| IIF-978 | 2-OtBu-Et | H | Ph-Et | i-Bu | 3.08 | 440 | H |
| IIF-979 | 2-OtBu-Et | H | Ph-Et | i-Pnt | 3.17 | 454 | H |
| IIF-980 | 4-tBuO-Bnzl | H | 4-F-Bnzl | Bnzl | 3.35 | 540 | H |
| IIF-981 | 4-tBuO-Bnzl | H | 4-F-Bnzl | i-Bu | 3.28 | 506 | H |
| IIF-982 | 4-tBuO-Bnzl | H | 4-F-Bnzl | 1-Npm | 3.47 | 590 | H |
| IIF-983 | tBOC-E | H | 4-F-Bnzl | Bnzl | 3.14 | 506 | H |
| IIF-984 | tBOC-E | H | 4-F-Bnzl | i-Bu | 3.11 | 472 | H |
| IIF-985 | tBOC-E | H | 4-F-Bnzl | 1-Npm | 3.32 | 556 | H |
| IIF-986 | 2-OtBu-Et | H | 4-F-Bnzl | i-Bu | 3.03 | 444 | H |
| IIF-987 | 2-OtBu-Et | H | 4-F-Bnzl | Ph-Et | 3.13 | 492 | H |
| IIF-988 | 2-OtBu-Et | H | 4-F-Bnzl | i-Pnt | 3.13 | 458 | H |
| IIF-989 | Bnzl | H | 2-OtBu-Et | Bnzl | 4.08 | 460 | H |
| IIF-990 | Bnzl | H | 2-OtBu-Et | i-Bu | 4.07 | 426 | H |
| IIF-991 | Bnzl | H | 2-OtBu-Et | 1-Npm | 4.26 | 510 | H |
| IIF-992 | Bnzl | H | 2-OtBu-Et | Ph-Et | 4.17 | 474 | H |
| IIF-993 | Bnzl | H | 2-OtBu-Et | i-Pnt | 4.15 | 440 | H |
| IIF-994 | i-Bu | H | 2-OtBu-Et | Bnzl | 4.12 | 426 | H |
| IIF-995 | i-Bu | H | 2-OtBu-Et | 1-Npm | 4.29 | 476 | H |
| IIF-996 | i-Bu | H | 2-OtBu-Et | Ph-Et | 4.16 | 440 | H |
| IIF-997 | 1-Npm | H | 2-OtBu-Et | i-Bu | 4.22 | 476 | H |
| IIF-998 | 1-Npm | H | 2-OtBu-Et | i-Pnt | 4.33 | 490 | H |
| IIF-999 | 4-tBuO-Bnzl | H | 2-OtBu-Et | i-Bu | 4.3 | 498 | H |
| IIF-1000 | Ph-Et | H | 2-OtBu-Et | Bnzl | 4.2 | 474 | H |
| IIF-1001 | Ph-Et | H | 2-OtBu-Et | i-Bu | 4.17 | 440 | H |
| IIF-1002 | Ph-Et | H | 2-OtBu-Et | 1-Npm | 4.35 | 524 | H |
| IIF-1003 | Ph-Et | H | 2-OtBu-Et | 4-tBuO-Bnzl | 4.36 | 546 | H |

TABLE 2-continued

| | | | | | | | |
|---|---|---|---|---|---|---|---|
| IIF-1004 | Ph-Et | H | 2-OtBu-Et | i-Pnt | 4.28 | 454 | H |
| IIF-1005 | 4-F-Bnzl | H | 2-OtBu-Et | Bnzl | 4.17 | 478 | H |
| IIF-1006 | 4-F-Bnzl | H | 2-OtBu-Et | i-Bu | 4.05 | 444 | H |
| IIF-1007 | 4-F-Bnzl | H | 2-OtBu-Et | 1-Npm | 4.3 | 528 | H |
| IIF-1008 | 4-F-Bnzl | H | 2-OtBu-Et | 4-tBuO-Bnzl | 4.35 | 550 | H |
| IIF-1009 | 4-F-Bnzl | H | 2-OtBu-Et | Ph-Et | 4.18 | 492 | H |
| IIF-1010 | 4-F-Bnzl | H | 2-OtBu-Et | i-Pnt | 4.18 | 458 | H |
| IIF-1011 | i-Pnt | H | 2-OtBu-Et | Bnzl | 4.15 | 440 | H |
| IIF-1012 | i-Pnt | H | 2-OtBu-Et | 1-Npm | 4.32 | 490 | H |
| IIF-1013 | i-Pnt | H | 2-OtBu-Et | 4-tBuO-Bnzl | 4.36 | 512 | H |
| IIF-1014 | i-Pnt | H | 2-OtBu-Et | Ph-Et | 4.26 | 454 | H |
| IIF-1015 | Chm | H | 2-OtBu-Et | Bnzl | 4.25 | 466 | H |
| IIF-1016 | Chm | H | 2-OtBu-Et | 4-tBuO-Bnzl | 4.41 | 538 | H |
| IIF-1017 | Chm | H | 2-OtBu-Et | Ph-Et | 4.28 | 480 | H |
| IIF-1018 | Bnzl | H | i-Pnt | 4-tBuO-Bnzl | 3.27 | 502 | H |
| IIF-1019 | Bnzl | H | i-Pnt | tBOC-E | 3.08 | 468 | H |
| IIF-1020 | 1-Npm | H | i-Pnt | 4-tBuO-Bnzl | 3.46 | 552 | H |
| IIF-1021 | 1-Npm | H | i-Pnt | tBOC-E | 3.25 | 518 | H |
| IIF-1022 | 4-tBuO-Bnzl | H | i-Pnt | Bnzl | 3.32 | 502 | H |
| IIF-1023 | 4-tBuO-Bnzl | H | i-Pnt | i-Bu | 3.3 | 468 | H |
| IIF-1024 | 4-tBuO-Bnzl | H | i-Pnt | 1-Npm | 3.53 | 552 | H |
| IIF-1025 | 4-tBuO-Bnzl | H | i-Pnt | Ph-Et | 3.37 | 516 | H |
| IIF-1026 | tBOC-E | H | i-Pnt | Bnzl | 3.18 | 468 | H |
| IIF-1027 | tBOC-E | H | i-Pnt | 1-Npm | 3.38 | 518 | H |
| IIF-1028 | tBOC-E | H | i-Pnt | Ph-Et | 3.22 | 482 | H |
| IIF-1029 | Ph-Et | H | i-Pnt | 4-tBuO-Bnzl | 3.39 | 516 | H |
| IIF-1030 | Ph-Et | H | i-Pnt | tBOC-E | 3.22 | 482 | H |
| IIF-1031 | 4-F-Bnzl | H | i-Pnt | 4-tBuO-Bnzl | 3.29 | 520 | H |
| IIF-1032 | 4-F-Bnzl | H | i-Pnt | tBOC-E | 2.35 | 486 | H |
| IIF-1033 | Chm | H | i-Pnt | 4-tBuO-Bnzl | 2.62 | 508 | H |
| IIF-1034 | Bnzl | H | Hxy | 4-tBuO-Bnzl | 2.63 | 516 | H |
| IIF-1035 | i-Bu | H | Hxy | 4-tBuO-Bnzl | 2.55 | 482 | H |
| IIF-1036 | 1-Npm | H | Hxy | 4-tBuO-Bnzl | 2.88 | 566 | H |
| IIF-1037 | 4-tBuO-Bnzl | H | Hxy | Bnzl | 2.63 | 516 | H |
| IIF-1038 | 4-tBuO-Bnzl | H | Hxy | i-Bu | 2.6 | 482 | H |
| IIF-1039 | 4-tBuO-Bnzl | H | Hxy | Ph-Et | 2.67 | 530 | H |
| IIF-1040 | 4-tBuO-Bnzl | H | Hxy | i-Pnt | 2.7 | 496 | H |
| IIF-1041 | tBOC-E | H | Hxy | Ph-Et | 2.55 | 496 | H |
| IIF-1042 | Ph-Et | H | Hxy | 4-tBuO-Bnzl | 2.68 | 530 | H |
| IIF-1043 | 4-F-Bnzl | H | Hxy | 4-tBuO-Bnzl | 2.63 | 534 | H |
| IIF-1044 | 2-OtBu-Et | H | Hxy | Bnzl | 2.47 | 454 | H |

TABLE 2-continued

| | | | | | | | |
|---|---|---|---|---|---|---|---|
| IIF-1045 | 2-OtBu-Et | H | Hxy | 1-Npm | 2.63 | 504 | H |
| IIF-1046 | 2-OtBu-Et | H | Hxy | Ph-Et | 2.5 | 468 | H |
| IIF-1047 | 1-Npm | H | 4-F-Bnzl | 2-OTBS-Et | 1.11 | 586.4 | C |

† Ring formed together by $R_{2A}$ and $R_{2B}$

| Compound number | Name of compound | LCMS $t_R$ (min) | Mass $(M + H)^+$ | Measurement condition | Yield (%) |
|---|---|---|---|---|---|
| IIF-1 | (3S*,3aR*,6S*,7R*,7aR*)-N,7-dibenzyl-1-isobutyl-1,2,3,3a,7,7a-hexahydro-6H-3,6-methanopyrrolo[3,2-c]pyridine-6-carboxamide | 1.14 | 416 | B | 10 |
| IIF-2 | (3S*,3aR*,6S*,7R*,7aR*)-N,1,7-triisobutyl-1,2,3,3a,7,7a-hexahydro-6H-3,6-methanopyrrolo[3,2-c]pyridine-6-carboxamide | 1.11 | 348 | B | 16 |
| IIF-3 | (3S*,3aR*,6S*,7R*,7aR*)-7-benzyl-N,1-diisobutyl-1,2,3,3a,7,7a-hexahydro-6H-3,6-methanopyrrolo[3,2-c]pyridine-6-carboxamide | 1.14 | 382 | B | 14 |
| IIF-4 | (3S*,3aR*,6S*,7R*,7aR*)-1-benzyl-N,7-diisobutyl-1,2,3,3a,7,7a-hexahydro-6H-3,6-methanopyrrolo[3,2-c]pyridine-6-carboxamide | 1.14 | 382 | B | 8 |
| IIF-5 | (3S*,3aR*,6S*,7R*,7aR*)-N-benzyl-1,7-diisobutyl-1,2,3,3a,7,7a-hexahydro-6H-3,6-methanopyrrolo[3,2-c]pyridine-6-carboxamide | 1.13 | 382 | B | 13 |
| IIF-6 | (3S*,3aR*,6S*,7R*,7aR*)-1,7-dibenzyl-N-isobutyl-1,2,3,3a,7,7a-hexahydro-6H-3,6-methanopyrrolo[3,2-c]pyridine-6-carboxamide | 1.15 | 416 | B | 19 |
| IIF-7 | (3S*,3aR*,6S*,7R*,7aR*)-N,1-dibenzyl-7-isobutyl-1,2,3,3a,7,7a-hexahydro-6H-3,6-methanopyrrolo[3,2-c]pyridine-6-carboxamide | 1.00 | 416 | B | 22 |
| IIF-8 | (3S*,3aR*,6S*,7R*,7aR*)-N,1,7-tribenzyl-1,2,3,3a,7,7a-hexahydro-6H-3,6-methanopyrrolo[3,2-c]pyridine-6-carboxamide | 1.16 | 450 | B | 21 |
| IIF-9 | (3S*,3aR*,6S*,7R*,7aR*)-N,7-dibenzyl-1-isopentyl-1,2,3,3a,7,7a-hexahydro-6H-3,6-methanopyrrolo[3,2-c]pyridine-6-carboxamide | 1.18 | 430 | B | 20 |
| IIF-10 | (3S*,3aR*,6S*,7R*,7aR*)-N,1-dibenzyl-7-isopentyl-1,2,3,3a,7,7a-hexahydro-6H-3,6-methanopyrrolo[3,2-c]pyridine-6-carboxamide | 1.18 | 430 | B | 11 |
| IIF-11 | (3S*,3aR*,6S*,7R*,7aR*)-N-benzyl-1-isobutyl-7-phenethyl-1,2,3,3a,7,7a-hexahydro-6H-3,6-methanopyrrolo[3,2-c]pyridine-6-carboxamide | 1.16 | 430 | B | 12 |
| IIF-12 | (3S*,3aR*,6S*,7R*,7aR*)-1-benzyl-7-isobutyl-N-phenethyl-1,2,3,3a,7,7a-hexahydro-6H-3,6-methanopyrrolo[3,2-c]pyridine-6-carboxamide | 1.16 | 430 | B | 12 |
| IIF-13 | (3S*,3aR*,6S*,7R*,7aR*)-N-benzyl-1-isobutyl-7-(3-methylbenzyl)-1,2,3,3a,7,7a-hexahydro-6H-3,6-methanopyrrolo[3,2-c]pyridine-6-carboxamide | 1.17 | 430 | B | 17 |

TABLE 2-continued

| | | | | | |
|---|---|---|---|---|---|
| IIF-14 | (3S*,3aR*,6S*,7R*,7aR*)-N-benzyl-1-isobutyl-7-(4-methylbenzyl)-1,2,3,3a,7,7a-hexahydro-6H-3,6-methanopyrrolo[3,2-c]pyridine-6-carboxamide | 1.16 | 430 | B | 15 |
| IIF-15 | (3S*,3aR*,6S*,7R*,7aR*)-7-benzyl-1-isobutyl-N-(3-methylbenzyl)-1,2,3,3a,7,7a-hexahydro-6H-3,6-methanopyrrolo[3,2-c]pyridine-6-carboxamide | 1.18 | 430 | B | 16 |
| IIF-16 | (3S*,3aR*,6S*,7R*,7aR*)-7-benzyl-1-isobutyl-N-(4-methylbenzyl)-1,2,3,3a,7,7a-hexahydro-6H-3,6-methanopyrrolo[3,2-c]pyridine-6-carboxamide | 1.18 | 430 | B | 15 |
| IIF-17 | (3S*,3aR*,6S*,7R*,7aR*)-7-benzyl-N-(3-chlorobenzyl)-1-isobutyl-1,2,3,3a,7,7a-hexahydro-6H-3,6-methanopyrrolo[3,2-c]pyridine-6-carboxamide | 1.18 | 450 | B | 14 |
| IIF-18 | (3S*,3aR*,6S*,7R*,7aR*)-7-benzyl-N-(4-chlorobenzyl)-1-isobutyl-1,2,3,3a,7,7a-hexahydro-6H-3,6-methanopyrrolo[3,2-c]pyridine-6-carboxamide | 1.17 | 450 | B | 13 |
| IIF-19 | (3S*,3aR*,6S*,7R*,7aR*)-N-benzyl-1-(3,4-dichlorobenzyl)-7-isobutyl-1,2,3,3a,7,7a-hexahydro-6H-3,6-methanopyrrolo[3,2-c]pyridine-6-carboxamide | 1.28 | 484 | B | 22 |
| IIF-20 | (3S*,3aR*,6S*,7R*,7aR*)-1-benzyl-N-(3,4-dichlorobenzyl)-7-isobutyl-1,2,3,3a,7,7a-hexahydro-6H-3,6-methanopyrrolo[3,2-c]pyridine-6-carboxamide | 1.25 | 484 | B | 21 |
| IIF-23 | (3S*,3aR*,6S*,7R*,7aR*)-7-benzyl-1-isobutyl-N-(4-(tert-butoxy)benzyl)-1,2,3,3a,7,7a-hexahydro-6H-3,6-methanopyrrolo[3,2-c]pyridine-6-carboxamide | 0.99 | 488 | A | 33 |
| IIF-24 | (3S*,3aR*,6S*,7R*,7aR*)-7-benzyl-1-isobutyl-N-(naphthalen-1-ylmethyl)-1,2,3,3a,7,7a-hexahydro-6H-3,6-methanopyrrolo[3,2-c]pyridine-6-carboxamide | 0.98 | 466 | A | 14 |
| IIF-25 | (3S*,3aR*,6S*,7R*,7aR*)-7-benzyl-N-(2-hydroxyethyl)-1-isobutyl-1,2,3,3a,7,7a-hexahydro-6H-3,6-methanopyrrolo[3,2-c]pyridine-6-carboxamide | 0.74 | 370 | A | 5 |
| IIF-26 | 3-((3S*,3aR*,6S*,7R*,7aR*)-7-benzyl-1-isobutyl-1,2,3,3a,7,7a-hexahydro-1H-3,6-methanopyrrolo[3,2-c]pyridine-6-carboxamide)propanoic acid | 0.75 | 398 | A | 100 |
| IIF-27 | (3S*,3aR*,6S*,7R*,7aR*)-7-benzyl-1-isobutyl-N-(2-(tert-butoxy)-2-oxoethyl)-1,2,3,3a,7,7a-hexahydro-6H-3,6-methanopyrrolo[3,2-c]pyridine-6-carboxamide | 0.92 | 454 | A | 20 |
| IIF-28 | (3S*,3aR*,6S*,7R*,7aR*)-7-benzyl-N-(3-amino-3-oxopropyl)-1-isobutyl-1,2,3,3a,7,7a-hexahydro-6H-3,6-methanopyrrolo[3,2-c]pyridine-6-carboxamide | 0.72 | 397 | A | 88 |
| IIF-29 | (3S*,3aR*,6S*,7R*,7aR*)-N-(4-aminobutyl)-7-benzyl-1-isobutyl-1,2,3,3a,7,7a-hexahydro-6H-3,6-methanopyrrolo[3,2-c]pyridine-6-carboxamide | 0.67 | 397 | A | 100 |
| IIF-30 | (3S*,3aR*,6S*,7R*,7aR*)-7-benzyl-1-isobutyl-N-(4-((tert-butoxycarbonyl)amino)butyl)-1,2,3,3a,7,7a-hexahydro-6H-3,6-methanopyrrolo[3,2-c]pyridine-6-carboxamide | 0.91 | 497 | A | 10 |

TABLE 2-continued

| ID | Name | | | | |
|---|---|---|---|---|---|
| IIF-31 | (3S*,3aR*,6S*,7R*,7aR*)-7-benzyl-N-cyclohexylmethyl-1-isobutyl-1,2,3,3a,7,7a-hexahydro-6H-3,6-methanopyrrolo[3,2-c]pyridine-6-carboxamide | 0.98 | 422 | A | 12 |
| IIF-32 | (3S*,3aR*,6S*,7R*,7aR*)-7-benzyl-1-isobutyl-N-((tetrahydro-2H-pyran-2-yl)methyl)-1,2,3,3a,7,7a-hexahydro-6H-3,6-methanopyrrolo[3,2-c]pyridine-6-carboxamide | 0.87 | 424 | A | 24 |
| IIF-34 | (3S*,3aR*,6S*,7R*,7aR*)-N-benzyl-1-isobutyl-7-(4-((tert-butoxycarbonyl)amino)butyl)-1,2,3,3a,7,7a-hexahydro-6H-3,6-methanopyrrolo[3,2-c]pyridine-6-carboxamide | 0.93 | 497 | A | 17 |
| IIF-36 | (3S*,3aR*,6S*,7R*,7aR*)-N-benzyl-1-isobutyl-7-(3-methoxy-3-oxopropyl)-1,2,3,3a,7,7a-hexahydro-6H-3,6-methanopyrrolo[3,2-c]pyridine-6-carboxamide | 0.82 | 412 | A | 5 |
| IIF-38 | (3S*,3aR*,6S*,7R*,7aR*)-N-benzyl-7-(cyclohexylmethyl)-1-isobutyl-1,2,3,3a,7,7a-hexahydro-6H-3,6-methanopyrrolo[3,2-c]pyridine-6-carboxamide | 0.99 | 422 | A | 23 |
| IIF-39 | (3S*,3aR*,6S*,7R*,7aR*)-N,7-dibenzyl-1-cyclohexylmethyl-1,2,3,3a,7,7a-hexahydro-6H-3,6-methanopyrrolo[3,2-c]pyridine-6-carboxamide | 0.96 | 456 | A | 22 |
| IIF-40 | (3S*,3aR*,6S*,7R*,7aR*)-N,7-dibenzyl-1-(4-hydroxybenzyl)-1,2,3,3a,7,7a-hexahydro-6H-3,6-methanopyrrolo[3,2-c]pyridine-6-carboxamide | 0.86 | 466 | A | 76 |
| IIF-41 | (3S*,3aR*,6S*,7R*,7aR*)-N,7-dibenzyl-1-(4-(tert-butoxy)benzyl)-1,2,3,3a,7,7a-hexahydro-6H-3,6-methanopyrrolo[3,2-c]pyridine-6-carboxamide | 1.00 | 522 | A | 14 |
| IIF-42 | (3S*,3aR*,6S*,7R*,7aR*)-N,7-dibenzyl-1-(naphthalen-1-ylmethyl)-1,2,3,3a,7,7a-hexahydro-6H-3,6-methanopyrrolo[3,2-c]pyridine-6-carboxamide | 0.97 | 500 | A | 4 |
| IIF-76 | tert-butyl 3-((3S*,3aR*,6S*,7R*,7aR*)-7-benzyl-6-(benzylcarbamoyl)-2,3,3a,6,7,7a-hexahydro-1H-3,6-methanopyrrolo[3,2-c]pyridin-1-yl)propanoate | 0.70 | 488 | B | 22 |
| IIF-77 | (3S*,3aR*,6S*,7R*,7aR*)-N,1-dibenzyl-7-(4-hydroxybenzyl)-1,2,3,3a,7,7a-hexahydro-6H-3,6-methanopyrrolo[3,2-c]pyridine-6-carboxamide | 0.80 | 466 | B | 19 |
| IIF-80 | (3S*,3aR*,6S*,7R*,7aR*)-N-benzyl-1-(naphthalen-1-ylmethyl)-7-propyl-1,2,3,3a,7,7a-hexahydro-6H-3,6-methanopyrrolo[3,2-c]pyridine-6-carboxamide | 1.01 | 452 | A | 6 |

Synthesis Example: IF-1

Synthesis of (3S*,3aS*,6S*,7R*,7aS*)-N,7-dibenzyl-1-isobutyloctahydro-6H-3,6-methanopyrrolo[3,2-c]pyridine-6-carboxamide(IF-1)

Sodium tetrahydroborate (1.86 mg, 0.0490 mmol) was added to a methanol (0.500 mL) solution of (3S*,3aR*,6S*,7R*,7aR*)-N,7-dibenzyl-1-isobutyl-1,2,3,3a,7,7a-hexahydro-6H-3,6-methanopyrrolo[3,2-c]pyridine-6-carboxamide (IIF-1) (10.2 mg, 0.0245 mmol) and stirred for 1 hour. After evaporating the solvent under reduced pressure, 5% sodium bicarbonate solution (1.00 mL) was added to the residue, which was extracted with ethyl acetate (3.00 mL). The organic layer was washed with water (1.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=85:15)

to obtain the aforementioned compound (6.37 mg, yield: 62%, RT=0.99 minutes (B method), [M+1]⁺=418).

¹H-NMR spectrum (400 MHz, CDCl₃) δ (ppm): 0.52 (3H, d), 0.58 (3H, d), 0.89-0.97 (1H, m), 1.57-1.62 (1H, m), 1.83-1.94 (3H, m), 2.01-2.07 (1H, m), 2.18-2.24 (2H, m), 2.29 (1H, d), 2.40-2.44 (1H, m), 2.71-2.75 (2H, m), 2.86-2.89 (1H, m), 3.10-3.19 (2H, m), 4.39-4.48 (2H, m), 7.24-7.38 (11H, m).

¹³C-NMR spectrum (100 MHz, CDCl₃) δ (ppm): 20.20, 26.99, 33.45, 35.79, 36.41, 39.83, 42.13, 42.79, 46.40, 56.95, 61.37, 61.78, 61.97, 125.50, 126.96, 127.39, 127.73, 128.25, 129.41, 138.20, 139.59, 175.20.

Figure 2:
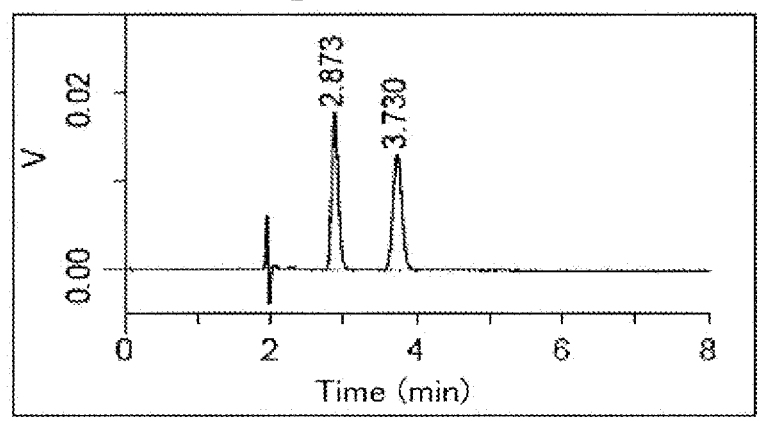
FIG. 2 shows a chromatogram upon separation of the racemate in Synthesis Example: IF-1 using a chiral column, CHIRALPAK IG (5 µm, 4.6×150 mm), mobile phase: methanol:diethylamine (100:0.1).
Figure 3:
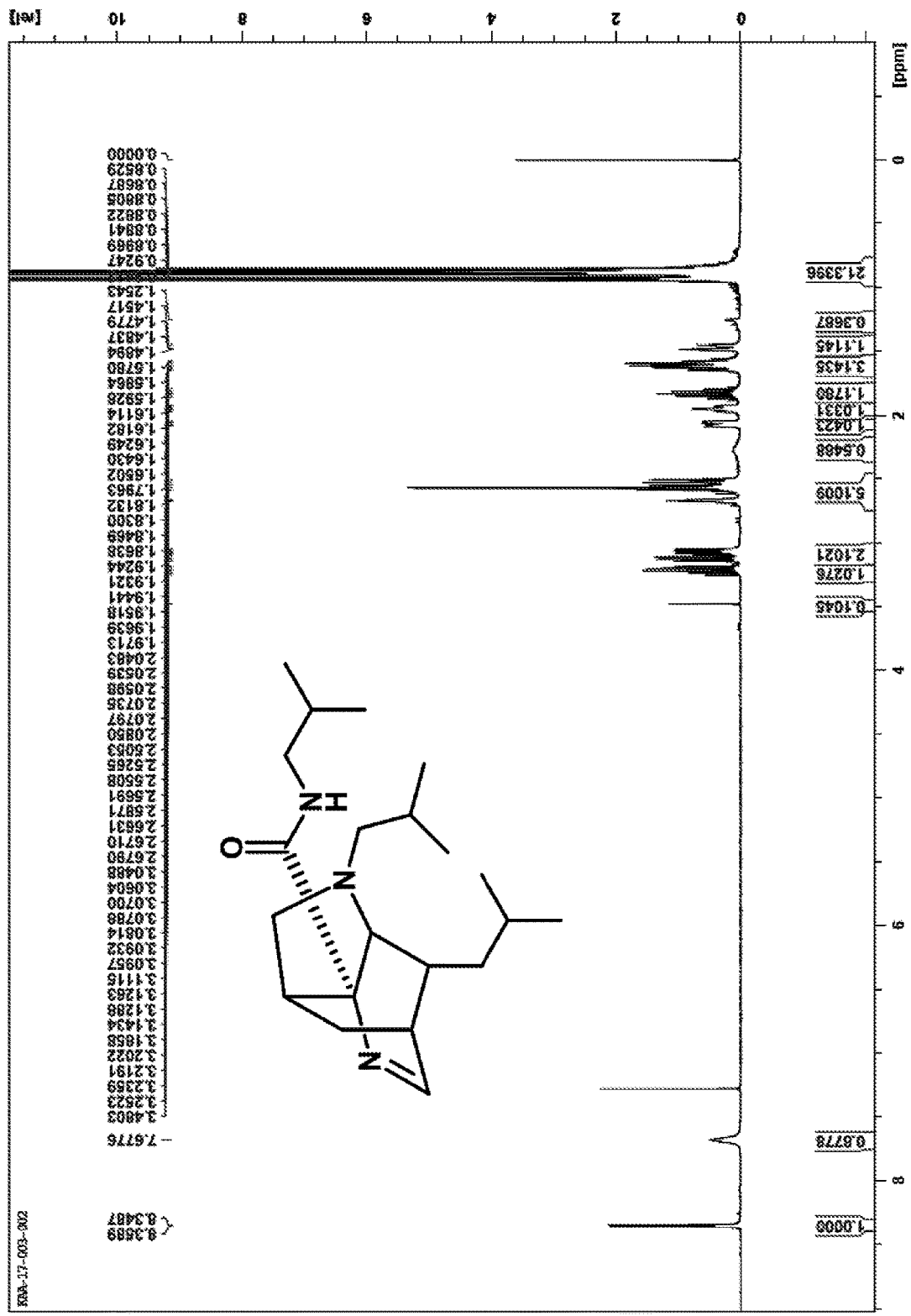
FIG. 3 shows the ¹H-NMR chart for an exemplary compound of the present disclosure (formula in the figure).
Figure 4:
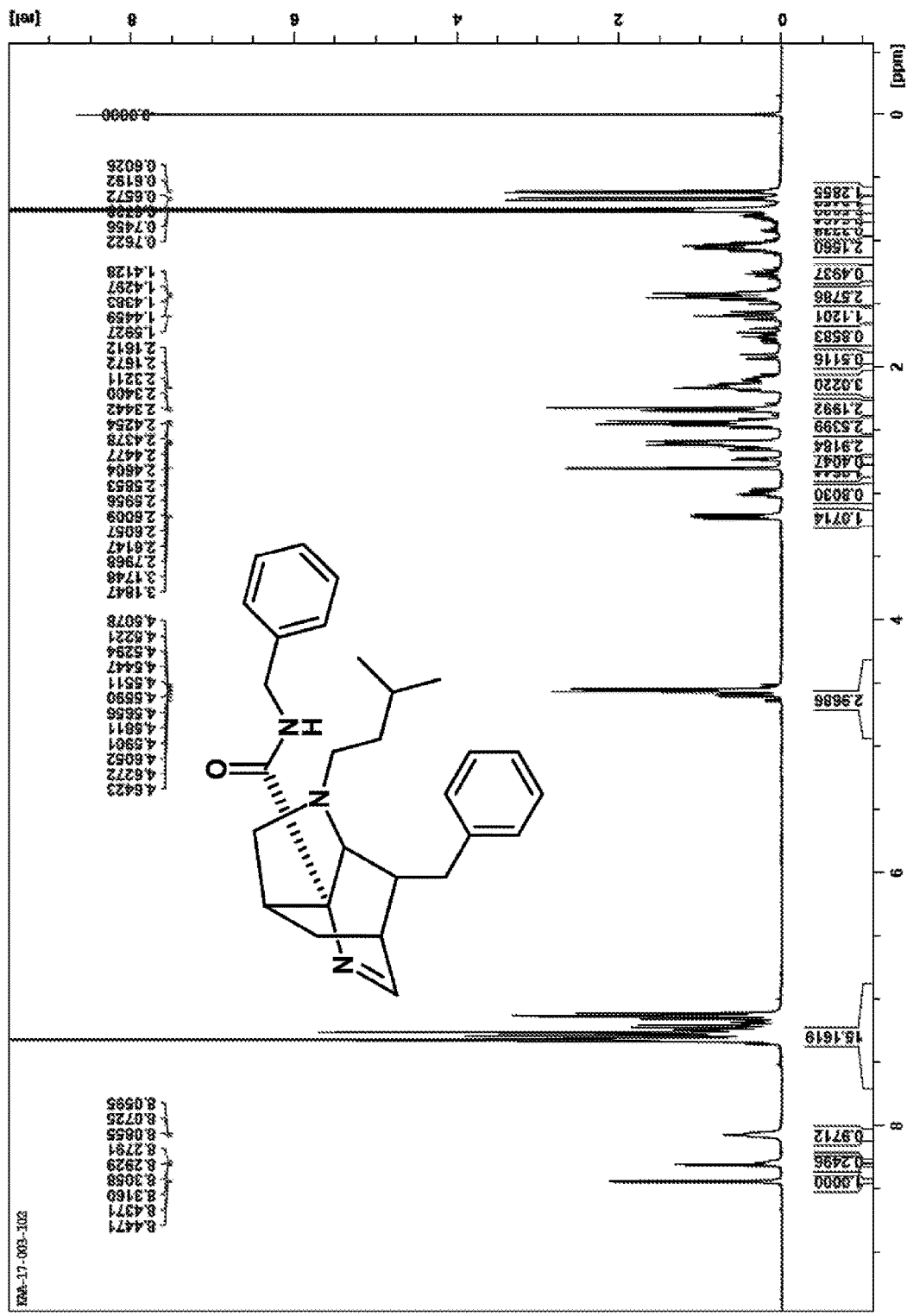
FIG. 4 shows the ¹H-NMR chart for an exemplary compound of the present disclosure (formula in the figure).
Figure 5:
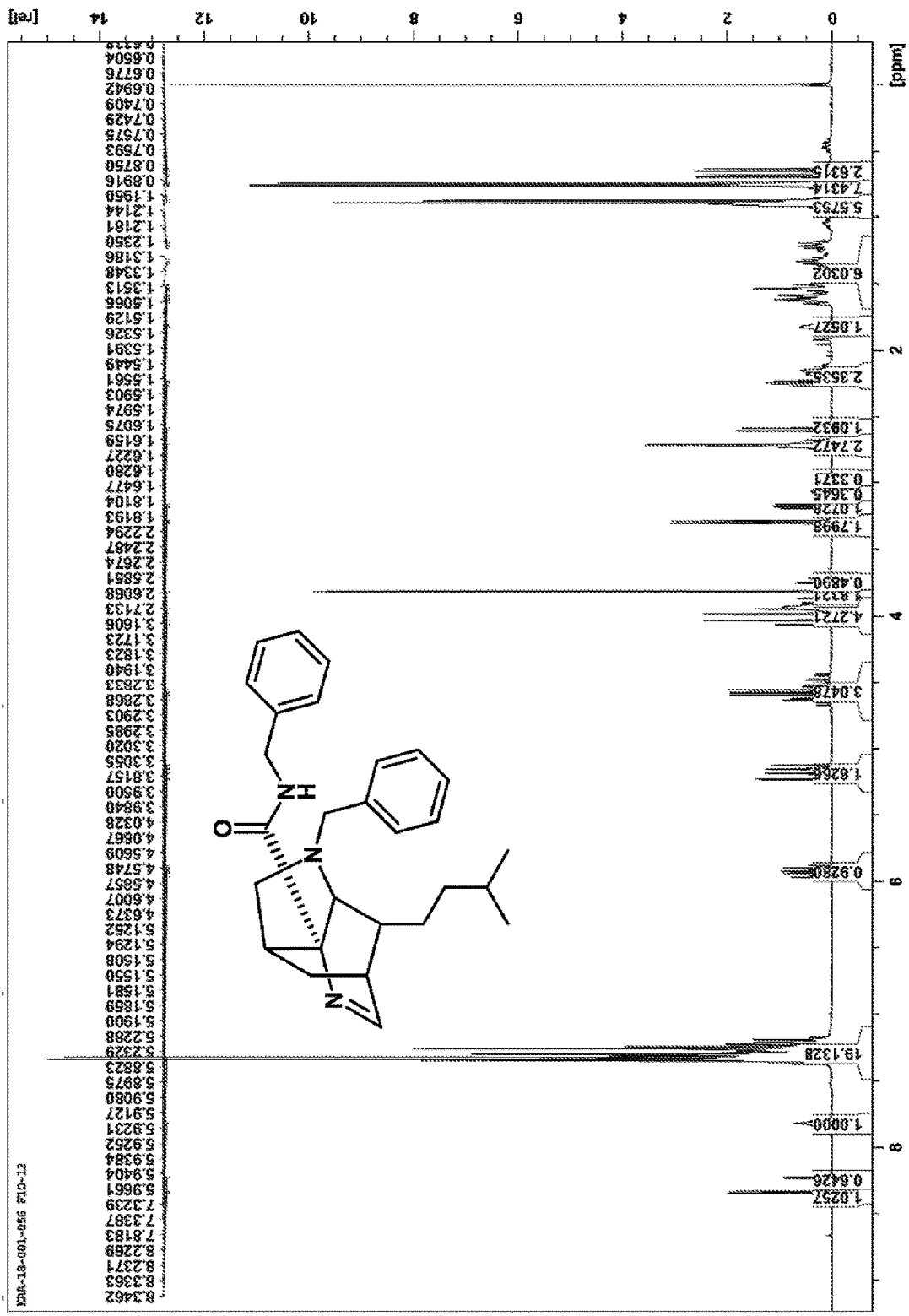
FIG. 5 shows the ¹H-NMR chart for an exemplary compound of the present disclosure (formula in the figure).
Figure 6:
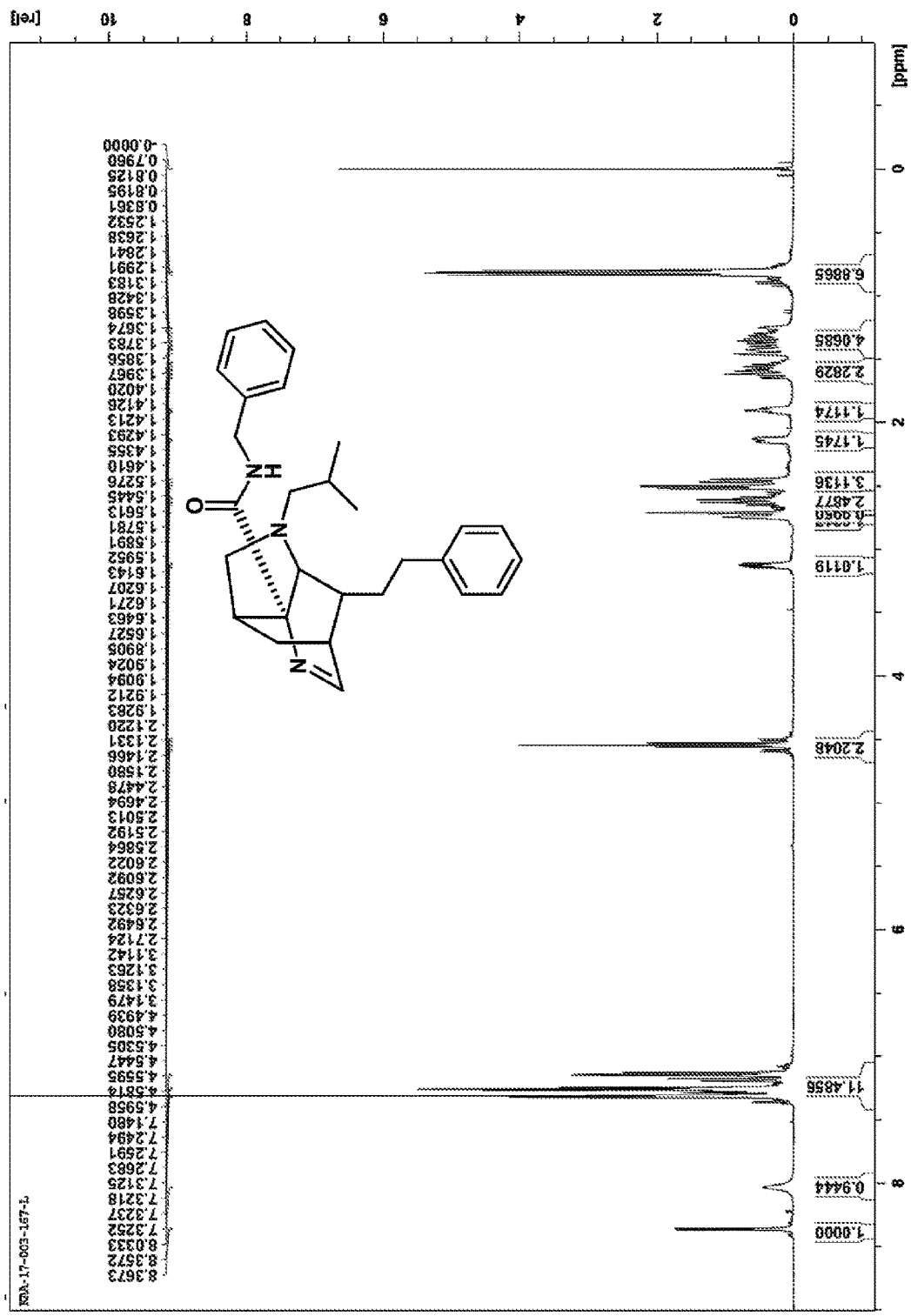
FIG. 6 shows the ¹H-NMR chart for an exemplary compound of the present disclosure (formula in the figure).
Figure 7:
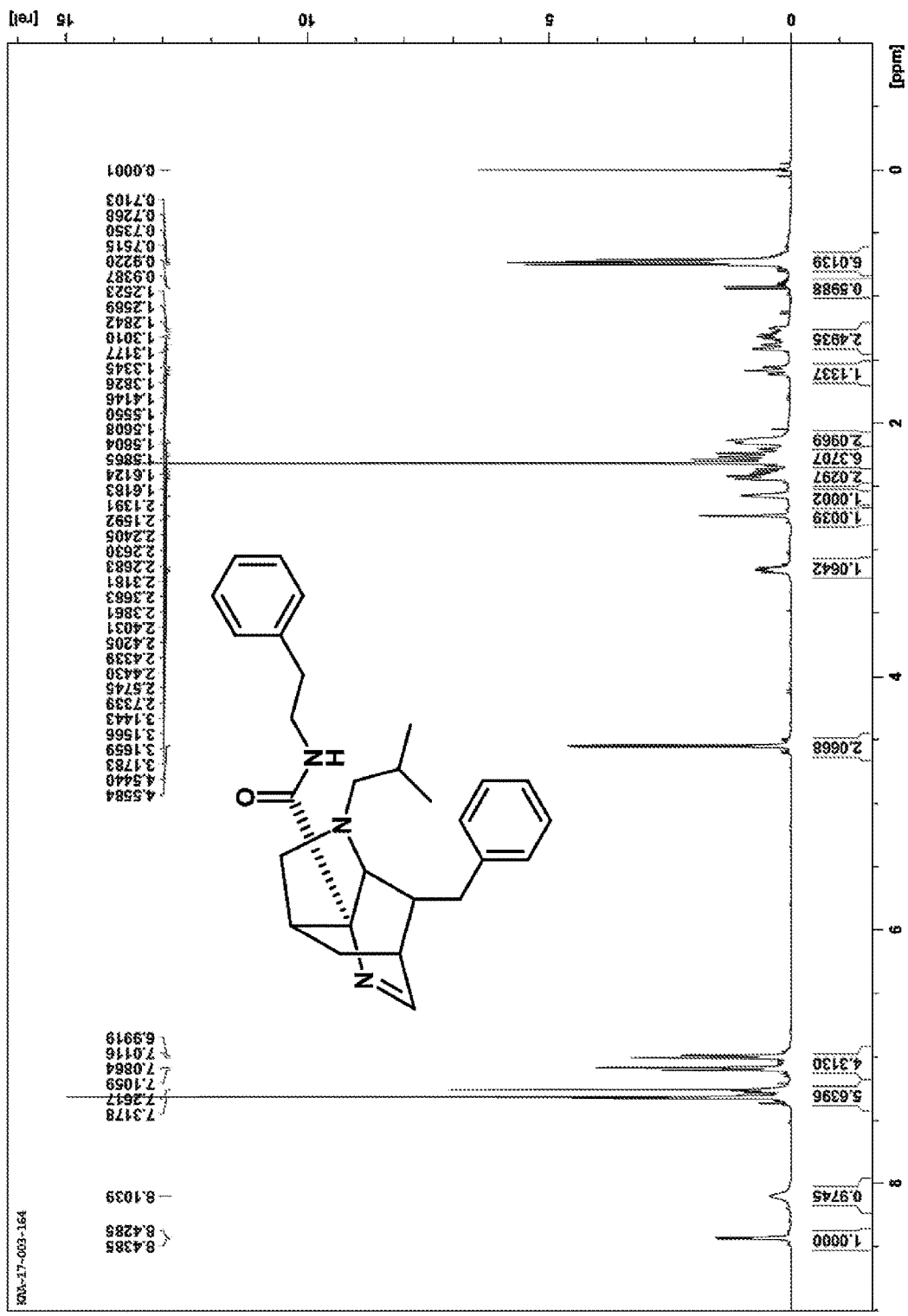
FIG. 7 shows the ¹H-NMR chart for an exemplary compound of the present disclosure (formula in the figure).
Figure 8:
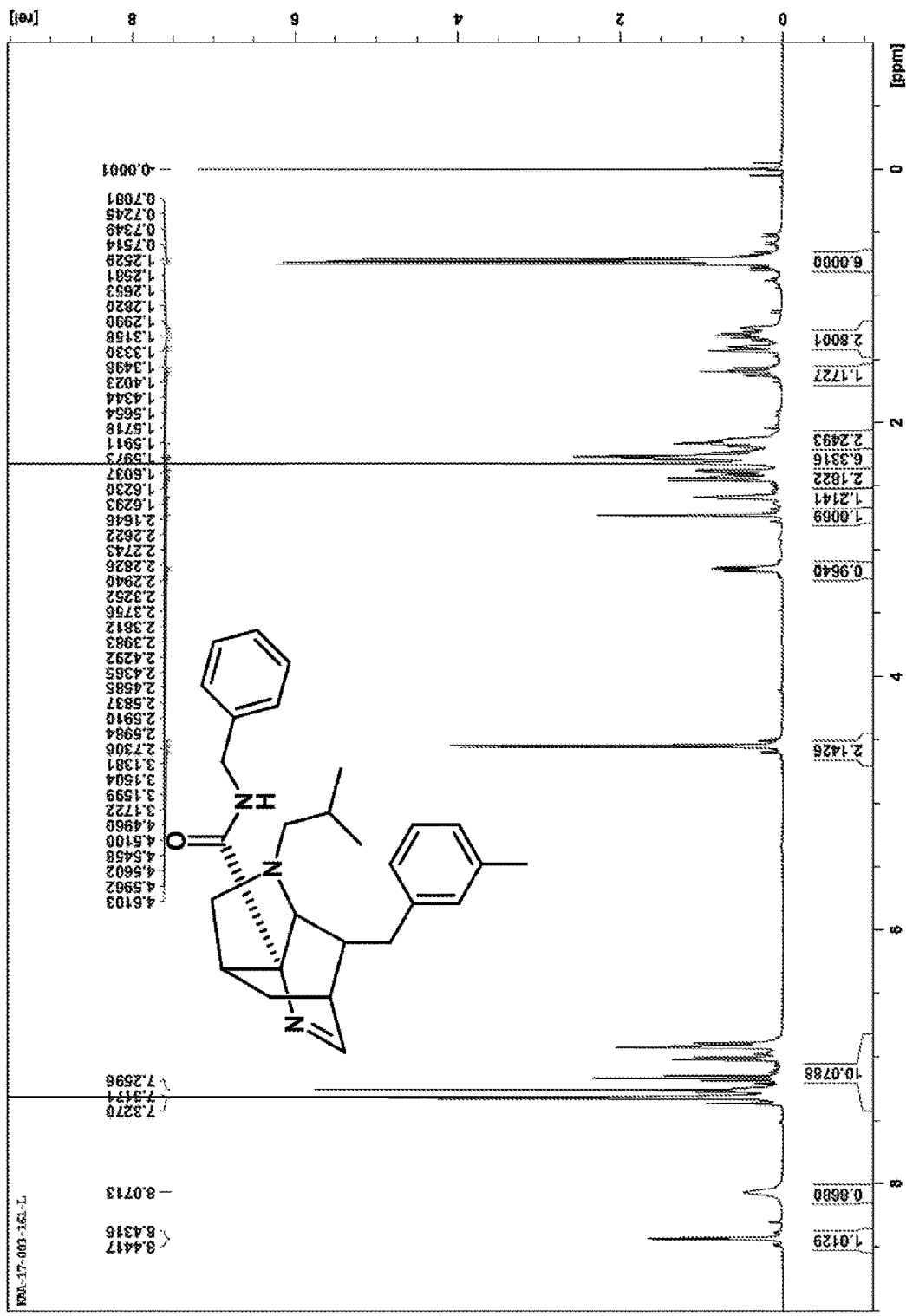
FIG. 8 shows the $^1$H-NMR chart for an exemplary compound of the present disclosure (formula in the figure).
Figure 9:
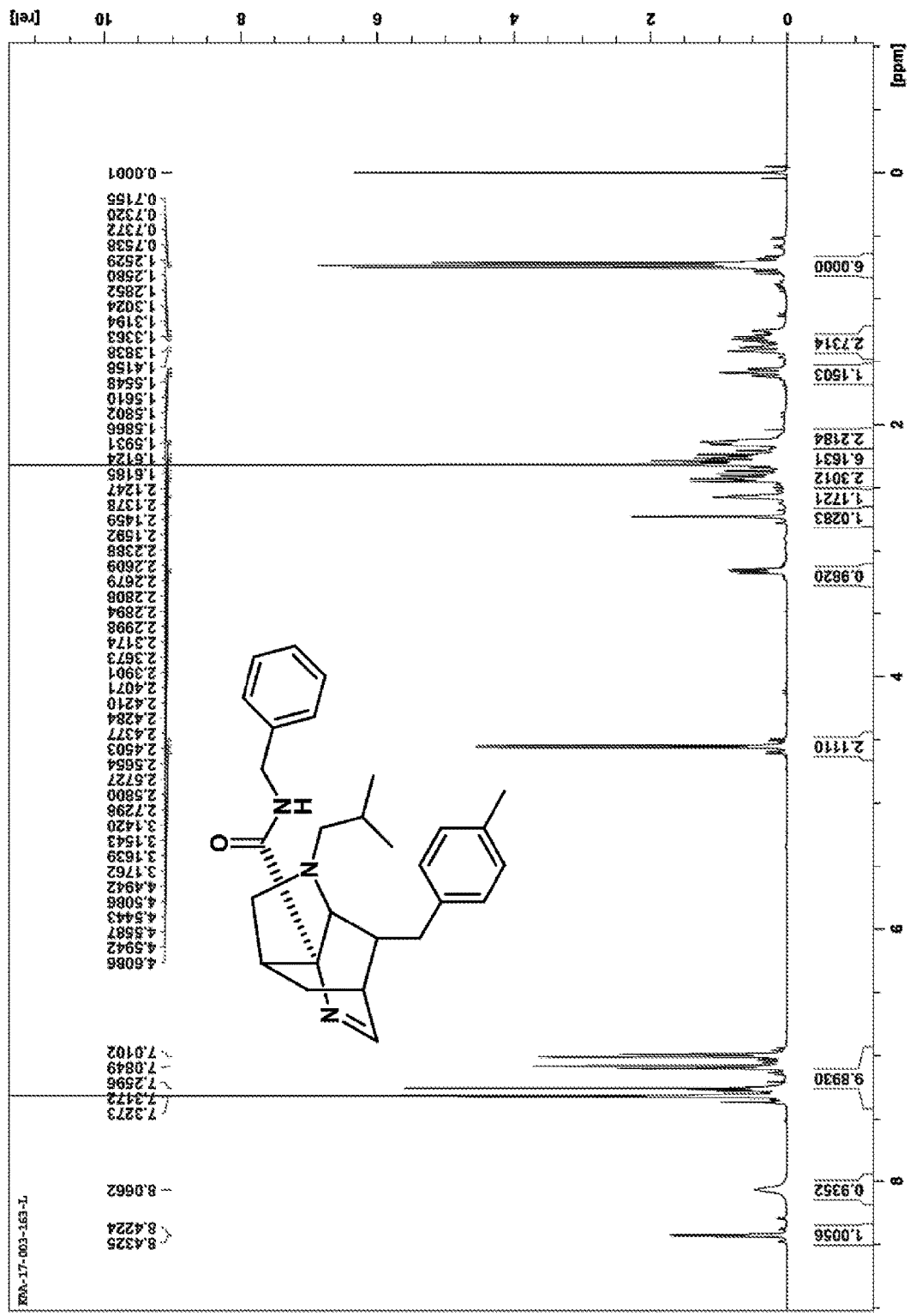
FIG. 9 shows the $^1$H-NMR chart for an exemplary compound of the present disclosure (formula in the figure).
Figure 10:
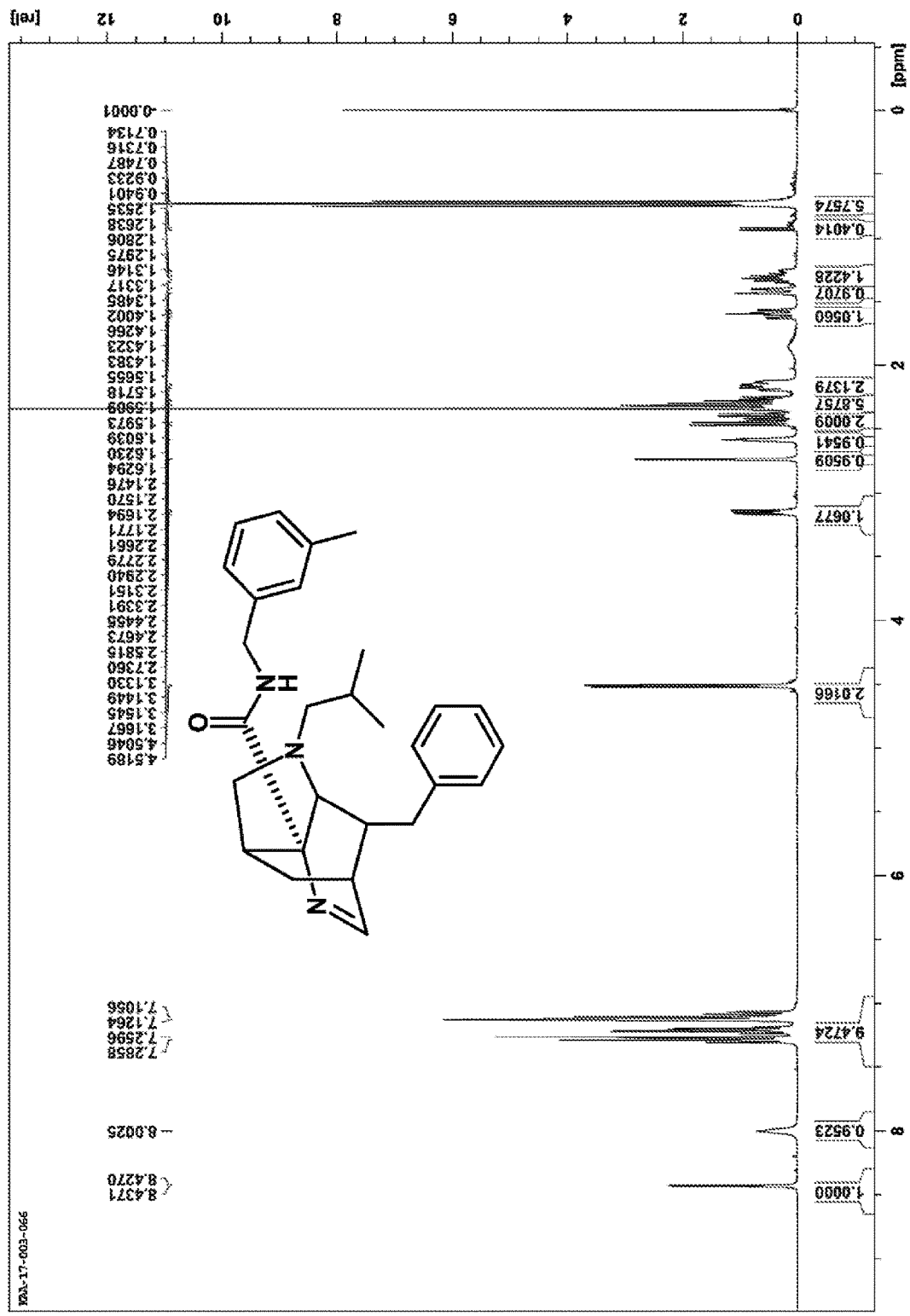
FIG. 10 shows the $^1$H-NMR chart for an exemplary compound of the present disclosure (formula in the figure).
Figure 11:
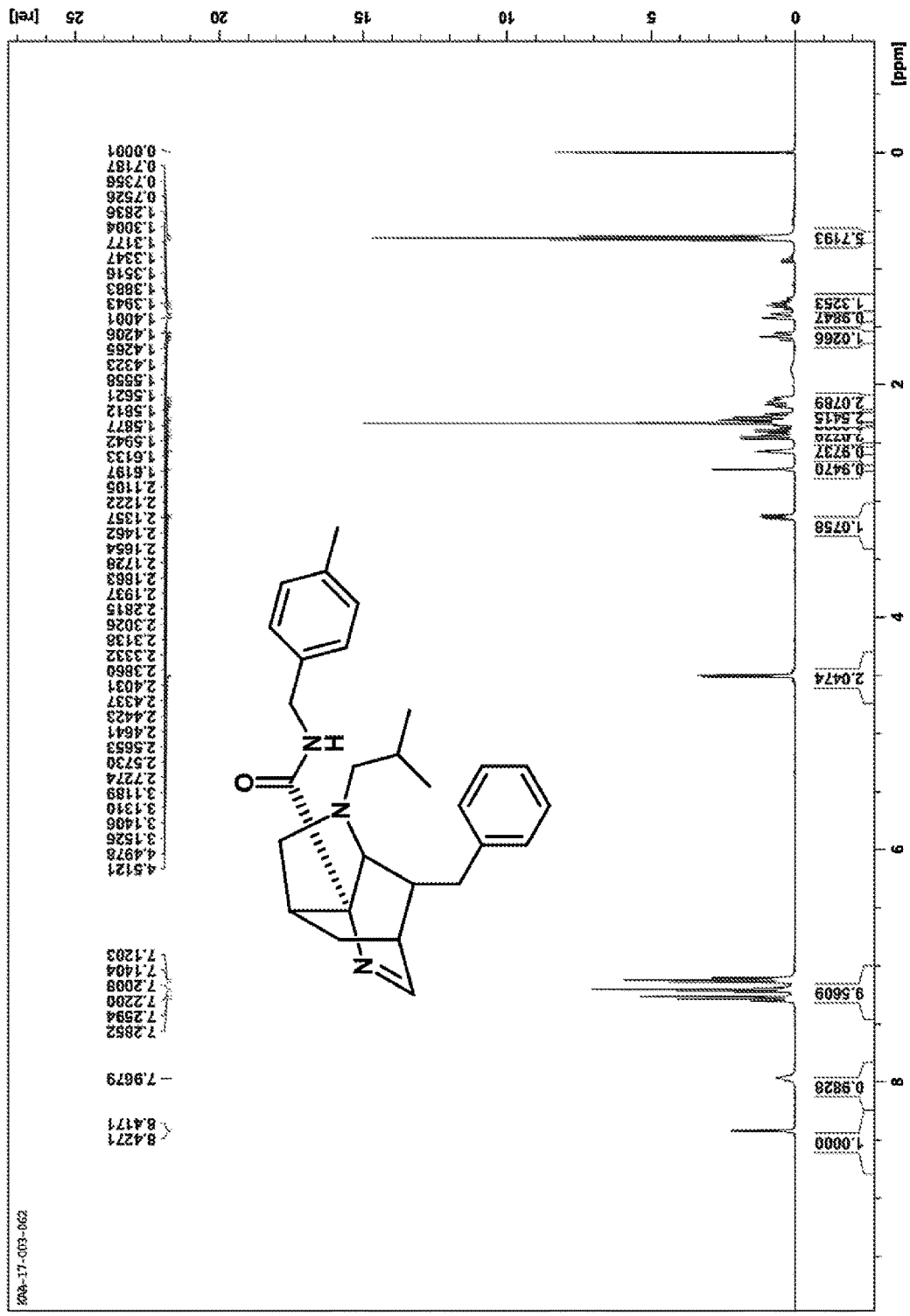
FIG. 11 shows the $^1$H-NMR chart for an exemplary compound of the present disclosure (formula in the figure).
Figure 12:
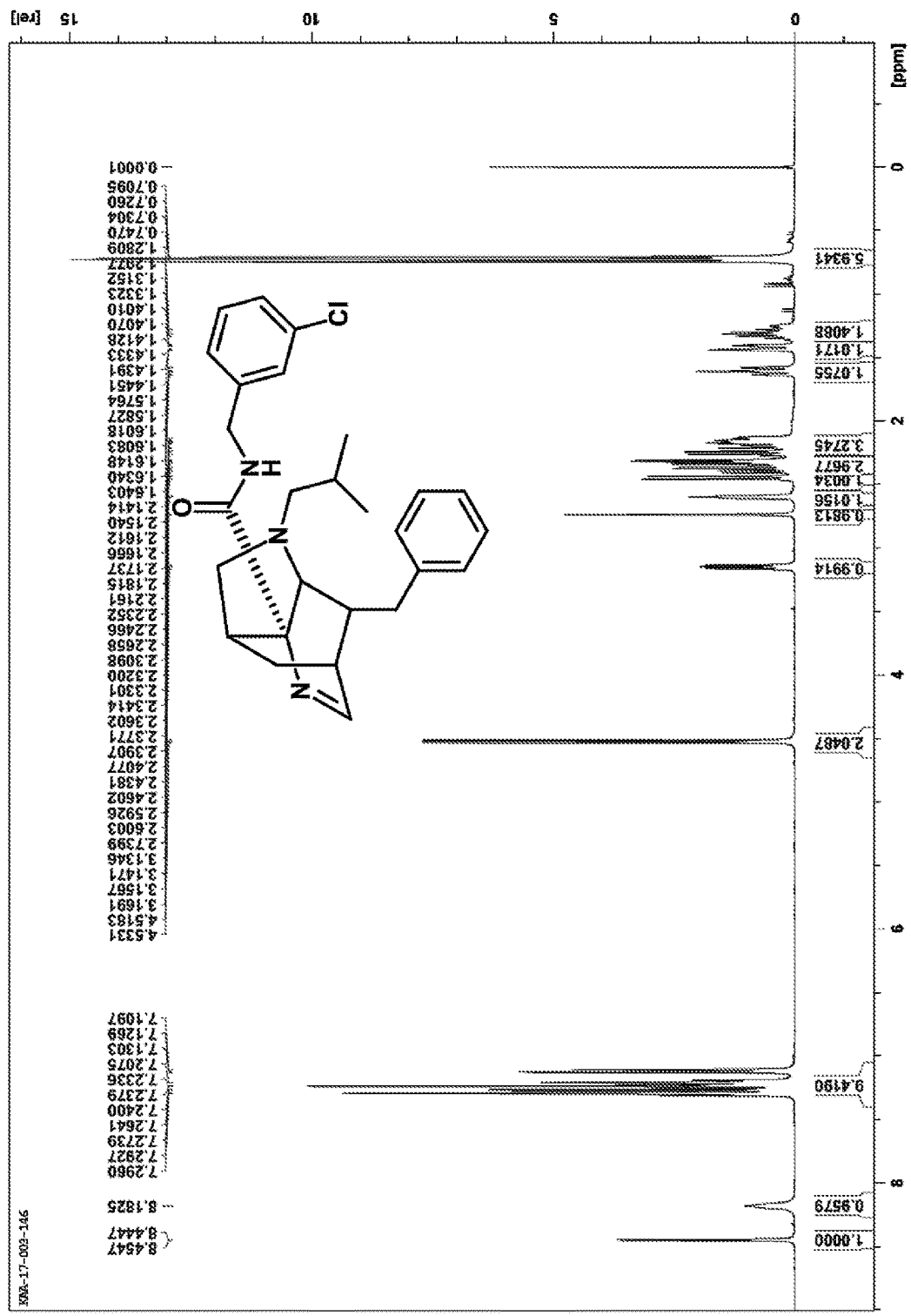
FIG. 12 shows the $^1$H-NMR chart for an exemplary compound of the present disclosure (formula in the figure).
Figure 13:
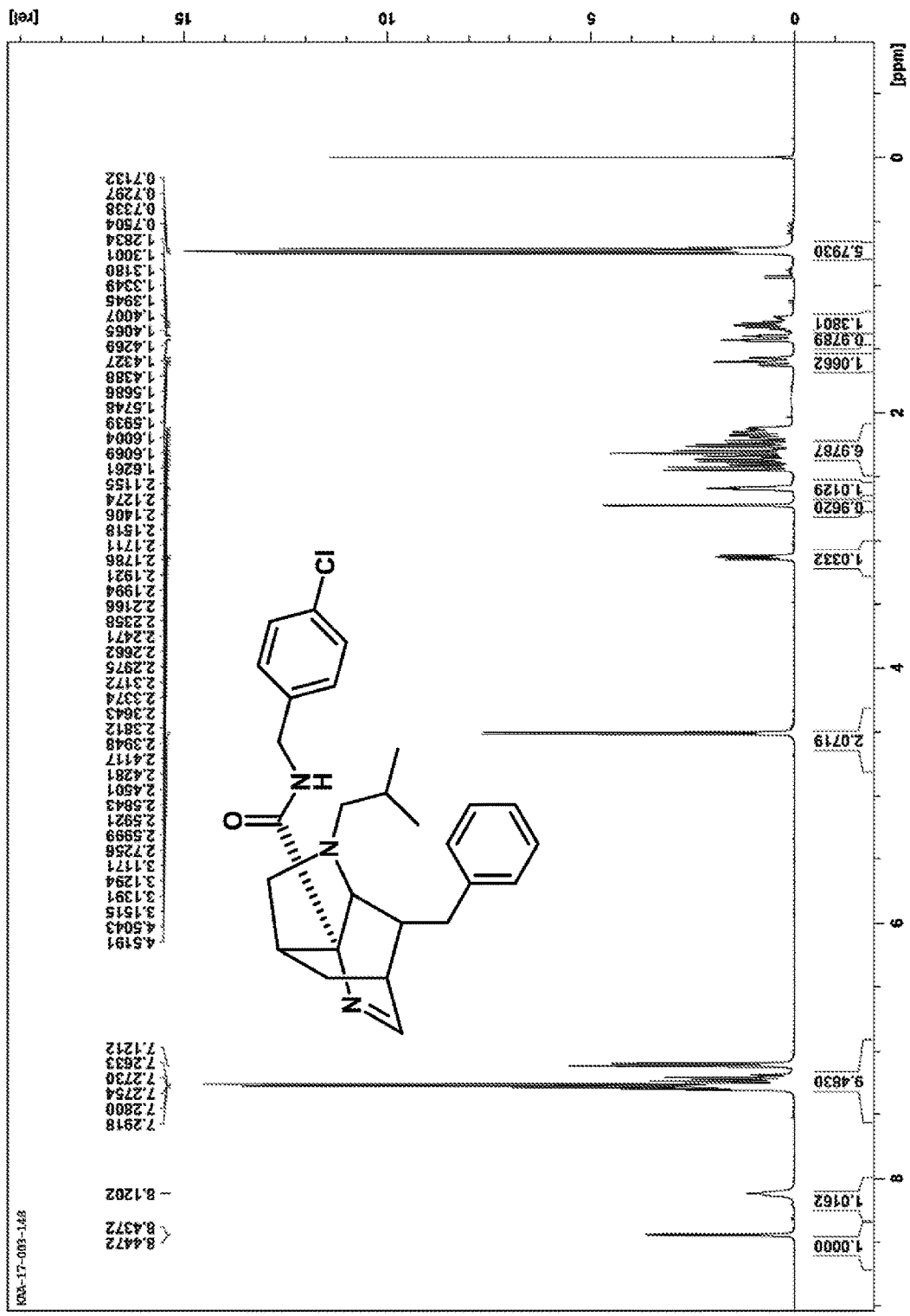
FIG. 13 shows the $^1$H-NMR chart for an exemplary compound of the present disclosure (formula in the figure).
Figure 14:
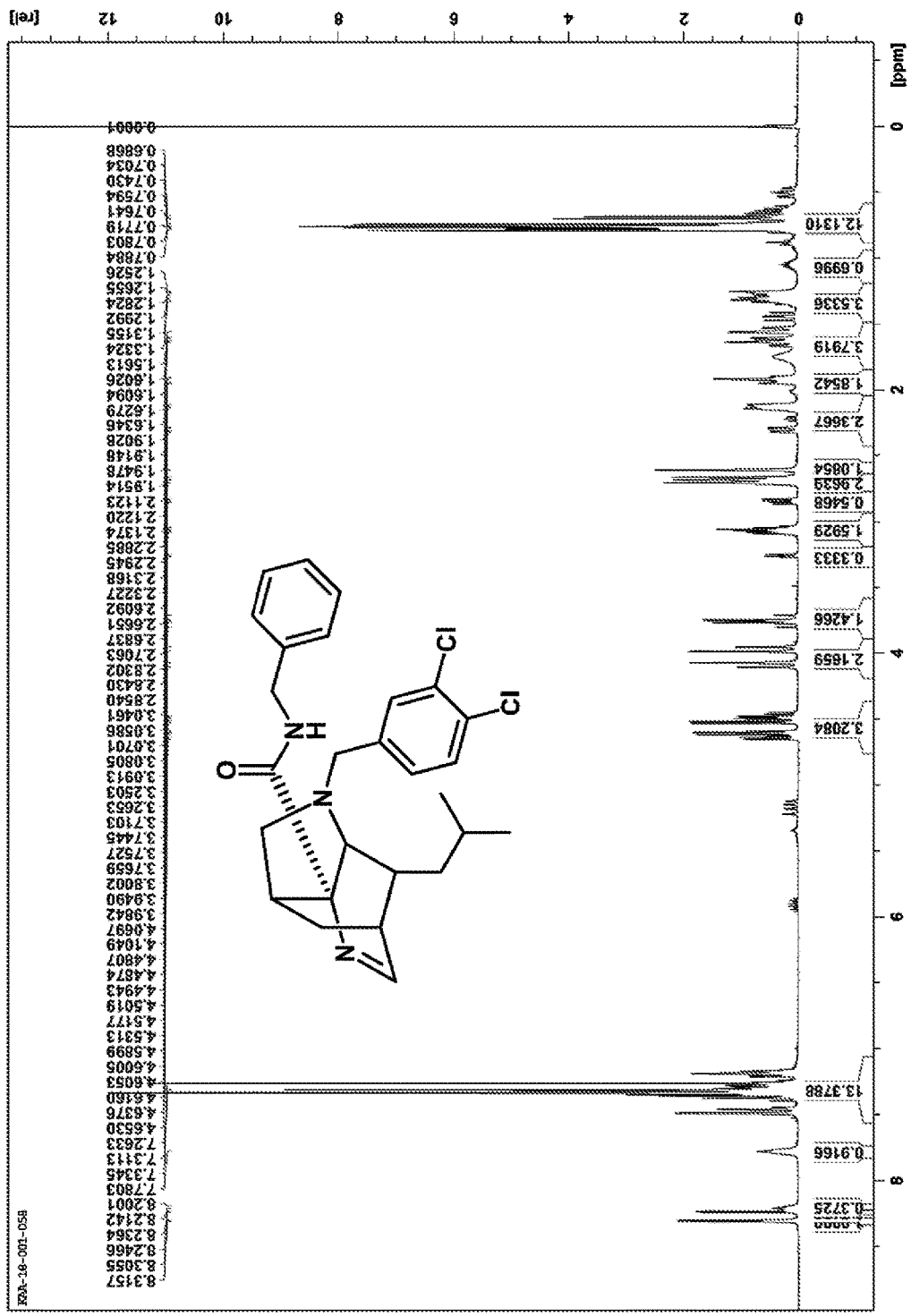
FIG. 14 shows the $^1$H-NMR chart for an exemplary compound of the present disclosure (formula in the figure).
Figure 15:
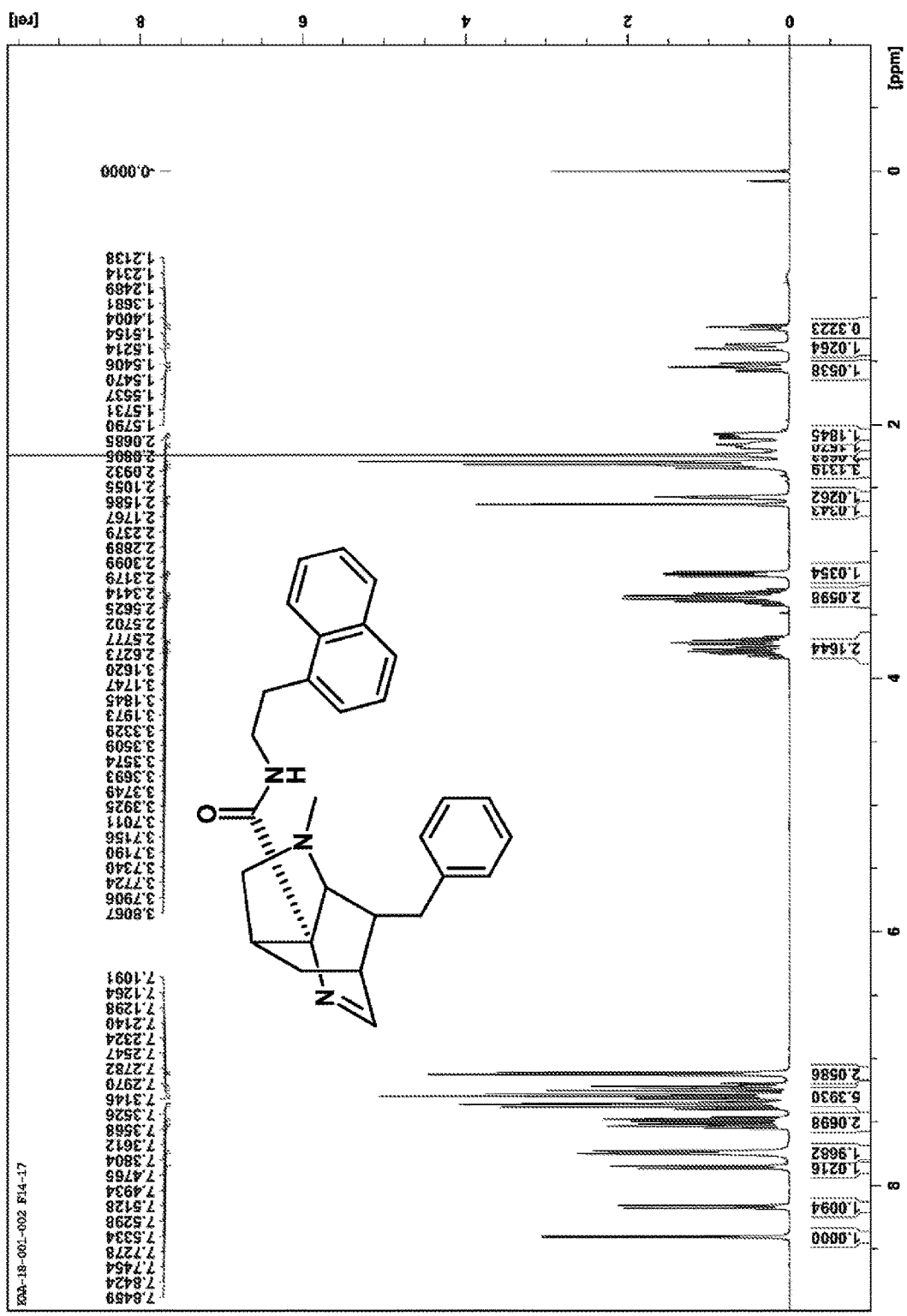
FIG. 15 shows the $^1$H-NMR chart for an exemplary compound of the present disclosure (formula in the figure).
Figure 16:
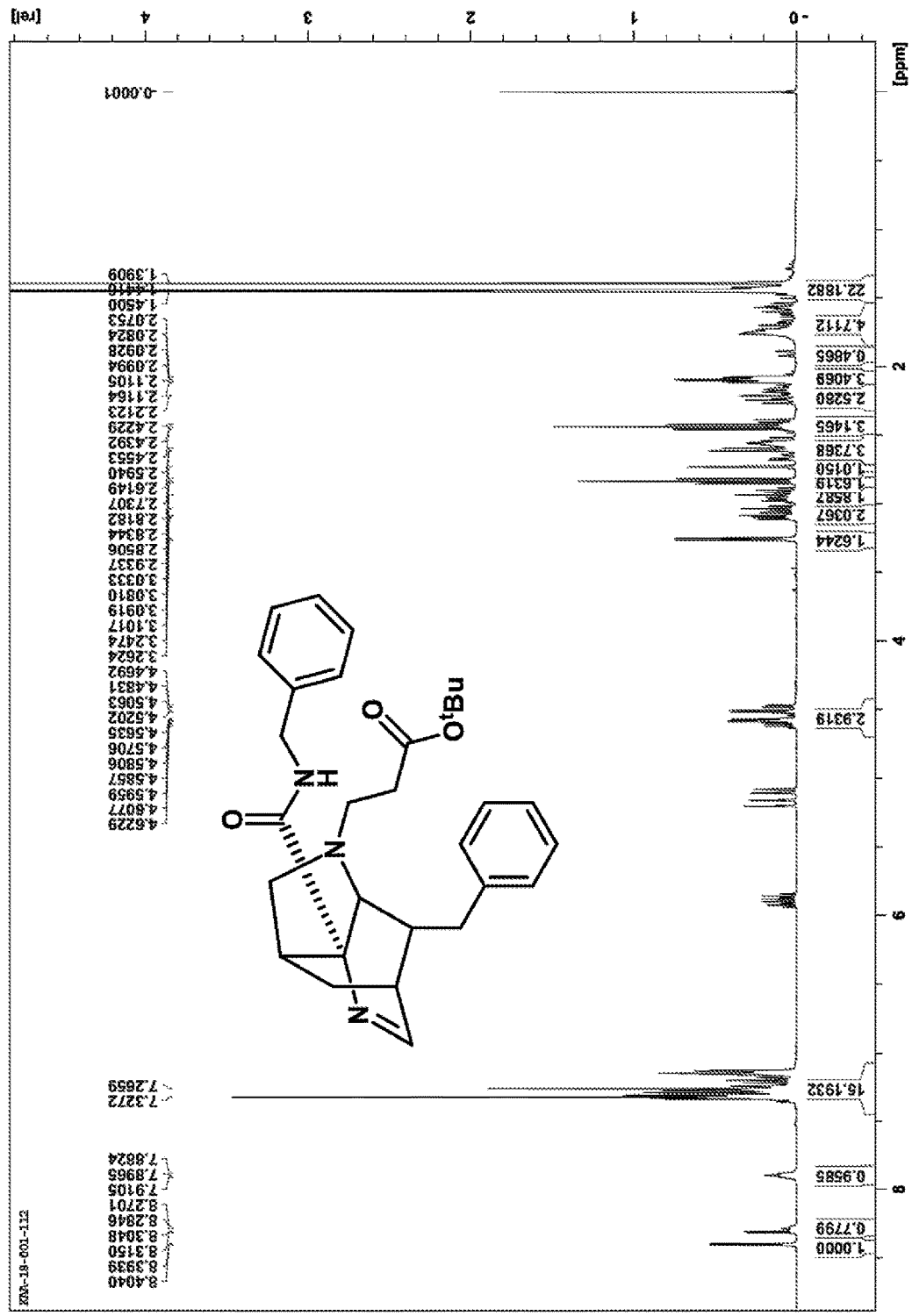
FIG. 16 shows the $^1$H-NMR chart for an exemplary compound of the present disclosure (formula in the figure).
Figure 17:
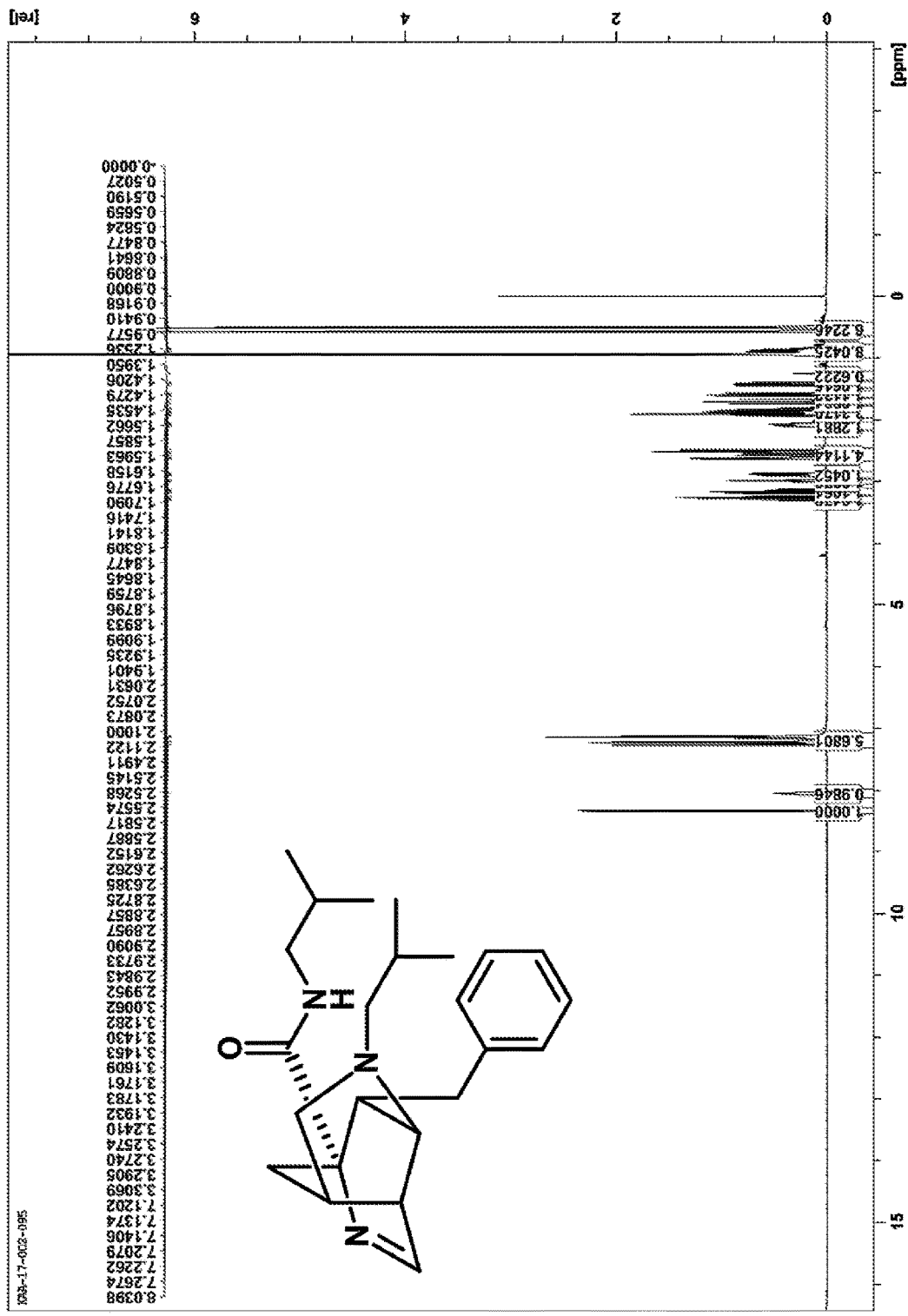
FIG. 17 shows the $^1$H-NMR chart for an exemplary compound of the present disclosure (formula in the figure).
Figure 18:
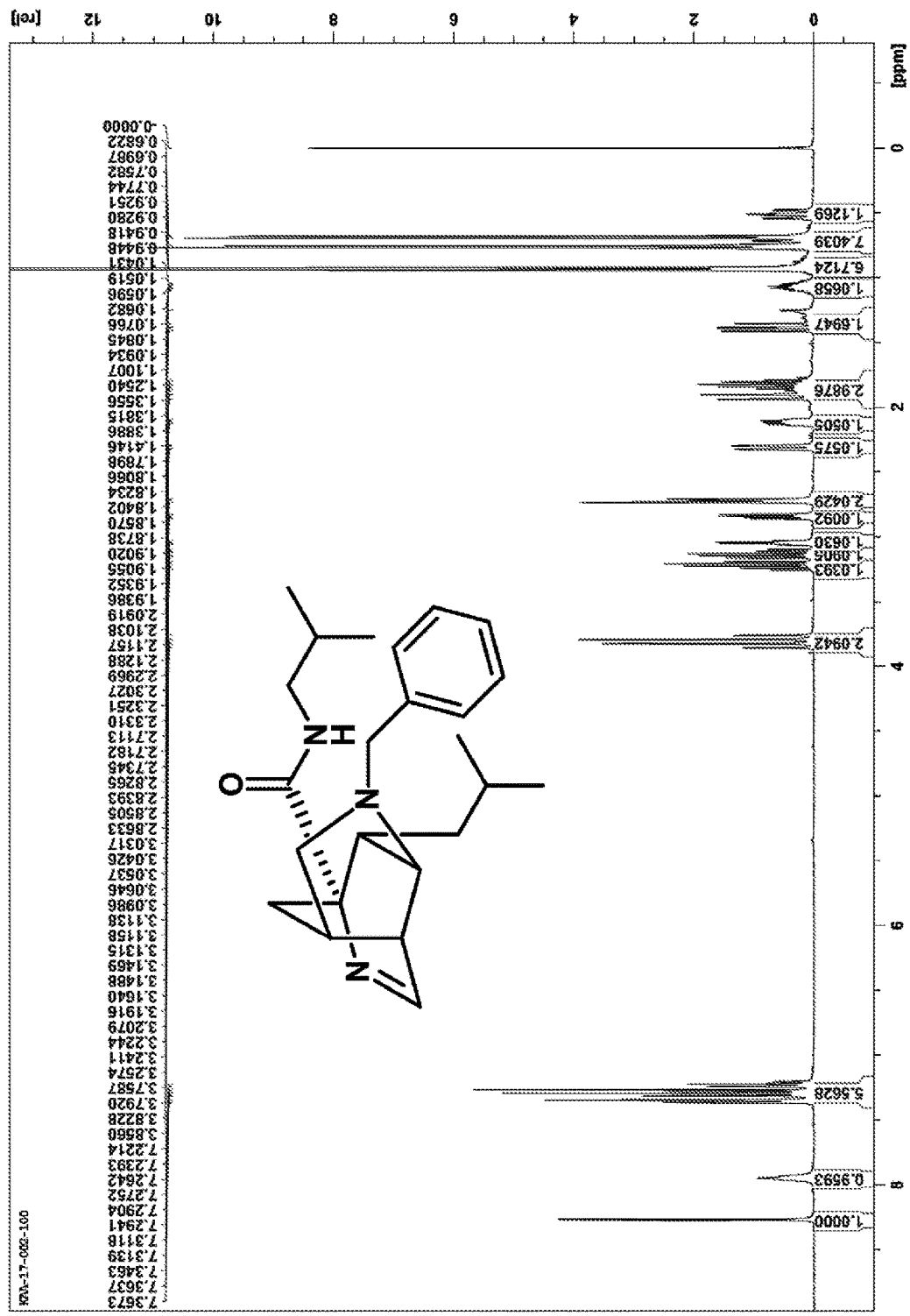
FIG. 18 shows the $^1$H-NMR chart for an exemplary compound of the present disclosure (formula in the figure).
Figure 19:
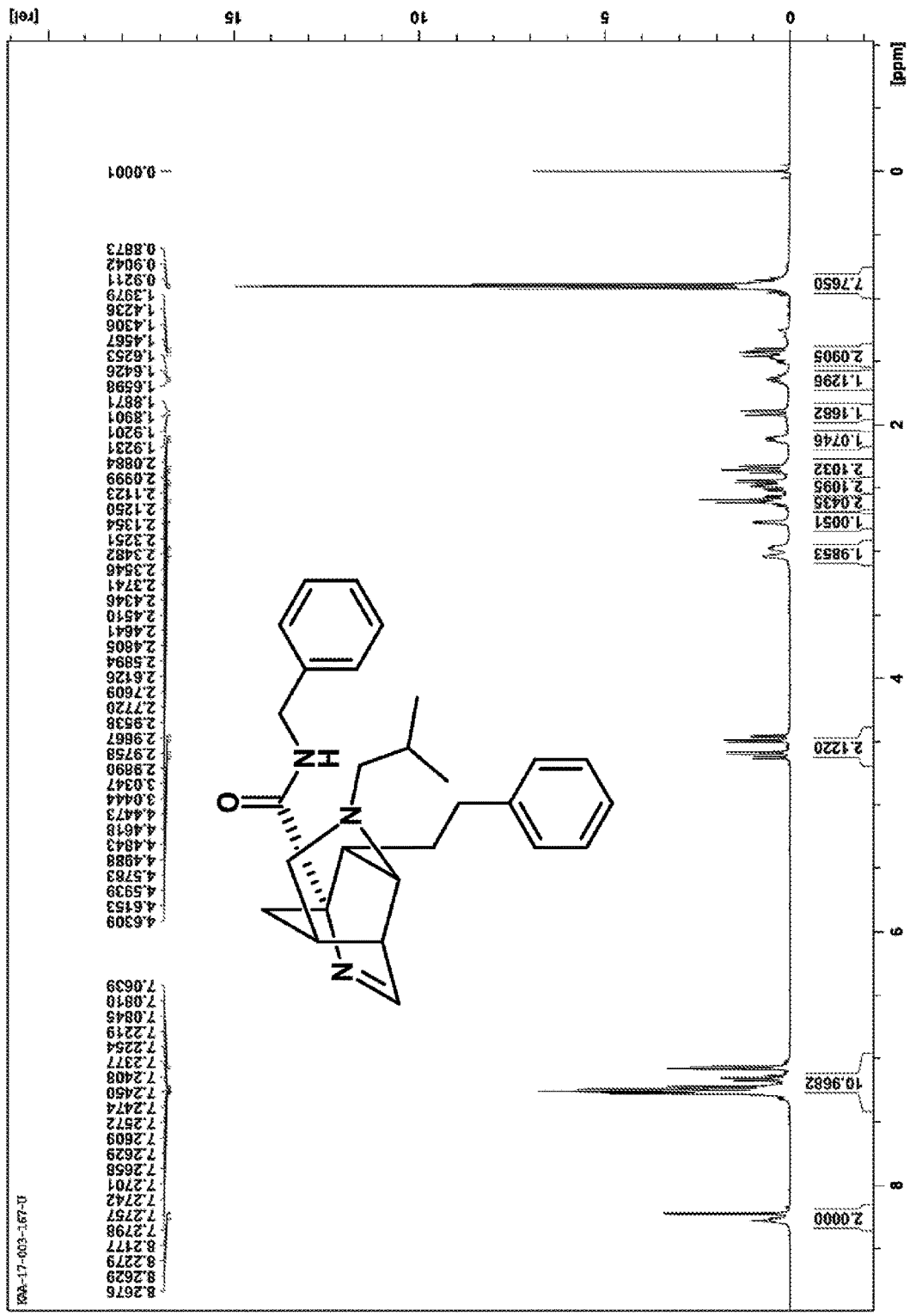
FIG. 19 shows the $^1$H-NMR chart for an exemplary compound of the present disclosure (formula in the figure).
Figure 20:
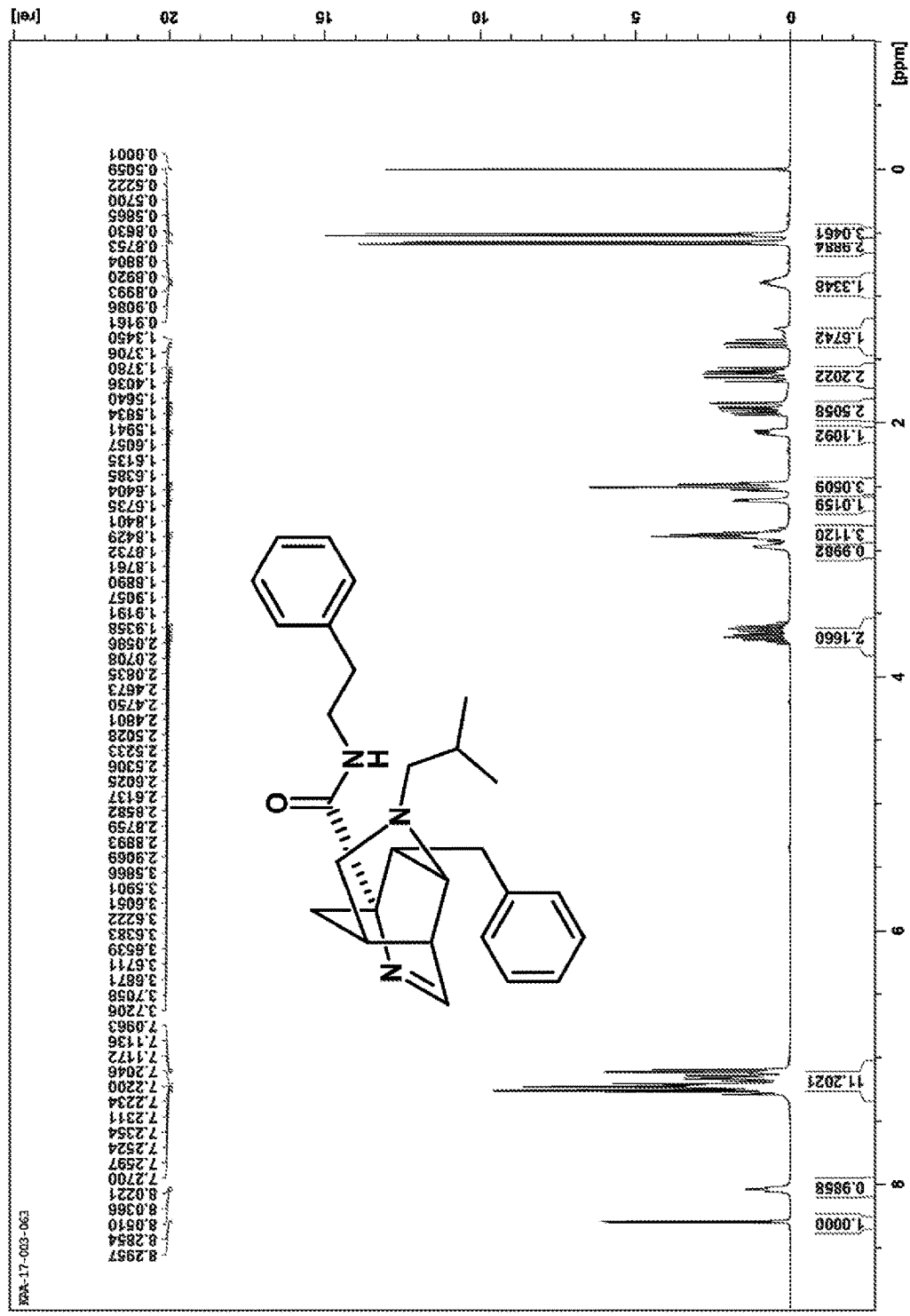
FIG. 20 shows the $^1$H-NMR chart for an exemplary compound of the present disclosure (formula in the figure).
Figure 21:
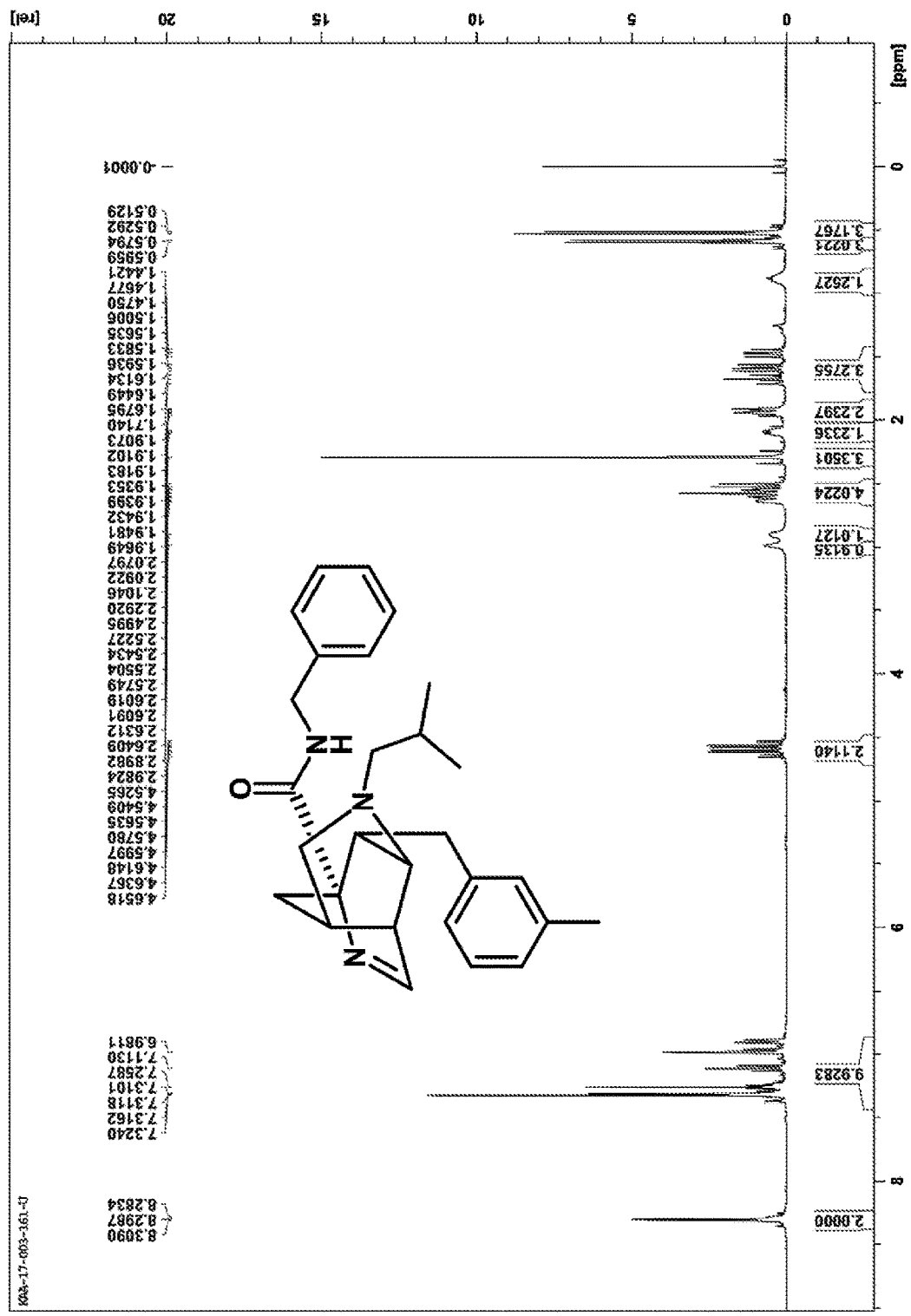
FIG. 21 shows the $^1$H-NMR chart for an exemplary compound of the present disclosure (formula in the figure).
Figure 22:
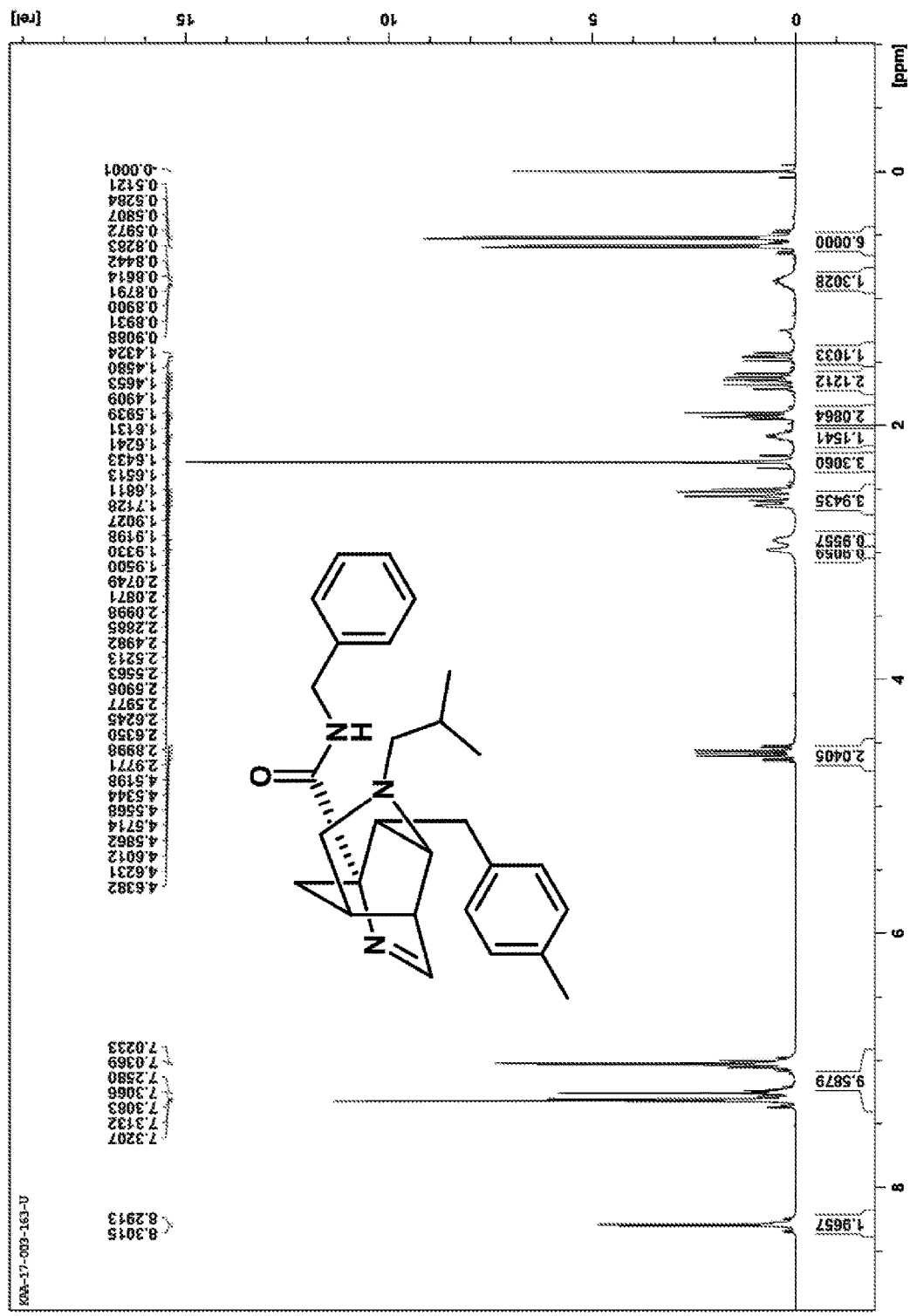
FIG. 22 shows the $^1$H-NMR chart for an exemplary compound of the present disclosure (formula in the figure).
Figure 23:
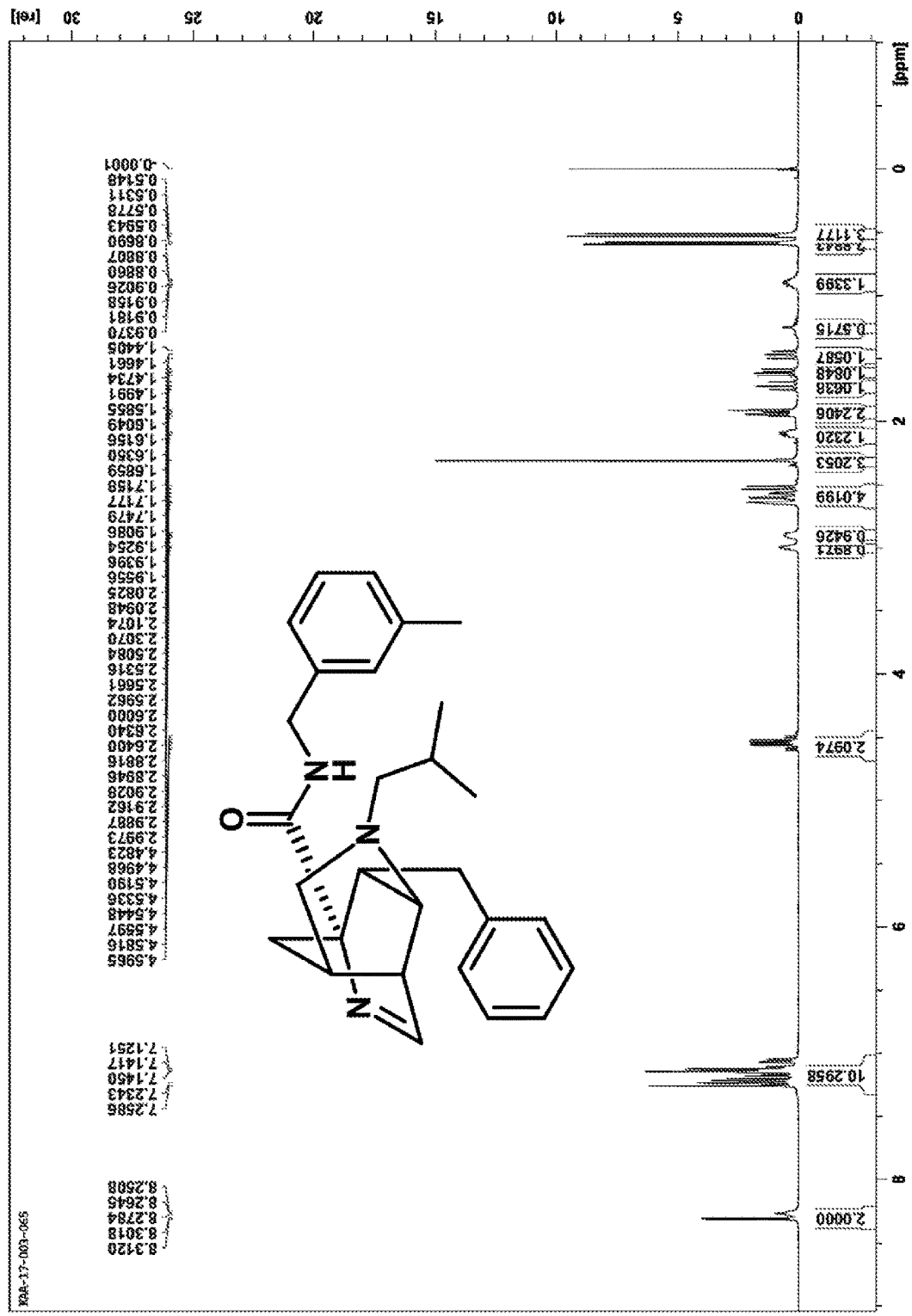
FIG. 23 shows the $^1$H-NMR chart for an exemplary compound of the present disclosure (formula in the figure).
Figure 24:
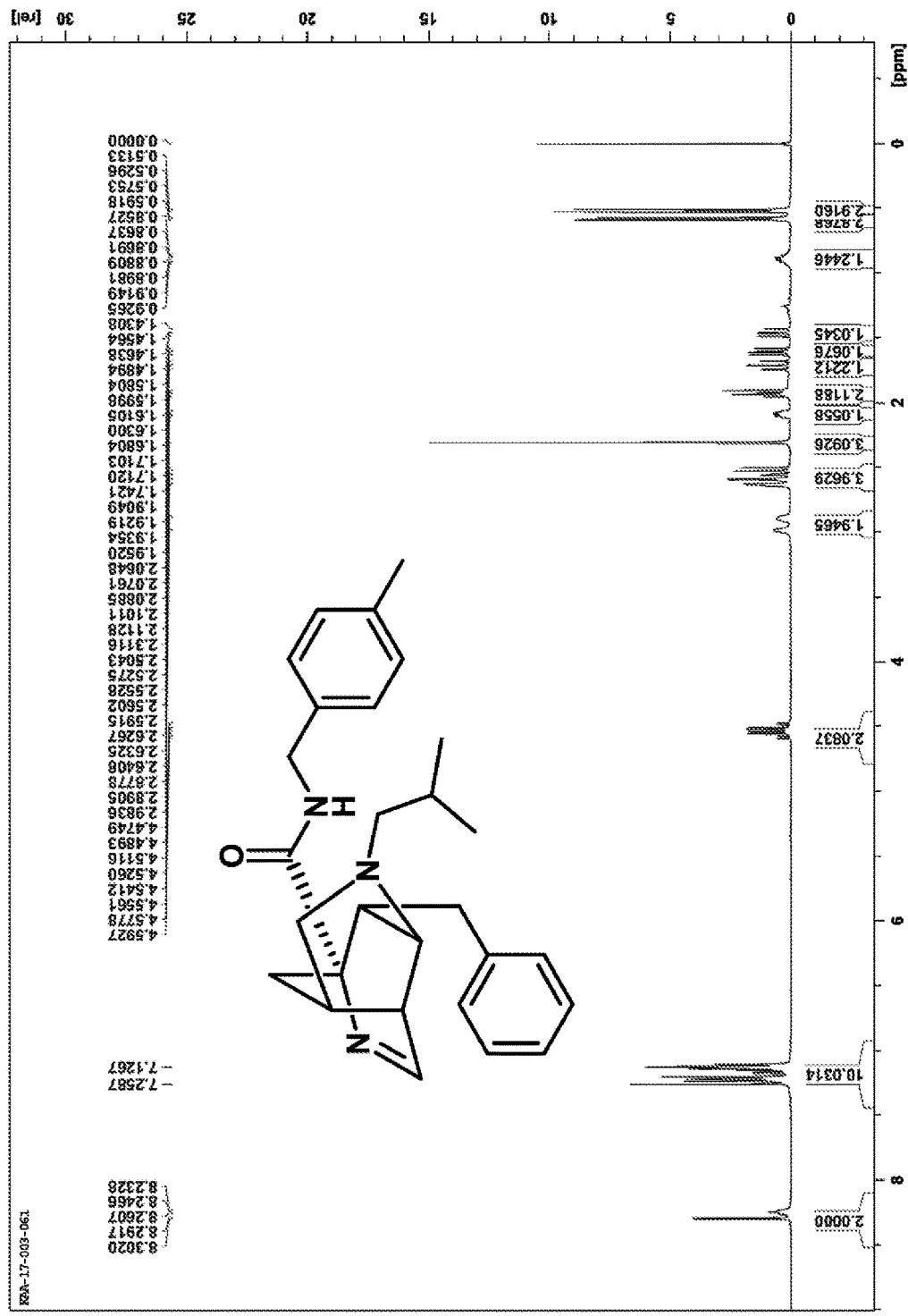
FIG. 24 shows the $^1$H-NMR chart for an exemplary compound of the present disclosure (formula in the figure).
Figure 25:
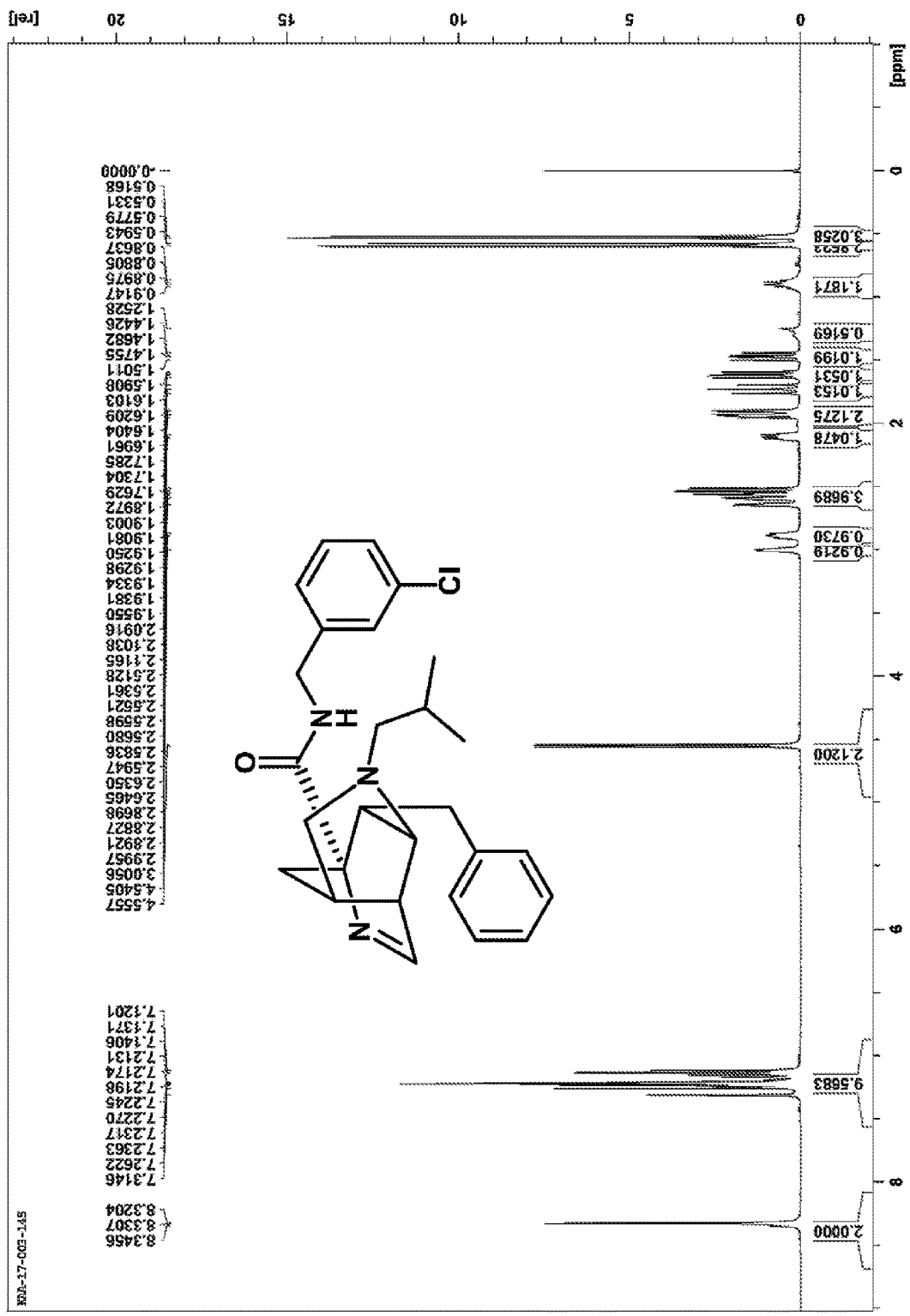
FIG. 25 shows the $^1$H-NMR chart for an exemplary compound of the present disclosure (formula in the figure).
Figure 26:
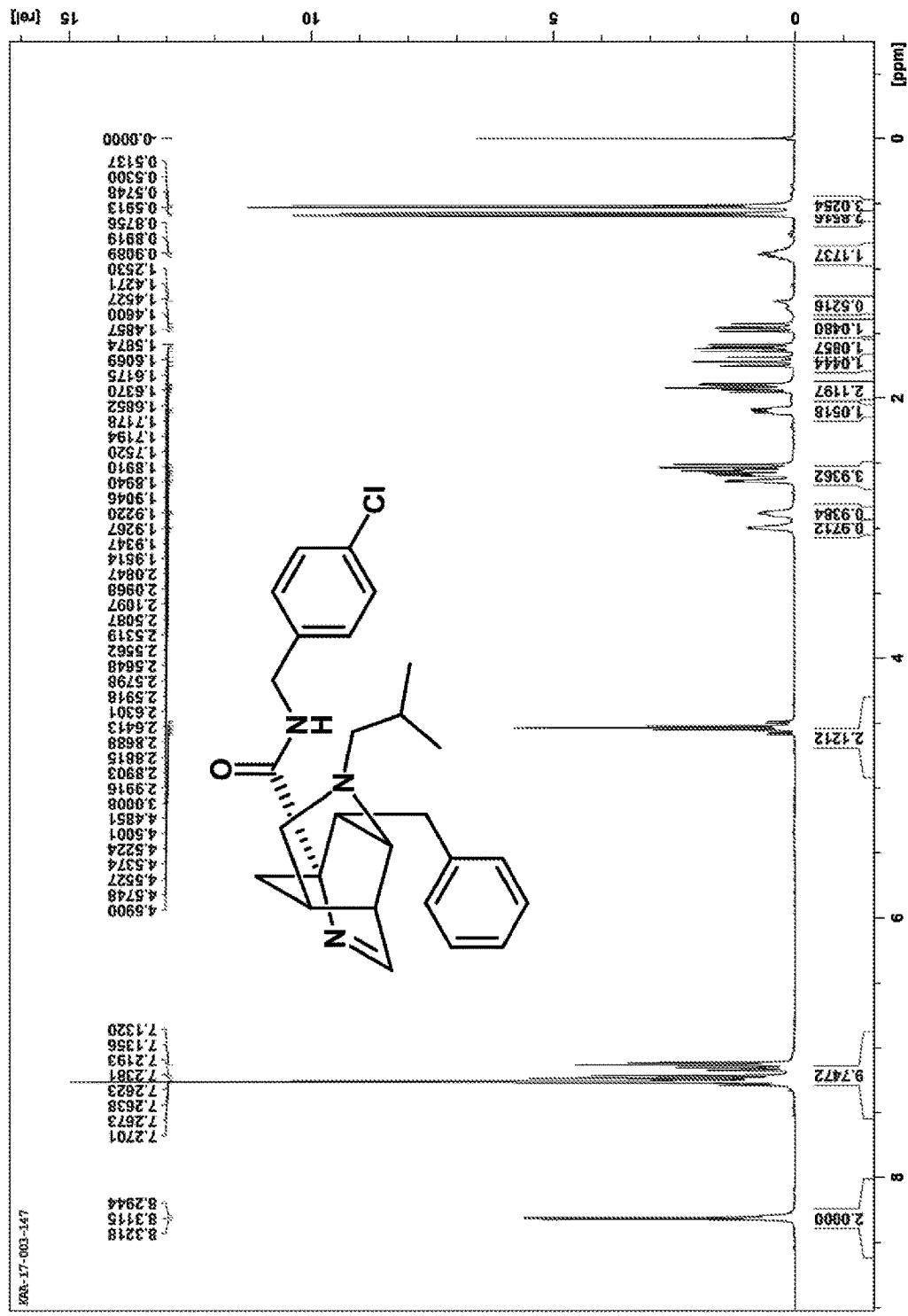
FIG. 26 shows the $^1$H-NMR chart for an exemplary compound of the present disclosure (formula in the figure).
Figure 27:
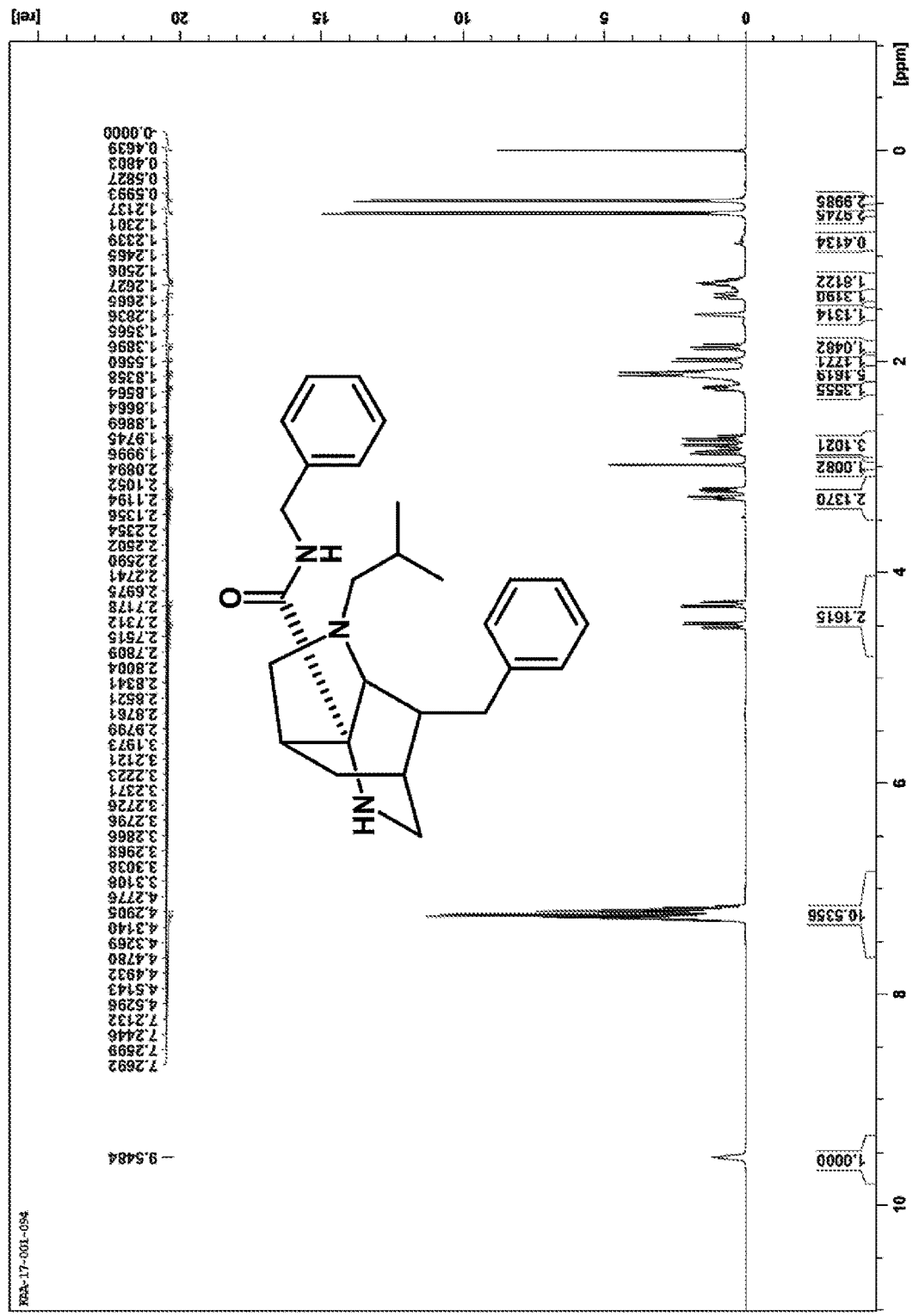
FIG. 27 shows the $^1$H-NMR chart for an exemplary compound of the present disclosure (formula in the figure).
Figure 28:
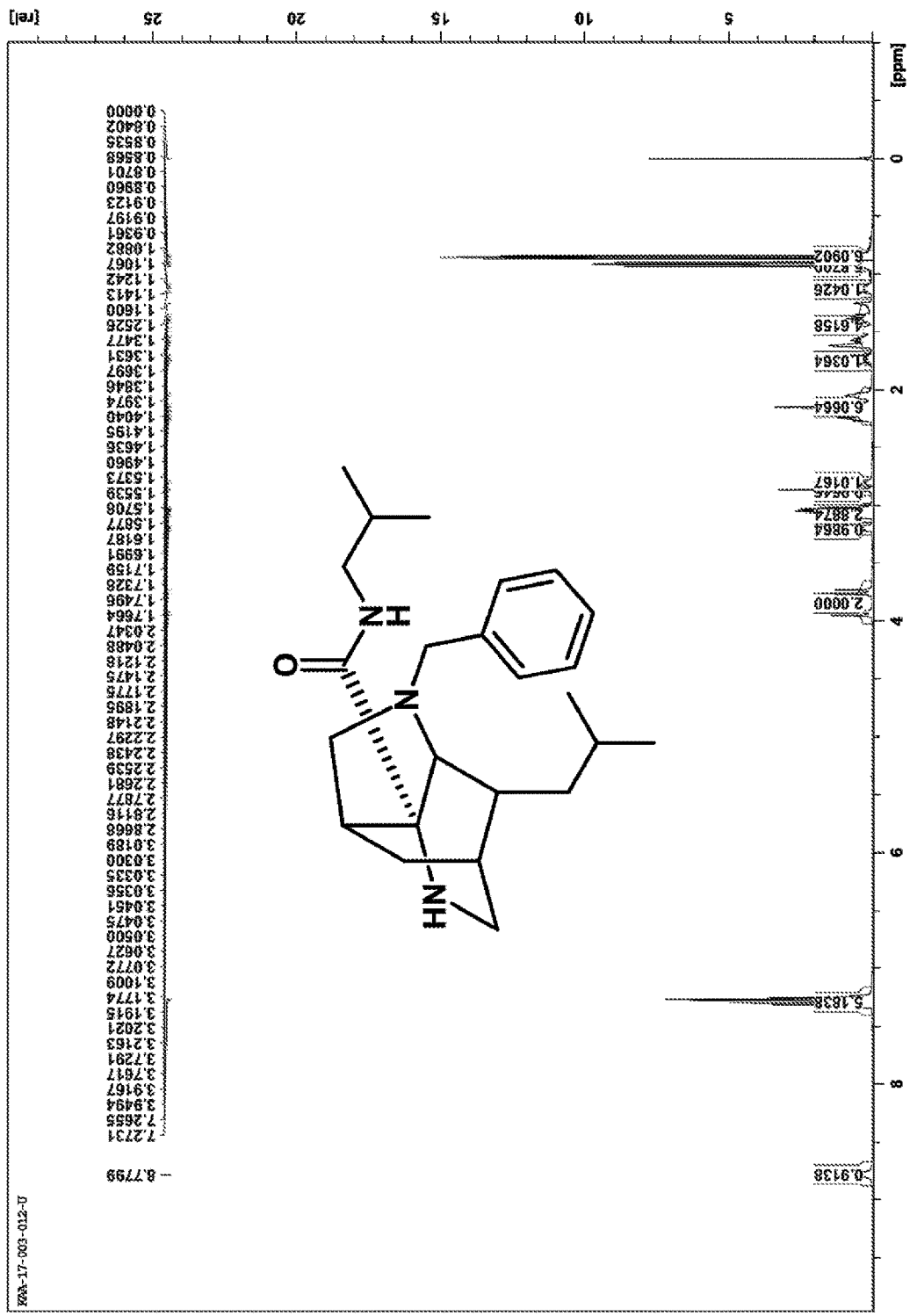
FIG. 28 shows the $^1$H-NMR chart for an exemplary compound of the present disclosure (formula in the figure).
Figure 29:
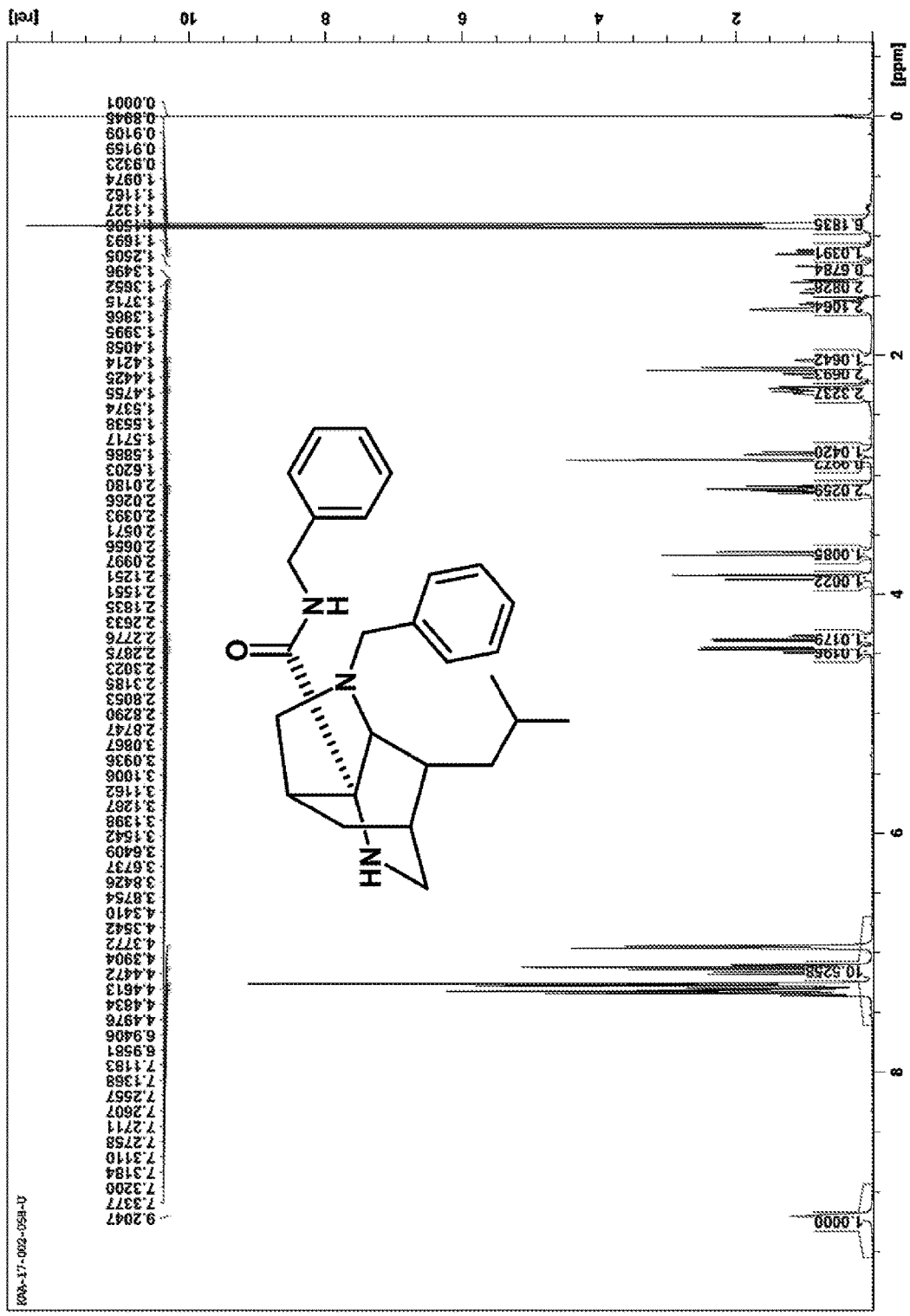
FIG. 29 shows the $^1$H-NMR chart for an exemplary compound of the present disclosure (formula in the figure).
Figure 30:
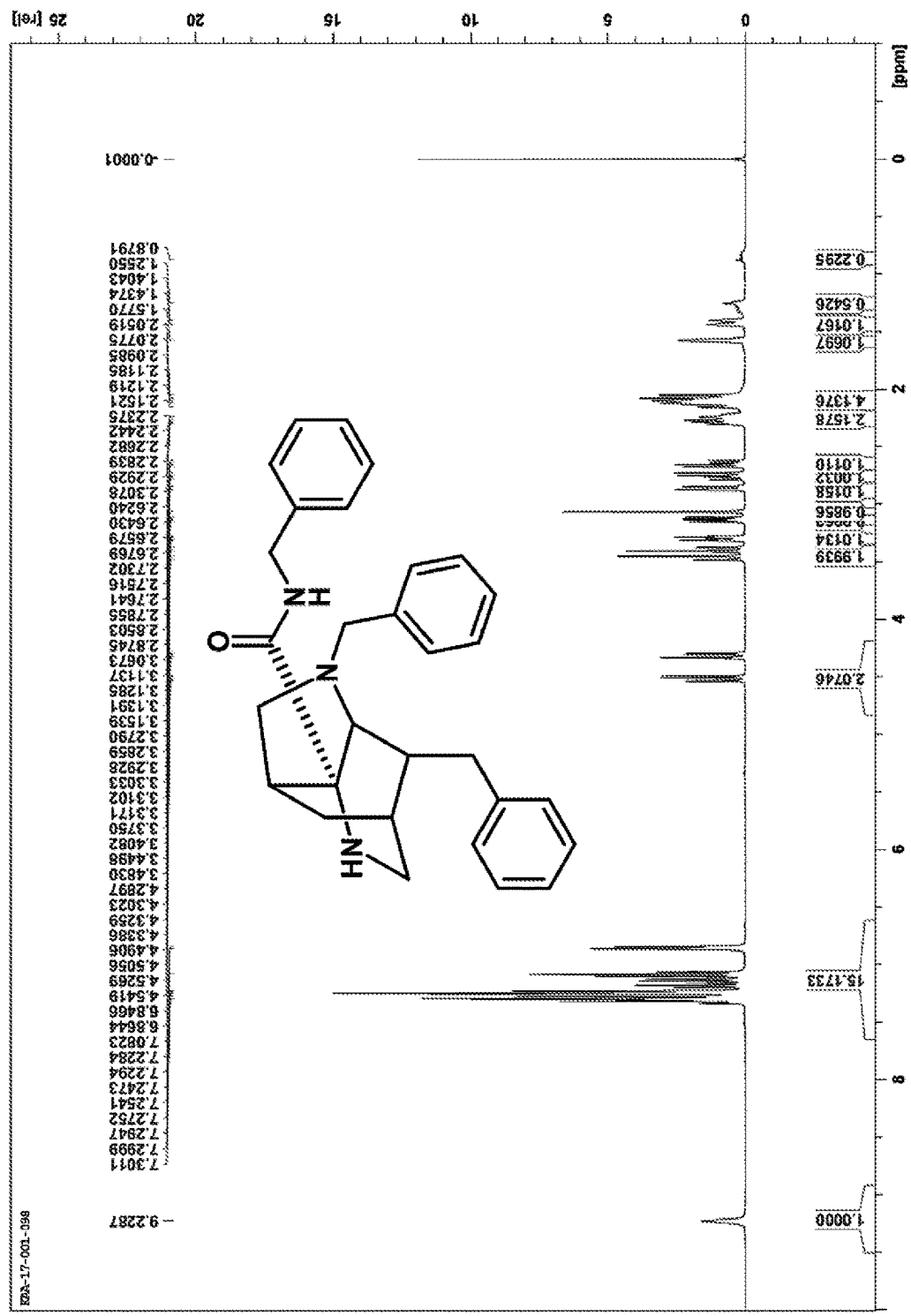
FIG. 30 shows the $^1$H-NMR chart for an exemplary compound of the present disclosure (formula in the figure).
Figure 31:
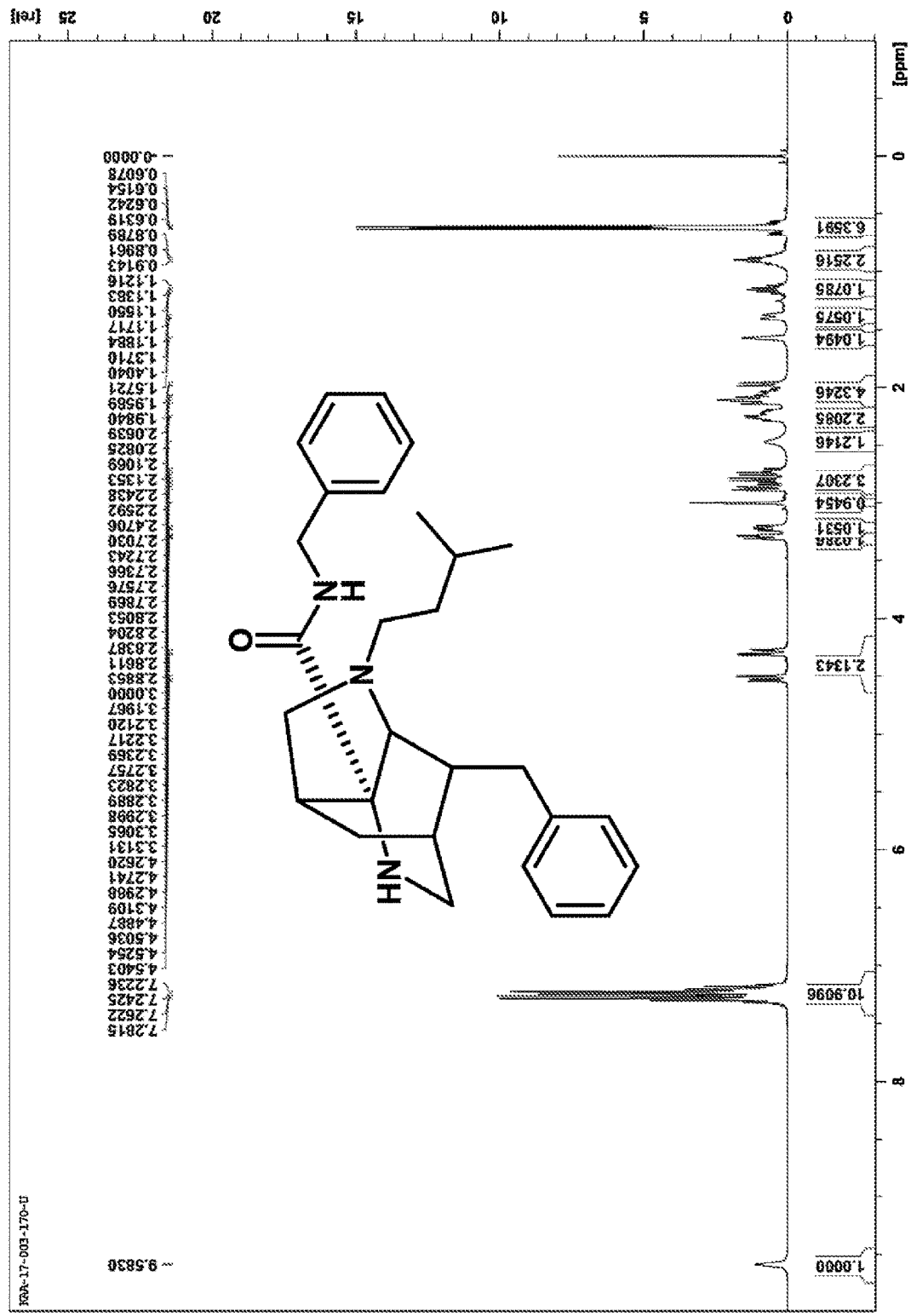
FIG. 31 shows the $^1$H-NMR chart for an exemplary compound of the present disclosure (formula in the figure).
Figure 32:
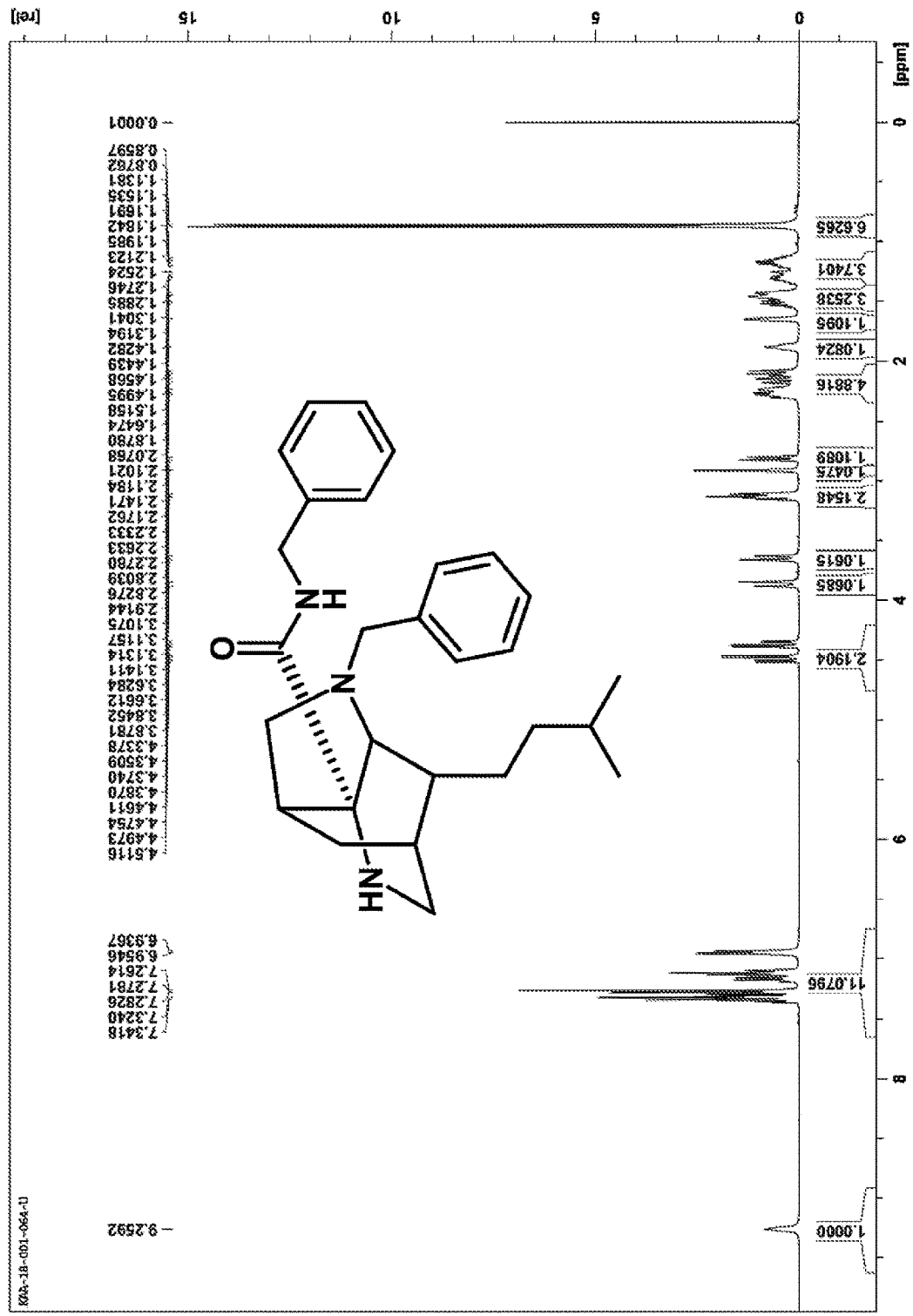
FIG. 32 shows the $^1$H-NMR chart for an exemplary compound of the present disclosure (formula in the figure).
Figure 33:
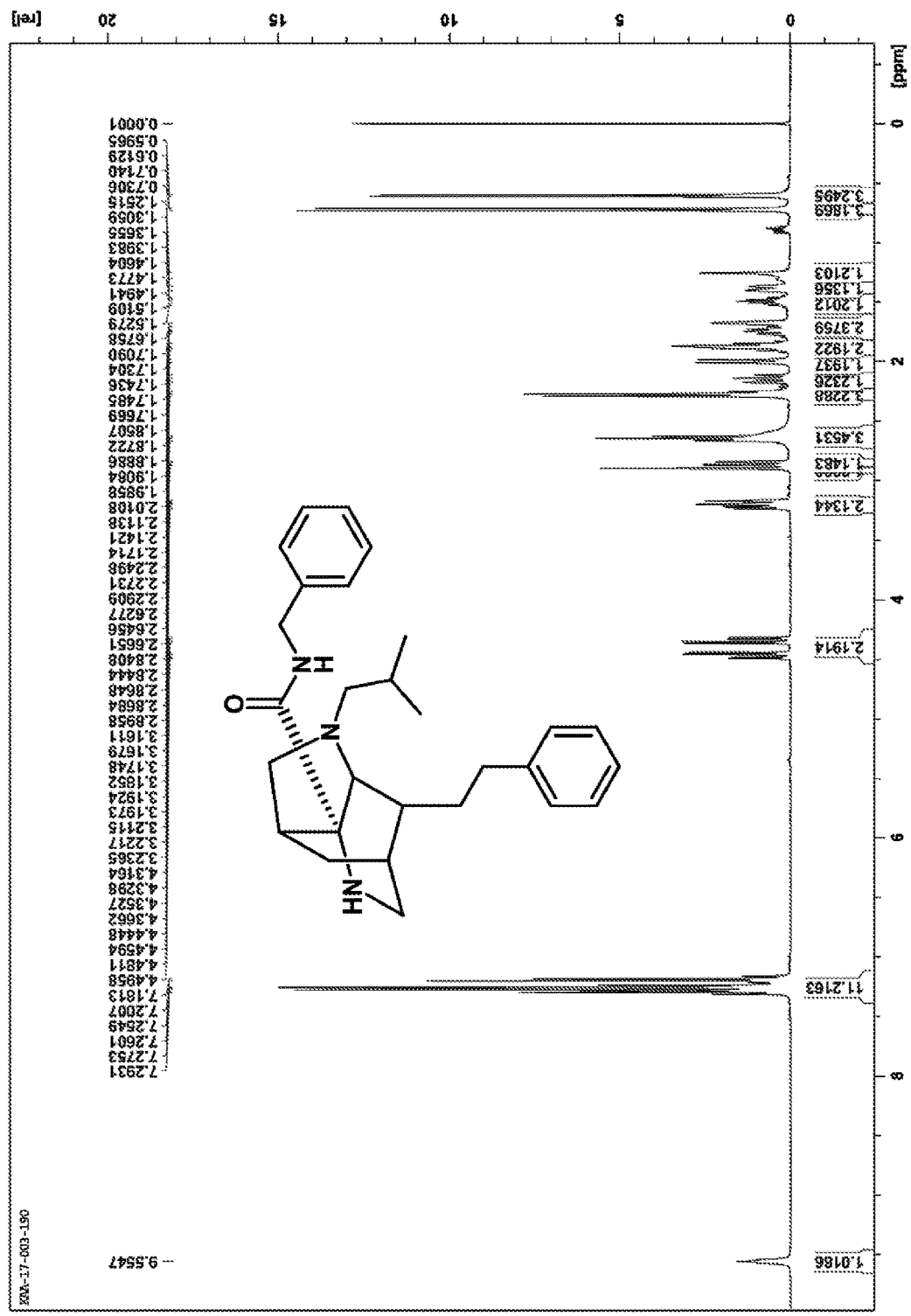
FIG. 33 shows the $^1$H-NMR chart for an exemplary compound of the present disclosure (formula in the figure).
Figure 34:
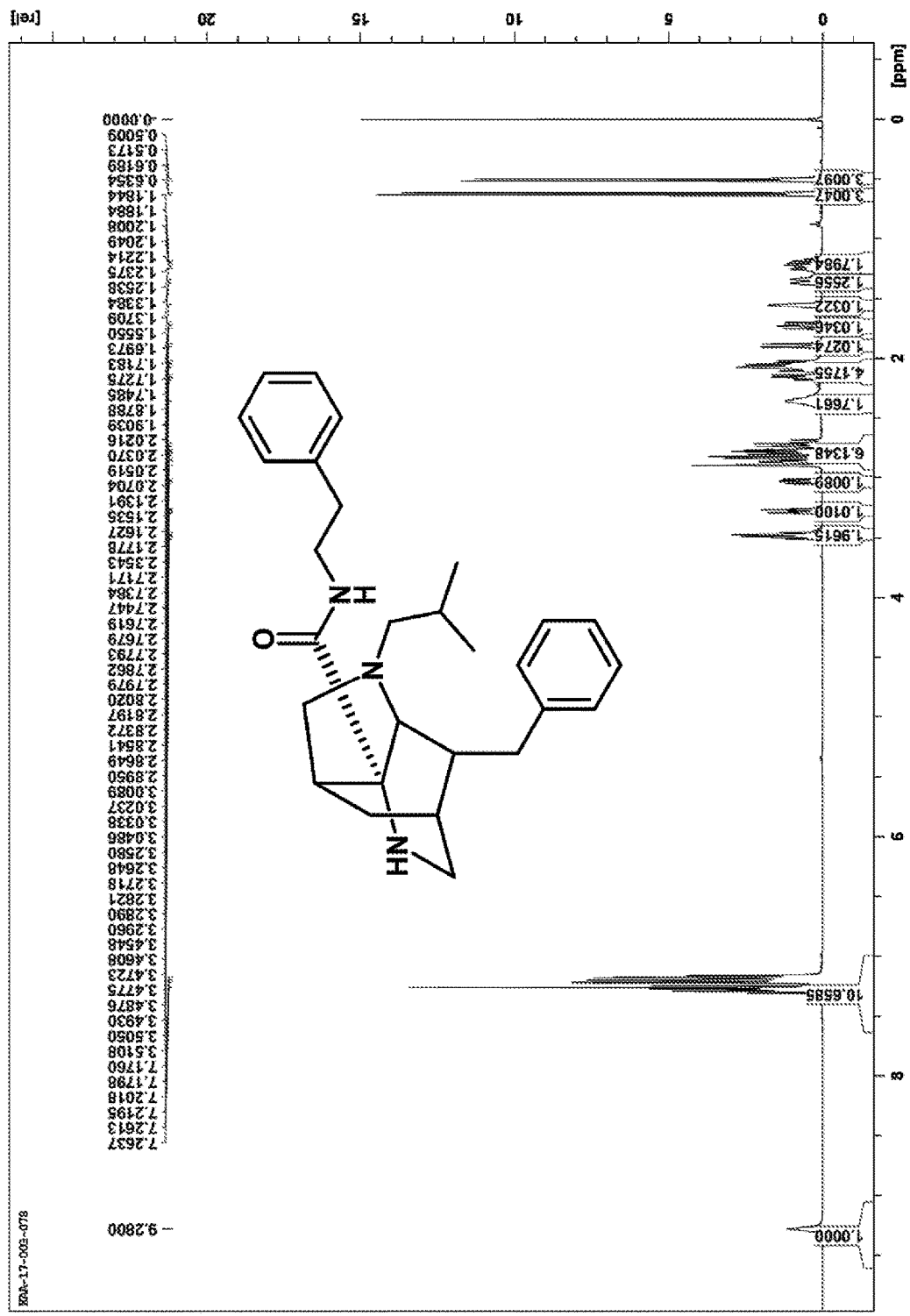
FIG. 34 shows the $^1$H-NMR chart for an exemplary compound of the present disclosure (formula in the figure).
Figure 35:
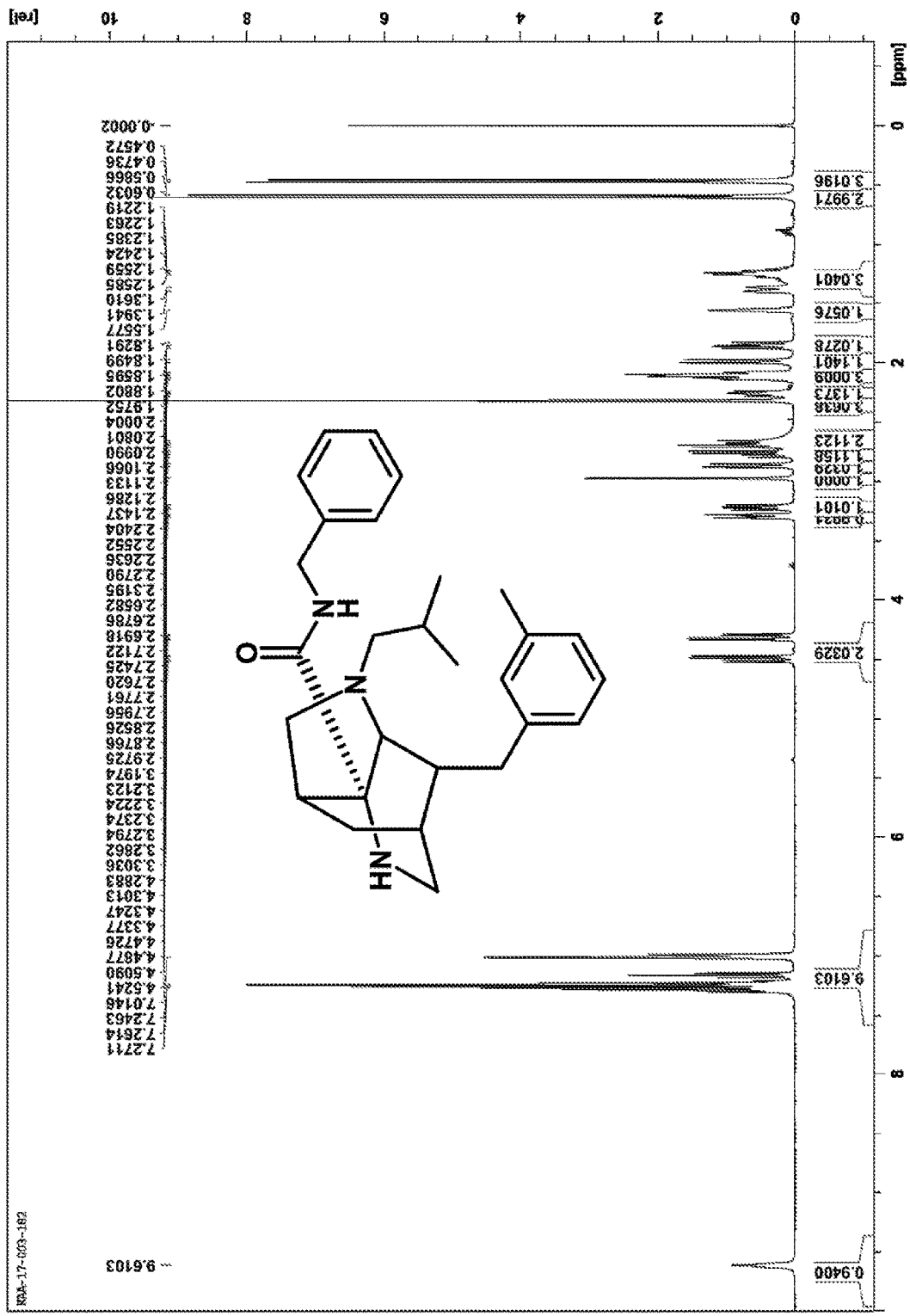
FIG. 35 shows the $^1$H-NMR chart for an exemplary compound of the present disclosure (formula in the figure).
Figure 36:
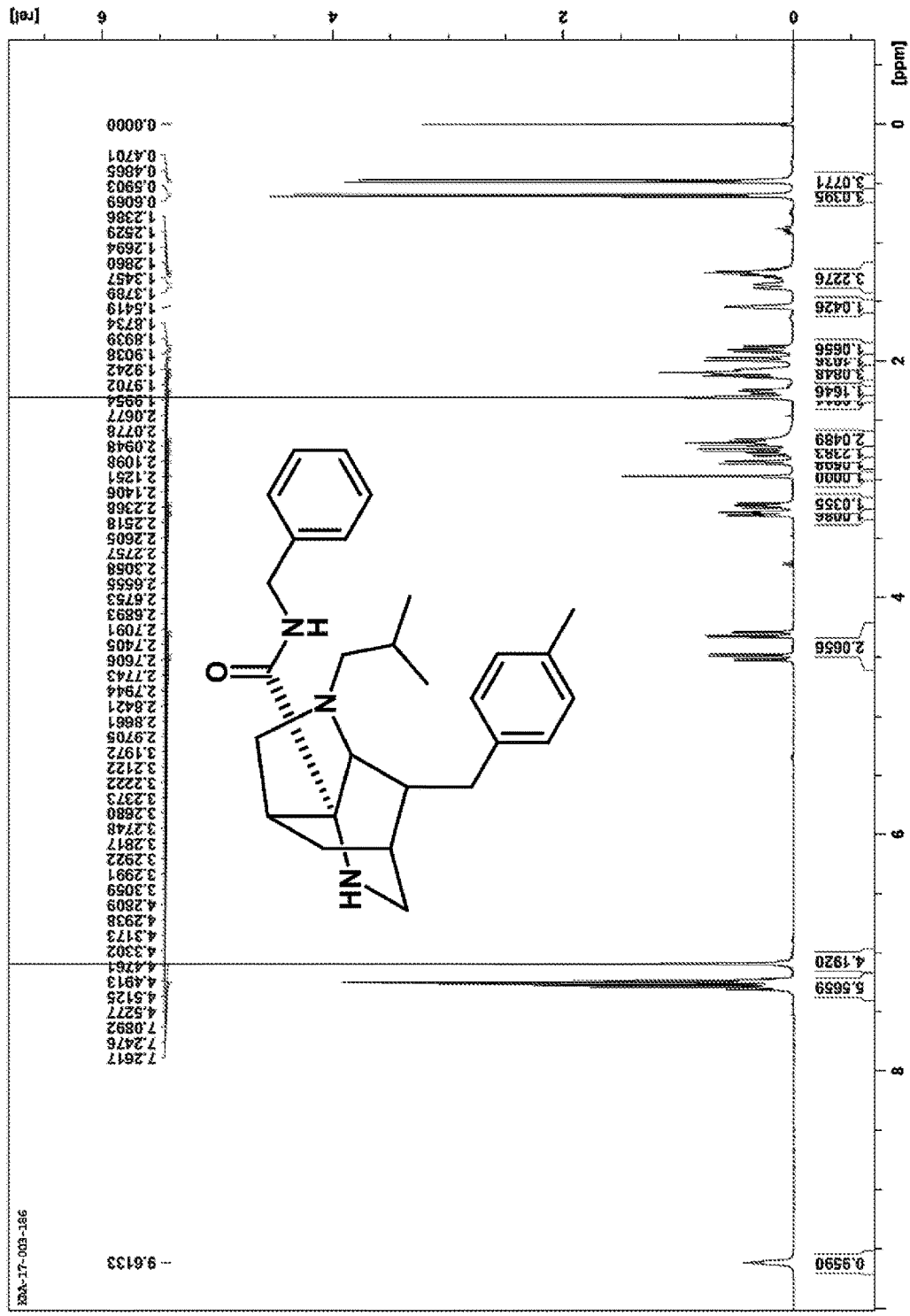
FIG. 36 shows the $^1$H-NMR chart for an exemplary compound of the present disclosure (formula in the figure).
Figure 37:
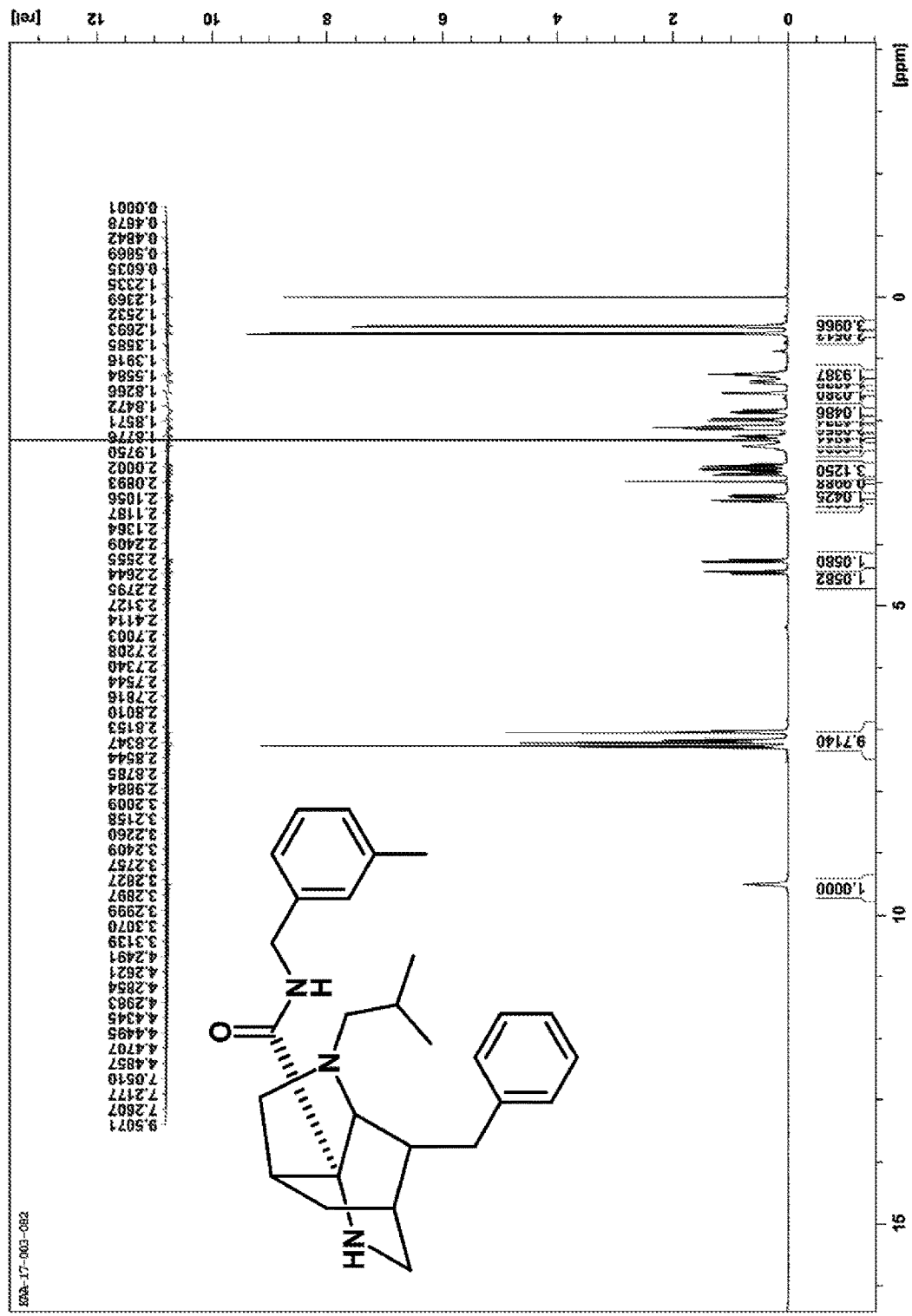
FIG. 37 shows the $^1$H-NMR chart for an exemplary compound of the present disclosure (formula in the figure).
Figure 38:
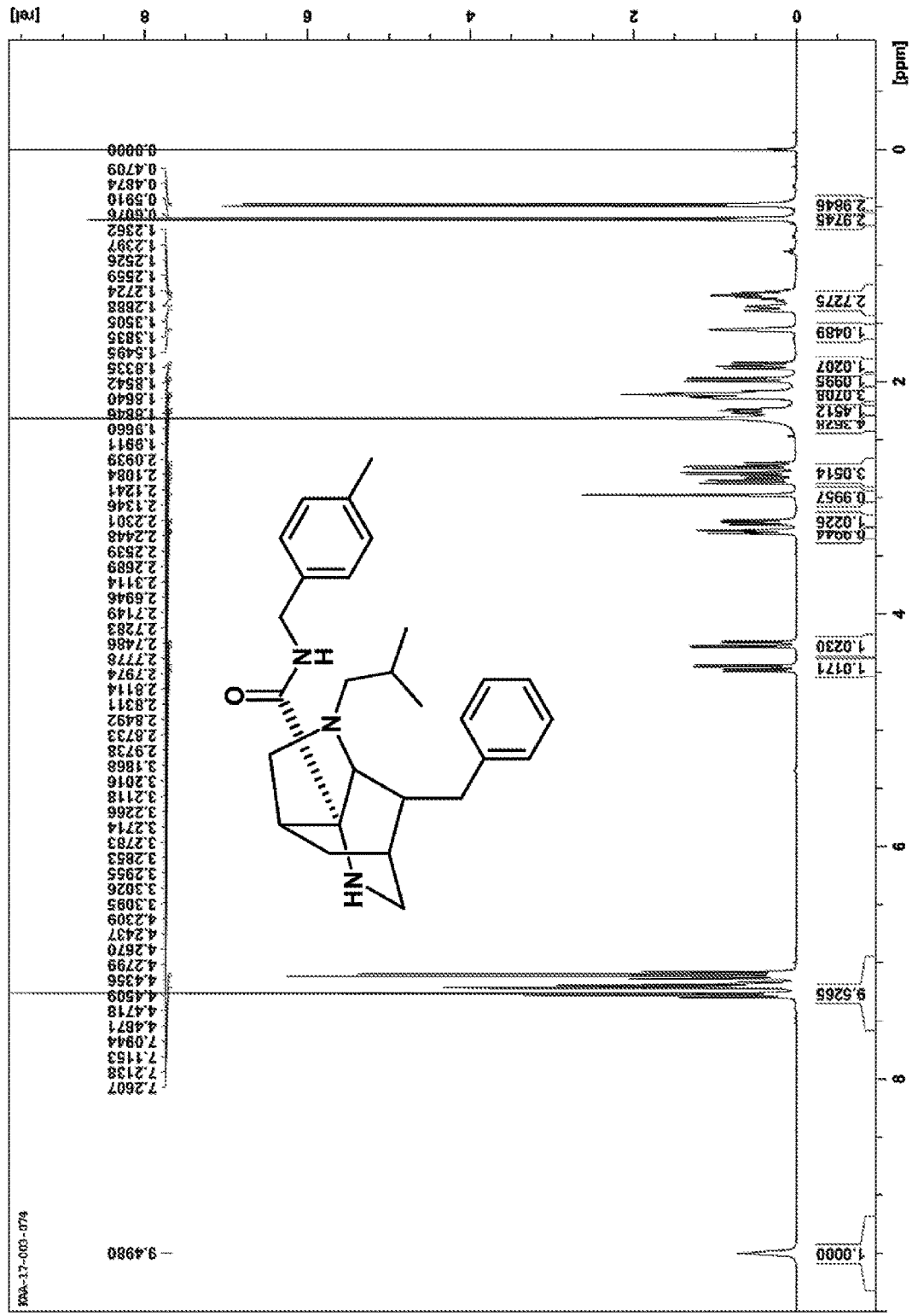
FIG. 38 shows the $^1$H-NMR chart for an exemplary compound of the present disclosure (formula in the figure).
Figure 39:
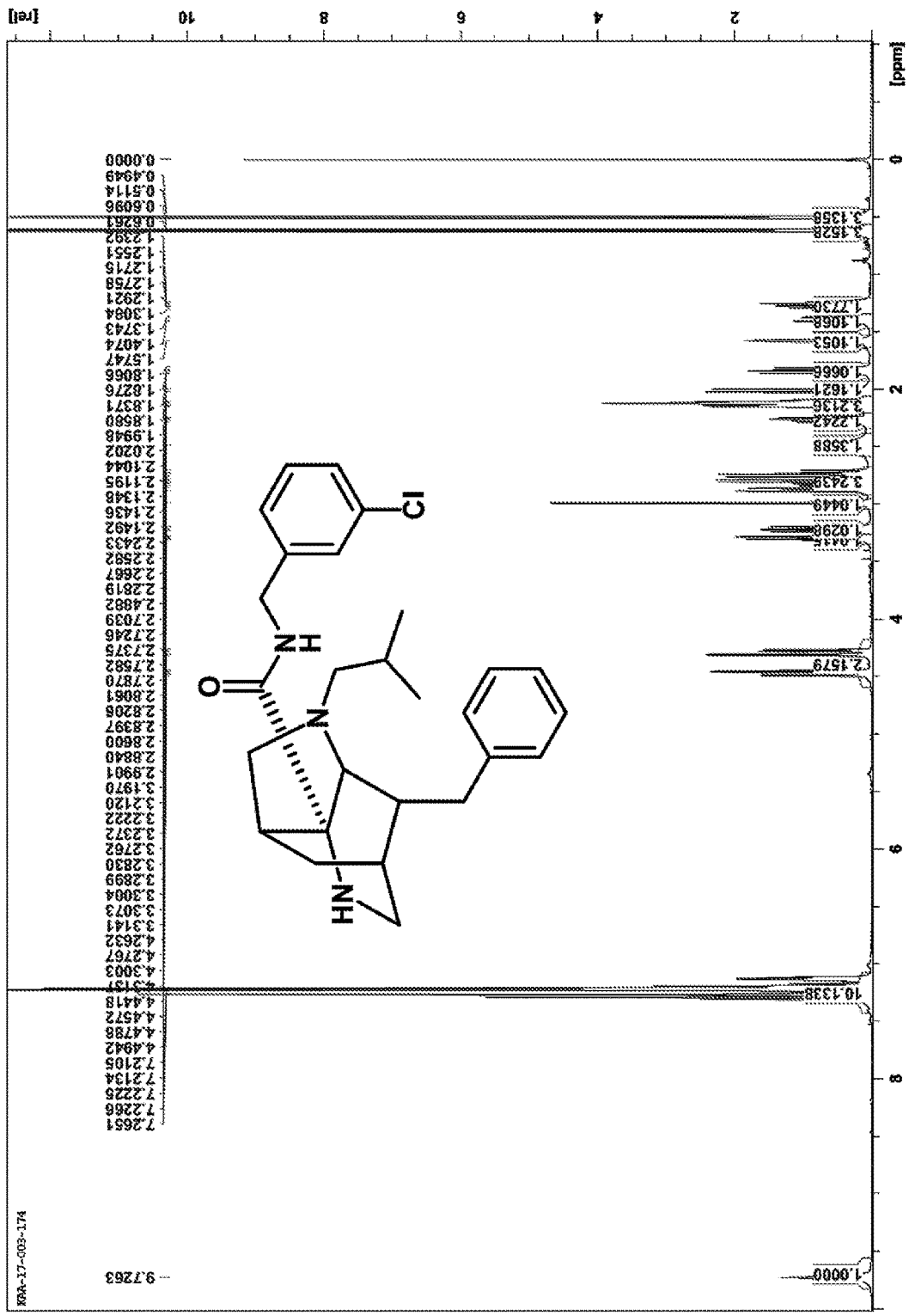
FIG. 39 shows the $^1$H-NMR chart for an exemplary compound of the present disclosure (formula in the figure).
Figure 40:
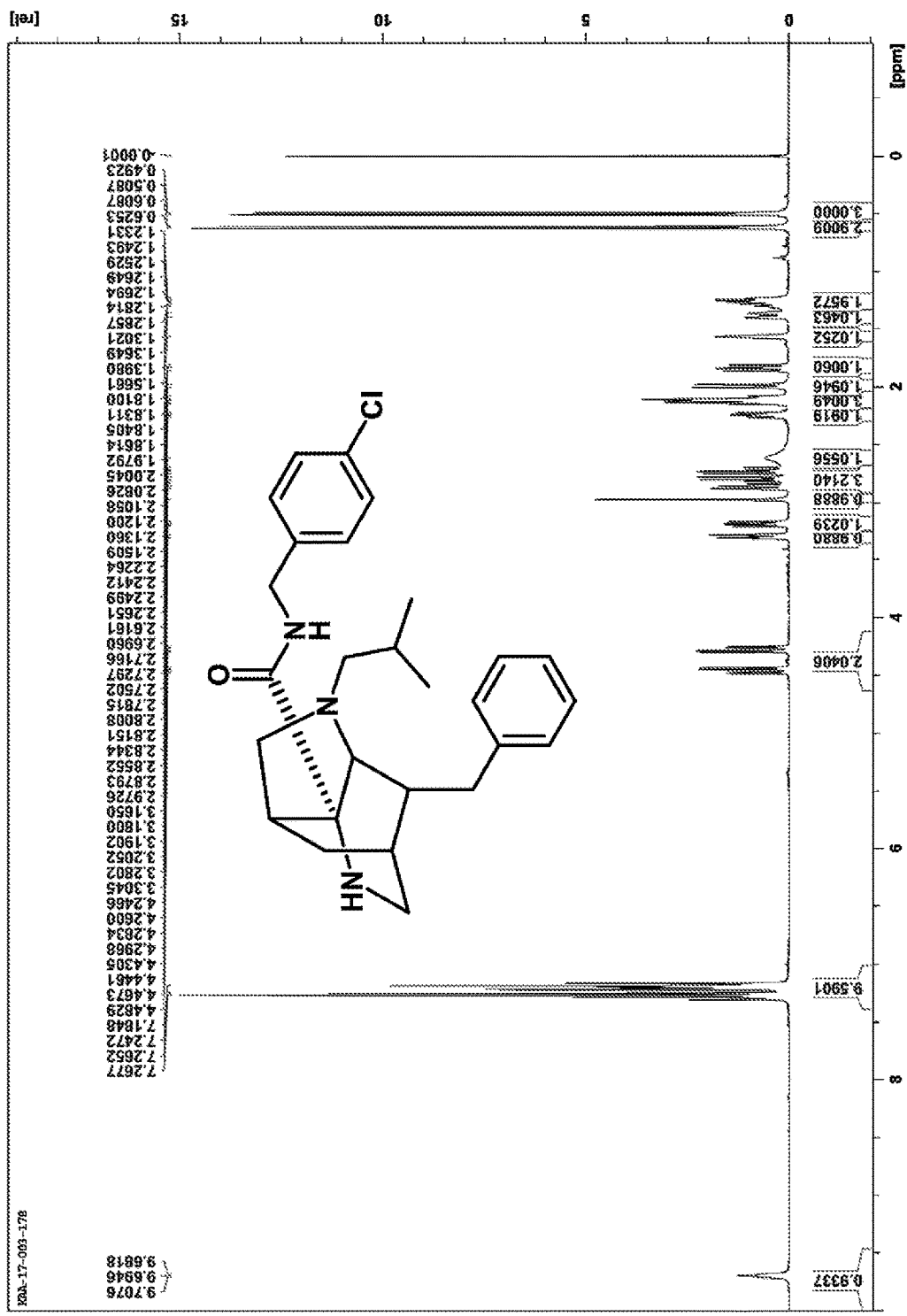
FIG. 40 shows the $^1$H-NMR chart for an exemplary compound of the present disclosure (formula in the figure).
Figure 41:
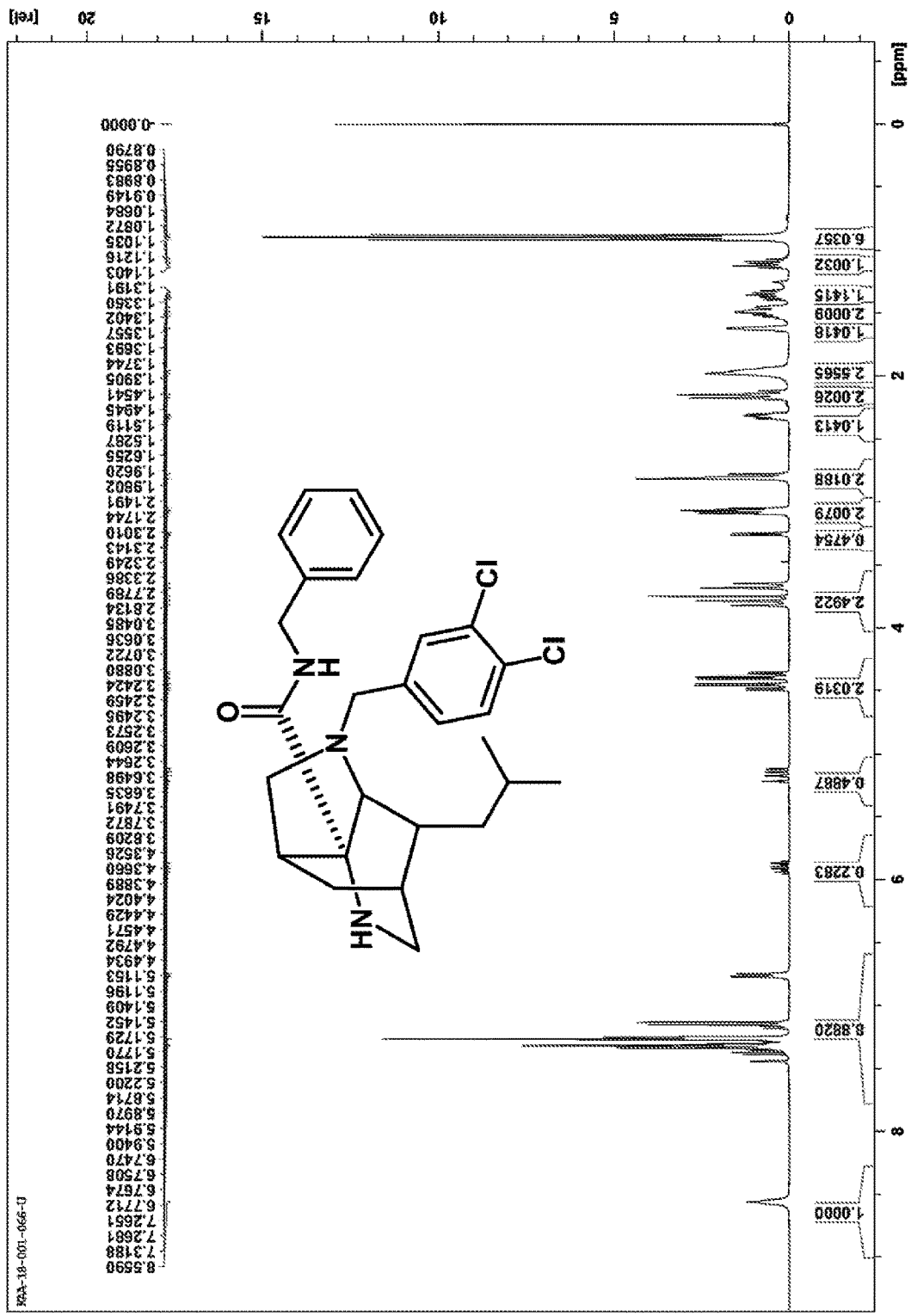
FIG. 41 shows the $^1$H-NMR chart for an exemplary compound of the present disclosure (formula in the figure).
Figure 42:
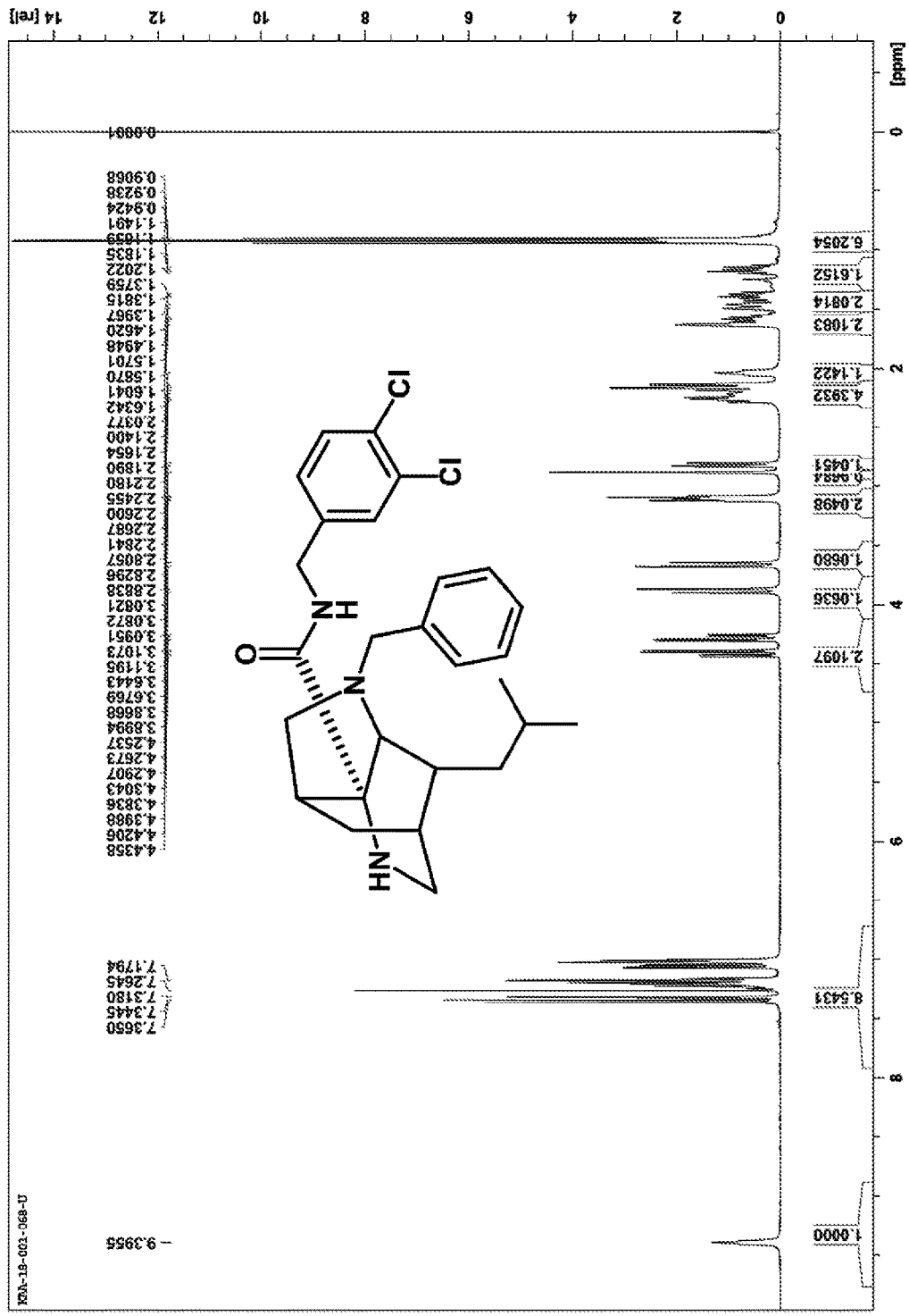
FIG. 42 shows the $^1$H-NMR chart for an exemplary compound of the present disclosure (formula in the figure).
Figure 43:
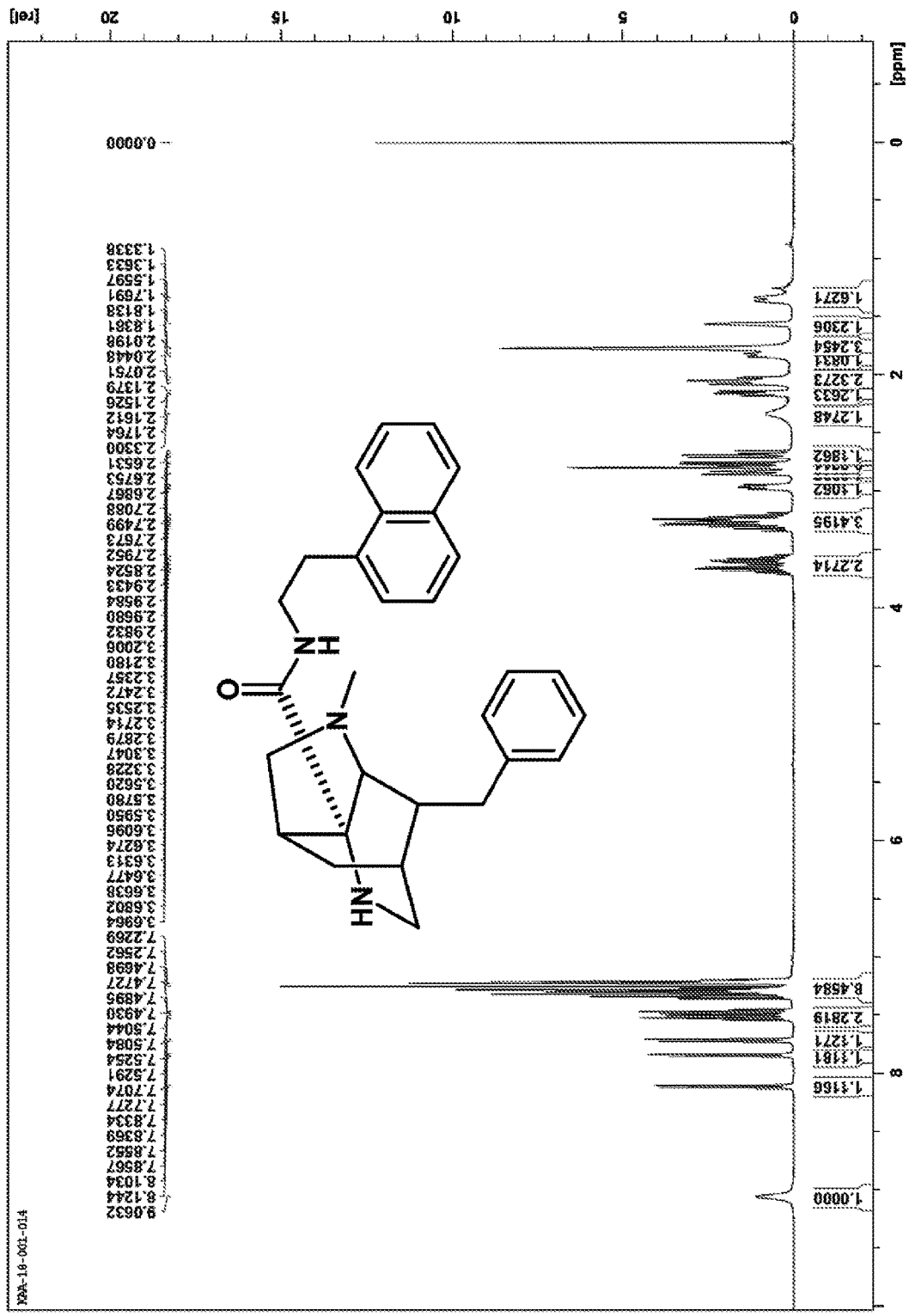
FIG. 43 shows the $^1$H-NMR chart for an exemplary compound of the present disclosure (formula in the figure).
Figure 44:
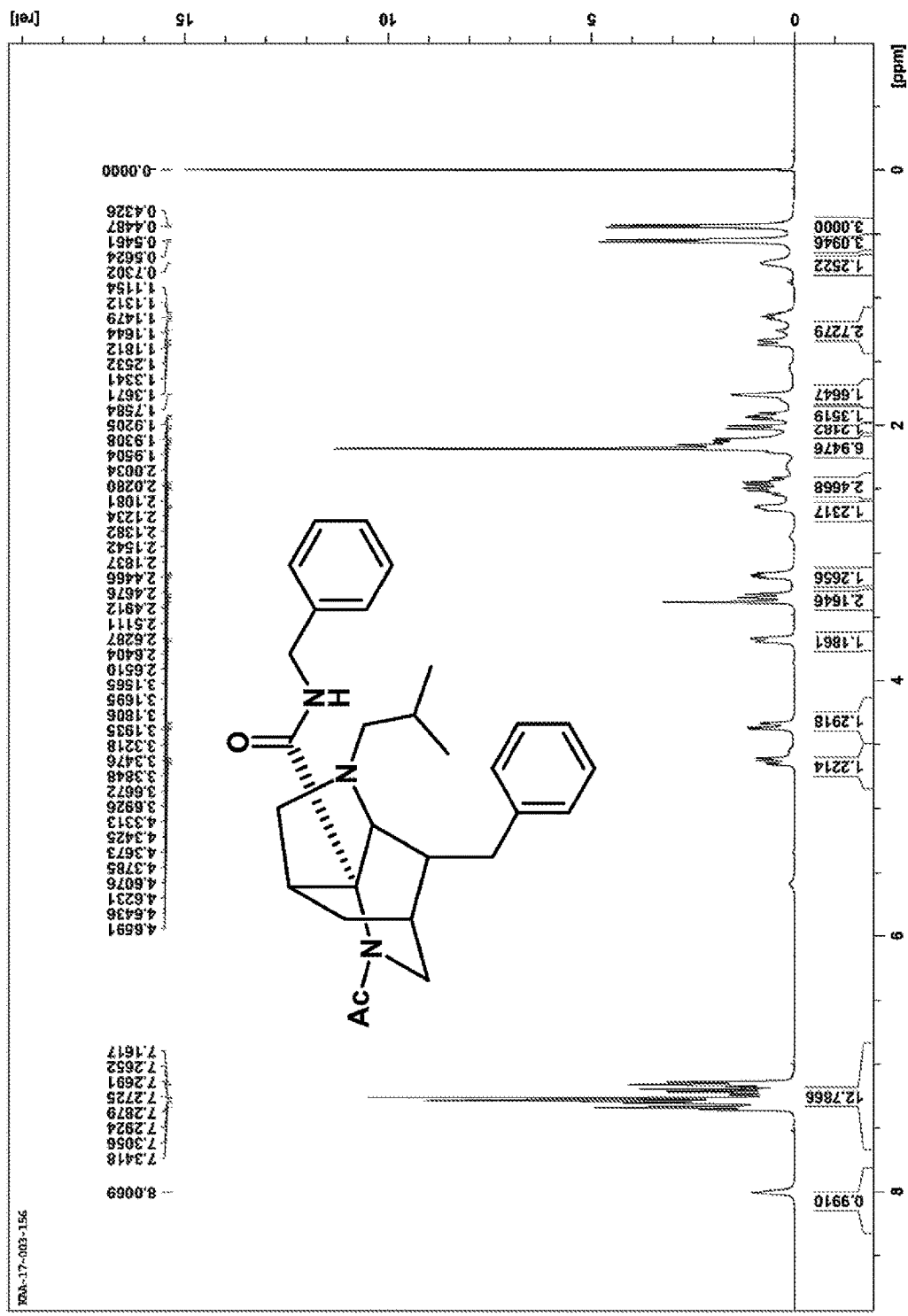
FIG. 44 shows the $^1$H-NMR chart for an exemplary compound of the present disclosure (formula in the figure).
Figure 45:
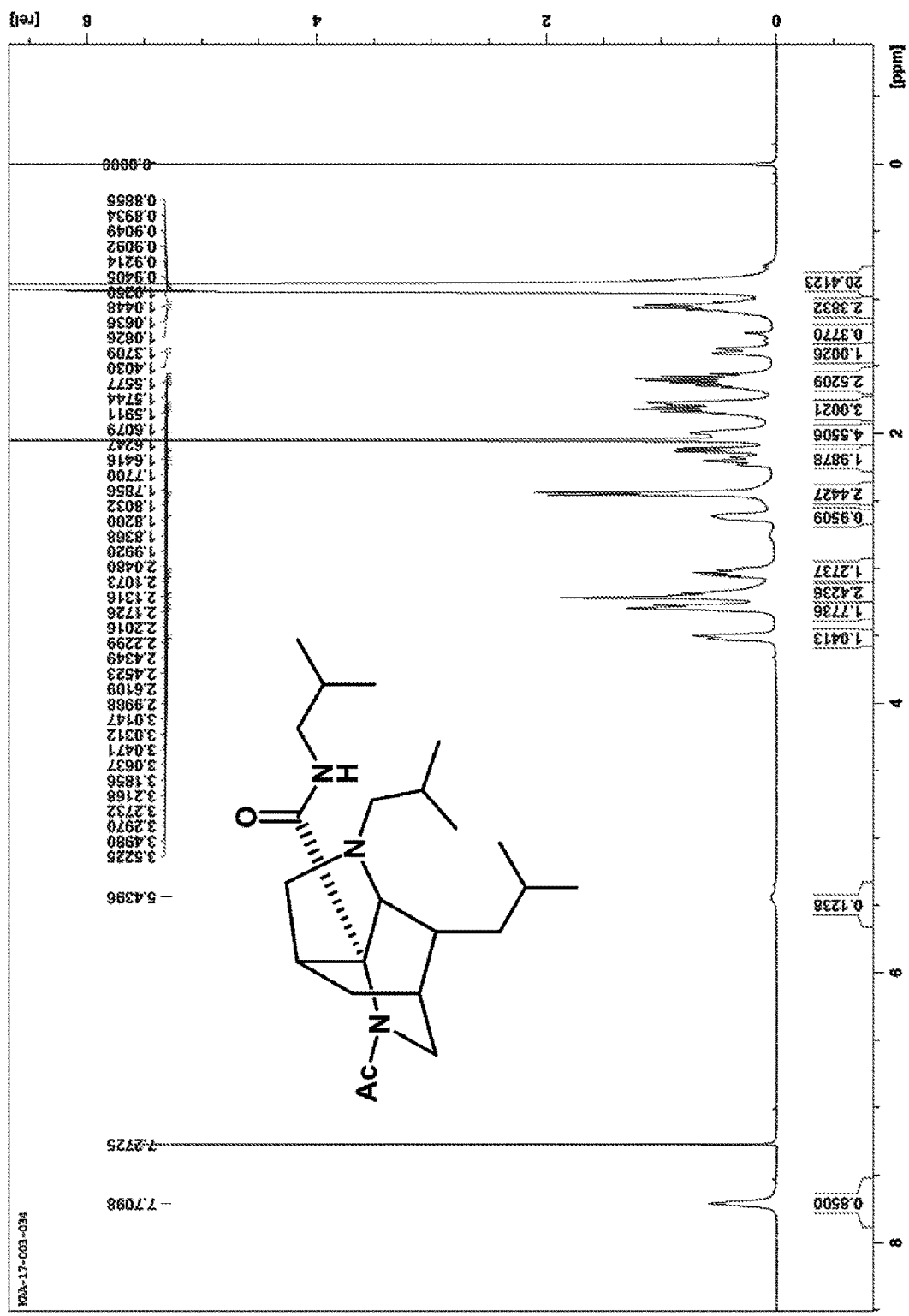
FIG. 45 shows the $^1$H-NMR chart for an exemplary compound of the present disclosure (formula in the figure).
Figure 46:
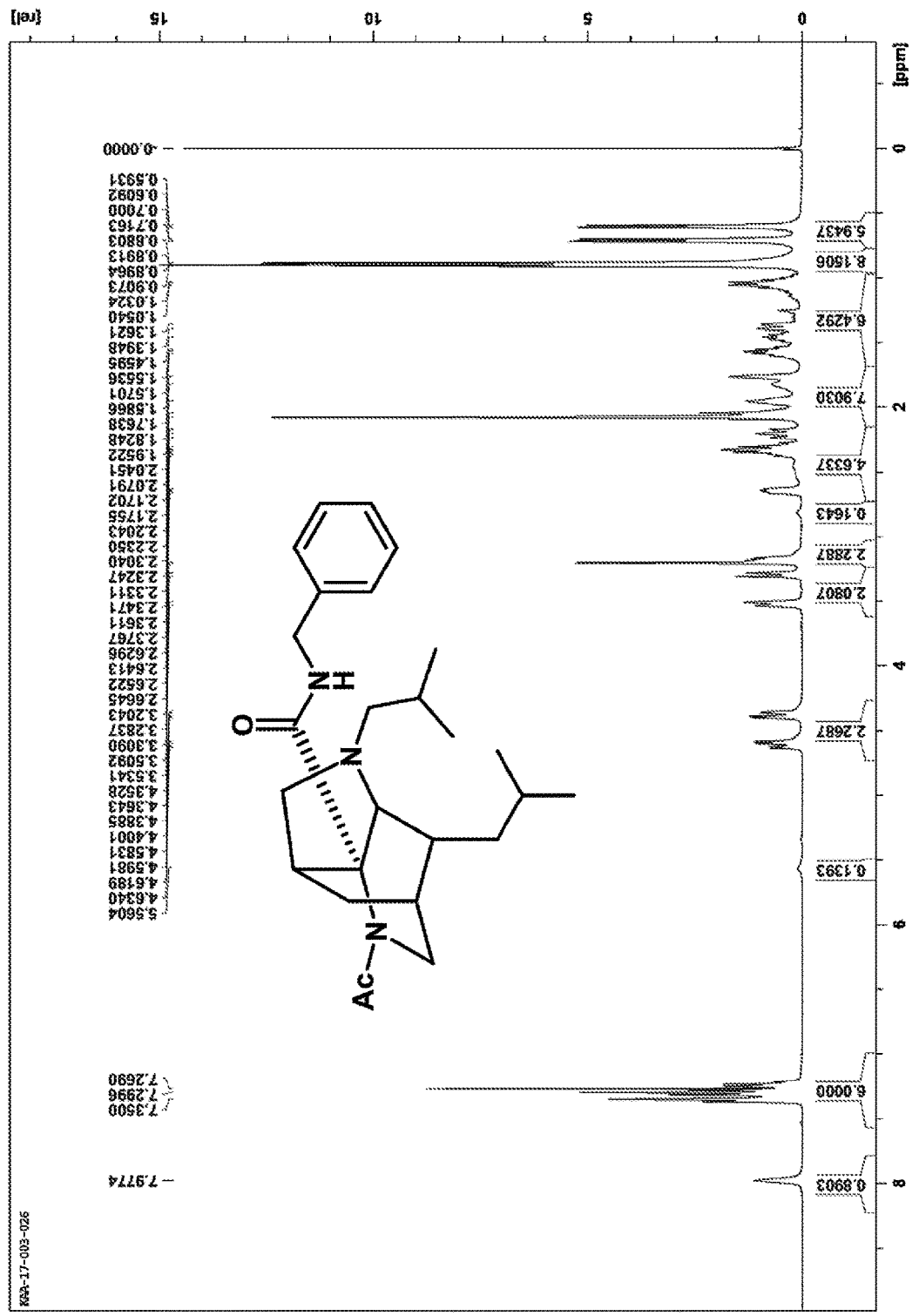
FIG. 46 shows the $^1$H-NMR chart for an exemplary compound of the present disclosure (formula in the figure).
Figure 47:
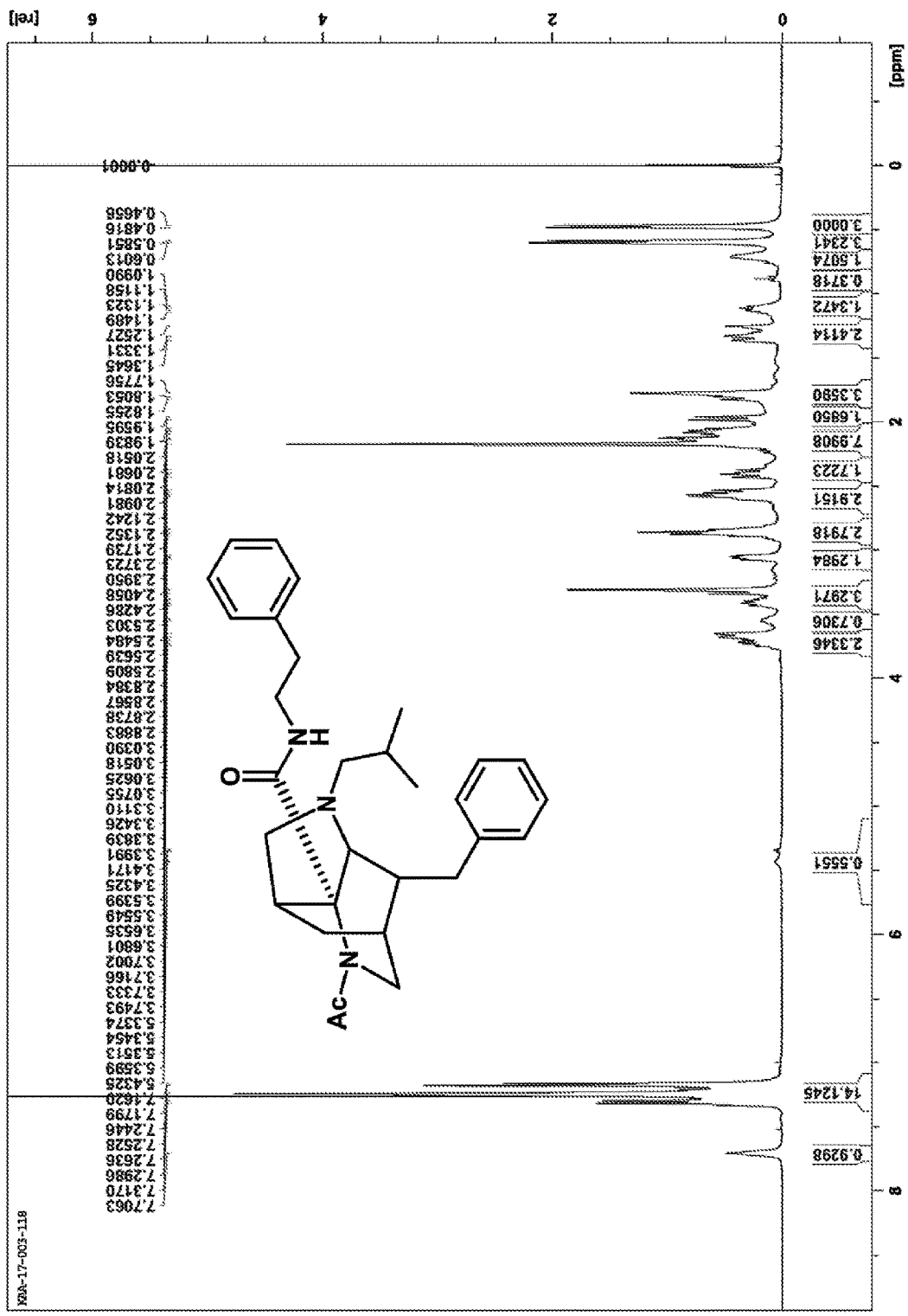
FIG. 47 shows the $^1$H-NMR chart for an exemplary compound of the present disclosure (formula in the figure).
Figure 48:
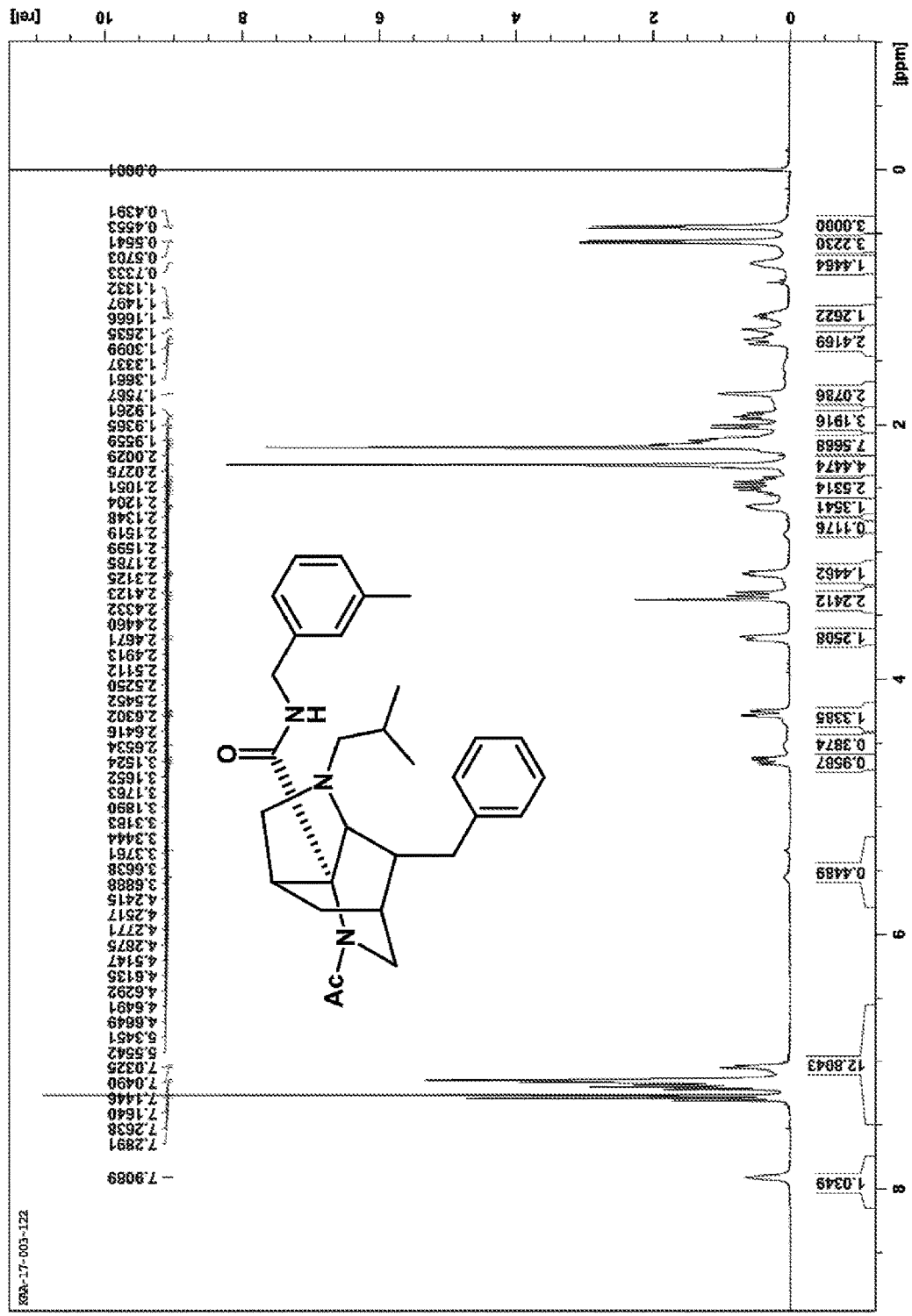
FIG. 48 shows the $^1$H-NMR chart for an exemplary compound of the present disclosure (formula in the figure).
Figure 49:
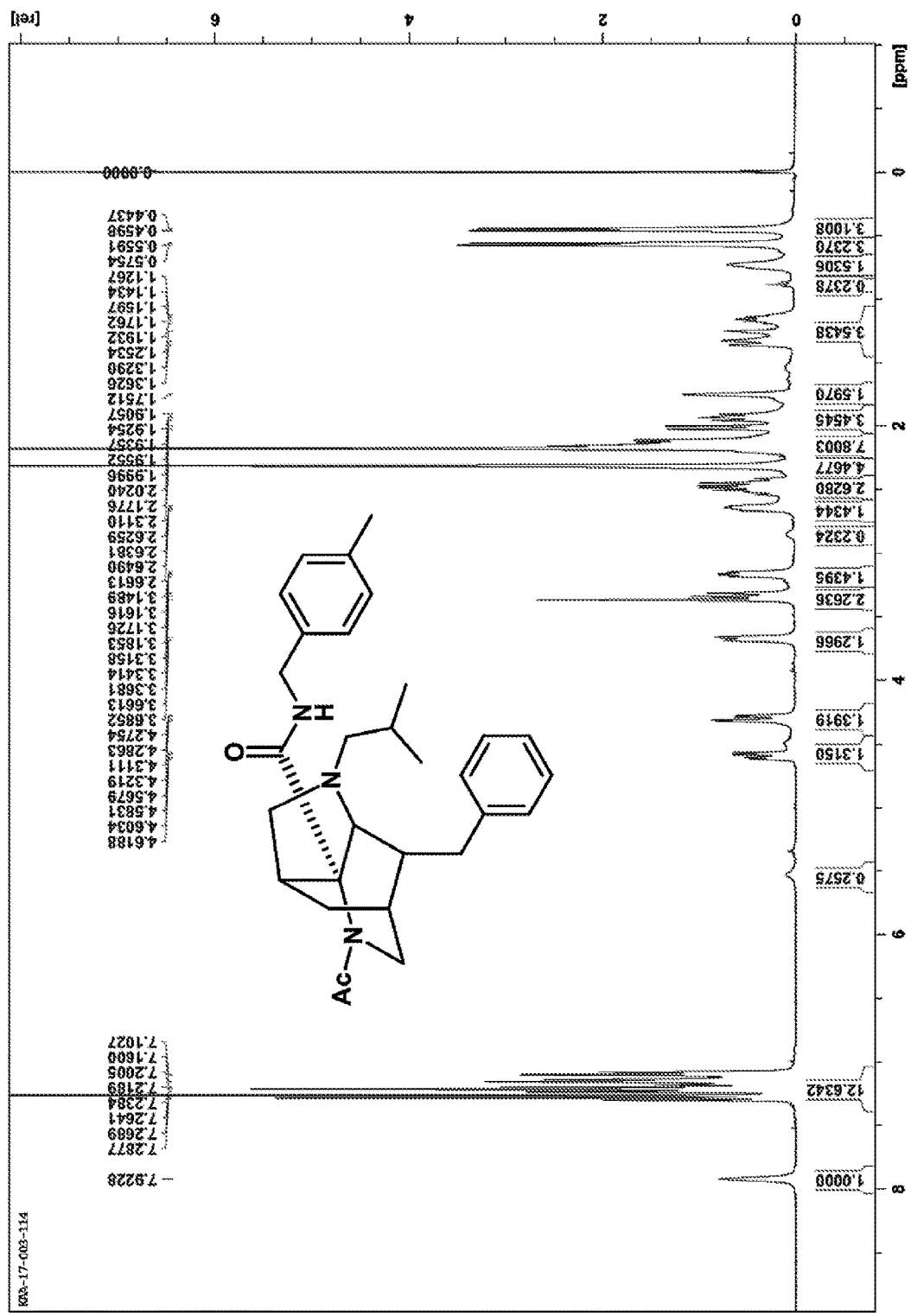
FIG. 49 shows the $^1$H-NMR chart for an exemplary compound of the present disclosure (formula in the figure).
Figure 50:
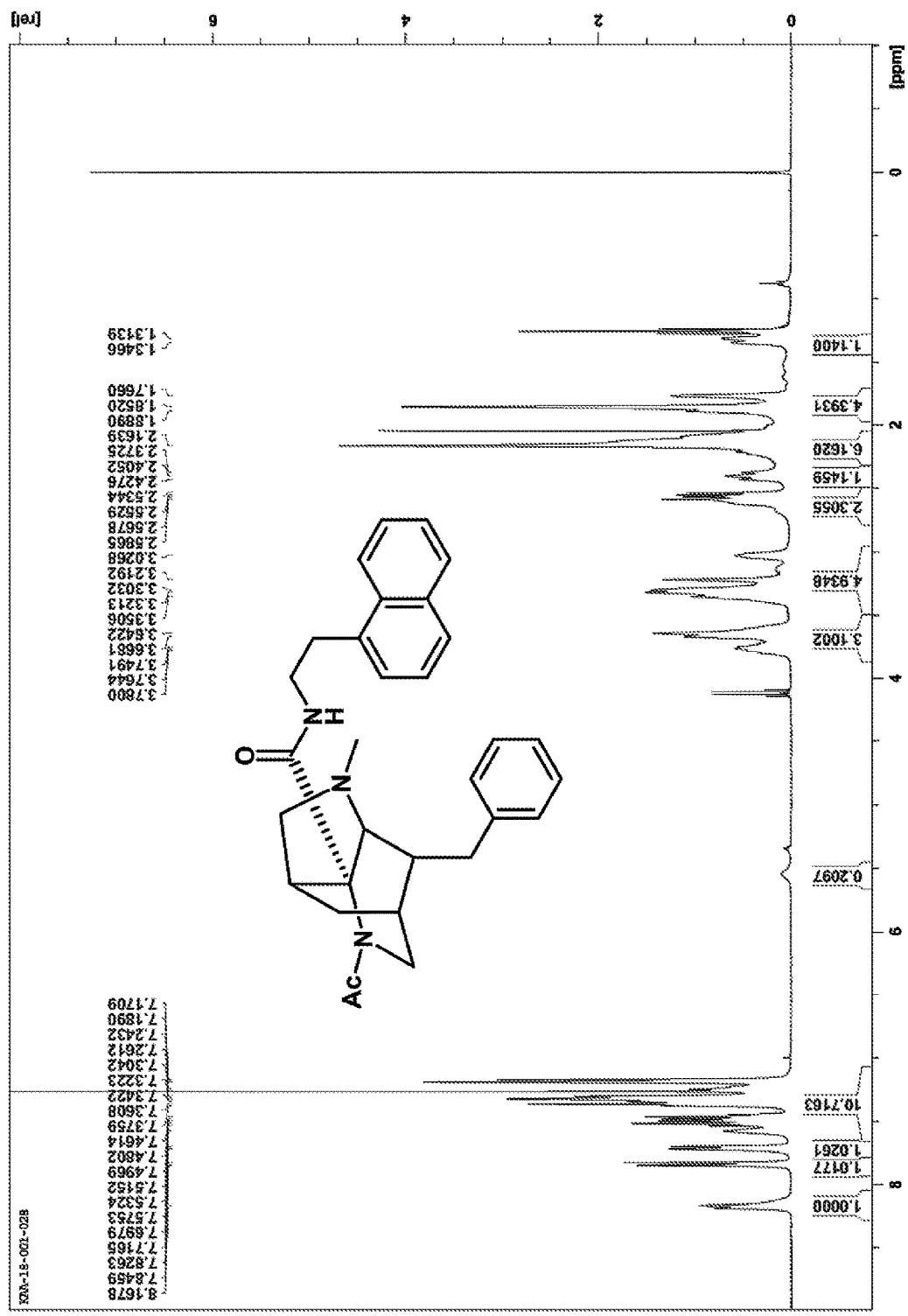
FIG. 50 shows the $^1$H-NMR chart for an exemplary compound of the present disclosure (formula in the figure).
Figure 51:
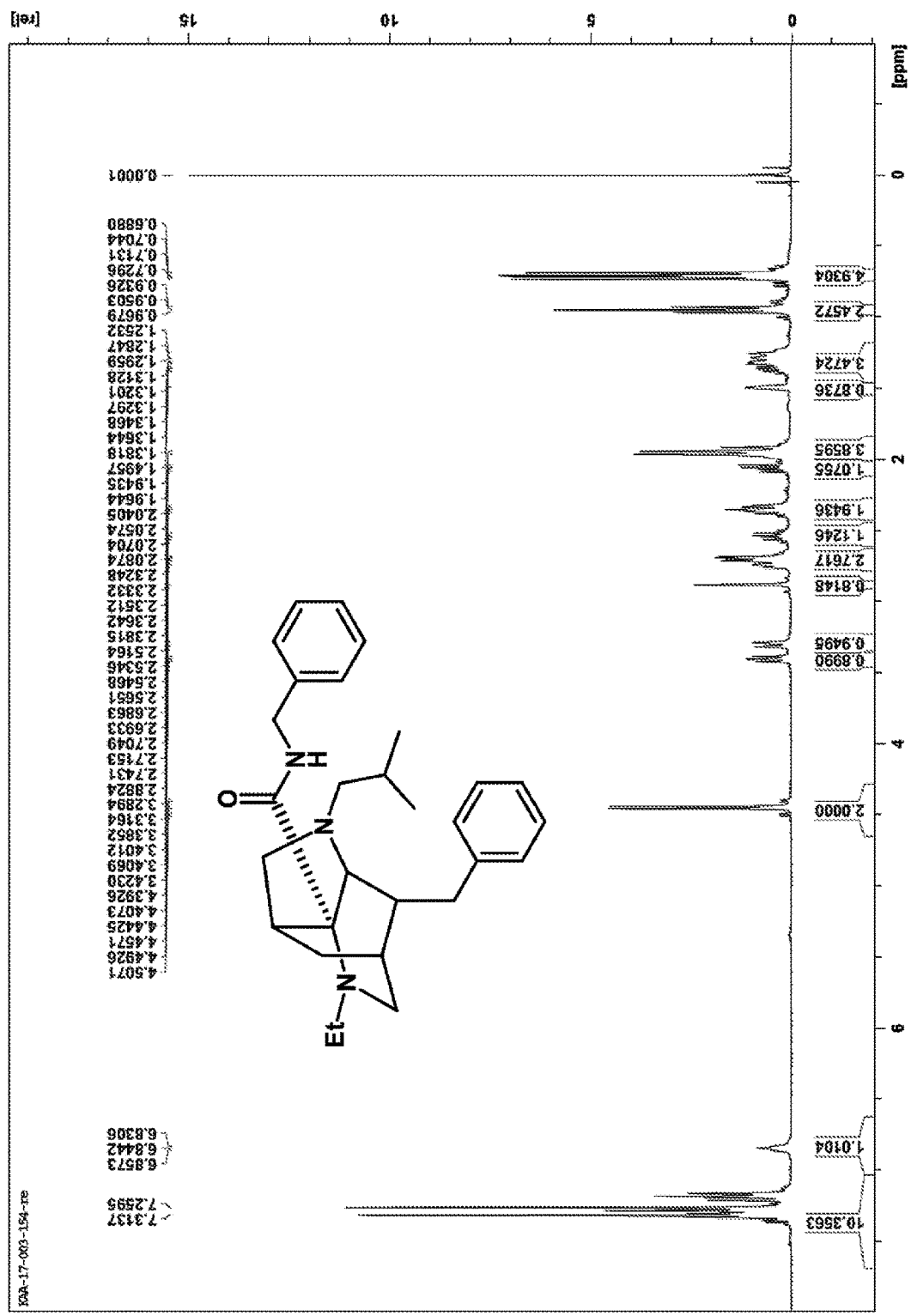
FIG. 51 shows the $^1$H-NMR chart for an exemplary compound of the present disclosure (formula in the figure).
Figure 52:
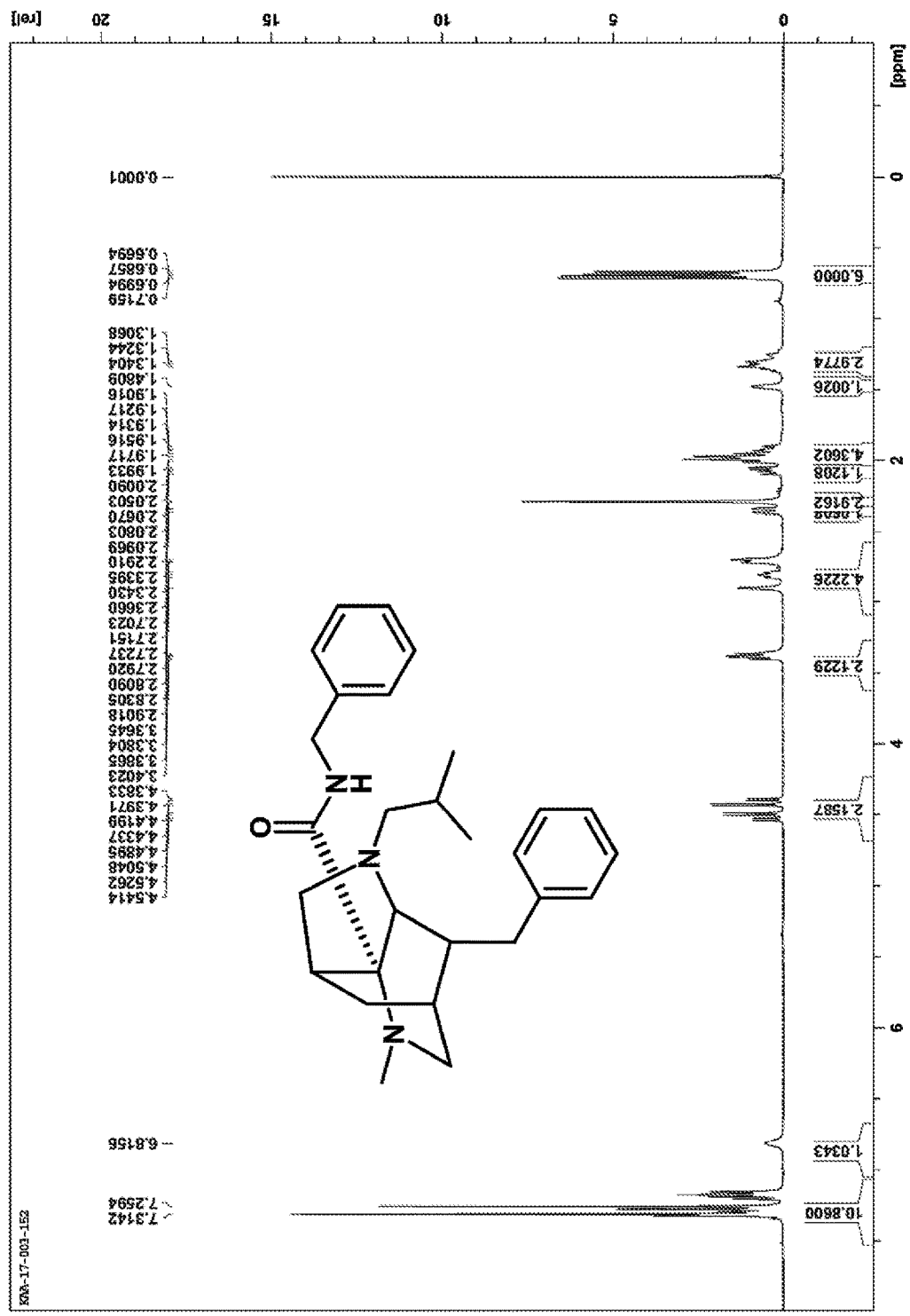
FIG. 52 shows the $^1$H-NMR chart for an exemplary compound of the present disclosure (formula in the figure).
Figure 53:
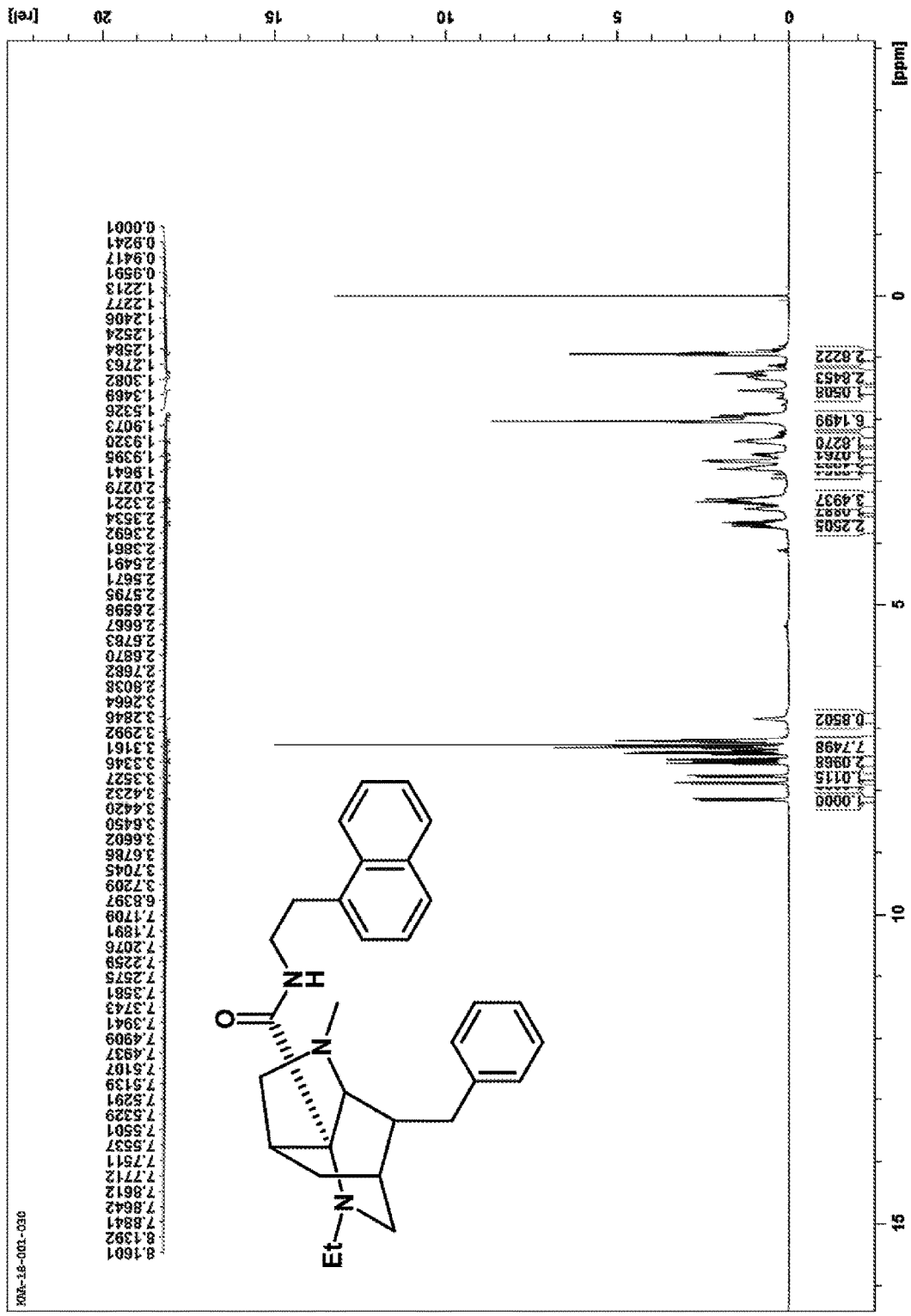
FIG. 53 shows the $^1$H-NMR chart for an exemplary compound of the present disclosure (formula in the figure).
Figure 54:
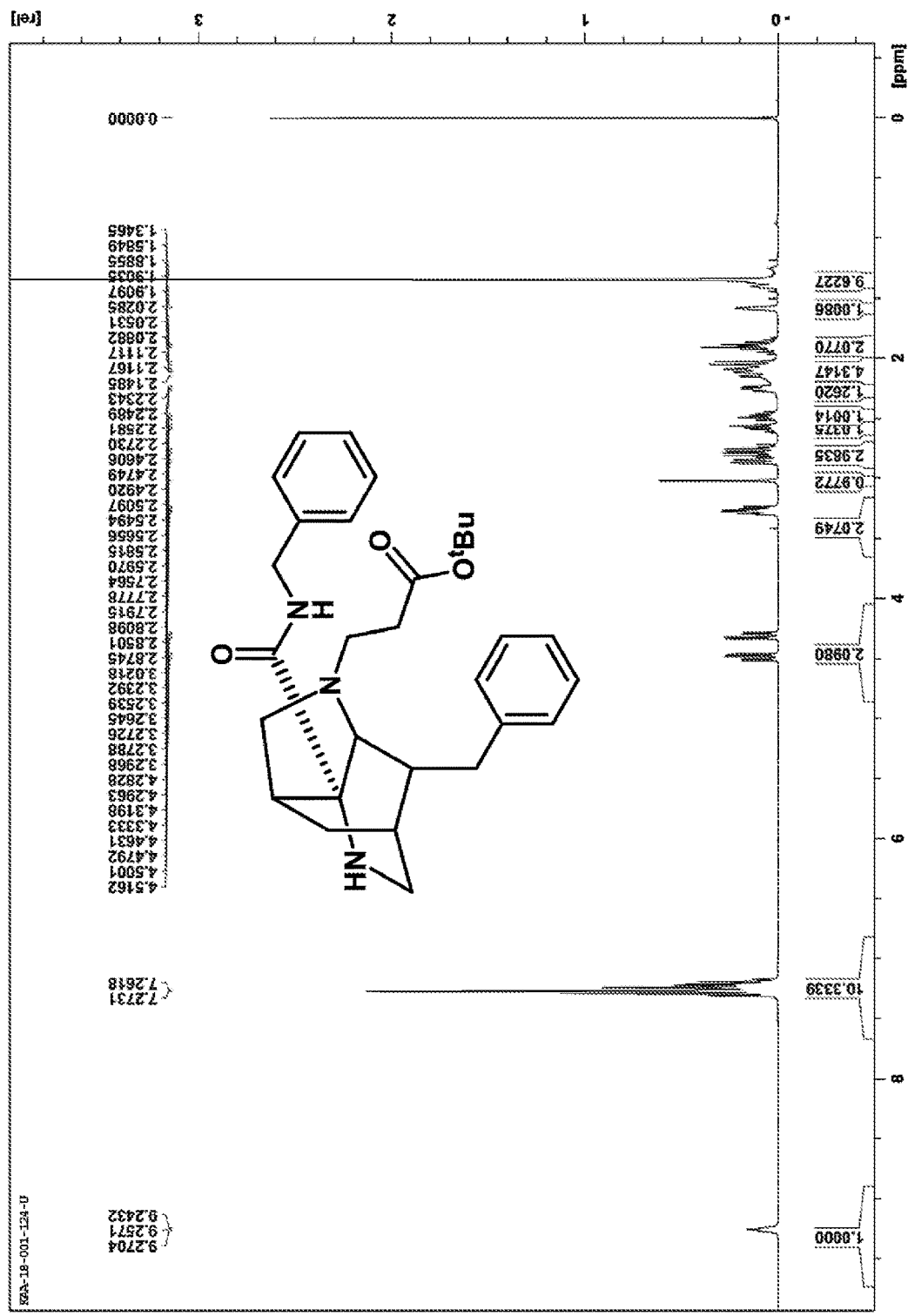
FIG. 54 shows the $^1$H-NMR chart for an exemplary compound of the present disclosure (formula in the figure).
Figure 55:
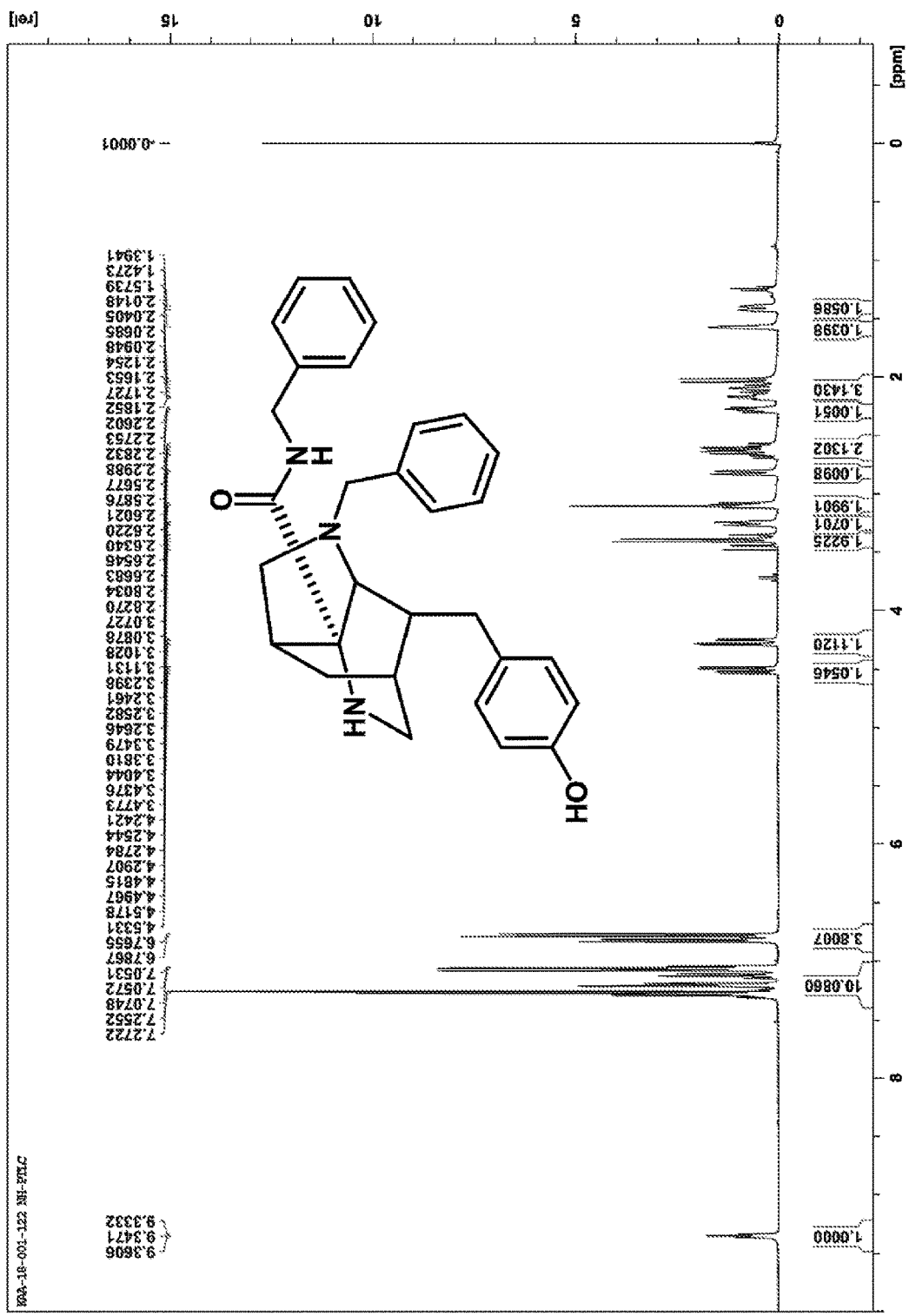
FIG. 55 shows the $^1$H-NMR chart for an exemplary compound of the present disclosure (formula in the figure).
Figure 56:
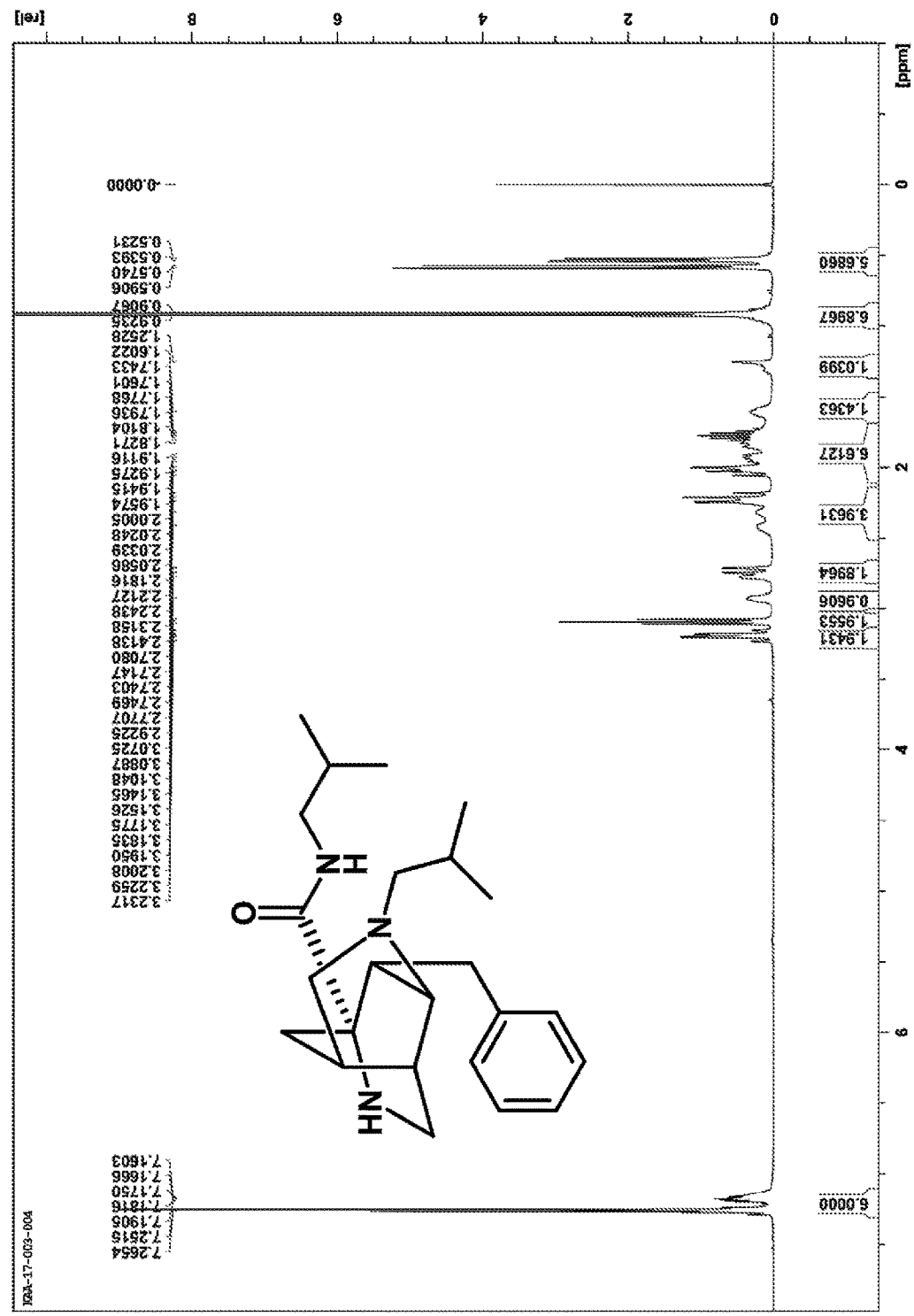
FIG. 56 shows the $^1$H-NMR chart for an exemplary compound of the present disclosure (formula in the figure).
Figure 57:
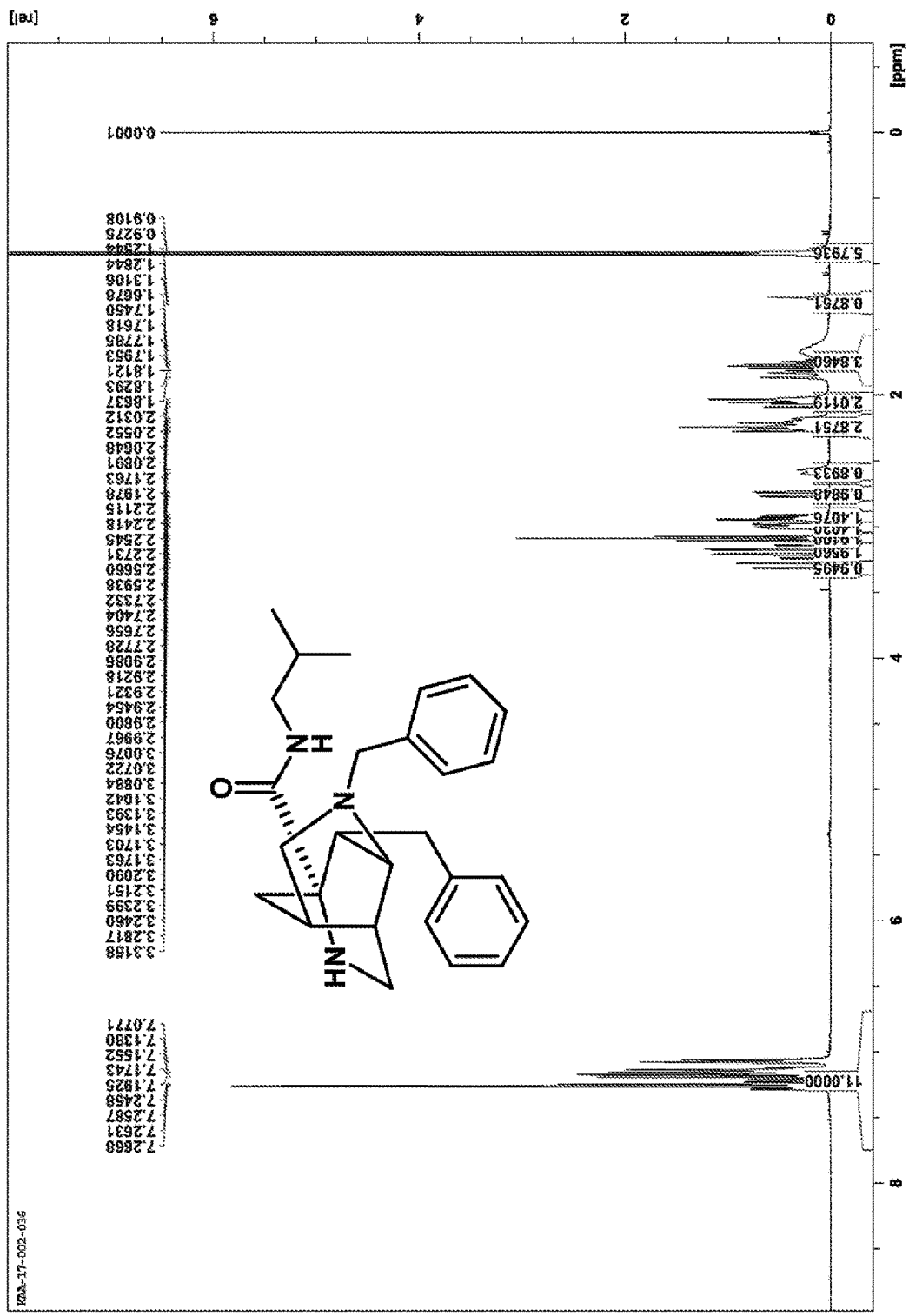
FIG. 57 shows the $^1$H-NMR chart for an exemplary compound of the present disclosure (formula in the figure).
Figure 58:
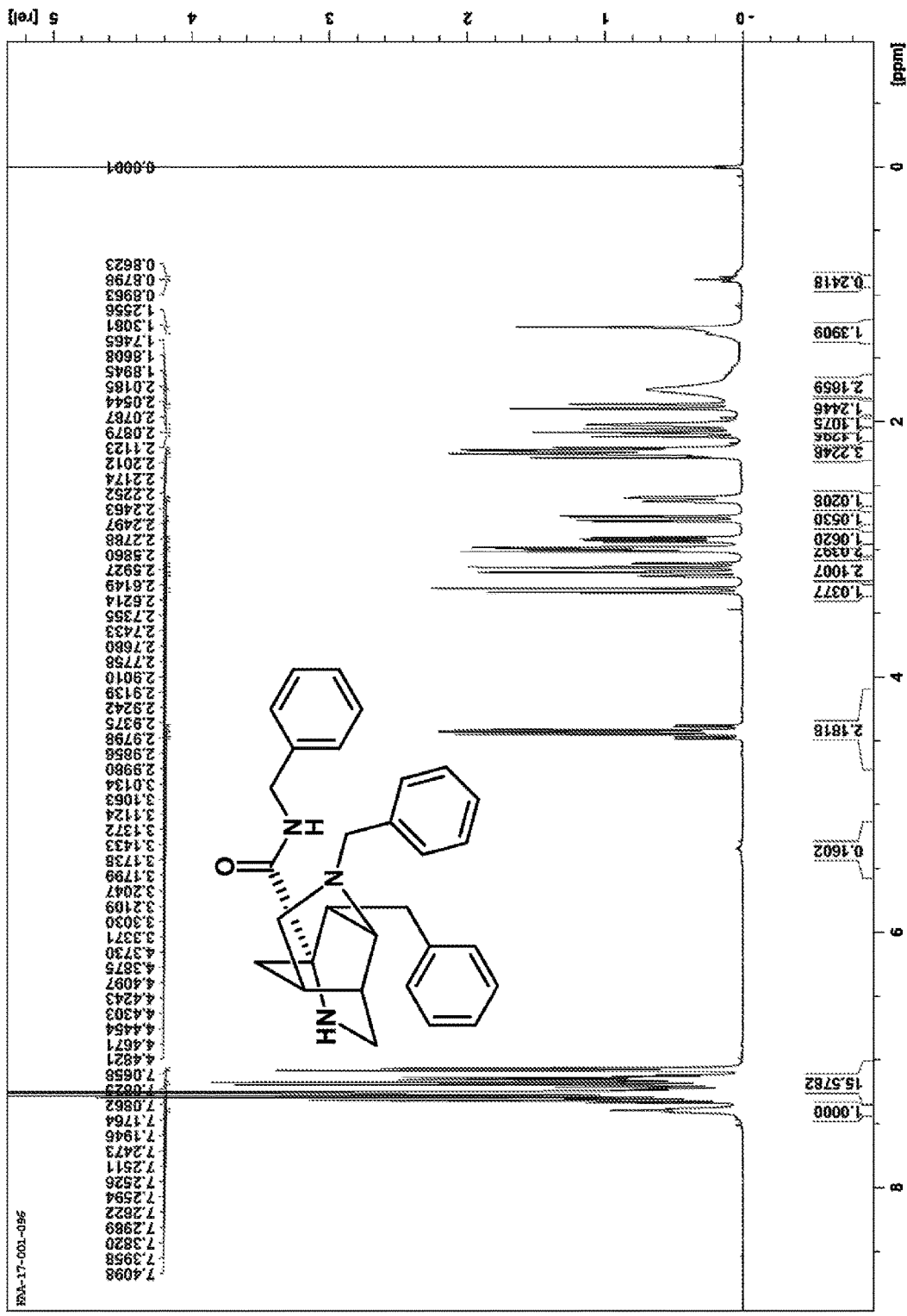
FIG. 58 shows the $^1$H-NMR chart for an exemplary compound of the present disclosure (formula in the figure).
Figure 59:
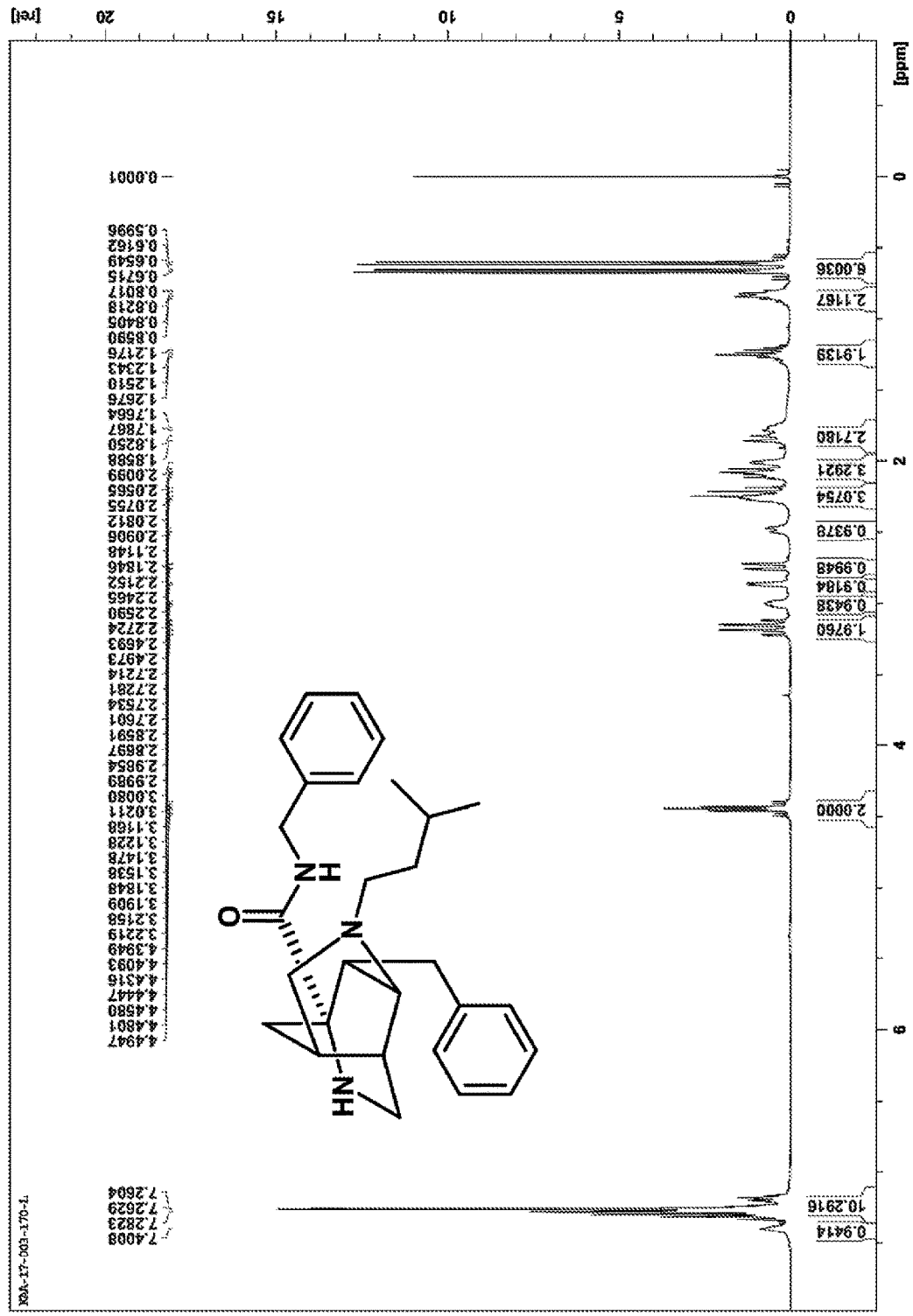
FIG. 59 shows the $^1$H-NMR chart for an exemplary compound of the present disclosure (formula in the figure).
Figure 60:
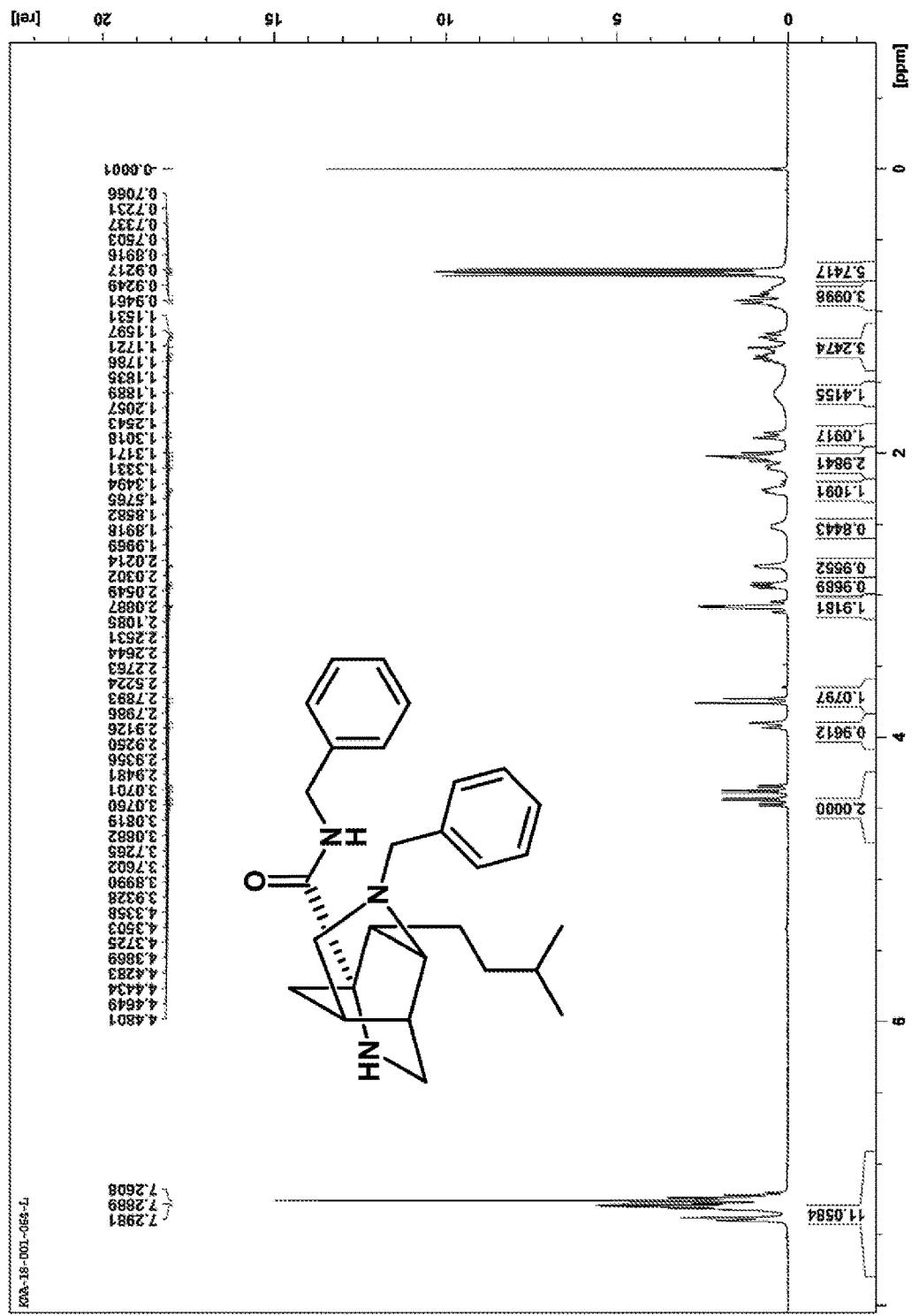
FIG. 60 shows the $^1$H-NMR chart for an exemplary compound of the present disclosure (formula in the figure).
Figure 61:
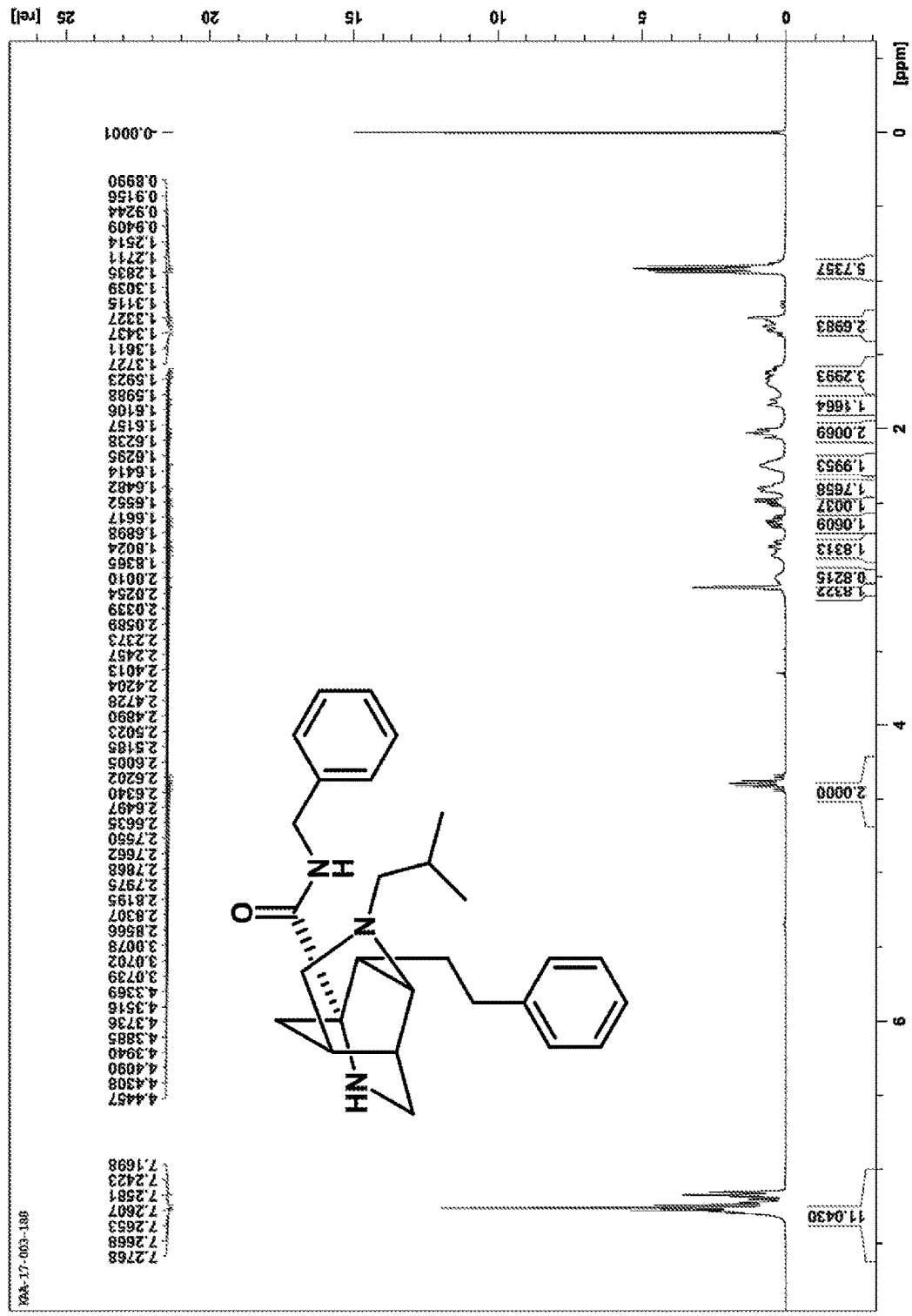
FIG. 61 shows the $^1$H-NMR chart for an exemplary compound of the present disclosure (formula in the figure).
Figure 62:
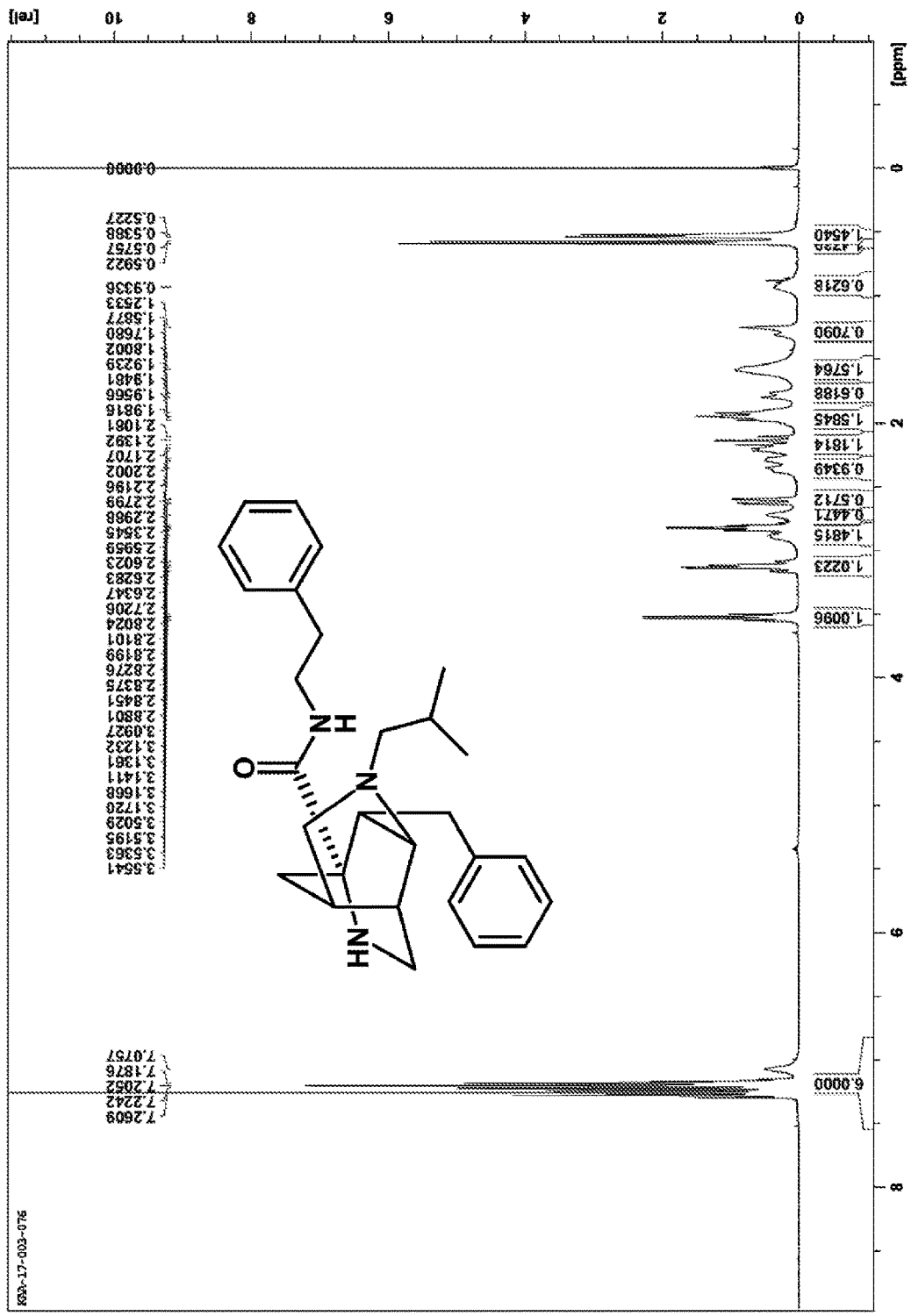
FIG. 62 shows the $^1$H-NMR chart for an exemplary compound of the present disclosure (formula in the figure).
Figure 63:
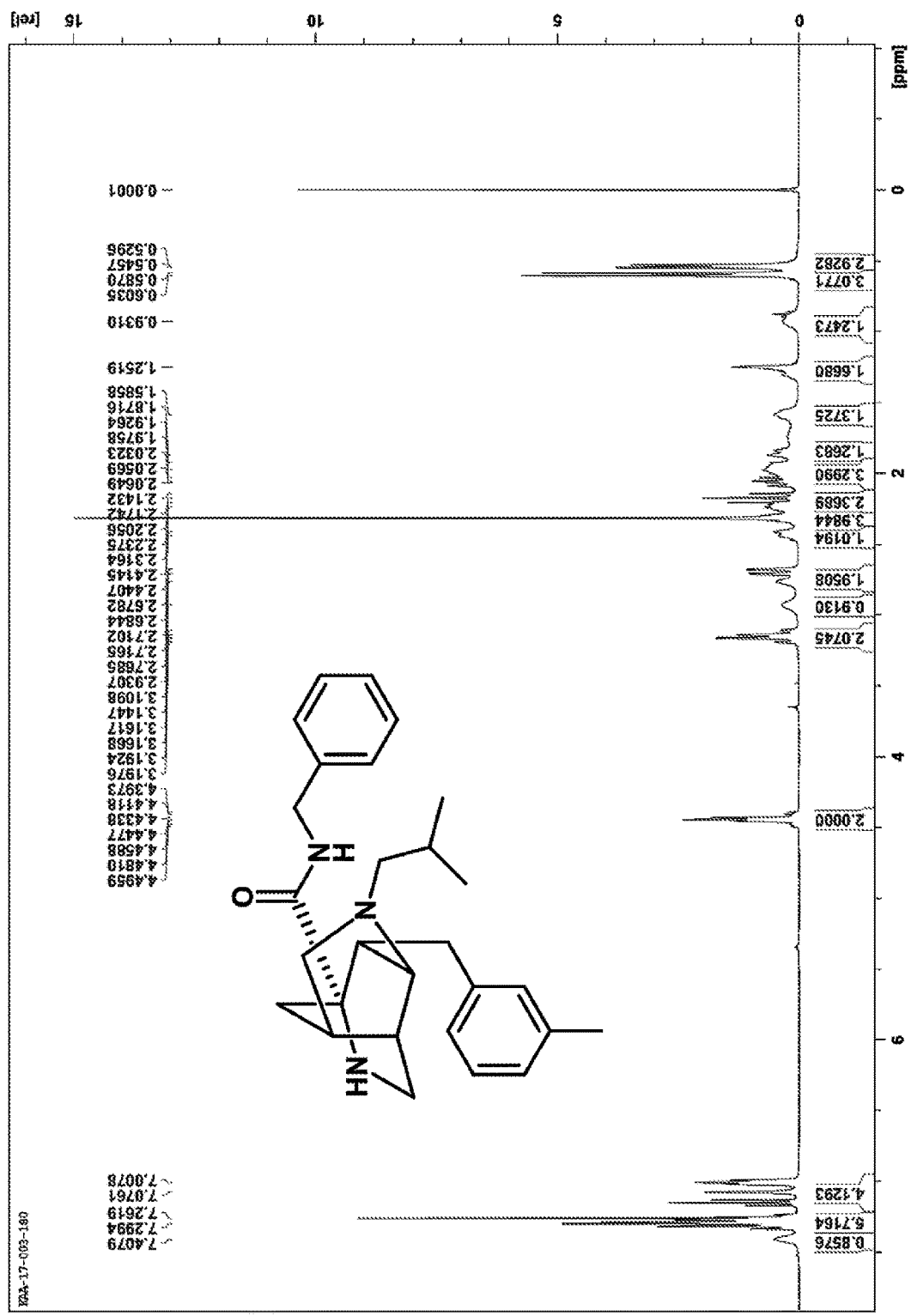
FIG. 63 shows the $^1$H-NMR chart for an exemplary compound of the present disclosure (formula in the figure).
Figure 64:
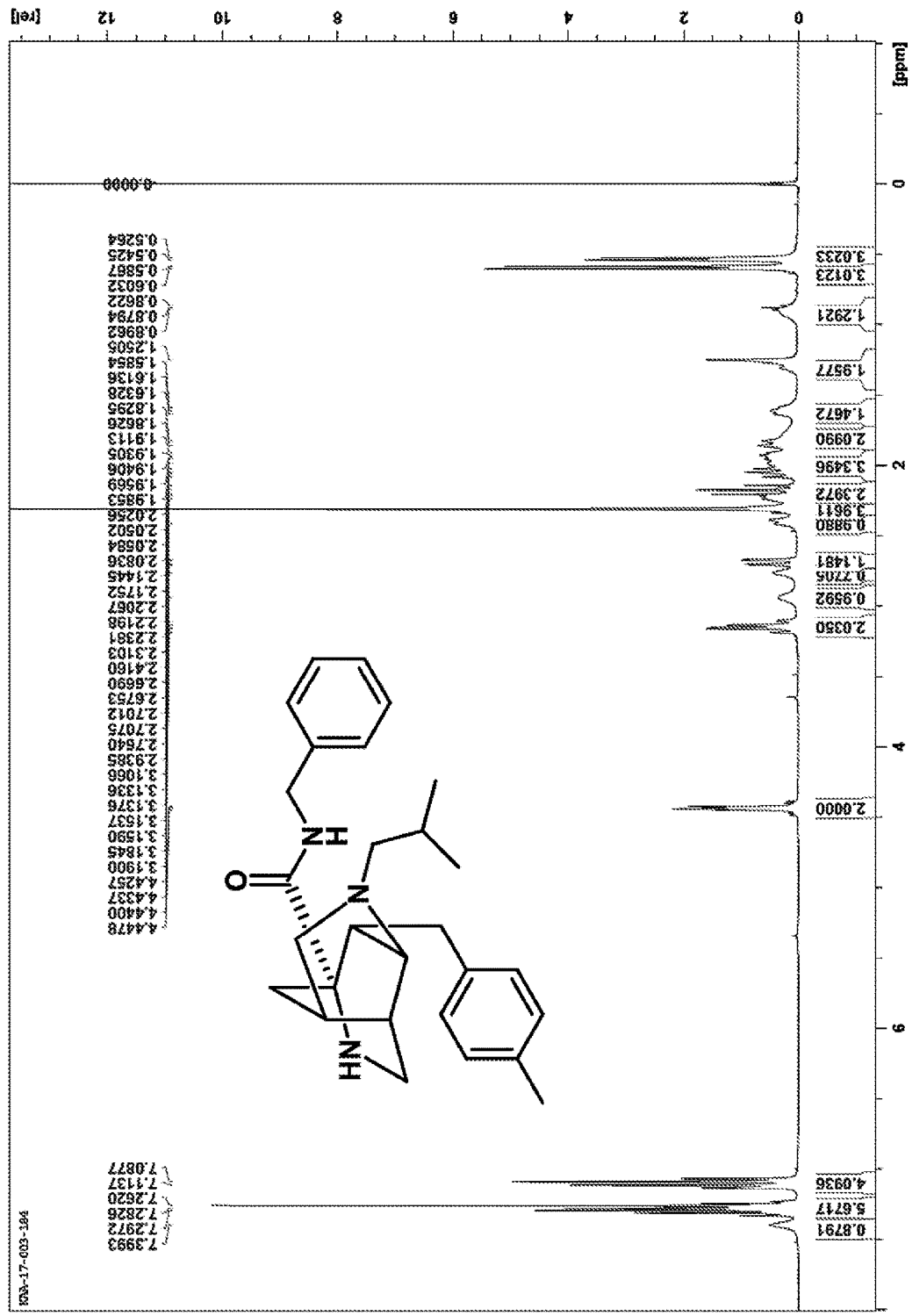
FIG. 64 shows the $^1$H-NMR chart for an exemplary compound of the present disclosure (formula in the figure).
Figure 65:
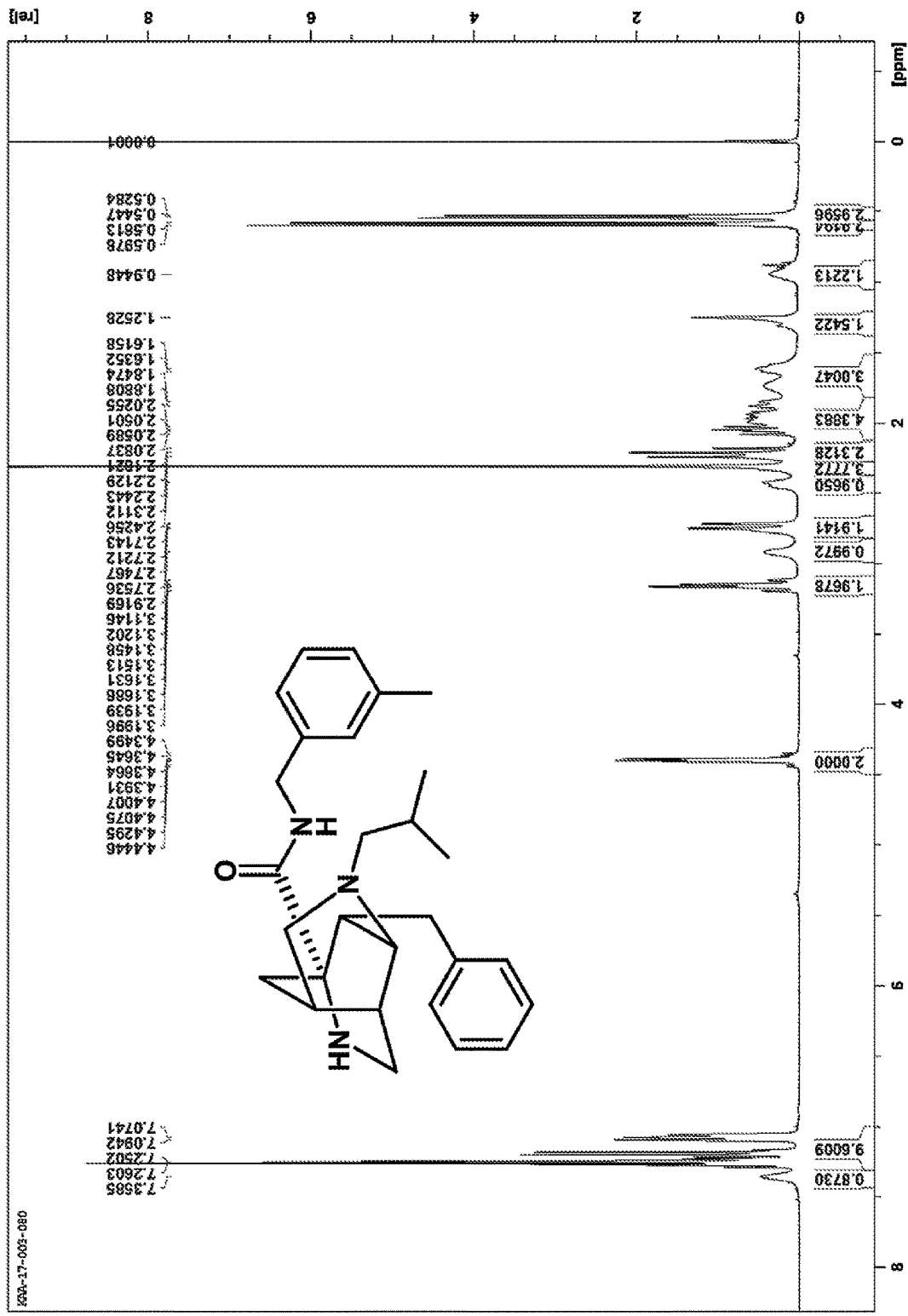
FIG. 65 shows the $^1$H-NMR chart for an exemplary compound of the present disclosure (formula in the figure).
Figure 66:
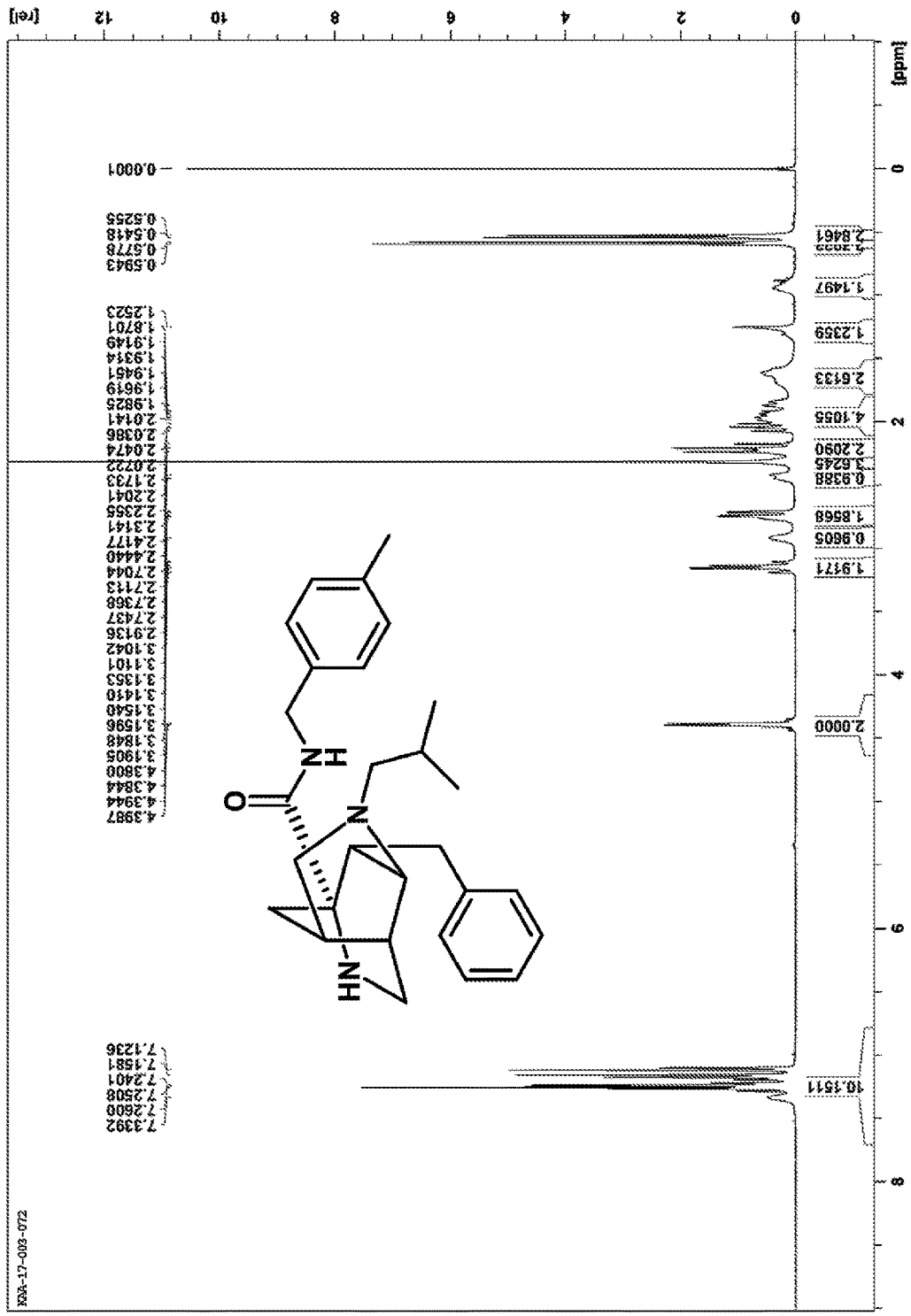
FIG. 66 shows the $^1$H-NMR chart for an exemplary compound of the present disclosure (formula in the figure).
Figure 67:
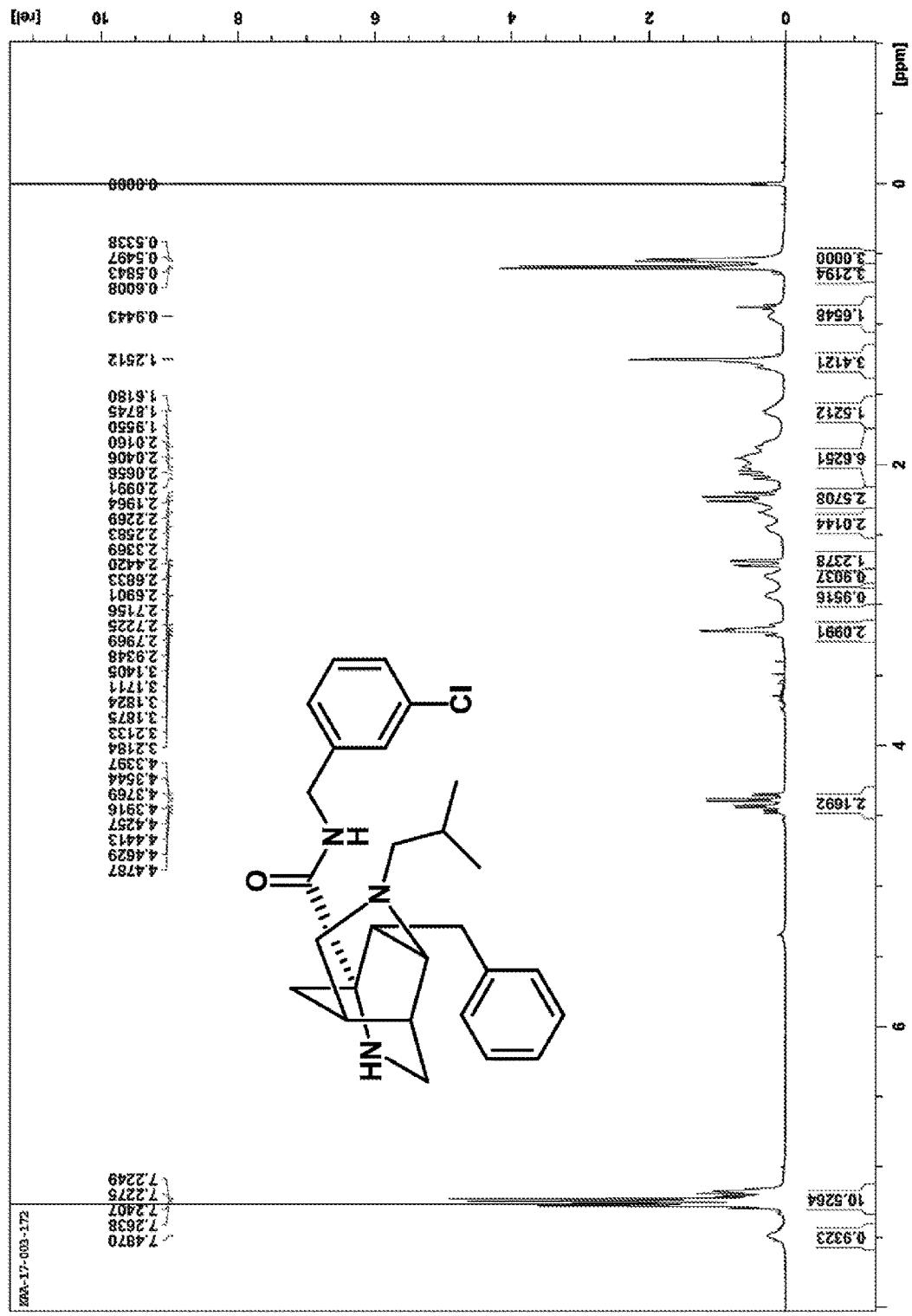
FIG. 67 shows the $^1$H-NMR chart for an exemplary compound of the present disclosure (formula in the figure).
Figure 68:
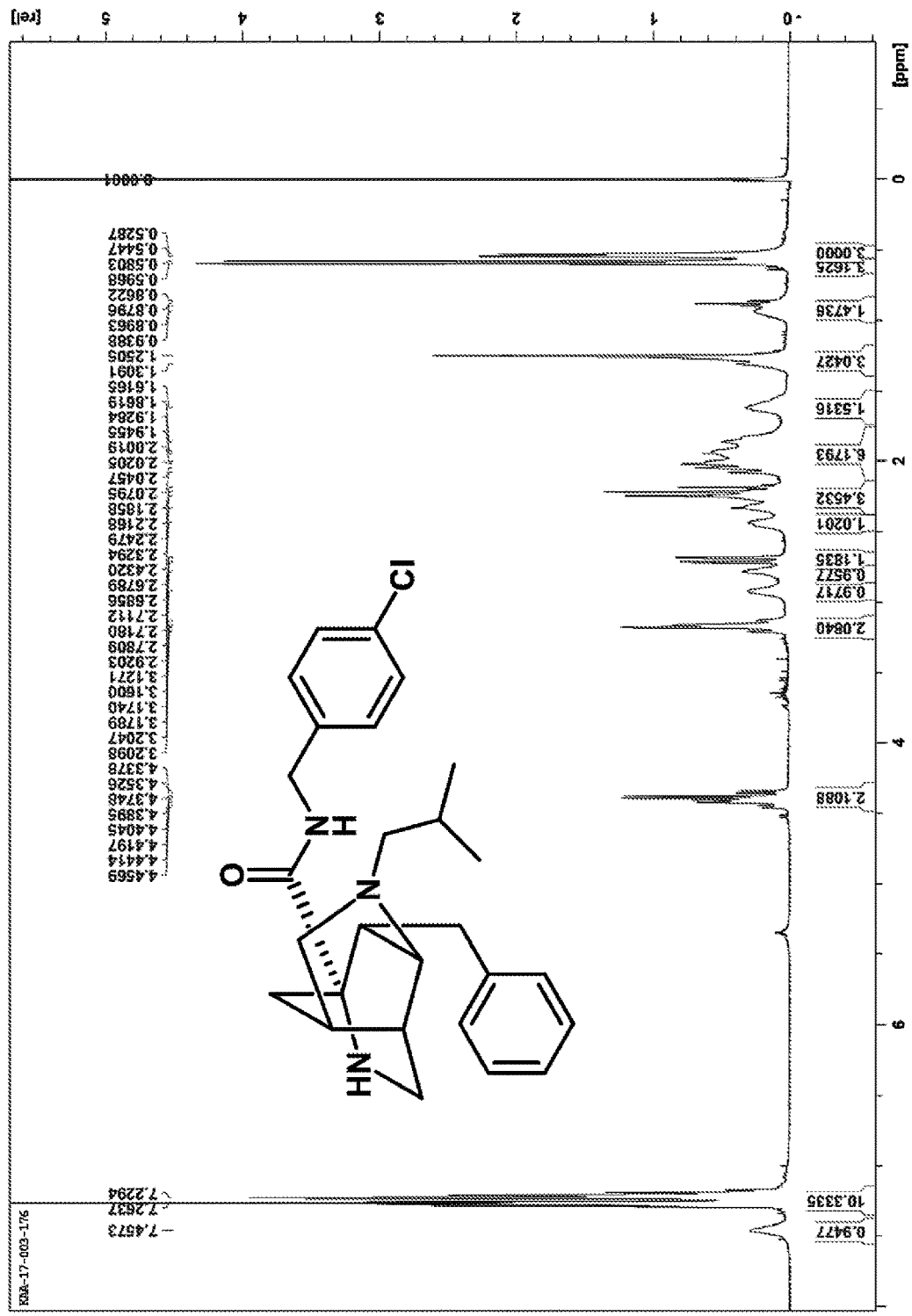
FIG. 68 shows the $^1$H-NMR chart for an exemplary compound of the present disclosure (formula in the figure).
Figure 69:
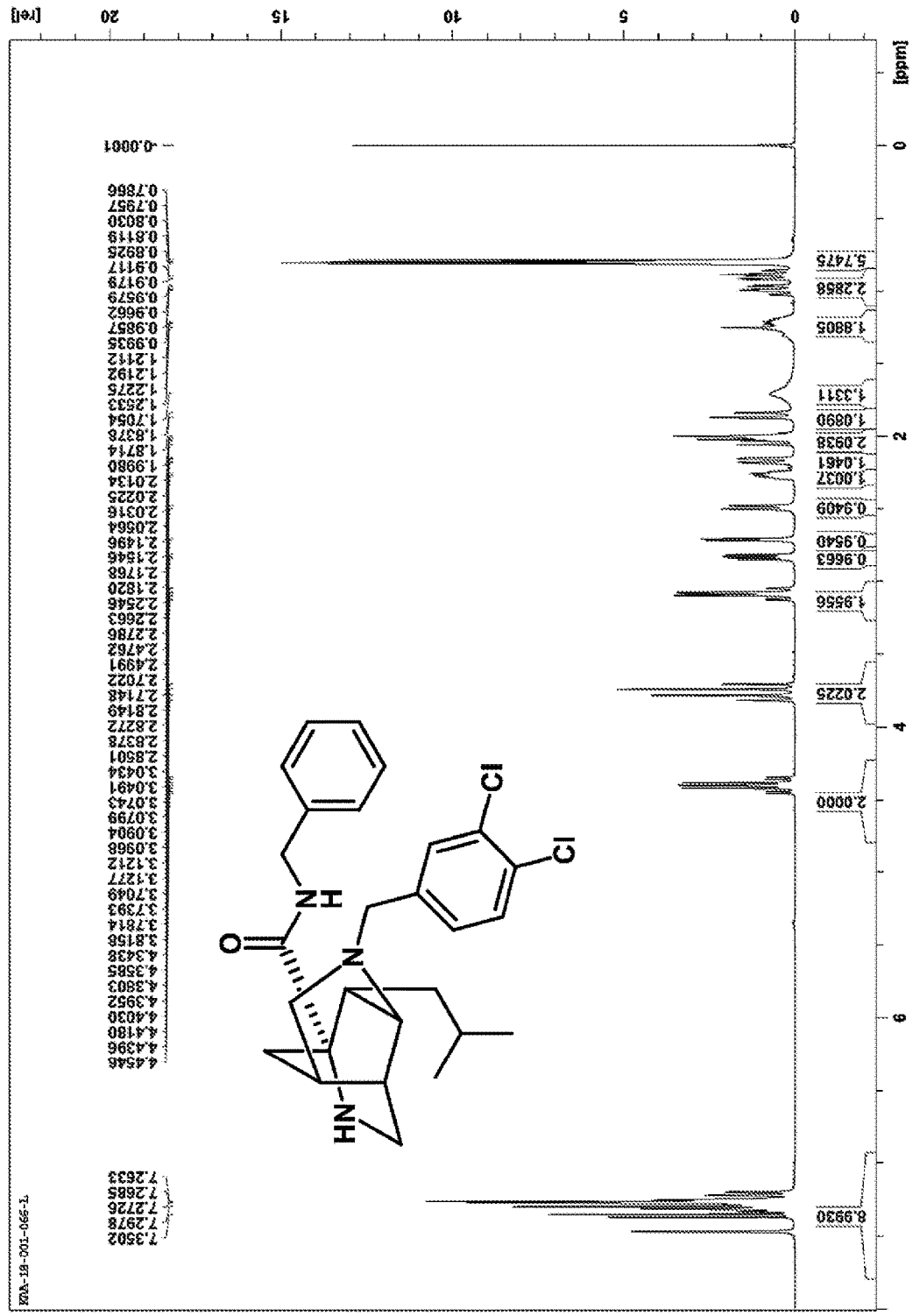
FIG. 69 shows the $^1$H-NMR chart for an exemplary compound of the present disclosure (formula in the figure).
Figure 70:
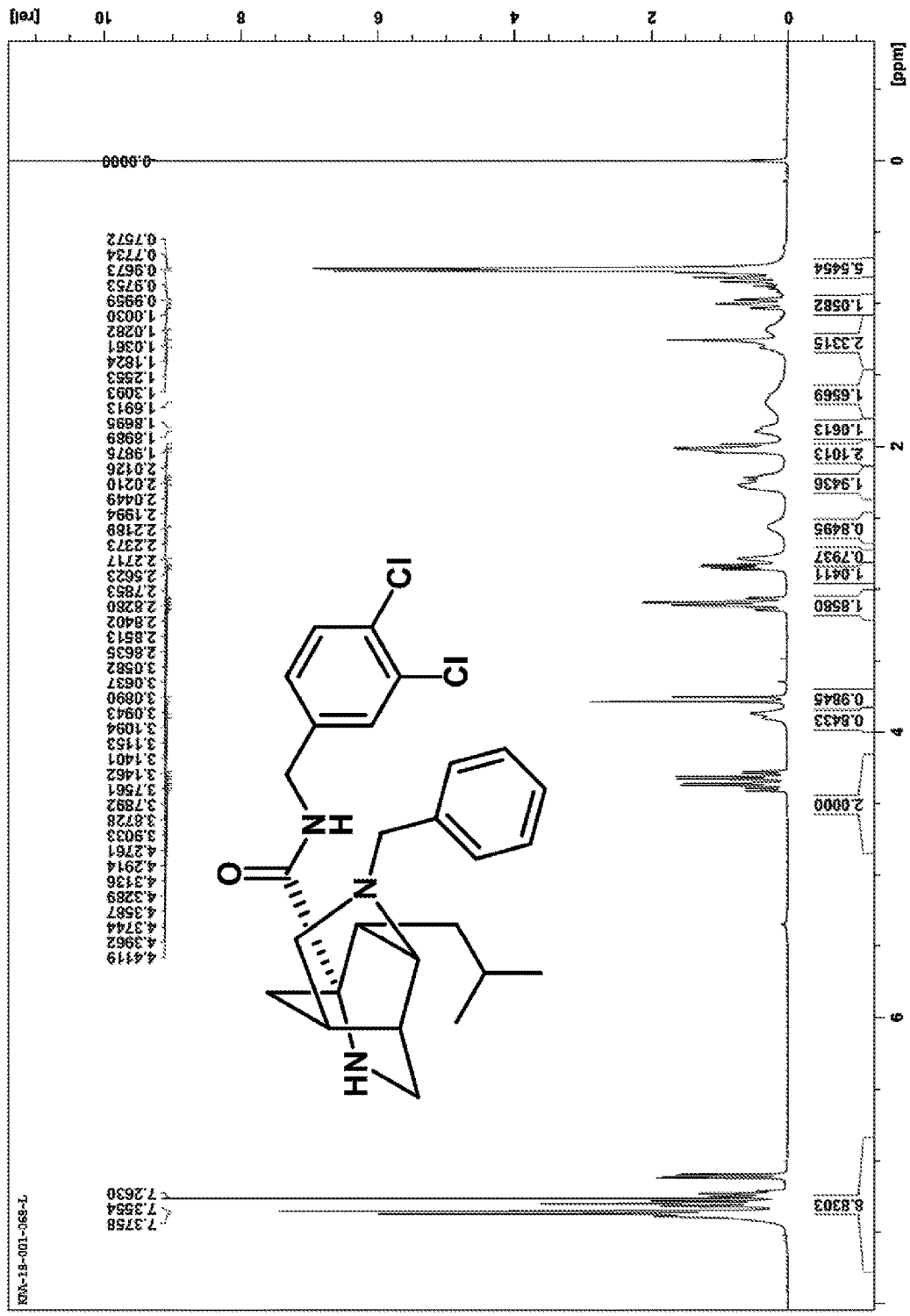
FIG. 70 shows the $^1$H-NMR chart for an exemplary compound of the present disclosure (formula in the figure).
Figure 71:
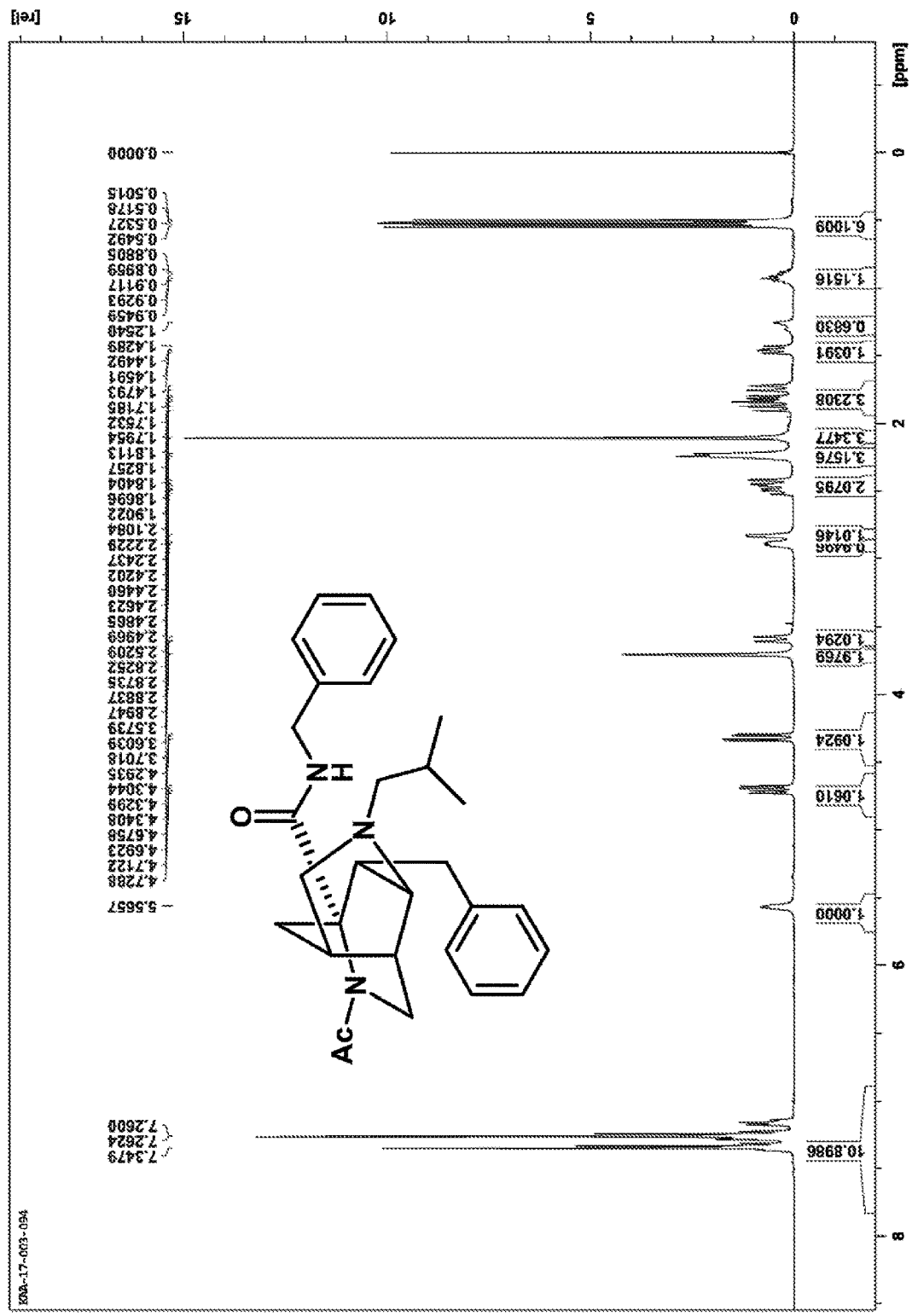
FIG. 71 shows the $^1$H-NMR chart for an exemplary compound of the present disclosure (formula in the figure).
Figure 72:
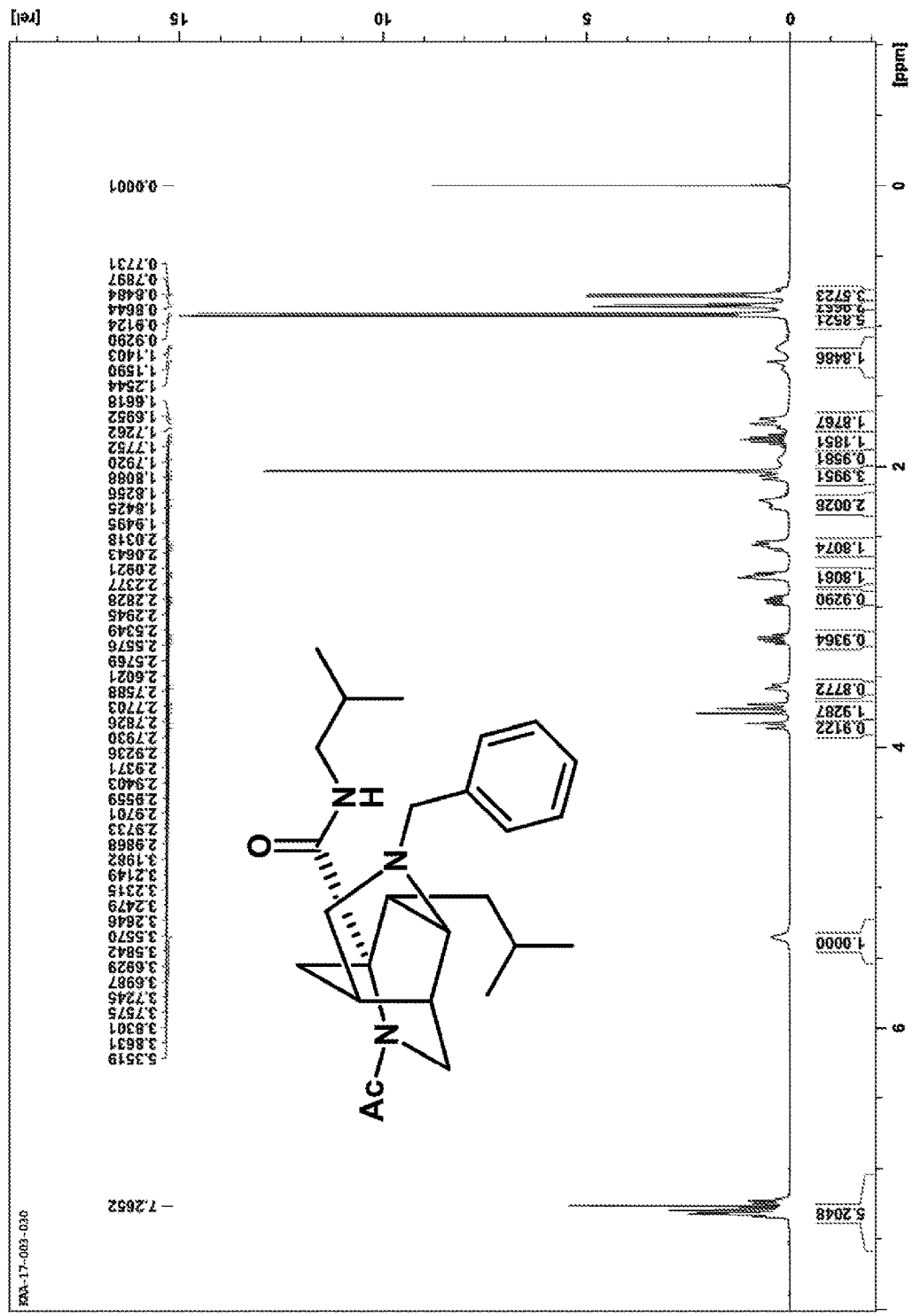
FIG. 72 shows the $^1$H-NMR chart for an exemplary compound of the present disclosure (formula in the figure).
Figure 73:
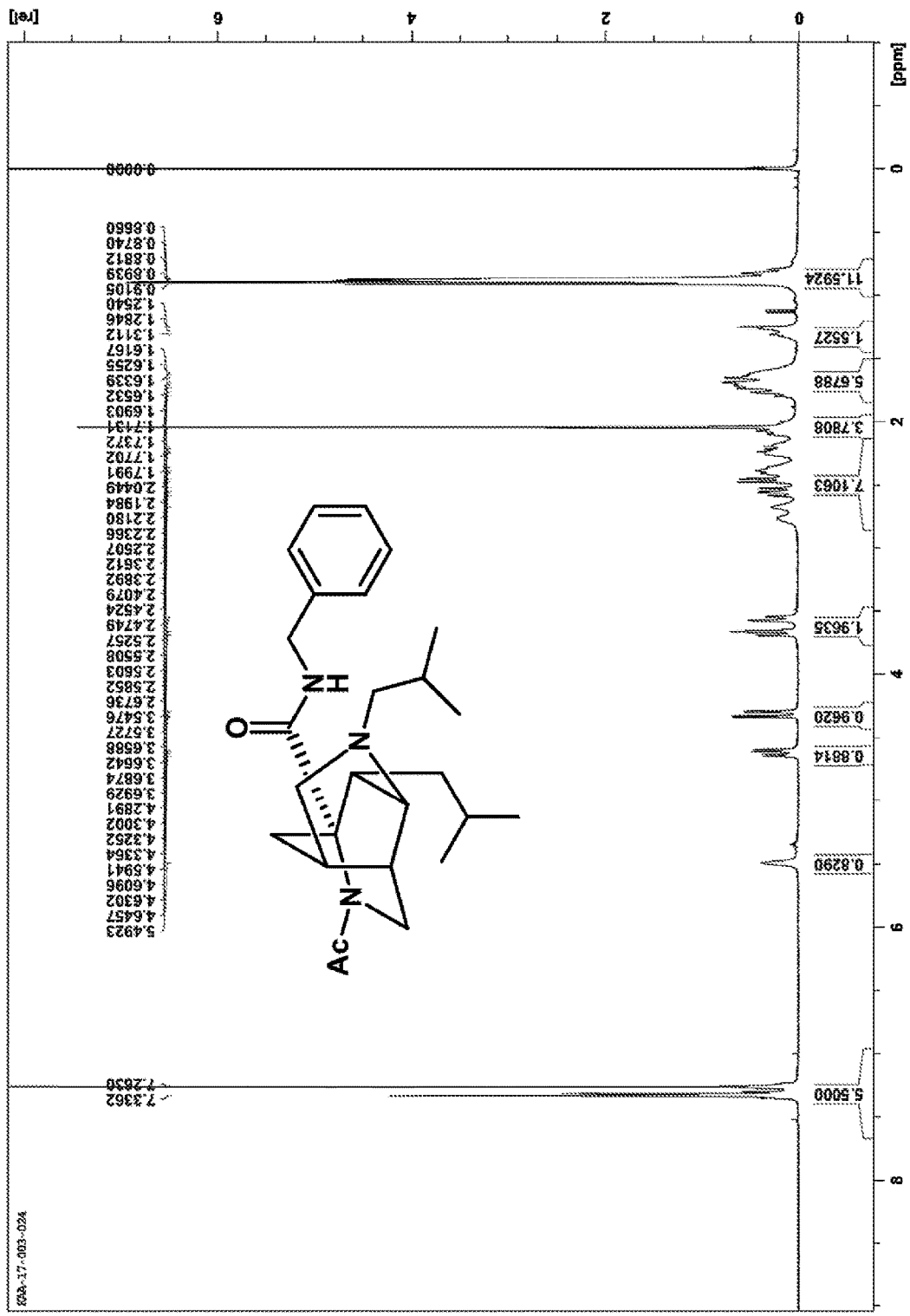
FIG. 73 shows the $^1$H-NMR chart for an exemplary compound of the present disclosure (formula in the figure).
Figure 74:
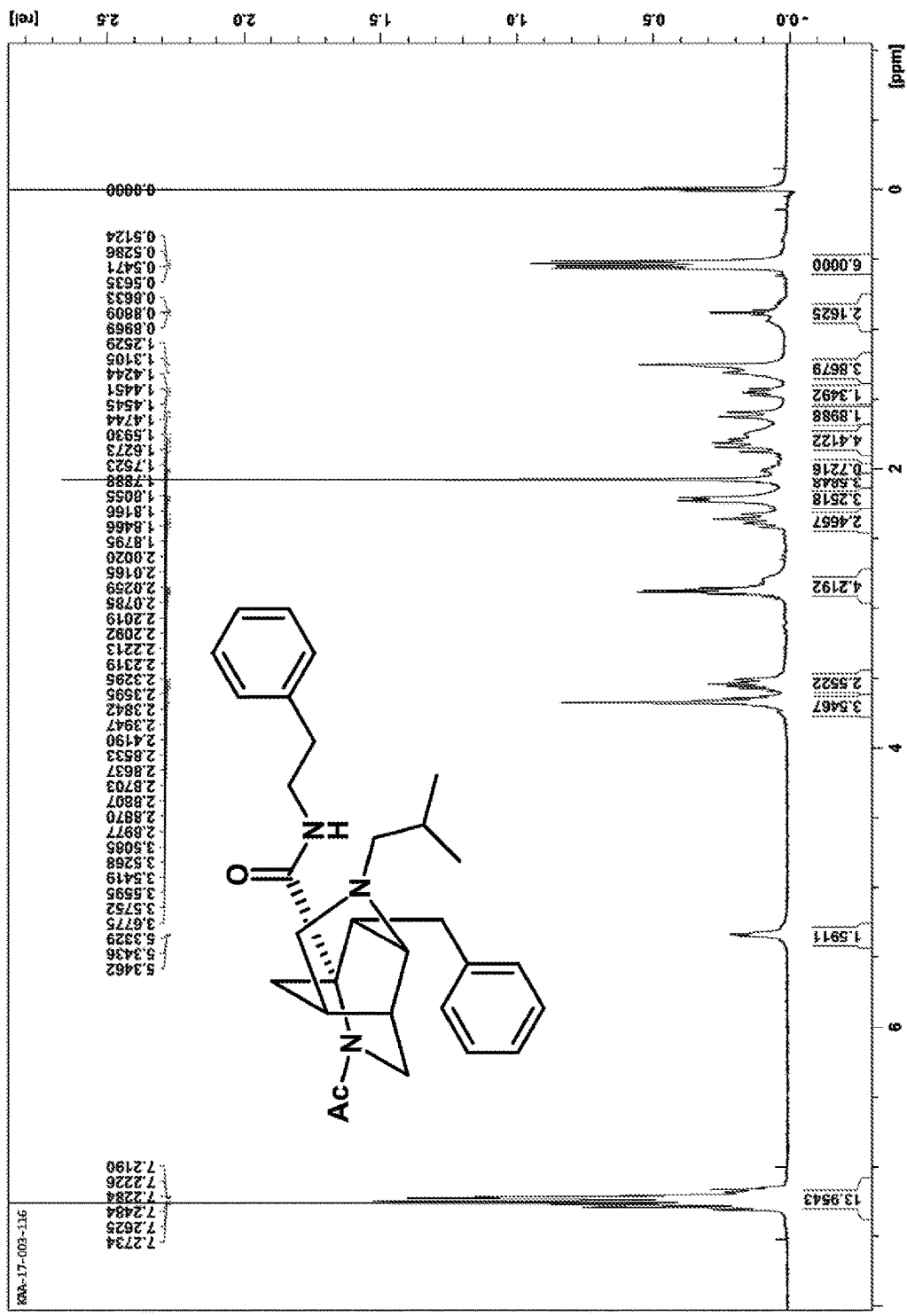
FIG. 74 shows the $^1$H-NMR chart for an exemplary compound of the present disclosure (formula in the figure).
Figure 75:
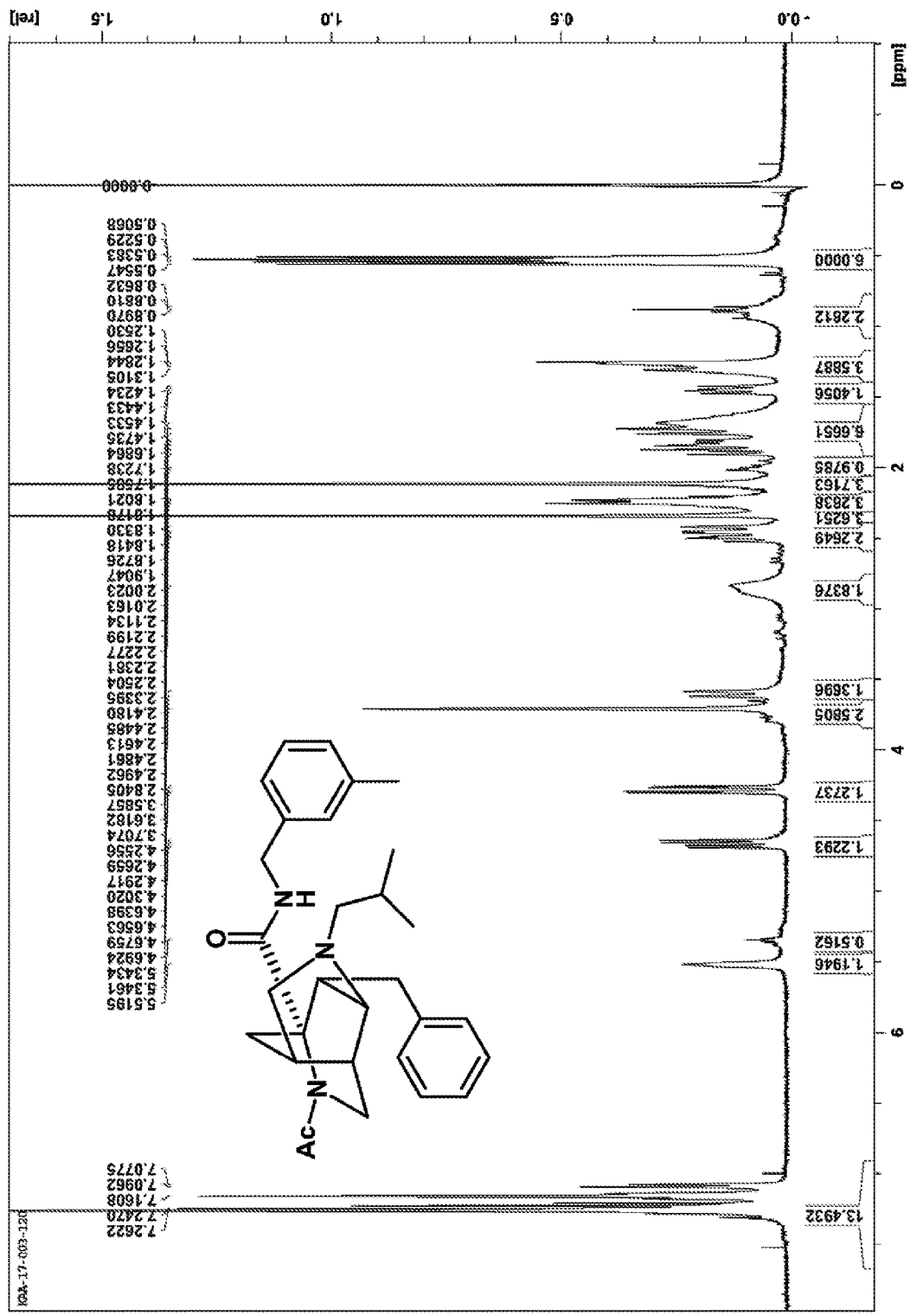
FIG. 75 shows the $^1$H-NMR chart for an exemplary compound of the present disclosure (formula in the figure).
Figure 76:
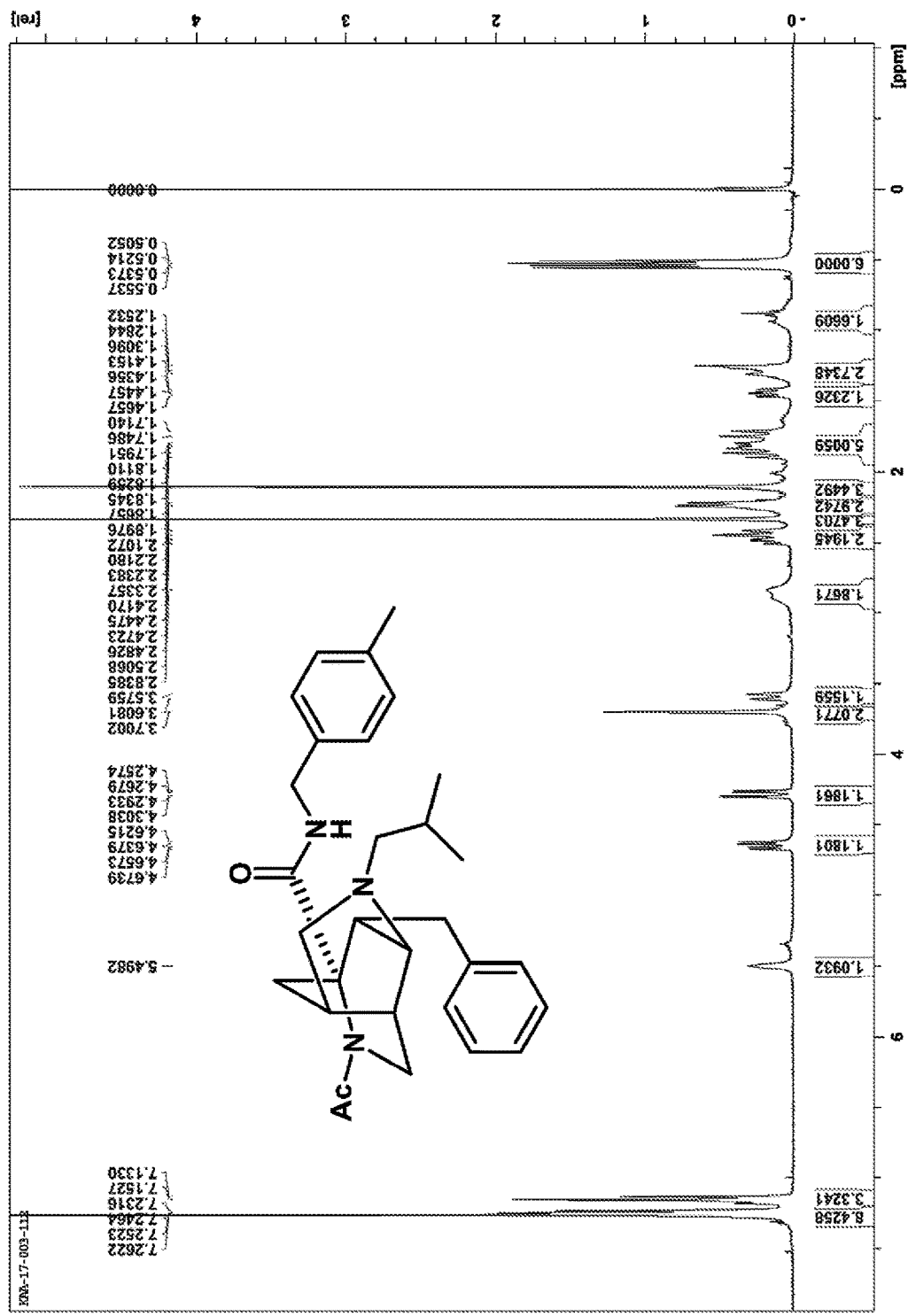
FIG. 76 shows the $^1$H-NMR chart for an exemplary compound of the present disclosure (formula in the figure).
Figure 77:
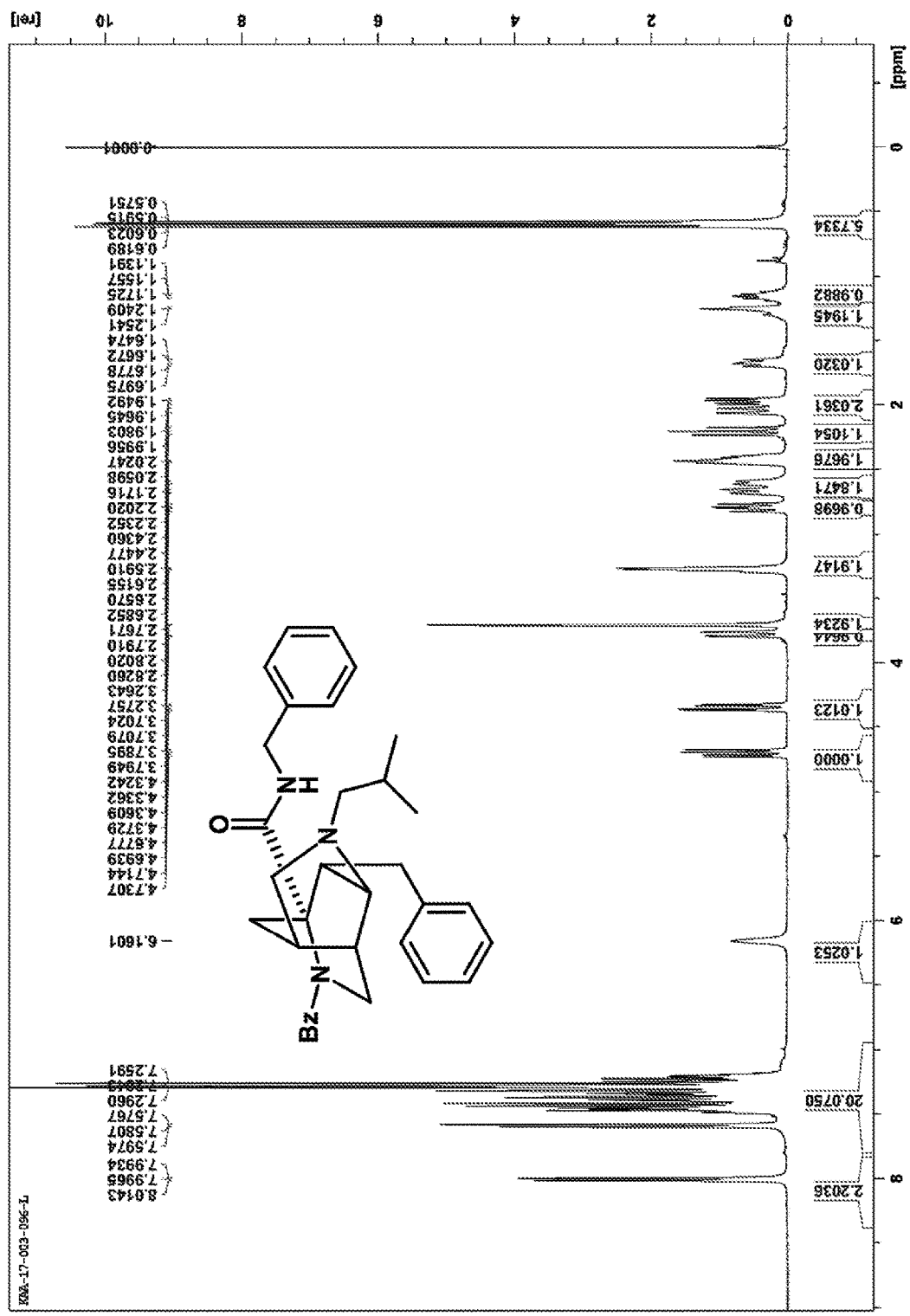
FIG. 77 shows the $^1$H-NMR chart for an exemplary compound of the present disclosure (formula in the figure).
Figure 78:
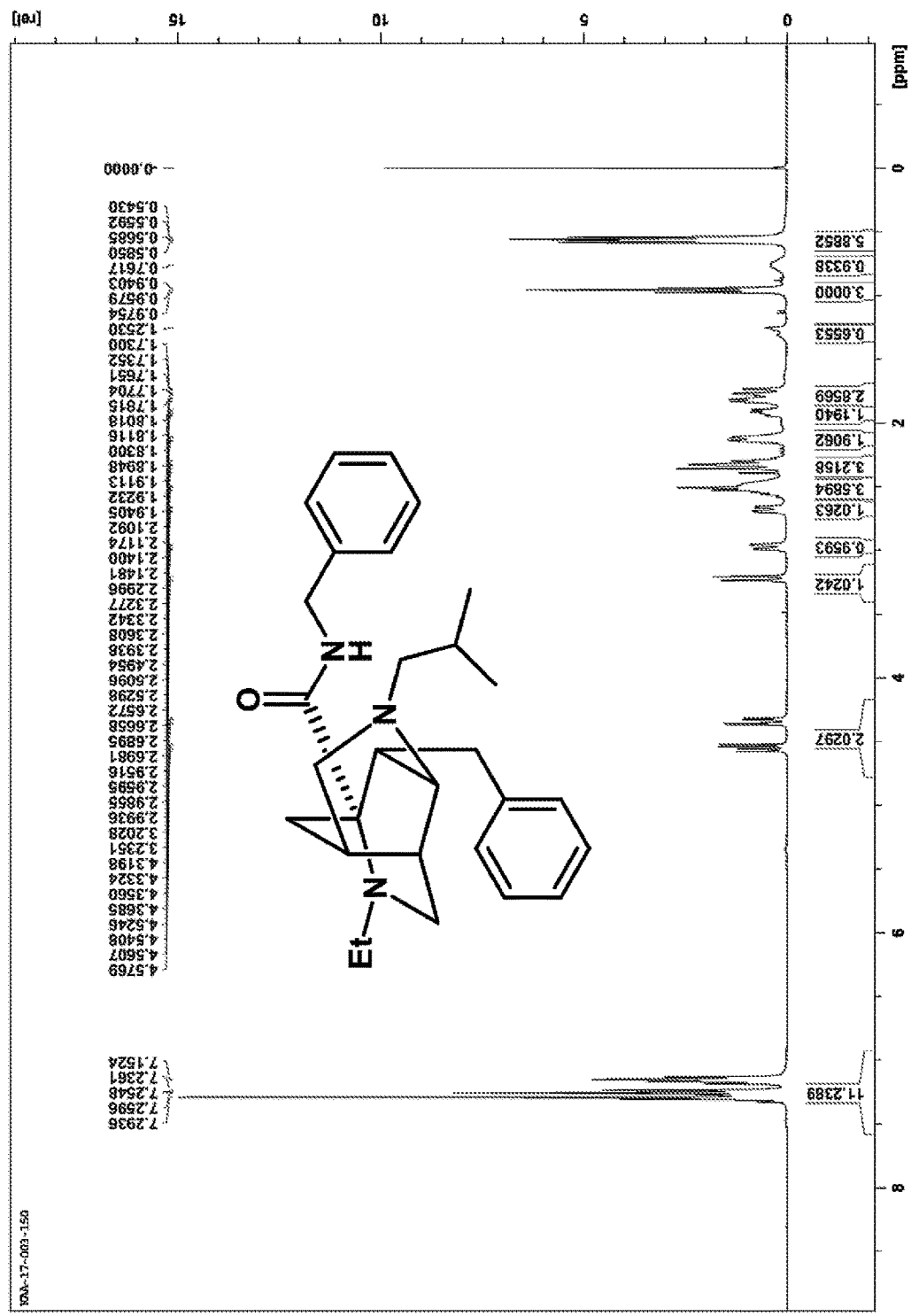
FIG. 78 shows the $^1$H-NMR chart for an exemplary compound of the present disclosure (formula in the figure).
Figure 79:
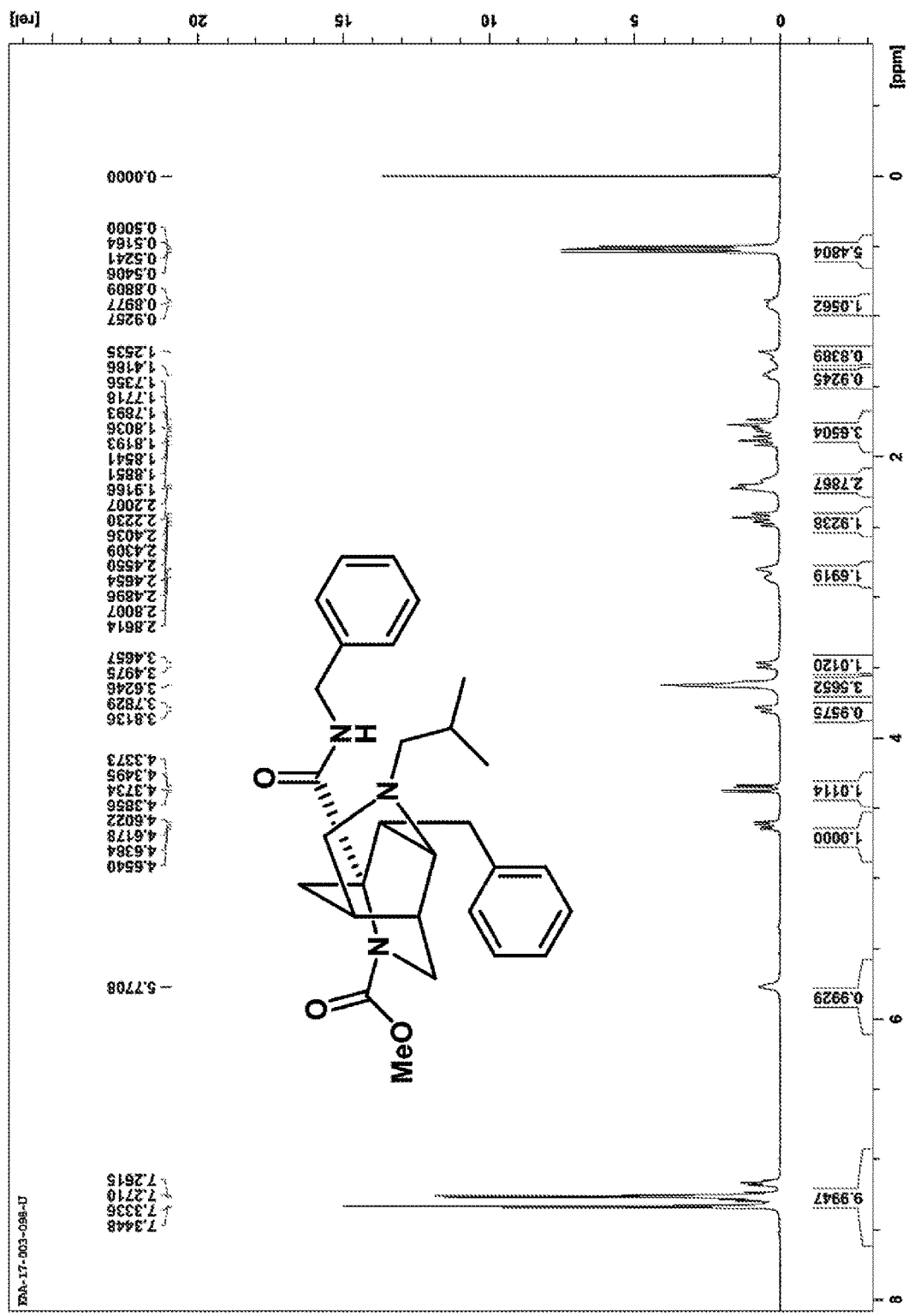
FIG. 79 shows the $^1$H-NMR chart for an exemplary compound of the present disclosure (formula in the figure).
Figure 80:
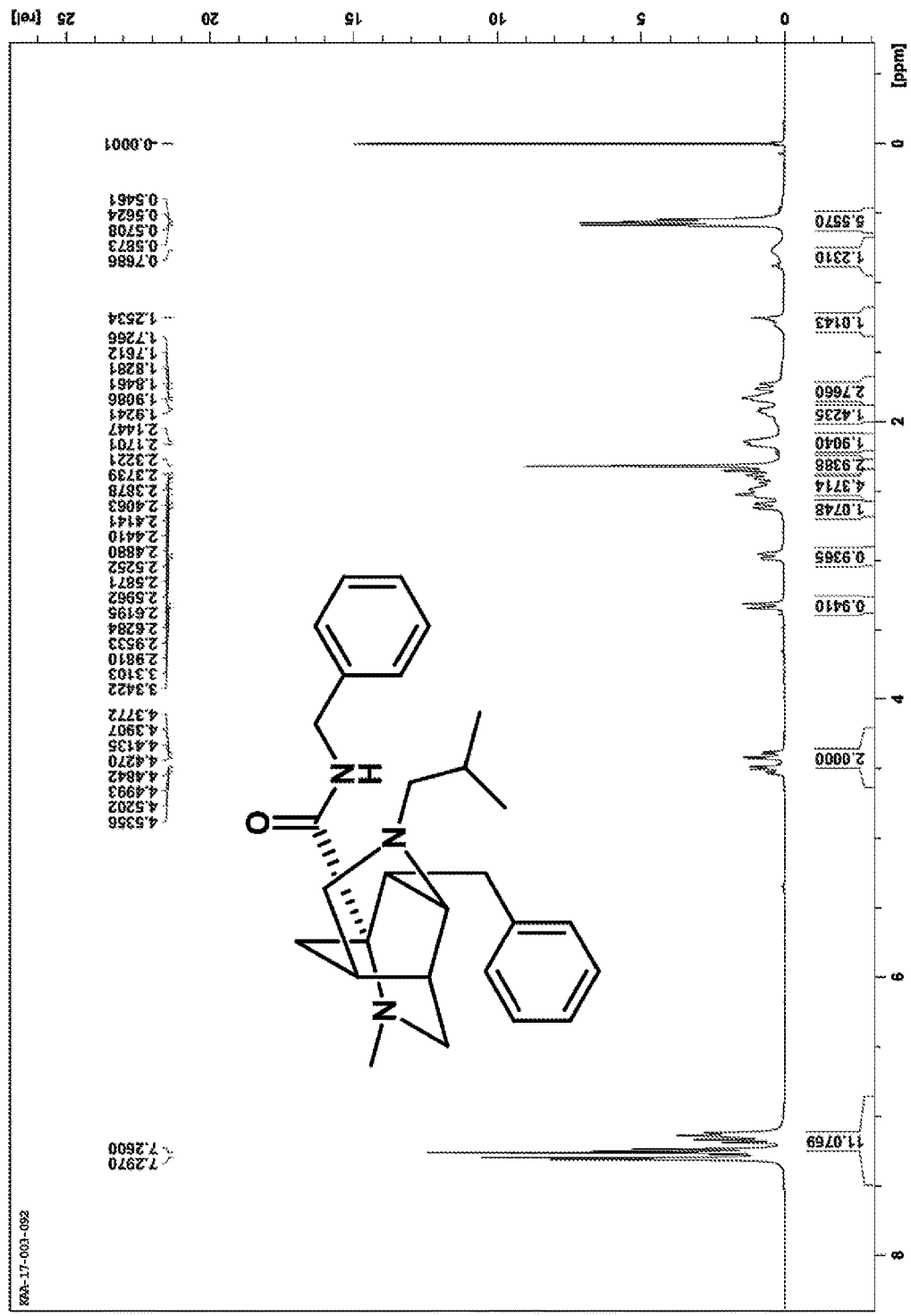
FIG. 80 shows the $^1$H-NMR chart for an exemplary compound of the present disclosure (formula in the figure).
Figure 81:
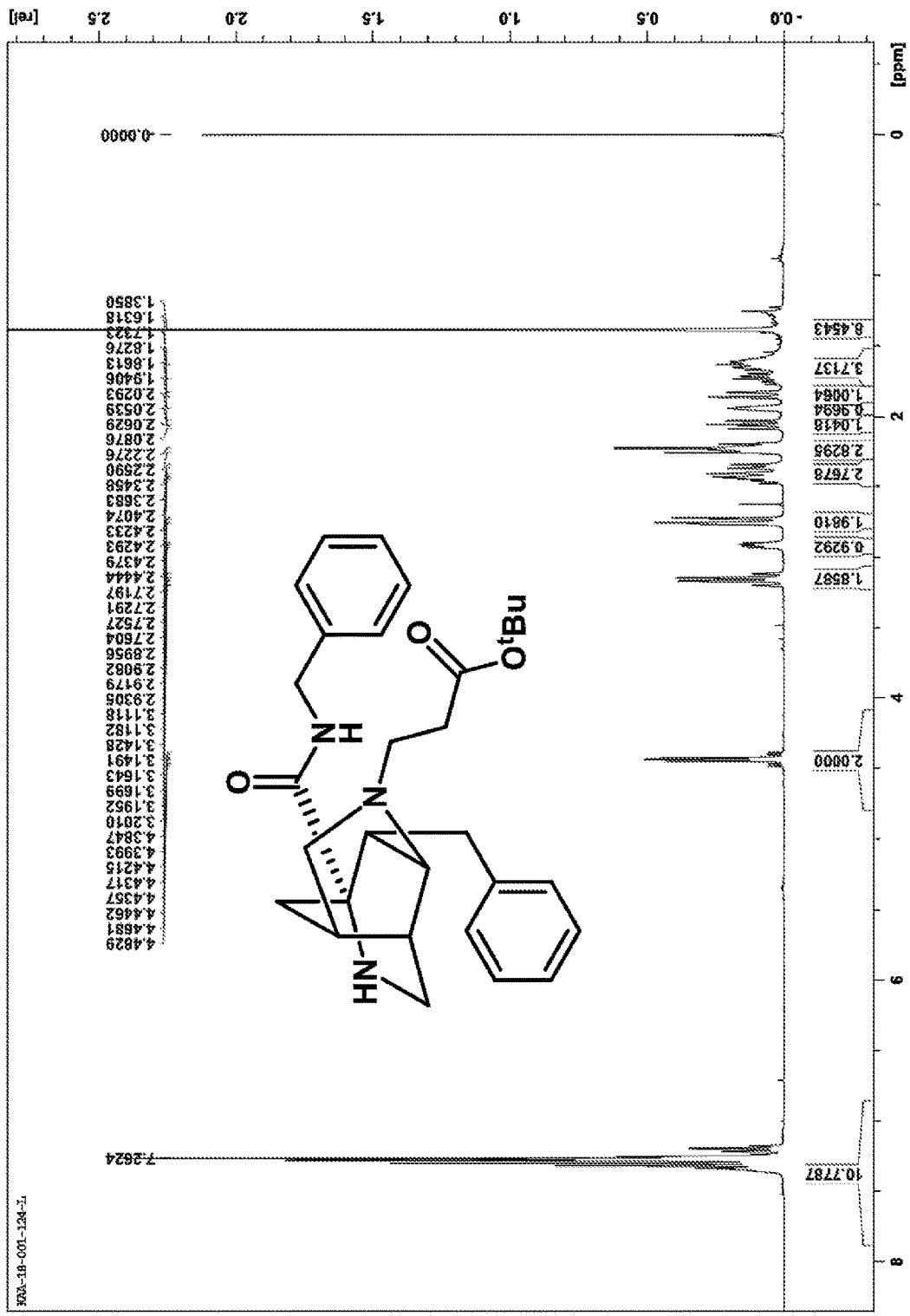
FIG. 81 shows the $^1$H-NMR chart for an exemplary compound of the present disclosure (formula in the figure).

The three-dimensional structure of the molecules was studied by X-ray crystallography. FIG. 1 shows an ORTEP diagram thereof. Daicel Corporation's chiral column, CHIRALPAK IG (5 μm, 4.6×150 mm), mobile phase: methanol:diethylamine (100:0.1) was used to confirm that the molecule was a racemate through analysis. FIG. 2 shows the chromatogram thereof.

Synthesis Example: D3-1

Synthesis of (3S*,3aS*,6R*,7R*,7aS*)-N,7-dibenzyl-1-isobutyloctahydro-3aH-3,6-methanopyrrolo[3,2-b]pyridine-3a-carboxamide (IB-1)

Sodium tetrahydroborate (3.83 mg, 0.101 mmol) was added to a methanol (1.00 mL) solution of (3S*,3aS*,6R*,7R*,7aS*)-N,7-dibenzyl-1-isobutyl-1,2,3,6,7,7a-hexahydro-3aH-3,6-methanopyrrolo[3,2-b]pyridine-3a-carboxamide (IIB-1) (21.0 mg, 0.0506 mmol) and stirred for 1 hour. After evaporating the solvent under reduced pressure, 5% sodium bicarbonate solution (1.00 mL) was added to the residue, which was extracted with ethyl acetate (4.00 mL). The organic layer was washed with water (1.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=90:10) to obtain the aforementioned compound (17.0 mg, yield: 81%, RT=1.21 minutes (B method), [M+1]⁺=418).

¹H-NMR spectrum (400 MHz, CDCl₃) δ (ppm): 0.48 (3H, d), 0.57 (3H, d), 1.18-1.28 (1H, m), 1.35-1.39 (1H, m), 1.55 (1H, s), 1.83-1.88 (1H, m), 2.09-2.14 (3H, m), 2.24-2.28 (1H, m), 2.45 (1H, s), 2.70-2.75 (1H, m), 2.78-2.88 (1H, m), 2.97 (1H, s), 3.20-3.27 (1H, m), 3.28-3.31 (1H, m), 4.28-4.33 (1H, m), 4.48-4.53 (1H, m), 7.21-7.27 (1H, m), 9.56 (1H, t).

¹³C-NMR spectrum (400 MHz, CDCl₃) δ (ppm): 20.20, 20.37, 25.84, 26.43, 38.09, 38.60, 39.25, 42.99, 58.19, 61.48, 62.33, 66.49, 125.58, 126.77, 127.49, 127.93, 128.07, 128.70, 138.22, 140.32, 173.83.

Synthesis Example: IB-29

Synthesis of (3S*,3aS*,6R*,7R*,7aS*)-N-(4-aminobutyl)-7-benzyl-1-isobutyloctahydro-3aH-3,6-methanopyrrolo[3,2-b]pyridine-3a-carboxamide (IB-29)

Formic acid (500 μL) was added to (3S*,3aS*,6R*,7R*,7aS*)-7-benzyl-1-isobutyl-N-(4-((tert-butoxycarbonyl)amino)butyl)octahydro-3aH-3,6-methanopyrrolo[3,2-b]pyridine-3a-carboxamide (IB-30) (7.70 mg, 0.0154 mmol) and incubated overnight at room temperature. The formic acid was evaporated under reduced pressure to obtain a triformic acid salt of the aforementioned compound (7.60 mg, yield: 92%, RT=0.75 minutes (A method), [M+1]⁺=399).

Synthesis Example: IB-40

Synthesis of (3S*,3aS*,6R*,7R*,7aS*)-N,7-dibenzyl-1-(4-hydroxybenzyl)octahydro-3aH-3,6-methanopyrrolo[3,2-b]pyridine-3a-carboxamide (IB-40)

Formic acid (250 μL) was added to (3S*,3aS*,6R*,7R*,7aS*)-N,7-dibenzyl-1-(4-(tert-butoxy)benzyl)octahydro-3aH-3,6-methanopyrrolo[3,2-b]pyridine-3a-carboxamide (IB-41) (7.80 mg, 0.0149 mmol) and incubated for 3 hours at room temperature. The formic acid was evaporated under reduced pressure to obtain a diformic acid salt of the aforementioned compound (6.30 mg, yield: 99%, RT=0.89 minutes (A method), [M+1]⁺=468).

Synthesis Example: IB-74

Synthesis of tert-butyl (3S*,3aS*,6R*,7R*,7aS*)-3a-(benzylcarbamoyl)-1-isobutyl-7-(3-methoxy-3-oxopropyl)octahydro-4H-3,6-methanopyrrolo[3,2-b]pyridine-4-carboxylate (IB-74)

(3S*,3aS*,6R*,7R*,7aS*)-N-benzyl-1-isobutyl-7-(3-methoxy-3-oxopropyl)octahydro-3aH-3,6-methanopyrrolo[3,2-b]pyridine-3a-carboxamide (IB-36) (23.5 mg, 0.0570 mmol) was dissolved in tetrahydrofuran (0.400 mL), and a 30% tetrahydrofuran solution (140 μL, 0.140 mmol) of di-tert-butyl dicarbonate was added and heated for 2 hours at 50° C. The solvent was evaporated under reduced pressure. The resulting residue was purified by preparative PLC (Merck 1.05744.0001 (layer thickness 0.500 mm) (ethyl acetate:methanol=9:1)) to obtain the aforementioned compound (22.0 mg, yield: 75%, RT=0.97 minutes (A method), [M+1]⁺=514).

Synthesis Example: IB-73

Synthesis of tert-butyl (3S*,3aS*,6R*,7R*,7aS*)-3a-(benzylcarbamoyl)-1-isobutyl-7-(2-carboxyethyl)octahydro-4H-3,6-methanopyrrolo[3,2-b]pyridine-4-carboxylate (IB-73)

tert-butyl (3S*,3aS*,6R*,7R*,7aS*)-3a-(benzylcarbamoyl)-1-isobutyl-7-(3-methoxy-3-oxopropyl)octahydro-4H-3,6-methanopyrrolo[3,2-b]pyridine-4-carboxylate (IB-74) (22.0 mg, 0.0430 mmol) was dissolved in methanol (1.00 mL), and lithium hydroxide monohydrate (18.0 mg, 0.430 mmol) was added and stirred overnight at room temperature. Methanol was evaporated under reduced pressure. 10% citric acid solvent (450 μL) and ethyl acetate were added thereto. The organic layer was dried with anhydrous sodium sulfate, and the solvent was evaporated under reduced pressure to obtain the aforementioned compound (21.40 mg, yield: 100%, RT=0.91 minutes (A method), [M+1]⁺=500).

Synthesis Example: IB-75

Synthesis of tert-butyl (3S*,3aS*,6R*,7R*,7aS*)-3a-(benzylcarbamoyl)-1-isobutyl-7-(3-amino-3-oxopropyl)octahydro-4H-3,6-methanopyrrolo[3,2-b]pyridine-4-carboxylate (IB-75)

tert-butyl (3S*,3aS*,6R*,7R*,7aS*)-3a-(benzylcarbamoyl)-1-isobutyl-7-(2-carboxyethyl)octahydro-4H-3,6- methanopyrrolo[3,2-b]pyridine-4-carboxylate (IB-73) (6.9 mg, 0.0130 mmol) was dissolved in tetrahydrofuran (0.200 mL), and carbonyldiimidazole (4.2 mg, 0.0260 mmol) was added and stirred overnight at room temperature. Ammonium water (13 M) (20.0 μL, 0.260 mmol) was added thereto and stirred for 1 hour. The solvent was evaporated. The resulting residue was purified by preparative PLC (Fuji Silysia Chemical's CHROMATOREX NH-TLC (layer thickness 0.200 mm) (ethyl acetate)) to obtain the aforementioned compound (1.70 mg, yield: 26%, RT=0.86 minutes (A method), [M+1]$^+$=499).

Synthesis Example: IB-79

Synthesis of (3S*,3aS*,6R*,7R*,7aS*)-N$^{3a}$,7-dibenzyl-1-(cyclohexylmethyl)-N$^4$-propylhexahydro-1H-3,6-methanopyrrolo[3,2-b]pyridine-3a,4-dicarboxamide (IB-79)

(3S*,3aS*,6R*,7R*,7aS*)-N,7-dibenzyl-1-cyclohexylmethyloctahydro-3aH-3,6-methanopyrrolo[3,2-b]pyridine-3a-carboxamide (IB-39) (4.6 mg, 0.0100 mmol) was dissolved in tetrahydrofuran (0.180 mL), then triethylamine (1.6 μL, 0.0120 mmol) and propylisocyanate (1.13 μL, 0.120 mmol) were added and incubated for 1 hour at room temperature. The reaction mixture was purified with preparative PLC silica gel 60F254 (layer thickness 0.250 mm) (ethyl acetate: methanol=5:1) to obtain the aforementioned compound (3.50 mg, yield: 65%, RT=1.05 minutes (A method), [M+1]$^+$=543).

Synthesis of 3-((3S*,3aS*,6R*,7R*,7aS*)-3a-(benzylcarbamoyl)-1-isobutyloctahydro-1H-3,6-methanopyrrolo[3,2-b]pyridin-7-yl)propanoic acid (IB-35)

Trifluoroacetic acid (200 μL) was added to tert-butyl (3S*,3aS*,6R*,7R*,7aS*)-3a-(benzylcarbamoyl)-1-isobutyl-7-(2-carboxyethyl)octahydro-4H-3,6-methanopyrrolo[3,2-b]pyridine-4-carboxylate (IB-73) (5.50 mg, 0.0110 mmol) and incubated overnight at room temperature. Trifluoroacetic acid was evaporated under reduced pressure to obtain a ditrifluoroacetic acid salt of the aforementioned compound (6.80 mg, yield: 100%, RT=0.83 minutes (A method), [M+1]$^+$=400).

Synthesis Example: IF-26

Synthesis of ((3S*,3aS*,6S*,7R*,7aS*)-7-benzyl-1-isobutyloctahydro-1H-3,6-methanopyrrolo[3,2-c]pyridine-6-carboxamide)propanoic acid (IF-26)

Formic acid (0.500 mL) was added to (3S*,3aS*,6S*, 7R*,7aS*)-7-benzyl-1-isobutyl-N-(2-(tert-butoxy)-2-oxoethyl)octahydro-6H-3,6-methanopyrrolo[3,2-c]pyridine-6-carboxamide (IF-27) (15.0 mg, 0.0330 mmol) and heated overnight at 45° C. The formic acid was evaporated under reduced pressure to obtain a diformic acid salt of the aforementioned compound (16.2 mg, yield: 100%, RT=0.66 minutes (A method), [M+1]$^+$=400).

Synthesis Example: IF-33

Synthesis of (3S*,3aS*,6S*,7R*,7aS*)-7-(4-aminobutyl)-N-benzyl-1-isobutyloctahydro-6H-3,6-methanopyrrolo[3,2-c]pyridine-6-carboxamide (IF-33)

Trifluoroacetic acid (200 μL) was added to (3S*,3aS*, 6S*,7R*,7aS*)-N-benzyl-1-isobutyl-7-(4-((tert-butoxycarbonyl)amino)butyl)octahydro-6H-3,6-methanopyrrolo[3,2-c]pyridine-6-carboxamide (IF-34) (7.80 mg, 0.0156 mmol) and incubated overnight at room temperature. The trifluoroacetic acid was evaporated under reduced pressure to obtain a tritrifluoroacetic acid salt of the aforementioned compound (7.80 mg, yield: 100%, RT=0.62 minutes (A method), [M+1]$^+$=399).

Synthesis Example: IF-41

Synthesis of (3S*,3aS*,6S*,7R*,7aS*)-N,7-dibenzyl-1-(4-(tert-butoxy)benzyl)octahydro-6H-3,6-methanopyrrolo[3,2-c]pyridine-6-carboxamide (IF-41)

9.50 mg of 10% palladium-carbon was added to a methanol (0.500 mL) solution of (3S*,3aR*,6S*,7R*,7aR*)-N,7-dibenzyl-1-(4-(tert-butoxy)benzyl)-1,2,3,3a,7,7a-hexahydro-6H-3,6-methanopyrrolo[3,2-c]pyridine-6-carboxamide (IIF-41) (11 mg, 0.0210 mmol) and stirred for a week under a hydrogen gas atmosphere. After filtering out the palladium-carbon, the solution was concentrated. The residue was purified with preparative PLC silica gel 60F254 (layer thickness 0.500 mm) (ethyl acetate:methanol=5:1) to obtain the aforementioned compound (5.70 mg, yield: 52%, RT=0.90 minutes (A method), [M+1]$^+$=524).

Synthesis Example: IF-40

Synthesis of (3S*,3aS*,6S*,7R*,7aS*)-N,7-dibenzyl-1-(4-hydroxybenzyl)octahydro-6H-3,6-methanopyrrolo[3,2-c]pyridine-6-carboxamide (IF-40)

Formic acid (250 μL) was added to (3S*,3aS*,6S*,7R*, 7aS*)-N,7-dibenzyl-1-(4-(tert-butoxy)benzyl)octahydro-6H-3,6-methanopyrrolo[3,2-c]pyridine-6-carboxamide (IF-41) (5.70 mg, 10.9 mmol) and incubated for 3 hours at room temperature. The formic acid was evaporated under reduced pressure to obtain a diformic acid salt of the aforementioned compound (3.20 mg, yield: 52%, RT=0.75 minutes (A method), [M+1]$^+$=468).

Synthesis Example: IF-71

Synthesis of (3S*,3aS*,6S*,7R*,7aS*)-N,7-dibenzyl-1-isobutyl-4-methyloctahydro-6H-3,6-methanopyrrolo[3,2-c]pyridine-6-carboxamide (IF-71)

A 37% formalin solution (0.06 mL, 0.736 mmol) was added to a tetrahydrofuran (2.00 mL) solution of (3S*,3aS*, 6S*,7R*,7aS*)-N,7-dibenzyl-1-isobutyloctahydro-6H-3,6-methanopyrrolo[3,2-c]pyridine-6-carboxamide (IF-1) (30.8 mg, 0.0736 mmol) and stirred for 15 minutes at room temperature. Sodium triacetoxyborohydride (46.8 mg, 0.221 mmol) was added to the reaction mixture, and stirred for 1 hour at room temperature. An aqueous 5% sodium bicarbonate solution (2.00 mL) was added to the reaction mixture, and the organic phase was extracted with ethyl acetate (5.00 mL). The organic layer was washed with water (2.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate: methanol=85:15) to obtain the aforementioned compound (12.1 mg, yield: 38%, RT=1.02 minutes (B method), [M+1]$^+$=432).

Synthesis Example: IF-43

Synthesis of (3S*,3aS*,6S*,7R*,7aS*)-4-acetyl-N,7-dibenzyl-1-isobutyloctahydro-6H-3,6-methanopyrrolo[3,2-c]pyridine-6-carboxamide (IF-43)

Triethylamine (0.0156 mL, 1.13 mmol) and acetyl chloride (0.00804 mL, 1.13 mmol) were added to a tetrahydrofuran (1.80 mL) solution of (3S*,3aS*,6S*,7R*,7aS*)-N,7-dibenzyl-1-isobutyloctahydro-6H-3,6-methanopyrrolo[3,2-c]pyridine-6-carboxamide (IF-1) (31.4 mg, 0.0751 mmol), and stirred for 30 minutes while cooling with ice. A 5% sodium bicarbonate solution (2.00 mL) was added to the reaction mixture, and the organic phase was extracted with ethyl acetate (5.00 mL). The organic layer was washed with water (2.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=85:15) to obtain the aforementioned compound (17.6 mg, yield: 51%, RT=1.08 minutes (B method), [M+1]$^+$=460).

Synthesis Example: IB-68

Synthesis of (3S*,3aS*,6R*,7R*,7aS*)-4-benzoyl-N,7-dibenzyl-1-isobutyloctahydro-3aH-3,6-methanopyrrolo[3,2-b]pyridine-3a-carboxamide (IB-68)

Triethylamine (0.0152 mL, 0.110 mmol) and benzoyl chloride (0.0127 mL, 1.10 mmol) were added to a tetrahydrofuran (2.00 mL) solution of (3S*,3aS*,6R*,7R*,7aS*)-N,7-dibenzyl-1-isobutyloctahydro-3aH-3,6-methanopyrrolo[3,2-b]pyridine-3a-carboxamide (IB-1) (30.6 mg, 0.0733 mmol) and stirred for 30 minutes while cooling with ice. An aqueous 5% sodium bicarbonate solution (2.00 mL) was added to the reaction mixture, and an organic phase was extracted with ethyl acetate (5.00 mL). The organic layer was washed with water (2.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=95:5) to obtain the aforementioned compound (14.8 mg, yield: 39%, RT=1.23 minutes (B method), [M+1]$^+$=522).

Synthesis Example: IB-69

Synthesis of (3S*,3aS*,6R*,7R*,7aS*)-N,7-dibenzyl-4-ethyl-1-isobutyloctahydro-3aH-3,6-methanopyrrolo[3,2-b]pyridine-3a-carboxamide (IB-69)

An acetaldehyde 2% N,N-dimethylformamide solution (0.870 mL, 0.395 mmol) was added to a tetrahydrofuran (2.00 mL) solution of (3S*,3aS*,6R*,7R*,7aS*)-N,7-dibenzyl-1-isobutyloctahydro-3aH-3,6-methanopyrrolo[3,2-b]pyridine-3a-carboxamide (IB-1) (33.0 mg, 0.790 mmol) and stirred for 15 minutes at room temperature. Sodium triacetoxyborohydride (50.2 mg, 0.273 mmol) was added to the reaction mixture, and further stirred for 2 hours at room temperature. An aqueous 5% sodium bicarbonate solution (10.0 mL) was added to the reaction mixture, and an organic phase was extracted with ethyl acetate (30.0 mL). The organic layer was washed twice with water (10.0 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=95:5) to obtain the aforementioned compound (9.85 mg, yield: 28%, RT=1.24 minutes (B method), [M+1]$^+$=446).

Synthesis Example: IB-70

Synthesis of (3S*,3aS*,6R*,7R*,7aS*)-N,7-dibenzyl-1-isobutyl-4-(methoxycarbonyl)octahydro-3aH-3,6-methanopyrrolo[3,2-b]pyridine-3a-carboxamide (IB-70)

Triethylamine (0.0157 mL, 0.113 mmol) and chloroformic acid methyl (0.00870 mL, 0.113 mmol) were added to a tetrahydrofuran (2.00 mL) solution of (3S*,3aS*,6R*,7R*,7aS*)-N,7-dibenzyl-1-isobutyloctahydro-3 aH-3,6-methanopyrrolo[3,2-b]pyridine-3a-carboxamide (IB-1) (31.5 mg, 0.0754 mmol), and stirred for 30 minutes while cooling with ice. After stirring for 30 minutes at room temperature, a 5% sodium bicarbonate solution (2.00 mL) was added to the reaction mixture, and the organic phase was extracted with ethyl acetate (5.00 mL). The organic layer was washed with water (2.00 mL), then dried with anhydrous sodium sulfate and filtered. The solvent was evaporated under reduced pressure. The resulting residue was purified with preparative PLC silica gel 60F254 (layer thickness 0.500 mm) (ethyl acetate:methanol=95:5) to obtain the aforementioned compound (31.0 mg, yield: 87%, RT=1.18 minutes (B method), [M+1]$^+$=476).

The following compounds were synthesized by the same method as the Synthesis Examples.

Compounds with a guanidinopropyl group in one of the substituents $R_1$, $R_2$, and $R_3$ were synthesized by the following method. Representative examples are provided below.

Synthesis of (3S*,3aS*,6R*,7R*,7aS*)-1-(3-guanidinopropyl)-7-isobutyl-N-(naphthalen-1-ylmethyl)octahydro-3aH-3,6-methanopyrrolo[3,2-b]pyridine-3a-carboxamide (IB-164) and (3S*,3aS*,6S*,7R*,7aS*)-1-(3-guanidinopropyl)-7-isobutyl-N-(naphthalen-1-ylmethyl)octahydro-6H-3,6-methanopyrrolo[3,2-c]pyridine-6-carboxamide (IF-162)

1. Synthesis of tert-butyl (3S*,3aR*,6S*,7R*,7aS*)-(3-(7-isobutyl-3a-((naphthalen-1-ylmethyl)carbamoyl)-2,3,3a,6,7,7a-hexahydro-1H-3,6-methanopyrrolo[3,2-b]pyridin-yl)propyl)carbamate and tert-butyl(3S*,3aR*,6S*,7R*,7aR*)-(3-(7-isobutyl-6-(naphthalen-1-ylmethyl)carbamoyl)-2,3,3a,6,7,7a-hexahydro-1H-3,6-methanopyrrolo[3,2-c]pyridin-1-yl)propyl)carbamate N,N-dimethylformamide (1 mL) was added to 4-methylpentanal (60.1 mg, 0.6 mmol), tert-butyl(3-(allylamino)propyl)carbamate (128.6 mg, 0.6 mmol), and molecular sieve 4 A (100 mg), and then N-(naphthalen-1-ylmethyl)-1,2,4-triazine-3-carboxamide (79.3 mg, 0.3 mmol) was added. The reaction mixture was heated for 16 hours at 85° C., and then filtered. The filtrate was purified by preparative HPLC (High Performance Liquid Chromatography). A fraction of the substance of interest was concentrated to obtain a mixture of the aforementioned compound.

2. Synthesis of (3S*,3aS*,6R*,7R*,7aS*)-1-(3-aminopropyl)-7-isobutyl-N-(naphthalen-1-ylmethyl)-1,2,3,6,7,7a-hexahydro-3aH-3,6-methanopyrrolo[3,2-b]pyridine-3a-carboxamide and (3S*,3aR*,6S*,7R*,7aR*)-1-(3-aminopropyl)-7-isobutyl-N-(naphthalen-1-ylmethyl)-1,2,3,3a,7,7a-hexahydro-6H-3,6-methanopyrrolo[3,2-c]pyridine-6-carboxamide Trifluoroacetic acid (0.3 mL) was added to the compound (mixture) obtained in 1. and stirred for 1 hour at room temperature. The trifluoroacetic acid was evaporated to obtain a trifluoroacetic acid salt of the aforementioned compound (mixture).

3. Synthesis of (3S*,3aS*,6R*,7R*,7aS*)-1-(3-(N,N'-di(tert-butoxycarbonyl)guanidino)propyl)-7-isobutyl-N-(naphthalen-1-ylmethyl)-1,2,3,6,7,7a-hexahydro-3aH-3,6-methanopyrrolo[3,2-b]pyridine-3a-carboxamide and (3S*,3aR*,6S*,7R*,7aR*)-1-(3-(N,N'-di(tert-butoxycarbonyl)guanidino)propyl)-7-isobutyl-N-(naphthalen-1-ylmethyl)-1,2,3,3a,7,7a-hexahydro-6H-3,6-methanopyrrolo[3,2-c]pyridine-6-carboxamide 1,3-di(tert-butoxycarbonyl)-2-(trifluoromethanesulfonyl)guanidine (234.8 mg, 0.6 mmol), triethylamine (60.7 mg, 0.6 mmol), and tetrahydrofuran (0.5 mL) were added to the compound (mixture) obtained in 2. and stirred for 3 hours at room temperature. The solvent was evaporated to obtain a mixture comprising the aforementioned compound. The mixture obtained in this step was used in synthesis of the next step without purification.

4. Synthesis of (3S*,3aS*,6R*,7R*,7aS*)-1-(3-(N,N'-di(tert-butoxycarbonyl)guanidino)propyl)-7-isobutyl-N-(naphthalen-1-ylmethyl)octahydro-3aH-3,6-methanopyrrolo[3,2-b]pyridine-3a-carboxamide and (3S*,3aS*,6S*,7R*,7aS*)-1-(3-(N,N'-di(tert-butoxycarbonyl)guanidino)propyl)-7-isobutyl-N-(naphthalen-1-ylmethyl)octahydro-6H-3,6-methanopyrrolo[3,2-c]pyridine-6-carboxamide The reaction mixture obtained in 3. was dissolved in methanol (1 mL), then sodium borohydride (22.7 mg, 0.6 mmol) was added and stirred for 2 hours at room temperature. The reaction mixture was purified by preparative HPLC. Fractions of substances of interest were concentrated to obtain each of the aforementioned compounds separately.

5. Synthesis of (3S*,3aS*,6S*,7R*,7aS*)-1-(3-guanidinopropyl)-7-isobutyl-N-(naphthalen-1-ylmethyl)octahydro-6H-3,6-methanopyrrolo[3,2-c]pyridine-6-carboxamide Trifluoroacetic acid (0.3 mL) was added to (3S*,3aS*,6S*,7R*,7aS*)-1-(3-(N,N'-di(tert-butoxycarbonyl)guanidino)propyl)-7-isobutyl-N-(naphthalen-1-ylmethyl)octahydro-6H-3,6-methanopyrrolo[3,2-c]pyridine-6-carboxamide obtained in 4. and stirred for 1 hour at room temperature. The trifluoroacetic acid was evaporated to obtain a trifluoroacetic acid salt of the aforementioned compound.

6. Synthesis of (3S*,3aS*,6R*,7R*,7aS*)-1-(3-guanidinopropyl)-7-isobutyl-N-(naphthalen-1-ylmethyl)octahydro-3aH-3,6-methanopyrrolo[3,2-b]pyridine-3a-carboxamide A trifluoroacetic acid salt of the aforementioned compound was obtained by the same method as 5. by using (3S*,3aS*,6R*,7R*,7aS*)-1-(3-(N,N'-di(tert-butoxycarbonyl)guanidino)propyl)-7-isobutyl-N-(naphthalen-1-ylmethyl)octahydro-3aH-3,6-methanopyrrolo[3,2-b]pyridine-3a-carboxamide obtained in 4.

Synthesis of (3S*,3aS*,6R*,7R*,7aS*)-N-benzyl-7-(2-((tert-butyldimethylsilyl)oxy)ethyl)-1-phenethyl-1,2,3,6,7,7a-hexahydro-3aH-3,6-methanopyrrolo[3,2-b]pyridine-3a-carboxamide and (3S*,3aR*,6S*,7R*,7aR*)-N-benzyl-7-(2-((tert-butyldimethylsilyl)oxy)ethyl)-1-phenethyl-1,2,3,3a,7,7a-hexahydro-6H-3,6-methanopyrrolo[3,2-c]pyridine-6H-carboxamide Chloroform (1 mL) was added to N-phenethyl prop-2-en-1-amine (58.4 mg, 0.4 mmol), 4-((tert-butyldimethylsilyl)oxy)butanal (80.0 mg, 0.4 mmol), and molecular sieve 4 A (400 mg), and then N-benzyl-1,2,4-triazine-3-carboxamide (43.8 mg, 0.2 mmol) and chloroform (1 mL) were further added. The reaction mixture was heated for 48 hours at 55° C. and filtered. The filtrate was concentrated under reduced pressure. The resulting residue was purified by preparative TLC (Merck 1.13895.001, layer thickness 1 mm) (ethyl acetate:methanol=9:1) to obtain a mixture of the aforementioned compound (73.3 mg, yield 69%, RT=1.08 minutes, 1.12 minutes (C method), [M+1]⁺=532).

Synthesis of (3S*,3aS*,6S*,7R*,7aS*)-N-benzyl-7-(2-((tert-butyldimethylsilyl)oxy)ethyl)-1-phenethyloctahydro-3aH-3,6-methanopyrrolo[3,2-b]pyridine-3a-carboxamide and (3S*,3aS*,6S*,7R*,7aS*)-N-benzyl-7-(2-((tert-butyldimethylsilyl)oxy)ethyl)-1-phenethyloctahydro-6H-3,6-methanopyrrolo[3,2-c]pyridine-6-carboxamide The mixture obtained in the above reaction (73.3 mg) was dissolved in methanol (1.5 mL), and sodium borohydride (9 mg, 0.24 mmol) was added and stirred for 12 hours at room temperature. Ethyl acetate was added to the reaction mixture, which was washed twice with saturated saline. The organic phase was dried with anhydrous sodium sulfate. The anhydrous sodium sulfate was filtered out. The filtrate was concentrated under reduced pressure and purified by preparative TLC (Merck 1.13895.001, layer thickness 1 mm) (ethyl acetate:methanol=4:1) to obtain (3S*,3aS*,6S*,7R*,7aS*)-N-benzyl-7-(2-((tert-butyldimethylsilyl)oxy)ethyl)-1-phenethyloctahydro-3aH-3,6-methanopyrrolo[3,2-b]pyridine-3a-carboxamide (47.6 mg, two-step yield of 43%, RT=1.13 minutes (C method), [M+1]⁺=534) and (3S*,3aS*,6S*,7R*,7aS*)-N-benzyl-7-(2-((tert-butyldimethylsilyl)oxy)ethyl)-1-phenethyloctahydro-6H-3,6-methanopyrrolo[3,2-c]pyridine-6-carboxamide (20.6 mg, two-step yield of 19%, RT=0.95 minutes (C method), [M+1]⁺=534).

Synthesis of (3S*,3aS*,6S*,7R*,7aS*)-N-benzyl-7-(2-hydroxyethyl)-1-phenethyloctahydro-3aH-3,6-methanopyrrolo[3,2-b]pyridine-3aH-carboxamide (3S*,3aS*,6S*,7R*,7aS*)-N-benzyl-7-(2-((tert-butyldimethylsilyl)oxy)ethyl)-1-phenethyloctahydro-3aH-3,6-methanopyrrolo[3,2-b]pyridine-a-carboxamide (46.7 mg, 0.087 mmol) was dissolved in tetrahydrofuran (1 mL), and tetrabutylammonium fluoride (approximately 1 mol/L tetrahydrofuran solution, 0.1 mL) was added and stirred overnight at room temperature. The reaction mixture was concentrated and ethyl acetate was added, and then transferred to a separatory funnel and washed with saturated saline. The organic phase was dried with anhydrous sodium sulfate, concentrated under reduced pressure, and purified by preparative TLC (Merck 1.05744.001, layer thickness 0.5 mm) (ethyl acetate:methanol=4:1) to obtain the aforementioned compound (35 mg, yield of 96%, RT=0.85 minutes (C method), [M+1]⁺=420).

Synthesis of (3S*,3aS*,6S*,7R*,7aS*)-N-benzyl-7-(2-hydroxyethyl)-1-phenethyloctahydro-6H-3,6-methanopyrrolo[3,2-c]pyridine-6H-carboxamide (3S*,3aS*,6S*,7R*,7aS*)-N-benzyl-7-(2-((tert-butyldimethylsilyl)oxy)ethyl)-1-phenethyloctahydro-6H-3,6-methanopyrrolo[3,2-c]pyridine-6-carboxamide (20.6 mg, 0.039 mmol) was dissolved in tetrahydrofuran (0.5 mL), and tetrabutylammonium fluoride (approximately 1 mol/L tetrahydrofuran solution, 0.05 mL) was added and stirred overnight at room temperature. The reaction mixture was concentrated, ethyl acetate was added and transferred to a separatory funnel, and washed twice with saturated saline. The organic phase was dried with anhydrous sodium sulfate, concentrated under reduced pressure, and purified by preparative TLC (Merck 105744.001, layer thickness 0.5 mm) (ethyl acetate:methanol=4:1) to obtain the aforementioned compound (16 mg, yield of 91%, RT=0.72 minutes (C method), [M+1]⁺=420).

Synthesis of (3S*,3aS*,6S*,7R*,7aS*)-N,4,7-tribenzyl-1-(naphthalen-1-ylmethyl)octahydro-3aH-3,6-methanopyrrolo[3,2-b]pyridine-3a-carboxamide (3S*,3aS*,6S*,7R*,7aS*)-N,7-dibenzyl-1-(naphthalen-1-ylmethyl)octahydro-3aH-3,6-methanopyrrolo[3,2-b]pyridine-3a-carboxamide (compound D3-42, 5 mg, 0.01 mmol) was dissolved in tetrahydrofuran (0.2 mL), then benzaldehyde (2.1 mg, 0.02 mmol), trifluoroacetic acid (3.4 mg, 0.03 mmol), and molecular sieve 4 A (40 mg) were added and heated for 18 hours at 50° C. Sodium triacetoxyborohydride (5 mg, 0.024 mmol) was added to the reaction mixture and stirred for 5 hours at room temperature. To the reaction mixture, ethyl acetate and saturated sodium bicarbonate water are added. The organic phase was washed twice with saturated saline. The organic phase was dried with anhydrous sodium sulfate, concentrated under reduced pressure, and purified by TLC (Merck 105715.001, layer thickness 0.25 mm) (hexane:ethyl acetate=2:1) to obtain the aforementioned compound (1.2 mg, yield of 20%, RT=1.14 minutes (C method), [M+1]⁺=592).

Tables 3 and 4 summarize the synthesized compounds of formula IB and compounds of IF. In the following tables, "EX" means that the synthesis method is described in the Examples.

TABLE 3

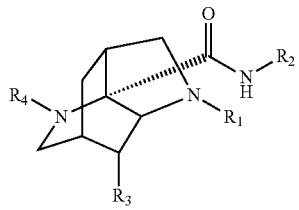

| Compound number | R₁ | R₂ | R₃ | R₄ | Synthesis method | Intermediate |
|---|---|---|---|---|---|---|
| IB-1 | i-Bu | Bnzl | Bnzl | H | EX | IIB-1 |
| IB-2 | i-Bu | i-Bu | i-Bu | H | IB-1 | IIB-2 |
| IB-3 | i-Bu | i-Bu | Bnzl | H | IB-1 | IIB-3 |
| IB-4 | Bnzl | i-Bu | i-Bu | H | IB-1 | IIB-4 |
| IB-5 | i-Bu | Bnzl | i-Bu | H | IB-1 | IIB-5 |
| IB-6 | Bnzl | i-Bu | Bnzl | H | IB-1 | IIB-6 |
| IB-7 | Bnzl | Bnzl | i-Bu | H | IB-1 | IIB-7 |
| IB-8 | Bnzl | Bnzl | Bnzl | H | IB-1 | IIB-8 |
| IB-9 | i-Pnt | Bnzl | Bnzl | H | IB-1 | IIB-9 |
| IB-10 | Bnzl | Bnzl | i-Pnt | H | IB-1 | IIB-10 |
| IB-11 | i-Bu | Bnzl | Ph-Et | H | IB-1 | IIB-11 |
| IB-12 | i-Bu | Ph-Et | Bnzl | H | IB-1 | IIB-12 |
| IB-13 | i-Bu | Bnzl | 3-Me-Bnzl | H | IB-1 | IIB-13 |
| IB-14 | i-Bu | Bnzl | 4-Me-Bnzl | H | IB-1 | IIB-14 |
| IB-15 | i-Bu | 3-Me-Bnzl | Bnzl | H | IB-1 | IIB-15 |
| IB-16 | i-Bu | 4-Me-Bnzl | Bnzl | H | IB-1 | IIB-16 |
| IB-17 | i-Bu | 3-Cl-Bnzl | Bnzl | H | IB-1 | IIB-17 |
| IB-18 | i-Bu | 4-Cl-Bnzl | Bnzl | H | IB-1 | IIB-18 |
| IB-19 | 3,4-Cl₂-Bnzl | Bnzl | i-Bu | H | IB-1 | IIB-19 |
| IB-20 | Bnzl | 3,4-Cl₂-Bnzl | i-Bu | H | IB-1 | IIB-20 |
| IB-21 | Me | Np-E | Bnzl | H | IB-1 | IIB-21 |
| IB-22 | i-Bu | 4-OH-Bnzl | Bnzl | H | IB-40 | IB-23 |
| IB-23 | i-Bu | 4-(tert-butoxy)benzyl | Bnzl | H | IB-1 | IIB-23 |
| IB-24 | i-Bu | Np-M | Bnzl | H | IB-1 | IIB-24 |
| IB-25 | i-Bu | Hdr-E | Bnzl | H | IB-1 | IIB-25 |
| IB-26 | i-Bu | Cbx-E | Bnzl | H | IF-26 | IB-27 |
| IB-27 | i-Bu | 2-(tert-butoxy)-2-oxoethyl | Bnzl | H | IB-1 | IIB-27 |
| IB-28 | i-Bu | Cbm-E | Bnzl | H | IB-1 | IIB-28 |
| IB-29 | i-Bu | 4-aminobutyl | Bnzl | H | EX | IB-30 |

TABLE 3-continued

| | | | | | | |
|---|---|---|---|---|---|---|
| IB-30 | i-Bu | 4-((tert-butoxycarbonyl)amino)butyl | Bnzl | H | IB-1 | IIB-30 |
| IB-31 | i-Bu | Chm | Bnzl | H | IB-1 | IIB-31 |
| IB-32 | i-Bu | (tetrahydro-2H-pyran-2-yl)methyl | Bnzl | H | IB-1 | IIB-32 |
| IB-33 | i-Bu | Bnzl | 4-amino-butyl | H | IF-33 | IB-34 |
| IB-34 | i-Bu | Bnzl | 4-((tert-butoxy carbon yl)amino) butyl | H | IB-1 | IIB-34 |
| IB-35 | i-Bu | Bnzl | Cbx-E | H | EX | IB-73 |
| IB-36 | i-Bu | Bnzl | 3-methoxy-3-oxopro-pyl | H | IB-1 | IIB-36 |
| IB-37 | i-Bu | Bnzl | Cbm-E | H | IF-33 | IB-75 |
| IB-38 | i-Bu | Bnzl | Chm | H | IB-1 | IIB-38 |
| IB-39 | Chm | Bnzl | Bnzl | H | IB-1 | IIB-39 |
| IB-40 | 4-OH-Bnzl | Bnzl | Bnzl | H | EX | IB-41 |
| IB-41 | 4-(tert-butoxy)benzyl | Bnzl | Bnzl | H | IB-1 | IIB-41 |
| IB-42 | Np-M | Bnzl | Bnzl | H | IB-1 | IIB-42 |
| IB-43 | i-Bu | Bnzl | Bnzl | Ac | IF-43 | IB-1 |
| IB-44 | i-Bu | i-Bu | i-Bu | Ac | IF-43 | IB-2 |
| IB-45 | i-Bu | i-Bu | Bnzl | Ac | IF-43 | IB-3 |
| IB-46 | Bnzl | i-Bu | i-Bu | Ac | IF-43 | IB-4 |
| IB-47 | i-Bu | Bnzl | i-Bu | Ac | IF-43 | IB-5 |
| IB-49 | Bnzl | Bnzl | i-Bu | Ac | IF-43 | IB-7 |
| IB-50 | Bnzl | Bnzl | Bnzl | Ac | IF-43 | IB-8 |
| IB-54 | i-Bu | Ph-Et | Bnzl | Ac | IF-43 | IB-12 |
| IB-57 | i-Bu | 3-Me-Bnzl | Bnzl | Ac | IF-43 | IB-15 |
| IB-58 | i-Bu | 4-Me-Bnzl | Bnzl | Ac | IF-43 | IB-16 |
| IB-64 | Me | Np-E | Bnzl | Ac | IF-43 | IB-21 |
| IB-68 | i-Bu | Bnzl | Bnzl | Bz | EX | IB-1 |
| IB-69 | i-Bu | Bnzl | Bnzl | Et | EX | IB-1 |
| IB-70 | i-Bu | Bnzl | Bnzl | methoxy-carbonyl | EX | IB-1 |
| IB-71 | i-Bu | Bnzl | Bnzl | Me | IF-71 | IB-1 |
| IB-72 | Me | Np-E | Bnzl | Et | IB-69 | IB-21 |
| IB-73 | i-Bu | Bnzl | Cbx-E | tBOC | EX | IB-74 |
| IB-74 | i-Bu | Bnzl | 3-methoxy-3-oxopropyl | tBOC | EX | IB-36 |
| IB-75 | i-Bu | Bnzl | Cbm-E | tBOC | EX | IB-73 |
| IB-76 | 3-(tert-butoxy)-3-oxopro-pyl | Bnzl | Bnzl | H | IB-1 | IIB-76 |
| IB-77 | Bnzl | Bnzl | 4-OH-Bnzl | H | IB-1 | IIB-77 |
| IB-78 | Me | 2-(1-(tert-butoxycarbonyl)-1H-indol-3-yl)ethyl | Bnzl | H | IB-1 | IIB-78 |
| IB-79 | Chm | Bnzl | Bnzl | pro-pyl carba-moyl | EX | IB-39 |
| IB-80 | Np-M | Bnzl | Pr | H | IB-1 | IIB-80 |

| Compound number | Name of compound | LCMS $t_R$ (min) | Mass $(M + H)^+$ | Elution condition | Yield (%) |
|---|---|---|---|---|---|
| IB-1 | (3S*,3aS*,6R*,7R*,7aS*)-N,7-dibenzyl-1-isobutyloctahydro-3aH-3,6-methanopyrrolo[3,2-b]pyridine-3a-carboxamide | 1.21 | 418 | B | 81 |

TABLE 3-continued

| | | | | | |
|---|---|---|---|---|---|
| IB-2 | (3S*,3aS*,6R*,7R*,7aS*)-N,1,7-triisobutyloctahydro-3aH-3,6-methanopyrrolo[3,2-b]pyridine-3a-carboxamide | 1.20 | 350 | B | 77 |
| IB-3 | (3S*,3aS*,6R*,7R*,7aS*)-7-benzyl-N,1-diisobutyloctahydro-3aH-3,6-methanopyrrolo[3,2-b]pyridine-3a-carboxamide | 1.19 | 384 | B | 75 |
| IB-4 | (3S*,3aS*,6R*,7R*,7aS*)-1-benzyl-N,7-diisobutyloctahydro-3aH-3,6-methanopyrrolo[3,2-b]pyridine-3a-carboxamide | 1.20 | 384 | B | 88 |
| IB-5 | (3S*,3aS*,6R*,7R*,7aS*)-N-benzyl-1,7-diisobutyloctahydro-3aH-3,6-methanopyrrolo[3,2-b]pyridine-3a-carboxamide | 1.20 | 384 | B | 76 |
| IB-6 | (3S*,3aS*,6R*,7R*,7aS*)-1,7-dibenzyl-N-isobutyloctahydro-3aH-3,6-methanopyrrolo[3,2-b]pyridine-3a-carboxamide | 1.20 | 418 | B | 54 |
| IB-7 | (3S*,3aS*,6R*,7R*,7aS*)-N,1-dibenzyl-7-isobutyloctahydro-3aH-3,6-methanopyrrolo[3,2-b]pyridine-3a-carboxamide | 1.21 | 418 | B | 81 |
| IB-8 | (3S*,3aS*,6R*,7R*,7aS*)-N,1,7-tribenzyloctahydro-3aH-3,6-methanopyrrolo[3,2-b]pyridine-3a-carboxamide | 1.21 | 452 | B | 76 |
| IB-9 | (3S*,3aS*,6R*,7R*,7aS*)-N,7-dibenzyl-1-isopentyloctahydro-3aH-3,6-methanopyrrolo[3,2-b]pyridine-3a-carboxamide | 1.23 | 432 | B | 81 |
| IB-10 | (3S*,3aS*,6R*,7R*,7aS*)-N,1-dibenzyl-7-isopentyloctahydro-3aH-3,6-methanopyrrolo[3,2-b]pyridine-3a-carboxamide | 1.23 | 432 | B | 37 |
| IB-11 | (3S*,3aS*,6R*,7R*,7aS*)-N-benzyl-1-isobutyl-7-phenethyloctahydro-3aH-3,6-methanopyrrolo[3,2-b]pyridine-3a-carboxamide | 1.22 | 432 | B | 63 |
| IB-12 | (3S*,3aS*,6R*,7R*,7aS*)-1-benzyl-7-isobutyl-N-phenethyloctahydro-3aH-3,6-methanopyrrolo[3,2-b]pyridine-3a-carboxamide | 1.23 | 432 | B | 65 |
| IB-13 | (3S*,3aS*,6R*,7R*,7aS*)-N-benzyl-1-isobutyl-7-(3-methylbenzyl)octahydro-3aH-3,6-methanopyrrolo[3,2-b]pyridine-3a-carboxamide | 1.24 | 432 | B | 64 |
| IB-14 | (3S*,3aS*,6R*,7R*,7aS*)-N-benzyl-1-isobutyl-7-(4-methylbenzyl)octahydro-3aH-3,6-methanopyrrolo[3,2-b]pyridine-3a-carboxamide | 1.23 | 432 | B | 74 |
| IB-15 | (3S*,3aS*,6R*,7R*,7aS*)-7-benzyl-1-isobutyl-N-(3-methylbenzyl)octahydro-3aH-3,6-methanopyrrolo[3,2-b]pyridine-3a-carboxamide | 1.24 | 432 | B | 66 |
| IB-16 | (3S*,3aS*,6R*,7R*,7aS*)-7-benzyl-1-isobutyl-N-(4-methylbenzyl)octahydro-3aH-3,6-methanopyrrolo[3,2-b]pyridine-3a-carboxamide | 1.25 | 432 | B | 72 |
| IB-17 | (3S*,3aS*,6R*,7R*,7aS*)-7-benzyl-N-(3-chlorobenzyl)-1-isobutyloctahydro-3aH-3,6-methanopyrrolo[3,2-b]pyridine-3a-carboxamide | 1.03 | 452 | B | 85 |
| IB-18 | (3S*,3aS*,6R*,7R*,7aS*)-7-benzyl-N-(4-chlorobenzyl)-1-isobutyloctahydro-3aH-3,6-methanopyrrolo[3,2-b]pyridine-3a-carboxamide | 1.24 | 452 | B | 79 |
| IB-19 | (3S*,3aS*,6R*,7R*,7aS*)-N-benzyl-1-(3,4-dichlorobenzyl)-7-isobutyloctahydro-3aH-3,6-methanopyrrolo[3,2-b]pyridine-3a-carboxamide | 1.13 | 486 | B | 43 |
| IB-20 | (3S*,3aS*,6R*,7R*,7aS*)-1-benzyl-N-(3,4-dichlorobenzyl)-7-isobutyloctahydro-3aH-3,6-methanopyrrolo[3,2-b]pyridine-3a-carboxamide | 1.26 | 486 | B | 84 |

TABLE 3-continued

| | | | | | |
|---|---|---|---|---|---|
| IB-21 | (3S*,3aS*,6R*,7R*,7aS*)-7-benzyl-1-isobutyl-N-(2-(naphthalen-1-yl)ethyl)octahydro-3aH-3,6-methanopyrrolo[3,2-b]pyridine-3a-carboxamide | 1.19 | 440 | B | 82 |
| IB-22 | (3S*,3aS*,6R*,7R*,7aS*)-7-benzyl-N-(4-hydroxybenzyl)-1-isobutyloctahydro-3aH-3,6-methanopyrrolo[3,2-b]pyridine-3a-carboxamide | 0.89 | 434 | A | 95 |
| IB-23 | (3S*,3aS*,6R*,7R*,7aS*)-7-benzyl-1-isobutyl-N-(4-(tert-butoxy)benzyl)octahydro-3aH-3,6-methanopyrrolo[3,2-b]pyridine-3a-carboxamide | 1.06 | 490 | A | 88 |
| IB-24 | (3S*,3aS*,6R*,7R*,7aS*)-7-benzyl-1-isobutyl-N-(naphthalen-1-ylmethyl)octahydro-3aH-3,6-methanopyrrolo[3,2-b]pyridine-3a-carboxamide | 1.05 | 468 | A | 84 |
| IB-25 | (3S*,3aS*,6R*,7R*,7aS*)-7-benzyl-N-(2-hydroxyethyl)-1-isobutyloctahydro-3aH-3,6-methanopyrrolo[3,2-b]pyridine-3a-carboxamide | 0.80 | 372 | A | 77 |
| IB-26 | 3-((3S*,3aS*,6R*,7R*,7aS*)-7-benzyl-1-isobutyloctahydro-1H-3,6-methanopyrrolo[3,2-b]pyridine-3a-carboxamide)propanoic acid | 0.82 | 400 | A | 95 |
| IB-27 | (3S*,3aS*,6R*,7R*,7aS*)-7-benzyl-1-isobutyl-N-(2-(tert-butoxy)-2-oxoethyl)octahydro-3aH-3,6-methanopyrrolo[3,2-b]pyridine-3a-carboxamide | 0.99 | 456 | A | 93 |
| IB-28 | (3S*,3aS*,6R*,7R*,7aS*)-N-(3-amino-3-oxopropyl)-7-benzyl-1-isobutyloctahydro-3aH-3,6-methanopyrrolo[3,2-b]pyridine-3a-carboxamide | 0.79 | 399 | A | 80 |
| IB-29 | (3S*,3aS*,6R*,7R*,7aS*)-N-(4-aminobutyl)-7-benzyl-1-isobutyloctahydro-3aH-3,6-methanopyrrolo[3,2-b]pyridine-3a-carboxamide | 0.75 | 399 | A | 100 |
| IB-30 | (3S*,3aS*,6R*,7R*,7aS*)-7-benzyl-1-isobutyl-N-(4-((tert-butoxycarbonyl)amino)butyl)octahydro-3aH-3,6-methanopyrrolo[3,2-b]pyridine-3a-carboxamide | 0.97 | 499 | A | 62 |
| IB-31 | (3S*,3aS*,6R*,7R*,7aS*)-7-benzyl-N-cyclohexylmethyl-1-isobutyloctahydro-3aH-3,6-methanopyrrolo[3,2-b]pyridine-3a-carboxamide | 1.05 | 424 | A | 42 |
| IB-32 | (3S*,3aS*,6R*,7R*,7aS*)-7-benzyl-1-isobutyl-N-((tetrahydro-2H-pyran-2-yl)methyl)octahydro-3aH-3,6-methanopyrrolo[3,2-b]pyridine-3a-carboxamide | 0.96 | 426 | A | 97 |
| IB-33 | (3S*,3aS*,6R*,7R*,7aS*)-7-(4-aminobutyl)-N-benzyl-1-isobutyloctahydro-3aH-3,6-methanopyrrolo[3,2-b]pyridine-3a-carboxamide | 0.74 | 399 | A | 100 |
| IB-34 | (3S*,3aS*,6R*,7R*,7aS*)-N-benzyl-1-isobutyl-7-(4-((tert-butoxycarbonyl)amino)butyl)octahydro-3aH-3,6-methanopyrrolo[3,2-b]pyridine-3a-carboxamide | 0.99 | 499 | A | 77 |
| IB-35 | 3-((3S*,3aS*,6R*,7R*,7aS*)-3a-(benzylcarbamoyl)-1-isobutyloctahydro-1H-3,6-methanopyrrolo[3,2-b]pyridin-7-yl)propanoic acid | 0.83 | 400 | A | 100 |
| IB-36 | (3S*,3aS*,6R*,7R*,7aS*)-N-benzyl-1-isobutyl-7-(3-methoxy-3-oxopropyl)octahydro-3aH-3,6-methanopyrrolo[3,2-b]pyridine-3a-carboxamide | 0.90 | 414 | A | 73 |

TABLE 3-continued

| | | | | | |
|---|---|---|---|---|---|
| IB-37 | (3S*,3aS*,6R*,7R*,7aS*)-7-(3-amino-3-oxopropyl)-N-benzyl-1-isobutyloctahydro-3aH-3,6-methanopyrrolo[3,2-b]pyridine-3a-carboxamide | 0.78 | 399 | A | 100 |
| IB-38 | (3S*,3aS*,6R*,7R*,7aS*)-N-benzyl-7-(cyclohexylmethyl)-1-isobutyloctahydro-3aH-3,6-methanopyrrolo[3,2-b]pyridine-3a-carboxamide | 1.07 | 424 | A | 82 |
| IB-39 | (3S*,3aS*,6R*,7R*,7aS*)-N,7-dibenzyl-1-cyclohexylmethyloctahydro-3aH-3,6-methanopyrrolo[3,2-b]pyridine-3a-carboxamide | 1.06 | 458 | A | 78 |
| IB-40 | (3S*,3aS*,6R*,7R*,7aS*)-N,7-dibenzyl-1-(4-hydroxybenzyl)octahydro-3aH-3,6-methanopyrrolo[3,2-b]pyridine-3a-carboxamide | 0.89 | 468 | A | 99 |
| IB-41 | (3S*,3aS*,6R*,7R*,7aS*)-N,7-dibenzyl-1-(4-(tert-butoxy)benzyl)octahydro-3aH-3,6-methanopyrrolo[3,2-b]pyridine-3a-carboxamide | 1.05 | 524 | A | 65 |
| IB-42 | (3S*,3aS*,6R*,7R*,7aS*)-N,7-dibenzyl-1-(naphthalen-1-ylmethyl)octahydro-3aH-3,6-methanopyrrolo[3,2-b]pyridine-3a-carboxamide | 1.05 | 502 | A | 63 |
| IB-43 | (3S*,3aS*,6R*,7R*,7aS*)-4-acetyl-N,7-dibenzyl-1-isobutyloctahydro-3aH-3,6-methanopyrrolo[3,2-b]pyridine-3a-carboxamide | 1.14 | 460 | B | 86 |
| IB-44 | (3S*,3aS*,6R*,7R*,7aS*)-4-acetyl-N,1,7-triisobutyloctahydro-3aH-3,6-methanopyrrolo[3,2-b]pyridine-3a-carboxamide | 1.10 | 392 | B | 86 |
| IB-45 | (3S*,3aS*,6R*,7R*,7aS*)-4-acetyl-7-benzyl-N,1-diisobutyloctahydro-3aH-3,6-methanopyrrolo[3,2-b]pyridine-3a-carboxamide | 1.10 | 426 | B | 82 |
| IB-46 | (3S*,3aS*,6R*,7R*,7aS*)-4-acetyl-1-benzyl-N,7-diisobutyloctahydro-3aH-3,6-methanopyrrolo[3,2-b]pyridine-3a-carboxamide | 1.10 | 426 | B | 91 |
| IB-47 | (3S*,3aS*,6R*,7R*,7aS*)-4-acetyl-N-benzyl-1,7-diIsobutyloctahydro-3aH-3,6-methanopyrrolo[3,2-b]pyridine-3a-carboxamide | 1.11 | 426 | B | 85 |
| IB-49 | (3S*,3aS*,6R*,7R*,7aS*)-4-acetyl-N,1-dibenzyl-7-isobutyloctahydro-3aH-3,6-methanopyrrolo[3,2-b]pyridine-3a-carboxamide | 1.13 | 460 | B | 86 |
| IB-50 | (3S*,3aS*,6R*,7R*,7aS*)-4-acetyl-N,1,7-tribenzyloctahydro-3aH-3,6-methanopyrrolo[3,2-b]pyridine-3a-carboxamide | 1.16 | 494 | B | 81 |
| IB-54 | (3S*,3aS*,6R*,7R*,7aS*)-4-acetyl-1-benzyl-7-isobutyl-N-phenethyloctahydro-3aH-3,6-methanopyrrolo[3,2-b]pyridine-3a-carboxamide | 1.15 | 474 | B | 82 |
| IB-57 | (3S*,3aS*,6R*,7R*,7aS*)-4-acetyl-7-benzyl-1-isobutyl-N-(3-methylbenzyl)octahydro-3aH-3,6-methanopyrrolo[3,2-b]pyridine-3a-carboxamide | 1.17 | 474 | B | 87 |
| IB-58 | (3S*,3aS*,6R*,7R*,7aS*)-4-acetyl-7-benzyl-1-isobutyl-N-(4-methylbenzyl)octahydro-3aH-3,6-methanopyrrolo[3,2-b]pyridine-3a-carboxamide | 1.17 | 474 | B | 80 |
| IB-64 | (3S*,3aS*,6R*,7R*,7aS*)-4-acetyl-7-benzyl-1-isobutyl-N-(2-(naphthalen-1-yl)ethyl)octahydro-3aH-3,6-methanopyrrolo[3,2-b]pyridine-3a-carboxamide | 1.12 | 482 | B | 100 |
| IB-68 | (3S*,3aS*,6R*,7R*,7aS*)-4-benzoyl-N,7-dibenzyl-1-isobutyloctahydro-3aH-3,6-methanopyrrolo[3,2-b]pyridine-3a-carboxamide | 1.23 | 522 | B | 39 |

TABLE 3-continued

| | | | | | |
|---|---|---|---|---|---|
| IB-69 | (3S*,3aS*,6R*,7R*,7aS*)-N,7-dibenzyl-4-ethyl-1-isobutyloctahydro-3aH-3,6-methanopyrrolo[3,2-b]pyridine-3a-carboxamide | 1.24 | 446 | B | 28 |
| IB-70 | (3S*,3aS*,6R*,7R*,7aS*)-N,7-dibenzyl-1-isobutyl-4-(methoxycarbonyl)octahydro-3aH-3,6-methanopyrrolo[3,2-b]pyridine-3a-carboxamide | 1.18 | 476 | B | 85 |
| IB-71 | (3S*,3aS*,6R*,7R*,7aS*)-N,7-dibenzyl-1-isobutyl-4-methyloctahydro-3aH-3,6-methanopyrrolo[3,2-b]pyridine-3a-carboxamide | 1.22 | 432 | B | 35 |
| IB-72 | (3S*,3aS*,6R*,7R*,7aS*)-7-benzyl-4-ethyl-1-isobutyl-N-(2-(naphthalen-1-yl)ethyl)octahydro-3aH-3,6-methanopyrrolo[3,2-b]pyridine-3a-carboxamide | 1.24 | 468 | B | 70 |
| IB-73 | tert-butyl (3S*,3aS*,6R*,7R*,7aS*)-3a-(benzylcarbamoyl)-1-isobutyl-7-(2-carboxyethyl)octahydro-4H-3,6-methanopyrrolo[3,2-b]pyridlne-4-carboxylate | 0.91 | 500 | A | 100 |
| IB-74 | tert-butyl (3S*,3aS*,6R*,7R*,7aS*)-3a-(benzylcarbamoyl)-1-isobutyl-7-(3-methoxy-3-oxopropyl)octahydro-4H-3,6-methanopyrrolo[3,2-b]pyridine-4-carboxylate | 0.97 | 514 | A | 75 |
| IB-75 | tert-butyl (3S*,3aS*,6R*,7R*,7aS*)-3a-(benzylcarbamoyl)-1-isobutyl-7-(3-amino-3-oxopropyl)octahydro-4H-3,6-methanopyrrolo[3,2-b]pyridine-4-carboxylate | 0.86 | 499 | A | 26 |
| IB-76 | tert-butyl 3-((3S*,3aS*,6R*,7R*,7aS*)-7-benzyl-3a-(benzylcarbamoyl)octahydro-1H-3,6-methanopyrrolo[3,2-b]pyridin-1-yl)propanoate | 1.20 | 490 | B | 68 |
| IB-77 | (3S*,3aS*,6R*,7R*,7aS*)-N,1-dibenzyl-7-(4-hydroxybenzyl)octahydro-3aH-3,6-methanopyrrolo[3,2-b]pyridine-3a-carboxamide | 1.13 | 468 | B | 60 |
| IB-78 | tert-butyl 3-((3S*,3aS*,6R*,7R*,7aS*)-2-(7-benzyl-1-methyloctahydro-1H-3,6-methanopyrrolo[3,2-b]pyridine-3a-carboxamide)ethyl)-1H-indole-1-carboxylate | 1.25 | 529 | B | 71 |
| IB-79 | (3S*,3aS*,6R*,7R*,7aS*)-N$^{3a}$,7-dibenzyl-1-(cyclohexylmethyl)-N$^4$-propylhexahydro-1H-3,6-methanopyrrolo[3,2-b]pyridine-3a,4-dicarboxamide | 1.05 | 543 | A | 65 |
| IB-80 | (3S*,3aS*,6R*,7R*,7aS*)-N-benzyl-1-(naphthalen-1-ylmethyl)-7-propyloctahydro-3aH-3,6-methanopyrrolo[3,2-b]pyridine-3a-carboxamide | 1.02 | 454 | A | 62 |

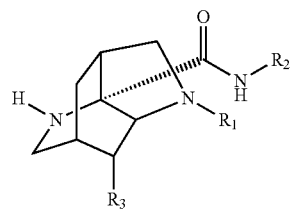

| Compound number | $R_1$ | $R_2$ | $R_3$ | Time of retention TR (min) | Mass $(M + H)^+$ | Measurement condition |
|---|---|---|---|---|---|---|
| IB-81 | Cbm-M | Np-M | i-Bu | 0.79 | 435 | C |
| IB-82 | Cbm-M | Np-M | Bnzl | 0.80 | 469 | C |
| IB-83 | Cbm-M | Np-M | 4-OH-Bnzl | 0.75 | 485 | C |
| IB-84 | Cbm-M | Np-M | i-Pnt | 0.83 | 449 | C |
| IB-85 | Cbm-M | Np-M | Ph-Et | 0.83 | 483 | C |

TABLE 3-continued

| | | | | | | |
|---|---|---|---|---|---|---|
| IB-86 | Cbm-M | Ph-Et | i-Bu | 0.74 | 399 | C |
| IB-87 | Cbm-M | Ph-Et | Bnzl | 0.75 | 433 | C |
| IB-88 | Cbm-M | Ph-Et | 4-OH-Bnzl | 0.69 | 449 | C |
| IB-89 | Cbm-M | Ph-Et | i-Pnt | 0.78 | 413 | C |
| IB-90 | Cbm-M | Np-M | Np-M | 0.84 | 519 | C |
| IB-91 | Cbm-M | 4-F-Bnzl | i-Bu | 0.74 | 403 | C |
| IB-92 | Cbm-M | 4-F-Bnzl | Bnzl | 0.75 | 437 | C |
| IB-93 | Cbm-M | 4-F-Bnzl | 4-OH-Bnzl | 0.69 | 453 | C |
| IB-94 | Cbm-M | 4-F-Bnzl | i-Pnt | 0.78 | 417 | C |
| IB-95 | Cbm-M | 4-F-Bnzl | Ph-Et | 0.78 | 451 | C |
| IB-96 | Cbm-M | 4-F-Bnzl | Np-M | 0.80 | 487 | C |
| IB-97 | Cbm-M | Ph-Et | Np-M | 0.82 | 483 | C |
| IB-98 | Cbm-M | i-Pnt | i-Bu | 0.73 | 365 | C |
| IB-99 | Cbm-M | i-Pnt | Bnzl | 0.74 | 399 | C |
| IB-100 | Cbm-M | i-Pnt | 4-OH-Bnzl | 0.70 | 415 | C |
| IB-101 | Cbm-M | i-Pnt | Cbx-E | 0.64 | 381 | C |
| IB-102 | Cbm-M | i-Pnt | Ph-Et | 0.78 | 413 | C |
| IB-103 | Cbm-M | i-Pnt | Np-M | 0.80 | 449 | C |
| IB-104 | Cbm-M | Hxy | i-Bu | 0.78 | 379 | C |
| IB-105 | Cbm-M | Hxy | Bnzl | 0.79 | 413 | C |
| IB-106 | Cbm-M | Hxy | 4-OH-Bnzl | 0.74 | 429 | C |
| IB-107 | Cbm-M | Hxy | Cbx-E | 0.70 | 395 | C |
| IB-108 | Cbm-M | Hxy | i-Pnt | 0.82 | 393 | C |
| IB-109 | Cbm-M | Hxy | Ph-Et | 0.82 | 427 | C |
| IB-110 | Cbm-M | Hxy | Np-M | 0.84 | 463 | C |
| IB-111 | Cbm-M | i-Pr | i-Bu | 0.65 | 337 | C |
| IB-112 | Cbm-M | i-Pr | Bnzl | 0.66 | 371 | C |
| IB-113 | Cbm-M | i-Pr | 4-OH-Bnzl | 0.59 | 387 | C |
| IB-114 | Cbm-M | i-Pr | Cbx-E | 0.98 | 353 | D |
| IB-115 | Cbm-M | i-Pr | i-Pnt | 0.70 | 351 | C |
| IB-116 | Cbm-M | i-Pr | Ph-Et | 0.72 | 385 | C |
| IB-117 | Cbm-M | i-Pr | Np-M | 0.74 | 421 | C |
| IB-118 | Cbm-M | i-Bu | i-Bu | 0.71 | 351 | C |
| IB-119 | Cbm-M | i-Bu | Bnzl | 0.72 | 385 | C |
| IB-120 | Cbm-M | i-Bu | 4-OH-Bnzl | 0.65 | 401 | C |
| IB-121 | Cbm-M | i-Bu | Cbx-E | 0.60 | 367 | C |
| IB-122 | Cbm-M | i-Bu | i-Pnt | 0.76 | 365 | C |
| IB-123 | Cbm-M | i-Bu | Ph-Et | 0.77 | 399 | C |
| IB-124 | Cbm-M | i-Bu | Np-M | 0.79 | 435 | C |
| IB-125 | Cbm-M | Bnzl | i-Bu | 0.74 | 385 | C |
| IB-126 | Cbm-M | Bnzl | Bnzl | 0.75 | 419 | C |
| IB-127 | Cbm-M | Bnzl | 4-OH-Bnzl | 0.69 | 435 | C |
| IB-128 | Cbm-M | Bnzl | Cbx-E | 0.63 | 401 | C |
| IB-129 | Cbm-M | Bnzl | i-Pnt | 0.79 | 399 | C |
| IB-130 | Cbm-M | Bnzl | Ph-Et | 0.80 | 433 | C |
| IB-131 | Cbm-M | Bnzl | Np-M | 0.81 | 469 | C |
| IB-132 | Cbm-M | 4-OH-Bnzl | i-Bu | 0.67 | 401 | C |
| IB-133 | Cbm-M | 4-OH-Bnzl | Bnzl | 0.69 | 435 | C |
| IB-134 | Cbm-M | 4-OH-Bnzl | Cbx-E | 0.98 | 417 | D |
| IB-135 | Cbm-M | 4-OH-Bnzl | i-Pnt | 0.73 | 415 | C |
| IB-136 | Cbm-M | 4-OH-Bnzl | Ph-Et | 0.74 | 449 | C |
| IB-137 | Cbm-M | 4-OH-Bnzl | Np-M | 0.76 | 485 | C |
| IB-138 | Cbm-M | Cbx-E | i-Bu | 0.61 | 367 | C |
| IB-139 | Cbm-M | Cbx-E | Bnzl | 0.62 | 401 | C |
| IB-140 | Cbm-M | Cbx-E | 4-OH-Bnzl | 0.98 | 417 | D |
| IB-141 | Cbm-M | Cbx-E | i-Pnt | 0.67 | 381 | C |
| IB-142 | Cbm-M | Cbx-E | Ph-Et | 0.69 | 415 | C |
| IB-143 | Cbm-M | Cbx-E | Np-M | 0.71 | 451 | C |
| IB-144 | Cbm-M | Cbm-E | i-Bu | 0.59 | 366 | C |
| IB-145 | Cbm-M | Cbm-E | Bnzl | 0.61 | 400 | C |
| IB-146 | Cbm-M | Cbm-E | 4-OH-Bnzl | 0.97 | 416 | D |
| IB-147 | Cbm-M | Cbm-E | Cbx-E | 0.20 | 382 | E |
| IB-148 | Cbm-M | Cbm-E | i-Pnt | 0.65 | 380 | C |
| IB-149 | Cbm-M | Cbm-E | Ph-Et | 0.67 | 414 | C |
| IB-150 | Cbm-M | Cbm-E | Np-M | 0.69 | 450 | C |
| IB-151 | Cbm-M | Gun-Pr | i-Bu | 0.59 | 394 | C |
| IB-152 | Cbm-M | Gun-Pr | Bnzl | 0.60 | 428 | C |
| IB-153 | Cbm-M | Gun-Pr | 4-OH-Bnzl | 0.91 | 444 | D |
| IB-154 | Cbm-M | Gun-Pr | i-Pnt | 0.63 | 408 | C |
| IB-155 | Cbm-M | Gun-Pr | Ph-Et | 0.65 | 442 | C |
| IB-156 | Cbm-M | Gun-Pr | Np-M | 1.15 | 478 | D |
| IB-157 | Cbm-M | Hdr-E | i-Bu | 0.60 | 339 | C |
| IB-158 | Cbm-M | Hdr-E | Bnzl | 0.61 | 373 | C |
| IB-159 | Cbm-M | Hdr-E | 4-OH-Bnzl | 0.98 | 389 | D |
| IB-160 | Cbm-M | Hdr-E | Cbx-E | 0.20 | 355 | E |
| IB-161 | Cbm-M | Hdr-E | i-Pnt | 0.65 | 353 | C |
| IB-162 | Cbm-M | Hdr-E | Ph-Et | 0.67 | 387 | C |
| IB-163 | Cbm-M | Hdr-E | Np-M | 0.70 | 423 | C |
| IB-164 | Gun-Pr | Np-M | i-Bu | 1.25 | 477 | D |
| IB-165 | Gun-Pr | Np-M | Bnzl | 0.73 | 511 | C |

TABLE 3-continued

| | | | | | | |
|---|---|---|---|---|---|---|
| IB-166 | Gun-Pr | Np-M | 4-OH-Bnzl | 0.71 | 527 | C |
| IB-167 | Gun-Pr | Np-M | i-Pnt | 1.30 | 491 | D |
| IB-168 | Gun-Pr | Np-M | Ph-Et | 1.31 | 525 | D |
| IB-169 | Gun-Pr | Np-M | Np-M | 1.31 | 561 | D |
| IB-170 | Gun-Pr | Hxy | i-Bu | 0.74 | 421 | C |
| IB-171 | Gun-Pr | Hxy | Bnzl | 0.74 | 455 | C |
| IB-172 | Gun-Pr | Hxy | 4-OH-Bnzl | 1.23 | 471 | D |
| IB-173 | Gun-Pr | Hxy | i-Pnt | 0.77 | 435 | C |
| IB-174 | Gun-Pr | Hxy | Ph-Et | 1.33 | 469 | D |
| IB-175 | Gun-Pr | Hxy | Np-M | 1.32 | 505 | D |
| IB-176 | Gun-Pr | i-Pr | i-Bu | 1.08 | 379 | D |
| IB-177 | Gun-Pr | i-Pr | 4-OH-Bnzl | 1.04 | 429 | D |
| IB-178 | Gun-Pr | i-Pr | i-Pnt | 1.15 | 393 | D |
| IB-179 | Gun-Pr | i-Pr | Ph-Et | 1.17 | 427 | D |
| IB-180 | Gun-Pr | i-Pr | Np-M | 1.18 | 463 | D |
| IB-181 | Gun-Pr | 4-F-Bnzl | i-Bu | 1.19 | 445 | D |
| IB-182 | Gun-Pr | 4-F-Bnzl | Bnzl | 0.70 | 479 | C |
| IB-183 | Gun-Pr | 4-F-Bnzl | 4-OH-Bnzl | 1.14 | 495 | D |
| IB-184 | Gun-Pr | 4-F-Bnzl | i-Pnt | 1.26 | 459 | D |
| IB-185 | Gun-Pr | 4-F-Bnzl | Ph-Et | 0.74 | 493 | C |
| IB-186 | Gun-Pr | 4-F-Bnzl | Np-M | 0.74 | 529 | C |
| IB-187 | i-Bu | i-Bu | Gun-Pr | 3.80 | 393 | G |
| IB-188 | i-Bu | Bnzl | Gun-Pr | 4.09 | 427 | G |
| IB-189 | i-Bu | 4-OH-Bnzl | Gun-Pr | 3.67 | 443 | G |
| IB-190 | i-Bu | Cbm-E | Gun-Pr | 3.04 | 408 | G |
| IB-191 | i-Bu | Hdr-E | Gun-Pr | 3.00 | 381 | G |
| IB-192 | i-Bu | i-Pnt | Gun-Pr | 4.15 | 407 | G |
| IB-193 | i-Bu | Ph-Et | Gun-Pr | 4.30 | 441 | G |
| IB-194 | i-Bu | Np-M | Gun-Pr | 4.70 | 477 | G |
| IB-195 | i-Bu | Hxy | Gun-Pr | 4.54 | 421 | G |
| IB-196 | i-Bu | i-Pr | Gun-Pr | 3.72 | 379 | G |
| IB-197 | i-Bu | 4-F-Bnzl | Gun-Pr | 4.29 | 445 | G |
| IB-198 | Bnzl | i-Bu | Gun-Pr | 2.65 | 427 | F |
| IB-199 | Bnzl | 4-OH-Bnzl | Gun-Pr | 3.88 | 477 | G |
| IB-200 | Bnzl | Cbm-E | Gun-Pr | 3.17 | 442 | G |
| IB-201 | Bnzl | Hdr-E | Gun-Pr | 3.20 | 415 | G |
| IB-202 | Bnzl | i-Pr | Gun-Pr | 3.82 | 413 | F |
| IB-203 | 4-OH-Bnzl | i-Bu | Gun-Pr | 3.65 | 443 | G |
| IB-204 | 4-OH-Bnzl | i-Pnt | Gun-Pr | 3.92 | 457 | G |
| IB-205 | 4-OH-Bnzl | Ph-Et | Gun-Pr | 3.95 | 491 | G |
| IB-206 | 4-OH-Bnzl | Np-M | Gun-Pr | 4.32 | 527 | G |
| IB-207 | 4-OH-Bnzl | 4-F-Bnzl | Gun-Pr | 3.94 | 495 | G |
| IB-208 | i-Pnt | i-Bu | Gun-Pr | 2.54 | 407 | F |
| IB-209 | i-Pnt | Bnzl | Gun-Pr | 2.65 | 441 | F |
| IB-210 | i-Pnt | 4-OH-Bnzl | Gun-Pr | 2.43 | 457 | F |
| IB-211 | i-Pnt | Cbm-E | Gun-Pr | 3.07 | 422 | G |
| IB-212 | i-Pnt | Hdr-E | Gun-Pr | 3.07 | 395 | G |
| IB-213 | i-Pnt | Ph-Et | Gun-Pr | 2.75 | 455 | F |
| IB-214 | i-Pnt | Np-M | Gun-Pr | 3.07 | 491 | F |
| IB-215 | i-Pnt | Hxy | Gun-Pr | 2.84 | 435 | F |
| IB-216 | i-Pnt | i-Pr | Gun-Pr | 3.59 | 393 | G |
| IB-217 | i-Pnt | 4-F-Bnzl | Gun-Pr | 2.74 | 459 | F |
| IB-218 | Ph-Et | Hdr-E | Gun-Pr | 3.63 | 429 | G |
| IB-219 | Np-M | i-Bu | Gun-Pr | 3.02 | 477 | F |
| IB-220 | Np-M | Bnzl | Gun-Pr | 4.80 | 511 | G |
| IB-221 | Np-M | 4-OH-Bnzl | Gun-Pr | 4.35 | 527 | G |
| IB-222 | Np-M | Cbm-E | Gun-Pr | 3.85 | 492 | G |
| IB-223 | Np-M | Hdr-E | Gun-Pr | 3.92 | 465 | G |
| IB-224 | Np-M | i-Pnt | Gun-Pr | 3.22 | 491 | F |
| IB-225 | Np-M | Ph-Et | Gun-Pr | 3.10 | 525 | F |
| IB-226 | Np-M | Np-M | Gun-Pr | 3.24 | 561 | F |
| IB-227 | Np-M | Hxy | Gun-Pr | 5.09 | 505 | G |
| IB-228 | Np-M | i-Pr | Gun-Pr | 2.82 | 463 | F |
| IB-229 | Np-M | 4-F-Bnzl | Gun-Pr | 4.87 | 529 | G |
| IB-230 | Chm | i-Bu | Gun-Pr | 2.82 | 433 | F |
| IB-231 | Chm | Bnzl | Gun-Pr | 2.95 | 467 | F |
| IB-232 | Chm | 4-OH-Bnzl | Gun-Pr | 2.67 | 483 | F |
| IB-233 | Chm | Cbm-E | Gun-Pr | 3.49 | 448 | G |
| IB-234 | Chm | Hdr-E | Gun-Pr | 3.50 | 421 | G |
| IB-235 | Chm | i-Pnt | Gun-Pr | 3.04 | 447 | F |
| IB-236 | Chm | Ph-Et | Gun-Pr | 2.94 | 481 | F |
| IB-237 | Chm | Np-M | Gun-Pr | 3.22 | 517 | F |
| IB-238 | Chm | Hxy | Gun-Pr | 3.15 | 461 | F |
| IB-239 | Chm | i-Pr | Gun-Pr | 2.69 | 419 | F |
| IB-240 | Chm | 4-F-Bnzl | Gun-Pr | 2.99 | 485 | F |
| IB-241 | 4-F-Bnzl | 4-OH-Bnzl | Gun-Pr | 4.00 | 495 | G |
| IB-242 | 4-F-Bnzl | Cbm-E | Gun-Pr | 3.29 | 460 | G |
| IB-243 | 4-F-Bnzl | Hdr-E | Gun-Pr | 3.27 | 433 | F |
| IB-244 | 4-F-Bnzl | i-Pr | Gun-Pr | 3.84 | 431 | G |
| IB-245 | Bnzl | Bnzl | Gun-Pr | 2.69 | 461 | F |

TABLE 3-continued

| | | | | | | |
|---|---|---|---|---|---|---|
| IB-246 | Bnzl | i-Pnt | Gun-Pr | 2.74 | 441 | F |
| IB-247 | Bnzl | Ph-Et | Gun-Pr | 2.77 | 475 | F |
| IB-248 | Bnzl | Np-M | Gun-Pr | 3.07 | 511 | F |
| IB-249 | Bnzl | Hxy | Gun-Pr | 2.97 | 455 | F |
| IB-250 | Bnzl | 4-F-Bnzl | Gun-Pr | 2.77 | 479 | F |
| IB-251 | Ph-Et | i-Bu | Gun-Pr | 2.75 | 441 | F |
| IB-252 | Ph-Et | Bnzl | Gun-Pr | 2.85 | 475 | F |
| IB-253 | Ph-Et | 4-OH-Bnzl | Gun-Pr | 2.60 | 491 | F |
| IB-254 | Ph-Et | i-Pnt | Gun-Pr | 2.85 | 455 | F |
| IB-255 | Ph-Et | Np-M | Gun-Pr | 3.25 | 525 | F |
| IB-256 | Ph-Et | Hxy | Gun-Pr | 3.15 | 469 | F |
| IB-257 | Ph-Et | i-Pr | Gun-Pr | 2.52 | 427 | F |
| IB-258 | Ph-Et | 4-F-Bnzl | Gun-Pr | 2.97 | 493 | F |
| IB-259 | 4-F-Bnzl | i-Bu | Gun-Pr | 2.67 | 445 | F |
| IB-260 | 4-F-Bnzl | Bnzl | Gun-Pr | 2.80 | 479 | F |
| IB-261 | 4-F-Bnzl | i-Pnt | Gun-Pr | 2.84 | 459 | F |
| IB-262 | 4-F-Bnzl | Ph-Et | Gun-Pr | 2.88 | 493 | F |
| IB-263 | 4-F-Bnzl | Np-M | Gun-Pr | 3.20 | 529 | F |
| IB-264 | 4-F-Bnzl | Hxy | Gun-Pr | 3.04 | 473 | F |
| IB-265 | i-Bu | Cbm-E | Cbx-E | 2.06 | 381 | H |
| IB-266 | i-Bu | Cbm-E | i-Pnt | 2.48 | 379 | H |
| IB-267 | i-Bu | Gun-Pr | i-Bu | 2.35 | 393 | H |
| IB-268 | i-Bu | Gun-Pr | Bnzl | 2.39 | 427 | H |
| IB-269 | i-Bu | Gun-Pr | 4-OH-Bnzl | 1.98 | 443 | H |
| IB-270 | i-Bu | Gun-Pr | i-Pnt | 2.24 | 407 | H |
| IB-271 | i-Bu | Gun-Pr | Ph-Et | 2.25 | 441 | H |
| IB-272 | i-Bu | Gun-Pr | Np-M | 2.28 | 477 | H |
| IB-273 | Bnzl | Cbm-E | Cbx-E | 1.90 | 415 | H |
| IB-274 | Bnzl | Cbm-E | i-Pnt | 2.28 | 413 | H |
| IB-275 | Bnzl | Gun-Pr | i-Bu | 2.17 | 427 | H |
| IB-276 | Bnzl | Gun-Pr | Bnzl | 2.25 | 461 | H |
| IB-277 | Bnzl | Gun-Pr | 4-OH-Bnzl | 2.07 | 477 | H |
| IB-278 | Bnzl | Gun-Pr | i-Pnt | 2.36 | 441 | H |
| IB-279 | Bnzl | Gun-Pr | Ph-Et | 2.28 | 475 | H |
| IB-280 | Bnzl | Gun-Pr | Np-M | 2.33 | 511 | H |
| IB-281 | 4-OH-Bnzl | Cbm-E | Cbx-E | 1.71 | 431 | H |
| IB-282 | 4-OH-Bnzl | Cbm-E | i-Pnt | 2.03 | 429 | H |
| IB-283 | 4-OH-Bnzl | Gun-Pr | i-Bu | 1.96 | 443 | H |
| IB-284 | 4-OH-Bnzl | Gun-Pr | Bnzl | 2.12 | 477 | H |
| IB-285 | 4-OH-Bnzl | Gun-Pr | i-Pnt | 2.03 | 457 | H |
| IB-286 | 4-OH-Bnzl | Gun-Pr | Ph-Et | 2.13 | 491 | H |
| IB-287 | 4-OH-Bnzl | Gun-Pr | Np-M | 2.22 | 527 | H |
| IB-288 | Cbx-E | Cbm-E | i-Pnt | 2.10 | 395 | H |
| IB-289 | Gun-Pr | i-Bu | i-Bu | 2.02 | 393 | H |
| IB-290 | Gun-Pr | i-Bu | Bnzl | 2.01 | 427 | H |
| IB-291 | Gun-Pr | i-Bu | 4-OH-Bnzl | 1.95 | 443 | H |
| IB-292 | Gun-Pr | i-Bu | i-Pnt | 2.04 | 407 | H |
| IB-293 | Gun-Pr | i-Bu | Ph-Et | 2.12 | 441 | H |
| IB-294 | Gun-Pr | i-Bu | Np-M | 2.14 | 477 | H |
| IB-295 | Gun-Pr | Bnzl | i-Bu | 2.03 | 427 | H |
| IB-296 | Gun-Pr | Bnzl | Bnzl | 2.06 | 461 | H |
| IB-297 | Gun-Pr | Bnzl | 4-OH-Bnzl | 1.98 | 477 | H |
| IB-298 | Gun-Pr | Bnzl | i-Pnt | 2.16 | 441 | H |
| IB-299 | Gun-Pr | Bnzl | Ph-Et | 2.19 | 475 | H |
| IB-300 | Gun-Pr | Bnzl | Np-M | 2.21 | 511 | H |
| IB-301 | Gun-Pr | 4-OH-Bnzl | i-Bu | 1.93 | 443 | H |
| IB-302 | Gun-Pr | 4-OH-Bnzl | Bnzl | 1.95 | 477 | H |
| IB-303 | Gun-Pr | 4-OH-Bnzl | i-Pnt | 2.05 | 457 | H |
| IB-304 | Gun-Pr | 4-OH-Bnzl | Ph-Et | 2.07 | 491 | H |
| IB-305 | Gun-Pr | 4-OH-Bnzl | Np-M | 2.11 | 527 | H |
| IB-306 | Gun-Pr | Cbm-E | i-Bu | 1.83 | 408 | H |
| IB-307 | Gun-Pr | Cbm-E | Bnzl | 1.85 | 442 | H |
| IB-308 | Gun-Pr | Cbm-E | 4-OH-Bnzl | 1.75 | 458 | H |
| IB-309 | Gun-Pr | Cbm-E | i-Pnt | 1.91 | 422 | H |
| IB-310 | Gun-Pr | Cbm-E | Ph-Et | 1.96 | 456 | H |
| IB-311 | Gun-Pr | Cbm-E | Np-M | 1.98 | 492 | H |
| IB-312 | Gun-Pr | Hdr-E | i-Bu | 1.81 | 381 | H |
| IB-313 | Gun-Pr | Hdr-E | Bnzl | 1.85 | 415 | H |
| IB-314 | Gun-Pr | Hdr-E | 4-OH-Bnzl | 1.73 | 431 | H |
| IB-315 | Gun-Pr | Hdr-E | i-Pnt | 1.92 | 395 | H |
| IB-316 | Gun-Pr | Hdr-E | Ph-Et | 1.94 | 429 | H |
| IB-317 | Gun-Pr | Hdr-E | Np-M | 1.98 | 465 | H |
| IB-318 | Gun-Pr | i-Pnt | i-Bu | 2.10 | 407 | H |
| IB-319 | Gun-Pr | i-Pnt | Bnzl | 2.11 | 441 | H |
| IB-320 | Gun-Pr | i-Pnt | 4-OH-Bnzl | 2.03 | 457 | H |
| IB-321 | Gun-Pr | i-Pnt | Ph-Et | 2.12 | 455 | H |
| IB-322 | Gun-Pr | i-Pnt | Np-M | 2.22 | 491 | H |
| IB-323 | Gun-Pr | Ph-Et | i-Bu | 2.12 | 441 | H |
| IB-324 | Gun-Pr | Ph-Et | Bnzl | 2.09 | 475 | H |
| IB-325 | Gun-Pr | Ph-Et | 4-OH-Bnzl | 2.02 | 491 | H |

TABLE 3-continued

| | | | | | | |
|---|---|---|---|---|---|---|
| IB-326 | Gun-Pr | Ph-Et | i-Pnt | 2.18 | 455 | H |
| IB-327 | Gun-Pr | Ph-Et | Np-M | 2.25 | 525 | H |
| IB-328 | Hdr-E | Cbm-E | i-Pnt | 1.98 | 367 | H |
| IB-329 | Hdr-E | Gun-Pr | i-Bu | 1.89 | 381 | H |
| IB-330 | Hdr-E | Gun-Pr | Bnzl | 1.96 | 415 | H |
| IB-331 | Hdr-E | Gun-Pr | 4-OH-Bnzl | 1.84 | 431 | H |
| IB-332 | Hdr-E | Gun-Pr | i-Pnt | 2.00 | 395 | H |
| IB-333 | Hdr-E | Gun-Pr | Ph-Et | 2.03 | 429 | H |
| IB-334 | Hdr-E | Gun-Pr | Np-M | 1.83 | 465 | H |
| IB-335 | i-Pnt | Cbm-E | Cbx-E | 1.85 | 395 | H |
| IB-336 | i-Pnt | Gun-Pr | i-Bu | 2.14 | 408 | H |
| IB-337 | i-Pnt | Gun-Pr | Bnzl | 2.17 | 441 | H |
| IB-338 | i-Pnt | Gun-Pr | 4-OH-Bnzl | 1.92 | 457 | H |
| IB-339 | i-Pnt | Gun-Pr | Ph-Et | 2.26 | 455 | H |
| IB-340 | i-Pnt | Gun-Pr | Np-M | 2.31 | 491 | H |
| IB-341 | Ph-Et | Cbm-E | Cbx-E | 2.00 | 429 | H |
| IB-342 | Ph-Et | Cbm-E | i-Pnt | 2.39 | 427 | H |
| IB-343 | Ph-Et | Gun-Pr | i-Bu | 2.22 | 441 | H |
| IB-344 | Ph-Et | Gun-Pr | Bnzl | 2.27 | 475 | H |
| IB-345 | Ph-Et | Gun-Pr | 4-OH-Bnzl | 2.10 | 491 | H |
| IB-346 | Ph-Et | Gun-Pr | i-Pnt | 2.33 | 455 | H |
| IB-347 | Ph-Et | Gun-Pr | Np-M | 2.38 | 525 | H |
| IB-348 | Np-M | Cbm-E | Cbx-E | 2.14 | 465 | H |
| IB-349 | Np-M | Cbm-E | i-Pnt | 2.57 | 463 | H |
| IB-350 | Np-M | Gun-Pr | i-Bu | 2.33 | 477 | H |
| IB-351 | Np-M | Gun-Pr | Bnzl | 2.31 | 511 | H |
| IB-352 | Np-M | Gun-Pr | 4-OH-Bnzl | 2.18 | 527 | H |
| IB-353 | Np-M | Gun-Pr | i-Pnt | 2.42 | 491 | H |
| IB-354 | Np-M | Gun-Pr | Ph-Et | 2.38 | 525 | H |
| IB-355 | Np-M | Gun-Pr | Np-M | 2.41 | 561 | H |
| IB-356 | Chm | Cbm-E | Cbx-E | 2.00 | 421 | H |
| IB-357 | Chm | Cbm-E | i-Pnt | 2.41 | 419 | H |
| IB-358 | Chm | Gun-Pr | i-Bu | 2.27 | 433 | H |
| IB-359 | Chm | Gun-Pr | Bnzl | 2.31 | 467 | H |
| IB-360 | Chm | Gun-Pr | 4-OH-Bnzl | 2.13 | 483 | H |
| IB-361 | Chm | Gun-Pr | i-Pnt | 2.33 | 447 | H |
| IB-362 | Chm | Gun-Pr | Ph-Et | 2.34 | 481 | H |
| IB-363 | Chm | Gun-Pr | Np-M | 2.42 | 517 | H |
| IB-364 | 4-F-Bnzl | Cbm-E | Cbx-E | 1.93 | 433 | H |
| IB-365 | 4-F-Bnzl | Cbm-E | i-Pnt | 2.29 | 431 | H |
| IB-366 | 4-F-Bnzl | Gun-Pr | i-Bu | 2.21 | 445 | H |
| IB-367 | 4-F-Bnzl | Gun-Pr | Bnzl | 2.26 | 478 | H |
| IB-368 | 4-F-Bnzl | Gun-Pr | 4-OH-Bnzl | 2.09 | 495 | H |
| IB-369 | 4-F-Bnzl | Gun-Pr | i-Pnt | 2.27 | 459 | H |
| IB-370 | 4-F-Bnzl | Gun-Pr | Ph-Et | 2.28 | 493 | H |
| IB-371 | 4-F-Bnzl | Gun-Pr | Np-M | 2.36 | 529 | H |
| IB-372 | Hdr-E | i-Bu | i-Pnt | 1.68 | 352 | I |
| IB-373 | Ph-Et | i-Bu | i-Pnt | 2.16 | 412 | I |
| IB-374 | Np-M | i-Bu | i-Pnt | 2.21 | 448 | I |
| IB-375 | Chm | i-Bu | i-Pnt | 2.28 | 404 | I |
| IB-376 | 4-F-Bnzl | i-Bu | i-Pnt | 2.09 | 416 | I |
| IB-377 | Bnzl | i-Bu | i-Pnt | 2.09 | 398 | I |
| IB-378 | i-Bu | i-Bu | i-Pnt | 2.06 | 364 | I |
| IB-379 | Hdr-E | Cbx-E | i-Bu | 1.33 | 354 | I |
| IB-380 | Hdr-E | 4-OH-Bnzl | Cbx-E | 1.11 | 404 | I |
| IB-381 | i-Pnt | Cbx-E | Np-M | 1.87 | 464 | I |
| IB-382 | Chm | Cbx-E | i-Bu | 1.87 | 406 | I |
| IB-383 | Chm | 4-OH-Bnzl | Cbx-E | 1.68 | 456 | I |
| IB-384 | 4-F-Bnzl | Cbx-E | Np-M | 1.90 | 502 | I |
| IB-385 | 4-F-Bnzl | 4-OH-Bnzl | Cbx-E | 1.53 | 468 | I |
| IB-386 | i-Pnt | 4-F-Bnzl | Cbx-E | 1.85 | 432 | I |
| IB-387 | Ph-Et | Hdr-E | Cbx-E | 1.37 | 402 | I |
| IB-388 | Np-M | Hdr-E | Cbx-E | 1.54 | 438 | I |
| IB-389 | Chm | Np-M | Cbx-E | 1.99 | 490 | I |
| IB-390 | 4-F-Bnzl | Np-M | Cbx-E | 1.86 | 502 | I |
| IB-391 | Cbx-E | Hdr-E | Bnzl | 1.35 | 388 | I |
| IB-392 | Cbx-E | Np-M | i-Bu | 1.80 | 450 | I |
| IB-393 | Cbx-E | Hxy | Bnzl | 1.79 | 428 | I |
| IB-394 | Cbx-E | 4-F-Bnzl | Bnzl | 1.70 | 452 | I |
| IB-395 | Cbx-E | Hdr-E | i-Pnt | 1.46 | 368 | I |
| IB-396 | Cbx-E | Hdr-E | Ph-Et | 1.45 | 402 | I |
| IB-397 | Cbx-E | Hdr-E | Np-M | 1.59 | 438 | I |
| IB-398 | Cbx-E | Np-M | i-Pnt | 1.83 | 464 | I |
| IB-399 | Cbx-E | 4-F-Bnzl | i-Pnt | 1.82 | 432 | I |
| IB-400 | Cbx-E | i-Bu | Bnzl | 1.53 | 400 | I |
| IB-401 | Cbx-E | Cbm-E | Ph-Et | 1.49 | 429 | I |
| IB-402 | Cbx-E | 4-OH-Bnzl | i-Pnt | 1.60 | 430 | I |
| IB-403 | Bnzl | Hdr-E | Cbx-E | 1.31 | 388 | I |
| IB-404 | Bnzl | Hxy | Cbx-E | 1.88 | 428 | I |
| IB-405 | Bnzl | 4-OH-Bnzl | Cbx-E | 1.54 | 450 | I |

TABLE 3-continued

| | | | | | | |
|---|---|---|---|---|---|---|
| IB-406 | i-Bu | Hxy | Cbx-E | 1.88 | 394 | I |
| IB-407 | i-Bu | Cbx-E | i-Bu | 1.62 | 366 | I |
| IB-408 | i-Bu | i-Bu | Cbx-E | 1.71 | 366 | I |
| IB-409 | i-Bu | 4-OH-Bnzl | Cbx-E | 1.47 | 416 | I |
| IB-410 | 4-OH-Bnzl | Cbx-E | Np-M | 1.70 | 500 | I |
| IB-411 | Ph-Et | i-Bu | Np-M | 2.32 | 482 | I |
| IB-412 | Ph-Et | 4-OH-Bnzl | Np-M | 2.02 | 532 | I |
| IB-413 | Np-M | i-Bu | Ph-Et | 2.23 | 482 | I |
| IB-414 | Np-M | i-Bu | Np-M | 2.25 | 518 | I |
| IB-415 | Np-M | i-Bu | Bnzl | 2.15 | 468 | I |
| IB-416 | Np-M | 4-OH-Bnzl | Ph-Et | 2.08 | 532 | I |
| IB-417 | Np-M | 4-OH-Bnzl | Np-M | 2.11 | 568 | I |
| IB-418 | 4-F-Bnzl | i-Bu | Np-M | 2.15 | 486 | I |
| IB-419 | 4-F-Bnzl | Ph-Et | Np-M | 2.17 | 534 | I |
| IB-420 | Bnzl | i-Bu | Np-M | 2.17 | 468 | I |
| IB-421 | Bnzl | 4-OH-Bnzl | Ph-Et | 1.92 | 482 | I |
| IB-422 | i-Bu | 4-OH-Bnzl | Ph-Et | 1.93 | 448 | I |
| IB-423 | 4-OH-Bnzl | Ph-Et | Np-M | 1.97 | 532 | I |
| IB-424 | 4-OH-Bnzl | i-Bu | i-Pnt | 1.82 | 414 | I |
| IB-425 | Hdr-E | Np-M | Cbx-E | 1.55 | 438 | I |
| IB-426 | i-Pnt | Np-M | Hdr-M | 1.91 | 422 | I |
| IB-427 | 4-F-Bnzl | Np-M | Hdr-M | 1.96 | 460 | I |
| IB-428 | Cbx-E | Ph-Et | 4-OH-Bnzl | 1.59 | 464 | I |
| IB-429 | Cbx-E | Np-M | Hdr-M | 1.55 | 424 | I |
| IB-430 | Cbx-E | i-Bu | Ph-Et | 1.66 | 414 | I |
| IB-431 | Cbx-E | i-Bu | Hdr-M | 1.21 | 340 | I |
| IB-432 | Cbx-E | i-Bu | 4-OH-Bnzl | 1.40 | 416 | I |
| IB-433 | Cbx-E | Cbm-E | Np-M | 1.56 | 465 | I |
| IB-434 | Cbx-E | Cbm-E | Bnzl | 1.41 | 415 | I |
| IB-435 | Cbx-E | Cbm-E | i-Bu | 1.37 | 381 | I |
| IB-436 | Cbx-E | Cbm-E | 4-OH-Bnzl | 1.19 | 431 | I |
| IB-437 | i-Bu | Np-M | Cbx-E | 1.86 | 450 | I |
| IB-438 | 4-OH-Bnzl | Ph-Et | Cbx-E | 1.60 | 464 | I |
| IB-439 | 4-OH-Bnzl | Np-M | Cbx-E | 1.69 | 500 | I |
| IB-440 | 4-OH-Bnzl | Np-M | Hdr-M | 1.70 | 458 | I |
| IB-441 | Hdr-E | Cbm-E | 4-OH-Bnzl | 1.18 | 403 | I |
| IB-442 | Hdr-E | 4-OH-Bnzl | i-Pnt | 1.58 | 402 | I |
| IB-443 | Hdr-E | 4-OH-Bnzl | Ph-Et | 1.60 | 436 | I |
| IB-444 | Hdr-E | 4-OH-Bnzl | Bnzl | 1.52 | 422 | I |
| IB-445 | i-Pnt | 4-OH-Bnzl | Np-M | 2.02 | 498 | I |
| IB-446 | i-Pnt | 4-OH-Bnzl | i-Bu | 1.90 | 414 | I |
| IB-447 | Ph-Et | 4-OH-Bnzl | i-Pnt | 2.02 | 462 | I |
| IB-448 | Ph-Et | 4-OH-Bnzl | Bnzl | 1.93 | 482 | I |
| IB-449 | Ph-Et | 4-OH-Bnzl | i-Bu | 1.90 | 448 | I |
| IB-450 | Np-M | 4-OH-Bnzl | i-Pnt | 2.08 | 498 | I |
| IB-451 | Np-M | 4-OH-Bnzl | Bnzl | 1.99 | 518 | I |
| IB-452 | Np-M | 4-OH-Bnzl | i-Bu | 2.00 | 484 | I |
| IB-453 | Chm | 4-OH-Bnzl | i-Pnt | 2.11 | 454 | I |
| IB-454 | Chm | 4-OH-Bnzl | Ph-Et | 2.08 | 488 | I |
| IB-455 | Chm | 4-OH-Bnzl | Np-M | 2.13 | 524 | I |
| IB-456 | Chm | 4-OH-Bnzl | Bnzl | 2.02 | 474 | I |
| IB-457 | 4-F-Bnzl | 4-OH-Bnzl | Np-M | 2.02 | 536 | I |
| IB-458 | 4-F-Bnzl | 4-OH-Bnzl | i-Bu | 1.87 | 452 | I |
| IB-459 | Np-M | Hdr-E | 4-OH-Bnzl | 1.64 | 472 | I |
| IB-460 | Chm | Hdr-E | Bnzl | 1.94 | 412 | I |
| IB-461 | Ph-Et | Hdr-E | i-Pnt | 1.86 | 400 | I |
| IB-462 | Bnzl | 4-OH-Bnzl | i-Pnt | 1.94 | 448 | I |
| IB-463 | Bnzl | 4-OH-Bnzl | Bnzl | 1.86 | 468 | I |
| IB-464 | Bnzl | 4-OH-Bnzl | i-Bu | 1.84 | 434 | I |
| IB-465 | i-Bu | 4-OH-Bnzl | i-Pnt | 1.96 | 414 | I |
| IB-466 | i-Bu | 4-OH-Bnzl | Np-M | 2.00 | 484 | I |
| IB-467 | i-Bu | 4-OH-Bnzl | i-Bu | 1.85 | 400 | I |
| IB-468 | 4-OH-Bnzl | Hdr-E | i-Bu | 1.40 | 388 | I |
| IB-469 | 4-OH-Bnzl | Hdr-E | i-Pnt | 1.55 | 402 | I |
| IB-470 | Hdr-E | 4-OH-Bnzl | Np-M | 1.68 | 472 | I |
| IB-471 | Ph-Et | i-Pr | 4-OH-Bnzl | 1.24 | 434 | I |
| IB-472 | Np-M | Bnzl | 4-OH-Bnzl | 1.98 | 518 | I |
| IB-473 | Chm | i-Pr | 4-OH-Bnzl | 1.20 | 426 | I |
| IB-474 | 4-F-Bnzl | Bnzl | Np-M | 2.16 | 520 | I |
| IB-475 | 4-F-Bnzl | i-Pr | 4-OH-Bnzl | 1.13 | 428 | I |
| IB-476 | Hdr-E | Hxy | Bnzl | 1.92 | 400 | I |
| IB-477 | Hdr-E | Hxy | i-Bu | 1.87 | 366 | I |
| IB-478 | Hdr-E | Hxy | 4-OH-Bnzl | 1.79 | 416 | I |
| IB-479 | Hdr-E | 4-F-Bnzl | Bnzl | 1.73 | 424 | I |
| IB-480 | i-Pnt | Hxy | 4-OH-Bnzl | 2.07 | 442 | I |
| IB-481 | i-Pnt | 4-F-Bnzl | 4-OH-Bnzl | 1.93 | 466 | I |
| IB-482 | Np-M | Hxy | i-Bu | 2.35 | | I |
| IB-483 | Np-M | Hxy | 4-OH-Bnzl | 2.17 | 512 | I |
| IB-484 | Chm | Ph-Et | Bnzl | 2.36 | | I |
| IB-485 | Chm | Hxy | Bnzl | 2.42 | | I |

TABLE 3-continued

| | | | | | | |
|---|---|---|---|---|---|---|
| IB-486 | Chm | Hxy | i-Bu | 2.44 | | I |
| IB-487 | Chm | Hxy | 4-OH-Bnzl | 2.18 | 468 | I |
| IB-488 | Chm | 4-F-Bnzl | i-Bu | 2.22 | 442 | I |
| IB-489 | 4-F-Bnzl | Ph-Et | Bnzl | 2.18 | 484 | I |
| IB-490 | Hdr-E | Hxy | i-Pnt | 1.99 | 380 | I |
| IB-491 | Hdr-E | Hxy | Np-M | 1.98 | 450 | I |
| IB-492 | Hdr-E | 4-F-Bnzl | Ph-Et | 1.80 | 438 | I |
| IB-493 | Np-M | Hdr-E | Np-M | 1.99 | 506 | I |
| IB-494 | Chm | Hxy | i-Pnt | 2.54 | | I |
| IB-495 | i-Bu | Ph-Et | i-Bu | 2.16 | 398 | I |
| IB-496 | i-Bu | Hxy | 4-OH-Bnzl | 2.04 | 428 | I |
| IB-497 | i-Bu | 4-F-Bnzl | i-Bu | 2.05 | 402 | I |
| IB-498 | i-Bu | 4-F-Bnzl | 4-OH-Bnzl | 1.89 | 452 | I |
| IB-499 | 4-OH-Bnzl | 4-F-Bnzl | i-Bu | 1.91 | 452 | I |
| IB-500 | 4-OH-Bnzl | Bnzl | Np-M | 1.92 | 518 | I |
| IB-501 | 4-OH-Bnzl | i-Pr | i-Pnt | 1.77 | 400 | I |
| IB-502 | 4-OH-Bnzl | i-Pr | Np-M | 1.83 | 470 | I |
| IB-503 | Hdr-E | Bnzl | Cbx-E | 1.37 | 388 | I |
| IB-504 | Hdr-E | i-Bu | Cbx-E | 1.28 | 354 | I |
| IB-505 | i-Pnt | Bnzl | Cbx-E | 1.79 | 414 | I |
| IB-506 | i-Pnt | i-Bu | Cbx-E | 1.75 | 380 | I |
| IB-507 | i-Pnt | 4-OH-Bnzl | Cbx-E | 1.49 | 430 | I |
| IB-508 | Ph-Et | i-Bu | Cbx-E | 1.71 | 414 | I |
| IB-509 | Np-M | i-Bu | Cbx-E | 1.93 | 450 | I |
| IB-510 | Chm | i-Bu | Cbx-E | 1.91 | 406 | I |
| IB-511 | 4-F-Bnzl | i-Pnt | Cbx-E | 1.88 | 432 | I |
| IB-512 | Cbx-E | i-Pnt | 4-OH-Bnzl | 1.55 | 430 | I |
| IB-513 | Cbx-E | i-Pnt | Ph-Et | 1.71 | 428 | I |
| IB-514 | Cbx-E | i-Pnt | Np-M | 1.83 | 464 | I |
| IB-515 | Cbx-E | 4-OH-Bnzl | Ph-Et | 1.63 | 464 | I |
| IB-516 | Cbx-E | 4-OH-Bnzl | Np-M | 1.68 | 500 | I |
| IB-517 | i-Bu | Cbx-E | Np-M | 1.81 | 450 | I |
| IB-518 | 4-OH-Bnzl | i-Pnt | Cbx-E | 1.61 | 430 | I |
| IB-519 | Hdr-E | Cbm-E | Np-M | 1.54 | 437 | I |
| IB-520 | Np-M | Cbm-E | i-Bu | 1.83 | 449 | I |
| IB-521 | Np-M | Cbm-E | 4-OH-Bnzl | 1.64 | 499 | I |
| IB-522 | Chm | Cbm-E | Np-M | 1.95 | 489 | I |
| IB-523 | Chm | Cbm-E | 4-OH-Bnzl | 1.57 | 455 | I |
| IB-524 | 4-F-Bnzl | Cbm-E | Ph-Et | 1.78 | 465 | I |
| IB-525 | 4-F-Bnzl | Cbm-E | Np-M | 1.86 | 501 | I |
| IB-526 | Hdr-E | Ph-Et | 4-OH-Bnzl | 1.53 | 436 | I |
| IB-527 | Hdr-E | Np-M | 4-OH-Bnzl | 1.69 | | I |
| IB-528 | Chm | Np-M | i-Bu | 2.35 | 474 | I |
| IB-529 | Chm | 4-F-Bnzl | 4-OH-Bnzl | 1.99 | 492 | I |
| IB-530 | 4-F-Bnzl | Np-M | 4-OH-Bnzl | 1.98 | 536 | I |
| IB-531 | Hdr-E | Ph-Et | i-Pnt | 1.80 | 400 | I |
| IB-532 | 4-F-Bnzl | Np-M | i-Pnt | 2.24 | 500 | I |
| IB-533 | Bnzl | 4-F-Bnzl | i-Bu | 2.07 | 436 | I |
| IB-534 | Bnzl | 4-F-Bnzl | 4-OH-Bnzl | 1.88 | 486 | I |
| IB-535 | Bnzl | Cbm-E | Ph-Et | 1.73 | 447 | I |
| IB-536 | i-Bu | Ph-Et | 4-OH-Bnzl | 1.85 | 448 | I |
| IB-537 | i-Bu | Np-M | 4-OH-Bnzl | 1.99 | 484 | I |
| IB-538 | i-Bu | Np-M | i-Pnt | 2.28 | 448 | I |
| IB-539 | i-Bu | Cbm-E | Ph-Et | 1.71 | 413 | I |
| IB-540 | 4-OH-Bnzl | Ph-Et | i-Bu | 1.80 | 448 | I |
| IB-541 | 4-OH-Bnzl | Np-M | i-Bu | 1.94 | 484 | I |
| IB-542 | 4-OH-Bnzl | Hxy | Bnzl | 1.98 | 462 | I |
| IB-543 | 4-OH-Bnzl | 4-F-Bnzl | Bnzl | 1.83 | 486 | I |
| IB-544 | 4-OH-Bnzl | Ph-Et | i-Pnt | 1.92 | 462 | I |
| IB-545 | 4-OH-Bnzl | Cbm-E | Bnzl | 1.53 | 449 | I |
| IB-546 | Ph-Et | Bnzl | Np-M | 2.22 | 516 | I |
| IB-547 | 4-F-Bnzl | Bnzl | Ph-Et | 2.15 | 484 | I |
| IB-548 | 4-F-Bnzl | Cbm-E | 4-OH-Bnzl | 1.48 | 467 | I |
| IB-549 | Hdr-E | 4-F-Bnzl | 4-OH-Bnzl | 1.51 | 440 | I |
| IB-550 | i-Pnt | Hxy | Bnzl | 2.22 | 426 | I |
| IB-551 | i-Pnt | Hxy | i-Bu | 2.24 | 392 | I |
| IB-552 | i-Pnt | 4-F-Bnzl | Bnzl | 2.11 | 450 | I |
| IB-553 | i-Pnt | 4-F-Bnzl | i-Bu | 2.10 | 416 | I |
| IB-554 | Ph-Et | Hxy | Bnzl | 2.27 | 460 | I |
| IB-555 | Ph-Et | 4-F-Bnzl | Bnzl | 2.13 | 484 | I |
| IB-556 | Ph-Et | 4-F-Bnzl | i-Bu | 2.12 | 450 | I |
| IB-557 | i-Pnt | Hxy | Ph-Et | 2.31 | 440 | I |
| IB-558 | i-Pnt | Hxy | Np-M | 2.35 | 476 | I |
| IB-559 | Ph-Et | 4-F-Bnzl | i-Pnt | 2.20 | 464 | I |
| IB-560 | Chm | 4-F-Bnzl | Np-M | 2.29 | 526 | I |
| IB-561 | Bnzl | i-Pnt | i-Bu | 2.13 | 398 | I |
| IB-562 | Bnzl | Hxy | Bnzl | 2.20 | 446 | I |
| IB-563 | Bnzl | Hxy | i-Bu | 2.22 | 412 | I |
| IB-564 | Bnzl | 4-F-Bnzl | Bnzl | 2.08 | 470 | I |
| IB-565 | Bnzl | Hxy | i-Pnt | 2.27 | 426 | I |

TABLE 3-continued

| | | | | | | |
|---|---|---|---|---|---|---|
| IB-566 | Bnzl | Hxy | Ph-Et | 2.24 | 460 | I |
| IB-567 | Bnzl | 4-F-Bnzl | i-Pnt | 2.13 | 450 | I |
| IB-568 | Bnzl | 4-F-Bnzl | Ph-Et | 2.12 | 484 | I |
| IB-569 | Bnzl | Cbm-E | 4-OH-Bnzl | 1.47 | 449 | I |
| IB-570 | i-Bu | Hxy | i-Bu | 2.22 | 378 | I |
| IB-571 | i-Bu | Hxy | i-Pnt | 2.31 | 392 | I |
| IB-572 | i-Bu | Hxy | Ph-Et | 2.25 | 426 | I |
| IB-573 | i-Bu | Hxy | Np-M | 2.48 | 462 | I |
| IB-574 | 4-OH-Bnzl | i-Pnt | Bnzl | 1.90 | 448 | I |
| IB-575 | Cbx-E | i-Bu | Np-M | 1.80 | 450 | I |
| IB-576 | i-Pnt | 4-OH-Bnzl | Ph-Et | 1.97 | 462 | I |
| IB-577 | i-Pnt | 4-OH-Bnzl | Bnzl | 1.87 | 448 | I |
| IB-578 | Np-M | Bnzl | Np-M | 2.24 | 552 | I |
| IB-579 | Np-M | i-Pr | Ph-Et | 2.15 | 468 | I |
| IB-580 | Np-M | i-Pr | Bnzl | 2.05 | 454 | I |
| IB-581 | Chm | 4-OH-Bnzl | i-Bu | 2.02 | 440 | I |
| IB-582 | 4-F-Bnzl | 4-OH-Bnzl | i-Pnt | 1.96 | 466 | I |
| IB-583 | 4-F-Bnzl | 4-OH-Bnzl | Bnzl | 1.88 | 486 | I |
| IB-584 | Hdr-E | Ph-Et | Bnzl | 1.75 | 420 | I |
| IB-585 | Hdr-E | Np-M | i-Bu | 1.80 | 422 | I |
| IB-586 | Hdr-E | 4-F-Bnzl | i-Bu | 1.62 | 390 | I |
| IB-587 | i-Pnt | Hdr-E | 4-OH-Bnzl | 1.36 | 402 | I |
| IB-588 | Np-M | Hdr-E | Bnzl | 1.89 | 456 | I |
| IB-589 | Np-M | Np-M | 4-OH-Bnzl | 2.06 | 568 | I |
| IB-590 | Np-M | 4-F-Bnzl | i-Bu | 2.16 | 486 | I |
| IB-591 | Chm | Hdr-E | 4-OH-Bnzl | 1.56 | 428 | I |
| IB-592 | Chm | 4-F-Bnzl | Bnzl | 2.23 | 476 | I |
| IB-593 | Ph-Et | Hdr-E | Np-M | 1.88 | 470 | I |
| IB-594 | Ph-Et | i-Pnt | Np-M | 2.24 | 496 | I |
| IB-595 | Ph-Et | Hxy | Np-M | 2.33 | 510 | I |
| IB-596 | Np-M | Hdr-E | Ph-Et | 1.94 | 470 | I |
| IB-597 | Np-M | Hxy | Ph-Et | 2.34 | 510 | I |
| IB-598 | Np-M | Hxy | Np-M | 2.36 | 546 | I |
| IB-599 | Np-M | 4-F-Bnzl | i-Pnt | 2.26 | 500 | I |
| IB-600 | Chm | 4-F-Bnzl | i-Pnt | 2.28 | 456 | I |
| IB-601 | Bnzl | Np-M | 4-OH-Bnzl | 1.98 | 518 | I |
| IB-602 | Bnzl | Hdr-E | Np-M | 1.85 | 456 | I |
| IB-603 | Bnzl | i-Pnt | Np-M | 2.29 | 482 | I |
| IB-604 | Bnzl | Hxy | Np-M | 2.29 | 496 | I |
| IB-605 | Bnzl | i-Pr | Np-M | 2.11 | 454 | I |
| IB-606 | Bnzl | 4-OH-Bnzl | Np-M | 1.96 | 518 | I |
| IB-607 | i-Bu | Hdr-E | 4-OH-Bnzl | 1.40 | 388 | I |
| IB-608 | i-Bu | 4-F-Bnzl | Np-M | 2.15 | 486 | I |
| IB-609 | i-Bu | Cbm-E | i-Bu | 1.59 | 365 | I |
| IB-610 | Hdr-E | Cbx-E | Np-M | 1.56 | 438 | I |
| IB-611 | i-Pnt | Cbx-E | i-Bu | 1.68 | 380 | I |
| IB-612 | Np-M | Cbx-E | Bnzl | 1.89 | 484 | I |
| IB-613 | Chm | Cbx-E | i-Pnt | 1.95 | 420 | I |
| IB-614 | Chm | Cbx-E | Np-M | 2.02 | 490 | I |
| IB-615 | 4-F-Bnzl | Cbx-E | 4-OH-Bnzl | 1.53 | 468 | I |
| IB-616 | Bnzl | Cbx-E | Np-M | 1.85 | 484 | I |
| IB-617 | Hdr-E | Bnzl | i-Pnt | 1.79 | 286 | I |
| IB-618 | Hdr-E | Bnzl | Ph-Et | 1.79 | 420 | I |
| IB-619 | Hdr-E | Bnzl | Bnzl | 1.71 | 406 | I |
| IB-620 | Hdr-E | i-Bu | Ph-Et | 1.74 | 386 | I |
| IB-621 | Hdr-E | i-Bu | Np-M | 1.80 | 422 | I |
| IB-622 | Hdr-E | i-Bu | Bnzl | 1.59 | 372 | I |
| IB-623 | Hdr-E | i-Bu | 4-OH-Bnzl | 1.48 | 388 | I |
| IB-624 | i-Pnt | Bnzl | Ph-Et | 2.17 | 446 | I |
| IB-625 | Ph-Et | i-Bu | 4-OH-Bnzl | 1.88 | 448 | I |
| IB-626 | Chm | Bnzl | i-Pnt | 2.35 | | I |
| IB-627 | Chm | Bnzl | 4-OH-Bnzl | 2.01 | 474 | I |
| IB-628 | 4-F-Bnzl | Bnzl | 4-OH-Bnzl | 1.94 | 486 | I |
| IB-629 | 4-F-Bnzl | i-Bu | Bnzl | 2.06 | 436 | I |
| IB-630 | 4-F-Bnzl | i-Bu | i-Bu | 2.03 | 402 | I |
| IB-631 | 4-F-Bnzl | i-Bu | 4-OH-Bnzl | 1.90 | 452 | I |
| IB-632 | Bnzl | Bnzl | Ph-Et | 2.12 | 466 | I |
| IB-633 | i-Bu | i-Bu | Ph-Et | 2.11 | 398 | I |
| IB-634 | 4-OH-Bnzl | Bnzl | Ph-Et | 1.87 | 482 | I |
| IB-635 | 4-OH-Bnzl | i-Bu | Np-M | 1.97 | 484 | I |
| IB-636 | i-Pnt | Cbm-E | Ph-Et | 1.80 | 427 | I |
| IB-637 | Chm | Cbm-E | Bnzl | 1.83 | 439 | I |
| IB-638 | i-Pnt | Hdr-E | Bnzl | 1.68 | 386 | I |
| IB-639 | i-Pnt | Hdr-E | i-Bu | 1.62 | 352 | I |
| IB-640 | Ph-Et | Hdr-E | Bnzl | 1.77 | 420 | I |
| IB-641 | Ph-Et | Hdr-E | i-Bu | 1.77 | 386 | I |
| IB-642 | Ph-Et | 4-F-Bnzl | 4-OH-Bnzl | 1.99 | 500 | I |
| IB-643 | Np-M | Hdr-E | i-Bu | 1.87 | 422 | I |
| IB-644 | Np-M | i-Pnt | i-Bu | 2.27 | 448 | I |
| IB-645 | Np-M | i-Pnt | 4-OH-Bnzl | 2.06 | 498 | I |

TABLE 3-continued

| | | | | | | |
|---|---|---|---|---|---|---|
| IB-646 | Chm | Hdr-E | i-Bu | 1.79 | 378 | I |
| IB-647 | Chm | i-Pnt | Bnzl | 2.32 | 438 | I |
| IB-648 | Chm | i-Pnt | 4-OH-Bnzl | 2.07 | 454 | I |
| IB-649 | 4-F-Bnzl | Hdr-E | Bnzl | 1.76 | 424 | I |
| IB-650 | 4-F-Bnzl | Hdr-E | i-Bu | 1.70 | 390 | I |
| IB-651 | 4-F-Bnzl | i-Pnt | Bnzl | 2.17 | 450 | I |
| IB-652 | 4-F-Bnzl | i-Pnt | i-Bu | 2.14 | 416 | I |
| IB-653 | 4-F-Bnzl | Np-M | i-Bu | 2.19 | 486 | I |
| IB-654 | 4-F-Bnzl | Hxy | Bnzl | 2.24 | 464 | I |
| IB-655 | 4-F-Bnzl | Hxy | i-Bu | 2.24 | | I |
| IB-656 | 4-F-Bnzl | Hxy | 4-OH-Bnzl | 2.02 | 480 | I |
| IB-657 | Hdr-E | 4-F-Bnzl | i-Pnt | 1.83 | 404 | I |
| IB-658 | i-Pnt | Hdr-E | Ph-Et | 1.79 | 400 | I |
| IB-659 | i-Pnt | Hdr-E | Np-M | 1.94 | 436 | I |
| IB-660 | Ph-Et | Hxy | i-Pnt | 2.39 | | I |
| IB-661 | Np-M | Hdr-E | i-Pnt | 1.98 | 436 | I |
| IB-662 | Np-M | Hxy | i-Pnt | 2.44 | | I |
| IB-663 | Chm | Hdr-E | Ph-Et | 1.89 | 426 | I |
| IB-664 | Chm | Hdr-E | Np-M | 1.98 | 462 | I |
| IB-665 | Chm | Hxy | Ph-Et | 2.50 | | I |
| IB-666 | Chm | Hxy | Np-M | 2.54 | | I |
| IB-667 | Chm | 4-F-Bnzl | Ph-Et | 2.31 | 490 | I |
| IB-668 | 4-F-Bnzl | Hdr-E | i-Pnt | 1.77 | 404 | I |
| IB-669 | 4-F-Bnzl | Hdr-E | Ph-Et | 1.78 | 438 | I |
| IB-670 | 4-F-Bnzl | Hdr-E | Np-M | 1.87 | 474 | I |
| IB-671 | 4-F-Bnzl | i-Pnt | Ph-Et | 2.21 | 464 | I |
| IB-672 | 4-F-Bnzl | i-Pnt | Np-M | 2.27 | 500 | I |
| IB-673 | 4-F-Bnzl | Hxy | i-Pnt | 2.30 | | I |
| IB-674 | 4-F-Bnzl | Hxy | Ph-Et | 2.31 | | I |
| IB-675 | 4-F-Bnzl | Hxy | Np-M | 2.37 | | I |
| IB-676 | Bnzl | Hdr-E | Bnzl | 1.70 | 406 | I |
| IB-677 | Bnzl | Hdr-E | i-Bu | 1.66 | 372 | I |
| IB-678 | Bnzl | i-Pnt | 4-OH-Bnzl | 1.95 | 448 | I |
| IB-679 | Bnzl | Hxy | 4-OH-Bnzl | 2.02 | 462 | I |
| IB-680 | Bnzl | Hdr-E | i-Pnt | 1.79 | 386 | I |
| IB-681 | Bnzl | Hdr-E | Ph-Et | 1.76 | 420 | I |
| IB-682 | i-Bu | Hdr-E | i-Bu | 1.62 | 338 | I |
| IB-683 | i-Bu | i-Pnt | i-Bu | 2.11 | 364 | I |
| IB-684 | i-Bu | i-Pnt | 4-OH-Bnzl | 1.88 | 414 | I |
| IB-685 | i-Bu | Hdr-E | i-Pnt | 1.71 | 352 | I |
| IB-686 | i-Bu | Hdr-E | Ph-Et | 1.74 | 386 | I |
| IB-687 | i-Bu | Hdr-E | Np-M | 1.82 | 422 | I |
| IB-688 | i-Bu | i-Pnt | Ph-Et | 2.17 | 412 | I |
| IB-689 | i-Bu | 4-F-Bnzl | i-Pnt | 2.13 | 416 | I |
| IB-690 | i-Bu | 4-F-Bnzl | Ph-Et | 2.22 | | I |
| IB-691 | Ph-Et | Bnzl | Cbx-E | 1.84 | 448 | I |
| IB-692 | 4-F-Bnzl | Bnzl | Cbx-E | 1.79 | 452 | I |
| IB-693 | Np-M | i-Pnt | Cbx-E | 1.99 | 464 | I |
| IB-694 | Cbx-E | Bnzl | i-Pnt | 1.79 | 414 | I |
| IB-695 | Cbx-E | Bnzl | i-Bu | 1.64 | 400 | I |
| IB-696 | Cbx-E | i-Bu | i-Pnt | 1.77 | 380 | I |
| IB-697 | Bnzl | i-Pnt | Cbx-E | 1.84 | 414 | I |
| IB-698 | Bnzl | Bnzl | Cbx-E | 1.82 | 434 | I |
| IB-699 | Bnzl | i-Bu | Cbx-E | 1.74 | 400 | I |
| IB-700 | i-Bu | i-Pnt | Cbx-E | 1.81 | 380 | I |
| IB-701 | Hdr-E | Cbm-E | Ph-Et | 1.46 | 401 | I |
| IB-702 | Hdr-E | Cbm-E | Bnzl | 1.39 | 387 | I |
| IB-703 | i-Pnt | Cbm-E | Np-M | 1.86 | 463 | I |
| IB-704 | i-Pnt | Cbm-E | Bnzl | 1.71 | 413 | I |
| IB-705 | i-Pnt | Cbm-E | i-Bu | 1.71 | 379 | I |
| IB-706 | i-Pnt | Cbm-E | 4-OH-Bnzl | 1.38 | 429 | I |
| IB-707 | Ph-Et | Cbm-E | Bnzl | 1.77 | 447 | I |
| IB-708 | Ph-Et | Cbm-E | i-Bu | 1.77 | 413 | I |
| IB-709 | Ph-Et | Cbm-E | 4-OH-Bnzl | 1.55 | 463 | I |
| IB-710 | Chm | Cbm-E | Ph-Et | 1.91 | 453 | I |
| IB-711 | Chm | Cbm-E | i-Bu | 1.84 | 405 | I |
| IB-712 | 4-F-Bnzl | Cbm-E | Bnzl | 1.76 | 451 | I |
| IB-713 | 4-F-Bnzl | Cbm-E | i-Bu | 1.71 | 417 | I |
| IB-714 | Hdr-E | i-Pnt | Bnzl | 1.72 | 386 | I |
| IB-715 | Hdr-E | i-Pnt | i-Bu | 1.71 | 352 | I |
| IB-716 | Hdr-E | i-Pnt | 4-OH-Bnzl | 1.61 | 402 | I |
| IB-717 | Hdr-E | Ph-Et | i-Bu | 1.74 | 386 | I |
| IB-718 | i-Pnt | Np-M | i-Bu | 2.29 | 448 | I |
| IB-719 | i-Pnt | Np-M | 4-OH-Bnzl | 2.02 | 498 | I |
| IB-720 | Ph-Et | i-Pnt | 4-OH-Bnzl | 1.99 | 462 | I |
| IB-721 | Np-M | Ph-Et | 4-OH-Bnzl | 2.09 | 532 | I |
| IB-722 | Chm | Ph-Et | i-Bu | 2.32 | 438 | I |
| IB-723 | Chm | Np-M | 4-OH-Bnzl | 2.13 | 524 | I |
| IB-724 | 4-F-Bnzl | i-Pnt | 4-OH-Bnzl | 2.00 | 466 | I |
| IB-725 | 4-F-Bnzl | Ph-Et | i-Bu | 2.16 | 450 | I |

TABLE 3-continued

| | | | | | | |
|---|---|---|---|---|---|---|
| IB-726 | 4-F-Bnzl | Ph-Et | 4-OH-Bnzl | 1.96 | 500 | I |
| IB-727 | Hdr-E | i-Pnt | Np-M | 1.88 | 436 | I |
| IB-728 | Np-M | i-Pnt | Ph-Et | 2.33 | 496 | I |
| IB-729 | Np-M | Ph-Et | Np-M | 2.38 | | I |
| IB-730 | Chm | i-Pnt | Ph-Et | 2.36 | | I |
| IB-731 | Chm | Np-M | i-Pnt | 2.46 | | I |
| IB-732 | 4-F-Bnzl | Ph-Et | i-Pnt | 2.22 | 464 | I |
| IB-733 | Bnzl | i-Pnt | Ph-Et | 2.20 | 446 | I |
| IB-734 | Bnzl | Cbm-E | Bnzl | 1.74 | 433 | I |
| IB-735 | i-Bu | Np-M | i-Bu | 2.25 | 434 | I |
| IB-736 | i-Bu | i-Pnt | Np-M | 2.27 | 448 | I |
| IB-737 | i-Bu | Cbm-E | Np-M | 1.84 | 449 | I |
| IB-738 | i-Bu | Cbm-E | 4-OH-Bnzl | 1.40 | 415 | I |
| IB-739 | 4-OH-Bnzl | i-Pnt | i-Bu | 1.84 | 414 | I |
| IB-740 | 4-OH-Bnzl | i-Pnt | Ph-Et | 1.95 | 462 | I |
| IB-741 | 4-OH-Bnzl | i-Pnt | Np-M | 2.01 | 498 | I |
| IB-742 | 4-OH-Bnzl | Cbm-E | Ph-Et | 1.59 | 463 | I |
| IB-743 | 4-OH-Bnzl | Cbm-E | Np-M | 1.75 | 499 | I |
| IB-744 | Hdr-E | Bnzl | i-Bu | 1.67 | 372 | I |
| IB-745 | Hdr-E | Bnzl | 4-OH-Bnzl | 1.51 | 422 | I |
| IB-746 | Hdr-E | i-Bu | i-Bu | 1.57 | 338 | I |
| IB-747 | i-Pnt | Bnzl | Np-M | 2.21 | 482 | I |
| IB-748 | i-Pnt | Bnzl | i-Bu | 2.10 | 398 | I |
| IB-749 | i-Pnt | Bnzl | 4-OH-Bnzl | 1.82 | 448 | I |
| IB-750 | i-Pnt | i-Bu | Ph-Et | 2.16 | 412 | I |
| IB-751 | i-Pnt | i-Bu | Np-M | 2.18 | 448 | I |
| IB-752 | i-Pnt | i-Bu | Bnzl | 2.06 | 398 | I |
| IB-753 | i-Pnt | i-Bu | i-Bu | 2.04 | 364 | I |
| IB-754 | i-Pnt | i-Bu | 4-OH-Bnzl | 2.34 | | I |
| IB-755 | Ph-Et | Bnzl | i-Pnt | 2.22 | 446 | I |
| IB-756 | Ph-Et | Bnzl | Bnzl | 2.10 | 466 | I |
| IB-757 | Ph-Et | Bnzl | i-Bu | 2.13 | 432 | I |
| IB-758 | Ph-Et | Bnzl | 4-OH-Bnzl | 1.90 | 482 | I |
| IB-759 | Ph-Et | i-Bu | Bnzl | 2.08 | 432 | I |
| IB-760 | Ph-Et | i-Bu | i-Bu | 2.10 | 398 | I |
| IB-761 | Np-M | Bnzl | i-Bu | 2.22 | 468 | I |
| IB-762 | Np-M | i-Bu | i-Bu | 2.16 | 434 | I |
| IB-763 | Np-M | i-Bu | 4-OH-Bnzl | 1.97 | 484 | I |
| IB-764 | Chm | Bnzl | Ph-Et | 2.31 | 472 | I |
| IB-765 | Chm | Bnzl | i-Bu | 2.24 | 424 | I |
| IB-766 | Chm | i-Bu | Ph-Et | 2.27 | 438 | I |
| IB-767 | Chm | i-Bu | Np-M | 2.32 | 474 | I |
| IB-768 | Chm | i-Bu | Bnzl | 2.19 | 424 | I |
| IB-769 | Chm | i-Bu | i-Bu | 2.22 | 390 | I |
| IB-770 | Chm | i-Bu | 4-OH-Bnzl | 1.99 | 440 | I |
| IB-771 | 4-F-Bnzl | Bnzl | i-Pnt | 2.18 | 450 | I |
| IB-772 | 4-F-Bnzl | Bnzl | Bnzl | 2.10 | 470 | I |
| IB-773 | 4-F-Bnzl | Bnzl | i-Bu | 2.12 | 436 | I |
| IB-774 | 4-F-Bnzl | i-Bu | Ph-Et | 2.11 | 450 | I |
| IB-775 | Ph-Et | i-Pnt | Bnzl | 2.18 | 446 | I |
| IB-776 | Bnzl | i-Pnt | Bnzl | 2.13 | 432 | I |
| IB-777 | Bnzl | Bnzl | Np-M | 2.20 | 502 | I |
| IB-778 | Bnzl | i-Bu | Ph-Et | 2.14 | 432 | I |
| IB-779 | Bnzl | i-Bu | 4-OH-Bnzl | 1.85 | 434 | I |
| IB-780 | i-Bu | i-Pnt | Bnzl | 2.15 | 398 | I |
| IB-781 | i-Bu | Bnzl | i-Pnt | 2.19 | 398 | I |
| IB-782 | i-Bu | Bnzl | Np-M | 2.16 | 468 | I |
| IB-783 | i-Bu | Bnzl | 4-OH-Bnzl | 1.85 | 434 | I |
| IB-784 | i-Bu | i-Bu | Np-M | 2.19 | 434 | I |
| IB-785 | i-Bu | i-Bu | 4-OH-Bnzl | 1.81 | 400 | I |
| IB-786 | 4-OH-Bnzl | Bnzl | i-Pnt | 1.90 | 448 | I |
| IB-787 | 4-OH-Bnzl | Bnzl | i-Bu | 1.80 | 434 | I |
| IB-788 | Ph-Et | Cbm-E | Np-M | 1.91 | 497 | I |
| IB-789 | Ph-Et | i-Pr | Np-M | 2.19 | 468 | I |
| IB-790 | Np-M | Cbm-E | Bnzl | 1.88 | 483 | I |
| IB-791 | i-Pnt | Np-M | Bnzl | 2.27 | 483 | I |
| IB-792 | Ph-Et | Np-M | i-Bu | 2.29 | 482 | I |
| IB-793 | Ph-Et | Np-M | 4-OH-Bnzl | 2.09 | 532 | I |
| IB-794 | Np-M | i-Pnt | Bnzl | 2.29 | 482 | I |
| IB-795 | Np-M | Ph-Et | Bnzl | 2.32 | 516 | I |
| IB-796 | Np-M | Np-M | i-Bu | 2.37 | 518 | I |
| IB-797 | Np-M | 4-F-Bnzl | Bnzl | 2.24 | 520 | I |
| IB-798 | Chm | Np-M | Bnzl | 2.41 | 508 | I |
| IB-799 | 4-F-Bnzl | Np-M | Bnzl | 2.25 | 520 | I |
| IB-800 | Ph-Et | Np-M | i-Pnt | 2.36 | 497 | I |
| IB-801 | Ph-Et | 4-F-Bnzl | Np-M | 2.27 | 534 | I |
| IB-802 | Np-M | i-Pnt | Np-M | 2.42 | 532 | I |
| IB-803 | Np-M | Np-M | i-Pnt | 2.41 | 532 | I |
| IB-804 | Np-M | Np-M | Ph-Et | 2.39 | 566 | I |
| IB-805 | Np-M | 4-F-Bnzl | Ph-Et | 2.28 | 534 | I |

TABLE 3-continued

| | | | | | | |
|---|---|---|---|---|---|---|
| IB-806 | Np-M | 4-F-Bnzl | Np-M | 2.36 | 570 | I |
| IB-807 | Chm | Np-M | Ph-Et | 2.47 | 522 | I |
| IB-808 | Chm | Np-M | Np-M | 2.47 | 558 | I |
| IB-809 | 4-F-Bnzl | Np-M | Ph-Et | 2.28 | 534 | I |
| IB-810 | 4-F-Bnzl | Np-M | Np-M | 2.31 | 570 | I |
| IB-811 | Bnzl | Np-M | i-Pnt | 2.30 | 482 | I |
| IB-812 | Bnzl | 4-F-Bnzl | Np-M | 2.21 | 520 | I |
| IB-813 | Bnzl | Cbm-E | Np-M | 1.86 | 483 | I |
| IB-814 | i-Bu | Np-M | Np-M | 2.39 | 518 | I |
| IB-815 | 4-OH-Bnzl | Np-M | Bnzl | 2.01 | 518 | I |
| IB-816 | 4-OH-Bnzl | Np-M | Ph-Et | 2.05 | 532 | I |
| IB-817 | Np-M | Bnzl | Ph-Et | 2.32 | 516 | I |
| IB-818 | Np-M | Cbm-E | Np-M | 2.00 | 533 | I |
| IB-819 | Chm | Bnzl | Np-M | 2.40 | 508 | I |
| IB-820 | Hdr-E | Np-M | Bnzl | 1.89 | 456 | I |
| IB-821 | i-Pnt | Ph-Et | 4-OH-Bnzl | 1.94 | 462 | I |
| IB-822 | Ph-Et | i-Pnt | i-Bu | 2.13 | 412 | I |
| IB-823 | Ph-Et | Np-M | Bnzl | 2.33 | 516 | I |
| IB-824 | Ph-Et | Hxy | i-Bu | 2.35 | 426 | I |
| IB-825 | Np-M | Np-M | Bnzl | 2.39 | 552 | I |
| IB-826 | Chm | Ph-Et | 4-OH-Bnzl | 2.02 | 488 | I |
| IB-827 | Hdr-E | i-Pnt | Ph-Et | 1.82 | 400 | I |
| IB-828 | Hdr-E | Np-M | i-Pnt | 1.98 | 436 | I |
| IB-829 | Hdr-E | Np-M | Ph-Et | 1.99 | 470 | I |
| IB-830 | Hdr-E | Np-M | Np-M | 2.02 | 506 | I |
| IB-831 | Hdr-E | 4-F-Bnzl | Np-M | 1.90 | 474 | I |
| IB-832 | i-Pnt | Np-M | Ph-Et | 2.45 | 496 | I |
| IB-833 | i-Pnt | Np-M | Np-M | 2.45 | 532 | I |
| IB-834 | i-Pnt | 4-F-Bnzl | Np-M | 2.24 | 500 | I |
| IB-835 | Chm | i-Pnt | Np-M | 2.46 | 488 | I |
| IB-836 | Bnzl | Ph-Et | 4-OH-Bnzl | 1.98 | 482 | I |
| IB-837 | Bnzl | Np-M | Bnzl | 2.30 | 502 | I |
| IB-838 | Bnzl | Ph-Et | Np-M | 2.28 | 516 | I |
| IB-839 | i-Bu | Hxy | Bnzl | 2.24 | 412 | I |
| IB-840 | i-Bu | 4-F-Bnzl | Bnzl | 2.11 | 436 | I |
| IB-841 | 4-OH-Bnzl | Hdr-E | Np-M | 1.72 | 472 | I |
| IB-842 | 4-OH-Bnzl | Np-M | Np-M | 2.08 | 568 | I |
| IB-843 | 4-OH-Bnzl | i-Bu | Ph-Et | 1.89 | 448 | I |
| IB-844 | Ph-Et | Cbx-E | i-Bu | 0.85 | 414 | C |
| IB-845 | Ph-Et | Cbx-E | i-Pnt | 0.89 | 428 | C |
| IB-846 | 4-OH-Bnzl | Cbx-E | i-Pnt | 0.73 | 430 | C |
| IB-847 | 4-OH-Bnzl | Cbx-E | Bnzl | 0.75 | 450 | C |
| IB-848 | 4-OH-Bnzl | Cbx-E | Ph-Et | 0.74 | | C |
| IB-849 | Bnzl | Cbx-E | i-Bu | 0.80 | 400 | C |
| IB-850 | Bnzl | Cbx-E | i-Pnt | 0.84 | 414 | C |
| IB-851 | Bnzl | Cbx-E | Ph-Et | 0.85 | 448 | C |
| IB-852 | i-Bu | Cbx-E | Ph-Et | 0.84 | 414 | C |
| IB-853 | i-Bu | Cbx-E | 4-OH-Bnzl | 0.54 | 416 | C |
| IB-854 | i-Pnt | Cbx-E | Ph-Et | 0.84 | 428 | C |
| IB-855 | i-Pnt | Cbx-E | 4-OH-Bnzl | 0.68 | 430 | C |
| IB-856 | Chm | Cbx-E | Ph-Et | 0.91 | 454 | C |
| IB-857 | Chm | Cbx-E | 4-OH-Bnzl | 0.77 | 456 | C |
| IB-858 | i-Pnt | Cbx-E | Bnzl | 0.80 | 414 | C |
| IB-859 | Chm | Cbx-E | Bnzl | 0.90 | 440 | C |
| IB-860 | 4-OH-Bnzl | Cbx-E | i-Bu | 0.69 | 416 | c |

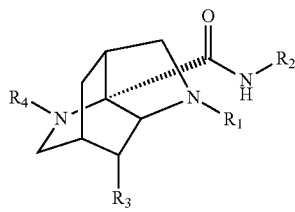

| Compound number | $R_1$ | $R_2$ | $R_3$ | $R_4$ | Retention RT (min) | Mass $(M + H)^+$ | Measurement condition |
|---|---|---|---|---|---|---|---|
| IB-861 | methyl | 2-(1H-indol-3-yl)ethyl | benzyl | H | 1.212 | 429 | B |
| IB-862 | benzyl | Np-M | i-Bu | H | 1.29 | 468 | B |
| IB-863 | benzyl | 4-(trifluoromethyl)benzyl | i-Bu | H | 1.298 | 486 | B |

TABLE 3-continued

| | | | | | | | |
|---|---|---|---|---|---|---|---|
| IB-864 | 4-Cl-Bnzl | benzyl | i-Bu | H | 1.288 | 452 | B |
| IB-865 | 3-Cl-Bnzl | benzyl | i-Bu | H | 1.293 | 452 | B |
| IB-866 | 4-methoxy-benzyl | benzyl | i-Bu | H | 1.263 | 448 | B |
| IB-867 | 4-methyl benzyl | benzyl | i-Bu | H | 1.288 | 432 | B |
| IB-868 | i-Pnt | 1-Bu | benzyl | H | 1.277 | 398 | B |
| IB-869 | i-Bu | 1-Bu | 4-Cl-Bnzl | H | 1.275 | 418 | B |
| IB-870 | i-Bu | 1-Pnt | benzyl | H | 1.287 | 398 | B |
| IB-871 | i-Bu | 4-Cl-Bnzl | i-Bu | H | 1.285 | 418 | B |
| IB-872 | 4-hydroxy-benzyl | benzyl | i-Bu | H | 1.187 | 434 | B |
| IB-873 | 4-(dimethyl-amino)benzyl | benzyl | i-Bu | H | 1.255 | 461 | B |
| IB-874 | 4-(tert-butyl)benzyl | benzyl | i-Bu | H | 1.345 | 474 | B |
| IB-875 | i-Bu | benzyl | i-Pnt | H | 1.283 | 398 | B |
| IB-876 | i-Pnt | benzyl | i-Bu | H | 1.067 | 398 | B |
| IB-877 | 4-(tri-fluoromethyl)benzyl | benzyl | i-Bu | H | 1.29 | 502 | B |
| IB-878 | 4-ethoxy benzyl | benzyl | i-Bu | H | 1.275 | 462 | B |
| IB-879 | benzyl | naphthalen-2-yl-methyl | i-Bu | H | 1.282 | 468 | B |
| IB-880 | 4-methyl benzyl | benzyl | i-Bu | ethyl | 1.332 | 460 | B |
| IB-881 | 4-methyl benzyl | benzyl | i-Bu | i-Bu | 1.495 | 488 | B |
| IB-882 | 4-methyl benzyl | benzyl | i-Bu | acetyl | 1.223 | 474 | B |
| IB-883 | 4-methyl benzyl | benzyl | i-Bu | 3-methyl-butanoyl | 1.312 | 516 | B |
| IB-884 | 4-methyl benzyl | benzyl | i-Bu | 2-phenyl-acetyl | 1.3 | 550 | B |
| IB-885 | 4-methyl benzyl | benzyl | i-Bu | methoxy-carbonyl | 1.267 | 490 | B |
| IB-886 | 4-methyl benzyl | benzyl | i-Bu | 2-methyl-propoxy carbonyl | 1.328 | 532 | B |
| IB-887 | 4-methyl benzyl | benzyl | i-Bu | benzyloxy-carbonyl | 1.347 | 566 | B |
| IB-888 | 4-methyl benzyl | benzyl | i-Bu | amino-carbonyl | 1.173 | 475 | B |
| IB-889 | 4-methyl benzyl | benzyl | i-Bu | N-benzyl-amino-carbonyl | 1.288 | 565 | B |
| IB-890 | benzyl | pyridin-4-ylmethyl | i-Bu | H | 1.11 | 419 | B |
| IB-891 | 4-(dimethyl-amino)-benzyl | 3-hydroxy-benzyl | i-Bu | H | 1.223 | 477 | B |
| IB-892 | 4-(dimethyl-amino)-benzyl | 4-hydroxy benzyl | i-Bu | H | 1.208 | 477 | B |
| IB-893 | 4-methoxy-benzyl | benzyl | benzyl | H | 0.98 | 482 | C |
| IB-894 | 4-methoxy-benzyl | benzyl | benzyl | tert-butoxy-carbonyl | 1.06 | 582 | C |
| IB-895 | methyl | benzyl | benzyl | tert-butoxy-carbonyl | 0.97 | 476 | C |
| IB-896 | methyl | benzyl | benzyl | H | 0.84 | 376 | C |
| IB-897 | phenethyl | benzyl | 2-(tert-butyl-dimethyl-silyloxy)ethyl | H | 1.13 | 534 | C |
| IB-898 | cyclopentyl-methyl | 4-(tert-butoxy)-benzyl | 2-(tert-butoxy-carbon-yl)ethyl | H | 1.16 | 554 | C |
| IB-899 | cyclopentyl-methyl | 4-(tert-butoxy)benzyl | 2-(tert-butoxy-carbonyl)ethyl | methoxy-carbonyl | 1.04 | 612 | C |
| IB-900 | cyclopentyl-methyl | 4-hydroxy-benzyl | 2-carboxy-ethyl | H | 0.77 | 442 | C |
| IB-901 | cyclopentyl-methyl | 4-hydroxy-benzyl | 2-carboxy-ethyl | methoxy-carbonyl | 0.76 | 500 | C |

TABLE 3-continued

| | | | | | | | |
|---|---|---|---|---|---|---|---|
| IB-902 | 4-nitro-benzyl | 4-(tert-butoxy)benzyl | 2-(tert-butoxycarbonyl)ethyl | H | 1.06 | 607 | C |
| IB-903 | phenethyl | benzyl | 2-hydroxyethyl | H | 0.85 | 420 | C |
| IB-904 | phenethyl | benzyl | 2-hydroxyethyl | acetyl | 0.81 | 462 | C |
| IB-905 | phenethyl | benzyl | 2-hydroxyethyl | methoxycarbonyl | 0.86 | 478 | C |
| IB-906 | phenethyl | benzyl | 2-hydroxyethyl | ethyl | 0.9 | 448 | C |
| IB-907 | 4-nitro-benzyl | 4-(tert-butoxy)benzyl | 2-(tert-butoxycarbonyl)ethyl | methoxycarbonyl | 1.04 | 665 | C |
| IB-908 | 1-naphthylmethyl | benzyl | benzyl | benzyl | 1.14 | 592 | C |
| IB-909 | 4-amino-benzyl | 4-(tert-butoxy)benzyl | 2-(tert-butoxycarbonyl)ethyl | methoxycarbonyl | 0.94 | 635 | C |
| IB-910 | 4-(cyclopentylcarbonylamino)benzyl | 4-(tert-butoxy)benzyl | 2-(tert-butoxycarbonyl)ethyl | methoxycarbonyl | 1.05 | 731 | C |
| IB-911 | 4-(2-carboxyethylcarbonylamino)benzyl | 4-(tert-butoxy)benzyl | 2-(tert-butoxycarbonyl)ethyl | methoxycarbonyl | 0.92 | 735 | C |
| IB-912 | 4-(2-carbamoylethylcarbonylamino)benzyl | 4-(tert-butoxy)benzyl | 2-(tert-butoxycarbonyl)ethyl | methoxycarbonyl | 0.9 | 734 | C |
| IB-913 | 4-nitro-benzyl | 4-hydroxy-benzyl | 2-carboxylethyl | H | 0.76 | 495 | C |
| IB-914 | 4-(cyclopentylcarbonylamino)benzyl | 4-hydroxy-benzyl | 2-carboxylethyl | methoxycarbonyl | 0.79 | 619 | C |
| IB-915 | 4-nitro-benzyl | 4-(tert-butoxy)benzyl | 2-(tert-butoxycarbonyl)ethyl | tert-butoxycarbonyl | 1.12 | 707 | C |
| IB-916 | 4-(cyclomethylcarbonylamino)benzyl | 4-(tert-butoxy)benzyl | 2-(tert-butoxycarbonyl)ethyl | methoxycarbonyl | 1.14 | 717 | C |
| IB-917 | 4-(cyclopentylcarbonylamino)benzyl | 4-(tert-butoxy)benzyl | 2-(tert-butoxycarbonyl)ethyl | tert-butoxycarbonyl | 1.14 | 774 | C |
| IB-918 | 4-(cyclomethylcarbonylamino)benzyl | 4-(tert-butoxy)benzyl | 2-(tert-butoxycarbonyl)ethyl | tert-butoxycarbonyl | 1.24 | 760 | C |
| IB-919 | 4-nitro-benzyl | 4-(tert-butoxy)benzyl | 2-(tert-butoxycarbonyl)ethyl | formyl | 0.98 | 635 | C |
| IB-920 | 4-(2-carbamoylethylcarbonylamino)benzyl | 4-hydroxy-benzyl | 2-carboxylethyl | methoxycarbonyl | 0.61 | 622 | C |
| IB-921 | 4-(cyclopentylmethylamino)benzyl | 4-hydroxy-benzyl | 2-carboxylethyl | methoxycarbonyl | 0.82 | 605 | C |
| IB-922 | 4-(cyclopentylcarbonylamino)benzyl | 4-hydroxy-benzyl | 2-carboxylethyl | H | 0.79 | 561 | C |

TABLE 3-continued

| IB-923 | 4-(cyclo-pentyl-methyl-amino)benzyl | 4-hydroxy-benzyl | 2-carboxyl ethyl | H | 0.75 | 547 | C |

Formula XXIB

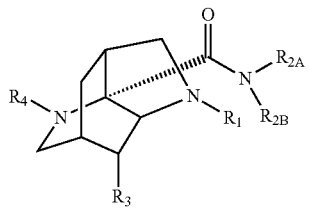

| Compound number | $R_1$ | $R_{2A}$ | $R_{2B}$ | $R_3$ | $R_4$ | Retention RT (min) | Mass $(M + H)^+$ | Measurement condition |
| --- | --- | --- | --- | --- | --- | --- | --- | --- |
| IB-924 | 4-Me-Bnzl | H | Bnzl | i-Bu | N-isobutyl-amino carbonyl | 2.88 | 531 | B1 |
| IB-925 | i-Bu | H | 4-Cl-Bnzl | Ph-Et | H | 2.93 | 466 | B1 |
| IB-926 | i-Bu | H | 3-Cl-Bnzl | Ph-Et | H | 2.94 | 466 | B1 |
| IB-927 | i-Bu | H | 4-MeO-Bnzl | Ph-Et | H | 2.84 | 462 | B1 |
| IB-928 | i-Bu | H | 4-Me-Bnzl | Ph-Et | H | 2.93 | 446 | B1 |
| IB-929 | i-Bu | H | 2-Npm | Ph-Et | H | 2.97 | 482 | B1 |
| IB-930 | i-Bu | H | Bnzl | Ph-Pr | H | 1.36 | 446 | B |
| IB-931 | i-Bu | H | 3-Cl-Bnzl | Ph-Pr | H | 1.31 | 480 | B |
| IB-932 | i-Bu | H | 3-F-Bnzl | Ph-Pr | H | 1.35 | 464 | B |
| IB-933 | i-Bu | H | 3-Me-Bnzl | Ph-Pr | H | 1.38 | 460 | B |
| IB-934 | i-Bu | H | 3-MeO-Bnzl | Ph-Pr | H | 1.36 | 476 | B |
| IB-935 | i-Bu | H | 3-Cl-Bnzl | Ph-Bu | H | 1.33 | 494 | B |
| IB-936 | i-Bu | H | 3-F-Bnzl | Ph-Bu | H | 1.29 | 478 | B |
| IB-937 | i-Bu | H | 3-Me-Bnzl | Ph-Bu | H | 1.38 | 474 | B |
| IB-938 | i-Bu | H | 3-MeO-Bnzl | Ph-Bu | H | 1.31 | 491 | B |
| IB-939 | i-Bu | H | Bnzl | Ph-Bu | H | 1.32 | 461 | B |
| IB-940 | i-Pnt | H | 3-F-Bnzl | Ph-Pr | H | 1.31 | 478 | B |
| IB-941 | 1-Npm | H | pentyl | Ph-Et | H | 1.08 | 496 | C |
| IB-942 | 1-Npm | H | cyclohexyl | Ph-Et | H | 1.08 | 508 | C |
| IB-943 | 1-Npm | H | cyclopentyl | Ph-Et | H | 1.06 | 494 | C |
| IB-944 | 1-Npm | piperidine† | | Ph-Et | H | 1.04 | 494 | C |
| IB-945 | 1-Npm | pyrrolidine† | | Ph-Et | H | 1.00 | 480 | C |
| IB-946 | 1-Npm | H | Hxy | 4-methyl-phen-ethyl | H | 1.14 | 524 | C |
| IB-947 | 1-Npm | H | Hxy | 2-(naph-thalen-2-yl)ethyl | H | 1.16 | 560 | C |

TABLE 3-continued

| | | | | | | | | |
|---|---|---|---|---|---|---|---|---|
| IB-948 | 1-Npm | H | heptyl | Ph-Et | H | 1.14 | 524 | C |
| IB-949 | 1-Npm | H | Hxy | 4-isopropyl-phenethyl | H | 1.19 | 552 | C |
| IB-950 | 1-Npm | H | Hxy | cyclohexyl ethyl | H | 1.19 | 516 | C |
| IB-951 | tBuO-E | H | 4-fluoro phenethyl | 1-Npm | H | 1.06 | 544 | C |
| IB-952 | H | H | 4-tBuO-Bnzl | tBOC-E | methoxycarbonyl | 0.93 | 530 | C |
| IB-953** | 2-phenylacetyl | H | 4-tBuO-Bnzl | tBOC-E | methoxycarbonyl | 1.17, 1.20 | 648 | C |
| IB-954** | 3-methyl butanoyl | H | 4-tBuO-Bnzl | tBOC-E | methoxycarbonyl | 1.16, 1.21 | 614 | C |
| IB-955** | 2-phenylacetyl | H | 4-OH-Bnzl | Cbx-E | methoxycarbonyl | 0.78, 0.83 | 536 | C |
| IB-956** | 3-methyl butanoyl | H | 4-OH-Bnzl | Cbx-E | methoxycarbonyl | 0.75, 0.81 | 502 | C |
| IB-957 | i-Bu | H | Ph-Et | Ph-Et | H | 2.89 | 446 | B1 |
| IB-958 | i-Bu | H | 1-Npm | Ph-Et | H | 2.97 | 482 | B1 |
| IB-959 | Chm | H | tBuO-E | 1-Npm | H | 1.10 | 518 | C |
| IB-960 | tBuO-E | H | Ph-Et | 1-Npm | H | 1.06 | 526 | C |
| IB-961 | Hdr-E | H | 4-fluorophen ethyl | 1-Npm | H | 0.90 | 488.3 | C |
| IB-962 | 3-tert-butoxy-propyl | H | 4-F-Bnzl | 1-Npm | H | 1.04 | 544.4 | C |
| IB-963 | tBuO-E | H | 4-Cl-Bnzl | 1-Npm | H | 1.07, 1.09 | 546.3 | C |
| IB-964 | Hdr-E | H | 4-Cl-Bnzl | 1-Npm | H | 0.92 | 490.3 | C |
| IB-965 | Hdr-E | H | 4-Cl-Bnzl | 1-Npm | H | 0.92 | 490.2 | C |
| IB-966 | 3-hydroxy-propyl | H | 4-F-Bnzl | 1-Npm | H | 0.87 | 488.3 | C |
| IB-967 | 1-Npm | H | Hxy | 3-methyl phen ethyl | H | 1.14 | 524.4 | C |
| IB-968 | 1-Npm | H | β-hydroxyphen-ethyl | Ph-Et | H | 1.01 | 546.4 | C |
| IB-969 | 1-Npm | H | α-hydroxymethyl-phen-ethyl | Ph-Et | H | 1.01 | 560.4 | C |
| IB-970 | 1-Npm | H | α-hydroxymethyl-phenethyl | Ph-Et | H | 1.03 | 560.4 | C |
| IB-971 | 4-Nt-Bnzl | H | Bnzl | tBOC-E | H | 0.97 | 535 | C |
| IB-972 | 4-Nt-Bnzl | H | Bnzl | tBOC-E | ethoxycarbonyl | 0.98 | 563 | C |
| IB-973 | H | H | Bnzl | tBOC-E | ethoxycarbonyl | 0.87 | 472 | C |
| IB-974 | phenyl-acetyl | H | Bnzl | tBOC-E | ethoxycarbonyl | 0.14, 0.16 | 590 | C |
| IB-975 | phenyl-acetyl | H | Bnzl | Cbx-E | ethoxycarbonyl | 0.91, 0.97 | 534 | C |
| IB-976 | 4-amino benzyl | H | Bnzl | tBOC-E | ethoxycarbonyl | 0.87 | 577 | C |

TABLE 3-continued

| | | | | | | | | |
|---|---|---|---|---|---|---|---|---|
| IB-977 | 4-(cyclopentylmethylamino)benzyl | H | Bnzl | tBOC-E | ethoxycarbonyl | 1.09 | 659 | C |
| IB-978 | 4-(cyclopentylmethylamino)benzyl | H | Bnzl | Cbx-E | ethoxycarbonyl | 0.93 | 603 | C |
| IB-979 | 4-(cyclopentylcarbonylamino)benzyl | H | Bnzl | tBOC-E | ethoxycarbonyl | 1.00 | 673 | C |
| IB-980** | 3-methylbutanoyl | H | Bnzl | tBOC-E | ethoxycarbonyl | 1.13, 1.16 | 556 | C |
| IB-981 | H | H | Bnzl | Bnzl | tert-butoxycarbonyl | 0.93 | 462 | C |
| IB-982** | 3-methylbutanoyl | H | Bnzl | Cbx-E | ethoxycarbonyl | 0.89, 0.96 | 500 | C |
| IB-983 | isopropoxycarbonyl | H | Bnzl | Cbx-E | ethoxycarbonyl | 0.94 | 502 | C |
| IB-984** | phenylacetyl | H | Bnzl | 3-ethoxy-3-oxo-propyl | ethoxycarbonyl | 1.05, 1.08 | 562 | C |
| IB-985 | benzoyl | H | Bnzl | Bnzl | tert-butoxycarbonyl | 1.22 | 566 | C |
| IB-986 | phenylacetyl | H | Bnzl | Bnzl | tert-butoxycarbonyl | 1.23 | 580 | C |
| IB-987 | 4-(cyclopentylcarbonylamino)benzyl | H | Bnzl | Cbx-E | ethoxycarbonyl | 0.87 | 617 | C |
| IB-988 | 1-Npm | H | 4-F-Bnzl | 2-OH-Et | H | 0.89 | 474.3 | C |
| IB-989 | 2-OH-Et | H | Ph-Et | 1-Npm | H | 0.89 | 470.3 | C |
| IB-990 | 4-tBuO-Bnzl | H | Bnzl | i-Bu | H | 1.02 | 490.3 | C |
| IB-991 | 4-tBuO-Bnzl | H | i-Bu | Bnzl | H | 1.03 | 490.4 | C |
| IB-992 | 2-OtBu-Et | H | Bnzl | 1-Npm | H | 1.04 | 512.4 | C |
| IB-993 | 2-OH-Et | H | Bnzl | 1-Npm | H | 0.87 | 456.3 | C |
| IB-994 | 4-OH-Bnzl | H | i-Bu | Bnzl | H | 0.85 | 434.3 | C |
| IB-995 | 1-Npm | H | 4-F-Bnzl | 2-OTBS-Et | H | 1.17 | 588.4 | C |

†Ring formed together by $R_{2A}$ and $R_{2B}$
**IB-953, 954, 955, 956, 980, 982, and 984 are mixtures of cis-trans isomers. For this reason, two values are shown for the retention of LCMS.

TABLE 4

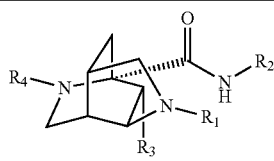

| Compound Number | R₁ | R₂ | R₃ | R₄ | Synthesis method | Intermediate |
| --- | --- | --- | --- | --- | --- | --- |
| IF-1 | i-Bu | Bnzl | Bnzl | H | EX | IIF-1 |
| IF-2 | i-Bu | i-Bu | i-Bu | H | IF-1 | IIF-2 |
| IF-3 | i-Bu | i-Bu | Bnzl | H | IF-1 | IIF-3 |
| IF-4 | Bnzl | i-Bu | i-Bu | H | IF-1 | IIF-4 |
| IF-5 | i-Bu | Bnzl | i-Bu | H | IF-1 | IIF-5 |
| IF-6 | Bnzl | i-Bu | Bnzl | H | IF-1 | IIF-6 |
| IF-7 | Bnzl | Bnzl | i-Bu | H | IF-1 | IIF-7 |
| IF-8 | Bnzl | Bnzl | Bnzl | H | IF-1 | IIF-8 |
| IF-9 | i-Pnt | Bnzl | Bnzl | H | IF-1 | IIF-9 |
| IF-10 | Bnzl | Bnzl | i-Pnt | H | IF-1 | IIF-10 |
| IF-11 | i-Bu | Bnzl | Ph-Et | H | IF-1 | IIF-11 |
| IF-12 | i-Bu | Ph-Et | Bnzl | H | IF-1 | IIF-12 |
| IF-13 | i-Bu | Bnzl | 3-Me-Bnzl | H | IF-1 | IIF-13 |
| IF-14 | i-Bu | Bnzl | 4-Me-Bnzl | H | IF-1 | IIF-14 |
| IF-15 | i-Bu | 3-Me-Bnzl | Bnzl | H | IF-1 | IIF-15 |
| IF-16 | i-Bu | 4-Me-Bnzl | Bnzl | H | IF-1 | IIF-16 |
| IF-17 | i-Bu | 3-Cl-Bnzl | Bnzl | H | IF-1 | IIF-17 |
| IF-18 | i-Bu | 4-Cl-Bnzl | Bnzl | H | IF-1 | IIF-18 |
| IF-19 | 3,4-Cl₂-Bnzl | Bnzl | i-Bu | H | IF-1 | IIF-19 |
| IF-20 | Bnzl | 3,4-Cl₂-Bnzl | i-Bu | H | IF-1 | IIF-20 |
| IF-22 | i-Bu | 4-OH-Bnzl | Bnzl | H | IF-40 | IF-23 |
| IF-23 | i-Bu | 4-(tert-butoxy)benzyl | Bnzl | H | IF-1 | IIF-23 |
| IF-24 | i-Bu | Np-M | Bnzl | H | IF-1 | IIF-24 |
| IF-25 | i-Bu | Hdr-E | Bnzl | H | IF-1 | IIF-25 |
| IF-26 | i-Bu | Cbx-E | Bnzl | H | EX | IF-27 |
| IF-27 | i-Bu | 2-(tert-butoxy)-2-oxoethyl | Bnzl | H | IF-1 | IIF-27 |
| IF-28 | i-Bu | Cbm-E | Bnzl | H | IF-1 | IIF-28 |
| IF-29 | i-Bu | 4-aminobutyl | Bnzl | H | IB-29 | IF-30 |
| IF-30 | i-Bu | 4-((tert-butoxycarbonyl)amino)butyl | Bnzl | H | IF-1 | IIF-30 |
| IF-31 | i-Bu | Chm | Bnzl | H | IF-1 | IIF-31 |
| IF-32 | i-Bu | (tetrahydro-2H-pyran-2-yl)methyl | Bnzl | H | IF-1 | IIF-32 |
| IF-33 | i-Bu | Bnzl | 4-aminobutyl | H | EX | IF-34 |
| IF-34 | i-Bu | Bnzl | 4-((tert-butoxycarbonyl)amino)butyl | H | IF-1 | IIF-34 |
| IF-35 | i-Bu | Bnzl | Cbx-E | H | IB-35 | IF-73 |
| IF-36 | i-Bu | Bnzl | 3-methoxy-3-oxopropyl | H | IF-1 | IIF-36 |
| IF-38 | i-Bu | Bnzl | Chm | H | IF-1 | IIF-38 |
| IF-39 | Chm | Bnzl | Bnzl | H | IF-1 | IIF-39 |
| IF-40 | 4-OH-Bnzl | Bnzl | Bnzl | H | EX | IF-41 |
| IF-41 | 4-(tert-butoxy)benzyl | Bnzl | Bnzl | H | EX | IIF-41 |
| IF-42 | Np-M | Bnzl | Bnzl | H | IF-1 | IIF-42 |
| IF-43 | i-Bu | Bnzl | Bnzl | Ac | EX | IF-1 |
| IF-44 | i-Bu | i-Bu | i-Bu | Ac | IF-43 | IF-2 |
| IF-45 | i-Bu | i-Bu | Bnzl | Ac | IF-43 | IF-3 |
| IF-46 | Bnzl | i-Bu | i-Bu | Ac | IF-43 | IF-4 |
| IF-47 | i-Bu | Bnzl | i-Bu | Ac | IF-43 | IF-5 |
| IF-49 | Bnzl | Bnzl | i-Bu | Ac | IF-43 | IF-7 |
| IF-50 | Bnzl | Bnzl | Bnzl | Ac | IF-43 | IF-8 |
| IF-54 | i-Bu | Ph-Et | Bnzl | Ac | IF-43 | IF-12 |
| IF-57 | i-Bu | 3-Me-Bnzl | Bnzl | Ac | IF-43 | IF-15 |
| IF-58 | i-Bu | 4-Me-Bnzl | Bnzl | Ac | IF-43 | IF-16 |
| IF-68 | i-Bu | Bnzl | Bnzl | Bz | IB-68 | IF-1 |
| IF-69 | i-Bu | Bnzl | Bnzl | Et | IB-69 | IF-1 |
| IF-70 | i-Bu | Bnzl | Bnzl | methoxycarbonyl | IB-70 | IF-1 |
| IF-71 | i-Bu | Bnzl | Bnzl | Me | EX | IF-1 |
| IF-72 | Bnzl | Bnzl | i-Bu | Et | IB-69 | IF-7 |
| IF-73 | i-Bu | Bnzl | Cbx-E | tBOC | IB-73 | IF-74 |
| IF-74 | i-Bu | Bnzl | 3-methoxy-3-oxopropyl | tBOC | IB-74 | IF-36 |

TABLE 4-continued

| | | | | | | |
|---|---|---|---|---|---|---|
| IF-76 | 3-(tert-butoxy)-3-oxopropyl | Bnzl | Bnzl | H | IF-1 | IIF-76 |
| IF-77 | Bnzl | Bnzl | 4-OH-Bnzl | H | IF-1 | IIF-77 |
| IF-80 | Np-M | Bnzl | Pr | H | IB-1 | IIF-80 |

| Compound number | Name of compound | LCMS $t_R$ (min) | Mass $(M + H)^+$ | Elution condition | Yield (%) |
|---|---|---|---|---|---|
| IF-1 | (3S*,3aS*,6S*,7R*,7aS*)-N,7-dibenzyl-1-isobutyloctahydro-6H-3,6-methanopyrrolo[3,2-c]pyridine-6-carboxamide | 0.99 | 418 | B | 62 |
| IF-2 | (3S*,3aS*,6S*,7R*,7aS*)-N,1,7-triisobutyloctahydro-6H-3,6-methanopyrrolo[3,2-c]pyridine-6-carboxamide | 0.93 | 350 | B | 73 |
| IF-3 | (3S*,3aS*,6S*,7R*,7aS*)-7-benzyl-N,1-diisobutyloctahydro-6H-3,6-methanopyrrolo[3,2-c]pyridine-6-carboxamide | 0.96 | 384 | B | 67 |
| IF-4 | (3S*,3aS*,6S*,7R*,7aS*)-1-benzyl-N,7-diisobutyloctahydro-6H-3,6-methanopyrrolo[3,2-c]pyridine-6-carboxamide | 0.97 | 384 | B | 82 |
| IF-5 | (3S*,3aS*,6S*,7R*,7aS*)-N-benzyl-1,7-diisobutyloctahydro-6H-3,6-methanopyrrolo[3,2-c]pyridine-6-carboxamide | 0.95 | 384 | B | 73 |
| IF-6 | (3S*,3aS*,6S*,7R*,7aS*)-1,7-dibenzyl-N-isobutyloctahydro-6H-3,6-methanopyrrolo[3,2-c]pyridine-6-carboxamide | 1.00 | 418 | B | 68 |
| IF-7 | (3S*,3aS*,6S*,7R*,7aS*)-N,1-dibenzyl-7-isobutyloctahydro-6H-3,6-methanopyrrolo[3,2-c]pyridine-6-carboxamide | 0.99 | 418 | B | 64 |
| IF-8 | (3S*,3aS*,6S*,7R*,7aS*)-N,1,7-tribenzyloctahydro-6H-3,6-methanopyrrolo[3,2-c]pyridine-6-carboxamide | 1.02 | 452 | B | 69 |
| IF-9 | (3S*,3aS*,6S*,7R*,7aS*)-N,7-dibenzyl-1-isopentyloctahydro-6H-3,6-methanopyrrolo[3,2-c]pyridine-6-carboxamide | 1.01 | 432 | B | 47 |
| IF-10 | (3S*,3aS*,6S*,7R*,7aS*)-N,1-dibenzyl-7-isopentyloctahydro-6H-3,6-methanopyrrolo[3,2-c]pyridine-6-carboxamide | 1.02 | 432 | B | 60 |
| IF-11 | (3S*,3aS*,6S*,7R*,7aS*)-N-benzyl-1-isobutyl-7-phenethyloctahydro-6H-3,6-methanopyrrolo[3,2-c]pyridine-6-carboxamide | 0.99 | 432 | B | 63 |
| IF-12 | (3S*,3aS*,6S*,7R*,7aS*)-1-benzyl-7-isobutyl-N-phenethyloctahydro-6H-3,6-methanopyrrolo[3,2-c]pyridine-6-carboxamide | 1.01 | 432 | B | 60 |
| IF-13 | (3S*,3aS*,6S*,7R*,7aS*)-N-benzyl-1-isobutyl-7-(3-methylbenzyl)octahydro-6H-3,6-methanopyrrolo[3,2-c]pyridine-6-carboxamide | 1.01 | 432 | B | 55 |
| IF-14 | (3S*,3aS*,6S*,7R*,7aS*)-N-benzyl-1-isobutyl-7-(4-methylbenzyl)octahydro-6H-3,6-methanopyrrolo[3,2-c]pyridine-6-carboxamide | 1.01 | 432 | B | 57 |
| IF-15 | (3S*,3aS*,6S*,7R*,7aS*)-7-benzyl-1-isobutyl-N-(3-methylbenzyl)octahydro-6H-3,6-methanopyrrolo[3,2-c]pyridine-6-carboxamide | 1.02 | 432 | B | 62 |
| IF-16 | (3S*,3aS*,6S*,7R*,7aS*)-7-benzyl-1-isobutyl-N-(4-methylbenzyl)octahydro-6H-3,6-methanopyrrolo[3,2-c]pyridine-6-carboxamide | 1.02 | 432 | B | 63 |
| IF-17 | (3S*,3aS*,6S*,7R*,7aS*)-7-benzyl-N-(3-chlorobenzyl)-1-isobutyloctahydro-6H-3,6-methanopyrrolo[3,2-c]pyridine-6-carboxamide | 1.03 | 452 | B | 69 |
| IF-18 | (3S*,3aS*,6S*,7R*,7aS*)-7-benzyl-N-(4-chlorobenzyl)-1-isobutyloctahydro-6H-3,6-methanopyrrolo[3,2-c]pyridine-6-carboxamide | 1.03 | 452 | B | 68 |
| IF-19 | (3S*,3aS*,6S*,7R*,7aS*)-N-benzyl-1-(3,4-dichlorobenzyl)-7-isobutyloctahydro-6H-3,6-methanopyrrolo[3,2-c]pyridine-6-carboxamide | 1.13 | 486 | B | 38 |
| IF-20 | (3S*,3aS*,6S*,7R*,7aS*)-1-benzyl-N-(3,4-dichlorobenzyl)-7-isobutyloctahydro-6H-3,6-methanopyrrolo[3,2-c]pyridine-6-carboxamide | 1.06 | 486 | B | 37 |
| IF-22 | (3S*,3aS*,6S*,7R*,7aS*)-7-benzyl-N-(4-hydroxybenzyl)-1-isobutyloctahydro-6H-3,6-methanopyrrolo[3,2-c]pyridine-6-carboxamide | 0.71 | 434 | A | 95 |
| IF-23 | (3S*,3aS*,6S*,7R*,7aS*)-7-benzyl-1-isobutyl-N-(4-(tert-butoxy)benzyl)octahydro-6H-3,6-methanopyrrolo[3,2-c]pyridine-6-carboxamide | 0.87 | 490 | A | 95 |
| IF-24 | (3S*,3aS*,6S*,7R*,7aS*)-7-benzyl-1-isobutyl-N-(naphthalen-1-ylmethyl)octahydro-6H-3,6-methanopyrrolo[3,2-c]pyridine-6-carboxamide | 0.85 | 468 | A | 77 |
| IF-25 | (3S*,3aS*,6S*,7R*,7aS*)-7-benzyl-N-(2-hydroxyethyl)-1-isobutyloctahydro-6H-3,6-methanopyrrolo[3,2-c]pyridine-6-carboxamide | 0.65 | 372 | A | 95 |

TABLE 4-continued

| | | | | | |
|---|---|---|---|---|---|
| IF-26 | 3-((3S*,3aS*,6S*,7R*,7aS*)-7-benzyl-1-isobutyloctahydro-1H-3,6-methanopyrrolo[3,2-c]pyridine-6-carboxamide)propanoic acid | 0.66 | 400 | A | 100 |
| IF-27 | (3S*,3aS*,6S*,7R*,7aS*)-7-benzyl-1-isobutyl-N-(2-(tert-butoxy)-2-oxoethyl)octahydro-6H-3,6-methanopyrrolo[3,2-c]pyridine-6-carboxamide | 0.81 | 456 | A | 100 |
| IF-28 | (3S*,3aS*,6S*,7R*,7aS*)-7-benzyl-N-(3-amino-3-oxopropyl)-1-isobutyloctahydro-6H-3,6-methanopyrrolo[3,2-c]pyridine-6-carboxamide | 0.67 | 399 | A | 53 |
| IF-29 | (3S*,3aS*,6S*,7R*,7aS*)-N-(4-aminobutyl)-7-benzyl-1-isobutyloctahydro-6H-3,6-methanopyrrolo[3,2-c]pyridine-6-carboxamide | 0.83 | 399 | A | 100 |
| IF-30 | (3S*,3aS*,6S*,7R*,7aS*)-7-benzyl-1-isobutyl-N-(4-((tert-butoxycarbonyl)amino)butyl)octahydro-6H-3,6-methanopyrrolo[3,2-c]pyridine-6-carboxamide | 0.81 | 499 | A | 80 |
| IF-31 | (3S*,3aS*,6S*,7R*,7aS*)-7-benzyl-N-cyclohexylmethyl-1-isobutyloctahydro-6H-3,6-methanopyrrolo[3,2-c]pyridine-6-carboxamide | 0.85 | 424 | A | 22 |
| IF-32 | (3S*,3aS*,6S*,7R*,7aS*)-7-benzyl-1-isobutyl-N-((tetrahydro-2H-pyran-2-yl)methyl)octahydro-6H-3,6-methanopyrrolo[3,2-c]pyridine-6-carboxamide | 0.76, 0.75 | 426 | A | 93 |
| IF-33 | (3S*,3aS*,6S*,7R*,7aS*)-7-(4-aminobutyl)-N-benzyl-1-isobutyloctahydro-6H-3,6-methanopyrrolo[3,2-c]pyridine-6-carboxamide | 0.62 | 399 | A | 100 |
| IF-34 | (3S*,3aS*,6S*,7R*,7aS*)-N-benzyl-1-isobutyl-7-(4-((tert-butoxycarbonyl)amino)butyl)octahydro-6H-3,6-methanopyrrolo[3,2-c]pyridine-6-carboxamide | 0.82 | 499 | A | 78 |
| IF-35 | 3-((3S*,3aS*,6S*,7R*,7aS*)-3a-(benzylcarbamoyl)-1-isobutyloctahydro-1H-3,6-methanopyrrolo[3,2-c]pyridin-7-yl)propanoic acid | 0.65 | 400 | A | 100 |
| IF-36 | (3S*,3aS*,6S*,7R*,7aS*)-N-benzyl-1-isobutyl-7-(3-methoxy-3-oxopropyl)octahydro-6H-3,6-methanopyrrolo[3,2-c]pyridine-6-carboxamide | 0.72 | 414 | A | — |
| IF-38 | (3S*,3aS*,6S*,7R*,7aS*)-N-benzyl-7-(cyclohexylmethyl)-1-isobutyloctahydro-6H-3,6-methanopyrrolo[3,2-c]pyridine-6-carboxamide | 0.86 | 424 | A | 83 |
| IF-39 | (3S*,3aS*,6S*,7R*,7aS*)-N,7-dibenzyl-1-cyclohexylmethyloctahydro-6H-3,6-methanopyrrolo[3,2-c]pyridine-6-carboxamide | 0.86 | 458 | A | 62 |
| IF-40 | (3S*,3aS*,6S*,7R*,7aS*)-N,7-dibenzyl-1-(4-hydroxybenzyl)octahydro-6H-3,6-methanopyrrolo[3,2-c]pyridine-6-carboxamide | 0.75 | 468 | A | 63 |
| IF-41 | (3S*,3aS*,6S*,7R*,7aS*)-N,7-dibenzyl-1-(4-(tert-butoxy)benzyl)octahydro-6H-3,6-methanopyrrolo[3,2-c]pyridine-6-carboxamide | 0.90 | 524 | A | 52 |
| IF-42 | (3S*,3aS*,6S*,7R*,7aS*)-N,7-dibenzyl-1-(naphthalen-1-ylmethyl)octahydro-6H-3,6-methanopyrrolo[3,2-c]pyridine-6-carboxamide | 0.88 | 502 | A | 65 |
| IF-43 | (3S*,3aS*,6S*,7R*,7aS*)-4-acetyl-N,7-dibenzyl-1-isobutyloctahydro-6H-3,6-methanopyrrolo[3,2-c]pyridine-6-carboxamide | 1.08 | 460 | B | 51 |
| IF-44 | (3S*,3aS*,6S*,7R*,7aS*)-4-acetyl-N,1,7-triisobutyloctahydro-6H-3,6-methanopyrrolo[3,2-c]pyridine-6-carboxamide | 1.04 | 392 | B | 82 |
| IF-45 | (3S*,3aS*,6S*,7R*,7c]pyridine-6-carboxamideaS*)-4-acetyl-7-benzyl-N,1-diisobutyloctahydro-6H-3,6-methanopyrrolo[3,2-c]pyridine-6-carboxamide | 1.05 | 426 | B | 83 |
| IF-46 | (3S*,3aS*,6S*,7R*,7aS*)-4-acetyl-1-benzyl-N,7-diisobutyloctahydro-6H-3,6-methanopyrrolo[3,2-c]pyridine-6-carboxamide | 1.05 | 426 | B | 79 |
| IF-47 | (3S*,3aS*,6S*,7R*,7aS*)-4-acetyl-N-benzyl-1,7-diisobutyloctahydro-6H-3,6-methanopyrrolo[3,2-c]pyridine-6-carboxamide | 1.06 | 426 | B | 88 |
| IF-49 | (3S*,3aS*,6S*,7R*,7aS*)-4-acetyl-N,1-dibenzyl-7-isobutyloctahydro-6H-3,6-methanopyrrolo[3,2-c]pyridine-6-carboxamide | 1.08 | 460 | B | 84 |
| IF-50 | (3S*,3aS*,6S*,7R*,7aS*)-4-acetyl-N,1,7-tribenzyloctahydro-6H-3,6-methanopyrrolo[3,2-c]pyridine-6-carboxamide | 1.10 | 494 | B | 75 |
| IF-54 | (3S*,3aS*,6S*,7R*,7aS*)-4-acetyl-1-benzyl-7-isobutyl-N-phenethyloctahydro-6H-3,6-methanopyrrolo[3,2-c]pyridine-6-carboxamide | 1.10 | 474 | B | 58 |
| IF-57 | (3S*,3aS*,6S*,7R*,7aS*)-4-acetyl-7-benzyl-1-isobutyl-N-(3-methylbenzyl)octahydro-6H-3,6-methanopyrrolo[3,2-c]pyridine-6-carboxamide | 1.12 | 474 | B | 40 |
| IF-58 | (3S*,3aS*,6S*,7R*,7aS*)-4-acetyl-7-benzyl-1-isobutyl-N-(4-methylbenzyl)octahydro-6H-3,6-methanopyrrolo[3,2-c]pyridine-6-carboxamide | 1.12 | 474 | B | 55 |

TABLE 4-continued

| | | RT (min) | Mass | | |
|---|---|---|---|---|---|
| IF-68 | (3S*,3aS*,6S*,7R*,7aS*)-4-benzoyl-N,7-dibenzyl-1-isobutyloctahydro-6H-3,6-methanopyrrolo[3,2-c]pyridine-6-carboxamide | 1.17 | 522 | B | 51 |
| IF-69 | (3S*,3aS*,6S*,7R*,7aS*)-N,7-dibenzyl-4-ethyl-1-isobutyloctahydro-6H-3,6-methanopyrrolo[3,2-c]pyridine-6-carboxamide | 1.06 | 446 | B | 57 |
| IF-70 | (3S*,3aS*,6S*,7R*,7aS*)-N,7-dibenzyl-1-isobutyl-4-(methoxycarbonyl)octahydro-6H-3,6-methanopyrrolo[3,2-c]pyridine-6-carboxamide | 1.13 | 476 | B | 32 |
| IF-71 | (3S*,3aS*,6S*,7R*,7aS*)-N,7-dibenzyl-1-isobutyl-4-methyloctahydro-6H-3,6-methanopyrrolo[3,2-c]pyridine-6-carboxamide | 1.02 | 432 | B | 38 |
| IF-72 | (3S*,3aS*,6S*,7R*,7aS*)-N,1-dibenzyl-4-ethyl-7-isobutyloctahydro-6H-3,6-methanopyrrolo[3,2-c]pyridine-6-carboxamide | 1.06 | 446 | B | 45 |
| IF-73 | tert-butyl (3S*,3aS*,6S*,7R*,7aS*)-6-(benzylcarbamoyl)-1-isobutyl-7-(2-carboxyethyl)octahydro-5H-3,6-methanopyrrolo[3,2-c]pyridine-5-carboxylate | 0.84 | 500 | A | 9 |
| IF-74 | tert-butyl (3S*,3aS*,6S*,7R*,7aS*)-3a-(benzylcarbamoyl)-1-isobutyl-7-(3-methoxy-3-oxopropyl)octahydro-4H-3,6-methanopyrrolo[3,2-b]pyridine-4-carboxylate | 0.91 | 514 | A | 71 |
| IF-76 | tert-butyl 3-((3S*,3aS*,6S*,7R*,7aS*)-7-benzyl-6-(benzylcarbamoyl)octahydro-1H-3,6-methanopyrrolo[3,2-c]pyridin-1-yl)propanoate | 1.04 | 490 | B | 53 |
| IF-77 | (3S*,3aS*,6S*,7R*,7aS*)-N,1-dibenzyl-7-(4-hydroxybenzyl)octahydro-6H-3,6-methanopyrrolo[3,2-c]pyridine-6-carboxamide | 0.93 | 468 | B | 60 |
| IF-80 | (3S*,3aS*,6S*,7R*,7aS*)-N-benzyl-1-(naphthalen-1-ylmethyl)-7-propyloctahydro-6H-3,6-methanopyrrolo[3,2-c]pyridine-6-carboxamide | 0.84 | 454 | A | 44 |

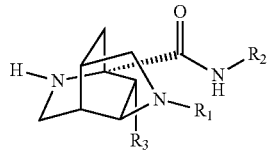

| Compound number | R₁ | R₂ | R₃ | Retention RT (min) | Mass (M + H)⁺ | Measurement condition |
|---|---|---|---|---|---|---|
| IF-81 | Cbm-M | Np-M | i-Bu | 0.71 | 435 | C |
| IF-82 | Cbm-M | Np-M | Bnzl | 0.72 | 469 | C |
| IF-83 | Cbm-M | Np-M | 4-OH-Bnzl | 0.67 | 485 | C |
| IF-84 | Cbm-M | Np-M | i-Pnt | 0.73 | 449 | C |
| IF-85 | Cbm-M | Np-M | Ph-Et | 0.75 | 483 | C |
| IF-86 | Cbm-M | Ph-Et | i-Bu | 0.66 | 399 | C |
| IF-87 | Cbm-M | Ph-Et | Bnzl | 0.68 | 433 | C |
| IF-88 | Cbm-M | Ph-Et | 4-OH-Bnzl | 0.63 | 449 | C |
| IF-89 | Cbm-M | Ph-Et | i-Pnt | 0.70 | 413 | C |
| IF-90 | Cbm-M | Ph-Et | Np-M | 0.74 | 483 | C |
| IF-91 | Cbm-M | Np-M | Np-M | 0.76 | 519 | C |
| IF-92 | Cbm-M | 4-F-Bnzl | i-Bu | 0.65 | 403 | C |
| IF-93 | Cbm-M | 4-F-Bnzl | Bnzl | 0.67 | 437 | C |
| IF-94 | Cbm-M | 4-F-Bnzl | 4-OH-Bnzl | 0.62 | 453 | C |
| IF-95 | Cbm-M | 4-F-Bnzl | i-Pnt | 0.69 | 417 | C |
| IF-96 | Cbm-M | 4-F-Bnzl | Ph-Et | 0.71 | 451 | C |
| IF-97 | Cbm-M | 4-F-Bnzl | Np-M | 0.73 | 487 | C |
| IF-98 | Cbm-M | i-Pnt | i-Bu | 0.66 | 365 | C |
| IF-99 | Cbm-M | i-Pnt | Bnzl | 0.67 | 399 | C |
| IF-100 | Cbm-M | i-Pnt | 4-OH-Bnzl | 0.62 | 415 | C |
| IF-101 | Cbm-M | i-Pnt | Cbx-E | 0.58 | 381 | C |
| IF-102 | Cbm-M | i-Pnt | Ph-Et | 0.71 | 413 | C |
| IF-103 | Cbm-M | i-Pnt | Np-M | 0.73 | 449 | C |
| IF-104 | Cbm-M | Hxy | i-Bu | 0.71 | 379 | C |
| IF-105 | Cbm-M | Hxy | Bnzl | 0.72 | 413 | C |
| IF-106 | Cbm-M | Hxy | 4-OH-Bnzl | 0.67 | 429 | C |
| IF-107 | Cbm-M | Hxy | Cbx-E | 0.63 | 395 | C |
| IF-108 | Cbm-M | Hxy | i-Pnt | 0.73 | 393 | C |
| IF-109 | Cbm-M | Hxy | Ph-Et | 0.75 | 427 | C |
| IF-110 | Cbm-M | Hxy | Np-M | 0.77 | 463 | C |
| IF-111 | Cbm-M | i-Pr | i-Bu | 1.03 | 337 | D |
| IF-112 | Cbm-M | i-Pr | Bnzl | 0.58 | 371 | C |
| IF-113 | Cbm-M | i-Pr | 4-OH-Bnzl | 0.97 | 387 | D |
| IF-114 | Cbm-M | i-Pr | Cbx-E | 0.22 | 353 | E |
| IF-115 | Cbm-M | i-Pr | i-Pnt | 1.09 | 351 | D |

TABLE 4-continued

| | | | | | |
|---|---|---|---|---|---|
| IF-116 | Cbm-M | i-Pr | Ph-Et | 0.63 | 385 | C |
| IF-117 | Cbm-M | i-Pr | Np-M | 0.65 | 421 | C |
| IF-118 | Cbm-M | i-Bu | i-Bu | 0.62 | 351 | C |
| IF-119 | Cbm-M | i-Bu | Bnzl | 0.64 | 385 | C |
| IF-120 | Cbm-M | i-Bu | 4-OH-Bnzl | 0.59 | 401 | C |
| IF-121 | Cbm-M | i-Bu | Cbx-E | 0.93 | 367 | D |
| IF-122 | Cbm-M | i-Bu | i-Pnt | 0.66 | 365 | C |
| IF-123 | Cbm-M | i-Bu | Ph-Et | 0.69 | 399 | C |
| IF-124 | Cbm-M | i-Bu | Np-M | 0.71 | 435 | C |
| IF-125 | Cbm-M | Bnzl | i-Bu | 0.65 | 385 | C |
| IF-126 | Cbm-M | Bnzl | Bnzl | 0.67 | 419 | C |
| IF-127 | Cbm-M | Bnzl | 4-OH-Bnzl | 0.62 | 435 | C |
| IF-128 | Cbm-M | Bnzl | Cbx-E | 0.99 | 401 | D |
| IF-129 | Cbm-M | Bnzl | i-Pnt | 0.69 | 399 | C |
| IF-130 | Cbm-M | Bnzl | Ph-Et | 0.71 | 433 | C |
| IF-131 | Cbm-M | Bnzl | Np-M | 0.73 | 469 | C |
| IF-132 | Cbm-M | 4-OH-Bnzl | i-Bu | 0.57 | 401 | C |
| IF-133 | Cbm-M | 4-OH-Bnzl | Bnzl | 0.59 | 435 | C |
| IF-134 | Cbm-M | 4-OH-Bnzl | Cbx-E | 0.87 | 417 | D |
| IF-135 | Cbm-M | 4-OH-Bnzl | i-Pnt | 0.60 | 415 | C |
| IF-136 | Cbm-M | 4-OH-Bnzl | Ph-Et | 0.63 | 449 | C |
| IF-137 | Cbm-M | 4-OH-Bnzl | Np-M | 0.65 | 485 | C |
| IF-138 | Cbm-M | Cbx-E | Bnzl | 0.94 | 401 | D |
| IF-139 | Cbm-M | Cbx-E | 4-OH-Bnzl | 0.47 | 417 | D |
| IF-140 | Cbm-M | Cbx-E | Ph-Et | 1.01 | 415 | D |
| IF-141 | Cbm-M | Cbx-E | Np-M | 0.60 | 451 | C |
| IF-142 | Cbm-M | Cbm-E | i-Bu | 0.23 | 366 | E |
| IF-143 | Cbm-M | Cbm-E | Bnzl | 0.88 | 400 | D |
| IF-144 | Cbm-M | Cbm-E | 4-OH-Bnzl | 0.23 | 416 | E |
| IF-145 | Cbm-M | Cbm-E | Cbx-E | 0.20 | 382 | E |
| IF-146 | Cbm-M | Cbm-E | i-Pnt | 0.91 | 380 | D |
| IF-147 | Cbm-M | Cbm-E | Ph-Et | 0.89 | 414 | D |
| IF-148 | Cbm-M | Cbm-E | Np-M | 0.57 | 450 | C |
| IF-149 | Cbm-M | Gun-Pr | i-Bu | 0.83 | 394 | D |
| IF-150 | Cbm-M | Gun-Pr | Bnzl | 0.92 | 428 | D |
| IF-151 | Cbm-M | Gun-Pr | 4-OH-Bnzl | 0.34 | 442[1] | E |
| IF-152 | Cbm-M | Gun-Pr | i-Pnt | 0.93 | 408 | D |
| IF-153 | Cbm-M | Gun-Pr | Ph-Et | 0.96 | 442 | D |
| IF-154 | Cbm-M | Gun-Pr | Np-M | 1.01 | 478 | D |
| IF-155 | Cbm-M | Hdr-E | i-Bu | 0.46 | 339 | E |
| IF-156 | Cbm-M | Hdr-E | Bnzl | 0.49 | 373 | C |
| IF-157 | Cbm-M | Hdr-E | 4-OH-Bnzl | 0.35 | 389 | E |
| IF-158 | Cbm-M | Hdr-E | Cbx-E | 0.20 | 355 | E |
| IF-159 | Cbm-M | Hdr-E | i-Pnt | 0.93 | 353 | D |
| IF-160 | Cbm-M | Hdr-E | Ph-Et | 0.98 | 387 | D |
| IF-161 | Cbm-M | Hdr-E | Np-M | 0.58 | 423 | C |
| IF-162 | Gun-Pr | Np-M | i-Bu | 1.25 | 477 | D |
| IF-163 | Gun-Pr | Np-M | Bnzl | 0.72 | 511 | C |
| IF-164 | Gun-Pr | Np-M | 4-OH-Bnzl | 0.69 | 527 | C |
| IF-165 | Gun-Pr | Np-M | i-Pnt | 1.28 | 491 | D |
| IF-166 | Gun-Pr | Np-M | Ph-Et | 0.75 | 525 | C |
| IF-167 | Gun-Pr | Np-M | Np-M | 1.31 | 561 | D |
| IF-168 | Gun-Pr | Hxy | i-Pnt | 0.74 | 435 | C |
| IF-169 | Gun-Pr | Hxy | Ph-Et | 1.30 | 469 | D |
| IF-170 | Gun-Pr | Hxy | Np-M | 1.33 | 505 | D |
| IF-171 | Gun-Pr | i-Pr | i-Bu | 1.08 | 379 | D |
| IF-172 | Gun-Pr | i-Pr | 4-OH-Bnzl | 1.04 | 429 | D |
| IF-173 | Gun-Pr | i-Pr | i-Pnt | 1.12 | 393 | D |
| IF-174 | Gun-Pr | i-Pr | Ph-Et | 1.15 | 427 | D |
| IF-175 | Gun-Pr | i-Pr | Np-M | 1.17 | 463 | D |
| IF-176 | Gun-Pr | 4-F-Bnzl | i-Bu | 1.17 | 445 | D |
| IF-177 | Gun-Pr | 4-F-Bnzl | Bnzl | 0.68 | 479 | C |
| IF-178 | Gun-Pr | 4-F-Bnzl | 4-OH-Bnzl | 1.13 | 495 | D |
| IF-179 | Gun-Pr | 4-F-Bnzl | i-Pnt | 1.21 | 459 | D |
| IF-180 | Gun-Pr | 4-F-Bnzl | Ph-Et | 0.71 | 493 | C |
| IF-181 | Gun-Pr | 4-F-Bnzl | Np-M | 0.72 | 529 | C |
| IF-182 | i-Bu | Hdr-E | Cbm-M | 0.63 | 339 | G |
| IF-183 | i-Bu | Ph-Et | Cbm-M | 3.40 | 399 | G |
| IF-184 | i-Bu | Np-M | Cbm-M | 3.87 | 435 | G |
| IF-185 | i-Bu | i-Bu | Gun-Pr | 3.15 | 393 | G |
| IF-186 | i-Bu | Bnzl | Gun-Pr | 3.42 | 427 | G |
| IF-187 | i-Bu | 4-OH-Bnzl | Gun-Pr | 3.09 | 443 | G |
| IF-188 | i-Bu | Hdr-E | Gun-Pr | 1.17 | 381 | G |
| IF-189 | i-Bu | Ph-Et | Gun-Pr | 3.57 | 441 | G |
| IF-190 | i-Bu | Np-M | Gun-Pr | 3.87 | 477 | G |
| IF-191 | i-Bu | Hxy | Gun-Pr | 3.79 | 421 | G |
| IF-192 | i-Bu | 4-F-Bnzl | Gun-Pr | 3.49 | 445 | G |
| IF-193 | Bnzl | Cbx-E | Cbm-M | 1.82 | 401 | G |
| IF-194 | Bnzl | Hdr-E | Cbm-M | 1.52 | 373 | G |
| IF-195 | Bnzl | i-Pnt | Cbm-M | 3.59 | 399 | G |

TABLE 4-continued

| | | | | | | |
|---|---|---|---|---|---|---|
| IF-196 | Bnzl | Ph-Et | Cbm-M | 3.62 | 433 | G |
| IF-197 | Bnzl | i-Pr | Cbm-M | 3.02 | 371 | G |
| IF-198 | Bnzl | 4-OH-Bnzl | Gun-Pr | 3.54 | 477 | G |
| IF-199 | Bnzl | Hdr-E | Gun-Pr | 2.74 | 415 | F |
| IF-200 | 4-OH-Bnzl | Ph-Et | Gun-Pr | 3.59 | 491 | G |
| IF-201 | 4-OH-Bnzl | Np-M | Gun-Pr | 3.90 | 527 | G |
| IF-202 | Cbx-E | i-Pr | Cbm-M | 0.95 | 353 | G |
| IF-203 | i-Pnt | i-Bu | Cbm-M | 3.25 | 365 | G |
| IF-204 | i-Pnt | Bnzl | Cbm-M | 3.47 | 399 | F |
| IF-205 | i-Pnt | 4-OH-Bnzl | Cbm-M | 3.13 | 415 | G |
| IF-206 | i-Pnt | Ph-Et | Cbm-M | 2.43 | 413 | F |
| IF-207 | i-Pnt | Np-M | Cbm-M | 2.62 | 449 | F |
| IF-208 | i-Pnt | Hxy | Cbm-M | 3.97 | 393 | G |
| IF-209 | i-Pnt | i-Pr | Cbm-M | 2.97 | 351 | G |
| IF-210 | i-Pnt | 4-F-Bnzl | Cbm-M | 3.60 | 417 | G |
| IF-211 | i-Pnt | Bnzl | Gun-Pr | 3.60 | 441 | G |
| IF-212 | i-Pnt | Ph-Et | Gun-Pr | 3.79 | 455 | G |
| IF-213 | i-Pnt | Np-M | Gun-Pr | 2.63 | 491 | G |
| IF-214 | i-Pnt | i-Pr | Gun-Pr | 3.25 | 393 | G |
| IF-215 | i-Pnt | 4-F-Bnzl | Gun-Pr | 3.72 | 459 | G |
| IF-216 | Ph-Et | Bnzl | Cbm-M | 2.45 | 433 | F |
| IF-217 | Ph-Et | 4-OH-Bnzl | Cbm-M | 3.40 | 449 | G |
| IF-218 | Ph-Et | Cbx-E | Cbm-M | 2.85 | 415 | G |
| IF-219 | Ph-Et | Cbm-E | Cbm-M | 2.67 | 414 | G |
| IF-220 | Ph-Et | Gun-Pr | Cbm-M | 2.94 | 442 | G |
| IF-221 | Ph-Et | Hdr-E | Cbm-M | 2.75 | 387 | G |
| IF-222 | Ph-Et | i-Pnt | Cbm-M | 3.87 | 413 | G |
| IF-223 | Ph-Et | Np-M | Cbm-M | 2.75 | 483 | F |
| IF-224 | Ph-Et | 4-F-Bnzl | Cbm-M | 2.52 | 451 | F |
| IF-225 | Ph-Et | Hdr-E | Gun-Pr | 3.05 | 429 | G |
| IF-226 | Np-M | i-Bu | Cbm-M | 2.49 | 435 | F |
| IF-227 | Np-M | Bnzl | Cbm-M | 2.62 | 469 | F |
| IF-228 | Np-M | Cbm-E | Cbm-M | 3.27 | 450 | G |
| IF-229 | Np-M | Gun-Pr | Cbm-M | 3.32 | 478 | G |
| IF-230 | Np-M | Hdr-E | Cbm-M | 3.29 | 423 | G |
| IF-231 | Np-M | Ph-Et | Cbm-M | 2.65 | 483 | F |
| IF-232 | Np-M | Np-M | Cbm-M | 2.84 | 519 | F |
| IF-233 | Np-M | i-Pr | Cbm-M | 3.62 | 421 | G |
| IF-234 | Np-M | 4-F-Bnzl | Cbm-M | 2.65 | 487 | F |
| IF-235 | Np-M | i-Bu | Gun-Pr | 3.70 | 477 | G |
| IF-236 | Np-M | Bnzl | Gun-Pr | 3.88 | 511 | G |
| IF-237 | Np-M | 4-OH-Bnzl | Gun-Pr | 3.62 | 527 | G |
| IF-238 | Np-M | Cbm-E | Gun-Pr | 3.22 | 492 | G |
| IF-239 | Np-M | Hdr-E | Gun-Pr | 3.20 | 465 | G |
| IF-240 | Np-M | i-Pnt | Gun-Pr | 3.95 | 491 | G |
| IF-241 | Np-M | Ph-Et | Gun-Pr | 4.07 | 525 | G |
| IF-242 | Np-M | Np-M | Gun-Pr | 4.27 | 561 | G |
| IF-243 | Np-M | Hxy | Gun-Pr | 4.25 | 505 | G |
| IF-244 | Np-M | i-Pr | Gun-Pr | 2.38 | 463 | F |
| IF-245 | Np-M | 4-F-Bnzl | Gun-Pr | 3.95 | 529 | G |
| IF-246 | Chm | Bnzl | Cbm-M | 3.75 | 425 | G |
| IF-247 | Chm | 4-OH-Bnzl | Cbm-M | 3.40 | 441 | G |
| IF-248 | Chm | Cbx-E | Cbm-M | 2.90 | 407 | G |
| IF-249 | Chm | Cbm-E | Cbm-M | 2.74 | 406 | G |
| IF-250 | Chm | i-Pnt | Cbm-M | 2.50 | 405 | F |
| IF-251 | Chm | Ph-Et | Cbm-M | 2.52 | 439 | F |
| IF-252 | Chm | Np-M | Cbm-M | 2.69 | 475 | F |
| IF-253 | Chm | Hxy | Cbm-M | 4.17 | 419 | G |
| IF-254 | Chm | i-Pr | Cbm-M | 3.29 | 377 | F |
| IF-255 | Chm | 4-F-Bnzl | Cbm-M | 2.54 | 443 | F |
| IF-256 | Chm | Bnzl | Gun-Pr | 3.79 | 467 | G |
| IF-257 | Chm | i-Pnt | Gun-Pr | 3.90 | 447 | G |
| IF-258 | Chm | Ph-Et | Gun-Pr | 3.95 | 481 | G |
| IF-259 | Chm | Np-M | Gun-Pr | 4.27 | 517 | G |
| IF-260 | Chm | Hxy | Gun-Pr | 4.12 | 461 | G |
| IF-261 | Chm | 4-F-Bnzl | Gun-Pr | 3.95 | 485 | G |
| IF-262 | 4-F-Bnzl | i-Bu | Cbm-M | 3.34 | 403 | G |
| IF-263 | 4-F-Bnzl | Bnzl | Cbm-M | 3.57 | 437 | G |
| IF-264 | 4-F-Bnzl | 4-OH-Bnzl | Cbm-M | 3.22 | 453 | G |
| IF-265 | 4-F-Bnzl | Cbx-E | Cbm-M | 2.34 | 419 | G |
| IF-266 | 4-F-Bnzl | Cbm-E | Cbm-M | 1.63 | 418 | G |
| IF-267 | 4-F-Bnzl | Hdr-E | Cbm-M | 1.79 | 391 | G |
| IF-268 | 4-F-Bnzl | i-Pnt | Cbm-M | 3.70 | 417 | G |
| IF-269 | 4-F-Bnzl | Ph-Et | Cbm-M | 2.43 | 451 | F |
| IF-270 | 4-F-Bnzl | Np-M | Cbm-M | 2.62 | 487 | F |
| IF-271 | 4-F-Bnzl | Hxy | Cbm-M | 2.60 | 431 | F |
| IF-272 | 4-F-Bnzl | i-Pr | Cbm-M | 3.10 | 389 | G |
| IF-273 | 4-F-Bnzl | Hdr-E | Gun-Pr | 2.70 | 433 | G |
| IF-274 | 4-F-Bnzl | i-Pr | Gun-Pr | 3.37 | 431 | G |
| IF-275 | Cbx-E | i-Bu | Cbm-M | 3.20 | 367 | G |

TABLE 4-continued

| | | | | | | |
|---|---|---|---|---|---|---|
| IF-276 | Cbx-E | i-Pnt | Cbm-M | 3.54 | 381 | G |
| IF-277 | Bnzl | Bnzl | Cbm-M | 2.38 | 419 | F |
| IF-278 | Bnzl | Np-M | Cbm-M | 4.09 | 469 | G |
| IF-279 | Bnzl | Hxy | Cbm-M | 4.02 | 413 | G |
| IF-280 | Bnzl | 4-F-Bnzl | Cbm-M | 2.43 | 437 | F |
| IF-281 | Bnzl | Bnzl | Gun-Pr | 2.40 | 461 | F |
| IF-282 | Bnzl | i-Pnt | Gun-Pr | 2.47 | 441 | F |
| IF-283 | Bnzl | Ph-Et | Gun-Pr | 2.50 | 475 | F |
| IF-284 | Bnzl | Np-M | Gun-Pr | 2.62 | 511 | F |
| IF-285 | Bnzl | Hxy | Gun-Pr | 2.62 | 455 | F |
| IF-286 | Bnzl | 4-F-Bnzl | Gun-Pr | 2.47 | 479 | F |
| IF-287 | Ph-Et | Bnzl | Gun-Pr | 2.52 | 475 | F |
| IF-288 | Ph-Et | 4-OH-Bnzl | Gun-Pr | 2.38 | 491 | F |
| IF-289 | Ph-Et | i-Pnt | Gun-Pr | 2.57 | 455 | F |
| IF-290 | Ph-Et | Np-M | Gun-Pr | 2.72 | 525 | F |
| IF-291 | Ph-Et | Hxy | Gun-Pr | 2.70 | 469 | F |
| IF-292 | Ph-Et | 4-F-Bnzl | Gun-Pr | 2.59 | 493 | F |
| IF-293 | 4-F-Bnzl | i-Bu | Gun-Pr | 2.34 | 445 | F |
| IF-294 | 4-F-Bnzl | Bnzl | Gun-Pr | 2.43 | 479 | F |
| IF-295 | 4-F-Bnzl | i-Pnt | Gun-Pr | 2.50 | 459 | F |
| IF-296 | 4-F-Bnzl | Ph-Et | Gun-Pr | 2.50 | 493 | F |
| IF-297 | 4-F-Bnzl | Np-M | Gun-Pr | 2.63 | 529 | F |
| IF-298 | 4-F-Bnzl | Hxy | Gun-Pr | 2.63 | 473 | F |
| IF-299 | i-Bu | Cbm-E | Cbx-E | 1.03 | 381 | H |
| IF-300 | i-Bu | Cbm-E | i-Pnt | 2.15 | 379 | H |
| IF-301 | i-Bu | Gun-Pr | i-Bu | 2.13 | 393 | H |
| IF-302 | i-Bu | Gun-Pr | Bnzl | 2.19 | 427 | H |
| IF-303 | i-Bu | Gun-Pr | 4-OH-Bnzl | 1.79 | 443 | H |
| IF-304 | i-Bu | Gun-Pr | i-Pnt | 1.95 | 407 | H |
| IF-305 | i-Bu | Gun-Pr | Ph-Et | 1.98 | 441 | H |
| IF-306 | i-Bu | Gun-Pr | Np-M | 2.08 | 477 | H |
| IF-307 | Bnzl | Cbm-E | Cbx-E | 1.76 | 415 | H |
| IF-308 | Bnzl | Cbm-E | i-Pnt | 2.02 | 413 | H |
| IF-309 | Bnzl | Gun-Pr | i-Bu | 1.82 | 427 | H |
| IF-310 | Bnzl | Gun-Pr | Bnzl | 2.02 | 461 | H |
| IF-311 | Bnzl | Gun-Pr | 4-OH-Bnzl | 1.87 | 477 | H |
| IF-312 | Bnzl | Gun-Pr | i-Pnt | 2.05 | 441 | H |
| IF-313 | Bnzl | Gun-Pr | Ph-Et | 2.08 | 475 | H |
| IF-314 | Bnzl | Gun-Pr | Np-M | 2.14 | 511 | H |
| IF-315 | 4-OH-Bnzl | Cbm-E | Cbx-E | 1.28 | 431 | H |
| IF-316 | 4-OH-Bnzl | Cbm-E | i-Pnt | 1.85 | 429 | H |
| IF-317 | 4-OH-Bnzl | Gun-Pr | i-Bu | 1.85 | 443 | H |
| IF-318 | 4-OH-Bnzl | Gun-Pr | Bnzl | 1.91 | 477 | H |
| IF-319 | 4-OH-Bnzl | Gun-Pr | i-Pnt | 1.89 | 457 | H |
| IF-320 | 4-OH-Bnzl | Gun-Pr | Ph-Et | 1.96 | 491 | H |
| IF-321 | 4-OH-Bnzl | Gun-Pr | Np-M | 2.00 | 527 | H |
| IF-322 | Cbx-E | Cbm-E | i-Pnt | 1.73 | 395 | H |
| IF-323 | Gun-Pr | i-Bu | i-Bu | 1.98 | 393 | H |
| IF-324 | Gun-Pr | i-Bu | Bnzl | 1.99 | 427 | H |
| IF-325 | Gun-Pr | i-Bu | 4-OH-Bnzl | 1.92 | 443 | H |
| IF-326 | Gun-Pr | i-Bu | i-Pnt | 2.10 | 407 | H |
| IF-327 | Gun-Pr | i-Bu | Ph-Et | 2.15 | 441 | H |
| IF-328 | Gun-Pr | i-Bu | Np-M | 2.14 | 477 | H |
| IF-329 | Gun-Pr | Bnzl | i-Bu | 2.06 | 427 | H |
| IF-330 | Gun-Pr | Bnzl | Bnzl | 2.08 | 461 | H |
| IF-331 | Gun-Pr | Bnzl | 4-OH-Bnzl | 1.98 | 47 | H |
| IF-332 | Gun-Pr | Bnzl | i-Pnt | 2.16 | 441 | H |
| IF-333 | Gun-Pr | Bnzl | Ph-Et | 2.19 | 475 | H |
| IF-334 | Gun-Pr | Bnzl | Np-M | 2.21 | 511 | H |
| IF-335 | Gun-Pr | 4-OH-Bnzl | i-Bu | 1.89 | 443 | H |
| IF-336 | Gun-Pr | 4-OH-Bnzl | Bnzl | 1.95 | 477 | H |
| IF-337 | Gun-Pr | 4-OH-Bnzl | i-Pnt | 1.92 | 457 | H |
| IF-338 | Gun-Pr | 4-OH-Bnzl | Ph-Et | 1.97 | 491 | H |
| IF-339 | Gun-Pr | 4-OH-Bnzl | Np-M | 2.01 | 527 | H |
| IF-340 | Gun-Pr | Cbm-E | i-Bu | 1.64 | 408 | H |
| IF-341 | Gun-Pr | Cbm-E | Bnzl | 1.72 | 442 | H |
| IF-342 | Gun-Pr | Cbm-E | 4-OH-Bnzl | 1.15 | 458 | H |
| IF-343 | Gun-Pr | Cbm-E | i-Pnt | 1.73 | 422 | H |
| IF-344 | Gun-Pr | Cbm-E | Ph-Et | 1.79 | 456 | H |
| IF-345 | Gun-Pr | Cbm-E | Np-M | 1.84 | 492 | H |
| IF-346 | Gun-Pr | Hdr-E | i-Bu | 1.70 | 381 | H |
| IF-347 | Gun-Pr | Hdr-E | Bnzl | 1.73 | 415 | H |
| IF-348 | Gun-Pr | Hdr-E | 4-OH-Bnzl | 1.59 | 431 | H |
| IF-349 | Gun-Pr | Hdr-E | i-Pnt | 1.78 | 395 | H |
| IF-350 | Gun-Pr | Hdr-E | Ph-Et | 1.82 | 429 | H |
| IF-351 | Gun-Pr | Hdr-E | Np-M | 1.84 | 465 | H |
| IF-352 | Gun-Pr | i-Pnt | i-Bu | 2.07 | 407 | H |
| IF-353 | Gun-Pr | i-Pnt | Bnzl | 2.10 | 441 | H |
| IF-354 | Gun-Pr | i-Pnt | 4-OH-Bnzl | 2.02 | 457 | H |
| IF-355 | Gun-Pr | i-Pnt | Ph-Et | 2.12 | 455 | H |

TABLE 4-continued

| | | | | | | |
|---|---|---|---|---|---|---|
| IF-356 | Gun-Pr | i-Pnt | Np-M | 2.22 | 491 | H |
| IF-357 | Gun-Pr | Ph-Et | i-Bu | 2.09 | 441 | H |
| IF-358 | Gun-Pr | Ph-Et | Bnzl | 2.10 | 475 | H |
| IF-359 | Gun-Pr | Ph-Et | 4-OH-Bnzl | 2.02 | 491 | H |
| IF-360 | Gun-Pr | Ph-Et | i-Pnt | 2.18 | 455 | H |
| IF-361 | Gun-Pr | Ph-Et | Np-M | 2.19 | 525 | H |
| IF-362 | Hdr-E | Cbm-E | Cbx-E | 0.41 | 369 | H |
| IF-363 | Hdr-E | Cbm-E | i-Pnt | 1.71 | 367 | H |
| IF-364 | Hdr-E | Gun-Pr | i-Bu | 1.64 | 381 | H |
| IF-365 | Hdr-E | Gun-Pr | Bnzl | 1.76 | 415 | H |
| IF-366 | Hdr-E | Gun-Pr | 4-OH-Bnzl | 1.84 | 431 | H |
| IF-367 | Hdr-E | Gun-Pr | i-Pnt | 1.75 | 395 | H |
| IF-368 | Hdr-E | Gun-Pr | Ph-Et | 1.81 | 429 | H |
| IF-369 | Hdr-E | Gun-Pr | Np-M | 1.83 | 465 | H |
| IF-370 | i-Pnt | Cbm-E | Cbx-E | 1.75 | 395 | H |
| IF-371 | i-Pnt | Gun-Pr | i-Bu | 2.01 | 407 | H |
| IF-372 | i-Pnt | Gun-Pr | Bnzl | 2.05 | 441 | H |
| IF-373 | i-Pnt | Gun-Pr | 4-OH-Bnzl | 1.91 | | H |
| IF-374 | i-Pnt | Gun-Pr | Ph-Et | 2.09 | 455 | H |
| IF-375 | i-Pnt | Gun-Pr | Np-M | 2.15 | 491 | H |
| IF-376 | Ph-Et | Cbm-E | Cbx-E | 1.85 | 429 | H |
| IF-377 | Ph-Et | Cbm-E | i-Pnt | 2.09 | 427 | H |
| IF-378 | Ph-Et | Gun-Pr | i-Bu | 2.05 | 441 | H |
| IF-379 | Ph-Et | Gun-Pr | Bnzl | 2.18 | | H |
| IF-380 | Ph-Et | Gun-Pr | 4-OH-Bnzl | 1.94 | 491 | H |
| IF-381 | Ph-Et | Gun-Pr | i-Pnt | 2.11 | 455 | H |
| IF-382 | Ph-Et | Gun-Pr | Np-M | 2.20 | 525 | H |
| IF-383 | Np-M | Cbm-E | Cbx-E | 1.91 | 465 | H |
| IF-384 | Np-M | Cbm-E | i-Pnt | 2.17 | 463 | H |
| IF-385 | Np-M | Gun-Pr | i-Bu | 1.82 | 477 | H |
| IF-386 | Np-M | Gun-Pr | Bnzl | 2.15 | 511 | H |
| IF-387 | Np-M | Gun-Pr | 4-OH-Bnzl | 1.97 | 527 | H |
| IF-388 | Np-M | Gun-Pr | i-Pnt | 2.17 | 491 | H |
| IF-389 | Np-M | Gun-Pr | Ph-Et | 2.20 | 525 | H |
| IF-390 | Np-M | Gun-Pr | Np-M | 2.22 | 561 | H |
| IF-391 | Chm | Cbm-E | Cbx-E | 1.83 | 421 | H |
| IF-392 | Chm | Cbm-E | i-Pnt | 2.10 | 419 | H |
| IF-393 | Chm | Gun-Pr | i-Bu | 2.06 | 433 | H |
| IF-394 | Chm | Gun-Pr | Bnzl | 2.13 | 467 | H |
| IF-395 | Chm | Gun-Pr | 4-OH-Bnzl | 1.91 | 483 | H |
| IF-396 | Chm | Gun-Pr | i-Pnt | 2.13 | 447 | H |
| IF-397 | Chm | Gun-Pr | Ph-Et | 2.15 | 481 | H |
| IF-398 | Chm | Gun-Pr | Np-M | 2.22 | 517 | H |
| IF-399 | 4-F-Bnzl | Cbm-E | Cbx-E | 1.78 | 433 | H |
| IF-400 | 4-F-Bnzl | Cbm-E | i-Pnt | 2.06 | 431 | H |
| IF-401 | 4-F-Bnzl | Gun-Pr | i-Bu | 2.03 | 445 | H |
| IF-402 | 4-F-Bnzl | Gun-Pr | Bnzl | 2.10 | 479 | H |
| IF-403 | 4-F-Bnzl | Gun-Pr | 4-OH-Bnzl | 1.90 | 495 | H |
| IF-404 | 4-F-Bnzl | Gun-Pr | i-Pnt | 2.10 | 459 | H |
| IF-405 | 4-F-Bnzl | Gun-Pr | Ph-Et | 2.13 | 493 | H |
| IF-406 | 4-F-Bnzl | Gun-Pr | Np-M | 2.19 | 529 | H |
| IF-407 | Ph-Et | i-Bu | i-Pnt | 1.54 | 412 | I |
| IF-408 | Np-M | i-Bu | i-Pnt | 1.68 | 448 | I |
| IF-409 | Chm | i-Bu | i-Pnt | 1.55 | 404 | I |
| IF-410 | 4-F-Bnzl | i-Bu | i-Pnt | 1.51 | 416 | I |
| IF-411 | Bnzl | i-Bu | i-Pnt | 1.46 | 398 | I |
| IF-412 | i-Bu | i-Bu | i-Pnt | 1.40 | 364 | I |
| IF-413 | i-Pnt | Cbx-E | Np-M | 1.41 | 464 | I |
| IF-414 | i-Pnt | Cbx-E | i-Bu | 1.15 | 380 | I |
| IF-415 | Chm | Cbx-E | i-Pnt | 1.15 | 420 | I |
| IF-416 | Chm | Cbx-E | Np-M | 1.51 | 490 | I |
| IF-417 | 4-F-Bnzl | Cbx-E | Np-M | 1.46 | 502 | I |
| IF-418 | i-Pnt | 4-F-Bnzl | Cbx-E | 1.18 | 432 | I |
| IF-419 | Chm | Np-M | Cbx-E | 1.40 | 490 | I |
| IF-420 | 4-F-Bnzl | Np-M | Cbx-E | 1.42 | 502 | I |
| IF-421 | Cbx-E | 4-F-Bnzl | i-Bu | 1.27 | 418 | I |
| IF-422 | Cbx-E | Np-M | i-Pnt | 1.48 | 464 | I |
| IF-423 | Cbx-E | 4-F-Bnzl | Np-M | 1.47 | 502 | I |
| IF-424 | Cbx-E | i-Bu | Bnzl | 1.20 | 400 | I |
| IF-425 | Cbx-E | 4-OH-Bnzl | Np-M | 1.28 | 500 | I |
| IF-426 | Bnzl | Hxy | Cbx-E | 1.31 | 428 | I |
| IF-427 | i-Bu | Hxy | Cbx-E | 1.24 | 394 | I |
| IF-428 | i-Bu | Cbx-E | Np-M | 1.35 | 450 | I |
| IF-429 | i-Bu | Cbx-E | i-Bu | 1.02 | 366 | I |
| IF-430 | Hdr-E | i-Bu | i-Pnt | 1.23 | 352 | I |
| IF-431 | Ph-Et | i-Bu | Np-M | 1.75 | 482 | I |
| IF-432 | Np-M | i-Bu | Ph-Et | 1.75 | 482 | I |
| IF-433 | Np-M | i-Bu | Np-M | 1.96 | 518 | I |
| IF-434 | Np-M | i-Bu | Bnzl | 1.73 | 468 | I |
| IF-435 | Np-M | Cbm-E | 4-OH-Bnzl | 1.17 | 499 | I |

TABLE 4-continued

| | | | | | | |
|---|---|---|---|---|---|---|
| IF-436 | 4-F-Bnzl | i-Bu | Np-M | 1.73 | 486 | I |
| IF-437 | i-Pnt | Ph-Et | i-Bu | 1.55 | 412 | I |
| IF-438 | Ph-Et | Hxy | i-Bu | 1.67 | 426 | I |
| IF-439 | Chm | Ph-Et | 4-OH-Bnzl | 1.43 | 488 | I |
| IF-440 | 4-F-Bnzl | Ph-Et | Np-M | 1.77 | 534 | I |
| IF-441 | Bnzl | i-Bu | Np-M | 1.65 | 468 | I |
| IF-442 | 4-OH-Bnzl | Hdr-E | Np-M | 1.26 | 472 | I |
| IF-443 | 4-OH-Bnzl | i-Bu | i-Pnt | 1.25 | 414 | I |
| IF-444 | Hdr-E | Cbx-E | Np-M | 1.15 | 438 | I |
| IF-445 | i-Pnt | 4-OH-Bnzl | Cbx-E | 0.97 | 430 | I |
| IF-446 | Chm | Cbx-E | i-Bu | 1.25 | 406 | I |
| IF-447 | Chm | 4-OH-Bnzl | Cbx-E | 1.12 | 456 | I |
| IF-448 | Np-M | Hdr-E | Cbx-E | 1.13 | 438 | I |
| IF-449 | Cbx-E | Np-M | i-Bu | 1.43 | 450 | I |
| IF-450 | Cbx-E | Hxy | i-Bu | 1.43 | 394 | I |
| IF-451 | Cbx-E | Hdr-E | Ph-Et | 0.91 | 402 | I |
| IF-452 | Cbx-E | Hdr-E | Np-M | 1.13 | 438 | I |
| IF-453 | Cbx-E | 4-F-Bnzl | Ph-Et | 1.41 | 466 | I |
| IF-454 | Cbx-E | i-Bu | Ph-Et | 1.30 | 414 | I |
| IF-455 | Cbx-E | i-Bu | 4-OH-Bnzl | 1.11 | 416 | I |
| IF-456 | Cbx-E | Cbm-E | Ph-Et | 0.95 | 429 | I |
| IF-457 | Cbx-E | Cbm-E | Np-M | 1.16 | 465 | I |
| IF-458 | Cbx-E | 4-OH-Bnzl | i-Pnt | 1.13 | 430 | I |
| IF-459 | Bnzl | Cbx-E | Np-M | 1.42 | 484 | I |
| IF-460 | i-Bu | Np-M | Cbx-E | 1.32 | 450 | I |
| IF-461 | 4-OH-Bnzl | Np-M | Cbx-E | 1.26 | | I |
| IF-462 | Hdr-E | 4-OH-Bnzl | Ph-Et | 1.20 | | I |
| IF-463 | Hdr-E | 4-OH-Bnzl | Np-M | 1.27 | 472 | I |
| IF-464 | i-Pnt | 4-OH-Bnzl | Ph-Et | 1.40 | 462 | I |
| IF-465 | i-Pnt | 4-OH-Bnzl | Np-M | 1.53 | 498 | I |
| IF-466 | i-Pnt | 4-OH-Bnzl | Bnzl | 1.37 | 448 | I |
| IF-467 | i-Pnt | 4-OH-Bnzl | i-Bu | 1.32 | 414 | I |
| IF-468 | Ph-Et | 4-OH-Bnzl | i-Pnt | 1.48 | 462 | I |
| IF-469 | Ph-Et | 4-OH-Bnzl | Bnzl | 1.46 | 482 | I |
| IF-470 | Ph-Et | 4-OH-Bnzl | i-Bu | 1.38 | 448 | I |
| IF-471 | Np-M | 4-OH-Bnzl | i-Pnt | 1.63 | 498 | I |
| IF-472 | Np-M | 4-OH-Bnzl | Bnzl | 1.58 | 518 | I |
| IF-473 | Np-M | 4-OH-Bnzl | i-Bu | 1.51 | 484 | I |
| IF-474 | Chm | 4-OH-Bnzl | i-Pnt | 1.46 | 454 | I |
| IF-475 | Chm | 4-OH-Bnzl | Ph-Et | 1.49 | 488 | I |
| IF-476 | Chm | 4-OH-Bnzl | Np-M | 1.62 | 524 | I |
| IF-477 | Chm | 4-OH-Bnzl | Bnzl | 1.43 | 474 | I |
| IF-478 | Chm | 4-OH-Bnzl | i-Bu | 1.41 | 440 | I |
| IF-479 | 4-F-Bnzl | 4-OH-Bnzl | i-Pnt | 1.41 | 466 | I |
| IF-480 | 4-F-Bnzl | 4-OH-Bnzl | Np-M | 1.58 | 536 | I |
| IF-481 | 4-F-Bnzl | 4-OH-Bnzl | Bnzl | 1.38 | 486 | I |
| IF-482 | 4-F-Bnzl | 4-OH-Bnzl | i-Bu | 1.32 | 452 | I |
| IF-483 | i-Pnt | Hdr-E | Bnzl | 1.23 | 386 | I |
| IF-484 | Ph-Et | Hdr-E | Bnzl | 1.30 | 420 | I |
| IF-485 | Np-M | Hdr-E | 4-OH-Bnzl | 1.17 | 472 | I |
| IF-486 | Chm | Hdr-E | Bnzl | 1.33 | 412 | I |
| IF-487 | 4-F-Bnzl | Hdr-E | Bnzl | 1.24 | 424 | I |
| IF-488 | 4-F-Bnzl | Hdr-E | 4-OH-Bnzl | 0.75 | 440 | I |
| IF-489 | i-Pnt | Hdr-E | Ph-Et | 1.29 | 400 | I |
| IF-490 | 4-F-Bnzl | Hdr-E | i-Pnt | 1.30 | 404 | I |
| IF-491 | 4-F-Bnzl | Hdr-E | Ph-Et | 1.34 | 438 | I |
| IF-492 | Bnzl | Hdr-E | i-Bu | 1.17 | 372 | I |
| IF-493 | Bnzl | 4-OH-Bnzl | i-Pnt | 1.40 | 448 | I |
| IF-494 | Bnzl | 4-OH-Bnzl | Bnzl | 1.37 | 468 | I |
| IF-495 | Bnzl | 4-OH-Bnzl | i-Bu | 1.29 | 434 | I |
| IF-497 | i-Bu | Hdr-E | i-Pnt | 1.12 | 352 | I |
| IF-498 | i-Bu | Hdr-E | Ph-Et | 1.18 | 386 | I |
| IF-499 | i-Bu | 4-OH-Bnzl | i-Pnt | 1.29 | 414 | I |
| IF-500 | i-Bu | 4-OH-Bnzl | Np-M | 1.46 | 484 | I |
| IF-501 | i-Bu | 4-OH-Bnzl | i-Bu | 1.22 | 400 | I |
| IF-502 | 4-OH-Bnzl | Hdr-E | i-Pnt | 0.99 | 402 | I |
| IF-503 | 4-OH-Bnzl | i-Pr | i-Pnt | 1.20 | 400 | I |
| IF-504 | 4-OH-Bnzl | i-Pr | Np-M | 1.39 | 470 | I |
| IF-505 | Np-M | Bnzl | 4-OH-Bnzl | 1.46 | 518 | I |
| IF-506 | 4-F--Bnzl | Bnzl | Np-M | 1.73 | 520 | I |
| IF-507 | Hdr-E | Hxy | i-Bu | 1.43 | 366 | I |
| IF-508 | Hdr-E | 4-F-Bnzl | Bnzl | 1.31 | 424 | I |
| IF-509 | i-Pnt | 4-F-Bnzl | 4-OH-Bnzl | 1.40 | 466 | I |
| IF-510 | Ph-Et | Hxy | 4-OH-Bnzl | 1.59 | 476 | I |
| IF-511 | Np-M | Hxy | i-Bu | 1.89 | 462 | I |
| IF-512 | Np-M | Hxy | 4-OH-Bnzl | 1.69 | 512 | I |
| IF-513 | Chm | Hxy | i-Bu | 1.75 | 418 | I |
| IF-514 | Chm | Hxy | 4-OH-Bnzl | 1.49 | 468 | I |
| IF-515 | Hdr-E | 4-F-Bnzl | i-Pnt | 1.42 | 404 | I |
| IF-516 | Hdr-E | 4-F-Bnzl | Ph-Et | 1.41 | 438 | I |

TABLE 4-continued

| | | | | | | |
|---|---|---|---|---|---|---|
| IF-517 | Ph-Et | Hxy | i-Pnt | 1.83 | 440 | I |
| IF-518 | Np-M | Hdr-E | Ph-Et | 1.46 | 470 | I |
| IF-519 | Np-M | Hxy | i-Pnt | 1.98 | 476 | I |
| IF-520 | Chm | Hxy | i-Pnt | 1.81 | 432 | I |
| IF-521 | Chm | 4-F-Bnzl | Ph-Et | 1.67 | 490 | I |
| IF-522 | 4-F--Bnzl | Hxy | Ph-Et | 1.85 | 478 | I |
| IF-523 | i-Bu | Hxy | 4-OH-Bnzl | 1.46 | 428 | I |
| IF-524 | i-Bu | 4-F-Bnzl | 4-OH-Bnzl | 1.37 | 452 | I |
| IF-525 | i-Bu | 4-F-Bnzl | Ph-Et | 1.63 | 450 | I |
| IF-526 | Np-M | i-Bu | Cbx-E | 1.39 | 450 | I |
| IF-527 | Ph-Et | i-Pnt | Cbx-E | 1.35 | 428 | I |
| IF-528 | Cbx-E | i-Pnt | Bnzl | 1.41 | 414 | I |
| IF-529 | Cbx-E | i-Pnt | Ph-Et | 1.46 | 428 | I |
| IF-530 | Cbx-E | i-Bu | i-Pnt | 1.30 | 380 | I |
| IF-531 | Hdr-E | Cbm-E | Np-M | 1.10 | 437 | I |
| IF-532 | Hdr-E | Cbm-E | i-Bu | 1.26 | 353 | I |
| IF-533 | Hdr-E | 4-F-Bnzl | i-Bu | 1.47 | 388 | I |
| IF-534 | Ph-Et | 4-OH-Bnzl | Np-M | 1.55 | 532 | I |
| IF-535 | Np-M | Cbm-E | i-Bu | 1.36 | 449 | I |
| IF-536 | Chm | Cbm-E | Np-M | 1.51 | 489 | I |
| IF-537 | Chm | Cbm-E | 4-OH-Bnzl | 1.01 | 455 | I |
| IF-538 | 4-F-Bnzl | Cbm-E | Ph-Et | 1.31 | 465 | I |
| IF-539 | 4-F-Bnzl | Cbm-E | Np-M | 1.41 | 501 | I |
| IF-540 | Hdr-E | Ph-Et | Bnzl | 1.32 | 420 | I |
| IF-541 | Hdr-E | Ph-Et | 4-OH-Bnzl | 1.25 | 436 | I |
| IF-542 | Hdr-E | Np-M | i-Bu | 1.42 | 422 | I |
| IF-543 | Hdr-E | Np-M | 4-OH-Bnzl | 1.34 | | I |
| IF-544 | Hdr-E | 4-F-Bnzl | i-Bu | 1.21 | 390 | I |
| IF-545 | i-Pnt | Ph-Et | 4-OH-Bnzl | 1.36 | 462 | I |
| IF-546 | i-Pnt | Hxy | i-Bu | 1.61 | 392 | I |
| IF-547 | i-Pnt | 4-F-Bnzl | Bnzl | 1.58 | 450 | I |
| IF-548 | i-Pnt | 4-F-Bnzl | i-Bu | 1.48 | 416 | I |
| IF-549 | Ph-Et | 4-F-Bnzl | Bnzl | 1.62 | 484 | I |
| IF-550 | Ph-Et | 4-F-Bnzl | i-Bu | 1.56 | 450 | I |
| IF-551 | Chm | Np-M | i-Bu | 1.75 | 474 | I |
| IF-552 | 4-F-Bnzl | Np-M | 4-OH-Bnzl | 1.48 | 536 | I |
| IF-553 | Hdr-E | Ph-Et | i-Pnt | 1.37 | 400 | I |
| IF-554 | i-Pnt | Hxy | Ph-Et | 1.77 | 440 | I |
| IF-555 | i-Pnt | Hxy | Np-M | 1.84 | 476 | I |
| IF-556 | Ph-Et | 4-F-Bnzl | i-Pnt | 1.66 | 464 | I |
| IF-557 | Chm | 4-F-Bnzl | i-Pnt | 1.66 | 456 | I |
| IF-558 | 4-F-Bnzl | Np-M | i-Pnt | 1.73 | 500 | I |
| IF-559 | Bnzl | Hxy | Bnzl | 1.70 | 446 | I |
| IF-560 | Bnzl | Hxy | i-Bu | 1.63 | 412 | I |
| IF-561 | Bnzl | 4-F-Bnzl | Bnzl | 1.55 | 470 | I |
| IF-562 | Bnzl | Hxy | i-Pnt | 1.67 | 426 | I |
| IF-563 | Bnzl | Hxy | Ph-Et | 1.74 | 460 | I |
| IF-564 | Bnzl | Cbm-E | Ph-Et | 1.31 | 447 | I |
| IF-565 | Bnzl | 4-OH-Bnzl | Ph-Et | 1.45 | 482 | I |
| IF-566 | Bnzl | 4-OH-Bnzl | Np-M | 1.53 | 518 | I |
| IF-567 | i-Bu | Ph-Et | 4-OH-Bnzl | 1.33 | 448 | I |
| IF-568 | i-Bu | Np-M | 4-OH-Bnzl | 1.42 | 484 | I |
| IF-569 | i-Bu | Hxy | i-Bu | 1.53 | 378 | I |
| IF-570 | i-Bu | Np-M | i-Pnt | 1.61 | 448 | I |
| IF-571 | i-Bu | Hxy | i-Pnt | 1.61 | 392 | I |
| IF-572 | i-Bu | Hxy | Ph-Et | 1.66 | 426 | I |
| IF-573 | i-Bu | Hxy | Np-M | 1.83 | 462 | I |
| IF-574 | i-Bu | 4-F-Bnzl | Np-M | 1.67 | 486 | I |
| IF-575 | i-Bu | Cbm-E | Ph-Et | 1.19 | 413 | I |
| IF-576 | i-Bu | 4-OH-Bnzl | Ph-Et | 1.31 | 448 | I |
| IF-577 | 4-OH-Bnzl | Ph-Et | Bnzl | 1.44 | 482 | I |
| IF-578 | 4-OH-Bnzl | Np-M | i-Bu | 1.47 | 484 | I |
| IF-579 | 4-OH-Bnzl | Hdr-E | Ph-Et | 1.59 | 436 | I |
| IF-580 | 4-OH-Bnzl | Ph-Et | Np-M | 1.61 | 532 | I |
| IF-581 | Np-M | 4-OH-Bnzl | Ph-Et | 1.64 | 532 | I |
| IF-582 | Np-M | 4-OH-Bnzl | Np-M | 1.80 | 568 | I |
| IF-583 | i-Pnt | Hxy | 4-OH-Bnzl | 1.50 | 442 | I |
| IF-584 | 4-F-Bnzl | i-Pnt | Bnzl | 1.65 | 450 | I |
| IF-585 | 4-F-Bnzl | i-Pnt | i-Bu | 1.57 | 416 | I |
| IF-586 | 4-F-Bnzl | Ph-Et | Bnzl | 1.69 | 484 | I |
| IF-587 | 4-F-Bnzl | Hxy | Bnzl | 1.79 | 464 | I |
| IF-588 | Chm | 4-F-Bnzl | Np-M | 1.79 | 526 | I |
| IF-589 | 4-F-Bnzl | i-Pnt | Np-M | 1.82 | 500 | I |
| IF-590 | 4-OH-Bnzl | Ph-Et | i-Bu | 1.40 | 448 | I |
| IF-591 | i-Pnt | Bnzl | Cbx-E | 1.23 | 414 | I |
| IF-592 | Ph-Et | Bnzl | Cbx-E | 1.31 | 448 | I |
| IF-593 | Np-M | i-Pnt | Cbx-E | 1.51 | 464 | I |
| IF-594 | Cbx-E | i-Bu | Np-M | 1.43 | 450 | I |
| IF-595 | Bnzl | Bnzl | Cbx-E | 1.19 | 434 | I |
| IF-596 | Np-M | i-Pr | Np-M | 1.81 | 504 | I |

TABLE 4-continued

| | | | | | | |
|---|---|---|---|---|---|---|
| IF-597 | i-Pnt | Hdr-E | i-Bu | 1.13 | 352 | I |
| IF-598 | i-Pnt | Hdr-E | 4-OH-Bnzl | 0.61 | 402 | I |
| IF-599 | i-Pnt | Hxy | Bnzl | 1.67 | 426 | I |
| IF-600 | Ph-Et | Hdr-E | i-Bu | 1.23 | 386 | I |
| IF-601 | Ph-Et | Hdr-E | 4-OH-Bnzl | 1.01 | 436 | I |
| IF-602 | Ph-Et | Hxy | Bnzl | 1.75 | 460 | I |
| IF-603 | Np-M | Hdr-E | Bnzl | 1.49 | 456 | I |
| IF-604 | Np-M | Hdr-E | i-Bu | 1.35 | 422 | I |
| IF-605 | Np-M | Hxy | Bnzl | 1.92 | 496 | I |
| IF-606 | Chm | Hdr-E | i-Bu | 1.23 | 378 | I |
| IF-607 | Chm | Hdr-E | 4-OH-Bnzl | 0.99 | 428 | I |
| IF-608 | Chm | 4-F-Bnzl | Bnzl | 1.61 | 476 | I |
| IF-609 | 4-F-Bnzl | Hdr-E | i-Bu | 1.17 | 390 | I |
| IF-610 | Hdr-E | Ph-Et | Np-M | 1.48 | 470 | I |
| IF-611 | i-Pnt | Hdr-E | Np-M | 1.45 | 436 | I |
| IF-612 | Ph-Et | Hdr-E | Np-M | 1.44 | 470 | I |
| IF-613 | Np-M | Hdr-E | i-Pnt | 1.43 | 436 | I |
| IF-614 | Np-M | Hdr-E | Np-M | 1.59 | 506 | I |
| IF-615 | Np-M | Hxy | Ph-Et | 1.96 | 510 | I |
| IF-616 | Np-M | Hxy | Np-M | 2.10 | 546 | I |
| IF-617 | Chm | Hdr-E | i-Pnt | 1.35 | 392 | I |
| IF-618 | Chm | Hdr-E | Ph-Et | 1.39 | 426 | I |
| IF-619 | Chm | Hdr-E | Np-M | 1.46 | 462 | I |
| IF-620 | 4-F--Bnzl | Hdr-E | Np-M | 1.43 | 474 | I |
| IF-621 | Bnzl | Hdr-E | Bnzl | 1.22 | 406 | I |
| IF-622 | Bnzl | Hdr-E | 4-OH-Bnzl | 0.75 | 422 | I |
| IF-623 | Bnzl | Hdr-E | Ph-Et | 1.31 | 420 | I |
| IF-624 | Bnzl | Hdr-E | Np-M | 1.42 | 456 | I |
| IF-625 | i-Bu | Hdr-E | Np-M | 1.33 | 422 | I |
| IF-627 | Hdr-E | Bnzl | i-Pnt | 1.34 | 386 | I |
| IF-628 | Hdr-E | Bnzl | Bnzl | 1.30 | 406 | I |
| IF-629 | Hdr-E | Bnzl | i-Bu | 1.25 | 372 | I |
| IF-630 | Hdr-E | Bnzl | 4-OH-Bnzl | 1.22 | 422 | I |
| IF-631 | Hdr-E | i-Bu | i-Bu | 1.15 | 338 | I |
| IF-632 | i-Pnt | Bnzl | Ph-Et | 1.62 | 446 | I |
| IF-634 | i-Pnt | Bnzl | 4-OH-Bnzl | 1.31 | 448 | I |
| IF-635 | i-Pnt | i-Bu | Ph-Et | 1.54 | 412 | I |
| IF-636 | i-Pnt | i-Bu | i-Bu | 1.42 | 364 | I |
| IF-637 | i-Pnt | i-Bu | 4-OH-Bnzl | 1.30 | 414 | I |
| IF-638 | Ph-Et | Bnzl | i-Pnt | 1.66 | 446 | I |
| IF-639 | Ph-Et | Bnzl | i-Bu | 1.56 | 432 | I |
| IF-640 | Ph-Et | Bnzl | 4-OH-Bnzl | 1.40 | 482 | I |
| IF-641 | Ph-Et | i-Bu | Bnzl | 1.58 | 432 | I |
| IF-642 | Np-M | Bnzl | i-Bu | 1.73 | 468 | I |
| IF-643 | Chm | Bnzl | Ph-Et | 1.66 | 472 | I |
| IF-644 | Chm | Bnzl | i-Bu | 1.59 | 424 | I |
| IF-645 | Chm | Bnzl | 4-OH-Bnzl | 1.34 | 474 | I |
| IF-646 | Chm | i-Bu | Np-M | 1.76 | 474 | I |
| IF-647 | Chm | i-Bu | 4-OH-Bnzl | 1.35 | 440 | I |
| IF-648 | 4-F-Bnzl | Bnzl | Ph-Et | 1.68 | 484 | I |
| IF-649 | 4-F-Bnzl | Bnzl | Bnzl | 1.60 | 470 | I |
| IF-650 | 4-F-Bnzl | Bnzl | i-Bu | 1.57 | 436 | I |
| IF-651 | 4-F-Bnzl | Bnzl | 4-OH-Bnzl | 1.32 | 486 | I |
| IF-652 | 4-F-Bnzl | i-Bu | Ph-Et | 1.59 | 450 | I |
| IF-653 | 4-F-Bnzl | i-Bu | Bnzl | 1.52 | 436 | I |
| IF-654 | 4-F-Bnzl | i-Bu | i-Bu | 1.48 | 402 | I |
| IF-655 | 4-F-Bnzl | i-Bu | 4-OH-Bnzl | 1.29 | 452 | I |
| IF-656 | Hdr-E | i-Pnt | Bnzl | 1.36 | 386 | I |
| IF-657 | Ph-Et | i-Pnt | i-Bu | 1.62 | 412 | I |
| IF-658 | Chm | i-Pnt | Bnzl | 1.65 | 438 | I |
| IF-659 | Chm | i-Pnt | i-Bu | 2.29 | 404 | I |
| IF-660 | Hdr-E | i-Pnt | Np-M | 1.53 | 436 | I |
| IF-661 | Np-M | i-Pnt | Ph-Et | 1.91 | 496 | I |
| IF-662 | Chm | i-Pnt | Ph-Et | 1.72 | 452 | I |
| IF-663 | Chm | i-Pnt | Np-M | 1.83 | 488 | I |
| IF-664 | 4-F-Bnzl | i-Pnt | Ph-Et | 1.68 | 464 | I |
| IF-665 | Bnzl | i-Pnt | Bnzl | 1.61 | 432 | I |
| IF-666 | Bnzl | i-Pnt | 4-OH-Bnzl | 1.36 | 448 | I |
| IF-667 | Bnzl | i-Pnt | Ph-Et | 1.65 | 446 | I |
| IF-670 | Bnzl | i-Bu | Ph-Et | 1.54 | 432 | I |
| IF-671 | i-Bu | i-Pnt | i-Bu | 1.44 | 364 | I |
| IF-672 | i-Bu | i-Pnt | 4-OH-Bnzl | 1.30 | 414 | I |
| IF-673 | i-Bu | i-Pnt | Ph-Et | 1.56 | 412 | I |
| IF-674 | i-Bu | i-Pnt | Np-M | 1.71 | 448 | I |
| IF-675 | i-Bu | Bnzl | i-Pnt | 1.53 | 398 | I |
| IF-678 | i-Bu | Bnzl | 4-OH-Bnzl | 1.23 | 434 | I |
| IF-679 | i-Bu | i-Bu | Ph-Et | 1.48 | 398 | I |
| IF-680 | i-Bu | i-Bu | Np-M | 1.59 | 434 | I |
| IF-683 | i-Bu | i-Bu | 4-OH-Bnzl | 1.23 | 400 | I |
| IF-684 | 4-OH-Bnzl | i-Pnt | Np-M | 1.62 | 498 | I |

TABLE 4-continued

| | | | | | | |
|---|---|---|---|---|---|---|
| IF-686 | i-Pnt | Cbm-E | Ph-Et | 1.28 | 427 | I |
| IF-687 | Np-M | i-Pnt | 4-OH-Bnzl | 1.56 | 498 | I |
| IF-688 | Chm | 4-F-Bnzl | i-Bu | 1.56 | 442 | I |
| IF-689 | 4-F-Bnzl | Hxy | 4-OH-Bnzl | 1.47 | 480 | I |
| IF-690 | Ph-Et | Hdr-E | i-Pnt | 1.30 | 400 | I |
| IF-691 | Bnzl | i-Pnt | i-Bu | 1.54 | 398 | I |
| IF-692 | Bnzl | Hxy | 4-OH-Bnzl | 1.45 | 462 | I |
| IF-693 | Cbx-E | Bnzl | Bnzl | 1.30 | 434 | I |
| IF-694 | Cbx-E | Bnzl | i-Bu | 1.24 | 400 | I |
| IF-695 | Bnzl | i-Pnt | Cbx-E | 1.26 | 414 | I |
| IF-696 | i-Pnt | Cbm-E | Np-M | 1.46 | 463 | I |
| IF-697 | i-Pnt | Cbm-E | Bnzl | 1.28 | 413 | I |
| IF-698 | Ph-Et | Cbm-E | Bnzl | 1.36 | 447 | I |
| IF-699 | Ph-Et | Cbm-E | i-Bu | 1.24 | 413 | I |
| IF-700 | Chm | Cbm-E | Ph-Et | 1.43 | 453 | I |
| IF-701 | Chm | Cbm-E | Bnzl | 1.36 | 439 | I |
| IF-702 | 4-F-Bnzl | Cbm-E | Bnzl | 1.27 | 451 | I |
| IF-703 | 4-F-Bnzl | Cbm-E | i-Bu | 1.23 | 417 | I |
| IF-704 | Hdr-E | Ph-Et | i-Bu | 1.31 | 386 | I |
| IF-705 | i-Pnt | Np-M | i-Bu | 1.69 | 448 | I |
| IF-706 | i-Pnt | Np-M | 4-OH-Bnzl | 1.50 | 498 | I |
| IF-707 | Ph-Et | i-Pnt | 4-OH-Bnzl | 1.47 | 462 | I |
| IF-708 | Np-M | Ph-Et | 4-OH-Bnzl | 1.57 | 532 | I |
| IF-709 | Chm | i-Pnt | 4-OH-Bnzl | 1.40 | 454 | I |
| IF-710 | Chm | Ph-Et | Bnzl | 1.72 | 472 | I |
| IF-711 | Chm | Ph-Et | i-Bu | 1.69 | 438 | I |
| IF-712 | Chm | Np-M | 4-OH-Bnzl | 1.58 | 524 | I |
| IF-713 | 4-F-Bnzl | i-Pnt | 4-OH-Bnzl | 1.38 | 466 | I |
| IF-714 | 4-F-Bnzl | Ph-Et | i-Bu | 1.62 | 450 | I |
| IF-715 | 4-F-Bnzl | Ph-Et | 4-OH-Bnzl | 1.42 | 500 | I |
| IF-716 | 4-F-Bnzl | Np-M | i-Bu | 1.71 | 486 | I |
| IF-717 | Chm | Ph-Et | i-Pnt | 1.76 | 452 | I |
| IF-718 | Chm | Ph-Et | Np-M | 1.94 | 522 | I |
| IF-719 | Chm | Np-M | i-Pnt | 1.81 | 488 | I |
| IF-720 | 4-F-Bnzl | Ph-Et | i-Pnt | 1.68 | 464 | I |
| IF-721 | Bnzl | Ph-Et | i-Bu | 1.58 | 432 | I |
| IF-722 | Bnzl | Ph-Et | 4-OH-Bnzl | 1.41 | 482 | I |
| IF-723 | Bnzl | Ph-Et | i-Pnt | 1.68 | 446 | I |
| IF-724 | Bnzl | Cbm-E | Bnzl | 1.24 | 433 | I |
| IF-725 | i-Bu | Ph-Et | i-Bu | 1.51 | 398 | I |
| IF-726 | i-Bu | Np-M | i-Bu | 1.62 | 434 | I |
| IF-727 | i-Bu | Ph-Et | i-Pnt | 1.62 | 412 | I |
| IF-728 | i-Bu | Cbm-E | Np-M | 1.37 | 449 | I |
| IF-730 | 4-OH-Bnzl | Np-M | i-Pnt | 1.62 | | I |
| IF-731 | 4-OH-Bnzl | Cbm-E | Np-M | 1.29 | 499 | I |
| IF-732 | i-Pnt | Bnzl | Np-M | 1.72 | 482 | I |
| IF-733 | i-Pnt | Bnzl | i-Bu | 1.49 | 398 | I |
| IF-734 | i-Pnt | i-Bu | Np-M | 1.66 | 448 | I |
| IF-735 | i-Pnt | i-Bu | Bnzl | 1.50 | 398 | I |
| IF-736 | Ph-Et | Bnzl | Np-M | 1.76 | 516 | I |
| IF-737 | Ph-Et | Bnzl | Bnzl | 1.61 | 466 | I |
| IF-738 | Ph-Et | i-Bu | i-Bu | 1.49 | 398 | I |
| IF-739 | Np-M | i-Bu | i-Bu | 1.66 | 434 | I |
| IF-740 | Chm | Bnzl | i-Pnt | 1.69 | 438 | I |
| IF-742 | Chm | i-Bu | i-Bu | 1.49 | 390 | I |
| IF-743 | 4-F-Bnzl | Bnzl | i-Pnt | 1.64 | 450 | I |
| IF-744 | Ph-Et | i-Pnt | Bnzl | 1.65 | 446 | I |
| IF-746 | Bnzl | Bnzl | Ph-Et | 1.58 | 466 | I |
| IF-747 | Bnzl | Bnzl | Np-M | 1.72 | 502 | I |
| IF-751 | Bnzl | i-Bu | 4-OH-Bnzl | 1.26 | 434 | I |
| IF-752 | i-Bu | i-Pnt | Bnzl | 1.50 | 398 | I |
| IF-753 | i-Bu | Bnzl | Np-M | 1.64 | 468 | I |
| IF-755 | 4-OH-Bnzl | Bnzl | i-Pnt | 1.42 | 448 | I |
| IF-756 | Ph-Et | Cbm-E | Np-M | 1.48 | 497 | I |
| IF-757 | Ph-Et | i-Pr | Np-M | 1.65 | 468 | I |
| IF-758 | Hdr-E | Np-M | Bnzl | 1.46 | 456 | I |
| IF-759 | i-Pnt | Np-M | Bnzl | 1.72 | 482 | I |
| IF-760 | Ph-Et | Np-M | i-Bu | 1.71 | 482 | I |
| IF-761 | Ph-Et | Np-M | 4-OH-Bnzl | 1.57 | 532 | I |
| IF-762 | Np-M | i-Pnt | Bnzl | 1.86 | 482 | I |
| IF-763 | Np-M | Np-M | i-Bu | 1.95 | 518 | I |
| IF-764 | Chm | Np-M | Bnzl | 1.77 | 508 | I |
| IF-765 | 4-F--Bnzl | Np-M | Bnzl | 1.76 | 520 | I |
| IF-766 | Ph-Et | Np-M | i-Pnt | 1.74 | 497 | I |
| IF-767 | Np-M | Np-M | i-Pnt | 1.96 | 532 | I |
| IF-768 | Np-M | 4-F-Bnzl | Np-M | 2.03 | 570 | I |
| IF-769 | Chm | Np-M | Ph-Et | 1.85 | 522 | I |
| IF-770 | Chm | Np-M | Np-M | 1.95 | 558 | I |
| IF-771 | 4-F-Bnzl | Np-M | Ph-Et | 1.80 | 534 | I |
| IF-772 | 4-F--Bnzl | Np-M | Np-M | 1.95 | 570 | I |

TABLE 4-continued

| | | | | | | |
|---|---|---|---|---|---|---|
| IF-773 | Bnzl | Np-M | i-Bu | 1.67 | 468 | I |
| IF-774 | Bnzl | Np-M | i-Pnt | 1.73 | 482 | I |
| IF-775 | Bnzl | 4-F-Bnzl | Np-M | 1.75 | 520 | I |
| IF-776 | Bnzl | Cbm-E | Np-M | 1.42 | 483 | I |
| IF-777 | i-Bu | Np-M | Ph-Et | 1.71 | 482 | I |
| IF-778 | i-Bu | Np-M | Np-M | 1.81 | 518 | I |
| IF-779 | 4-OH-Bnzl | Np-M | Np-M | 1.71 | 568 | I |
| IF-780 | Hdr-E | i-Bu | Ph-Et | 1.34 | 386 | I |
| IF-781 | Hdr-E | i-Bu | 4-OH-Bnzl | 1.12 | 388 | I |
| IF-782 | Ph-Et | i-Bu | 4-OH-Bnzl | 1.44 | | I |
| IF-783 | Ph-Et | Cbm-E | 4-OH-Bnzl | 1.03 | 463 | I |
| IF-784 | Np-M | Bnzl | i-Pnt | 1.84 | 482 | I |
| IF-785 | Np-M | Bnzl | Ph-Et | 1.88 | 516 | I |
| IF-786 | Np-M | Bnzl | Np-M | 2.03 | 552 | I |
| IF-787 | Np-M | i-Bu | 4-OH-Bnzl | 1.40 | 484 | I |
| IF-788 | Np-M | Cbm-E | Np-M | 1.65 | 533 | I |
| IF-789 | Np-M | i-Pr | Ph-Et | 1.69 | 468 | I |
| IF-790 | Np-M | i-Pr | Bnzl | 1.67 | 454 | I |
| IF-791 | Chm | Bnzl | Np-M | 1.80 | 508 | I |
| IF-792 | Hdr-E | i-Pnt | i-Bu | 1.30 | 352 | I |
| IF-793 | Ph-Et | Np-M | Bnzl | 1.80 | 516 | I |
| IF-794 | Np-M | Np-M | Bnzl | 2.05 | 552 | I |
| IF-795 | Np-M | 4-F-Bnzl | Bnzl | 1.89 | 520 | I |
| IF-796 | Hdr-E | i-Pnt | Ph-Et | 1.44 | 400 | I |
| IF-797 | Hdr-E | Np-M | i-Pnt | 1.50 | 436 | I |
| IF-798 | Hdr-E | Np-M | Ph-Et | 1.50 | 470 | I |
| IF-799 | i-Pnt | Np-M | Ph-Et | 1.78 | 496 | I |
| IF-800 | i-Pnt | 4-F-Bnzl | Ph-Et | 1.63 | 464 | I |
| IF-801 | i-Pnt | 4-F-Bnzl | Np-M | 1.71 | 500 | I |
| IF-802 | Ph-Et | i-Pnt | Np-M | 1.77 | 496 | I |
| IF-803 | Ph-Et | Np-M | Np-M | 1.93 | 566 | I |
| IF-804 | Ph-Et | 4-F-Bnzl | Np-M | 1.84 | 534 | I |
| IF-805 | Bnzl | Np-M | Bnzl | 1.72 | 502 | I |
| IF-806 | Bnzl | Np-M | 4-OH-Bnzl | 1.45 | 518 | I |
| IF-807 | Bnzl | 4-F-Bnzl | i-Bu | 1.55 | 436 | I |
| IF-808 | Bnzl | 4-F-Bnzl | 4-OH-Bnzl | 1.39 | 486 | I |
| IF-809 | Bnzl | i-Pnt | Np-M | 1.79 | 482 | I |
| IF-810 | Bnzl | Np-M | Ph-Et | 1.81 | 516 | I |
| IF-811 | Bnzl | 4-F-Bnzl | i-Pnt | 1.60 | 450 | I |
| IF-812 | Bnzl | i-Pr | Np-M | 1.54 | 454 | I |
| IF-814 | i-Bu | Hxy | Bnzl | 1.62 | 412 | I |
| IF-815 | i-Bu | 4-F-Bnzl | Bnzl | 1.52 | 436 | I |
| IF-816 | 4-OH-Bnzl | i-Pnt | Ph-Et | 1.51 | 462 | I |
| IF-817 | 4-OH-Bnzl | Bnzl | Ph-Et | 1.43 | 482 | I |
| IF-818 | 4-OH-Bnzl | Bnzl | i-Bu | 1.32 | 434 | I |
| IF-819 | 4-OH-Bnzl | i-Bu | i-Bu | 1.25 | 400 | I |
| IF-820 | i-Pnt | Cbx-E | Bnzl | 0.70 | 414 | C |
| IF-821 | Ph-Et | Cbx-E | i-Pnt | 0.73 | 428 | C |
| IF-822 | Chm | Cbx-E | Bnzl | 0.72 | 440 | C |
| IF-823 | 4-OH-Bnzl | Cbx-E | i-Pnt | 0.61 | 430 | C |
| IF-824 | 4-OH-Bnzl | Cbx-E | Ph-Et | 0.65 | 464 | C |
| IF-825 | Bnzl | Cbx-E | i-Bu | 0.67 | 400 | C |
| IF-826 | Bnzl | Cbx-E | i-Pnt | 0.70 | 414 | C |
| IF-827 | Bnzl | Cbx-E | Ph-Et | 0.71 | 448 | C |
| IF-828 | i-Bu | Cbx-E | Ph-Et | 0.67 | 414 | C |
| IF-829 | i-Bu | Cbx-E | 4-OH-Bnzl | 0.70 | 416 | C |
| IF-830 | i-Pnt | Cbx-E | Ph-Et | 0.72 | 428 | C |
| IF-831 | i-Pnt | Cbx-E | 4-OH-Bnzl | 0.59 | 430 | C |
| IF-832 | Chm | Cbx-E | Ph-Et | 0.74 | 454 | C |
| IF-833 | Chm | Cbx-E | 4-OH-Bnzl | 0.62 | 456 | C |
| IF-835 | Ph-Et | Cbx-E | i-Bu | 0.69 | 414 | C |
| IF-836 | 4-OH-Bnzl | Cbx-E | i-Bu | 0.58 | 416 | C |

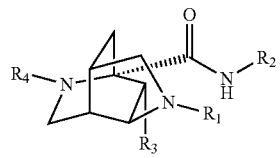

| Compound number | $R_1$ | $R_2$ | $R_3$ | $R_4$ | Retention RT (min) | Mass $(M + H)^+$ | Measurement condition |
|---|---|---|---|---|---|---|---|
| IF-837 | Bnzl | Np-M | i-Bu | H | 1.127 | 468 | B |
| IF-838 | Bnzl | 4-(trifluoromethyl)benzyl | i-Bu | H | 1.14 | 486 | B |

TABLE 4-continued

| | | | | | | | |
|---|---|---|---|---|---|---|---|
| IF-839 | 4-Cl-Bnzl | Bnzl | i-Bu | H | 1.13 | 452 | B |
| IF-840 | 3-Cl-Bnzl | Bnzl | i-Bu | H | 1.14 | 452 | B |
| IF-841 | 4-methoxybenzyl | Bnzl | i-Bu | H | 1.072 | 448 | B |
| IF-842 | 4-methylbenzyl | Bnzl | i-Bu | H | 1.097 | 432 | B |
| IF-843 | i-Pnt | i-Bu | Bnzl | H | 1.278 | 398 | B |
| IF-844 | i-Bu | i-Bu | 4-Cl-Bnzl | H | 1.275 | 418 | B |
| IF-845 | i-Bu | i-Pnt | Bnzl | H | 1.082 | 398 | B |
| IF-846 | i-Bu | 4-Cl-Bnzl | i-Bu | H | 1.085 | 418 | B |
| IF-847 | 4-hydroxybenzyl | Bnzl | i-Bu | H | 1.187 | 434 | B |
| IF-848 | 4-(dimethylamino)benzyl | Bnzl | i-Bu | H | 1.097 | 461 | B |
| IF-849 | 4-(tert-butyl)benzyl | Bnzl | i-Bu | H | 1.175 | 474 | B |
| IF-850 | i-Bu | Bnzl | i-Pnt | H | 1.075 | 398 | B |
| IF-851 | i-Pnt | Bnzl | i-Bu | H | 1.29 | 398 | B |
| IF-852 | 4-(trifluoromethyl)benzyl | Bnzl | i-Bu | H | 1.18 | 502 | B |
| IF-853 | 4-ethoxybenzyl | Bnzl | i-Bu | H | 1.112 | 462 | B |
| IF-854 | Bnzl | naphthalen-2-ylmethyl | i-Bu | H | 1.142 | 468 | B |
| IF-855 | 4-methylbenzyl | Bnzl | i-Bu | ethyl | 1.172 | 460 | B |
| IF-856 | 4-methylbenzyl | Bnzl | i-Bu | i-Bu | 1.303 | 488 | B |
| IF-857 | 4-methylbenzyl | Bnzl | i-Bu | acetyl | 1.187 | 474 | B |
| IF-858 | 4-methylbenzyl | Bnzl | i-Bu | 3-methyl-butanoyl | 1.247 | 516 | B |
| IF-859 | 4-methylbenzyl | Bnzl | i-Bu | 2-phenyl-acetyl | 1.253 | 550 | B |
| IF-860 | 4-methylbenzyl | Bnzl | i-Bu | methoxy-carbonyl | 1.23 | 490 | B |
| IF-861 | 4-methylbenzyl | Bnzl | i-Bu | 2-methyl-propoxy-carbonyl | 1.292 | 532 | B |
| IF-862 | 4-methylbenzyl | Bnzl | i-Bu | benzyl-oxy-carbonyl | 1.297 | 566 | B |
| IF-863 | 4-methylbenzyl | Bnzl | i-Bu | amino-carbonyl | 1.157 | 475 | B |
| IF-864 | 4-methylbenzyl | Bnzl | i-Bu | N-benzyl-amino-carbonyl | 1.252 | 565 | B |
| IF-865 | Bnzl | pyridin-4-ylmethyl | i-Bu | H | 1.11 | 419 | B |
| IF-866 | 4-(dimethylamino)benzyl | 3-hydroxybenzyl | i-Bu | H | 1.223 | 477 | B |
| IF-867 | 4-(dimethylamino)benzyl | 4-hydroxybenzyl | i-Bu | H | 1.208 | 477 | B |
| IF-868 | 2-hydroxyethyl | 4-fluorobenzyl | Np-M | H | 0.76 | 474 | C |
| IF-869 | 4-methoxybenzyl | Bnzl | Bnzl | H | 0.83 | 482 | C |
| IF-870 | 4-methoxybenzyl | Bnzl | Bnzl | tert-butoxy-carbonyl | 1.01 | 582 | C |
| IF-871 | ethyl | Bnzl | Bnzl | tert-butoxy-carbonyl | 0.94 | 490 | C |
| IF-872 | phenethyl | Bnzl | 2-(tert-butyldimethyl-silyloxy)ethyl | H | 0.95 | 534 | C |
| IF-873 | cyclopentyl-methyl | 4-(tert-butoxy)benzyl | 2-(tert-butoxycarbonyl)ethyl | H | 0.93 | 554 | C |
| IF-874 | 4-nitrobenzyl | 4-(tert-butoxy)benzyl | 2-(tert-butoxycarbonyl)ethyl | H | 0.97 | 607 | C |
| IF-875 | phenethyl | Bnzl | 2-hydroxyethyl | H | 0.72 | 420 | C |
| IF-876 | cyclopentyl-methyl | 4-(tert-butoxy)benzyl | 2-(tert-butoxycarbonyl)ethyl | methoxy-carbonyl | 1.03 | 612 | C |
| IF-877 | cyclopentyl-methyl | 4-hydroxybenzyl | 2-carboxyethyl | methoxy-carbonyl | 0.71 | 500 | C |
| IF-878 | cyclopentyl-methyl | 4-hydroxybenzyl | 2-carboxyethyl | H | 0.64 | 442 | C |
| IF-879 | phenethyl | Bnzl | 2-hydroxyethyl | methoxy-carbonyl | 0.8 | 478 | C |
| IF-880 | 4-aminobenzyl | 4-(tert-butoxy)benzyl | 2-(tert-butoxycarbonyl)ethyl | formyl | 0.89 | 605 | C |

TABLE 4-continued

| | | | | | | | |
|---|---|---|---|---|---|---|---|
| IF-881 | 4-(cyclopentyl-carbonylamino)benzyl | 4-(tert-butoxy)benzyl | 2-(tert-butoxycarbonyl)ethyl | formyl | 1 | 701 | C |
| IF-882 | 4-(cyclopentyl-methylamino)benzyl | 4-(tert-butoxy)benzyl | 2-(tert-butoxycarbonyl)ethyl | formyl | 1.07 | 687 | C |
| IF-883 | 4-(cyclopentyl-methylamino)benzyl | 4-hydroxybenzyl | 2-methoxy-carbonylethyl | H | 0.81 | 561 | C |
| IF-884 | 4-(cyclopentyl-methylamino)benzyl | 4-hydroxybenzyl | 2-carboxyethyl | H | 0.75 | 547 | C |

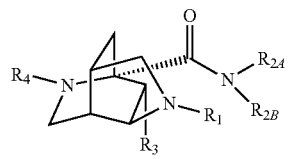

| Compound number | $R_1$ | $R_{2A}$ | $R_{2B}$ | $R_3$ | $R_4$ | Retention RT (min) | Mass $(M + H)^+$ | Measurement condition |
|---|---|---|---|---|---|---|---|---|
| IF-885 | i-Bu | H | 4-Cl-Bnzl | Ph-Et | H | 1.99 | 466 | B1 |
| IF-886 | i-Bu | H | 3-Cl-Bnzl | Ph-Et | H | 1.98 | 466 | B1 |
| IF-887 | i-Bu | H | 4-MeO-Bnzl | Ph-Et | H | 1.75 | 462 | B1 |
| IF-888 | i-Bu | H | 4-Me-Bnzl | Ph-Et | H | 1.92 | 446 | B1 |
| IF-889 | i-Bu | H | 2-Npm | Ph-Et | H | 2.07 | 482 | B1 |
| IF-890 | i-Bu | H | Bnzl | Ph-Pr | H | 1.89 | 446 | B |
| IF-891 | i-Bu | H | 3-Cl-Bnzl | Ph-Pr | H | 1.16 | 480 | B |
| IF-892 | i-Bu | H | 3-F-Bnzl | Ph-Pr | H | 1.14 | 464 | B |
| IF-893 | i-Bu | H | 3-Me-Bnzl | Ph-Pr | H | 1.13 | 460 | B |
| IF-894 | i-Bu | H | 3-MeO-Bnzl | Ph-Pr | H | 1.10 | 476 | B |
| IF-895 | i-Bu | H | 3-Cl-Bnzl | Ph-Bu | H | 1.16 | 494 | B |
| IF-896 | i-Bu | H | 3-F-Bnzl | Ph-Bu | H | 1.12 | 478 | B |
| IF-897 | i-Bu | H | 3-Me-Bnzl | Ph-Bu | H | 1.16 | 474 | B |
| IF-898 | i-Bu | H | 3-MeO-Bnzl | Ph-Bu | H | 1.12 | 491 | B |
| IF-899 | i-Bu | H | Bnzl | Ph-Bu | H | 1.13 | 460 | B |
| IF-900 | i-Pnt | H | 3-F-Bnzl | Ph-Pr | H | 1.14 | 478 | B |
| IF-901 | 1-Npm | H | pentyl | Ph-Et | H | 0.92 | 496 | C |
| IF-902 | 1-Npm | H | cyclohexyl | Ph-Et | H | 0.92 | 508 | C |
| IF-903 | 1-Npm | H | cyclopentyl | Ph-Et | H | 0.90 | 494 | C |
| IF-904 | 1-Npm | H | Hxy | 4-methylphenethyl | H | 0.99 | 524 | C |
| IF-905 | 1-Npm | H | Hxy | 2-(naphthalen-2-yl)ethyl | H | 1.02 | 560 | C |
| IF-906 | 1-Npm | H | heptyl | Ph-Et | H | 1.00 | 524 | C |
| IF-907 | 1-Npm | H | Hxy | 4-isopropyl-phenethyl | H | 1.05 | 552 | C |
| IF-908 | 1-Npm | H | Hxy | cyclohexylethyl | H | 1.03 | 516 | C |
| IF-909 | i-Bu | H | Ph-Et | Ph-Et | H | 1.87 | 444 | B1 |
| IF-910 | Chm | H | tBuO-E | 1-Npm | H | 0.87 | 518 | C |
| IF-911 | tBuO-E | H | Ph-Et | 1-Npm | H | 0.88 | 526 | C |
| IF-912 | Ph-Et | H | Hxy | 1-Npm | H | 0.95 | 510 | C |
| IF-913 | tBuO-E | H | 4-fluoro-phenethyl | 1-Npm | H | 0.89 | 544.4 | C |
| IF-914 | Hdr-E | H | 4-fluoro-phenethyl | 1-Npm | H | 0.77 | 488.3 | C |
| IF-915 | 3-tert-butoxy-propyl | H | 4-F-Bnzl | 1-Npm | H | 0.89 | 544.4 | C |
| IF-916 | tBuO-E | H | 4-Cl-Bnzl | 1-Npm | H | 0.9 | 546.3 | C |
| IF-917 | 3-hydroxy-propyl | H | 4-F-Bnzl | 1-Npm | H | 0.76 | 488.3 | C |
| IF-918 | Hdr-E | H | 4-Cl-Bnzl | 1-Npm | H | 0.78 | 490.3 | C |
| IF-919 | 1-Npm | H | Hxy | 3-methylphenethyl | H | 0.99 | 524.4 | C |
| IF-920 | 1-Npm | H | β-hydroxy-phenethyl | Ph-Et | H | 0.84 | 546.4 | C |
| IF-921 | 1-Npm | H | α-hydroxy-methyl-phenethyl | Ph-Et | H | 0.88 | 560.4 | C |

TABLE 4-continued

| | | | | | | | | |
|---|---|---|---|---|---|---|---|---|
| IF-922 | 1-Npm | H | α-hydroxy-methyl-phenethyl | Ph-Et | H | 0.85 | 560.4 | C |
| IF-923 | 4-Nt-Bnzl | H | Bnzl | tBOC-E | H | 0.86 | 535 | C |
| IF-924 | 4-Nt-Bnzl | H | Bnzl | tBOC-E | ethoxy-carbonyl | 0.94 | 607 | C |
| IF-925 | 1-Npm | H | 4-F-Bnzl | 2-OH-Et | H | 0.73 | 474.3 | C |
| IF-926 | 4-tBuO-Bnzl | H | Bnzl | i-Bu | H | 0.91 | 490.4 | C |
| IF-927 | 4-tBuO-Bnzl | H | i-Bu | Bnzl | H | 0.88 | 490.4 | C |
| IF-928 | 2-OtBu-Et | H | Bnzl | 1-Npm | H | 0.85 | 512.4 | C |
| IF-929 | 2-OH-Et | H | Bnzl | 1-Npm | H | 0.74 | 456.3 | C |
| IF-930 | 4-OH-Bnzl | H | i-Bu | Bnzl | H | 0.73 | 434.3 | C |
| IF-931 | 1-Npm | H | 4-F-Bnzl | 2-OTBS-Et | H | 1.01 | 588.4 | C |

[1] $(M - H)^-$

Example 2: Assay Method for Anti-Rabies Virus Activity

Each tested compound prepared as a 10 mM with DMSO was first diluted to 100 μM or 40 μM with 10% fetal bovine serum-supplemented Eagle's minimal essential medium (hereinafter, medium), and further diluted with the medium to the final concentration of interest. Fifty microlitter of the diluted medium was added dropwise to each well of a 96-well plate. Furthermore, 50 μL of medium comprising $4 \times 10^2$ infectious units of the recombinant rabies virus 1088 strain expressing Gaussia Luciferase (GLuc) (1088/GLuc) and $4 \times 10^4$ Neuro-2a cells were added to each well. The plate was shaken for 30 seconds with a multiple microplate mixer NS-4P (AS ONE Corporation) and then cultured for 3 days at 37° C. in the presence of 5% $CO_2$. After incubation, 25 μL of coelenterazine, which is a substrate of the luciferase, was added dropwise to each well of the plate, and the plate was immediately loaded into a luminescent plate reader LuMate (Awareness Technology) and shaken for 10 seconds. The relative light unit (RLU) was then measured.

The synthesized compounds were tested. It was found that the compounds described in Table 5 exhibited the higher anti-rabies virus activity compared to T-705 (generic name: Favipiravir) ($IC_{50}$=30 μM), which is examined as an anti-rabies antiviral drug.

The compounds are classified as A if $IC_{50}$ is 5 μM or less, B if greater than 5 μM and less than or equal to 10 μM, and C if greater than 10 μM and less than 30 μM. The 'na' indicates not applicable.

TABLE 5

| Compound number | Name of compound | $IC_{50}$ (μM) |
|---|---|---|
| IB-3 | (3S*,3aS*,6R*,7R*,7aS*)-7-benzyl-N,1-diisobutyloctahydro-3aH-3,6-methanopyrrolo[3,2-b]pyridine-3a-carboxamide | 19.6 |
| IB-4 | (3S*,3aS*,6R*,7R*,7aS*)-1-benzyl-N,7-diisobutyloctahydro-3aH-3,6-methanopyrrolo[3,2-b]pyridine-3a-carboxamide | 19.2 |
| IB-5 | (3S*,3aS*,6R*,7R*,7aS*)-N-benzyl-1,7-diisobutyloctahydro-3aH-3,6-methanopyrrolo[3,2-b]pyridine-3a-carboxamide | 18.2 |
| IB-9 | (3S*,3aS*,6R*,7R*,7aS*)-N,7-dibenzyl-1-isopentyloctahydro-3aH-3,6-methanopyrrolo[3,2-b]pyridine-3a-carboxamide | 17.0 |
| IB-12 | (3S*,3aS*,6R*,7R*,7aS*)-1-benzyl-7-isobutyl-N-phenethyloctahydro-3aH-3,6-methanopyrrolo[3,2-b]pyridine-3a-carboxamide | 15.5 |
| IB-13 | (3S*,3aS*,6R*,7R*,7aS*)-N-benzyl-1-isobutyl-7-(3-methylbenzyl)octahydro-3aH-3,6-methanopyrrolo[3,2-b]pyridine-3a-carboxamide | 14.3 |
| IB-15 | (3S*,3aS*,6R*,7R*,7aS*)-7-benzyl-1-isobutyl-N-(3-methylbenzyl)octahydro-3aH-3,6-methanopyrrolo[3,2-b]pyridine-3a-carboxamide | 15.9 |
| IF-1 | (3S*,3aS*,6S*,7R*,7aS*)-N,7-dibenzyl-1-isobutyloctahydro-6H-3,6-methanopyrrolo[3,2-c]pyridine-6-carboxamide | 12.6 |
| IF-6 | (3S*,3aS*,6S*,7R*,7aS*)-1,7-dibenzyl-N-isobutyloctahydro-6H-3,6-methanopyrrolo[3,2-c]pyridine-6-carboxamide | 16.3 |
| IF-7 | (3S*,3aS*,6S*,7R*,7aS*)-N,1-dibenzyl-7-isobutyloctahydro-6H-3,6-methanopyrrolo[3,2-c]pyridine-6-carboxamide | 8.5 |
| IF-9 | (3S*,3aS*,6S*,7R*,7aS*)-N,7-dibenzyl-1-isopentyloctahydro-6H-3,6-methanopyrrolo[3,2-c]pyridine-6-carboxamide | 15.6 |
| IF-11 | (3S*,3aS*,6S*,7R*,7aS*)-N-benzyl-1-isobutyl-7-phenethyloctahydro-6H-3,6-methanopyrrolo[3,2-c]pyridine-6-carboxamide | 17.5 |

TABLE 5-continued

| | | |
|---|---|---|
| IF-13 | (3S*,3aS*,6S*,7R*,7aS*)-N-benzyl-1-isobutyl-7-(3-methylbenzyl)octahydro-6H-3,6-methanopyrrolo[3,2-c]pyridine-6-carboxamide | 13.1 |
| IF-14 | (3S*,3aS*,6S*,7R*,7aS*)-N-benzyl-1-isobutyl-7-(4-methylbenzyl)octahydro-6H-3,6-methanopyrrolo[3,2-c]pyridine-6-carboxamide | 14.1 |
| IF-15 | (3S*,3aS*,6S*,7R*,7aS*)-7-benzyl-1-isobutyl-N-(3-methylbenzyl)octahydro-6H-3,6-methanopyrrolo[3,2-c]pyridine-6-carboxamide | 17.1 |
| IF-20 | (3S*,3aS*,6S*,7R*,7aS*)-1-benzyl-N-(3,4-dichlorobenzyl)-7-isobutyloctahydro-6H-3,6-methanopyrrolo[3,2-c]pyridine-6-carboxamide | 11.6 |
| IF-69 | (3S*,3aS*,6S*,7R*,7aS*)-N,7-dibenzyl-4-ethyl-1-isobutyloctahydro-6H-3,6-methanopyrrolo[3,2-c]pyridine-6-carboxamide | 16.5 |
| IIB-4 | (3S*,3aS*,6R*,7R*,7aS*)-1-benzyl-N,7-diisobutyl-1,2,3,6,7,7a-hexahydro-3aH-3,6-methanopyrrolo[3,2-b]pyridine-3a-carboxamide | 8.9 |
| IIF-16 | (3S*,3aR*,6S*,7R*,7aR*)-7-benzyl-1-isobutyl-N-(4-methylbenzyl)-1,2,3,3a,7,7a-hexahydro-6H-3,6-methanopyrrolo[3,2-c]pyridine-6-carboxamide | 28.7 |

Table. Anti-rabies activity of compound of formula IB
(A: $IC_{50} \leq 5$ μM, B: 5 μM < $IC_{50} \leq 10$ μM, C: 10 μM < $IC_{50} < 30$ μM)

| Compound number | R₁ | R₂ | R₃ | R₄ | Anti-rabies activity |
|---|---|---|---|---|---|
| IB-3 | i-Bu | i-Bu | Bnzl | H | C |
| IB-4 | Bnzl | i-Bu | i-Bu | H | C |
| IB-5 | i-Bu | Bnzl | i-Bu | H | C |
| IB-9 | i-Pnt | Bnzl | Bnzl | H | C |
| IB-12 | i-Bu | phenethyl | Bnzl | H | C |
| IB-13 | i-Bu | Bnzl | 3-methylbenzyl | H | C |
| IB-15 | i-Bu | 3-methylbenzyl | Bnzl | H | C |
| IB-42 | Np-M | Bnzl | Bnzl | H | C |
| IB-81 | carbamoylmethyl | 1-naphthylmethyl | i-Bu | H | C |
| IB-82 | carbamoylmethyl | 1-naphthylmethyl | Bnzl | H | C |
| IB-83 | carbamoylmethyl | 1-naphthylmethyl | 4-hydroxybenzyl | H | C |
| IB-84 | carbamoylmethyl | 1-naphthylmethyl | i-Pnt | H | C |
| IB-86 | carbamoylmethyl | 2-phenylethyl | i-Bu | H | C |
| IB-87 | carbamoylmethyl | 2-phenylethyl | Bnzl | H | A |
| IB-89 | carbamoylmethyl | 2-phenylethyl | i-Pnt | H | A |
| IB-90 | carbamoylmethyl | 1-naphthylmethyl | 1-naphthylmethyl | H | A |
| IB-92 | carbamoylmethyl | 4-fluorobenzyl | Bnzl | H | C |
| IB-95 | carbamoylmethyl | 4-fluorobenzyl | 2-phenylethyl | H | A |
| IB-96 | carbamoylmethyl | 4-fluorobenzyl | 1-naphthylmethyl | H | C |
| IB-97 | carbamoylmethyl | 2-phenylethyl | 1-naphthylmethyl | H | A |
| IB-102 | carbamoylmethyl | i-Pnt | 2-phenylethyl | H | A |
| IB-103 | carbamoylmethyl | i-Pnt | 1-naphthylmethyl | H | C |
| IB-105 | carbamoylmethyl | hexyl | Bnzl | H | C |
| IB-108 | carbamoylmethyl | hexyl | i-Pnt | H | C |
| IB-109 | carbamoylmethyl | hexyl | 2-phenylethyl | H | C |
| IB-110 | carbamoylmethyl | hexyl | 1-naphthylmethyl | H | A |
| IB-130 | carbamoylmethyl | Bnzl | 2-phenylethyl | H | C |
| IB-164 | 3-guanidinopropyl | 1-naphthylmethyl | i-Bu | H | A |
| IB-174 | 3-guanidinopropyl | hexyl | 2-phenylethyl | H | C |

TABLE 5-continued

| | | | | | |
|---|---|---|---|---|---|
| IB-176 | 3-guanidinopropyl | isopropyl | i-Bu | H | C |
| IB-179 | 3-guanidinopropyl | isopropyl | 2-phenylethyl | H | C |
| IB-182 | 3-guanidinopropyl | 4-fluorobenzyl | Bnzl | H | C |
| IB-187 | i-Bu | i-Bu | 3-guanidinopropyl | H | C |
| IB-192 | i-Bu | i-Pnt | 3-guanidinopropyl | H | A |
| IB-198 | Bnzl | i-Bu | 3-guanidinopropyl | H | C |
| IB-203 | 4-hydroxybenzyl | i-Bu | 3-guanidinopropyl | H | C |
| IB-207 | 4-hydroxybenzyl | 4-fluorobenzyl | 3-guanidinopropyl | H | C |
| IB-247 | Bnzl | phenethyl | 3-guanidinopropyl | H | C |
| IB-249 | Bnzl | hexyl | 3-guanidinopropyl | H | C |
| IB-250 | Bnzl | 4-fluorobenzyl | 3-guanidinopropyl | H | C |
| IB-256 | phenethyl | hexyl | 3-guanidinopropyl | H | C |
| IB-260 | 4-fluorobenzyl | Bnzl | 3-guanidinopropyl | H | C |
| IB-262 | 4-fluorobenzyl | phenethyl | 3-guanidinopropyl | H | C |
| IB-274 | Bnzl | 3-amino-3-oxopropyl | i-Pnt | H | C |
| IB-276 | Bnzl | 3-guanidinopropyl | Bnzl | H | C |
| IB-279 | Bnzl | 3-guanidinopropyl | phenethyl | H | C |
| IB-280 | Bnzl | 3-guanidinopropyl | Np-M | H | C |
| IB-300 | 3-guanidinopropyl | Bnzl | Np-M | H | C |
| IB-327 | 3-guanidinopropyl | phenethyl | Np-M | H | C |
| IB-342 | phenethyl | 3-amino-3-oxopropyl | i-Pnt | H | C |
| IB-344 | phenethyl | 3-guanidinopropyl | Bnzl | H | C |
| IB-346 | phenethyl | 3-guanidinopropyl | i-Pnt | H | C |
| IB-347 | phenethyl | 3-guanidinopropyl | Np-M | H | C |
| IB-349 | Np-M | 3-amino-3-oxopropyl | i-Pnt | H | A |
| IB-350 | Np-M | 3-guanidinopropyl | i-Bu | H | C |
| IB-351 | Np-M | 3-guanidinopropyl | Bnzl | H | C |
| IB-353 | Np-M | 3-guanidinopropyl | i-Pnt | H | A |
| IB-354 | Np-M | 3-guanidinopropyl | phenethyl | H | A |
| IB-357 | cyclohexylmethyl | 3-amino-3-oxopropyl | i-Pnt | H | C |
| IB-361 | cyclohexylmethyl | 3-guanidinopropyl | i-Pnt | H | C |
| IB-362 | cyclohexylmethyl | 3-guanidinopropyl | phenethyl | H | A |
| IB-365 | 4-fluorobenzyl | 3-amino-3-oxopropyl | i-Pnt | H | C |
| IB-369 | 4-fluorobenzyl | 3-guanidinopropyl | i-Pnt | H | C |
| IB-372 | 2-hydroxyethyl | i-Bu | i-Pnt | H | C |
| IB-378 | i-Bu | i-Bu | i-Pnt | H | A |
| IB-381 | i-Pnt | 2-carboxyethyl | Np-M | H | C |
| IB-384 | 4-fluorobenzyl | 2-carboxyethyl | Np-M | H | C |
| IB-386 | i-Pnt | 4-fluorobenzyl | 2-carboxyethyl | H | C |
| IB-389 | cyclohexylmethyl | Np-M | 2-carboxyethyl | H | C |

TABLE 5-continued

| | | | | | |
|---|---|---|---|---|---|
| IB-390 | 4-fluorobenzyl | Np-M | 2-carboxyethyl | H | C |
| IB-392 | 2-carboxyethyl | Np-M | i-Bu | H | C |
| IB-394 | 2-carboxyethyl | 4-fluorobenzyl | Bnzl | H | C |
| IB-398 | 2-carboxyethyl | Np-M | i-Pnt | H | C |
| IB-399 | 2-carboxyethyl | 4-fluorobenzyl | i-Pnt | H | C |
| IB-402 | 2-carboxyethyl | 4-hydroxybenzyl | i-Pnt | H | C |
| IB-410 | 4-hydroxybenzyl | 2-carboxyethyl | Np-M | H | C |
| IB-417 | Np-M | 4-hydroxybenzyl | Np-M | H | C |
| IB-425 | 2-hydroxyethyl | Np-M | 2-carboxyethyl | H | C |
| IB-426 | i-Pnt | Np-M | hydroxymethyl | H | A |
| IB-430 | 2-carboxyethyl | i-Bu | phenethyl | H | A |
| IB-431 | 2-carboxyethyl | i-Bu | hydroxymethyl | H | C |
| IB-449 | phenethyl | 4-hydroxybenzyl | i-Bu | H | C |
| IB-458 | 4-fluorobenzyl | 4-hydroxybenzyl | i-Bu | H | C |
| IB-459 | Np-M | 2-hydroxyethyl | 4-hydroxybenzyl | H | C |
| IB-461 | phenethyl | 2-hydroxyethyl | i-Pnt | H | C |
| IB-464 | Bnzl | 4-hydroxybenzyl | i-Bu | H | A |
| IB-465 | i-Bu | 4-hydroxybenzyl | i-Pnt | H | C |
| IB-470 | 2-hydroxyethyl | 4-hydroxybenzyl | Np-M | H | C |
| IB-476 | 2-hydroxyethyl | hexyl | Bnzl | H | A |
| IB-477 | 2-hydroxyethyl | hexyl | i-Bu | H | A |
| IB-478 | 2-hydroxyethyl | hexyl | 4-hydroxybenzyl | H | C |
| IB-479 | 2-hydroxyethyl | 4-fluorobenzyl | Bnzl | H | C |
| IB-481 | i-Pnt | 4-fluorobenzyl | 4-hydroxybenzyl | H | A |
| IB-484 | cyclohexylmethyl | phenethyl | Bnzl | H | A |
| IB-490 | 2-hydroxyethyl | hexyl | i-Pnt | H | A |
| IB-492 | 2-hydroxyethyl | 4-fluorobenzyl | phenethyl | H | A |
| IB-495 | i-Bu | phenethyl | i-Bu | H | A |
| IB-498 | i-Bu | 4-fluorobenzyl | 4-hydroxybenzyl | H | A |
| IB-499 | 4-hydroxybenzyl | 4-fluorobenzyl | i-Bu | H | A |
| IB-501 | 4-hydroxybenzyl | isopropyl | i-Pnt | H | A |
| IB-502 | 4-hydroxybenzyl | isopropyl | Np-M | H | A |
| IB-505 | i-Pnt | Bnzl | 2-carboxyethyl | H | C |
| IB-508 | phenethyl | i-Bu | 2-carboxyethyl | H | C |
| IB-510 | cyclohexylmethyl | i-Bu | 2-carboxyethyl | H | C |
| IB-515 | 2-carboxyethyl | 4-hydroxybenzyl | phenethyl | H | C |
| IB-516 | 2-carboxyethyl | 4-hydroxybenzyl | Np-M | H | C |
| IB-520 | Np-M | 3-amino-3-oxopropyl | i-Bu | H | A |
| IB-521 | Np-M | 3-amino-3-oxopropyl | 4-hydroxybenzyl | H | C |
| IB-522 | cyclohexylmethyl | 3-amino-3-oxopropyl | Np-M | H | C |
| IB-525 | 4-fluorobenzyl | 3-amino-3-oxopropyl | Np-M | H | C |

TABLE 5-continued

| | | | | | |
|---|---|---|---|---|---|
| IB-527 | 2-hydroxyethyl | Np-M | 4-hydroxybenzyl | H | C |
| IB-531 | 2-hydroxyethyl | phenethyl | i-Pnt | H | C |
| IB-535 | Bnzl | 3-amino-3-oxopropyl | phenethyl | H | C |
| IB-536 | i-Bu | phenethyl | 4-hydroxybenzyl | H | C |
| IB-539 | i-Bu | 3-amino-3-oxopropyl | phenethyl | H | C |
| IB-540 | 4-hydroxybenzyl | phenethyl | i-Bu | H | C |
| IB-541 | 4-hydroxybenzyl | Np-M | i-Bu | H | A |
| IB-544 | 4-hydroxybenzyl | phenethyl | i-Pnt | H | C |
| IB-549 | 2-hydroxyethyl | 4-fluorobenzyl | 4-hydroxybenzyl | H | C |
| IB-551 | i-Pnt | hexyl | i-Bu | H | A |
| IB-553 | i-Pnt | 4-fluorobenzyl | i-Bu | H | A |
| IB-562 | Bnzl | hexyl | Bnzl | H | C |
| IB-568 | Bnzl | 4-fluorobenzyl | phenethyl | H | C |
| IB-574 | 4-hydroxybenzyl | i-Pnt | Bnzl | H | C |
| IB-575 | 2-carboxyethyl | i-Bu | Np-M | H | C |
| IB-576 | i-Pnt | 4-hydroxybenzyl | phenethyl | H | C |
| IB-577 | i-Pnt | 4-hydroxybenzyl | Bnzl | H | C |
| IB-581 | cyclohexylmethyl | 4-hydroxybenzyl | i-Bu | H | C |
| IB-582 | 4-fluorobenzyl | 4-hydroxybenzyl | i-Pnt | H | C |
| IB-583 | 4-fluorobenzyl | 4-hydroxybenzyl | Bnzl | H | C |
| IB-585 | 2-hydroxyethyl | Np-M | i-Bu | H | C |
| IB-588 | Np-M | 2-hydroxyethyl | Bnzl | H | A |
| IB-593 | phenethyl | 2-hydroxyethyl | Np-M | H | C |
| IB-602 | Bnzl | 2-hydroxyethyl | Np-M | H | C |
| IB-610 | 2-hydroxyethyl | 2-carboxyethyl | Np-M | H | C |
| IB-611 | i-Pnt | 2-carboxyethyl | i-Bu | H | C |
| IB-613 | cyclohexylmethyl | 2-carboxyethyl | i-Pnt | H | C |
| IB-614 | cyclohexylmethyl | 2-carboxyethyl | Np-M | H | C |
| IB-616 | Bnzl | 2-carboxyethyl | Np-M | H | C |
| IB-618 | 2-hydroxyethyl | Bnzl | phenethyl | H | A |
| IB-619 | 2-hydroxyethyl | Bnzl | Bnzl | H | C |
| IB-621 | 2-hydroxyethyl | i-Bu | Np-M | H | A |
| IB-625 | phenethyl | i-Bu | 4-hydroxybenzyl | H | C |
| IB-630 | 4-fluorobenzyl | i-Bu | i-Bu | H | A |
| IB-631 | 4-fluorobenzyl | i-Bu | 4-hydroxybenzyl | H | C |
| IB-633 | i-Bu | i-Bu | phenethyl | H | A |
| IB-636 | i-Pnt | 3-amino-3-oxopropyl | phenethyl | H | C |
| IB-637 | cyclohexylmethyl | 3-amino-3-oxopropyl | Bnzl | H | A |
| IB-640 | phenethyl | 2-hydroxyethyl | Bnzl | H | A |
| IB-641 | phenethyl | 2-hydroxyethyl | i-Bu | H | C |
| IB-642 | phenethyl | 4-fluorobenzyl | 4-hydroxybenzyl | H | A |

TABLE 5-continued

| | | | | | |
|---|---|---|---|---|---|
| IB-643 | Np-M | 2-hydroxyethyl | i-Bu | H | C |
| IB-646 | cyclohexylmethyl | 2-hydroxyethyl | i-Bu | H | C |
| IB-648 | cyclohexylmethyl | i-Pnt | 4-hydroxybenzyl | H | C |
| IB-649 | 4-fluorobenzyl | 2-hydroxyethyl | Bnzl | H | C |
| IB-650 | 4-fluorobenzyl | 2-hydroxyethyl | i-Bu | H | C |
| IB-656 | 4-fluorobenzyl | hexyl | 4-hydroxybenzyl | H | A |
| IB-657 | 2-hydroxyethyl | 4-fluorobenzyl | i-Pnt | H | C |
| IB-658 | i-Pnt | 2-hydroxyethyl | phenethyl | H | C |
| IB-659 | i-Pnt | 2-hydroxyethyl | Np-M | H | A |
| IB-663 | cyclohexylmethyl | 2-hydroxyethyl | phenethyl | H | A |
| IB-668 | 4-fluorobenzyl | 2-hydroxyethyl | i-Pnt | H | A |
| IB-669 | 4-fluorobenzyl | 2-hydroxyethyl | phenethyl | H | C |
| IB-676 | Bnzl | 2-hydroxyethyl | Bnzl | H | C |
| IB-678 | Bnzl | i-Pnt | 4-hydroxybenzyl | H | A |
| IB-680 | Bnzl | 2-hydroxyethyl | i-Pnt | H | C |
| IB-681 | Bnzl | 2-hydroxyethyl | phenethyl | H | C |
| IB-684 | i-Bu | i-Pnt | 4-hydroxybenzyl | H | C |
| IB-687 | i-Bu | 2-hydroxyethyl | Np-M | H | C |
| IB-688 | i-Bu | i-Pnt | phenethyl | H | A |
| IB-694 | 2-carboxyethyl | Bnzl | i-Pnt | H | C |
| IB-703 | i-Pnt | 3-amino-3-oxopropyl | Np-M | H | A |
| IB-707 | phenethyl | 3-amino-3-oxopropyl | Bnzl | H | A |
| IB-708 | phenethyl | 3-amino-3-oxopropyl | i-Bu | H | A |
| IB-710 | cyclohexylmethyl | 3-amino-3-oxopropyl | phenethyl | H | A |
| IB-712 | 4-fluorobenzyl | 3-amino-3-oxopropyl | Bnzl | H | A |
| IB-714 | 2-hydroxyethyl | i-Pnt | Bnzl | H | A |
| IB-725 | 4-fluorobenzyl | phenethyl | i-Bu | H | A |
| IB-727 | 2-hydroxyethyl | i-Pnt | Np-M | H | A |
| IB-729 | Np-M | phenethyl | Np-M | H | A |
| IB-734 | Bnzl | 3-amino-3-oxopropyl | Bnzl | H | C |
| IB-737 | i-Bu | 3-amino-3-oxopropyl | Np-M | H | C |
| IB-739 | 4-hydroxybenzyl | i-Pnt | i-Bu | H | C |
| IB-743 | 4-hydroxybenzyl | 3-amino-3-oxopropyl | Np-M | H | A |
| IB-749 | i-Pnt | Bnzl | 4-hydroxybenzyl | H | C |
| IB-753 | i-Pnt | i-Bu | i-Bu | H | A |
| IB-757 | phenethyl | Bnzl | i-Bu | H | A |
| IB-759 | phenethyl | i-Bu | Bnzl | H | A |
| IB-760 | phenethyl | i-Bu | i-Bu | H | A |
| IB-762 | Np-M | i-Bu | i-Bu | H | A |
| IB-763 | Np-M | i-Bu | 4-hydroxybenzyl | H | C |
| IB-770 | cyclohexylmethyl | i-Bu | 4-hydroxybenzyl | H | C |
| IB-772 | 4-fluorobenzyl | Bnzl | Bnzl | H | A |
| IB-773 | 4-fluorobenzyl | Bnzl | i-Bu | H | A |

TABLE 5-continued

| | | | | | |
|---|---|---|---|---|---|
| IB-774 | 4-fluorobenzyl | i-Bu | phenethyl | H | A |
| IB-777 | Bnzl | Bnzl | Np-M | H | A |
| IB-780 | i-Bu | i-Pnt | Bnzl | H | A |
| IB-783 | i-Bu | Bnzl | 4-hydroxybenzyl | H | C |
| IB-786 | 4-hydroxybenzyl | Bnzl | i-Pnt | H | C |
| IB-787 | 4-hydroxybenzyl | Bnzl | i-Bu | H | C |
| IB-804 | Np-M | Np-M | phenethyl | H | A |
| IB-813 | Bnzl | 3-amino-3-oxopropyl | Np-M | H | A |
| IB-831 | 2-hydroxyethyl | 4-fluorobenzyl | Np-M | H | A |
| IB-864 | 4-Cl-Bnzl | Bnzl | i-Bu | H | B |
| IB-865 | 3-Cl-Bnzl | Bnzl | i-Bu | H | B |
| IB-866 | 4-methoxybenzyl | Bnzl | i-Bu | H | B |
| IB-867 | 4-methylbenzyl | Bnzl | i-Bu | H | B |
| IB-870 | i-Bu | i-Pnt | Bnzl | H | C |
| IB-871 | i-Bu | 4-Cl-Bnzl | i-Bu | H | C |
| IB-873 | 4-(dimethylamino)benzyl | Bnzl | i-Bu | H | B |
| IB-874 | 4-(tert-butyl)benzyl | Bnzl | i-Bu | H | B |
| IB-875 | i-Bu | Bnzl | i-Pnt | H | C |
| IB-876 | i-Pnt | Bnzl | i-Bu | H | C |
| IB-877 | 4-(trifluoromethyl)benzyl | Bnzl | i-Bu | H | B |
| IB-878 | 4-ethoxybenzyl | Bnzl | i-Bu | H | C |
| IB-879 | Bnzl | naphthalen-2-ylmethyl | i-Bu | H | A |
| IB-880 | 4-methylbenzyl | Bnzl | i-Bu | ethyl | A |
| IB-881 | 4-methylbenzyl | Bnzl | i-Bu | i-Bu | A |
| IB-883 | 4-methylbenzyl | Bnzl | i-Bu | 3-methylbutanoyl | A |
| IB-884 | 4-methylbenzyl | Bnzl | i-Bu | 2-phenylacetyl | A |
| IB-885 | 4-methylbenzyl | Bnzl | i-Bu | methoxycarbonyl | B |
| IB-886 | 4-methylbenzyl | Bnzl | i-Bu | 2-methylpropoxycarbonyl | B |
| IB-887 | 4-methylbenzyl | Bnzl | i-Bu | benzyloxycarbonyl | B |
| IB-888 | 4-methylbenzyl | Bnzl | i-Bu | aminocarbonyl | C |
| IB-889 | 4-methylbenzyl | Bnzl | i-Bu | N-benzylaminocarbonyl | B |
| IB-891 | 4-(dimethylamino)benzyl | 3-hydroxybenzyl | i-Bu | H | C |
| IB-892 | 4-(dimethylamino)benzyl | 4-hydroxybenzyl | i-Bu | H | C |

Table. Anti-rabies activity of compounds of formula XXIB

| Compound number | $R_1$ | $R_{2A}$ | $R_{2B}$ | $R_3$ | $R_4$ | Anti-rabies activity |
|---|---|---|---|---|---|---|
| IB-924 | 4-Me-Bnzl | H | Bnzl | i-Bu | N-isobutylaminocarbonyl | na |
| IB-925 | i-Bu | H | 4-Cl-Bnzl | Ph-Et | H | A |
| IB-926 | i-Bu | H | 3-Cl-Bnzl | Ph-Et | H | A |
| IB-927 | i-Bu | H | 4-MeO-Bnzl | Ph-Et | H | A |
| IB-928 | i-Bu | H | 4-Me-Bnzl | Ph-Et | H | A |
| IB-929 | i-Bu | H | 2-Npm | Ph-Et | H | A |
| IB-930 | i-Bu | H | Bnzl | Ph-Pr | H | A |
| IB-931 | i-Bu | H | 3-Cl-Bnzl | Ph-Pr | H | A |
| IB-932 | i-Bu | H | 3-F-Bnzl | Ph-Pr | H | A |
| IB-933 | i-Bu | H | 3-Me-Bnzl | Ph-Pr | H | A |
| IB-934 | i-Bu | H | 3-MeO-Bnzl | Ph-Pr | H | A |
| IB-935 | i-Bu | H | 3-Cl-Bnzl | Ph-Bu | H | A |
| IB-936 | i-Bu | H | 3-F-Bnzl | Ph-Bu | H | A |
| IB-937 | i-Bu | H | 3-Me-Bnzl | Ph-Bu | H | A |
| IB-938 | i-Bu | H | 3-MeO-Bnzl | Ph-Bu | H | A |

TABLE 5-continued

| | | | | | | |
|---|---|---|---|---|---|---|
| IB-939 | i-Bu | H | Bnzl | Ph-Bu | H | A |
| IB-940 | i-Pnt | H | 3-F-Bnzl | Ph-Pr | H | A |
| IB-957 | i-Bu | H | Ph-Et | Ph-Et | H | A |
| IB-958 | i-Bu | H | 1-Npm | Ph-Et | H | A |

Table. Anti-rabies activity of compounds of formula IF
(A: $IC_{50} \leq 5$ μM, B: $5$ μM $< IC_{50} \leq 10$ μM, C: $10$ μM $< IC_{50} < 30$ μM)

| Compound number | $R_1$ | $R_2$ | $R_3$ | $R_4$ | Anti-rabies activity |
|---|---|---|---|---|---|
| IF-1 | i-Bu | Bnzl | Bnzl | H | C |
| IF-6 | Bnzl | i-Bu | Bnzl | H | C |
| IF-7 | Bnzl | Bnzl | i-Bu | H | B |
| IF-9 | i-Pnt | Bnzl | Bnzl | H | C |
| IF-11 | i-Bu | Bnzl | phenethyl | H | C |
| IF-13 | i-Bu | Bnzl | 3-methylbenzyl | H | C |
| IF-14 | i-Bu | Bnzl | 4-methylbenzyl | H | C |
| IF-15 | i-Bu | 3-methylbenzyl | Bnzl | H | C |
| IF-20 | Bnzl | 3,4-dichlorobenzyl | i-Bu | H | C |
| IF-38 | i-Bu | Bnzl | cyclohexylmethyl | H | C |
| IF-42 | Np-M | Bnzl | Bnzl | H | C |
| IF-69 | i-Bu | Bnzl | Bnzl | ethyl | C |
| IF-81 | 2-amino-2-oxoethyl | Np-M | i-Bu | H | C |
| IF-82 | 2-amino-2-oxoethyl | Np-M | Bnzl | H | C |
| IF-84 | 2-amino-2-oxoethyl | Np-M | i-Pnt | H | C |
| IF-85 | 2-amino-2-oxoethyl | Np-M | phenethyl | H | C |
| IF-90 | 2-amino-2-oxoethyl | phenethyl | Np-M | H | C |
| IF-91 | 2-amino-2-oxoethyl | Np-M | Np-M | H | A |
| IF-95 | 2-amino-2-oxoethyl | 4-fluorobenzyl | i-Pnt | H | C |
| IF-97 | 2-amino-2-oxoethyl | 4-fluorobenzyl | Np-M | H | C |
| IF-109 | 2-amino-2-oxoethyl | hexyl | phenethyl | H | C |
| IF-110 | 2-amino-2-oxoethyl | hexyl | Np-M | H | A |
| IF-137 | 2-amino-2-oxoethyl | 4-hydroxybenzyl | Np-M | H | A |
| IF-214 | i-Pnt | isopropyl | 3-guanidinopropyl | H | C |
| IF-219 | phenethyl | 3-amino-3-oxopropyl | 2-amino-2-oxoethyl | H | C |
| IF-223 | phenethyl | Np-M | 2-amino-2-oxoethyl | H | C |
| IF-226 | Np-M | i-Bu | 2-amino-2-oxoethyl | H | C |
| IF-230 | Np-M | 2-hydroxyethyl | 2-amino-2-oxoethyl | H | C |
| IF-235 | Np-M | i-Bu | 3-guanidinopropyl | H | C |
| IF-236 | Np-M | Bnzl | 3-guanidinopropyl | H | C |
| IF-239 | Np-M | 2-hydroxyethyl | 3-guanidinopropyl | H | C |
| IF-243 | Np-M | hexyl | 3-guanidinopropyl | H | A |
| IF-244 | Np-M | isopropyl | 3-guanidinopropyl | H | A |
| IF-245 | Np-M | 4-fluorobenzyl | 3-guanidinopropyl | H | A |
| IF-246 | cyclohexylmethyl | Bnzl | 2-amino-2-oxoethyl | H | C |
| IF-247 | cyclohexylmethyl | 4-hydroxybenzyl | 2-amino-2-oxoethyl | H | C |
| IF-251 | cyclohexylmethyl | phenethyl | 2-amino-2-oxoethyl | H | C |
| IF-260 | cyclohexylmethyl | hexyl | 3-guanidinopropyl | H | C |
| IF-262 | 4-fluorobenzyl | i-Bu | 2-amino-2-oxoethyl | H | A |

TABLE 5-continued

| | | | | | |
|---|---|---|---|---|---|
| IF-269 | 4-fluorobenzyl | phenethyl | 2-amino-2-oxoethyl | H | C |
| IF-274 | 4-fluorobenzyl | isopropyl | 3-guanidinopropyl | H | C |
| IF-284 | Bnzl | Np-M | 3-guanidinopropyl | H | C |
| IF-285 | Bnzl | hexyl | 3-guanidinopropyl | H | C |
| IF-297 | 4-fluorobenzyl | Np-M | 3-guanidinopropyl | H | C |
| IF-298 | 4-fluorobenzyl | hexyl | 3-guanidinopropyl | H | C |
| IF-300 | i-Bu | 3-amino-3-oxopropyl | i-Pnt | H | C |
| IF-356 | 3-guanidinopropyl | i-Pnt | Np-M | H | C |
| IF-359 | 3-guanidinopropyl | phenethyl | 4-hydroxybenzyl | H | C |
| IF-384 | Np-M | 3-amino-3-oxopropyl | i-Pnt | H | C |
| IF-386 | Np-M | 3-guanidinopropyl | Bnzl | H | C |
| IF-389 | Np-M | 3-guanidinopropyl | phenethyl | H | A |
| IF-390 | Np-M | 3-guanidinopropyl | Np-M | H | C |
| IF-411 | Bnzl | i-Bu | i-Pnt | H | A |
| IF-412 | i-Bu | i-Bu | i-Pnt | H | A |
| IF-413 | i-Pnt | 2-carboxyethyl | Np-M | H | C |
| IF-416 | cyclohexylmethyl | 2-carboxyethyl | Np-M | H | C |
| IF-417 | 4-fluorobenzyl | 2-carboxyethyl | Np-M | H | C |
| IF-419 | cyclohexylmethyl | Np-M | 2-carboxyethyl | H | C |
| IF-422 | 2-carboxyethyl | Np-M | i-Pnt | H | C |
| IF-428 | i-Bu | 2-carboxyethyl | Np-M | H | C |
| IF-435 | Np-M | 3-amino-3-oxopropyl | 4-hydroxybenzyl | H | A |
| IF-437 | i-Pnt | phenethyl | i-Bu | H | C |
| IF-439 | cyclohexylmethyl | phenethyl | 4-hydroxybenzyl | H | A |
| IF-444 | 2-hydroxyethyl | 2-carboxyethyl | Np-M | H | C |
| IF-445 | i-Pnt | 4-hydroxybenzyl | 2-carboxyethyl | H | C |
| IF-447 | cyclohexylmethyl | 4-hydroxybenzyl | 2-carboxyethyl | H | C |
| IF-452 | 2-carboxyethyl | 2-hydroxyethyl | Np-M | H | C |
| IF-454 | 2-carboxyethyl | i-Bu | phenethyl | H | C |
| IF-455 | 2-carboxyethyl | i-Bu | 4-hydroxybenzyl | H | C |
| IF-458 | 2-carboxyethyl | 4-hydroxybenzyl | i-Pnt | H | C |
| IF-464 | i-Pnt | 4-hydroxybenzyl | phenethyl | H | C |
| IF-465 | i-Pnt | 4-hydroxybenzyl | Np-M | H | C |
| IF-466 | i-Pnt | 4-hydroxybenzyl | Bnzl | H | C |
| IF-468 | phenethyl | 4-hydroxybenzyl | i-Pnt | H | C |
| IF-469 | phenethyl | 4-hydroxybenzyl | Bnzl | H | C |
| IF-470 | phenethyl | 4-hydroxybenzyl | i-Bu | H | C |
| IF-472 | Np-M | 4-hydroxybenzyl | Bnzl | H | A |
| IF-473 | Np-M | 4-hydroxybenzyl | i-Bu | H | A |
| IF-474 | cyclohexylmethyl | 4-hydroxybenzyl | i-Pnt | H | A |
| IF-475 | cyclohexylmethyl | 4-hydroxybenzyl | phenethyl | H | C |
| IF-477 | cyclohexylmethyl | 4-hydroxybenzyl | Bnzl | H | A |

TABLE 5-continued

| | | | | | |
|---|---|---|---|---|---|
| IF-478 | cyclohexylmethyl | 4-hydroxybenzyl | i-Bu | H | A |
| IF-479 | 4-fluorobenzyl | 4-hydroxybenzyl | i-Pnt | H | A |
| IF-481 | 4-fluorobenzyl | 4-hydroxybenzyl | Bnzl | H | C |
| IF-482 | 4-fluorobenzyl | 4-hydroxybenzyl | i-Bu | H | C |
| IF-486 | cyclohexylmethyl | 2-hydroxyethyl | Bnzl | H | C |
| IF-490 | 4-fluorobenzyl | 2-hydroxyethyl | i-Pnt | H | C |
| IF-493 | Bnzl | 4-hydroxybenzyl | i-Pnt | H | A |
| IF-494 | Bnzl | 4-hydroxybenzyl | Bnzl | H | C |
| IF-500 | i-Bu | 4-hydroxybenzyl | Np-M | H | C |
| IF-503 | 4-hydroxybenzyl | isopropyl | i-Pnt | H | A |
| IF-504 | 4-hydroxybenzyl | isopropyl | Np-M | H | C |
| IF-505 | Np-M | Bnzl | 4-hydroxybenzyl | H | A |
| IF-508 | 2-hydroxyethyl | 4-fluorobenzyl | Bnzl | H | C |
| IF-514 | cyclohexylmethyl | hexyl | 4-hydroxybenzyl | H | A |
| IF-516 | 2-hydroxyethyl | 4-fluorobenzyl | phenethyl | H | A |
| IF-525 | i-Bu | 4-fluorobenzyl | phenethyl | H | C |
| IF-536 | cyclohexylmethyl | 3-amino-3-oxopropyl | Np-M | H | A |
| IF-539 | 4-fluorobenzyl | 3-amino-3-oxopropyl | Np-M | H | A |
| IF-542 | 2-hydroxyethyl | Np-M | i-Bu | H | A |
| IF-543 | 2-hydroxyethyl | Np-M | 4-hydroxybenzyl | H | C |
| IF-545 | i-Pnt | phenethyl | 4-hydroxybenzyl | H | C |
| IF-546 | i-Pnt | hexyl | i-Bu | H | C |
| IF-547 | i-Pnt | 4-fluorobenzyl | Bnzl | H | A |
| IF-548 | i-Pnt | 4-fluorobenzyl | i-Bu | H | C |
| IF-560 | Bnzl | hexyl | i-Bu | H | A |
| IF-561 | Bnzl | 4-fluorobenzyl | Bnzl | H | A |
| IF-565 | Bnzl | 4-hydroxybenzyl | phenethyl | H | A |
| IF-567 | i-Bu | phenethyl | 4-hydroxybenzyl | H | C |
| IF-568 | i-Bu | Np-M | 4-hydroxybenzyl | H | A |
| IF-569 | i-Bu | hexyl | i-Bu | H | C |
| IF-576 | i-Bu | 4-hydroxybenzyl | phenethyl | H | C |
| IF-578 | 4-hydroxybenzyl | Np-M | i-Bu | H | A |
| IF-580 | 4-hydroxybenzyl | phenethyl | Np-M | H | C |
| IF-583 | i-Pnt | hexyl | 4-hydroxybenzyl | H | A |
| IF-584 | 4-fluorobenzyl | i-Pnt | Bnzl | H | A |
| IF-585 | 4-fluorobenzyl | i-Pnt | i-Bu | H | A |
| IF-586 | 4-fluorobenzyl | phenethyl | Bnzl | H | C |
| IF-596 | Np-M | isopropyl | Np-M | H | C |
| IF-599 | i-Pnt | hexyl | Bnzl | H | C |
| IF-602 | phenethyl | hexyl | Bnzl | H | C |
| IF-603 | Np-M | 2-hydroxyethyl | Bnzl | H | C |
| IF-604 | Np-M | 2-hydroxyethyl | i-Bu | H | C |
| IF-606 | cyclohexylmethyl | 2-hydroxyethyl | i-Bu | H | C |
| IF-610 | 2-hydroxyethyl | phenethyl | Np-M | H | C |
| IF-611 | i-Pnt | 2-hydroxyethyl | Np-M | H | C |
| IF-612 | phenethyl | 2-hydroxyethyl | Np-M | H | C |

TABLE 5-continued

| | | | | | |
|---|---|---|---|---|---|
| IF-613 | Np-M | 2-hydroxyethyl | i-Pnt | H | C |
| IF-614 | Np-M | 2-hydroxyethyl | Np-M | H | C |
| IF-619 | cyclohexylmethyl | 2-hydroxyethyl | Np-M | H | C |
| IF-620 | 4-fluorobenzyl | 2-hydroxyethyl | Np-M | H | A |
| IF-624 | Bnzl | 2-hydroxyethyl | Np-M | H | C |
| IF-635 | i-Pnt | i-Bu | phenethyl | H | C |
| IF-639 | phenethyl | Bnzl | i-Bu | H | A |
| IF-640 | phenethyl | Bnzl | 4-hydroxybenzyl | H | C |
| IF-641 | phenethyl | i-Bu | Bnzl | H | A |
| IF-644 | cyclohexylmethyl | Bnzl | i-Bu | H | A |
| IF-645 | cyclohexylmethyl | Bnzl | 4-hydroxybenzyl | H | C |
| IF-646 | cyclohexylmethyl | i-Bu | Np-M | H | A |
| IF-649 | 4-fluorobenzyl | Bnzl | Bnzl | H | A |
| IF-650 | 4-fluorobenzyl | Bnzl | i-Bu | H | A |
| IF-652 | 4-fluorobenzyl | i-Bu | phenethyl | H | A |
| IF-653 | 4-fluorobenzyl | i-Bu | Bnzl | H | C |
| IF-654 | 4-fluorobenzyl | i-Bu | i-Bu | H | A |
| IF-656 | 2-hydroxyethyl | i-Pnt | Bnzl | H | C |
| IF-657 | phenethyl | i-Pnt | i-Bu | H | A |
| IF-658 | cyclohexylmethyl | i-Pnt | Bnzl | H | A |
| IF-659 | cyclohexylmethyl | i-Pnt | i-Bu | H | C |
| IF-660 | 2-hydroxyethyl | i-Pnt | Np-M | H | C |
| IF-665 | Bnzl | i-Pnt | Bnzl | H | A |
| IF-670 | Bnzl | i-Bu | phenethyl | H | A |
| IF-673 | i-Bu | i-Pnt | phenethyl | H | A |
| IF-674 | i-Bu | i-Pnt | Np-M | H | C |
| IF-675 | i-Bu | Bnzl | i-Pnt | H | A |
| IF-679 | i-Bu | i-Bu | phenethyl | H | A |
| IF-680 | i-Bu | i-Bu | Np-M | H | C |
| IF-684 | 4-hydroxybenzyl | i-Pnt | Np-M | H | C |
| IF-691 | benzyl | i-Pnt | i-Bu | H | C |
| IF-692 | Bnzl | hexyl | 4-hydroxybenzyl | H | A |
| IF-699 | phenethyl | 3-amino-3-oxopropyl | i-Bu | H | C |
| IF-705 | i-Pnt | Np-M | i-Bu | H | A |
| IF-706 | i-Pnt | Np-M | 4-hydroxybenzyl | H | A |
| IF-707 | phenethyl | i-Pnt | 4-hydroxybenzyl | H | A |
| IF-708 | Np-M | i-Pnt | phenethyl | H | A |
| IF-709 | cyclohexylmethyl | i-Pnt | 4-hydroxybenzyl | H | C |
| IF-710 | cyclohexylmethyl | phenethyl | Bnzl | H | A |
| IF-711 | cyclohexylmethyl | phenethyl | i-Bu | H | C |
| IF-714 | 4-fluorobenzyl | phenethyl | i-Bu | H | A |
| IF-715 | 4-fluorobenzyl | phenethyl | 4-hydroxybenzyl | H | A |
| IF-717 | cyclohexylmethyl | phenethyl | i-Pnt | H | A |
| IF-718 | cyclohexylmethyl | phenethyl | Np-M | H | A |
| IF-721 | Bnzl | phenethyl | i-Bu | H | A |
| IF-722 | Bnzl | phenethyl | 4-hydroxybenzyl | H | A |
| IF-723 | Bnzl | phenethyl | i-Pnt | H | C |
| IF-725 | i-Bu | phenethyl | i-Bu | H | C |
| IF-726 | i-Bu | Np-M | i-Bu | H | C |
| IF-727 | i-Bu | phenethyl | i-Pnt | H | A |
| IF-730 | 4-hydroxybenzyl | Np-M | i-Pnt | H | C |
| IF-733 | i-Pnt | Bnzl | i-Bu | H | A |
| IF-734 | i-Pnt | Bnzl | Np-M | H | A |
| IF-735 | i-Pnt | i-Bu | Bnzl | H | C |
| IF-738 | phenethyl | i-Bu | i-Bu | H | C |
| IF-739 | Np-M | i-Bu | i-Bu | H | A |
| IF-740 | cyclohexylmethyl | Bnzl | i-Pnt | H | C |
| IF-742 | cyclohexylmethyl | i-Bu | i-Bu | H | C |
| IF-743 | 4-fluorobenzyl | Bnzl | i-Pnt | H | C |

TABLE 5-continued

| | | | | | |
|---|---|---|---|---|---|
| IF-744 | phenethyl | i-Pnt | Bnzl | H | A |
| IF-753 | i-Bu | Bnzl | Np-M | H | C |
| IF-758 | 2-hydroxyethyl | Np-M | Bnzl | H | A |
| IF-778 | i-Bu | Np-M | Np-M | H | A |
| IF-779 | 4-hydroxybenzyl | Np-M | Np-M | H | C |
| IF-789 | Np-M | isopropyl | phenethyl | H | C |
| IF-805 | Bnzl | Np-M | Bnzl | H | C |
| IF-807 | Bnzl | 4-fluorobenzyl | i-Bu | H | A |
| IF-815 | i-Bu | 4-fluorobenzyl | Bnzl | H | A |
| IF-830 | i-Pnt | 2-carboxyethyl | phenethyl | H | C |
| IF-837 | Bnzl | Np-M | i-Bu | H | B |
| IF-838 | Bnzl | 4-(trifluoromethyl)benzyl | i-Bu | H | C |
| IF-839 | 4-Cl-Bnzl | Bnzl | i-Bu | H | B |
| IF-840 | 3-Cl-Bnzl | Bnzl | i-Bu | H | B |
| IF-841 | 4-methoxybenzyl | Bnzl | i-Bu | H | B |
| IF-842 | 4-methylbenzyl | Bnzl | i-Bu | H | A |
| IF-845 | i-Bu | i-Pnt | Bnzl | H | C |
| IF-846 | i-Bu | 4-Cl-Bnzl | i-Bu | H | C |
| IF-848 | 4-(dimethyl-amino)benzyl | Bnzl | i-Bu | H | B |
| IF-849 | 4-(tert-butyl)benzyl | Bnzl | i-Bu | H | B |
| IF-850 | i-Bu | Bnzl | i-Pnt | H | B |
| IF-851 | i-Pnt | Bnzl | i-Bu | H | C |
| IF-852 | 4-(trifluoro-methyl)benzyl | Bnzl | i-Bu | H | B |
| IF-853 | 4-ethoxybenzyl | Bnzl | i-Bu | H | B |
| IF-854 | Bnzl | naphthalen-2-ylmethyl | i-Bu | H | B |
| IF-855 | 4-methylbenzyl | Bnzl | i-Bu | ethyl | B |
| IF-856 | 4-methylbenzyl | Bnzl | i-Bu | i-Bu | A |
| IF-859 | 4-methylbenzyl | Bnzl | i-Bu | 2-phenylacetyl | B |
| IF-860 | 4-methylbenzyl | Bnzl | i-Bu | methoxycarbonyl | C |
| IF-861 | 4-methylbenzyl | Bnzl | i-Bu | 2-methylpropoxycarbonyl | B |
| IF-862 | 4-methylbenzyl | Bnzl | i-Bu | benzyloxycarbonyl | B |
| IF-864 | 4-methylbenzyl | Bnzl | i-Bu | N-benzylaminocarbonyl | C |
| IF-866 | 4-(dimethylamino)benzyl | 3-hydroxybenzyl | i-Bu | H | C |
| IF-867 | 4-(dimethylamino)benzyl | 4-hydroxybenzyl | i-Bu | H | C |

Table. Anti-rabies activity of compounds of formula XXIF

| Compound number | $R_1$ | $R_{2A}$ | $R_{2B}$ | $R_3$ | $R_4$ | Anti-rabies activity |
|---|---|---|---|---|---|---|
| IF-885 | i-Bu | H | 4-Cl-Bnzl | Ph-Et | H | A |
| IF-886 | i-Bu | H | 3-Cl-Bnzl | Ph-Et | H | A |
| IF-887 | i-Bu | H | 4-MeO-Bnzl | Ph-Et | H | A |
| IF-888 | i-Bu | H | 4-Me-Bnzl | Ph-Et | H | A |
| IF-889 | i-Bu | H | 2-Npm | Ph-Et | H | A |
| IF-890 | i-Bu | H | Bnzl | Ph-Pr | H | B |
| IF-891 | i-Bu | H | 3-Cl-Bnzl | Ph-Pr | H | A |
| IF-892 | i-Bu | H | 3-F-Bnzl | Ph-Pr | H | A |
| IF-893 | i-Bu | H | 3-Me-Bnzl | Ph-Pr | H | B |
| IF-894 | i-Bu | H | 3-MeO-Bnzl | Ph-Pr | H | A |
| IF-895 | i-Bu | H | 3-Cl-Bnzl | Ph-Bu | H | A |
| IF-896 | i-Bu | H | 3-F-Bnzl | Ph-Bu | H | A |
| IF-897 | i-Bu | H | 3-Me-Bnzl | Ph-Bu | H | A |
| IF-898 | i-Bu | H | 3-MeO-Bnzl | Ph-Bu | H | B |
| IF-899 | i-Bu | H | Bnzl | Ph-Bu | H | B |

TABLE 5-continued

| | | | | | | |
|---|---|---|---|---|---|---|
| IF-900 | i-Pnt | H | 3-F-Bnzl | Ph-Pr | H | A |
| IF-909 | i-Bu | H | Ph-Et | Ph-Et | H | A |

Table. Anti-rabies activity of compounds of formula IIB
(A: $IC_{50} \leq 5~\mu M$, B: $5~\mu M < IC_{50} \leq 10~\mu M$, C: $10~\mu M < IC_{50} < 30~\mu M$)

| Compound number | $R_1$ | $R_2$ | $R_3$ | Anti-rabies activity |
|---|---|---|---|---|
| IIB-4 | Bnzl | i-Bu | i-Bu | B |
| IIB-83 | 4-Cl-Bnzl | Bnzl | i-Bu | A |
| IIB-84 | 3-Cl-Bnzl | Bnzl | i-Bu | A |
| IIB-85 | 4-methoxybenzyl | Bnzl | i-Bu | B |
| IIB-86 | 4-methylbenzyl | Bnzl | i-Bu | B |
| IIB-94 | 4-(dimethylamino)benzyl | Bnzl | i-Bu | B |
| IIB-95 | 4-(tert-butyl)benzyl | Bnzl | i-Bu | B |
| IIB-96 | 4-(trifluoromethoxy)benzyl | Bnzl | i-Bu | B |
| IIB-97 | 4-ethoxybenzyl | Bnzl | i-Bu | C |
| IIB-101 | 4-hydroxybenzyl | Bnzl | i-Pnt | B |
| IIB-102 | Bnzl | naphthalen-2-ylmethyl | i-Bu | A |
| IIB-103 | i-Pnt | 4-Cl-Bnzl | i-Bu | B |
| IIB-104 | i-Pnt | 4-fluorobenzyl | i-Bu | B |

Anti-rabies activity of compounds of formula XXIIB

| Compound number | $R_1$ | $R_{2A}$ | $R_{2B}$ | $R_3$ | Anti-rabies activity |
|---|---|---|---|---|---|
| IIF-325 | i-Pnt | H | 3-Cl-Bnzl | Bnzl | A |
| IIF-328 | i-Pnt | H | 4-Me-Bnzl | Bnzl | A |
| IIF-329 | i-Pnt | H | 4-MeO-Bnzl | Bnzl | A |
| IIB-329 | Me | H | quinolin-8-ylethyl | Bnzl | A |
| IIB-330 | Me | H | quinolin-5-ylethyl | Bnzl | A |
| IIB-331 | i-Bu | H | 4-Cl-Bnzl | Ph-Et | A |
| IIB-332 | i-Bu | H | 3-Cl-Bnzl | Ph-Et | A |
| IIB-333 | i-Bu | H | 4-MeO-Bnzl | Ph-Et | A |
| IIB-334 | i-Bu | H | 4-Me-Bnzl | Ph-Et | A |
| IIB-335 | i-Bu | H | 2-Npm | Ph-Et | A |
| IIB-336 | i-Bu | H | Bnzl | Ph-Pr | A |
| IIB-337 | i-Bu | H | 3-Cl-Bnzl | Ph-Pr | A |
| IIB-338 | i-Bu | H | 3-F-Bnzl | Ph-Pr | A |
| IIB-339 | Cpm | H | 4-OH-Bnzl | 2-Cbx-Et | na |
| IIB-340 | i-Bu | H | 3-Me-Bnzl | Ph-Pr | A |
| IIB-341 | i-Bu | H | 3-MeO-Bnzl | Ph-Pr | A |
| IIB-342 | i-Bu | H | 3-Cl-Bnzl | Ph-Bu | B |
| IIB-343 | i-Bu | H | 3-F-Bnzl | Ph-Bu | A |
| IIB-344 | i-Bu | H | 3-Me-Bnzl | Ph-Bu | A |
| IIB-345 | i-Bu | H | 3-MeO-Bnzl | Ph-Bu | A |
| IIB-346 | i-Bu | H | Bnzl | Ph-Bu | A |
| IIB-347 | i-Pnt | H | 3-F-Bnzl | Ph-Pr | A |
| IIF-327 | i-Pnt | H | 4-F-Bnzl | Bnzl | A |
| IIF-370 | i-Pnt | H | Ph-Et | Bnzl | A |
| IIF-371 | i-Pnt | H | 1-Npm | Bnzl | A |
| IIB-374 | i-Bu | H | 4-F-Bnzl | Ph-Et | A |
| IIB-375 | i-Bu | H | Ph-Et | Ph-Et | A |
| IIB-376 | i-Bu | H | 1-Npm | Ph-Et | A |
| IIB-378 | 4-F-Bnzl | H | 1-Npm | i-Bu | A |

Table. Anti-rabies activity of compounds of formula IIF
(A: $IC_{50} \leq 5~\mu M$, B: $5~\mu M < IC_{50} \leq 10~\mu M$, C: $10~\mu M < IC_{50} < 30~\mu M$)

| Compound number | $R_1$ | $R_2$ | $R_3$ | Anti-rabies activity |
|---|---|---|---|---|
| IIF-16 | i-Bu | 4-Me-Bnzl | Bnzl | C |
| IIF-83 | 4-Cl-Bnzl | Bnzl | i-Bu | A |
| IIF-84 | 3-Cl-Bnzl | Bnzl | i-Bu | B |
| IIF-85 | 4-methoxybenzyl | Bnzl | i-Bu | B |
| IIF-86 | 4-methylbenzyl | Bnzl | i-Bu | A |
| IIF-94 | 4-(dimethylamino)benzyl | Bnzl | i-Bu | B |
| IIF-95 | 4-(tert-butyl)benzyl | Bnzl | i-Bu | A |
| IIF-96 | 4-(trifluoromethoxy)benzyl | Bnzl | i-Bu | B |
| IIF-97 | 4-ethoxybenzyl | Bnzl | i-Bu | C |
| IIF-101 | 4-hydroxybenzyl | Bnzl | i-Pnt | B |
| IIF-102 | Bnzl | naphthalen-2-ylmethyl | i-Bu | A |

TABLE 5-continued

| | | | | |
|---|---|---|---|---|
| IIF-103 | i-Pnt | 4-Cl-Bnzl | i-Bu | B |
| IIF-104 | i-Pnt | 4-fluorobenzyl | i-Bu | B |

Table. Anti-rabies activity of compounds of formula XXIIF

| Compound number | $R_1$ | $R_{2A}$ | $R_{2B}$ | $R_3$ | Anti-rabies activity |
|---|---|---|---|---|---|
| IIF-325 | i-Pnt | H | 3-Cl-Bnzl | Bnzl | A |
| IIF-326 | i-Pnt | H | 4-Cl-Bnzl | Bnzl | A |
| IIF-327 | i-Pnt | H | 4-F-Bnzl | Bnzl | A |
| IIF-328 | i-Pnt | H | 4-Me-Bnzl | Bnzl | A |
| IIF-329 | i-Pnt | H | 4-MeO-Bnzl | Bnzl | A |
| IIF-330 | i-Bu | H | 4-Cl-Bnzl | Ph-Et | A |
| IIF-331 | i-Bu | H | 3-Cl-Bnzl | Ph-Et | A |
| IIF-332 | i-Bu | H | 4-MeO-Bnzl | Ph-Et | A |
| IIF-333 | i-Bu | H | 4-Me-Bnzl | Ph-Et | A |
| IIF-334 | i-Bu | H | 2-Npm | Ph-Et | A |
| IIF-335 | i-Bu | H | Bnzl | Ph-Pr | A |
| IIF-336 | i-Bu | H | 3-Cl-Bnzl | Ph-Pr | A |
| IIF-337 | i-Bu | H | 3-F-Bnzl | Ph-Pr | A |
| IIF-338 | Cpm | H | 4-OH-Bnzl | 2-Cbx-Et | na |
| IIF-339 | i-Bu | H | 3-Me-Bnzl | Ph-Pr | A |
| IIF-340 | i-Bu | H | 3-MeO-Bnzl | Ph-Pr | A |
| IIF-341 | i-Bu | H | 3-Cl-Bnzl | Ph-Bu | A |
| IIF-342 | i-Bu | H | 3-F-Bnzl | Ph-Bu | A |
| IIF-343 | i-Bu | H | 3-Me-Bnzl | Ph-Bu | A |
| IIF-344 | i-Bu | H | 3-MeO-Bnzl | Ph-Bu | A |
| IIF-345 | i-Bu | H | Bnzl | Ph-Bu | A |
| IIF-346 | i-Pnt | H | 3-F-Bnzl | Ph-Pr | A |
| IIF-370 | i-Pnt | H | Ph-Et | Bnzl | A |
| IIF-371 | i-Pnt | H | 1-Npm | Bnzl | A |
| IIF-372 | i-Bu | H | 4-F-Bnzl | Ph-Et | A |
| IIF-373 | i-Bu | H | Ph-Et | Ph-Et | A |
| IIF-374 | i-Bu | H | 1-Npm | Ph-Et | A |
| IIF-376 | 4-F-Bnzl | H | 1-Npm | i-Bu | A |

Example 3: Efficacy in a Mouse Model of Rabies

In this example, it was tested whether the compound of the present disclosure is effective in a rabies mouse model.

(Materials and Methods)

Recombinant rabies virus 1088 strain expressing Red Firefly Luciferase (RFLuc) (1088/RFLuc) was generated by replacing the E2Cr gene of the recombinant virus 1088/E2Cr with the RFLuc gene (Isomura M, Yamada K, Noguchi K, Nishizono A. Near-infrared fluorescent protein iRFP720 is optimal for in vivo fluorescence imaging of rabies virus infection. J Gen Virol. 2017, 98(11): 2689-2698. doi: 10.1099/jgv.0.000950.). Hairless mice (Hos: HR-1, 6-week old, female; Hoshino Laboratory Animals) were inoculated with $1\times10^5$ infectious units of 1088/RFLuc intramuscularly into the right hindlimb and administered the test compound intraperitoneally for 6 days (Day 0 to Day 6), beginning 1 hour after inoculation. Actually, 0.5 mL of the solution (2% DMSO, 2% Solutol HS 15, and penicillin/streptomycin-added Dulbecco's phosphate buffered saline, available from Nacalai tesque, Sigma-Aldrich, etc.) supplemented with/without the compound (25 mg/kgBW) was administered twice daily with a 6-hour interval between doses. The inoculated mice were monitored for clinical signs and weighed everyday. The viral dynamics in the treated mice were observed longitudinally using in vivo imaging as follows; mice were administered D-Luciferin solution (150 mg/kgBW; Wako Pure Chemical Industry) intraperitoneally and then imaged (exposure time of 2 minutes and electron-multiplying gain of 300) with the Lumazone imaging system (Nippon Roper) under 2% isoflurane inhalation anesthesia after 15 minutes of substrate injection. The obtained images (16-bit TIFF) were processed and analysed using the ImageJ software. The compounds listed in Table 5 that were evaluated in Example 2 were tested as the test compounds.

(Results)

On days 6 and 8 after virus inoculation, the viral dynamics and the effect of the test compounds were observed in the mice, where the virus-driven luciferase luminescence served as an indicator. It was observed that the viral propagation and dissemination in the brain and spinal cord were significantly suppressed in three of four infected mice that were given the test compound at 50 mg/kgBW/day for 6 days (Days 0 to 5) compared to the solvent administered group, indicating that the antiviral effect of the test compounds on rabies virus was also confirmed in the infected mouse model. In other words, the compounds listed in Table 5 that were evaluated in Example 2 were confirmed to attain a significant therapeutic/prophylactic effect. For the nucleic acid analog drug favipiravir (product name: Avigan tablet/Toyama Chemical), which was confirmed to be effective on rabies virus, a significant prophylactic effect was confirmed in ddY mice given in a dose of 300 mg/kgBW/day, but not 100 mg/kgBW/day, for 7 days immediately after viral inoculation (Yamada K, Noguchi K, Komeno T, Furuta Y, Nishizono A. Efficacy of Favipiravir (T-705) in Rabies Postexposure Prophylaxis. J Infect Dis. 2016, 213(8): 1253-1261.doi:10.1093/infdis/jiv586.). Therefore, the present compound can be provided as a novel and highly effective rabies therapeutic agent that has a different mechanism of action from favipiravir.

Example 4: Anti-Cancer Cell Activity Evaluation Method

The minimum inhibitory concentration (MIC) with respect to cells was evaluated for compounds in Example 2 with which cell dealth of the host, i.e., mouse neuroblastoma cell strain Neuro-2A, was observed.

Each tested compound prepared as a 10 mM with DMSO was first diluted to 100 µM or 40 µM with 10% fetal bovine serum-supplemented medium, and further diluted with the medium to the final concentration of interest. Fifty microlitter of the diluted medium was added dropwise to each well of a 96-well plate. Furthermore, 50 µM of medium comprising $4 \times 10^2$ infectious units of 1088/GLuc and $4 \times 10^4$ Neuro-2a cells were added to each well. The plate was shaken for 30 seconds with the microplate mixer NS-4P and then cultured for 3 days at 37° C. in the presence of 5% $CO_2$. After incubation, 25 µL of coelenterazine was added dropwise to each well of the plate, and the plate was immediately loaded into the luminescent plate reader LuMate and shaken for 10 seconds. The relative light unit (RLU) was then measured, and entries in which a cell death caused due to virus infection were excluded.

The following tables show the results of evaluating the compounds. Some compounds were evaluated as a mixture as shown in the following tables. The compounds are classified as a if the minimum inhibitory concentration (MIC) is 10 µM or less, b if greater than 10 µM and less than or equal to 20 µM, and c if greater than 20 µM and less than or equal to 40 µM. The 'na' indicates not applicable.

TABLE 6

Table. Anti-cancer cell activity of compounds of formula XXIB
(a: MIC ≤ 10 µM, b: 10 µM < MIC ≤ 20 µM, c: 20 µM < MIC ≤ 40 µM)

| Compound number | $R_1$ | $R_{2A}$ | $R_{2B}$ | $R_3$ | $R_4$ | Anti-cancer cell activity |
|---|---|---|---|---|---|---|
| IB-924 | 4-Me-Bnzl | H | Bnzl | i-Bu | N-isobutylaminocarbonyl | na |
| IB-925 | i-Bu | H | 4-Cl-Bnzl | Ph-Et | H | c |
| IB-926 | i-Bu | H | 3-Cl-Bnzl | Ph-Et | H | b |
| IB-927 | i-Bu | H | 4-MeO-Bnzl | Ph-Et | H | c |
| IB-928 | i-Bu | H | 4-Me-Bnzl | Ph-Et | H | c |
| IB-929 | i-Bu | H | 2-Npm | Ph-Et | H | b |
| IB-930 | i-Bu | H | Bnzl | Ph-Pr | H | c |
| IB-931 | i-Bu | H | 3-Cl-Bnzl | Ph-Pr | H | c |
| IB-932 | i-Bu | H | 3-F-Bnzl | Ph-Pr | H | c |
| IB-933 | i-Bu | H | 3-Me-Bnzl | Ph-Pr | H | b |
| IB-934 | i-Bu | H | 3-MeO-Bnzl | Ph-Pr | H | b |
| IB-935 | i-Bu | H | 3-Cl-Bnzl | Ph-Bu | H | c |
| IB-936 | i-Bu | H | 3-F-Bnzl | Ph-Bu | H | b |
| IB-937 | i-Bu | H | 3-Me-Bnzl | Ph-Bu | H | c |
| IB-938 | i-Bu | H | 3-MeO-Bnzl | Ph-Bu | H | c |
| IB-939 | i-Bu | H | Bnzl | Ph-Bu | H | c |
| IB-940 | i-Pnt | H | 3-F-Bnzl | Ph-Pr | H | c |
| IB-957 | i-Bu | H | Ph-Et | Ph-Et | H | c |
| IB-958 | i-Bu | H | 1-Npm | Ph-Et | H | b |

Table. Anti-cancer cell activity of compounds of formula XXIF

| Compound number | $R_1$ | $R_{2A}$ | $R_{2B}$ | $R_3$ | $R_4$ | Anti-cancer cell activity |
|---|---|---|---|---|---|---|
| IF-885 | i-Bu | H | 4-Cl-Bnzl | Ph-Et | H | c |
| IF-886 | i-Bu | H | 3-Cl-Bnzl | Ph-Et | H | c |
| IF-887 | i-Bu | H | 4-MeO-Bnzl | Ph-Et | H | c |
| IF-888 | i-Bu | H | 4-Me-Bnzl | Ph-Et | H | na |
| IF-889 | i-Bu | H | 2-Npm | Ph-Et | H | b |
| IF-890 | i-Bu | H | Bnzl | Ph-Pr | H | c |
| IF-891 | i-Bu | H | 3-Cl-Bnzl | Ph-Pr | H | b |
| IF-892 | i-Bu | H | 3-F-Bnzl | Ph-Pr | H | c |
| IF-893 | i-Bu | H | 3-Me-Bnzl | Ph-Pr | H | c |
| IF-894 | i-Bu | H | 3-MeO-Bnzl | Ph-Pr | H | c |
| IF-895 | i-Bu | H | 3-Cl-Bnzl | Ph-Bu | H | b |
| IF-896 | i-Bu | H | 3-F-Bnzl | Ph-Bu | H | b |
| IF-897 | i-Bu | H | 3-Me-Bnzl | Ph-Bu | H | b |
| IF-898 | i-Bu | H | 3-MeO-Bnzl | Ph-Bu | H | c |
| IF-899 | i-Bu | H | Bnzl | Ph-Bu | H | c |
| IF-900 | i-Pnt | H | 3-F-Bnzl | Ph-Pr | H | c |
| IF-909 | i-Bu | H | Ph-Et | Ph-Et | H | na |

Table. Anti-cancer cell activity of compounds of formula XXIIB and formula XXIIF

| Compound number | $R_1$ | $R_{2A}$ | $R_{2B}$ | $R_3$ | Anti-cancer cell activity |
|---|---|---|---|---|---|
| Mixture of IIB-326 and IIF-325 | i-Pnt | H | 3-Cl-Bnzl | Bnzl | c |
| Mixture of IIB-327 and IIF-328 | i-Pnt | H | 4-Me-Bnzl | Bnzl | c |

TABLE 6-continued

| | | | | | |
|---|---|---|---|---|---|
| Mixture of IIB-328 and IIF-329 | i-Pnt | H | 4-MeO-Bnzl | Bnzl | na |
| IIB-329 | Me | H | quinolin-8-ylethyl | Bnzl | na |
| IIB-330 | Me | H | quinolin-5-ylethyl | Bnzl | na |
| IIB-331 | i-Bu | H | 4-Cl-Bnzl | Ph-Et | c |
| IIB-332 | i-Bu | H | 3-Cl-Bnzl | Ph-Et | b |
| IIB-333 | i-Bu | H | 4-MeO-Bnzl | Ph-Et | na |
| IIB-334 | i-Bu | H | 4-Me-Bnzl | Ph-Et | c |
| IIB-335 | i-Bu | H | 2-Npm | Ph-Et | c |
| IIB-336 | i-Bu | H | Bnzl | Ph-Pr | c |
| IIB-337 | i-Bu | H | 3-Cl-Bnzl | Ph-Pr | c |
| IIB-338 | i-Bu | H | 3-F-Bnzl | Ph-Pr | c |
| IIB-339 | Cpm | H | 4-OH-Bnzl | 2-Cbx-Et | na |
| IIB-340 | i-Bu | H | 3-Me-Bnzl | Ph-Pr | c |
| IIB-341 | i-Bu | H | 3-MeO-Bnzl | Ph-Pr | c |
| IIB-342 | i-Bu | H | 3-Cl-Bnzl | Ph-Bu | b |
| IIB-343 | i-Bu | H | 3-F-Bnzl | Ph-Bu | c |
| IIB-344 | i-Bu | H | 3-Me-Bnzl | Ph-Bu | b |
| IIB-345 | i-Bu | H | 3-MeO-Bnzl | Ph-Bu | c |
| IIB-346 | i-Bu | H | Bnzl | Ph-Bu | b |
| IIB-347 | i-Pnt | H | 3-F-Bnzl | Ph-Pr | c |
| Mixture of IIB-371 and IIF-327 | i-Pnt | H | 4-F-Bnzl | Bnzl | b |
| Mixture of IIB-372 and IIF-370 | i-Pnt | H | Ph-Et | Bnzl | na |
| Mixture of IIB-373 and IIF-371 | i-Pnt | H | 1-Npm | Bnzl | c |
| IIB-374 | i-Bu | H | 4-F-Bnzl | Ph-Et | c |
| IIB-375 | i-Bu | H | Ph-Et | Ph-Et | na |
| IIB-376 | i-Bu | H | 1-Npm | Ph-Et | c |
| IIB-378 | 4-F-Bnzl | H | 1-Npm | i-Bu | b |
| IIF-326 | i-Pnt | H | 4-Cl-Bnzl | Bnzl | b |
| IIF-330 | i-Bu | H | 4-Cl-Bnzl | Ph-Et | c |
| IIF-331 | i-Bu | H | 3-Cl-Bnzl | Ph-Et | c |
| IIF-332 | i-Bu | H | 4-MeO-Bnzl | Ph-Et | na |
| IIF-333 | i-Bu | H | 4-Me-Bnzl | Ph-Et | c |
| IIF-334 | i-Bu | H | 2-Npm | Ph-Et | c |
| IIF-335 | i-Bu | H | Bnzl | Ph-Pr | na |
| IIF-336 | i-Bu | H | 3-Cl-Bnzl | Ph-Pr | c |
| IIF-337 | i-Bu | H | 3-F-Bnzl | Ph-Pr | b |
| IIF-338 | Cpm | H | 4-OH-Bnzl | 2-Cbx-Et | na |
| IIF-339 | i-Bu | H | 3-Me-Bnzl | Ph-Pr | c |
| IIF-340 | i-Bu | H | 3-MeO-Bnzl | Ph-Pr | na |
| IIF-341 | i-Bu | H | 3-Cl-Bnzl | Ph-Bu | b |
| IIF-342 | i-Bu | H | 3-F-Bnzl | Ph-Bu | c |
| IIF-343 | i-Bu | H | 3-Me-Bnzl | Ph-Bu | c |
| IIF-344 | i-Bu | H | 3-MeO-Bnzl | Ph-Bu | c |
| IIF-345 | i-Bu | H | Bnzl | Ph-Bu | c |
| IIF-346 | i-Pnt | H | 3-F-Bnzl | Ph-Pr | c |
| IIF-372 | i-Bu | H | 4-F-Bnzl | Ph-Et | c |
| IIF-373 | i-Bu | H | Ph-Et | Ph-Et | c |
| IIF-374 | i-Bu | H | 1-Npm | Ph-Et | c |
| IIF-376 | 4-F-Bnzl | H | 1-Npm | i-Bu | c |

[Note]

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application is a continuation-in-part application that claims priority to Japanese Patent Application No. 2018-153227 filed on Aug. 16, 2018 and International Publication No. PCT/JP2019/032032 filed on Aug. 15, 2019 with the Japan Patent Office. The entire content thereof is incorporated herein by reference.

INDUSTRIAL APPLICABILITY

The present disclosure is useful in the field of rabies and cancer treatment and prophylaxis.

The invention claimed is:
1. A compound represented by formula XXIIF:

[Chemical Formula 53]

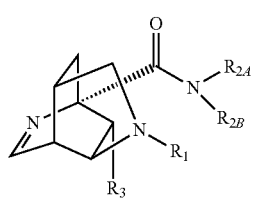

Formula XXIIF or formula XXIIB

[Chemical Formula 54]

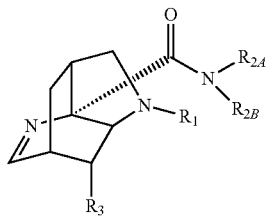

Formula XXIIB or an enantiomer thereof, or a salt thereof, or a solvate thereof, wherein,
$R_1$ and $R_3$ are each independently,
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl,
$R_{2A}$ and $R_{2B}$ are each independently,
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl, or
$R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

2. The compound or an enantiomer thereof, or a salt thereof,
or a solvate thereof according to claim 1, wherein
the alkyl, alkenyl, alkynyl, cycloalkyl, heterocycloalkyl, aryl, heteroaryl, and carbonyl of $R_1$ and $R_3$ are each independently and optionally substituted with one to the maximum substitutable number of the same or different substituents selected from substituent group I, and
the alkyl, alkenyl, alkynyl, cycloalkyl, heterocycloalkyl, aryl, heteroaryl, and carbonyl, and the non-aryl heterocycle and the heteroaryl ring of $R_{2A}$ and $R_{2B}$ are each independently and optionally substituted with one to the maximum substitutable number of the same or different substituents selected from substituent group I;
wherein substituent group I consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, unsubstituted or substituted alkyl, unsubstituted or substituted alkenyl, unsubstituted or substituted alkynyl, unsubstituted or substituted aryl, unsubstituted or substituted cycloalkyl, unsubstituted or substituted heteroaryl, unsubstituted or substituted heterocycloalkyl, unsubstituted or substituted alkyloxy, unsubstituted or substituted alkenyloxy, unsubstituted or substituted alkynyloxy, unsubstituted or substituted aryl-Lx-oxy, unsubstituted or substituted cycloalkyl-Lx-oxy, unsubstituted or substituted heteroaryl-Lx-oxy, unsubstituted or substituted heterocycloalkyl-Lx-oxy, unsubstituted or substituted alkyloxyalkyl, unsubstituted or substituted alkenyloxyalkyl, unsubstituted or substituted alkynyloxyalkyl, unsubstituted or substituted aryloxyalkyl, unsubstituted or substituted cycloalkyloxyalkyl, unsubstituted or substituted heteroaryloxyalkyl, unsubstituted or substituted heterocycloalkyloxyalkyl, unsubstituted or substituted alkyloxyalkyloxy, unsubstituted or substituted alkenyloxyalkyloxy, unsubstituted or substituted alkynyloxyalkyloxy, unsubstituted or substituted aryloxyalkyloxy, unsubstituted or substituted cycloalkyloxyalkyloxy, unsubstituted or substituted heteroaryloxyalkyloxy, unsubstituted or substituted heterocycloalkyloxyalkyloxy, unsubstituted or substituted alkylcarbonyl, unsubstituted or substituted alkenylcarbonyl, unsubstituted or substituted alkynylcarbonyl, unsubstituted or substituted aryl-Lx-carbonyl, unsubstituted or substituted cycloalkyl-Lx-carbonyl, unsubstituted or substituted heteroaryl-Lx-carbonyl, unsubstituted or substituted heterocycloalkyl-Lx-carbonyl, unsubstituted or substituted alkylcarbonyloxy, unsubstituted or substituted alkenylcarbonyloxy, unsubstituted or substituted alkynylcarbonyloxy, unsubstituted or substituted aryl-Lx-carbonyloxy, unsubstituted or substituted cycloalkyl-Lx-carbonyloxy, unsubstituted or substituted heteroaryl-Lx-carbonyloxy, unsubstituted or substituted heterocycloalkyl-Lx-carbonyloxy, unsubstituted or substituted alkylcarbonylamino, unsubstituted or substituted alkenylcarbonylamino, unsubstituted or substituted alkynylcarbonylamino, unsubstituted or substituted aryl-Lx-carbonylamino, unsubstituted or substituted cycloalkyl-Lx-carbonylamino, unsubstituted or substituted heteroaryl-Lx-carbonylamino, unsubstituted or substituted heterocycloalkyl-Lx-carbonylamino, unsubstituted or substituted alkylcarbonylthio, unsubstituted or substituted alkenylcarbonylthio, unsubstituted or substituted alkynylcarbonylthio, unsubstituted or substituted aryl-Lx-carbonylthio, unsubstituted or substituted cycloalkyl-Lx-carbonylthio, unsubstituted or substituted heteroaryl-Lx-carbonylthio, unsubstituted or substituted heterocycloalkyl-Lx-carbonylthio, unsubstituted or substituted alkylcarbonylimino, unsubstituted or substituted alkenylcarbonylimino, unsubstituted or substituted alkynylcarbonylimino, unsubstituted or substituted aryl-Lx-carbonylimino, unsubstituted or substituted cycloalkyl-Lx-carbonylimino, unsubstituted or substituted heteroaryl-Lx-carbonylimino, unsubstituted or substituted heterocycloalkyl-Lx-carbonylimino, unsubstituted or substituted alkylthio, unsubstituted or substituted alkenylthio, unsubstituted or substituted alkynylthio, unsubstituted or substituted aryl-Lx-thio, unsubstituted or substituted cycloalkyl-Lx-thio, unsubstituted or substituted heteroaryl-Lx-thio, unsubstituted or substituted heterocycloalkyl-Lx-thio, unsubstituted or substituted alkylamino, unsubstituted or substituted alkenylamino, unsubstituted or substituted alkynylamino, unsubstituted or substituted alkynylamino, unsubstituted or substituted aryl-Lx-amino, unsubstituted or substituted cycloalkyl-Lx-amino, unsubstituted or substituted heteroaryl-Lx-amino, unsubstituted or substituted heterocycloalkyl-Lx-amino, unsubstituted or substituted alkylsulfonyl, unsubstituted or substituted alkenylsulfonyl, unsubstituted or substituted alkynylsulfonyl, unsubstituted or substituted aryl-Lx-sulfonyl, unsubstituted or substituted cycloalkyl-Lx-sulfonyl, unsubstituted or substituted heteroaryl-Lx-sulfonyl, unsubstituted or substituted heterocycloalkyl-Lx-sulfonyl, unsubstituted or substituted alkylsulfonylamino, unsubstituted or substituted alkenylsulfonylamino, unsubstituted or substituted alkynylsulfonylamino, unsubstituted or substituted aryl-Lx-sulfonylamino, unsubstituted or substituted cycloalkyl-Lx-sulfonylamino, unsubstituted or substituted heteroaryl-Lx-sulfonylamino, unsubstituted or substituted heterocycloalkyl-Lx-sulfonylamino, unsubstituted or substituted alkylimino, unsubstituted or substituted alkenylimino, unsubstituted or substituted alkynylimino, unsubstituted or substituted aryl-Lx-imino, unsubstituted or substituted cycloalkyl-Lx-imino, unsubstituted or substituted heteroaryl-Lx-imino, unsubstituted or substituted heterocycloalkyl-Lx-imino, unsubstituted or substituted alkyloxyimino, unsubstituted or substituted alkenyloxyimino, unsubstituted or substituted alkynyloxyimino, unsubstituted or substituted aryl-Lx-oxyimino, unsubstituted or substituted cycloalkyl-Lx-oxyimino, unsubstituted or substituted heteroaryl-Lx-oxyimino, unsubstituted or substituted heterocycloalkyl-Lx-oxyimino, unsubstituted or substituted alkyloxycarbonyl, unsubstituted or substituted alkenyloxycarbonyl, unsubstituted or substituted alkynyloxycarbonyl, unsubstituted or substituted aryl-Lx-oxycarbonyl, unsubstituted or substituted cycloalkyl-Lx-oxycarbonyl, unsubstituted or substituted heteroaryl-Lx-oxycarbonyl, unsubstituted or substituted heterocycloalkyl-Lx-oxycarbonyl, unsubstituted or substituted alkyloxycarbonylamino, unsubstituted or substituted alkenyloxycarbonylamino, unsubstituted or substituted alkynyloxycarbonylamino, unsubstituted or substituted aryl-Lx-oxycarbonylamino, unsubstituted or substituted cycloalkyl-Lx-oxycarbonylamino, unsubstituted or substituted heteroaryl-Lx-oxycarbonylamino, unsubstituted or substituted heterocycloalkyl-Lx-oxycarbonylamino, unsubstituted or substituted alkylsulfanyl, unsubstituted or substituted alkenylsulfanyl, unsubstituted or substituted alkynylsulfanyl, unsubstituted or substituted aryl-Lx-sulfanyl, unsubstituted or substituted cycloalkyl-Lx-sulfanyl, unsubstituted or substituted heteroaryl-Lx-sulfanyl, unsubstituted or substituted heterocycloalkyl-Lx-sulfanyl, unsubstituted or substituted alkylsulfinyl, unsubstituted or substituted alkenylsulfinyl, unsubstituted or substituted alkynylsulfinyl, unsubstituted or substituted aryl-Lx-sulfinyl, unsubstituted or substituted cycloalkyl-Lx-sulfinyl, unsubstituted or substituted heteroaryl-Lx-sulfinyl, unsubstituted or substituted heterocycloalkyl-Lx-sulfinyl, unsubstituted or substituted alkylcarbamoyl, unsubstituted or substituted alkenylcarbamoyl, unsubstituted or substituted alkynylcarbamoyl, unsubstituted or substituted aryl-Lx-carbamoyl, unsubstituted or substituted cycloalkyl-Lx-carbamoyl, unsubstituted or substituted heteroaryl-Lx-carbamoyl, unsubstituted or substituted heterocycloalkyl-Lx-carbamoyl, unsubstituted or substituted alkylsulfamoyl, unsubstituted or substituted alkenylsulfamoyl, unsubstituted or substituted alkynylsulfamoyl, unsubstituted or substituted aryl-Lx-sulfamoyl, unsubstituted or substituted cycloalkyl-Lx-sulfamoyl, unsubstituted or substituted heteroaryl-Lx-sulfamoyl, and unsubstituted or substituted heterocycloalkyl-Lx-sulfamoyl, wherein Lx is a single bond or unsubstituted or substituted alkylene, wherein the substituted alkyl, substituted alkenyl, substituted alkynyl, substituted aryl, substituted cycloalkyl, substituted heteroaryl, substituted heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, alkyl, alkenyl, alkynyl, aryl, cycloalkyl, heteroaryl, heterocycloalkyl, alkyloxy, alkenyloxy, alkynyloxy, aryl-Lx-oxy, cycloalkyl-Lx-oxy, heteroaryl-Lx-oxy, heterocycloalkyl-Lx-oxy, alkyloxyalkyl, alkenyloxyalkyl, alkynyloxyalkyl, aryloxyalkyl, cycloalkyloxyalkyl, heteroaryloxyalkyl, heterocycloalkyloxyalkyl, alkyloxyalkyloxy, alkenyloxyalkyloxy, alkynyloxyalkyloxy, aryloxyalkyloxy, cycloalkyloxyalkyloxy, heteroaryloxyalkyloxy, heterocycloalkyloxyalkyloxy, alkylcarbonyl, alkenylcarbonyl, alkynylcarbonyl, aryl-Lx-carbonyl, cycloalkyl-Lx-carbonyl, heteroaryl-Lx-carbonyl, heterocycloalkyl-Lx-carbonyl, alkylcarbonyloxy, alkenylcarbonyloxy, alkynylcarbonyloxy, aryl-Lx-carbonyloxy, cycloalkyl-Lx-carbonyloxy, heteroaryl-Lx-carbonyloxy, heterocycloalkyl-Lx-carbonyloxy, alkylcarbonylamino, alkenylcarbonylamino, alkynylcarbonylamino, aryl-Lx-carbonylamino, cycloalkyl-Lx-carbonylamino, heteroaryl-Lx-carbonylamino, heterocycloalkyl-Lx-carbonylamino, alkylcarbonylthio, alkenylcarbonylthio, alkynylcarbonylthio, aryl-Lx-carbonylthio, cycloalkyl-Lx-carbonylthio, heteroaryl-Lx-carbonylthio, heterocycloalkyl-Lx-carbonylthio, alkylcarbonylimino, alkenylcarbonylimino, alkynylcarbonylimino, aryl-Lx-carbonylimino, cycloalkyl-Lx-carbonylimino, heteroaryl-Lx-carbonylimino, heterocycloalkyl-Lx-carbonylimino, alkylthio, alkenylthio, alkynylthio, aryl-Lx-thio, cycloalkyl-Lx-thio, heteroaryl-Lx-thio, heterocycloalkyl-Lx-thio, alkylamino, alkenylamino, alkynylamino, alkynylamino, aryl-Lx-amino, cycloalkyl-Lx-amino, heteroaryl-Lx-amino, heterocycloalkyl-Lx-amino, alkylsulfonyl, alkenylsulfonyl, alkynylsulfonyl, aryl-Lx-sulfonyl, cycloalkyl-Lx-sulfonyl, heteroaryl-Lx-sulfonyl, heterocycloalkyl-Lx-sulfonyl, alkylsulfonylamino, alkenylsulfonylamino, alkynylsulfonylamino, aryl-Lx-sulfonylamino, cycloalkyl-Lx-sulfonylamino, heteroaryl-Lx-sulfonylamino, heterocycloalkyl-Lxsulfonylamino, alkylimino, alkenylimino, alkynylimino, aryl-Lx-imino, cycloalkyl-Lx-imino, heteroaryl-Lx-imino, heterocycloalkyl-Lx-imino, alkyloxyimino, alkenyloxyimino, alkynyloxyimino, aryl-Lx-oxyimino, cycloalkyl-Lx-oxyimino, heteroaryl-Lx-oxyimino, heterocycloalkyl-Lx-oxyimino, alkyloxycarbonyl, alkenyloxycarbonyl, alkynyloxycarbonyl, aryl-Lx-oxycarbonyl, cycloalkyl-Lx-oxycarbonyl, heteroaryl-Lx-oxycarbonyl, heterocycloalkyl-Lx-oxycarbonyl, alkyloxycarbonylamino, alkenyloxycarbonylamino, alkynyloxycarbonylamino, aryl-Lx-oxycarbonylamino, cycloalkyl-Lx-oxycarbonylamino, heteroaryl-Lx-oxycarbonylamino, heterocycloalkyl-Lx-oxycarbonylamino, alkylsulfanyl, alkenylsulfanyl, alkynylsulfanyl, aryl-Lx-sulfanyl, cycloalkyl-Lx-sulfanyl, heteroaryl-Lx-sulfanyl, heterocycloalkyl-Lx-sulfanyl, alkylsulfinyl, alkenylsulfinyl, alkynylsulfinyl, aryl-Lx-sulfinyl, cycloalkyl-Lx-sulfinyl, heteroaryl-Lx-sulfinyl, heterocycloalkyl-Lx-sulfinyl, alkylcarbamoyl, alkenylcarbamoyl, alkynylcarbamoyl, aryl-Lx-carbamoyl, cycloalkyl-Lx-carbamoyl, heteroaryl-Lx-carbamoyl, heterocycloalkyl-Lx-carbamoyl, alkylsulfamoyl, alkenylsulfamoyl, alkynylsulfamoyl, aryl-Lx-sulfamoyl, cycloalkyl-Lx-sulfamoyl, heteroaryl-Lx-sulfamoyl, and heterocycloalkyl-Lx-sulfamoyl.

3. A compound represented by formula XXIIF:

[Chemical Formula 53]

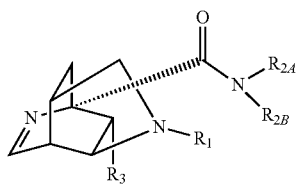

Formula XXIIF or formula XXIIB

[Chemical Formula 54]

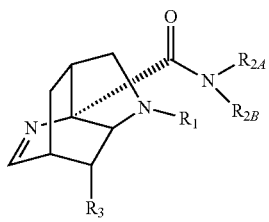

Formula XXIIB or an enantiomer thereof, or a salt thereof, or a solvate thereof, wherein
$R_1$ and $R_3$ are each independently,
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, and $R_{2A}$ and $R_{2B}$ are each independently,
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, or
$R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

4. The compound or an enantiomer thereof, or a salt thereof,
or a solvate thereof according to claim 1, wherein
$R_1$ and $R_3$ are each independently,
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$ and $R_3$ are optionally substituted with one to the maximum substitutable number of the same or different substituents selected from substituent group II, and
$R_{2A}$ and $R_{2B}$ are each independently,
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl, wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, forms a 5- to 6-membered non-aryl heterocycle, wherein the non-aryl heterocycle is optionally substituted with one to the maximum substitutable number of the same or different substituents selected from substituent group II;

wherein substituent group II consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, unsubstituted or substituted $C_{1-12}$ alkyl, unsubstituted or substituted $C_{2-12}$ alkenyl, unsubstituted or substituted $C_{2-12}$ alkynyl, unsubstituted or substituted $C_{6-10}$ aryl, unsubstituted or substituted $C_{3-10}$ cycloalkyl, unsubstituted or substituted 5- to 10-membered heteroaryl, unsubstituted or substituted 5- to 10-membered heterocycloalkyl, unsubstituted or substituted $C_{1-12}$ alkyloxy, unsubstituted or substituted $C_{2-12}$ alkenyloxy, unsubstituted or substituted $C_{2-12}$ alkynyloxy, unsubstituted or substituted $C_{6-10}$ aryl-Lx-oxy, unsubstituted or substituted $C_{3-10}$ cycloalkyl-Lx-oxy, unsubstituted or substituted 5- to 10-membered heteroaryl-Lx-oxy, unsubstituted or substituted 5- to 10-membered heterocycloalkyl-Lx-oxy, unsubstituted or substituted $C_{1-12}$ alkyloxy $C_{1-12}$ alkyl, unsubstituted or substituted $C_{2-12}$ alkenyloxy $C_{1-12}$ alkyl, unsubstituted or substituted $C_{2-12}$ alkynyloxy $C_{1-12}$ alkyl, unsubstituted or substituted $C_{6-10}$ aryloxy $C_{1-12}$ alkyl, unsubstituted or substituted $C_{3-10}$ cycloalkyloxy $C_{1-12}$ alkyl, unsubstituted or substituted 5- to 10-membered heteroaryloxy $C_{1-12}$ alkyl, unsubstituted or substituted 5- to 10-membered heterocycloalkyloxy $C_{1-12}$ alkyl, unsubstituted or substituted $C_{1-12}$ alkyloxy $C_{1-12}$ alkyloxy, unsubstituted or substituted $C_{2-12}$ alkenyloxy $C_{1-12}$ alkyloxy, unsubstituted or substituted $C_{2-12}$ alkynyloxy $C_{1-12}$ alkyloxy, unsubstituted or substituted $C_{6-10}$ aryloxy $C_{1-12}$ alkyloxy, unsubstituted or substituted $C_{3-10}$ cycloalkyloxy $C_{1-12}$ alkyloxy, unsubstituted or substituted 5- to 10-membered heteroaryloxy $C_{1-12}$ alkyloxy, unsubstituted or substituted 5- to 10-membered heterocycloalkyloxy $C_{1-12}$ alkyloxy, unsubstituted or substituted $C_{1-12}$ alkylcarbonyl, unsubstituted or substituted $C_{2-12}$ alkenylcarbonyl, unsubstituted or substituted $C_{2-12}$ alkynylcarbonyl, unsubstituted or substituted $C_{6-10}$ aryl-Lx-carbonyl, unsubstituted or substituted $C_{3-10}$ cycloalkyl-Lx-carbonyl, unsubstituted or substituted 5- to 10-membered heteroaryl-Lx-carbonyl, unsubstituted or substituted 5- to 10-membered heterocycloalkyl-Lx-carbonyl, unsubstituted or substituted $C_{1-12}$ alkylcarbonyloxy, unsubstituted or substituted $C_{2-12}$ alkenylcarbonyloxy, unsubstituted or substituted $C_{2-12}$ alkynylcarbonyloxy, unsubstituted or substituted $C_{6-10}$ aryl-Lx-carbonyloxy, unsubstituted or substituted $C_{3-10}$ cycloalkyl-Lx-carbonyloxy, unsubstituted or substituted 5- to 10-membered heteroaryl-Lx-carbonyloxy, unsubstituted or substituted 5- to 10-membered heterocycloalkyl-Lx-carbonyloxy, unsubstituted or substituted $C_{1-12}$ alkylcarbonylamino, unsubstituted or substituted $C_{2-12}$ alkenylcarbonylamino, unsubstituted or substituted $C_{2-12}$ alkynylcarbonylamino, unsubstituted or substituted $C_{6-10}$ aryl-Lx-carbonylamino, unsubstituted or substituted $C_{3-10}$ cycloalkyl-Lx-carbonylamino, unsubstituted or substituted 5- to 10-membered heteroaryl-Lx-carbonylamino, unsubstituted or substituted 5- to 10-membered heterocycloalkyl-Lx-carbonylamino, unsubstituted or substituted $C_{1-12}$ alkylcarbonylthio, unsubstituted or substituted $C_{2-12}$ alkenylcarbonylthio, unsubstituted or substituted $C_{2-12}$ alkynylcarbonylthio, unsubstituted or substituted $C_{6-10}$ aryl-Lx-carbonylthio, unsubstituted or substituted $C_{3-10}$ cycloalkyl-Lx-carbonylthio, unsubstituted or substituted 5- to 10-membered heteroaryl-Lx-carbonylthio, unsubstituted or substituted 5- to 10-membered heterocycloalkyl-Lx-carbonylthio, unsubstituted or substituted $C_{1-12}$ alkylcarbonylimino, unsubstituted or substituted $C_{2-12}$ alkenylcarbonylimino, unsubstituted or substituted $C_{2-12}$ alkynylcarbonylimino, unsubstituted or substituted $C_{6-10}$ aryl-Lx-carbonylimino, unsubstituted or substituted $C_{3-10}$ cycloalkyl-Lx-carbonylimino, unsubstituted or substituted 5- to 10-membered heteroaryl-Lx-carbonylimino, unsubstituted or substituted 5- to 10-membered heterocycloalkyl-Lx-carbonylimino, unsubstituted or substituted $C_{1-12}$ alkylthio, unsubstituted or substituted $C_{2-12}$ alkenylthio, unsubstituted or substituted $C_{2-12}$ alkynylthio, unsubstituted or substituted $C_{6-10}$ aryl-Lx-thio, unsubstituted or substituted $C_{3-10}$ cycloalkyl-Lx-thio, unsubstituted or substituted 5- to 10-membered heteroaryl-Lx-thio, unsubstituted or substituted 5- to 10-membered heterocycloalkyl-Lx-thio, unsubstituted or substituted $C_{1-12}$ alkylamino, unsubstituted or substituted $C_{2-12}$ alkenylamino, unsubstituted or substituted $C_{2-12}$ alkynylamino, unsubstituted or substituted $C_{2-12}$ alkynylamino, unsubstituted or substituted $C_{6-10}$ aryl-Lx-amino, unsubstituted or substituted $C_{3-10}$ cycloalkyl-Lx-amino, unsubstituted or substituted 5- to 10-membered heteroaryl-Lx-amino, unsubstituted or substituted 5- to 10-membered heterocycloalkyl-Lx-amino, unsubstituted or substituted $C_{1-12}$ alkylsulfonyl, unsubstituted or substituted $C_{2-12}$ alkenylsulfonyl, unsubstituted or substituted $C_{2-12}$ alkynylsulfonyl, unsubstituted or substituted $C_{6-10}$ aryl-Lx-sulfonyl, unsubstituted or substituted $C_{3-10}$ cycloalkyl-Lx-sulfonyl, unsubstituted or substituted 5- to 10-membered heteroaryl-Lx-sulfonyl, unsubstituted or substituted 5- to 10-membered heterocycloalkyl-Lx-sulfonyl, unsubstituted or substituted $C_{1-12}$ alkylsulfonylamino, unsubstituted or substituted $C_{2-12}$ alkenylsulfonylamino, unsubstituted or substituted $C_{2-12}$ alkynylsulfonylamino, unsubstituted or substituted $C_{6-10}$ aryl-Lx-sulfonylamino, unsubstituted or substituted $C_{3-10}$ cycloalkyl-Lx-sulfonylamino, unsubstituted or substituted 5- to 10-membered heteroaryl-Lx-sulfonylamino, unsubstituted or substituted 5- to 10-membered heterocycloalkyl-Lx-sulfonylamino, unsubstituted or substituted $C_{1-12}$ alkylimino, unsubstituted or substituted $C_{2-12}$ alkenylimino, unsubstituted or substituted $C_{2-12}$ alkynylimino, unsubstituted or substituted $C_{6-10}$ aryl-Lx-imino, unsubstituted or substituted $C_{3-10}$ cycloalkyl-Lx-imino, unsubstituted or substituted 5- to 10-membered heteroaryl-Lx-imino, unsubstituted or substituted 5- to 10-membered heterocycloalkyl-Lx-imino, unsubstituted or substituted $C_{1-12}$ alkyloxyimino, unsubstituted or substituted $C_{2-12}$ alkenyloxyimino, unsubstituted or substituted $C_{2-12}$ alkynyloxyimino, unsubstituted or substituted $C_{6-10}$ aryl-Lx-oxyimino, unsubstituted or substituted $C_{3-10}$ cycloalkyl-Lx-oxyimino, unsubstituted or substituted 5- to 10-membered heteroaryl-Lx-oxyimino, unsubstituted or substituted 5- to 10-membered heterocycloalkyl-Lx-oxyimino, unsubstituted or substituted $C_{1-12}$ alkyloxycarbonyl, unsubstituted or substituted $C_{2-12}$ alkenyloxycarbonyl, unsubstituted or substituted $C_{2-12}$ alkynyloxycarbonyl, unsubstituted or substituted $C_{6-10}$ aryl-Lx-oxycarbonyl, unsubstituted or substituted $C_{3-10}$ cycloalkyl-Lx-oxycarbonyl, unsubstituted or substituted 5- to 10-membered heteroaryl-Lx-oxycarbonyl, unsubstituted or substituted 5- to 10-membered heterocycloalkyl-Lx-oxycarbonyl, unsubstituted or substituted $C_{1-12}$ alkyloxycarbonylamino, unsubstituted or substituted $C_{2-12}$ alkenyloxycarbonylamino, unsubstituted or substituted $C_{2-12}$ alkynyloxycarbonylamino, unsubstituted or substituted $C_{6-10}$ aryl-Lx-oxycarbonylamino, unsubstituted or substituted $C_{3-10}$ cycloalkyl-Lx-oxycarbonylamino, unsubstituted or substituted 5- to 10-membered heteroaryl-Lx-oxycarbonylamino, unsubstituted or substituted 5- to 10-membered heterocycloalkyl-Lx-oxycarbonylamino, unsubstituted or substituted $C_{1-12}$ alkylsulfanyl, unsubstituted or substituted $C_{2-12}$ alkenylsulfanyl, unsubstituted or substituted $C_{2-12}$ alkynylsulfanyl, unsubstituted or substituted $C_{6-10}$ aryl-Lx-sulfanyl, unsubstituted or substituted $C_{3-10}$ cycloalkyl-Lx-sulfanyl, unsubstituted or substituted 5- to 10-membered heteroaryl-Lx-sulfanyl, unsubstituted or substituted 5- to 10-membered heterocycloalkyl-Lx-sulfanyl, unsubstituted or substituted $C_{1-12}$ alkylsulfinyl, unsubstituted or substituted $C_{2-12}$ alkenylsulfinyl, unsubstituted or substituted $C_{2-12}$ alkynylsulfinyl, unsubstituted or substituted $C_{6-10}$ aryl-Lx-sulfinyl, unsubstituted or substituted $C_{3-10}$ cycloalkyl-Lx-sulfinyl, unsubstituted or substituted 5- to 10-membered heteroaryl-Lx-sulfinyl, unsubstituted or substituted 5- to 10-membered heterocycloalkyl-Lx-sulfinyl, unsubstituted or substituted $C_{1-12}$ alkylcarbamoyl, unsubstituted or substituted $C_{2-12}$ alkenylcarbamoyl, unsubstituted or substituted $C_{2-12}$ alkynylcarbamoyl, unsubstituted or substituted $C_{6-10}$ aryl-Lx-carbamoyl, unsubstituted or substituted $C_{3-10}$ cycloalkyl-Lx-carbamoyl, unsubstituted or substituted 5- to 10-membered heteroaryl-Lx-carbamoyl, unsubstituted or substituted 5- to 10-membered heterocycloalkyl-Lx-carbamoyl, unsubstituted or substituted $C_{1-12}$ alkylsulfamoyl, unsubstituted or substituted $C_{2-12}$ alkenylsulfamoyl, unsubstituted or substituted $C_{2-12}$ alkynylsulfamoyl, unsubstituted or substituted $C_{6-10}$ aryl-Lx-sulfamoyl, unsubstituted or substituted $C_{3-10}$ cycloalkyl-Lx-sulfamoyl, unsubstituted or substituted 5- to 10-membered heteroaryl-Lx-sulfamoyl, and unsubstituted or substituted 5- to 10-membered heterocycloalkyl-Lx-sulfamoyl, wherein Lx is a single bond or unsubstituted or substituted $C_{1-12}$ alkylene, wherein the substituted $C_{1-12}$ alkyl, substituted $C_{2-12}$ alkenyl, substituted $C_{2-12}$ alkynyl, substituted $C_{6-10}$ aryl, substituted $C_{3-10}$ cycloalkyl, substituted 5- to 10-membered heteroaryl, substituted 5- to 10-membered heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, amidinoamino, $C_{1-12}$ alkyl, $C_{1-12}$ haloalkyl, $C_{2-12}$ alkenyl, $C_{2-12}$ alkynyl, $C_{6-10}$ aryl, $C_{3-10}$ cycloalkyl, 5- to 10-membered heteroaryl, 5- to 10-membered heterocycloalkyl, $C_{1-12}$ alkyloxy, $C_{1-12}$ haloalkyloxy, $C_{2-12}$ alkenyloxy, $C_{2-12}$ alkynyloxy, $C_{6-10}$ aryl-Lx-oxy, $C_{3-10}$ cycloalkyl-Lx-oxy, 5- to 10-membered heteroaryl-Lx-oxy, 5- to 10-membered heterocycloalkyl-Lx-oxy, $C_{1-12}$ alkyloxyalkyl, $C_{2-12}$ alkenyloxyalkyl, $C_{2-12}$ alkynyloxyalkyl, $C_{6-10}$ aryloxyalkyl, $C_{3-10}$ cycloalkyloxyalkyl, 5- to 10-membered heteroaryloxyalkyl, 5- to 10-membered heterocycloalkyloxyalkyl, $C_{1-12}$ alkyloxyalkyloxy, $C_{2-12}$ alkenyloxyalkyloxy, $C_{2-12}$ alkynyloxyalkyloxy, $C_{6-10}$ aryloxyalkyloxy, $C_{3-10}$ cycloalkyloxyalkyloxy, 5- to 10-membered heteroaryloxyalkyloxy, 5- to 10-membered heterocycloalkyloxyalkyloxy, $C_{1-12}$ alkylcarbonyl, $C_{2-12}$ alkenylcarbonyl, $C_{2-12}$ alkynylcarbonyl, $C_{6-10}$ aryl-Lx-carbonyl, $C_{3-10}$ cycloalkyl-Lx-carbonyl, 5- to 10-membered heteroaryl-Lx-carbonyl, 5- to 10-membered heterocycloalkyl-Lx-carbonyl, $C_{1-12}$ alkylcarbonyloxy, $C_{2-12}$ alkenylcarbonyloxy, $C_{2-12}$ alkynylcarbonyloxy, $C_{6-10}$ aryl-Lx-carbonyloxy, $C_{3-10}$ cycloalkyl-Lx-carbonyloxy, 5- to 10-membered heteroaryl-Lx-carbonyloxy, 5- to 10-membered heterocycloalkyl-Lx-carbonyloxy, $C_{1-12}$ alkylcarbonylamino, $C_{2-12}$ alkenylcarbonylamino, $C_{2-12}$ alkynylcarbonylamino, $C_{6-10}$ aryl-Lx-carbonylamino, $C_{3-10}$ cycloalkyl-Lx-carbonylamino, 5- to 10-membered heteroaryl-Lx-carbonylamino, 5- to 10-membered heterocycloalkyl-Lx-carbonylamino, $C_{1-12}$ alkylcarbonylthio, $C_{2-12}$ alkenylcarbonylthio, $C_{2-12}$ alkynylcarbonylthio, $C_{6-10}$ aryl-Lx-carbonylthio, $C_{3-10}$ cycloalkyl-Lx-carbonylthio, 5- to 10-membered heteroaryl-Lx-carbonylthio, 5- to 10-membered heterocycloalkyl-Lx-carbonylthio, $C_{1-12}$ alkylcarbonylimino, $C_{2-12}$ alkenylcarbonylimino, $C_{2-12}$ alkynylcarbonylimino, $C_{6-10}$ aryl-Lx-carbonylimino, $C_{3-10}$ cycloalkyl-Lx-carbonylimino, 5- to 10-membered heteroaryl-Lx-carbonylimino, 5- to 10-membered heterocycloalkyl-Lx-carbonylimino, $C_{1-12}$ alkylthio, $C_{2-12}$ alkenylthio, $C_{2-12}$ alkynylthio, $C_{6-10}$ aryl-Lx-thio, $C_{3-10}$ cycloalkyl-Lx-thio, 5- to 10-membered heteroaryl-Lx-thio, 5- to 10-membered heterocycloalkyl-Lx-thio, $C_{1-12}$ alkylamino, $C_{2-12}$ alkenylamino, $C_{2-12}$ alkynylamino, $C_{2-12}$ alkynylamino, $C_{6-10}$ aryl-Lx-amino, $C_{3-10}$ cycloalkyl-Lx-amino, 5- to 10-membered heteroaryl-Lx-amino, 5- to 10-membered heterocycloalkyl-Lx-amino, $C_{1-12}$ alkylsulfonyl, $C_{2-12}$ alkenylsulfonyl, $C_{2-12}$ alkynylsulfonyl, $C_{6-10}$ aryl-Lx-sulfonyl, $C_{3-10}$ cycloalkyl-Lx-sulfonyl, 5- to 10-membered heteroaryl-Lx-sulfonyl, 5- to 10-membered heterocycloalkyl-Lx-sulfonyl, $C_{1-12}$ alkylsulfonylamino, $C_{2-12}$ alkenylsulfonylamino, $C_{2-12}$ alkynylsulfonylamino, $C_{6-10}$ aryl-Lx-sulfonylamino, $C_{3-10}$ cycloalkyl-Lxsulfonylamino, 5- to 10-membered heteroaryl-Lx-sulfonylamino, 5- to 10-membered heterocycloalkyl-Lx-sulfonylamino, $C_{1-12}$ alkylimino, $C_{2-12}$ alkenylimino, $C_{2-12}$ alkynylimino, $C_{6-10}$ aryl-Lx-imino, $C_{3-10}$ cycloalkyl-Lx-imino, 5- to 10-membered heteroaryl-Lx-imino, 5- to 10-membered heterocycloalkyl-Lx-imino, $C_{1-12}$ alkyloxyimino, $C_{2-12}$ alkenyloxyimino, $C_{2-12}$ alkynyloxyimino, $C_{6-10}$ aryl-Lx-oxyimino, $C_{3-10}$ cycloalkyl-Lx-oxyimino, 5- to 10-membered heteroaryl-Lx-oxyimino, 5- to 10-membered heterocycloalkyl-Lx-oxyimino, $C_{1-12}$ alkyloxycarbonyl, $C_{2-12}$ alkenyloxycarbonyl, $C_{2-12}$ alkynyloxycarbonyl, $C_{6-10}$ aryl-Lx-oxycarbonyl, $C_{3-10}$ cycloalkyl-Lx-oxycarbonyl, 5- to 10-membered heteroaryl-Lx-oxycarbonyl, 5- to 10-membered heterocycloalkyl-Lx-oxycarbonyl, $C_{1-12}$ alkyloxycarbonylamino, $C_{2-12}$ alkenyloxycarbonylamino, $C_{2-12}$ alkynyloxycarbonylamino, $C_{6-10}$ aryl-Lx-oxycarbonylamino, $C_{3-10}$ cycloalkyl-Lx-oxycarbonylamino, 5- to 10-membered heteroaryl-Lx-oxycarbonylamino, 5- to 10-membered heterocycloalkyl-Lx-oxycarbonylamino, $C_{1-12}$ alkylsulfanyl, $C_{2-12}$ alkenylsulfanyl, $C_{2-12}$ alkynylsulfanyl, $C_{6-10}$ aryl-Lx-sulfanyl, $C_{3-10}$ cycloalkyl-Lx-sulfanyl, 5- to 10-membered heteroaryl-Lx-sulfanyl, 5- to 10-membered heterocycloalkyl-Lx-sulfanyl, $C_{1-12}$ alkylsulfinyl, $C_{2-12}$ alkenylsulfinyl, $C_{2-12}$ alkynylsulfinyl, $C_{6-10}$ aryl-Lx-sulfinyl, $C_{3-10}$ cycloalkyl-Lx-sulfinyl, 5- to 10-membered heteroaryl-Lx-sulfinyl, 5- to 10-membered heterocycloalkyl-Lx-sulfinyl, $C_{1-12}$ alkylcarbamoyl, $C_{2-12}$ alkenylcarbamoyl, $C_{2-12}$ alkynylcarbamoyl, $C_{6-10}$ aryl-Lx-carbamoyl, $C_{3-10}$ cycloalkyl-Lx-carbamoyl, 5- to 10-membered heteroaryl-Lx-carbamoyl, 5- to 10-membered heterocycloalkyl-Lx-carbamoyl, $C_{1-12}$ alkylsulfamoyl, $C_{2-12}$ alkenylsulfamoyl, $C_{2-12}$ alkynylsulfamoyl, $C_{6-10}$ aryl-Lx-sulfamoyl, $C_{3-10}$ cycloalkyl-Lx-sulfamoyl, 5- to 10-membered heteroaryl-Lx-sulfamoyl, and 5- to 10-membered heterocycloalkyl-Lx-sulfamoyl.

5. The compound or an enantiomer thereof, or a salt thereof,
or a solvate thereof according to claim 1, wherein
$R_1$ and $R_3$ are each independently,
hydrogen,
optionally substituted $C_{1-12}$ alkyl,
optionally substituted $C_{6-10}$ aryl $C_{1-12}$ alkyl,
optionally substituted $C_{3-10}$ cycloalkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted 5- to 10-membered heteroarylcarbonyl,
optionally substituted 5- to 10-membered heteroaryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or
optionally substituted 5- to 10-membered heterocycloalkylcarbamoyl,
wherein the groups of $R_1$ and $R_3$ are optionally substituted with one to the maximum substitutable number of the same or different substituents selected from substituent group III, and
$R_{2A}$ and $R_{2B}$ are each independently,
hydrogen,
optionally substituted $C_{1-12}$ alkyl,
optionally substituted $C_{6-10}$ aryl $C_{1-12}$ alkyl,
optionally substituted $C_{3-10}$ cycloalkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted 5- to 10-membered heteroarylcarbonyl,
optionally substituted 5- to 10-membered heteroaryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or
optionally substituted 5- to 10-membered heterocycloalkylcarbamoyl,
wherein the groups of $R_{2A}$ and $R_{2B}$ are optionally substituted with one to the maximum substitutable number of the same or different substituents selected from substituent group III, or
$R_{2A}$ and $R_{2B}$, together with the nitrogen atom to which they are attached, form a 5- to 6-membered non-aryl heterocycle, wherein the non-aryl heterocycle is optionally substituted with one to the maximum substitutable number of the same or different substituents selected from substituent group III;
wherein substituent group III consists of halogen, hydroxy, carboxy, amino, carbamoyl, nitro, amidinoamino, alkyl, aryl, cycloalkyl, heteroaryl, alkyloxy, alkylcarbonyl, cycloalkylcarbonyl, alkylcarbonylamino, cycloalkylcarbonylamino, alkylamino, cycloalkylalkylamino, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

6. The compound or an enantiomer thereof, or a salt thereof,
or a solvate thereof according to claim 1, wherein
$R_1$ and $R_3$ are each independently,
hydrogen,
optionally substituted alkyl,
optionally substituted arylalkyl,
optionally substituted cycloalkyl,
formyl,
optionally substituted alkylcarbonyl,
optionally substituted alkoxycarbonyl,
optionally substituted arylcarbonyl,
optionally substituted aryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$ and $R_3$ are optionally substituted with one to the maximum substitutable number of the same or different substituents selected from substituent group III;
wherein substituent group III consists of halogen, hydroxy, carboxy, amino, carbamoyl, nitro, amidinoamino, alkyl, aryl, cycloalkyl, heteroaryl, alkyloxy, alkylcarbonyl, cycloalkylcarbonyl, alkylcarbonylamino, cycloalkylcarbonylamino, alkylamino, cycloalkylalkylamino, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

7. The compound or an enantiomer thereof, or a salt thereof,
or a solvate thereof according to claim 1, wherein
$R_1$ is
hydrogen,
alkyl,
$C_{1-12}$ alkyl substituted with one to the maximum substitutable number of the same or different substituents selected from the group consisting of amino, substituted amino, hydroxy, substituted oxy, formyl, substituted carbonyl, cycloalkyl, and substituted cycloalkyl,
arylalkyl,
arylalkyl substituted with one to the maximum substitutable number of the same or different substituents selected from the group consisting of halogen, alkyl, substituted alkyl, hydroxy, substituted oxy, amino, substituted amino, and nitro,
formyl, or
substituted carbonyl,
wherein the substituted amino, substituted oxy, substituted carbonyl, substituted cycloalkyl, and substituted alkyl in $R_1$ each independently have one to the maximum substitutable number of the same or different substituents selected from substituent group IV;
wherein substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

8. The compound or an enantiomer thereof, or a salt thereof,
or a solvate thereof according to claim 1, wherein
$R_1$ is
hydrogen,
alkyl,
$C_{1-12}$ alkyl substituted with one to the maximum substitutable number of the same or different substituents selected from the group consisting of amidinoamino, alkoxycarbonyl-substituted amidinoamino, alkoxy, alkoxycarbonyl, carbamoyl, carboxy, hydroxy, trialkylsilyloxy, and cycloalkyl,
arylalkyl,
arylalkyl substituted with one to the maximum substitutable number of the same or different substituents selected from the group consisting of halogen, alkyl, haloalkyl, alkoxy, haloalkoxy, amino, substituted amino, nitro, and hydroxy,
formyl,
alkylcarbonyl,
arylalkylcarbonyl,
alkoxycarbonyl,
arylcarbonyl,
aryloxycarbonyl,
carbamoyl,
alkylcarbamoyl, or
arylalkylcarbamoyl,
wherein the substituted amino has one to the maximum substitutable number of the same or different substituents selected from substituent group IV;
wherein substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

9. The compound or an enantiomer thereof, or a salt thereof,
or a solvate thereof according to claim 1, wherein
$R_3$ is
hydrogen,
alkyl,
formyl,
substituted carbonyl, or
alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl,
arylalkyl,
arylalkyl substituted with one to the maximum substitutable number of the same or different substituents selected from the group consisting of halogen, nitro, hydroxy, substituted oxy, amino, substituted amino, alkyl, and substituted alkyl,
heteroarylalkyl, or
substituted heteroarylalkyl,
wherein the substituted carbonyl, substituted oxy, substituted amino, substituted cycloalkyl, substituted heterocycloalkyl, substituted alkyl, and substituted heteroarylalkyl in $R_3$ each independently have one to the maximum substitutable number of the same or different substituents selected from substituent group IV;
wherein substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

10. The compound or an enantiomer thereof, or a salt thereof,
or a solvate thereof according to claim 1, wherein
$R_{2A}$ and $R_{2B}$ are each independently,
hydrogen,
alkyl,
formyl,
substituted carbonyl,
alkyl substituted with one to the maximum substitutable number of the same or different substituents selected from the group consisting of hydroxy, substituted oxy, substituted carbonyl, amino, substituted amino, cycloalkyl, substituted cycloalkyl, heterocycloalkyl, and substituted heterocycloalkyl,
arylalkyl,
arylalkyl substituted with one to the maximum substitutable number of the same or different substituents selected from the group consisting of halogen, nitro, hydroxy, substituted oxy, amino, substituted amino, alkyl, and substituted alkyl,
heteroarylalkyl, or
substituted heteroarylalkyl,
wherein the substituted carbonyl, substituted oxy, substituted amino, substituted cycloalkyl, substituted heterocycloalkyl, substituted alkyl, and substituted heteroarylalkyl in $R_{2A}$ and $R_{2B}$ each independently have one to the maximum substitutable number of the same or different substituents selected from substituent group IV,
wherein substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl, or
$R_{2A}$ and $R_{2B}$, together with the nitrogen atom to which they are attached, form a non-aryl heterocycle, wherein the non-aryl heterocycle is optionally substituted with one or up to the maximum substitutable number of the same or different substituents selected from substituent group VI;
wherein substituent group VI consists of halogen, hydroxy, carboxy, amino, formyl, carbamoyl, cyano, nitro, amidino, amidinoamino, alkyl, alkyloxy, haloalkyl, haloalkyloxy, alkylamino, formyl, alkylcarbonyl, alkyloxycarbonyl, and alkylcarbamoyl.

11. The compound or an enantiomer thereof, or a salt thereof,
or a solvate thereof according to claim 1, wherein
$R_1$ is
alkyl,
alkyl substituted with one to the maximum substitutable number of the same or different substituents selected from the group consisting of amidinoamino, carbamoyl, carboxy, hydroxy, and cycloalkyl,
arylalkyl, or
arylalkyl substituted with one to the maximum substitutable number of the same or different substituents selected from the group consisting of halogen, alkyl, haloalkyl, alkoxy, haloalkoxy, substituted amino, and hydroxy,
wherein the substituted amino has one to the maximum substitutable number of the same or different substituents selected from substituent group IV,
wherein substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

12. A compound represented by formula XXIIF:

[Chemical Formula 53]

Formula XXIIF

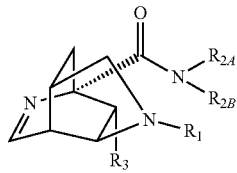

or formula XXIIB

[Chemical Formula 54]

Formula XXIIB

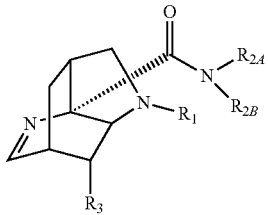

or an enantiomer thereof, or a salt thereof, or a solvate thereof, wherein
$R_1$ and $R_3$ are each independently,
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl,
$R_{2A}$ is hydrogen, and
$R_{2B}$ is
alkyl,
alkyl substituted with one to the maximum substitutable number of the same or different substituents selected from the group consisting of amidinoamino, carbamoyl, carboxy, hydroxy, and cycloalkyl,
arylalkyl, or
arylalkyl substituted with one to the maximum substitutable number of the same or different substituents selected from the group consisting of halogen and alkyl.

13. The compound or an enantiomer thereof, or a salt thereof, or a solvate thereof according to claim 12, wherein
$R_3$ is
alkyl,
alkyl substituted with one to the maximum substitutable number of the same or different substituents selected from the group consisting of amidinoamino, carbamoyl, carboxy, hydroxy, and cycloalkyl, or
arylalkyl.

14. A method for the prophylaxis or treatment of rabies, comprising administering a therapeutically effective amount of the compound according to claim 1, or a pharmaceutically acceptable salt thereof, to a subject in need thereof.

* * * * *

UNITED STATES PATENT AND TRADEMARK OFFICE
CERTIFICATE OF CORRECTION

| | | |
|---|---|---|
| PATENT NO. | : 11,780,841 B2 | Page 1 of 1 |
| APPLICATION NO. | : 17/679075 | |
| DATED | : October 10, 2023 | |
| INVENTOR(S) | : Hiroyuki Kouji et al. | |

It is certified that error appears in the above-identified patent and that said Letters Patent is hereby corrected as shown below:

On the Title Page

Item (57) Abstract:

"

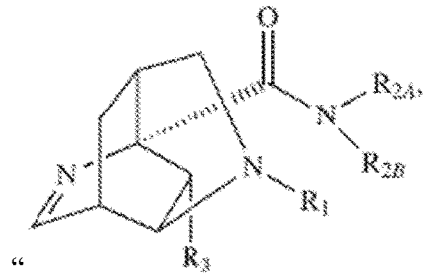

Should read:

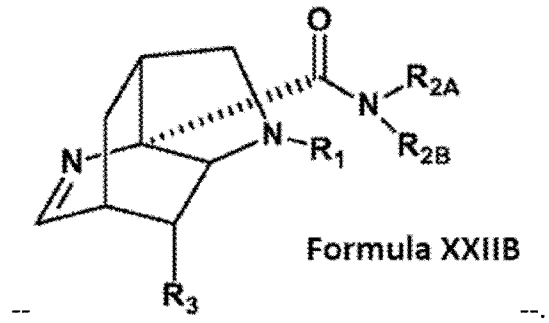

--.

In the Claims

Column 352, Claim 11, Line 38:
"group IV,"
Should read:
-- group IV; --.

Signed and Sealed this
Eighth Day of July, 2025

Coke Morgan Stewart
*Acting Director of the United States Patent and Trademark Office*